US009561231B2

(12) United States Patent
Hubbard et al.

(10) Patent No.: US 9,561,231 B2
(45) Date of Patent: Feb. 7, 2017

(54) PYRIDINONE AND PYRIDAZINONE DERIVATIVES

(71) Applicant: AbbVie Inc., North Chicago, IL (US)

(72) Inventors: Robert D. Hubbard, San Diego, CA (US); Le Wang, Vernon Hills, IL (US); Chang H Park, Wadsworth, IL (US); Chaohong Sun, Gurnee, IL (US); Keith F McDaniel, Wauconda, IL (US); John K Pratt, Kenosha, WI (US); Todd N Soltwedel, Chicago, IL (US); Michael D Wendt, Vernon Hills, IL (US); James H Holms, Gurnee, IL (US); Dachun Liu, Vernon Hills, IL (US); George S Sheppard, Wilmette, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/796,437

(22) Filed: Mar. 12, 2013

(65) Prior Publication Data

US 2013/0331382 A1    Dec. 12, 2013

(30) Foreign Application Priority Data

Jun. 12, 2012    (WO) ................ PCT/CN2012/076748

(51) Int. Cl.
| | | |
|---|---|---|
| A61K 31/541 | (2006.01) | |
| A61K 31/50 | (2006.01) | |
| A61K 31/4412 | (2006.01) | |
| A61K 31/501 | (2006.01) | |
| A61K 31/5377 | (2006.01) | |
| A61K 45/06 | (2006.01) | |
| C07D 237/14 | (2006.01) | |
| C07D 213/64 | (2006.01) | |
| C07D 401/04 | (2006.01) | |
| C07D 401/10 | (2006.01) | |
| C07D 403/04 | (2006.01) | |
| C07D 403/10 | (2006.01) | |
| C07D 413/10 | (2006.01) | |
| C07D 417/10 | (2006.01) | |
| C07D 403/12 | (2006.01) | |
| C07D 401/14 | (2006.01) | |
| C07D 213/74 | (2006.01) | |
| C07D 213/81 | (2006.01) | |
| C07D 401/02 | (2006.01) | |
| C07D 401/12 | (2006.01) | |
| C07D 407/04 | (2006.01) | |
| C07D 407/12 | (2006.01) | |
| C07D 409/04 | (2006.01) | |
| C07D 417/04 | (2006.01) | |

(Continued)

(52) U.S. Cl.
CPC ......... *A61K 31/541* (2013.01); *A61K 31/4412* (2013.01); *A61K 31/50* (2013.01); *A61K 31/501* (2013.01); *A61K 31/5377* (2013.01); *A61K 45/06* (2013.01); *C07D 213/30* (2013.01); *C07D 213/64* (2013.01); *C07D 213/68* (2013.01); *C07D 213/74* (2013.01); *C07D 213/81* (2013.01); *C07D 237/14* (2013.01); *C07D 401/02* (2013.01); *C07D 401/04* (2013.01); *C07D 401/10* (2013.01); *C07D 401/12* (2013.01); *C07D 401/14* (2013.01); *C07D 403/04* (2013.01); *C07D 403/10* (2013.01); *C07D 403/12* (2013.01); *C07D 407/04* (2013.01); *C07D 407/12* (2013.01); *C07D 409/04* (2013.01); *C07D 413/10* (2013.01); *C07D 417/04* (2013.01); *C07D 417/10* (2013.01); *C07D 417/12* (2013.01); *C07D 498/04* (2013.01)

(58) Field of Classification Search
None
See application file for complete search history.

(56) References Cited

U.S. PATENT DOCUMENTS 4,289,774 A    9/1981    Schacht et al.
4,397,854 A    8/1983    Sircar
(Continued)

FOREIGN PATENT DOCUMENTS

CN    101910182 A    12/2010
DE    1445510 A1    3/1969
(Continued)

OTHER PUBLICATIONS

Ach, F., J. Chem. Soc., Abstr. 58, 70-1(1890) (CAS Abstract).*
(Continued)

*Primary Examiner* — Timothy R Rozof
(74) *Attorney, Agent, or Firm* — Glen Gesicki

(57) ABSTRACT

The present invention provides for compounds of formula (I)

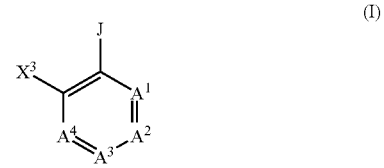

wherein $A^1$, $A^2$, $A^3$, $A^4$, J, and $X^3$ have any of the values defined therefor in the specification, and pharmaceutically acceptable salts thereof, that are useful as agents in the treatment of diseases and conditions, including inflammatory diseases, diabetes, obesity, cancer, and AIDS. Also provided are pharmaceutical compositions comprising one or more compounds of formula I.

43 Claims, No Drawings

(51) Int. Cl.
　　　*C07D 417/12*　　　(2006.01)
　　　*C07D 498/04*　　　(2006.01)
　　　*C07D 213/30*　　　(2006.01)
　　　*C07D 213/68*　　　(2006.01)

(56) References Cited

U.S. PATENT DOCUMENTS

| | | |
|---|---|---|
| 4,404,203 A | 9/1983 | Sircar |
| 4,657,906 A | 4/1987 | Emmett et al. |
| 4,699,914 A | 10/1987 | Hilboll et al. |
| 4,734,415 A | 3/1988 | Sircar et al. |
| 5,385,925 A | 1/1995 | Narr et al. |
| 5,401,738 A | 3/1995 | Mederski et al. |
| 5,574,030 A | 11/1996 | Masaki et al. |
| 5,587,393 A | 12/1996 | Narr et al. |
| 5,664,029 A | 9/1997 | Callahan et al. |
| 5,741,793 A | 4/1998 | Young et al. |
| 5,763,440 A | 6/1998 | Ross et al. |
| 5,814,651 A | 9/1998 | Duplantier et al. |
| 5,852,006 A | 12/1998 | Masaki et al. |
| 5,958,925 A | 9/1999 | Ross et al. |
| 6,063,781 A | 5/2000 | Lai et al. |
| 6,143,751 A | 11/2000 | Cheshire et al. |
| 6,200,982 B1 | 3/2001 | Collins et al. |
| 6,284,755 B1 | 9/2001 | DeSolms et al. |
| 6,300,500 B1 | 10/2001 | Muraoka et al. |
| 6,352,994 B2 | 3/2002 | Collins et al. |
| 6,452,008 B2 | 9/2002 | Muraoka et al. |
| 6,531,496 B1 | 3/2003 | Uhr et al. |
| 7,087,622 B2 | 8/2006 | Li |
| 7,329,680 B2 | 2/2008 | Whitehouse et al. |
| 7,410,984 B2 | 8/2008 | Witherington et al. |
| 7,459,453 B2 | 12/2008 | Dal Piaz et al. |
| 7,473,669 B2 | 1/2009 | Shaber et al. |
| 7,491,794 B2 | 2/2009 | Blatt et al. |
| 7,511,013 B2 | 3/2009 | Molino et al. |
| 7,511,038 B2 | 3/2009 | Dal Piaz et al. |
| 7,514,068 B2 | 4/2009 | Tung |
| 7,521,421 B2 | 4/2009 | Naicker et al. |
| 7,528,131 B2 | 5/2009 | Persichetti et al. |
| 7,531,685 B2 | 5/2009 | Czarnik |
| 7,534,814 B2 | 5/2009 | Ascher et al. |
| 7,538,189 B2 | 5/2009 | Naicker et al. |
| 7,790,723 B2 | 9/2010 | Eggenweiler et al. |
| 7,947,835 B2 | 5/2011 | Brittelli et al. |
| 2001/0018438 A1 | 8/2001 | Collins et al. |
| 2001/0051732 A1 | 12/2001 | Muraoka et al. |
| 2002/0037888 A1 | 3/2002 | DeSolms et al. |
| 2004/0067955 A1 | 4/2004 | Tabuchi et al. |
| 2004/0259863 A1 | 12/2004 | Eggenweiler et al. |
| 2005/0003135 A1 | 1/2005 | Schmidhalter et al. |
| 2005/0004114 A1 | 1/2005 | Whitehouse et al. |
| 2005/0043315 A1 | 2/2005 | Tsutsumi et al. |
| 2005/0070529 A1 | 3/2005 | Sutter et al. |
| 2005/0222034 A1 | 10/2005 | Hsu et al. |
| 2005/0222160 A1 | 10/2005 | Eggenweiler et al. |
| 2005/0256137 A1 | 11/2005 | Li |
| 2005/0267018 A1 | 12/2005 | Blatt et al. |
| 2005/0288337 A1 | 12/2005 | Witherington et al. |
| 2006/0052379 A1 | 3/2006 | Dal Piaz et al. |
| 2006/0229337 A1 | 10/2006 | Brittelli et al. |
| 2006/0252755 A1 | 11/2006 | Shaber et al. |
| 2007/0197536 A1 | 8/2007 | Dal Piaz et al. |
| 2007/0225291 A1 | 9/2007 | Boys et al. |
| 2008/0027041 A1 | 1/2008 | Hudkins et al. |
| 2008/0090827 A1 | 4/2008 | Taylor et al. |
| 2008/0146574 A1 | 6/2008 | Whitehouse et al. |
| 2008/0269235 A1 | 10/2008 | Dal Piaz et al. |
| 2008/0280933 A1 | 11/2008 | Efremov et al. |
| 2009/0029996 A1 | 1/2009 | Aguilar et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105254 A1 | 4/2009 | Mustelin et al. |
| 2009/0105307 A1 | 4/2009 | Galley et al. |
| 2009/0105338 A1 | 4/2009 | Czarnik |
| 2009/0105471 A1 | 4/2009 | Blatt et al. |
| 2009/0111840 A1 | 4/2009 | Herold et al. |
| 2009/0111969 A1 | 4/2009 | Blatt et al. |
| 2009/0111982 A1 | 4/2009 | Blatt et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2009/0253708 A1 | 10/2009 | Kelly et al. |
| 2009/0286843 A1 | 11/2009 | Blatt et al. |
| 2010/0009991 A1 | 1/2010 | Terasaka et al. |
| 2010/0041637 A1 | 2/2010 | Claremon et al. |
| 2010/0137317 A1 | 6/2010 | Ripka et al. |
| 2010/0160292 A1 | 6/2010 | Whitney et al. |
| 2010/0168104 A1 | 7/2010 | Guillemont et al. |
| 2010/0179148 A1 | 7/2010 | Stieber et al. |
| 2010/0179149 A1 | 7/2010 | Stieber et al. |
| 2010/0197655 A1 | 8/2010 | Beaudoin et al. |
| 2010/0267132 A1 | 10/2010 | McPhail et al. |
| 2010/0273779 A1 | 10/2010 | Bacon et al. |
| 2010/0280007 A1 | 11/2010 | Bacon et al. |
| 2010/0286127 A1 | 11/2010 | Miyoshi et al. |
| 2010/0292238 A1 | 11/2010 | Ripka et al. |
| 2011/0098320 A1 | 4/2011 | Claremon et al. |
| 2011/0105504 A1 | 5/2011 | Claremon et al. |
| 2011/0112082 A1 | 5/2011 | Claremon et al. |

FOREIGN PATENT DOCUMENTS

| | | |
|---|---|---|
| DE | 10010429 A1 | 9/2001 |
| EP | 0096517 A2 | 12/1983 |
| EP | 0365486 A2 | 4/1990 |
| EP | 0711759 A1 | 5/1996 |
| EP | 0760208 A2 | 3/1997 |
| EP | 0856255 A2 | 8/1998 |
| EP | 0989131 A1 | 3/2000 |
| EP | 1054190 A1 | 11/2000 |
| EP | 1308441 A1 | 5/2003 |
| EP | 1887008 A1 | 2/2008 |
| EP | 2239264 A1 | 10/2010 |
| JP | S5795964 A | 6/1982 |
| JP | H0578250 A | 3/1993 |
| JP | H05148222 A | 6/1993 |
| JP | H1149755 A | 2/1999 |
| JP | 2000178258 A | 6/2000 |
| JP | 2003313169 A | 11/2003 |
| JP | 2005255675 A | 9/2005 |
| JP | 2008156311 A | 7/2008 |
| WO | 9417059 A1 | 8/1994 |
| WO | 9507271 A1 | 3/1995 |
| WO | 9610559 A1 | 4/1996 |
| WO | 9633994 A1 | 10/1996 |
| WO | 9710223 A1 | 3/1997 |
| WO | 9720822 A1 | 6/1997 |
| WO | 9855480 A1 | 12/1998 |
| WO | 0138377 A1 | 5/2001 |
| WO | 0172812 A1 | 10/2001 |
| WO | 2004022540 A2 | 3/2004 |
| WO | 2004035564 A1 | 4/2004 |
| WO | 2005049581 A1 | 6/2005 |
| WO | 2005065688 A1 | 7/2005 |
| WO | 2005095403 A2 | 10/2005 |
| WO | 2005099353 A2 | 10/2005 |
| WO | 2006008754 A1 | 1/2006 |
| WO | 2006032470 A1 | 3/2006 |
| WO | 2007008144 A1 | 1/2007 |
| WO | 2007133561 A1 | 11/2007 |
| WO | 2008012622 A2 | 1/2008 |
| WO | 2008013838 A2 | 1/2008 |
| WO | 2008033854 A1 | 3/2008 |
| WO | 2008072784 A1 | 6/2008 |
| WO | 2009084693 A1 | 7/2009 |
| WO | 2010002655 A2 | 1/2010 |
| WO | 2010029299 A1 | 3/2010 |
| WO | 2010069504 A1 | 6/2010 |
| WO | 2011054553 A1 | 5/2011 |
| WO | 2011054843 A1 | 5/2011 |

(56) References Cited

FOREIGN PATENT DOCUMENTS

| WO | 2011054844 A1 | 5/2011 |
|---|---|---|
| WO | 2011054845 A1 | 5/2011 |
| WO | 2011054846 A1 | 5/2011 |
| WO | 2011054848 A1 | 5/2011 |
| WO | 2011054851 A1 | 5/2011 |
| WO | 2011109261 A1 | 9/2011 |
| WO | 2012075456 A1 | 6/2012 |
| WO | 2012129013 A1 | 9/2012 |
| WO | 2013045519 A1 | 4/2013 |

OTHER PUBLICATIONS

Knops et al., 24(29) Tetrahedron Letts. 2973-6 (1983) (CAS Abstract).*
Limaye et al., 3 J. Univ. Bombay, Sci.: Phys. Sci., Math., Bio. Sci. & Med. 135-40 (1934) (CAS Abstract).*
El-Mobayed et al., 8(3) Arab Gulf J. Sci. Res. 29-38 (1990) (citing CAS Abstract).*
Banerjee C., et al., "BET Bromodomain Inhibition as a Novel Strategy for Reactivation of HIV-1," Journal of Leukocyte Biology, 2012, vol. 92 (6), pp. 1147-1154.
Berge, S. M. et al., "Pharmaceutical Salts," Journal of Pharmaceutical Sciences, 1977, vol. 66 (1), pp. 1-19.
Blagojevic, N. et al., "Role of heavy water in Boron Neutron Capture Therapy," Topics in Dosimetry & Treatment Planning for Neutron Capture Therapy, 1994, pp. 125-134.
Blake, M. I. et al., "Studies With Deuterated Drugs," Journal of Pharmaceutical Sciences, 1975, vol. 64 (3), pp. 367-391.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Chung C.W., et al., "Discovery and Characterization of Small Molecule Inhibitors of the BET Family Bromodomains," Journal of Medicinal Chemistry, 2011, vol. 54 (11), pp. 3827-3838.
Chung C.W., "Small Molecule Bromodomain Inhibitors: Extending the Druggable Genome," Progress in Medicinal Chemistry, 2012, vol. 51, pp. 1-55.
Coates W.J., et al., "One-Pot Preparation of 6-Substituted 3(2H)-Pyridazinones from Ketones," Synthesis, 1993, vol. 1993 (3), pp. 334-342.
Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Czajka, D. M. et al., "Effect of Deuterium Oxide on the Reproductive Potential of Mice," Annals of the New York Academy of Sciences, 1960, vol. 84, pp. 770-779.
Czajka, D. M. et al., "Physiological Effects of Deuterium on Dogs," American Journal of Physiology, 1961, vol. 201 (2), pp. 357-362.
Dawson M.A., et al., "Inhibition of BET Recruitment to Chromatin as an Effective Treatment for MLL-fusion Leukaemia," Nature, 2011, vol. 478 (7370), pp. 529-533.
Delmore J.E., et al., "BET Bromodomain Inhibition as a Therapeutic Strategy to Target c-Myc," Cell, 2011, vol. 146 (6), pp. 904-917.
Denis G.V., "Bromodomain Coactivators in Cancer, Obesity, type 2 Diabetes, and Inflammation," Discovery Medicine, 2010, vol. 10 (55), pp. 489-499.
Filippakopoulos P., et al., "Selective Inhibition of BET Bromodomains," Nature, 2010, vol. 468 (7327), pp. 1067-1073.
Foster, A. B. et al., "Deuterium Isotope Effects in the Metabolism of Drugs and Xenobiotics: Implications for Drug Design," Advances in Drug Research, 1985, vol. 14, pp. 2-36.
Greene T.W., et al., in: Protective Groups in Organic Synthesis, 3rd Edition, John Wiley and Sons, Inc., 1999, Preface, Table of Contents, Abbreviations.
Hewings D.s., et al., "3,5-Dimethylisoxazoles Act as Acetyl-Lysine-Mimetic Bromodomain Ligands," Journal of Medicinal Chemistry, 2011, vol. 54 (19), pp. 6761-6770.
Hewings D.S., et al., "Progress in the Development and Application of Small Molecule Inhibitors of Bromodomain-acetyl-lysine Interactions," Journal of Medicinal Chemistry, 2012, vol. 55 (22), pp. 9393-9413.
Huang B., et al., "Brd4 Coactivates Transcriptional Activation of NF-kappaB via Specific Binding to Acetylated RelA," Molecular and Cellular Biology, 2009, vol. 29 (5), pp. 1375-1387.
International Search Report and Written Opinion for Application No. PCT/CN2012/076748, mailed on 21 Mar. 2013, 14 pages.
International Search Report and Written Opinion for Application No. PCT/US2013/045151, mailed on Aug. 16, 2013, 20 pages.
International Search Report for Application No. PCT/EP2010/066695, mailed on Feb. 7, 2011, 2 pages.
Jang M.K., et al., "The Bromodomain Protein Brd4 is a Positive Regulatory Component of P-TEFb and Stimulates RNA Polymerase II-dependent Transcription," Molecular Cell, 2005, vol. 19 (4), pp. 523-534.
Kato, S. et al., "Synthesis of Deuterated Mosapride Citrate," Journal of Labelled Compounds and Radiopharmaceuticals, 1995, vol. 36 (10), pp. 927-932.
Kushner, et al., "Pharmacological uses and perspectives of heavy water and deuterated compounds," Canadian Journal of Physiology and Pharmacology, 1999, vol. 77 (2), pp. 79-88.
Leroy G., et al., "The Double Bromodomain Proteins Brd2 and Brd3 Couple Histone Acetylation to Transcription," Molecular Cell, 2008, vol. 30 (1), pp. 51-60.
Lizondo, J. et al., "Linezolid: Oxazolidinone antibacterial," Drugs of the Future, 1996, vol. 21 (11), pp. 1116-1123.
Maha A.H., et al., "Design and Synthesis of New 6-Substituted Pyridazine Derivatives as Hypotensive Agents," Bulletin of the Faculty of Pharmacy, 2008, vol. 46 (3), pp. 45-56.
Mallesham, B. et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.
Matzuk M.M., et al., "Small-molecule Inhibition of BRDT for Male Contraception," Cell, 2012, vol. 150 (4), pp. 673-684.
Mertz J.A., et al., "Targeting MYC Dependence in Cancer by Inhibiting BET Bromodomains," Proceedings of the National Academy of Sciences, 2011, vol. 108 (40), pp. 16669-16674.
Miyaura N., et al., "Palladium-Catalyzed Cross-Coupling Reactions of Organoboron Compounds," Chemical Reviews, 1995, vol. 95 (7), pp. 2457-2483.
Nicodeme E., et al., "Suppression of Inflammation by a Synthetic Histone Mimic," Nature, 2010, vol. 468 (7327), pp. 1119-1123.
Prescott D.M., "Methods in Cell Biology", Academic Press, 1976, Table of Contents.
Prinjha R.K., et al., "Place your BETs: the Therapeutic Potential of Bromodomains," Trends in Pharmacological Sciences, 2012, vol. 33 (3), pp. 146-153.
Shatalov G.V., et al., "Vinylation of 3-Pyridazones," Chemistry of Heterocyclic Compounds, 1980, No. 3, pp. 394-397.
Sundar B.G., et al., "Amine-Constrained Pyridazinone Histamine H, Receptor Antagonists," Bioorganic & Medicinal Chemistry Letters, 2011, vol. 21 (18), pp. 5543-5546.
Suzuki A., "Recent Advances in the Cross-Coupling Reactions of organoboron Derivates with organic Electrophiles, 1995-1998," Journal of Organometallic Chemistry, 1999, vol. 576, pp. 147-168.
Thomson, J.F., "Physiological Effects of D20 in Mammals," Annals of the New York Academy of Sciences, 1960, vol. 84, pp. 736-744.
Tiryaki D., et al., "Synthesis of Some New 2,6-Disubstituded-3(2H)-Pyridazinone Derivatives and Investigation of their Analgesic, Anti-Inflammatory and Antimicrobial Activities," Medicinal Chemistry Research, 2012, vol. 22 (6), pp. 2553-2560.
Toshihiro Y., et al., "Pyridazinones. IV. Synthesis, Antisecretory and Antiulcer Activities of Urea Derivatives," European Journal of Medicinal Chemistry, 1983, vol. 18 (3), pp. 209-214.
Wang F., et al., "Brd2 Disruption in Mice Causes Severe Obesity without Type 2 Diabetes," Biochemical Journal, 2010, vol. 425, pp. 71-83.

(56) References Cited

OTHER PUBLICATIONS

Yang Z., et al., "Brd4 Recruits P-TEFb to Chromosomes at Late Mitosis to Promote G1 Gene Expression and Cell Cycle Progression," Molecular and Cellular Biology, 2008, vol. 28 (3), pp. 967-976.

Zhang G., et al., "Down-regulation of NF-κB Transcriptional Activity in HIV-associated Kidney Disease by BRD4 Inhibition," Journal of Biological Chemistry, 2012, vol. 287 (34), pp. 28840-28851.

Zuber J., et al., "RNAi Screen Identifies Brd4 as a Therapeutic Target in Acute Myeloid Leukaemia," Nature, 2011, vol. 478 (7370), pp. 524-528.

Garnier J.M., et al., "BET Bromodomain Inhibitors: A Patent Review," Expert Opinion on Therapeutic Patents, 2014, vol. 24 (2), pp. 185-199.

Roberts D.A., et al., "1,2,4-Triazolo[4,3-a]pyrazine Derivatives with Human Renin Inhibitory Activity. 1. Synthesis and Biological Properties of Alkyl Alcohol and Statine Derivatives," Journal of Medicinal Chemistry, 1990, vol. 33 (9), pp. 2326-2334.

Supplementary European Search Report for Application No. EP12878861, mailed on Oct. 9, 2015, 8 pages.

* cited by examiner

PYRIDINONE AND PYRIDAZINONE DERIVATIVES

CROSS-REFERENCES TO RELATED APPLICATIONS

This application claims the benefit of PCT Application No. PCT/CN2012/076748, filed on Jun. 12, 2012, the teachings of which are herein incorporated by reference.

BACKGROUND

Bromodomains refer to conserved protein structural folds which bind to N-acetylated lysine residues that are found in some proteins. The BET family of bromodomain containing proteins is comprised of four members (BRD2, BRD3, BRD4 and BRDt). Each member of the BET family employs two bromodomains to recognize N-acetylated lysine residues found primarily, but not exclusively, on the amino-terminal tails of histone proteins. These interactions modulate gene expression by recruiting transcription factors to specific genome locations within chromatin. For example, histone-bound BRD4 recruits the transcription factor P-TEFb to promoters, resulting in the expression of a subset of genes involved in cell cycle progression (Yang et al., Mol. Cell. Biol. 28: 967-976 (2008)). BRD2 and BRD3 also function as transcriptional regulators of growth promoting genes (LeRoy et al., Mol. Cell 30: 51-60 (2008)). BET family members were recently established as being important for the maintenance of several cancer types (Zuber et al., Nature 478: 524-528 (2011); Mertz et al; Proc. Nat'l. Acad. Sci. 108: 16669-16674 (2011); Delmore et al., Cell 146: 1-14, (2011); Dawson et al., Nature 478: 529-533 (2011)). BET family members have also been implicated in mediating acute inflammatory responses through the canonical NF-KB pathway (Huang et al., Mol. Cell. Biol. 29: 1375-1387 (2009)) resulting in the upregulation of genes associated with the production of cytokines (Nicodeme et al., Nature 468: 1119-1123, (2010)). Suppression of cytokine induction by BET bromodomain inhibitors has been shown to be an effective approach to treat inflammation-mediated kidney disease in an animal model (Zhang, et al., J. Biol. Chem. 287: 28840-28851 (2012)). BRD2 function has been linked to predisposition for dyslipidemia or improper regulation of adipogenesis, elevated inflammatory profiles and increased susceptibility to autoimmune diseases (Denis, Discovery Medicine 10: 489-499 (2010)). The human immunodeficiency virus utilizes BRD4 to initiate transcription of viral RNA from stably integrated viral DNA (Jang et al., Mol. Cell, 19: 523-534 (2005)). BET bromodomain inhibitors have also been shown to reactivate HIV transcription in models of latent T cell infection and latent monocyte infection (Banerjee, et al, J. Leukocyte Biol. doi:10.1189/jlb.0312165). BRDt has an important role in spermatogenesis that is blocked by BET bromodomain inhibitors (Matzuk, et al., Cell 150: 673-684 (2012)). Accordingly, there is an ongoing medical need to develop new drugs to treat these indications.

SUMMARY

In one aspect, the present invention relates to compounds of Formula (I) or a pharmaceutically acceptable salt thereof,

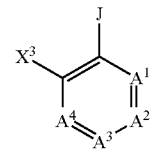

(I)

Wherein J is a group of formula IIa or IIb:

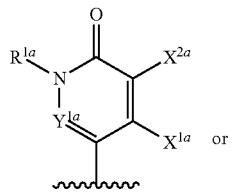

(IIa)

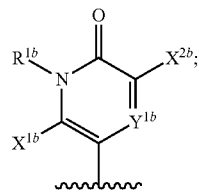

(IIb)

wherein
$R^{1a}$ is $C_1$-$C_3$ alkyl, $C_2$-$C_3$ alkylene-OH, or $C_1$-$C_3$ haloalkyl;
$Y^{1a}$ is N or $CR^{xa}$, wherein $R^{xa}$ is H, halo, $C_1$-$C_3$ alkyl, —O—$C_1$-$C_3$ alkyl, $C_1$-$C_3$ haloalkyl, —O—$C_1$-$C_3$ haloalkyl, aryl, aryl-$C_1$-$C_3$alkylene-OH, aryl-$C_1$-$C_3$alkylene-heterocycloalkyl, $C(O)NR^{10}R^{12}$, wherein heterocycloalkyl of aryl-$C_1$-$C_3$alkylene-heterocycloalkyl may be substituted with one to three $C_1$-$C_3$alkyl,
$R^{1b}$ is H, $C_1$-$C_3$ alkyl, $C_2$-$C_3$ alkylene-OH, or $C_1$-$C_3$ haloalkyl;
$Y^{1b}$ is N or $CR^{xb}$, wherein $R^{xb}$ is heteroaryl, H, halo, $C_1$-$C_3$ alkyl, —O—$C_1$-$C_3$ alkyl, $C_1$-$C_3$ haloalkyl, —O—$C_1$-$C_3$ haloalkyl, aryl, aryl-$C_1$-$C_3$alkylene-OH, aryl-$C_1$-$C_3$alkylene-heterocycloalkyl, $C(O)NR^{10}R^{12}$, wherein heterocycloalkyl of aryl-$C_1$-$C_3$alkylene-heterocycloalkyl may be substituted with one to three $C_1$-$C_3$alkyl; wherein said heteroaryl may be substituted with one to three groups selected from the group consisting of: $C_1$-$C_6$ alkyl, $C_1$-$C_3$alkylene-aryl, $C_1$-$C_3$alkylene-heteroaryl, $C_1$-$C_3$alkylene-heterocycloalkyl, COOH, and COO—$C_1$-$C_4$alkyl,
$X^{2a}$ is selected from the group consisting of: H, —$NR^{10}R^{12}$, halo, OH, —O—$C_1$-$C_4$ alkyl, aryl, heteroaryl, —$NR^{10}C(O)$—$C_1$-$C_4$ alkyl, $NR^{10}C(O)O$—$C_1$-$C_6$ alkyl, and $NR^{10}S(O)_2$—$C_1$-$C_6$ alkyl;
$X^{2b}$ is $C_1$-$C_3$ alkyl, $C_2$-$C_3$ alkylene-OH, or $C_1$-$C_3$ haloalkyl;
$X^{1a}$ and $X^{1b}$ are each selected from the group consisting of: hydrogen, halo, $C_1$-$C_6$ alkyl, $C_1$-$C_4$ haloalkyl, $C_2$-$C_4$ alkenyl, —$C_2$-$C_4$ alkenylene-O—$C_1$-$C_6$ alkyl, $C_2$-$C_4$ alkynyl, —$C_2$-$C_4$ alkynylene-N($C_1$-$C_6$ alkyl)$_2$, —O—$C_1$-$C_6$ alkyl, —O—$CD_2CH_3$, —O—$CD_2CD_3$, —O—$C_3$-$C_7$ cycloalkyl, —O-heterocycloalkyl, —O-aryl, —O—$C_1$-$C_3$ alkylene-$C_3$-$C_7$ cycloalkyl, —O—$C_1$-$C_3$ alkylene-heterocycloalkyl, —O—$C_1$-$C_3$ alkylene-aryl, wherein the aryl groups of the —O-aryl and —O—$C_1$-$C_3$ alkylene-aryl, the $C_3$-$C_7$ cycloalkyl groups of the —O—$C_3$-$C_7$ cycloalkyl and —O—$C_1$-$C_3$ alkylene-$C_3$-$C_7$ cycloalkyl, and the heterocycloalkyl groups of the —O-heterocycloalkyl and —O—$C_1$-$C_3$ alkylene-heterocycloalkyl may be substituted with 1, 2, or 3 substituents independently selected from the group consisting of oxo, halo, —CN, $C_1$-$C_6$ alkyl, $C_1$-$C_6$ haloalkyl, $NH_2$, N(H)(alkyl), N(alkyl)$_2$, —C(O)O$C_1$-$C_6$ alkyl, and $C_1$-$C_3$ alkylene-heterocycloalkyl, —O—$C_1$-$C_4$ haloalkyl, OH, —O—$C_1$-$C_6$ alkylene-OH, —O—$C_1$-$C_6$ alkylene-N($R^{10}$)$_2$, —O—$C_1$-$C_3$ alkylene-C(O)O—$C_1$-$C_4$ alkyl, —$NR^{10}$—$C_1$-$C_6$ alkyl, —$NR^{10}$—$C_1$-$C_6$ haloalkyl, —$NR^{10}$—C(O)O$C_1$-$C_6$ alkyl, —$NR^{10}$—C(O)O$C_1$-$C_6$haloalkyl, —$NR^{10}$—C(O)$NR^{10}R^{12}$, —$NR^{10}$—$SO_2R^{12}$, —$NR^{10}$—$C_3$-$C_7$ cycloalkyl, —$NR^{10}$—$C_1$-$C_3$ alkylene-$C_3$-$C_7$ cycloalkyl, $C_1$-$C_4$ alkylene-OH, —$C_1$-$C_3$ alkylene-C(O)O$C_1$-$C_4$ alkyl, $C_1$-$C_3$ alkylene-$NR^{10}$C(O)—$C_1$-$C_4$ alkyl, —$C_1$-$C_3$ alkylene-C(O)$NR^{10}R^{12}$, —$C_2$-$C_4$ alkenylene-O—$C_1$-$C_4$ alkyl, —O—$C_1$-$C_4$ alkyl, C(O)O $C_1$-$C_4$ alkyl, C(O)$NR^{10}R^{12}$, —$NR^{10}$C(O)—$C_1$-$C_4$ alkyl, —$NR^{10}$—$C_1$-$C_3$ alkylene-C(O)—$C_1$-$C_4$ alkyl, —$NR^{10}$—$C_1$-$C_3$ alkylene-C(O)O—$C_1$-$C_4$ alkyl, —$SO_2NR^{10}R^{12}$, and any of groups i-v:

i) $C_3$-$C_{14}$ cycloalkyl, which may be substituted with 1 to 3 of $R^2$, where $R^2$ is selected from the group consisting of: halo, oxo, CN, —O—$C_1$-$C_4$ alkyl, —O—$C_1$-$C_4$ haloalkyl, —$NR^{10}R^{12}$, C(O)$NR^{10}R^{12}$, $C_1$-$C_4$ alkyl, $C_1$-$C_4$ haloalkyl, C(O)—$C_1$-$C_4$ alkyl, —C(O)O—$C_1$-$C_4$ alkyl, $SO_2NR^{10}R^{12}$, $SO_2$—$C_1$-$C_4$ alkyl, and aryl, wherein said aryl may be substituted with 1 to 3 substituents independently selected from group consisting of: halo, $C_1$-$C_3$ alkyl, C(O)—$C_1$-$C_3$alkyl, C(O)OH, C(O)$NR^{10}R^{12}$, and heteroaryl;

ii) heterocycloalkenyl, which may be substituted with 1 to 3 of $R^2$, where $R^2$ is selected from the group consisting of: halo, oxo, CN, —O—$C_1$-$C_4$ alkyl, —O—$C_1$-$C_4$ haloalkyl, —$NR^{10}R^{12}$, C(O)$NR^{10}R^{12}$, $C_1$-$C_4$ alkyl, $C_1$-$C_4$ haloalkyl, C(O)—$C_1$-$C_4$ alkyl, —C(O)O—$C_1$-$C_4$ alkyl, $SO_2NR^{10}R^{12}$, $SO_2$—$C_1$-$C_4$ alkyl, and aryl, wherein said aryl may be substituted with 1 to 3 substituents independently selected from group consisting of: halo, $C_1$-$C_3$ alkyl, C(O)—$C_1$-$C_3$alkyl, C(O)OH, C(O)$NR^{10}R^{12}$, and heteroaryl;

iii) heterocycloalkyl, which may be substituted with 1 to 3 of $R^3$, where $R^3$ is selected from the group consisting of: halo, oxo, CN, —O—$C_1$-$C_4$ alkyl, —O—$C_1$-$C_4$ haloalkyl, —$NR^{10}R^{12}$, C(O)$NR^{10}R^{12}$, $C_1$-$C_4$ alkyl, $C_1$-$C_4$ haloalkyl, C(O)—$C_1$-$C_4$ alkyl, —C(O)O—$C_1$-$C_4$ alkyl, $SO_2NR^{10}R^{12}$, $SO_2$—$C_1$-$C_4$ alkyl, and aryl, wherein said aryl may be substituted with 1 to 3 substituents independently selected from group consisting of: halo, $C_1$-$C_3$ alkyl, C(O)—$C_1$-$C_3$alkyl, C(O)OH, C(O)$NR^{10}R^{12}$, and heteroaryl;

iv) heteroaryl, which may be substituted with 1 to 3 of $R^4$, where $R^4$ is selected from the group consisting of: halo, oxo, CN, —O—$C_1$-$C_4$ alkyl, —O—$C_1$-$C_4$ haloalkyl, —$NR^{10}R^{12}$, —C(O)H, C(O)$NR^{10}R^{12}$, $C_1$-$C_6$ alkyl, $C_1$-$C_4$ haloalkyl, $C_1$-$C_6$ alkylene-heterocycloalkyl, $C_1$-$C_6$alkylene-aryl, $C_1$-$C_6$ alkylene-heteroaryl, C(O)—$C_1$-$C_4$ alkyl, —C(O)O—$C_1$-$C_4$ alkyl, $SO_2NR^{10}R^{12}$, $SO_2$—$C_1$-$C_4$ alkyl, —$NR^{14}$C(O)$C_1$-$C_4$-alkyl, heterocycloalkyl, and aryl, wherein said aryl may be substituted with 1 to 3 substituents independently selected from group consisting of: halo, $C_1$-$C_3$ alkyl, C(O)—$C_1$-$C_3$alkyl, C(O)OH, C(O)$NR^{10}R^{12}$, and heteroaryl, wherein said heterocycloalkyl or heterocycloalkyl group of $C_1$-$C_6$ alkylene-heterocycloalkyl may be substituted with 1 to 3 independently selected $C_1$-$C_3$ alkyl groups, and wherein said heteroaryl group of $C_1$-$C_6$ alkylene-heteroaryl and said aryl groups of $C_1$-$C_6$ alkylene-aryl may be substituted with substituents 1 to 3 groups independently selected from $C_1$-$C_3$ alkyl and $NR^{14}R^{16}$;

v) aryl, which may be substituted with 1 to 3 of $R^6$, where $R^6$ is selected from the group consisting of: halo, CN, —$NR^{14}R^{16}$, N($R^{14}$)C(O)—$C_1$-$C_4$ alkyl, —$NR^{14}SO_2$—$C_1$-$C_4$ alkyl, C(O)H, C(O)$C_1$-$C_6$ alkyl, C(O)heterocycloalkyl, C(O)$NR^{14}R^{16}$, —$C_1$-$C_4$ alkylene-$NR^{14}R^{16}$, $SO_2NR^{14}R^{16}$, C(O)O$C_1$-$C_4$ alkyl, —$SO_2$-heterocycloalkyl, —$SO_2$—$C_1$-$C_6$ alkyl, —$C_1$-$C_6$ alkyl, —OH, —O—$C_1$-$C_6$ alkyl, —$C_1$-$C_6$ haloalkyl, —O—$C_1$-$C_6$ haloalkyl, —$C_1$-$C_6$ alkylene-OH, —C(H)(OH)($C_3$-$C_7$ cycloalkyl), —C(H)(OH)(phenyl), $C_2$-$C_4$ alkenylene-OH, —$C_1$-$C_6$ alkylene-O—$C_1$-$C_6$ alkyl, —$C_1$-$C_6$ alkylene-OC(O)—$C_1$-$C_6$ alkyl, —$C_1$-$C_6$ alkylene-C(O)O—$C_1$-$C_6$ alkyl, —$C_1$-$C_6$ alkylene-N(H)$SO_2$—$C_1$-$C_6$ alkyl, —$C_1$-$C_6$ alkylene-N(H)C(O)—$C_1$-$C_6$ alkyl, —$C_1$-$C_6$ alkylene-CN, —$C_1$-$C_6$ alkylene-heterocycloalkyl, $C_1$-$C_6$ alkylene-aryl, $C_1$-$C_6$ alkylene-heteroaryl, heteroaryl, and heterocycloalkyl, wherein said heterocycloalkyl and said heterocycloalkyl of said C(O)heterocycloalkyl and said $C_1$-$C_6$ alkylene-heterocycloalkyl may be substituted with 1 to 3 groups independently selected from the group consisting of $C_1$-$C_6$ alkyl, and $C_1$-$C_4$ alkylene-aryl, wherein said heteroaryl and the heteroaryl of said $C_1$-$C_6$ alkylene-heteroaryl, and the aryl of said $C_1$-$C_6$ alkylene-aryl may be substituted with 1 to 3 groups independently selected from the group consisting of $C_1$-$C_4$ alkyl, $C_1$-$C_4$ haloalkyl, halo, —$C_1$-$C_3$ alkylene-CN, —$C_1$-$C_3$ alkylene-OH, —$C_1$-$C_3$ alkylene-C(O)O—$C_1$-$C_3$ alkyl, —$C_1$-$C_3$ alkylene-O—$C_1$-$C_3$ alkyl, —$C_1$-$C_3$ alkylene-OC(O)—$C_1$-$C_3$ alkyl, —$C_1$-$C_3$ alkylene-$NR^{14}$-aryl, $C_1$-$C_3$ alkylene-$NR^{14}$—C(O)—$C_1$-$C_4$alkyl, —$C_1$-$C_3$ alkylene-$NR^{14}SO_2$—$C_1$-$C_4$ alkyl, —C(O)—$C_1$-$C_3$ alkyl, and —C(O)-heterocycloalkyl, wherein said heterocycloalkyl of C(O)-heterocycloalkyl may be substituted with 1 to 3 groups independently selected from the group consisting of: $C_1$-$C_6$ alkyl, —C(O)—$NHCH_2$-aryl, —CH═(OH)—$C_1$-$C_6$ alkyl, —CH(OH)—$C_2$-$C_6$ alkenyl, —CH(OH)—$C_3$-$C_7$ cycloalkyl, —CH(OH)-phenyl, —C(O)$NR^{14}R^{16}$—$C_3$-$C_{14}$cycloalkyl, —C(O)$NR^{14}$—$C_1$-$C_3$ alkylene-$NR^{14}R^{16}$, —C(O)$NR^{14}$—$C_1$-$C_3$ alkylene-CN, —C(O)$NR^{14}$—$C_1$-$C_3$ alkylene-$NR^{14}R^{16}$, —C(O)$NR^{14}R^{16}$, —C(O)NH—$C_3$-$C_{14}$ cycloalkyl, —C(O)NH—$C_1$-$C_3$ alkylene-O—$C_1$-$C_3$ alkyl, C(O)NH—$C_1$-$C_3$ alkylene-OH, —$NR^{14}$—$C_3$-$C_{14}$ cycloalkyl, —$NR^{14}$—$C_1$-$C_3$ alkylene-heterocycloalkyl, —$NR^{14}$C(O)—$C_1$-$C_4$ alkyl, heterocycloalkyl, and heteroaryl, wherein said heterocycloalkyl or heteroaryl may be substituted with 1-3 substituents independently selected from the group consisting of: halo, $C_1$-$C_4$ alkyl, $C_1$-$C_4$ haloalkyl, and aryl;

where $R^{14}$ and $R^{16}$ are independently selected from the group consisting of: $C_1$-$C_4$ alkyl, $C_3$-$C_7$-cycloalkyl, —$C_1$-$C_3$-alkylene-$NR^{10}R^{12}$, —$C_1$-$C_3$-alkylene-$OR^{12}$, —$C_1$-$C_3$-alkylene-CN, aryl, $C_3$-$C_7$ cycloalkyl, $C_1$-$C_3$-alkylene-aryl, and H, where $R^{10}$ and $R^{12}$ are at each occurrence independently selected from the group consisting of H, $C_1$-$C_6$ alkyl, $C_1$-$C_3$-alkylene-aryl, $C_1$-$C_3$-alkylene-heteroaryl, $C_1$-$C_3$-alkylene-$C_3$-$C_7$-cycloalkyl, —$C_1$-$C_3$-alkylene-heterocycloalkyl, and $C_3$-$C_7$ cycloalkyl;

where $X^3$ is hydrogen or is L-G, where L is absent or is selected from the group consisting of:
—O—, —O—$C_1$-$C_3$ alkylene-, —$NR^{30}$—, —$NR^{30}$—$C_1$-$C_3$ alkylene-, —C(O)—, —$C_1$-$C_3$ alkylene- wherein said $C_1$-$C_3$ alkylene may be substituted with one to two substituents independently selected from the group consisting of: OH, —$NR^{20}R^{22}$, —NH-heterocycloalkyl, and —O—$C_1$-$C_3$ alkyl, and wherein $R^{30}$ is H, $C_1$-$C_4$ alkyl, or $C_1$-$C_4$ haloalkyl; and G is selected from the group consisting of:
aryl, heteroaryl, $C_1$-$C_6$ alkyl, $C_3$-$C_7$ cycloalkyl, and heterocycloalkyl, wherein G may be substituted with 1 to 3 groups independently selected from the group consisting of halo, CN, OH, —$C_1$-$C_4$ alkyl, —$C_2$-$C_4$ alkynyl substituted with a $C_2$-$C_4$ alkenyl or OH, —$C_1$-$C_4$ haloalkyl, —$SO_2$—$R^{32}$, —O—$R^{32}$, —C(O)—$R^{32}$, —C(O)O—$R^{32}$, —C(O)$NR^{20}R^{22}$, —$NR^{20}R^{22}$, —$NR^{20}$C(O)$OR^{32}$, —$NR^{20}$C(O)$R^{32}$, —$NR^{20}SO_2R^{34}$, —$NR^{20}$C(O)$NR^{36}R^{38}$, —O-heterocycloalkyl, aryl, and heterocycloalkyl, and the aryl and the heterocycloalkyl may be substituted with one to three groups independently selected from the group consisting of halo, CN, OH, —$C_1$-$C_4$ alkyl, C(O)O$C_1$-$C_6$ alkyl, O—$C_1$-$C_4$ haloalkyl, and —$C_1$-$C_4$ haloalkyl,
wherein $R^{32}$ is selected from —$C_1$-$C_4$ alkyl and —$C_1$-$C_4$ haloalkyl,
wherein $R^{34}$ is selected from —$C_1$-$C_4$ alkyl and —$C_1$-$C_4$ haloalkyl,
wherein $R^{36}$ and $R^{38}$ are independently selected from the group consisting of hydrogen, —$C_1$-$C_4$ alkyl, and —$C_1$-$C_3$ haloalkyl;

where one of $A^1$, $A^2$, $A^3$, and $A^4$ is $CR^{18}$, one of $A^1$, $A^2$, $A^3$, and $A^4$ is N or $CR^{19}$, and two of $A^1$, $A^2$, $A^3$, and $A^4$ are $CR^{19}$, where $R^{19}$ is independently selected from the group consisting of: H, —$OR^{20}$, CN, —$NR^{20}R^{22}$, halo, $C_1$-$C_4$ alkyl, $C_1$-$C_4$ haloalkyl, and $SO_2R^{20}$, wherein $R^{18}$ is selected from the group consisting of: H, $NO_2$, CN, $C_1$-$C_3$ alkyene-$SO_2$—$C_1$-$C_6$ alkyl, $C_1$-$C_3$ alkyene-$SO_2$—$C_1$-$C_6$ haloalkyl, $C_1$-$C_3$ alkyene-$SO_2$—$NR^{20}R^{22}$, —$NR^{20}R^{22}$, —$NHSO_2$—$NR^{20}R^{22}$, —$NR^{40}SO_2$—$C_1$-$C_4$ alkyl, —$NR^{40}SO_2$—$C_1$-$C_4$ haloalkyl, —$NR^{40}SO_2$—$CH_2$—C(O)OH, —$NR^{40}SO_2$—$CH_2$—C(O)O$C_1$-$C_4$ alkyl, —$NR^{40}SO_2$—$C_3$-$C_7$ cycloalkyl, —$NR^{40}SO_2$-aryl, —$NR^{40}SO_2$-heteroaryl, —$NR^{40}SO_2$—$C_1$-$C_3$ alkylene-$C_3$-$C_{14}$ cycloalkyl, —$NR^{40}SO_2$—$C_1$-$C_3$ alkylene-heterocycloalkyl, —$NR^{40}SO_2$—$C_1$-$C_3$ alkylene-heteroaryl, —$NR^{40}SO_2$—$C_1$-$C_3$ alkylene-aryl, —$SO_2$—$NR^{40}R^{42}$, —$SO_2$—$NR^{40}$—$C_1$-$C_4$ haloalkyl, —$SO_2$—$NR^{40}$—$C_3$-$C_{14}$ cycloalkyl, —$SO_2$—$NR^{40}$—C(O)$NR^{20}R^{22}$, —$SO_2$—$NR^{40}$-heterocycloalkyl, —$SO_2$—$NR^{40}$-heteroaryl, —$SO_2$—$NR^{40}$-aryl, —$SO_2$—$C_1$-$C_6$ alkyl, —$SO_2$—$C_1$-$C_6$ haloalkyl, —$SO_2$—$C_3$-$C_{14}$ cycloalkyl, —$SO_2$-heterocycloalkyl, —$SO_2$-heteroaryl, —$SO_2$-aryl, —$NR^{40}SO_2$—$NR^{20}R^{22}$, —$NR^{40}$C(O)—$C_1$-$C_6$ alkyl, —$NR^{40}$C(O)NH—$C_1$-$C_4$ alkyl, —$NR^{40}$C(O)-heteroaryl, —$NR^{40}$C(O)-heterocycloalkyl, —$NR^{40}$C(O)-aryl, —$NR^{40}$C(O)—$C_3$-$C_{14}$ cycloalkyl, —$NR^{40}$C(O)O—$C_1$-$C_4$ alkyl, —$NR^{40}$C(O)O-heteroaryl, —$NR^{40}$C(O)—$CH_2$NH—C(O)O—$C_1$-$C_4$ alkyl, —$NR^{40}$C(O)—$CH_2NR^{20}R^{22}$, —C(O)$CH_2$—$NR^{20}R^{22}$, —C(O)$NR^{20}R^{22}$, C(O)OH, —$C_1$-$C_3$ alkylene-$NR^{40}$—C(O)—$C_1$-$C_4$ alkyl, —$C_1$-$C_3$ alkylene-$NR^{40}$—C(O)—$C_1$-$C_3$ haloalkyl, —$NR^{40}$-heteroaryl, $C_3$-$C_{14}$ cycloalkyl, heterocycloalkyl, heterocycloalkyl-aryl, heteroaryl, aryl, —$C_1$-$C_3$ alkylene-cycloalkyl, —$C_1$-$C_3$ alkylene-heterocycloalkyl, —$C_1$-$C_3$ alkylene-heteroaryl, and —$C_1$-$C_3$ alkylene-aryl,
wherein any of the cycloalkyl, $C_3$-$C_7$ cycloalkyl, $C_3$-$C_{14}$cycloalkyl, heterocycloalkyl, heteroaryl, or aryl groups of $R^{18}$ may be substituted with 1 to 3 of $C_1$-$C_4$ alkyl, $C_1$-$C_4$ haloalkyl, halo, oxo, —OH, —O—$C_1$-$C_6$ alkyl, —O—$C_1$-$C_6$ haloalkyl, —$OG^1$, —$S(O)_2$—$C_1$-$C_6$ alkyl, —$N(R^{40})_2$, —$N(R^{40})C(O)C_1$-$C_6$ alkyl, $G^1$, —$C_1$-$C_6$ alkylene-$G^1$, or —$C_1$-$C_6$ alkylene-$OG^1$, wherein $G^1$ is cycloalkyl, heterocycloalkyl, heteroaryl, or aryl, and each $G^1$ may be substituted with 1 to 3 of oxo, $C_1$-$C_4$ alkyl, $C_1$-$C_4$ haloalkyl, or halo,
wherein $R^{40}$ and $R^{42}$ are independently selected from the group consisting of: H and $C_1$-$C_4$ alkyl, and
wherein $R^{20}$ and $R^{22}$ are at each occurrence independently selected from the group consisting of: H and $C_1$-$C_6$ alkyl.

In certain embodiments,
J is a group of formula IIa or IIb:

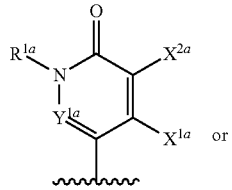

(IIa)

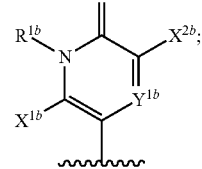

(IIb)

wherein
$R^{1a}$ is $C_1$-$C_3$ alkyl, $C_2$-$C_3$ alkylene-OH, or $C_1$-$C_3$ haloalkyl;
$Y^{1a}$ is N or $CR^{xa}$, wherein $R^{xa}$ is H, halo, $C_1$-$C_3$ alkyl, —O—$C_1$-$C_3$ alkyl, $C_1$-$C_3$ haloalkyl, —O—$C_1$-$C_3$ haloalkyl, aryl, aryl-$C_1$-$C_3$alkylene-OH, aryl-$C_1$-$C_3$alkylene-heterocycloalkyl, C(O)$NR^{10}R^{12}$, wherein heterocycloalkyl of aryl-$C_1$-$C_3$alkylene-heterocycloalkyl may be substituted with one to three $C_1$-$C_3$alkyl,
$R^{1b}$ is H, $C_1$-$C_3$ alkyl, $C_2$-$C_3$ alkylene-OH, or $C_1$-$C_3$ haloalkyl;
$Y^{1b}$ is N or $CR^{xb}$, wherein $R^{xb}$ is heteroaryl, H, halo, $C_1$-$C_3$ alkyl, —O—$C_1$-$C_3$ alkyl, $C_1$-$C_3$ haloalkyl, —O—$C_1$-$C_3$ haloalkyl, aryl, aryl-$C_1$-$C_3$alkylene-OH, aryl-$C_1$-$C_3$alkylene-heterocycloalkyl, C(O)NR$^{10}$R$^{12}$, wherein heterocycloalkyl of aryl-$C_1$-$C_3$alkylene-heterocycloalkyl may be substituted with one to three $C_1$-$C_3$alkyl; wherein said heteroaryl may be substituted with one to three groups selected from the group consisting of: $C_1$-$C_6$ alkyl, $C_1$-$C_3$alkylene-aryl, $C_1$-$C_3$alkylene-heteroaryl, $C_1$-$C_3$alkylene-heterocycloalkyl, COOH, and COO—$C_1$-$C_4$alkyl, $X^{2a}$ is selected from the group consisting of: H, —NR$^{10}$R$^{12}$, halo, OH, —O—$C_1$-$C_4$ alkyl, aryl, heteroaryl, and —NR$^{10}$C(O)—$C_1$-$C_4$ alkyl;

$X^{2b}$ is $C_1$-$C_3$ alkyl, $C_2$-$C_3$ alkylene-OH, or $C_1$-$C_3$ haloalkyl;

$X^{1a}$ and $X^{1b}$ are each selected from the group consisting of: hydrogen, halo, $C_1$-$C_6$ alkyl, $C_1$-$C_4$ haloalkyl, —O—$C_1$-$C_4$ alkyl, —O—$C_1$-$C_6$ cycloalkyl, —O—$C_1$-$C_3$ alkylene-$C_3$-$C_7$ cycloalkyl, —O—$C_1$-$C_4$ haloalkyl, —O—$C_1$-$C_3$ alkylene-heterocycloalkyl, —O—$C_1$-$C_6$ alkylene-OH, —O—$C_1$-$C_6$alkylene-N(R$^{10}$)$_2$—O—$C_1$-$C_3$ alkylene-C(O)O—$C_1$-$C_4$ alkyl, —NR$^{10}$—$C_1$-$C_6$ alkyl, —NR$^{10}$—$C_1$-$C_6$ haloalkyl, —NR$^{10}$—C(O)OC$_1$-$C_6$ alkyl, —NR$^{10}$—C(O)OC$_1$-$C_6$ haloalkyl, —NR$^{10}$—C(O)NR$^{10}$R$^{12}$, —NR$^{10}$—SO$_2$R$^{12}$, —NR$^{10}$—$C_3$-$C_7$ cycloalkyl, —O—$C_1$-$C_3$ alkylene-C(O)O—$C_1$-$C_4$ alkyl, —NR$^{10}$—$C_1$-$C_6$ alkyl, —NR$^{10}$—$C_1$-$C_6$ haloalkyl, —NR$^{10}$—$C_1$-$C_3$ alkylene-$C_3$-$C_7$ cycloalkyl, $C_1$-$C_4$ alkylene-OH, —$C_1$-$C_3$ alkylene-C(O)OC$_1$-$C_4$ alkyl, $C_1$-$C_3$ alkylene-NR$^{10}$C(O)—$C_1$-$C_4$ alkyl, —$C_1$-$C_3$ alkylene-C(O)NR$^{10}$R$^{12}$, —$C_2$-$C_4$ alkenylene-C(O)—O—$C_1$-$C_4$ alkyl, —C(O)—$C_1$-$C_4$ alkyl, C(O)O—$C_1$-$C_4$ alkyl, C(O)NR$^{10}$R$^{12}$, —NR$^{10}$C(O)—$C_1$-$C_4$ alkyl, —NR$^{10}$SO$_2$—$C_1$-$C_4$ alkyl, —NR$^{10}$—$C_1$-$C_3$ alkylene-C(O)—$C_1$-$C_4$ alkyl, —NR$^{10}$—$C_1$-$C_3$ alkylene-C(O)O—$C_1$-$C_4$ alkyl, —SO$_2$NR$^{10}$R$^{12}$, and any of groups i-v:

i) $C_3$-$C_{14}$ cycloalkyl, which may be substituted with 1 to 3 of R$^2$, where R$^2$ is selected from the group consisting of: halo, oxo, CN, —O—$C_1$-$C_4$ alkyl, —O—$C_1$-$C_4$ haloalkyl, —NR$^{10}$R$^{12}$, C(O)NR$^{10}$R$^{12}$, $C_1$-$C_4$ alkyl, $C_1$-$C_4$ haloalkyl, C(O)—$C_1$-$C_4$ alkyl, —C(O)O—$C_1$-$C_4$ alkyl, SO$_2$NR$^{10}$R$^{12}$, SO$_2$—$C_1$-$C_4$ alkyl, and aryl, wherein said aryl may be substituted with 1 to 3 substituents independently selected from group consisting of: halo, $C_1$-$C_3$ alkyl, C(O)—$C_1$-$C_3$alkyl, C(O)OH, C(O)NR$^{10}$R$^{12}$, and heteroaryl;

ii) heterocycloalkenyl, which may be substituted with 1 to 3 of R$^2$, where R$^2$ is selected from the group consisting of: halo, oxo, CN, —O—$C_1$-$C_4$ alkyl, —O—$C_1$-$C_4$ haloalkyl, —NR$^{10}$R$^{12}$, C(O)NR$^{10}$R$^{12}$, $C_1$-$C_4$ alkyl, $C_1$-$C_4$ haloalkyl, C(O)—$C_1$-$C_4$ alkyl, —C(O)O—$C_1$-$C_4$ alkyl, SO$_2$NR$^{10}$R$^{12}$, SO$_2$—$C_1$-$C_4$ alkyl, and aryl, wherein said aryl may be substituted with 1 to 3 substituents independently selected from group consisting of: halo, $C_1$-$C_3$ alkyl, C(O)—$C_1$-$C_3$alkyl, C(O)OH, C(O)NR$^{10}$R$^{12}$, and heteroaryl;

iii) heterocycloalkyl, which may be substituted with 1 to 3 of R$^3$, where R$^3$ is selected from the group consisting of: halo, oxo, CN, —O—$C_1$-$C_4$ alkyl, —O—$C_1$-$C_4$ haloalkyl, —NR$^{10}$R$^{12}$, C(O)NR$^{10}$R$^{12}$, $C_1$-$C_4$ alkyl, $C_1$-$C_4$ haloalkyl, C(O)—$C_1$-$C_4$ alkyl, —C(O)O—$C_1$-$C_4$ alkyl, SO$_2$NR$^{10}$R$^{12}$, SO$_2$—$C_1$-$C_4$ alkyl, and aryl, wherein said aryl may be substituted with 1 to 3 substituents independently selected from group consisting of: halo, $C_1$-$C_3$ alkyl, C(O)—$C_1$-$C_3$alkyl, C(O)OH, C(O)NR$^{10}$R$^{12}$, and heteroaryl;

iv) heteroaryl, which may be substituted with 1 to 3 of R$^4$, where R$^4$ is selected from the group consisting of: halo, oxo, CN, —O—$C_1$-$C_4$ alkyl, —O—$C_1$-$C_4$ haloalkyl, —NR$^{10}$R$^{12}$, C(O)NR$^{10}$R$^{12}$, $C_1$-$C_6$ alkyl, $C_1$-$C_4$ haloalkyl, $C_1$-$C_6$ alkylene-heterocycloalkyl, $C_1$-$C_6$alkylene-aryl, $C_1$-$C_6$alkylene-heteroaryl, C(O)—$C_1$-$C_4$ alkyl, —C(O)O—$C_1$-$C_4$ alkyl, SO$_2$NR$^{10}$R$^{12}$, SO$_2$—$C_1$-$C_4$ alkyl, —NR$^{14}$C(O)C$_1$-$C_4$-alkyl, NH—$C_1$-$C_4$ alkylene-aryl, heterocycloalkyl, and aryl, wherein said aryl may be substituted with 1 to 3 substituents independently selected from group consisting of: halo, $C_1$-$C_3$ alkyl, C(O)—$C_1$-$C_3$alkyl, C(O)OH, C(O)NR$^{10}$R$^{12}$, and heteroaryl, wherein said heterocycloalkyl or heterocycloalkyl group of $C_1$-$C_6$ alkylene-heterocycloalkyl may be substituted with 1 to 3 independently selected $C_1$-$C_3$ alkyl groups, and wherein said heteroaryl group of $C_1$-$C_6$ alkylene-heteroaryl and said aryl groups of $C_1$-$C_6$ alkylene-aryl and NH—$C_1$-$C_4$ alkylene-aryl may be substituted with substituents 1 to 3 groups independently selected from $C_1$-$C_3$ alkyl and NR$^{14}$R$^{16}$;

v) aryl, which may be substituted with 1 to 3 of R$^6$, where R$^6$ is selected from the group consisting of: halo, CN, —NR$^{14}$R$^{16}$, —NR$^{14}$SO$_2$—$C_1$-$C_4$ alkyl, C(O)H, —$C_1$-$C_4$ alkylene-NR$^{14}$R$^{16}$, SO$_2$NR$^{14}$R$^{16}$, C(O)OC$_1$-$C_4$ alkyl, —SO$_2$-heterocycloalkyl, —SO$_2$—$C_1$-$C_6$ alkyl, —$C_1$-$C_6$ alkyl, —O—$C_1$-$C_6$ alkyl, —$C_1$-$C_6$ haloalkyl, —O—$C_1$-$C_6$ haloalkyl, —$C_1$-$C_6$ alkylene-heterocycloalkyl, $C_1$-$C_6$alkylene-aryl, and $C_1$-$C_6$alkylene-heteroaryl, wherein said heterocycloalkyl of said $C_1$-$C_6$ alkylene-heterocycloalkyl may be substituted with 1 to 3 groups independently selected from the group consisting of $C_1$-$C_6$ alkyl and —CH$_2$-phenyl, and $C_1$-$C_4$ alkylene-aryl, wherein the heteroaryl of said $C_1$-$C_6$ alkylene-heteroaryl and the aryl of said $C_1$-$C_6$ alkylene-aryl may be substituted with 1 to 3 groups independently selected from the group consisting of $C_1$-$C_4$ alkyl, $C_1$-$C_4$ haloalkyl, and halo-$C_1$-$C_3$ alkylene-CN, —$C_1$-$C_3$ alkylene-OH, —$C_1$-$C_3$ alkylene-C(O)O—$C_1$-$C_3$ alkyl, —$C_1$-$C_3$ alkylene-O—$C_1$-$C_3$ alkyl, —$C_1$-$C_3$ alkylene-OC(O)—$C_1$-$C_3$ alkyl, —$C_1$-$C_3$ alkylene-NR$^{14}$-aryl, $C_1$-$C_3$ alkylene-NR$^{14}$—C(O)—$C_1$-$C_4$alkyl, —$C_1$-$C_3$ alkylene-NR$^{14}$SO$_2$—$C_1$-$C_4$ alkyl, —C(O)—$C_1$-$C_3$ alkylene, and —C(O)-heterocycloalkyl, wherein said heterocycloalkyl of C(O)-heterocycloalkyl may be substituted with 1 to 3 groups independently selected from the group consisting of: $C_1$-$C_6$ alkyl, —C(O)—NHCH$_2$-aryl, —CH—(OH)—$C_1$-$C_6$ alkyl, —CH(OH)—$C_2$-$C_6$ alkenyl, —CH(OH)—$C_3$-$C_7$ cycloalkyl, —CH(OH)-phenyl, —C(O)NR$^{14}$R$^{16}$—$C_3$-$C_{14}$cycloalkyl, —C(O)NR$^{14}$—$C_1$-$C_3$ alkylene-NR$^{14}$R$^{16}$, —C(O)NR$^{14}$—$C_1$-$C_3$ alkylene-CN, —C(O)NR$^{14}$—$C_1$-$C_3$ alkylene-NR$^{14}$R$^{16}$, —C(O)NR$^{14}$R$^{16}$, —C(O)NH—$C_3$-$C_{14}$ cycloalkyl, —C(O)NH—$C_1$-$C_3$ alkylene-O—$C_1$-$C_3$ alkyl, C(O)NH—$C_1$-$C_3$ alkylene-OH, —NR$^{14}$—$C_3$-$C_{14}$ cycloalkyl, —NR$^{14}$—$C_1$-$C_3$ alkylene-heterocycloalkyl, —NR$^{14}$C(O)—$C_1$-$C_4$ alkyl, heterocycloalkyl, and heteroaryl, wherein said heterocycloalkyl or heteroaryl may be substituted with 1-3 substituents independently selected from the group consisting of: halo, $C_1$-$C_4$ alkyl, $C_1$-$C_4$ haloalkyl and aryl;

where $R^{14}$ and $R^{16}$ are independently selected from the group consisting of: $C_1$-$C_4$ alkyl, $C_3$-$C_7$-cycloalkyl, —$C_1$-$C_3$-alkylene-$NR^{10}R^{12}$, aryl, and H, where $R^{10}$ and $R^{12}$ are at each occurrence independently selected from the group consisting of H, $C_1$-$C_4$ alkyl, $C_1$-$C_3$-alkylene-aryl, $C_1$-$C_3$-alkylene-heteroarylaryl, $C_1$-$C_3$-alkylene-$C_3$-$C_7$-cycloalkyl, and cyclopropyl;

where $X^3$ is absent or is L-G, where L is absent or is selected from the group consisting of:
—O—, —O—$C_1$-$C_3$ alkylene-, —$NR^{30}$—, —C(O)—, —$C_1$-$C_3$ alkylene-, wherein said $C_1$-$C_3$ alkylene may be substituted with one to two substituents independently selected from the group consisting of: OH, —$NR^{20}R^{22}$, —NH-heterocycloalkyl, and —O—$C_1$-$C_3$ alkyl, and wherein $R^{30}$ is H or $C_1$-$C_4$ alkyl, or $C_1$-$C_4$ haloalkyl; and G is selected from the group consisting of:
aryl, heteroaryl, $C_1$-$C_6$ alkyl, $C_3$-$C_7$ cycloalkyl, heterocycloalkyl, wherein G may be substituted with 1 to 3 groups independently selected from the group consisting of halo, CN, OH, —$C_1$-$C_4$ alkyl, —$C_1$-$C_4$ haloalkyl, —$SO_2$—$R^{32}$, —O—$R^{32}$, —C(O)—$R^{32}$, —C(O)O—$R^{32}$, —$NR^{20}R^{22}$, $NR^{20}C(O)OR^{32}$, —$NR^{20}C(O)R^{32}$, —$NR^{20}SO_2OR^{34}$, —$NR^{20}C(O)NR^{36}R^{38}$, aryl, and aryl substituted with one to three groups independently selected from the group consisting of halo, CN, OH, —$C_1$-$C_4$ alkyl, and —$C_1$-$C_4$ haloalkyl,
wherein $R^{32}$ is selected from —$C_1$-$C_4$ alkyl and —$C_1$-$C_4$ haloalkyl,
wherein $R^{34}$ is selected from —$C_1$-$C_4$ alkyl and —$C_1$-$C_4$ haloalkyl,
wherein $R^{36}$ and $R^{38}$ are independently selected from the group consisting of hydrogen, —$C_1$-$C_4$ alkyl, and —$C_1$-$C_3$ haloalkyl;

where one of $A^1$, $A^2$, $A^3$, and $A^4$ is $CR^{18}$, one of $A^1$, $A^2$, $A^3$, and $A^4$ is N or $CR^{19}$, and two of $A^1$, $A^2$, $A^3$, and $A^4$ are $CR^{19}$, where $R^{19}$ is independently selected from the group consisting of: H, —$OR^{20}$, CN, —$NR^{20}R^{22}$, halo, $C_1$-$C_4$ alkyl, $C_1$-$C_4$ haloalkyl, and $SO_2R^{20}$, wherein $R^{18}$ is selected from the group consisting of: H, $NO_2$, $C_1$-$C_3$ alkyene-$SO_2$—$C_1$-$C_6$ alkyl, $C_1$-$C_3$ alkyene-$SO_2$—$C_1$-$C_6$ haloalkyl, $C_1$-$C_3$ alkyene-$SO_2$—$NR^{20}R^{22}$, —$NR^{20}R^{22}$, —$NHSO_2$—$NH_2$, —$NR^{40}SO_2$—$C_1$-$C_4$ alkyl, —$NR^{40}SO_2$—$C_1$-$C_4$ haloalkyl, —$NR^{40}SO_2$—$CH_2$—C(O)OH, —$NR^{40}SO_2$—$CH_2$—C(O)O$C_1$-$C_4$, —$NR^{40}SO_2$—$C_1$-$C_4$ alkyl, —$NR^{40}SO_2$—$C_1$-$C_4$ haloalkyl, —$NR^{40}SO_2$—$C_3$-$C_7$ cycloalkyl, —$NR^{40}SO_2$-aryl, —$NR^{40}SO_2$-heteroaryl, —$NR^{40}SO_2$—$C_1$-$C_4$ alkyl, —$NR^{40}SO_2$—$C_1$-$C_4$ haloalkyl, —$NR^{40}SO_2$—$C_1$-$C_3$ alkylene-$C_3$-$C_{14}$ cycloalkyl, —$NR^{40}SO_2$—$C_1$-$C_3$ alkylene-heterocycloalkyl, —$NR^{40}SO_2$—$C_1$-$C_3$ alkylene-heteroaryl, —$NR^{40}SO_2$—$C_1$-$C_3$ alkylene-aryl, —$SO_2$—$NR^{40}R^{42}$, —$SO_2$—$NR^{40}$—$C_1$-$C_4$ alkyl, —$SO_2$—$NR^{40}$—$C_1$-$C_4$ haloalkyl, —$SO_2$—$NR^{40}$—$C_3$-$C_{14}$ cycloalkyl, —$SO_2$—$NR^{40}$—C(O)$NR^{20}R^{22}$, —$SO_2$—$NR^{40}$-heterocycloalkyl, —$SO_2$—$NR^{40}$-heteroaryl, —$SO_2$—$NR^{40}$-aryl, —$SO_2$—$C_1$-$C_6$ alkyl, —$SO_2$—$C_1$-$C_6$ haloalkyl, —$SO_2$—$C_3$-$C_{14}$ cycloalkyl, —$SO_2$-heterocycloalkyl, —$SO_2$-heteroaryl, —$SO_2$-aryl, —$NR^{40}SO_2$—$NR^{20}R^{22}$, —$NR^{40}C(O)$—$C_1$-$C_4$ alkyl, —$NR^{40}C(O)NH$—$C_1$-$C_4$ alkyl, —$NR^{40}C(O)$-heteroaryl, —$NR^{40}C(O)$-aryl, —$NR^{40}C(O)$-$C_1$-$C_4$ alkyl, —$NR^{40}C(O)O$-heteroaryl, —$NR^{40}C(O)$-aryl, —$NR^{40}C(O)$—$CH_2NH$—C(O)O—$C_1$-$C_4$ alkyl, —C(O)$CH_2$—$NR^{20}R^{22}$, —C(O)$NR^{20}R^{22}$, C(O)OH, $C_1$-$C_3$ alkylene-$NR^{40}$—C(O)—$C_1$-$C_4$ alkyl, $C_1$-$C_3$ alkylene-$NR^{40}$—C(O)—$C_1$-$C_3$ haloalkyl, —$NR^{40}$-heteroaryl, $C_3$-$C_{14}$ cycloalkyl, heterocycloalkyl, heterocycloalkyl-aryl, heteroaryl, aryl, $C_1$-$C_3$ alkylene-cycloalkyl, $C_1$-$C_3$ alkylene-heterocycloalkyl, $C_1$-$C_3$ alkylene-heteroaryl, and $C_1$-$C_3$ alkylene-aryl, wherein any of the cycloalkyl, heterocycloalkyl, heteroaryl, or aryl groups of $R^{18}$ may be substituted with 1 to 3 of $C_1$-$C_4$ alkyl, $C_1$-$C_4$ haloalkyl or halo, wherein $R^{40}$ and $R^{42}$ are independently selected from the group consisting of: H and $C_1$-$C_4$ alkyl, and wherein $R^{20}$ and $R^{22}$ are at each occurrence independently selected from the group consisting of: H and $C_1$-$C_4$ alkyl.

In certain embodiments, $A^1$ is $CR^{19}$, $A^2$ is $CR^{18}$, $A^3$ is $CR^{19}$, and $A^4$ is $CR^{19}$. In some such embodiments, $R^{19}$ is H or $C_1$-$C_4$ alkyl (e.g. $CH_3$).

In certain embodiments, $A^1$ is CH, $A^2$ is $CR^{18}$, $A^3$ is CH, and $A^4$ is CH. In certain embodiments, $R^{18}$ is selected from the group consisting of:

$NO_2$, $NR^{20}R^{22}$, $NHSO_2$—$NH_2$, $NR^{40}SO_2$—$C_1$-$C_4$ alkyl, $NR^{40}SO_2$—$C_1$-$C_4$ haloalkyl, $NR^{40}SO_2$—$CH_2$—C(O)OH, $NR^{40}SO_2$—$CH_2$—C(O)O$C_1$-$C_4$, —$NR^{40}SO_2$—$C_1$-$C_4$ alkyl, —$NR^{40}SO_2$—$C_1$-$C_4$ haloalkyl, $NR^{40}SO_2$—$C_3$-$C_7$ cycloalkyl, —$NR^{40}SO_2$-aryl, —$NR^{40}SO_2$-heteroaryl, —$NR^{40}SO_2$—$C_1$-$C_4$ alkyl, —$NR^{40}SO_2$—$C_1$-$C_4$ haloalkyl, —$NR^{40}SO_2$—$C_1$-$C_3$ alkylene-$C_3$-$C_{14}$ cycloalkyl, —$NR^{40}SO_2$—$C_1$-$C_3$ alkylene-heterocycloalkyl, —$NR^{40}SO_2$—$C_1$-$C_3$ alkylene-heteroaryl, —$NR^{40}SO_2$—$C_1$-$C_3$ alkylene-aryl, —$SO_2$—$NR^{40}R^{42}$, —$SO_2$—$NR^{40}$—$C_1$-$C_4$ alkyl, —$SO_2$—$NR^{40}$—$C_1$-$C_4$ haloalkyl, —$SO_2$—$NR^{40}$—$C_3$-$C_{14}$ cycloalkyl, —$SO_2$—$NR^{40}$-heterocycloalkyl, —$SO_2$—$NR^{40}$-heteroaryl, —$SO_2$—$NR^{40}$-aryl, —$SO_2$—$C_1$-$C_6$ alkyl, —$SO_2$—$C_1$-$C_6$ haloalkyl, —$SO_2$—$C_3$-$C_{14}$ cycloalkyl, —$SO_2$-heterocycloalkyl, —$SO_2$-heteroaryl, —$SO_2$-aryl, —$NR^{40}SO_2$—$NR^{20}R^{22}$, —$NR^{40}C(O)$—$C_1$-$C_4$ alkyl, —$NR^{40}C(O)NH$—$C_1$-$C_4$ alkyl, —$NR^{40}C(O)$-heteroaryl, $NR^{40}C(O)$-aryl, $NR^{40}C(O)O$—$C_1$-$C_4$ alkyl, —$NR^{40}C(O)O$-heteroaryl, $NR^{40}C(O)$-aryl, —$NR^{40}C(O)$—$CH_2NH$—C(O)O—$C_1$-$C_4$ alkyl, —C(O)$CH_2$—$NR^{20}R^{22}$, —C(O)$NR^{20}R^{22}$, C(O)OH, $C_1$-$C_3$ alkylene-$NR^{40}$—C(O)—$C_1$-$C_4$ alkyl, $C_1$-$C_3$ alkylene-$NR^{40}$—C(O)—$C_1$-$C_3$ haloalkyl, $NR^{40}$-heteroaryl, $C_3$-$C_{14}$ cycloalkyl, heterocycloalkyl, heteroaryl, aryl, $C_1$-$C_3$ alkylene-$C_3$-$C_{14}$ cycloalkyl, $C_1$-$C_3$ alkylene-heterocycloalkyl, $C_1$-$C_3$ alkylene-heteroaryl, and $C_1$-$C_3$ alkylene-aryl.

In certain embodiments, $R^{18}$ is selected from the group consisting of:

$NR^{40}SO_2$—$C_1$-$C_4$ alkyl, $NR^{40}SO_2$—$C_1$-$C_4$ haloalkyl, —$SO_2$—$NR^{40}$—$C_1$-$C_4$ alkyl, —$SO_2$—$NR^{40}$—$C_1$-$C_4$ haloalkyl, —$SO_2$—$C_1$-$C_6$ alkyl, and —$SO_2$—$C_1$-$C_6$ haloalkyl.

In certain embodiments, $R^{40}$ is H. In certain embodiments, $X^3$ is L-G and L is —O—, or —O—$C_1$-$C_3$ alkylene-. In certain embodiments, $X^3$ is L-G and L is $NR^{30}$— or —$NR^{30}$—$C_1$-$C_3$ alkylene-, and $R^{30}$ is H. In certain embodiments, G is aryl or $C_3$-$C_7$ cycloalkyl, wherein G is optionally substituted as described herein above. In certain embodiments, G is optionally substituted heteroaryl (e.g. optionally substituted pyridinyl). In certain embodiments, G is optionally substituted heterocycloalkyl (e.g. tetrahydropyranyl, tetrahydropyranyl, piperidinyl, each of which is optionally substituted). In certain embodiments, G is aryl or $C_3$-$C_7$ cycloalkyl, wherein G may be substituted with 1 to 3 groups independently selected from the group consisting of CN, OH, $NR^{20}R^{22}$, —$C_1$-$C_4$ haloalkyl, —$SO_2$—$C_1$-$C_4$ alkyl, halo, C(O)—$C_1$-$C_4$-alkyl, O—$C_1$-$C_4$ alkyl, —O—$C_1$-$C_4$ haloalkyl, —$C_1$-$C_4$ alkyl, —$NR^{20}C(O)R^{32}$, —$NR^{20}SO_2OR^{34}$, —$NR^{20}C(O)NR^{36}R^{38}$,
  wherein $R^{32}$ is selected from —$C_1$-$C_4$ alkyl and —$C_1$-$C_4$ haloalkyl,
  wherein $R^{34}$ is selected from —$C_1$-$C_4$ alkyl and —$C_1$-$C_4$ haloalkyl,
  wherein $R^{36}$ and $R^{38}$ are independently selected from the group consisting of hydrogen, —$C_1$-$C_4$ alkyl, and —$C_1$-$C_3$ haloalkyl.

In certain embodiments, L is —O—, and G is phenyl substituted with 1 to 3 halo. In certain embodiments, L is —$NR^{30}$— wherein $R^{30}$ is H, and G is $C_3$-$C_7$ cycloalkyl which is optionally substituted with 1 to 3 halo. In certain embodiments, L is —O— and G is phenyl substituted with 1 to 3 fluoro. In certain embodiments, G is 2,4-difluorophenyl. In certain embodiments, L is —O—$C_1$-$C_3$ alkyene, and G is $C_3$-$C_7$ cycloalkyl. In certain embodiments, L is —$NR^{30}$—$C_1$-$C_3$ alkyene wherein $R^{30}$ is H, and G is $C_3$-$C_7$ cycloalkyl or phenyl, each of which is optionally substituted with 1 or 3 halo. In certain embodiments, J is IIa, $Y^{1a}$ is N, $R^{1a}$ is methyl, and $X^{2a}$ is hydrogen. In certain embodiments, J is IIa, $Y^{1a}$ is $CR^{xa}$, wherein $R^{xa}$ is H, $R^{1a}$ is methyl, and $X^{2a}$ is hydrogen. In certain embodiments, $X^{1a}$ is hydrogen. In certain embodiments, $X^{1a}$ is selected from the group consisting of:
  halo, —O—$C_1$-$C_4$ alkyl, and aryl, wherein said aryl may be substituted with 1 to 3 of $R^6$, where $R^6$ is selected from the group consisting of: $NR^{14}SO_2$—$C_1$-$C_4$ alkyl, —$C_1$-$C_3$ alkylene-$NR^{14}R^{16}$, —$C_1$-$C_6$ alkylene-heterocycloalkyl, wherein said heterocycloalkyl of said $C_1$-$C_6$ alkylene-heterocycloalkyl may be substituted with 1 to 3 groups independently selected from the group consisting of $C_1$-$C_6$ alkyl and —$CH_2$-phenyl, wherein said aryl of said $C_1$-$C_6$ alkylene-aryl may be substituted with 1 to 3 groups independently selected from the group consisting of: —$C_1$-$C_3$ alkylene-OH, and heterocycloalkyl, wherein said heterocycloalkyl may be substituted with 1-3 substituents independently selected from the group consisting of: $C_1$-$C_4$ alkyl, $C_1$-$C_4$ haloalkyl and aryl.

In certain embodiments, J is IIb, $R^{1b}$ is hydrogen, $X^{2b}$ is methyl, $Y^{1b}$ is $CR^{xb}$, and $R^{xb}$ is H. In certain embodiments, $X^{1b}$ is hydrogen. In certain embodiments, L is —O—, and G is phenyl substituted with 1 to 3 halo. In certain embodiments, G is phenyl substituted with 1 to 3 halo. In certain embodiments, G is 2,4-difluoro-phenyl.

In certain embodiments, $X^{1b}$ is H, and $R^{18}$ is $NR^{40}SO_2C_1$-$C_4$ alkyl.

In certain embodiments,
  $A^1$ is CH, $A^2$ is $CR^{18}$, $A^3$ is CH, and $A^4$ is CH;
  J is formula IIa,
  $R^{1a}$ is methyl,
  $Y^{1a}$ is N or CH,
  $X^{2a}$ is H or halo,
  $X^3$ is L-G wherein L is —O— or —O—$C_1$-$C_3$ alkylene-, and G is phenyl or $C_3$-$C_7$ cycloalkyl, wherein G is optionally substituted with 1 to 3 halo, and
  $R^{18}$ is selected from the group consisting of H, $NR^{40}SO_2$—$C_1$-$C_4$ alkyl, —$NR^{40}SO_2$—$C_1$-$C_4$ haloalkyl, —$SO_2$—$NR^{40}R^{42}$, —$SO_2$—$NR^{40}$—$C_1$-$C_4$ haloalkyl, —$SO_2$—$C_1$-$C_6$ alkyl, and —$SO_2$—$C_1$-$C_6$ haloalkyl.

In certain embodiments,
  $A^1$ is CH, $A^2$ is $CR^{18}$, $A^3$ is CH, and $A^4$ is CH;
  J is formula IIa,
  $R^{1a}$ is methyl,
  $Y^{1a}$ is N or CH,
  $X^{2a}$ is H or halo,
  $X^3$ is L-G wherein L is —O— or —O—$C_1$-$C_3$ alkylene-, and G is phenyl or $C_3$-$C_7$ cycloalkyl, wherein G is optionally substituted with 1 to 3 halo,
  $R^{18}$ is selected from the group consisting of H, $NR^{40}SO_2$—$C_1$-$C_4$ alkyl, and —$SO_2$—$C_1$-$C_6$ alkyl, and
  $X^{1a}$ is selected from the group consisting of H, —O—$C_1$-$C_6$ alkyl, —O—$C_1$-$C_4$ haloalkyl, optionally substituted phenyl, optionally substituted heteroaryl, and —O—$C_1$-$C_3$ alkylene-$C_3$-$C_7$ cycloalkyl wherein said $C_3$-$C_7$ cycloalkyl of —O—$C_1$-$C_3$ alkylene-$C_3$-$C_7$ cycloalkyl is optionally substituted.

In certain embodiments, a compound of formula (I) is selected from the group consisting of:
N-[4-(4-chlorophenoxy)-3-(4-ethoxy-1-methyl-6-oxo-1,6-dihydropyridin-3-yl)phenyl]ethanesulfonamide;
N-{4-(2,4-difluorophenoxy)-3-[1-methyl-6-oxo-4-(2,2,2-trifluoroethoxy)-1,6-dihydropyridin-3-yl]phenyl}ethanesulfonamide;
N-[4-(2,4-difluorophenoxy)-3-(4-ethoxy-1-methyl-6-oxo-1,6-dihydropyridin-3-yl)phenyl]ethanesulfonamide;
5-[2-(2,4-difluorophenoxy)-5-(ethylsulfonyl)phenyl]-4-ethoxy-1-methylpyridin-2(1H)-one;
N-[4-(2,4-difluorophenoxy)-3-(4-methoxy-1-methyl-6-oxo-1,6-dihydropyridin-3-yl)phenyl]ethanesulfonamide;
N-(3-(4-(cyclopropylmethoxy)-1-methyl-6-oxo-1,6-dihydropyridin-3-yl)-4-(2,4-difluorophenoxy)phenyl)ethanesulfonamide;
N-[4-(2,4-difluorophenoxy)-3-{1-methyl-4-[1-(2-methylpropyl)-1H-pyrazol-4-yl]-6-oxo-1,6-dihydropyridin-3-yl]phenyl}ethanesulfonamide;
N-[4-(2,4-difluorophenoxy)-3-(1-methyl-6-oxo-1,6-dihydropyridin-3-yl)phenyl]methanesulfonamide;
N-[4-(2,4-difluorophenoxy)-3-(4-ethoxy-1-methyl-6-oxo-1,6-dihydropyridin-3-yl)phenyl]methanesulfonamide;
N-[4-(2,4-difluorophenoxy)-3-{1-methyl-4-[4-(morpholin-4-yl)phenyl]-6-oxo-1,6-dihydropyridin-3-yl]phenyl}ethanesulfonamide;
N-[4-(2,4-difluorophenoxy)-3-(4-{4-[(dimethylamino)methyl]phenyl}-1-methyl-6-oxo-1,6-dihydropyridin-3-yl)phenyl]ethanesulfonamide;
N-[4-(2,4-difluorophenoxy)-3-{1-methyl-4-[4-(morpholin-4-yl)phenyl]-6-oxo-1,6-dihydropyridin-3-yl]phenyl}methanesulfonamide;
N-[4-(2,4-difluorophenoxy)-3-(1-methyl-4-{4-[(4-methylpiperazin-1-yl)methyl]phenyl}-6-oxo-1,6-dihydropyridin-3-yl)phenyl]methanesulfonamide;
N-[4-(2,4-difluorophenoxy)-3-(1-methyl-6-oxo-1,6-dihydropyridin-3-yl)phenyl]ethanesulfonamide;
N-[4-(2,4-difluorophenoxy)-3-{4-[4-(hydroxymethyl)phenyl]-1-methyl-6-oxo-1,6-dihydropyridin-3-yl]phenyl}ethanesulfonamide;
N-[3-(5-chloro-1-methyl-6-oxo-1,6-dihydropyridin-3-yl)-4-(2,4-difluorophenoxy)phenyl]ethanesulfonamide;
N-[3-(1-methyl-4-{4-[(4-methylpiperazin-1-yl)methyl]phenyl}-6-oxo-1,6-dihydropyridazin-3-yl)-4-phenoxyphenyl]methanesulfonamide;
5-[2-(cyclopropylmethoxy)-5-(ethylsulfonyl)phenyl]-4-methoxy-1-methylpyridin-2(1H)-one;
N-[4-(2,4-difluorophenoxy)-3-(5-methyl-6-oxo-1,6-dihydropyridin-3-yl)phenyl]ethanesulfonamide; and N-[4-(2,4-difluorophenoxy)-3-(1-methyl-4-{4-[(4-methyl-piperazin-1-yl)methyl]phenyl}-6-oxo-1,6-dihydropyridin-3-yl)phenyl]ethanesulfonamide.

In certain embodiments, a compound of formula I is selected from the group consisting of:

1-methyl-5-(2-phenoxyphenyl)pyridin-2(1H)-one;
N-[3-(1-methyl-6-oxo-1,6-dihydropyridin-3-yl)-4-phenoxyphenyl]methanesulfonamide;
methyl{[3-(1-methyl-6-oxo-1,6-dihydropyridin-3-yl)-4-phenoxyphenyl]sulfamoyl}acetate;
{[3-(1-methyl-6-oxo-1,6-dihydropyridin-3-yl)-4-phenoxyphenyl]sulfamoyl}acetic acid;
1-methyl-N-[3-(1-methyl-6-oxo-1,6-dihydropyridin-3-yl)-4-phenoxyphenyl]-1H-imidazole-4-sulfonamide;
N-[3-(1-methyl-6-oxo-1,6-dihydropyridin-3-yl)-4-phenoxyphenyl]-1H-imidazole-4-sulfonamide;
2,2,2-trifluoro-N-[3-(1-methyl-6-oxo-1,6-dihydropyridin-3-yl)-4-phenoxyphenyl]ethanesulfonamide;
N-methyl-N'-[3-(1-methyl-6-oxo-1,6-dihydropyridin-3-yl)-4-phenoxyphenyl]sulfuric diamide;
N-{3-(1-methyl-6-oxo-1,6-dihydropyridin-3-yl)-4-[4-(trifluoromethyl)phenoxy]phenyl}methanesulfonamide;
N-[4-(4-fluorophenoxy)-3-(1-methyl-6-oxo-1,6-dihydropyridin-3-yl)phenyl]methanesulfonamide;
N-[4-(4-chlorophenoxy)-3-(1-methyl-6-oxo-1,6-dihydropyridin-3-yl)phenyl]methanesulfonamide;
N-[3-(1-methyl-6-oxo-1,6-dihydropyridin-3-yl)-4-(pyridin-3-yloxy)phenyl]methanesulfonamide;
N-[4-(2-chlorophenoxy)-3-(1-methyl-6-oxo-1,6-dihydropyridin-3-yl)phenyl]methanesulfonamide;
N-{3-(1-methyl-6-oxo-1,6-dihydropyridin-3-yl)-4-[2-(trifluoromethyl)phenoxy]phenyl}methanesulfonamide;
N-[4-(2-cyanophenoxy)-3-(1-methyl-6-oxo-1,6-dihydropyridin-3-yl)phenyl]methanesulfonamide;
N-[4-(2-methoxyphenoxy)-3-(1-methyl-6-oxo-1,6-dihydropyridin-3-yl)phenyl]methanesulfonamide;
N-[4-(2-fluorophenoxy)-3-(1-methyl-6-oxo-1,6-dihydropyridin-3-yl)phenyl]methanesulfonamide;
N-[4-(2,4-difluorophenoxy)-3-(1-methyl-6-oxo-1,6-dihydropyridin-3-yl)phenyl]methanesulfonamide;
N-[4-(2,4-difluorophenoxy)-3-(1-methyl-6-oxo-1,6-dihydropyridin-3-yl)phenyl]ethanesulfonamide;
N-[4-(3,5-difluorophenoxy)-3-(1-methyl-6-oxo-1,6-dihydropyridin-3-yl)phenyl]methanesulfonamide;
N-[4-(3-chlorophenoxy)-3-(1-methyl-6-oxo-1,6-dihydropyridin-3-yl)phenyl]methanesulfonamide;
N-{3-(1-methyl-6-oxo-1,6-dihydropyridin-3-yl)-4-[3-(trifluoromethyl)phenoxy]phenyl}methanesulfonamide;
N-[4-(3-cyanophenoxy)-3-(1-methyl-6-oxo-1,6-dihydropyridin-3-yl)phenyl]methanesulfonamide;
N-[4-(3-fluorophenoxy)-3-(1-methyl-6-oxo-1,6-dihydropyridin-3-yl)phenyl]methanesulfonamide;
N-[4-(cyclohexyloxy)-3-(1-methyl-6-oxo-1,6-dihydropyridin-3-yl)phenyl]methanesulfonamide;
N-[4-(cyclopentyloxy)-3-(1-methyl-6-oxo-1,6-dihydropyridin-3-yl)phenyl]methanesulfonamide;
N-[3-(1-methyl-6-oxo-1,6-dihydropyridin-3-yl)-4-(tetrahydrofuran-3-yloxy)phenyl]methanesulfonamide;
N-[3-(1-methyl-6-oxo-1,6-dihydropyridin-3-yl)-4-(tetrahydro-2H-pyran-4-ylmethoxy)phenyl]methanesulfonamide;
N-[3-(1-methyl-6-oxo-1,6-dihydropyridin-3-yl)-4-phenoxyphenyl]-1H-pyrrole-2-carboxamide;
tert-butyl (2-{[3-(1-methyl-6-oxo-1,6-dihydropyridin-3-yl)-4-phenoxyphenyl]amino}-2-oxoethyl)carbamate;
N-[3-(1-methyl-6-oxo-1,6-dihydropyridin-3-yl)-4-phenoxyphenyl]glycinamide;
1-methyl-5-[2-phenoxy-5-(pyridin-2-ylamino)phenyl]pyridin-2(1H)-one;
N-ethyl-3-(1-methyl-6-oxo-1,6-dihydropyridin-3-yl)-4-phenoxybenzenesulfonamide;
3-(1-methyl-6-oxo-1,6-dihydropyridin-3-yl)-4-phenoxybenzenesulfonamide;
N-[2-methyl-5-(1-methyl-6-oxo-1,6-dihydropyridin-3-yl)-4-phenoxyphenyl]methanesulfonamide;
4-methoxy-1-methyl-5-(2-phenoxyphenyl)pyridin-2(1H)-one;
N-[3-(4-methoxy-1-methyl-6-oxo-1,6-dihydropyridin-3-yl)-4-phenoxyphenyl]methanesulfonamide;
N-{4-(2,4-difluorophenoxy)-3-[1-methyl-6-oxo-4-(trifluoromethyl)-1,6-dihydropyridin-3-yl]phenyl}ethanesulfonamide;
N-[3-(4-chloro-1-methyl-6-oxo-1,6-dihydropyridin-3-yl)-4-(2,4-difluorophenoxy)phenyl]methanesulfonamide;
N-[4-(2,4-difluorophenoxy)-3-(4-methoxy-1-methyl-6-oxo-1,6-dihydropyridin-3-yl)phenyl]methanesulfonamide;
N-[4-(2,4-difluorophenoxy)-3-(4-methoxy-1-methyl-6-oxo-1,6-dihydropyridin-3-yl)phenyl]ethanesulfonamide;
N-[4-(2,4-difluorophenoxy)-3-{4-[4-(hydroxymethyl)phenyl]-1-methyl-6-oxo-1,6-dihydropyridin-3-yl}phenyl]methanesulfonamide;
N-[4-(2,4-difluorophenoxy)-3-(1-methyl-4-{4-[(4-methylpiperazin-1-yl)methyl]phenyl}-6-oxo-1,6-dihydropyridin-3-yl)phenyl]methanesulfonamide;
N-[4-(2,4-difluorophenoxy)-3-{1-methyl-4-[4-(morpholin-4-yl)phenyl]-6-oxo-1,6-dihydropyridin-3-yl}phenyl]methanesulfonamide;
5-[2-(cyclopropylmethoxy)-5-(ethylsulfonyl)phenyl]-4-methoxy-1-methylpyridin-2(1H)-one;
5-{2-(2,4-difluorophenoxy)-5-[(methylsulfonyl)amino]phenyl}-N,1-dimethyl-2-oxo-1,2-dihydropyridine-4-carboxamide;
N-[4-(2,4-difluorophenoxy)-3-(4-ethoxy-1-methyl-6-oxo-1,6-dihydropyridin-3-yl)phenyl]methanesulfonamide;
N-[4-(2,4-difluorophenoxy)-3-{4-[4-(hydroxymethyl)phenyl]-1-methyl-6-oxo-1,6-dihydropyridin-3-yl}phenyl]ethanesulfonamide;
N-[4-(2,4-difluorophenoxy)-3-(1-methyl-4-{4-[(4-methylpiperazin-1-yl)methyl]phenyl}-6-oxo-1,6-dihydropyridin-3-yl)phenyl]ethanesulfonamide;
N-[4-(2,4-difluorophenoxy)-3-(4-{4-[(dimethylamino)methyl]phenyl}-1-methyl-6-oxo-1,6-dihydropyridin-3-yl)phenyl]ethanesulfonamide;
3-chloro-1-methyl-5-(2-phenoxyphenyl)pyridin-2(1H)-one;
N-[3-(5-chloro-1-methyl-6-oxo-1,6-dihydropyridin-3-yl)-4-(2,4-difluorophenoxy)phenyl]methanesulfonamide;
N-[3-(5-chloro-1-methyl-6-oxo-1,6-dihydropyridin-3-yl)-4-(2,4-difluorophenoxy)phenyl]ethanesulfonamide;
N-[4-(2,4-difluorophenoxy)-3-{1-methyl-4-[4-(morpholin-4-yl)phenyl]-6-oxo-1,6-dihydropyridin-3-yl}phenyl]ethanesulfonamide;
4-{4-[(ethylsulfonyl)amino]-2-[1-methyl-6-oxo-4-(2,2,2-trifluoroethoxy)-1,6-dihydropyridin-3-yl]phenoxy}benzamide;
N-[4-(2,4-difluorophenoxy)-3-(4-ethoxy-1-methyl-6-oxo-1,6-dihydropyridin-3-yl)phenyl]-2-oxo-1-phenylpyrrolidine-3-carboxamide;
N-[4-(2,4-difluorophenoxy)-3-(4-ethoxy-1-methyl-6-oxo-1,6-dihydropyridin-3-yl)phenyl]-3,3-dimethylbutanamide;
N-[4-(2,4-difluorophenoxy)-3-(4-ethoxy-1-methyl-6-oxo-1,6-dihydropyridin-3-yl)phenyl]-4-(phenoxymethyl)benzamide;
N-[4-(2,4-difluorophenoxy)-3-(4-ethoxy-1-methyl-6-oxo-1,6-dihydropyridin-3-yl)phenyl]-4-methylpentanamide;

N-[4-(2,4-difluorophenoxy)-3-(4-ethoxy-1-methyl-6-oxo-1,6-dihydropyridin-3-yl)phenyl]-1-phenylcyclopropanecarboxamide;

4-(acetylamino)-N-[4-(2,4-difluorophenoxy)-3-(4-ethoxy-1-methyl-6-oxo-1,6-dihydropyridin-3-yl)phenyl]benzamide;

N-[4-(2,4-difluorophenoxy)-3-(4-ethoxy-1-methyl-6-oxo-1,6-dihydropyridin-3-yl)phenyl]-4-(propan-2-yloxy)benzamide;

N-[4-(2,4-difluorophenoxy)-3-(4-ethoxy-1-methyl-6-oxo-1,6-dihydropyridin-3-yl)phenyl]-2-(2-phenylethyl)benzamide;

4-(diethylamino)-N-[3-[4-(2,4-difluorophenoxy)-3-(4-ethoxy-1-methyl-6-oxo-1,6-dihydropyridin-3-yl)phenyl]benzamide;

N-[4-(2,4-difluorophenoxy)-3-(4-ethoxy-1-methyl-6-oxo-1,6-dihydropyridin-3-yl)phenyl]biphenyl-4-carboxamide;

5-{2-(2,4-difluorophenoxy)-5-[(2,2-dimethylpropyl)amino]phenyl}-4-ethoxy-1-methylpyridin-2(1H)-one;

5-{2-(2,4-difluorophenoxy)-5[(3,3-dimethylbutyl)amino]phenyl}-4-ethoxy-1-methylpyridin-2(1H)-one;

N-[4-(2,4-difluorophenoxy)-3-(4-ethoxy-1-methyl-6-oxo-1,6-dihydropyridin-3-yl)phenyl]-4-(methylsulfonyl)benzenesulfonamide;

N-[4-(2,4-difluorophenoxy)-3-(4-ethoxy-1-methyl-6-oxo-1,6-dihydropyridin-3-yl)phenyl]-4-(trifluoromethoxy)benzenesulfonamide;

N-[4-(2,4-difluorophenoxy)-3-(4-ethoxy-1-methyl-6-oxo-1,6-dihydropyridin-3-yl)phenyl]biphenyl-4-sulfonamide;

N-[4-(2,4-difluorophenoxy)-3-(4-ethoxy-1-methyl-6-oxo-1,6-dihydropyridin-3-yl)phenyl]-1-[(1S,4R)-7,7-dimethyl-2-oxobicyclo[2.2.1]hept-1-yl]methanesulfonamide;

N-[4-(2,4-difluorophenoxy)-3-(4-ethoxy-1-methyl-6-oxo-1,6-dihydropyridin-3-yl)phenyl]-1-phenylmethanesulfonamide;

5-[2-(cyclopropylmethoxy)-4-(3-methyl-1H-pyrazol-5-yl)phenyl]-1-methylpyridin-2(1H)-one;

5-{2-[2-(but-3-en-1-yn-1-yl)phenoxy]-5-(ethylsulfonyl)phenyl}-4-hydroxy-1-methylpyridin-2(1H)-one;

4-chloro-5-{5-(ethylsulfonyl)-2-[2-(3-hydroxyprop-1-yn-1-yl)phenoxy]phenyl}-1-methylpyridin-2(1H)-one;

N-[4-(2,4-difluorophenoxy)-3-(1-methyl-4-{[4-(morpholin-4-ylmethyl)benzyl]oxy}-6-oxo-1,6-dihydropyridin-3-yl)phenyl]ethanesulfonamide;

N-{4-(2,4-difluorophenoxy)-3-[1-methyl-4-(oxetan-3-yloxy)-6-oxo-1,6-dihydropyridin-3-yl]phenyl}ethanesulfonamide;

4-(2,4-difluorophenoxy)-5-[2-(2,4-difluorophenoxy)-5-(ethylsulfonyl)phenyl]-1-methylpyridin-2(1H)-one;

5-[2-(2,4-difluorophenoxy)-5-(ethylsulfonyl)phenyl]-1-methyl-4-(oxetan-3-yloxy)pyridin-2(1H)-one;

tert-butyl 4-[(5-{2-(2,4-difluorophenoxy)-5-[(ethylsulfonyl)amino]phenyl}-1-methyl-2-oxo-1,2-dihydropyridin-4-yl)oxy]piperidine-1-carboxylate;

tert-butyl 4-{[5-(2-{4-[1-(tert-butoxycarbonyl)piperidin-4-yl]-2-fluorophenoxy}-5-[(ethylsulfonyl)amino]phenyl)-1-methyl-2-oxo-1,2-dihydropyridin-4-yl]oxy}piperidine-1-carboxylate;

N-[4-(2,4-difluorophenoxy)-3-(4-{[trans-4-(dimethylamino)cyclohexyl]oxy}-1-methyl-6-oxo-1,6-dihydropyridin-3-yl)phenyl]ethanesulfonamide;

N-{4-(2,4-difluorophenoxy)-3-[1-methyl-6-oxo-4-(piperidin-4-yloxy)-1,6-dihydropyridin-3-yl]phenyl}ethanesulfonamide;

N-[4-(2,4-difluorophenoxy)-3-{1-methyl-4-[1-methylpyrrolidin-3-yl)methoxy]-6-oxo-1,6-dihydropyridin-3-yl}phenyl]ethanesulfonamide;

tert-butyl 4-{[(5-{2-(2,4-difluorophenoxy)-5-[(ethylsulfonyl)amino]phenyl}-1-methyl-2-oxo-1,2-dihydropyridin-4-yl)oxy]methyl}piperidine-1-carboxylate;

tert-butyl 6-[(5-{2-(2,4-difluorophenoxy)-5-[(ethylsulfonyl)amino]phenyl}-1-methyl-2-oxo-1,2-dihydropyridin-4-yl)oxy]-2-azaspiro[3.3]heptane-2-carboxylate;

N-{3-[4-(2-azaspiro[3.3]hept-6-yloxy)-1-methyl-6-oxo-1,6-dihydropyridin-3-yl]-4-(2,4-difluorophenoxy)phenyl}ethanesulfonamide;

5-{2-[(cyclopropylmethyl)amino]-5-(methylsulfonyl)phenyl}-4-[(E)-2-ethoxyethenyl]-1-methylpyridin-2(1H)-one;

N-[3-(4-{[4-(diethylamino)but-2-yn-1-yl]oxy}-1-methyl-6-oxo-1,6-dihydropyridin-3-yl)-4-(2,4-difluorophenoxy)phenyl]ethanesulfonamide;

N-[4-(2,4-difluorophenoxy)-3-{1-methyl-6-oxo-4-[(1E)-prop-1-en-1-yl]-1,6-dihydropyridin-3-yl}phenyl]ethanesulfonamide;

N-[4-(2,4-difluorophenoxy)-3-{1-methyl-4-[4-(4-methylpiperazin-1-yl)phenyl]-6-oxo-1,6-dihydropyridin-3-yl}phenyl]ethanesulfonamide;

N-{4-(2,4-difluorophenoxy)-3-[4-(2-hydroxyphenyl)-1-methyl-6-oxo-1,6-dihydropyridin-3-yl]phenyl}ethanesulfonamide;

N-{4-(2,4-difluorophenoxy)-3-[4-(4-formylthiophen-3-yl)-1-methyl-6-oxo-1,6-dihydropyridin-3-yl]phenyl}ethanesulfonamide;

N-[4-(2,4-difluorophenoxy)-3-{4-[(1,1-$^2$H$_2$)ethyloxy]-1-methyl-6-oxo-1,6-dihydropyridin-3-yl}phenyl]ethanesulfonamide;

N-[4-(2,4-difluorophenoxy)-3-{4-[($^2$H$_5$)ethyloxy]-1-methyl-6-oxo-1,6-dihydropyridin-3-yl}phenyl]ethanesulfonamide;

N-[3-{4-[(2,2-difluoro-1-methylcyclopropyl)methoxy]-1-methyl-6-oxo-1,6-dihydropyridin-3-yl}-4-(2,4-difluorophenoxy)phenyl]ethanesulfonamide;

N-{4-[2-fluoro-4-(oxetan-3-yloxy)phenoxy]-3-[1-methyl-4-(oxetan-3-yloxy)-6-oxo-1,6-dihydropyridin-3-yl]phenyl}ethanesulfonamide;

5-{2-[(cyclopropylmethyl)amino]-5-(methylsulfonyl)phenyl}-4-[(Z)-2-ethoxyethenyl]-1-methylpyridin-2(1H)-one;

ethyl{5-[2-(cyclopropylmethoxy)-5-(ethylsulfonyl)phenyl]-1-methyl-2-oxo-1,2-dihydropyridin-3-yl}carbamate;

N-{5-[2-(cyclopropylmethoxy)-5-(ethylsulfonyl)phenyl]-1-methyl-2-oxo-1,2-dihydropyridin-3-yl}methanesulfonamide;

5-{2-[(cyclopropylmethyl)amino]-5-(methylsulfonyl)phenyl}-4-ethoxy-1-methylpyridin-2(1H)-one;

5-{2-[(cyclopropylmethyl)amino]-5-(methylsulfonyl)phenyl}-4-[(3-hydroxy-2,3-dimethylbutan-2-yl)oxy]-1-methylpyridin-2(1H)-one;

N-{4-(2,4-difluorophenoxy)-3-[1-methyl-4-(1-methyl-1H-pyrazol-4-yl)-6-oxo-1,6-dihydropyridin-3-yl]phenyl}ethanesulfonamide;

N-[4-(2,4-difluorophenoxy)-3-(4-ethoxy-1-methyl-6-oxo-1,6-dihydropyridin-3-yl)phenyl]naphthalene-1-sulfonamide;

N-[4-(2,4-difluorophenoxy)-3-(4-ethoxy-1-methyl-6-oxo-1,6-dihydropyridin-3-yl)phenyl]benzenesulfonamide;

N-[4-(2,4-difluorophenoxy)-3-(1-methyl-4-{1-[2-(morpholin-4-yl)ethyl]-1H-pyrazol-4-yl}-6-oxo-1,6-dihydropyridin-3-yl)phenyl]ethanesulfonamide;

N-{4-(2,4-difluorophenoxy)-3-[1-methyl-6-oxo-4-(1H-pyrazol-1-yl)-1,6-dihydropyridin-3-yl]phenyl}ethanesulfonamide;

N-[4-(2,4-difluorophenoxy)-3-(4-ethoxy-1-methyl-6-oxo-1,6-dihydropyridin-3-yl)phenyl]-4-(propan-2-yl)benzenesulfonamide;

4-chloro-N-[4-(2,4-difluorophenoxy)-3-(4-ethoxy-1-methyl-6-oxo-1,6-dihydropyridin-3-yl)phenyl]-2-fluorobenzenesulfonamide;

N-[4-(2,4-difluorophenoxy)-3-(4-ethoxy-1-methyl-6-oxo-1,6-dihydropyridin-3-yl)phenyl]propane-1-sulfonamide;

1-(2-chloro-5-fluorophenyl)-N-[4-(2,4-difluorophenoxy)-3-(4-ethoxy-1-methyl-6-oxo-1,6-dihydropyridin-3-yl)phenyl]methanesulfonamide;

N-[4-(2,4-difluorophenoxy)-3-(4-ethoxy-1-methyl-6-oxo-1,6-dihydropyridin-3-yl)phenyl]-1-(2-fluorophenyl)methanesulfonamide;

N-[4-(2,4-difluorophenoxy)-3-(5-fluoro-1-methyl-6-oxo-1,6-dihydropyridin-3-yl)phenyl]ethanesulfonamide;

N-[3-{4-[(cyclopropylmethyl)amino]-1-methyl-6-oxo-1,6-dihydropyridin-3-yl}-4-(2,4-difluorophenoxy)phenyl]ethanesulfonamide;

5-[2-(cyclopropylmethoxy)-6-methylphenyl]-1-methylpyridin-2(1H)-one;

3-amino-5-[2-(cyclopropylmethoxy)-5-(ethylsulfonyl)phenyl]-1-methylpyridin-2(1H)-one;

N-[4-(4-cyanophenoxy)-3-(4-ethoxy-1-methyl-6-oxo-1,6-dihydropyridin-3-yl)phenyl]ethanesulfonamide;

N-[4-(2,4-difluorophenoxy)-3-(1-methyl-6-oxo-4-propyl-1,6-dihydropyridin-3-yl)phenyl]ethanesulfonamide;

5-{5-(ethylsulfonyl)-2-[(cis-4-methoxy-4-methylcyclohexyl)oxy]phenyl}-1-methylpyridin-2(1H)-one;

N-{5-[2-(cyclopropylmethoxy)-5-(ethylsulfonyl)phenyl]-1-methyl-2-oxo-1,2-dihydropyridin-3-yl}acetamide;

N-{3-[4-(cyclopropylamino)-1-methyl-6-oxo-1,6-dihydropyridin-3-yl]-4-(2,4-difluorophenoxy)phenyl}ethanesulfonamide;

N-{4-(2,4-difluorophenoxy)-3-[4-(ethylamino)-1-methyl-6-oxo-1,6-dihydropyridin-3-yl]phenyl}ethanesulfonamide;

5-[2-(2,4-difluorophenoxy)-5-(propan-2-ylsulfonyl)phenyl]-1-methylpyridin-2(1H)-one;

N-[4-(cyclopropylmethoxy)-2-methyl-3-(1-methyl-6-oxo-1,6-dihydropyridin-3-yl)phenyl]ethanesulfonamide;

N-[4-(cyclopropylmethoxy)-2-methyl-5-(1-methyl-6-oxo-1,6-dihydropyridin-3-yl)phenyl]ethanesulfonamide;

N-{3-[4-(cyclobutyloxy)-1-methyl-6-oxo-1,6-dihydropyridin-3-yl]-4-(2,4-difluorophenoxy)phenyl}ethanesulfonamide;

5-{2-[(2,2-difluorocyclopropyl)methoxy]-5-(ethylsulfonyl)phenyl}-4-ethoxy-1-methylpyridin-2(1H)-one;

5-[2-(2,4-difluorophenoxy)-5-(propan-2-ylsulfonyl)phenyl]-4-ethoxy-1-methylpyridin-2(1H)-one;

5-{2-(2,4-difluorophenoxy)-5-[(methylsulfonyl)methyl]phenyl}-4-ethoxy-1-methylpyridin-2(1H)-one;

5-[5-(cyclopropylsulfonyl)-2-(2,4-difluorophenoxy)phenyl]-4-ethoxy-1-methylpyridin-2(1H)-one;

N-{4-(2,4-difluorophenoxy)-3-[4-(3-hydroxy-3-methylbutoxy)-1-methyl-6-oxo-1,6-dihydropyridin-3-yl]phenyl}ethanesulfonamide;

5-[2-(cyclopropylamino)-5-(ethylsulfonyl)phenyl]-4-ethoxy-1-methylpyridin-2(1H)-one;

N-{4-(4-cyanophenoxy)-3-[1-methyl-6-oxo-4-(2,2,2-trifluoroethoxy)-1,6-dihydropyridin-3-yl]phenyl}ethanesulfonamide;

5-[2-(2,4-difluorophenoxy)-5-(ethylsulfonyl)phenyl]-4-ethoxy-1-methylpyridin-2(1H)-one;

N-{4-(2,4-difluorophenoxy)-3-[4-(2-hydroxy-2-methylpropoxy)-1-methyl-6-oxo-1,6-dihydropyridin-3-yl]phenyl}ethanesulfonamide;

4-ethoxy-5-{5-(ethylsulfonyl)-2-[4-(trifluoromethoxy)phenoxy]phenyl}-1-methylpyridin-2(1H)-one;

4-[2-(4-ethoxy-1-methyl-6-oxo-1,6-dihydropyridin-3-yl)-4-(ethylsulfonyl)phenoxy]benzonitrile;

5-{2-(2,4-difluorophenoxy)-5-[(ethylsulfonyl)methyl]phenyl}-4-ethoxy-1-methylpyridin-2(1H)-one;

5-{2-(2,4-difluorophenoxy)-5-[2-(ethylsulfonyl)propan-2-yl]phenyl}-4-ethoxy-1-methylpyridin-2(1H)-one;

N-[4-(cyclopropylmethoxy)-3-(4-ethoxy-1-methyl-6-oxo-1,6-dihydropyridin-3-yl)phenyl]ethanesulfonamide;

4-chloro-5-[2-(2,4-difluorophenoxy)-5-(ethylsulfonyl)phenyl]-1-methylpyridin-2(1H)-one;

N-[4-(2-cyclopropylethoxy)-3-(4-ethoxy-1-methyl-6-oxo-1,6-dihydropyridin-3-yl)phenyl]ethanesulfonamide;

N-[4-(cyclobutyloxy)-3-(4-ethoxy-1-methyl-6-oxo-1,6-dihydropyridin-3-yl)phenyl]ethanesulfonamide;

N-{4-[(4,4-difluorocyclohexyl)oxy]-3-(4-ethoxy-1-methyl-6-oxo-1,6-dihydropyridin-3-yl)phenyl}ethanesulfonamide;

N-{3-(4-ethoxy-1-methyl-6-oxo-1,6-dihydropyridin-3-yl)-4-[4-(trifluoromethyl)phenoxy]phenyl}ethanesulfonamide;

N-{3-(4-ethoxy-1-methyl-6-oxo-1,6-dihydropyridin-3-yl)-4-[4-(trifluoromethoxy)phenoxy]phenyl}ethanesulfonamide;

ethyl 4-{2-(4-ethoxy-1-methyl-6-oxo-1,6-dihydropyridin-3-yl)-4-[(ethylsulfonyl)amino]phenoxy}piperidine-1-carboxylate;

N-{4-[(1-acetylpiperidin-4-yl)oxy]-3-(4-ethoxy-1-methyl-6-oxo-1,6-dihydropyridin-3-yl)phenyl}ethanesulfonamide;

N-{3-[4-(1-benzyl-1H-pyrazol-4-yl)-1-methyl-6-oxo-1,6-dihydropyridin-3-yl]-4-(2,4-difluorophenoxy)phenyl}ethanesulfonamide;

N-[4-(2,4-difluorophenoxy)-3-{1-methyl-4-[1-(2-methylpropyl)-1H-pyrazol-4-yl]-6-oxo-1,6-dihydropyridin-3-yl}phenyl]ethanesulfonamide;

N-{4-(2,4-difluorophenoxy)-3-[4-(furan-2-yl)-1-methyl-6-oxo-1,6-dihydropyridin-3-yl]phenyl}ethanesulfonamide;

N-{4-(2,4-difluorophenoxy)-3-[4-(furan-3-yl)-1-methyl-6-oxo-1,6-dihydropyridin-3-yl]phenyl}ethanesulfonamide;

N-[4-(2,3-dihydro-1H-inden-2-yloxy)-3-(4-ethoxy-1-methyl-6-oxo-1,6-dihydropyridin-3-yl)phenyl]ethanesulfonamide;

tert-butyl(trans-4-{2-(4-ethoxy-1-methyl-6-oxo-1,6-dihydropyridin-3-yl)-4-[(ethylsulfonyl)amino]phenoxy}cyclohexyl)carbamate;

N-[3-(4-ethoxy-1-methyl-6-oxo-1,6-dihydropyridin-3-yl)-4-(4-fluorophenoxy)phenyl]ethanesulfonamide;

5-[2-(cyclopropylmethoxy)-5-(2,3-dihydro-1H-indol-1-ylsulfonyl)phenyl]-4-ethoxy-1-methylpyridin-2(1H)-one;

4-[2-(2,4-difluorophenoxy)-5-(ethylsulfonyl)phenyl]-1-methyl-5-(2,2,2-trifluoroethoxy)pyridin-2(1H)-one;

N-{4-(2,4-difluorophenoxy)-3-[1-methyl-6-oxo-4-(piperidin-4-ylmethoxy)-1,6-dihydropyridin-3-yl]phenyl}ethanesulfonamide;

N-[4-(4-chlorophenoxy)-3-(4-ethoxy-1-methyl-6-oxo-1,6-dihydropyridin-3-yl)phenyl]ethanesulfonamide;

N-[4-(3,4-difluorophenoxy)-3-(4-ethoxy-1-methyl-6-oxo-1,6-dihydropyridin-3-yl)phenyl]ethanesulfonamide;

N-[3-(4-ethoxy-1-methyl-6-oxo-1,6-dihydropyridin-3-yl)-4-(3,4,5-trifluorophenoxy)phenyl]ethanesulfonamide;

N-[4-(4-chloro-2-fluorophenoxy)-3-(4-ethoxy-1-methyl-6-oxo-1,6-dihydropyridin-3-yl)phenyl]ethanesulfonamide;

N-[4-(4-chloro-2,6-difluorophenoxy)-3-(4-ethoxy-1-methyl-6-oxo-1,6-dihydropyridin-3-yl)phenyl]ethanesulfonamide;

N-[3-(4-ethoxy-1-methyl-6-oxo-1,6-dihydropyridin-3-yl)-4-(pyridin-3-yloxy)phenyl]ethanesulfonamide;
5-[5-amino-2-(2,4-difluorophenoxy)phenyl]-4-ethoxy-1-methylpyridin-2(1H)-one;
N-{4-(2,4-difluorophenoxy)-3-[1-methyl-4-(5-methylthiophen-2-yl)-6-oxo-1,6-dihydropyridin-3-yl]phenyl}ethanesulfonamide;
N-[4-(4-cyano-2-fluorophenoxy)-3-(4-ethoxy-1-methyl-6-oxo-1,6-dihydropyridin-3-yl)phenyl]ethanesulfonamide;
5-{2-[(2,4-difluorobenzyl)amino]-5-(methylsulfonyl)phenyl}-4-ethoxy-1-methylpyridin-2(1H)-one;
N-[3-(4-ethoxy-1-methyl-6-oxo-1,6-dihydropyridin-3-yl)-4-({1-[4-(trifluoromethyl)phenyl]piperidin-4-yl}oxy)phenyl]ethanesulfonamide;
N-[4-(2,4-difluorophenoxy)-3-(4-ethoxy-1-methyl-6-oxo-1,6-dihydropyridin-3-yl)phenyl]-1,3-thiazole-5-carboxamide;
2,5-dichloro-N-[4-(2,4-difluorophenoxy)-3-(4-ethoxy-1-methyl-6-oxo-1,6-dihydropyridin-3-yl)phenyl]benzamide;
N-[4-(2,4-difluorophenoxy)-3-(4-ethoxy-1-methyl-6-oxo-1,6-dihydropyridin-3-yl)phenyl]-4-(propan-2-yl)benzamide;
N-[4-(2,4-difluorophenoxy)-3-(4-ethoxy-1-methyl-6-oxo-1,6-dihydropyridin-3-yl)phenyl]-5-methylpyrazine-2-carboxamide;
N-[4-(2,4-difluorophenoxy)-3-(4-ethoxy-1-methyl-6-oxo-1,6-dihydropyridin-3-yl)phenyl]pyridine-2-carboxamide;
4-tert-butyl-N-[4-(2,4-difluorophenoxy)-3-(4-ethoxy-1-methyl-6-oxo-1,6-dihydropyridin-3-yl)phenyl]benzenesulfonamide;
2,4-dichloro-N-[4-(2,4-difluorophenoxy)-3-(4-ethoxy-1-methyl-6-oxo-1,6-dihydropyridin-3-yl)phenyl]benzenesulfonamide;
N-[4-(2,4-difluorophenoxy)-3-(4-ethoxy-1-methyl-6-oxo-1,6-dihydropyridin-3-yl)phenyl]naphthalene-2-sulfonamide;
5-[2-(2,4-difluorophenoxy)-5-(2,3-dihydro-1H-indol-1-ylsulfonyl)phenyl]-4-ethoxy-1-methylpyridin-2(1H)-one; and
N-[4-(2,4-difluorophenoxy)-3-(4-ethoxy-1-methyl-6-oxo-1,6-dihydropyridin-3-yl)phenyl]-N-methyl-1-phenylmethanesulfonamide.

In certain embodiments, a compound of formula I is selected from the group consisting of:
2-methyl-6-(2-phenoxyphenyl)pyridazin-3(2H)-one;
6-[2-(benzyloxy)phenyl]-2-methylpyridazin-3(2H)-one;
6-[2-(1-methyl-6-oxo-1,6-dihydropyridazin-3-yl)phenoxy]benzonitrile;
6-[2-(cyclopentyloxy)phenyl]-2-methylpyridazin-3(2H)-one;
6-[2-(4-hydroxybutoxy)phenyl]-2-methylpyridazin-3(2H)-one;
2-methyl-6-[2-(pyridin-2-yloxy)phenyl]pyridazin-3(2H)-one;
2-methyl-6-{2-[4-(trifluoromethyl)phenoxy]phenyl}pyridazin-3(2H)-one;
2-methyl-6-{2-[4-(methylsulfonyl)phenoxy]phenyl}pyridazin-3(2H)-one;
2-methyl-6-(5-nitro-2-phenoxyphenyl)pyridazin-3(2H)-one;
6-(5-amino-2-phenoxyphenyl)-2-methylpyridazin-3(2H)-one;
4-methyl-N-[3-(1-methyl-6-oxo-1,6-dihydropyridazin-3-yl)-4-phenoxyphenyl]benzenesulfonamide;
N-[3-(1-methyl-6-oxo-1,6-dihydropyridazin-3-yl)-4-phenoxyphenyl]acetamide;
3-(1-methyl-6-oxo-1,6-dihydropyridazin-3-yl)-4-phenoxybenzonitrile;
3-(1-methyl-6-oxo-1,6-dihydropyridazin-3-yl)-4-phenoxybenzamide;
3-(1-methyl-6-oxo-1,6-dihydropyridazin-3-yl)-4-phenoxybenzoic acid;
N-[3-(1-methyl-6-oxo-1,6-dihydropyridazin-3-yl)-4-phenoxybenzyl]acetamide;
2,2,2-trifluoro-N-[3-(1-methyl-6-oxo-1,6-dihydropyridazin-3-yl)-4-phenoxybenzyl]acetamide;
5-methoxy-2-methyl-6-(2-phenoxyphenyl)pyridazin-3(2H)-one;
N-[3-(4-methoxy-1-methyl-6-oxo-1,6-dihydropyridazin-3-yl)phenyl]methanesulfonamide;
6-(5-amino-2-phenoxyphenyl)-5-methoxy-2-methylpyridazin-3(2H)-one;
N-[3-(4-methoxy-1-methyl-6-oxo-1,6-dihydropyridazin-3-yl)-4-phenoxyphenyl]acetamide;
N-[3-(4-methoxy-1-methyl-6-oxo-1,6-dihydropyridazin-3-yl)-4-phenoxyphenyl]methanesulfonamide;
N-[3-(4-methoxy-1-methyl-6-oxo-1,6-dihydropyridazin-3-yl)-4-phenoxyphenyl]-N-methylmethanesulfonamide;
N-[3-(4-methoxy-1-methyl-6-oxo-1,6-dihydropyridazin-3-yl)-4-phenoxyphenyl]propane-1-sulfonamide;
2,2,2-trifluoro-N-[3-(4-methoxy-1-methyl-6-oxo-1,6-dihydropyridazin-3-yl)-4-phenoxyphenyl]ethanesulfonamide;
N-[3-(4-methoxy-1-methyl-6-oxo-1,6-dihydropyridazin-3-yl)-4-phenoxyphenyl]cyclopentanesulfonamide;
N-[3-(4-methoxy-1-methyl-6-oxo-1,6-dihydropyridazin-3-yl)-4-phenoxyphenyl]-1-phenylmethanesulfonamide;
3,3,3-trifluoro-N-[3-(4-methoxy-1-methyl-6-oxo-1,6-dihydropyridazin-3-yl)-4-phenoxyphenyl]propane-1-sulfonamide;
Ethyl[3-(4-methoxy-1-methyl-6-oxo-1,6-dihydropyridazin-3-yl)-4-phenoxyphenyl]carbamate;
1-ethyl-3-[3-(4-methoxy-1-methyl-6-oxo-1,6-dihydropyridazin-3-yl)-4-phenoxyphenyl]urea;
N'-[3-(4-methoxy-1-methyl-6-oxo-1,6-dihydropyridazin-3-yl)-4-phenoxyphenyl]-N,N-dimethylsulfuric diamide;
4-[2-(4-methoxy-1-methyl-6-oxo-1,6-dihydropyridazin-3-yl)phenoxy]benzonitrile;
6-[2-(4-fluorophenoxy)phenyl]-5-methoxy-2-methylpyridazin-3(2H)-one;
6-[2-(3-chloro-4-fluorophenoxy)phenyl]-5-methoxy-2-methylpyridazin-3(2H)-one;
5-methoxy-6-[2-(4-methoxyphenoxy)phenyl]-2-methylpyridazin-3(2H)-one;
6-[2-(3-fluorophenoxy)phenyl]-5-methoxy-2-methylpyridazin-3(2H)-one;
6-[2-(4-chlorophenoxy)phenyl]-5-methoxy-2-methylpyridazin-3(2H)-one;
methyl{[1-methyl-6-oxo-3-(2-phenoxyphenyl)-1,6-dihydropyridazin-4-yl]oxy}acetate;
6-[2-(cyclohexyloxy)phenyl]-5-methoxy-2-methylpyridazin-3(2H)-one;
5-methoxy-2-methyl-6-[2-(pyridin-2-ylmethoxy)phenyl]pyridazin-3(2H)-one;
6-[2-(1H-indazol-5-ylmethoxy)phenyl]-5-methoxy-2-methylpyridazin-3(2H)-one;
6-[2-(2-cyclohexylethoxy)phenyl]-5-methoxy-2-methylpyridazin-3(2H)-one;
tert-butyl 4-{[2-(4-methoxy-1-methyl-6-oxo-1,6-dihydropyridazin-3-yl)phenoxy]methyl}piperidine-1-carboxylate;
5-methoxy-2-methyl-6-[2-(piperidin-4-ylmethoxy)phenyl]pyridazin-3(2H)-one;

5-methoxy-2-methyl-6-[2-(pyridin-4-ylmethoxy)phenyl]pyridazin-3(2H)-one;
6-[2-(cyclopentylmethoxy)phenyl]-5-methoxy-2-methylpyridazin-3(2H)-one;
5-methoxy-2-methyl-6-[2-(tetrahydro-2H-pyran-4-ylmethoxy)phenyl]pyridazin-3(2H)-one;
methyl 1-[1-methyl-6-oxo-3-(2-phenoxyphenyl)-1,6-dihydropyridazin-4-yl]pyrrolidine-3-carboxylate;
Ethyl 1-[1-methyl-6-oxo-3-(2-phenoxyphenyl)-1,6-dihydropyridazin-4-yl]pyrrolidine-3-carboxylate;
methyl N-[1-methyl-6-oxo-3-(2-phenoxyphenyl)-1,6-dihydropyridazin-4-yl]glycinate;
2-methyl-5-(4-methyl-3-oxopiperazin-1-yl)-6-(2-phenoxyphenyl)pyridazin-3(2H)-one;
6-(biphenyl-2-yl)-2-methylpyridazin-3(2H)-one;
2'-(1-methyl-6-oxo-1,6-dihydropyridazin-3-yl)biphenyl-3-carbonitrile;
5-(2-fluoropyridin-4-yl)-2-methyl-6-(2-phenoxyphenyl)pyridazin-3(2H)-one;
2-methyl-5-(2-oxo-1,2-dihydropyridin-4-yl)-6-(2-phenoxyphenyl)pyridazin-3(2H)-one;
2-methyl-5-(1-methyl-2-oxo-1,2-dihydropyridin-4-yl)-6-(2-phenoxyphenyl)pyridazin-3(2H)-one;
5-(2-methoxypyridin-4-yl)-2-methyl-6-(2-phenoxyphenyl)pyridazin-3(2H)-one;
N-{3-[4-(2-methoxypyridin-4-yl)-1-methyl-6-oxo-1,6-dihydropyridazin-3-yl]-4-phenoxyphenyl}methanesulfonamide;
Ethyl 3-[1-methyl-6-oxo-3-(2-phenoxyphenyl)-1,6-dihydropyridazin-4-yl]benzoate;
2-methyl-5-{3-[(4-methylpiperazin-1-yl)methyl]phenyl}-6-(2-phenoxyphenyl)pyridazin-3(2H)-one;
2-methyl-5-{4-[(4-methylpiperazin-1-yl)methyl]phenyl}-6-(2-phenoxyphenyl)pyridazin-3(2H)-one;
N-[3-(1-methyl-4-{4-[(4-methylpiperazin-1-yl)methyl]phenyl}-6-oxo-1,6-dihydropyridazin-3-yl)-4-phenoxyphenyl]methanesulfonamide;
N-{3-[1-methyl-4-(4-methylphenyl)-6-oxo-1,6-dihydropyridazin-3-yl]-4-phenoxyphenyl}methanesulfonamide;
5-(3-amino-4-methylphenyl)-2-methyl-6-(2-phenoxyphenyl)pyridazin-3(2H)-one;
4-[1-methyl-6-oxo-3-(2-phenoxyphenyl)-1,6-dihydropyridazin-4-yl]benzaldehyde;
2-methyl-5-[4-(morpholin-4-ylmethyl)phenyl]-6-(2-phenoxyphenyl)pyridazin-3(2H)-one;
2-methyl-6-(2-phenoxyphenyl)-5-[4-(piperidin-1-ylmethyl)phenyl]pyridazin-3(2H)-one;
2-methyl-5-{4-[(4-methylpiperidin-1-yl)methyl]phenyl}-6-(2-phenoxyphenyl)pyridazin-3(2H)-one;
5-{4-[(diethylamino)methyl]phenyl}-2-methyl-6-(2-phenoxyphenyl)pyridazin-3(2H)-one;
2-methyl-6-(2-phenoxyphenyl)-5-[4-(piperazin-1-ylmethyl)phenyl]pyridazin-3(2H)-one;
2-methyl-6-(2-phenoxyphenyl)-5-[4-(pyrrolidin-1-ylmethyl)phenyl]pyridazin-3(2H)-one;
5-[4-(1-hydroxypropyl)phenyl]-2-methyl-6-(2-phenoxyphenyl)pyridazin-3(2H)-one;
5-[4-(1-hydroxy-2-methylpropyl)phenyl]-2-methyl-6-(2-phenoxyphenyl)pyridazin-3(2H)-one;
5-{4-[cyclopentyl(hydroxy)methyl]phenyl}-2-methyl-6-(2-phenoxyphenyl)pyridazin-3(2H)-one;
5-[4-(1-hydroxyethyl)phenyl]-2-methyl-6-(2-phenoxyphenyl)pyridazin-3(2H)-one;
5-{4-[hydroxy(phenyl)methyl]phenyl}-2-methyl-6-(2-phenoxyphenyl)pyridazin-3(2H)-one;
5-[4-(1-hydroxybut-3-en-1-yl)phenyl]-2-methyl-6-(2-phenoxyphenyl)pyridazin-3(2H)-one;
5-[4-(hydroxymethyl)phenyl]-2-methyl-6-(2-phenoxyphenyl)pyridazin-3(2H)-one;
5-[4-(methoxymethyl)phenyl]-2-methyl-6-(2-phenoxyphenyl)pyridazin-3(2H)-one;
4-[1-methyl-6-oxo-3-(2-phenoxyphenyl)-1,6-dihydropyridazin-4-yl]benzyl acetate;
tert-butyl 4-[1-methyl-6-oxo-3-(2-phenoxyphenyl)-1,6-dihydropyridazin-4-yl]-3,6-dihydropyridine-1(2H)-carboxylate;
2-methyl-6-(2-phenoxyphenyl)-5-(1,2,3,6-tetrahydropyridin-4-yl)pyridazin-3(2H)-one;
2-methyl-5-(1-methyl-1,2,3,6-tetrahydropyridin-4-yl)-6-(2-phenoxyphenyl)pyridazin-3(2H)-one;
5-(1-acetyl-1,2,3,6-tetrahydropyridin-4-yl)-2-methyl-6-(2-phenoxyphenyl)pyridazin-3(2H)-one;
2-methyl-5-[1-(methylsulfonyl)-1,2,3,6-tetrahydropyridin-4-yl]-6-(2-phenoxyphenyl)pyridazin-3(2H)-one;
tert-butyl 4-[1-methyl-6-oxo-3-(2-phenoxyphenyl)-1,6-dihydropyridazin-4-yl]piperidine-1-carboxylate;
2-methyl-6-(2-phenoxyphenyl)-5-(piperidin-4-yl)pyridazin-3(2H)-one;
2-methyl-5-(1-methylpiperidin-4-yl)-6-(2-phenoxyphenyl)pyridazin-3(2H)-one;
5-(1-acetylpiperidin-4-yl)-2-methyl-6-(2-phenoxyphenyl)pyridazin-3(2H)-one;
2-methyl-5-[1-(methylsulfonyl)piperidin-4-yl]-6-(2-phenoxyphenyl)pyridazin-3(2H)-one;
2-methyl-5-[4-(5-methyl-1,3,4-oxadiazol-2-yl)phenyl]-6-(2-phenoxyphenyl)pyridazin-3(2H)-one;
methyl 3-{4-[1-methyl-6-oxo-3-(2-phenoxyphenyl)-1,6-dihydropyridazin-4-yl]phenyl}propanoate;
5-(4-benzylphenyl)-2-methyl-6-(2-phenoxyphenyl)pyridazin-3(2H)-one;
{4-[1-methyl-6-oxo-3-(2-phenoxyphenyl)-1,6-dihydropyridazin-4-yl]phenyl}acetonitrile;
5-[4-(5,6-dihydro-4H-1,3-oxazin-2-yl)phenyl]-2-methyl-6-(2-phenoxyphenyl)pyridazin-3(2H)-one;
2-methyl-5-[4-(2-methylpropyl)phenyl]-6-(2-phenoxyphenyl)pyridazin-3(2H)-one;
Ethyl {4-[1-methyl-6-oxo-3-(2-phenoxyphenyl)-1,6-dihydropyridazin-4-yl]phenyl}acetate;
N-{4-[1-methyl-6-oxo-3-(2-phenoxyphenyl)-1,6-dihydropyridazin-4-yl]benzyl}methanesulfonamide;
N-{4-[1-methyl-6-oxo-3-(2-phenoxyphenyl)-1,6-dihydropyridazin-4-yl]benzyl}acetamide;
N-(2-{4-[1-methyl-6-oxo-3-(2-phenoxyphenyl)-1,6-dihydropyridazin-4-yl]phenyl}ethyl)acetamide;
5-[4-(3-hydroxypropyl)phenyl]-2-methyl-6-(2-phenoxyphenyl)pyridazin-3(2H)-one;
methyl 4-[1-methyl-6-oxo-3-(2-phenoxyphenyl)-1,6-dihydropyridazin-4-yl]benzoate;
2-methyl-5-(1-methyl-1H-pyrazol-4-yl)-6-(2-phenoxyphenyl)pyridazin-3(2H)-one;
2-methyl-6-(2-phenoxyphenyl)-5-(pyridin-4-yl)pyridazin-3(2H)-one;
N-{4-[1-methyl-6-oxo-3-(2-phenoxyphenyl)-1,6-dihydropyridazin-4-yl]phenyl}acetamide;
N-{3-[1-methyl-6-oxo-3-(2-phenoxyphenyl)-1,6-dihydropyridazin-4-yl]phenyl}acetamide;
5-(4-ethoxy-3-fluorophenyl)-2-methyl-6-(2-phenoxyphenyl)pyridazin-3(2H)-one;
N,N-dimethyl-4-[1-methyl-6-oxo-3-(2-phenoxyphenyl)-1,6-dihydropyridazin-4-yl]benzamide;
N,N-dimethyl-3-[1-methyl-6-oxo-3-(2-phenoxyphenyl)-1,6-dihydropyridazin-4-yl]benzamide;
2-methyl-5-[3-(2-methylpropoxy)phenyl]-6-(2-phenoxyphenyl)pyridazin-3(2H)-one;

5-[3-fluoro-4-(propan-2-yloxy)phenyl]-2-methyl-6-(2-phenoxyphenyl)pyridazin-3(2H)-one;

4-[1-methyl-6-oxo-3-(2-phenoxyphenyl)-1,6-dihydropyridazin-4-yl]benzenesulfonamide;

5-(1-benzyl-1H-pyrazol-4-yl)-2-methyl-6-(2-phenoxyphenyl)pyridazin-3(2H)-one;

N-cyclopropyl-4-[1-methyl-6-oxo-3-(2-phenoxyphenyl)-1,6-dihydropyridazin-4-yl]benzamide;

5-(3,5-dimethyl-1H-pyrazol-4-yl)-2-methyl-6-(2-phenoxyphenyl)pyridazin-3(2H)-one;

5-(6-methoxypyridin-3-yl)-2-methyl-6-(2-phenoxyphenyl)pyridazin-3(2H)-one;

5-(4-ethoxyphenyl)-2-methyl-6-(2-phenoxyphenyl)pyridazin-3(2H)-one;

5-(isoquinolin-4-yl)-2-methyl-6-(2-phenoxyphenyl)pyridazin-3(2H)-one;

N-{4-[1-methyl-6-oxo-3-(2-phenoxyphenyl)-1,6-dihydropyridazin-4-yl]phenyl}methanesulfonamide;

N-{3-[1-methyl-6-oxo-3-(2-phenoxyphenyl)-1,6-dihydropyridazin-4-yl]phenyl}methanesulfonamide;

N-{5-[1-methyl-6-oxo-3-(2-phenoxyphenyl)-1,6-dihydropyridazin-4-yl]pyridin-3-yl}acetamide;

N-methyl-5-[1-methyl-6-oxo-3-(2-phenoxyphenyl)-1,6-dihydropyridazin-4-yl]pyridine-3-carboxamide;

2-methyl-6-(2-phenoxyphenyl)-5-[6-(propan-2-yloxy)pyridin-3-yl]pyridazin-3(2H)-one;

5-(3-acetyl-2-fluorophenyl)-2-methyl-6-(2-phenoxyphenyl)pyridazin-3(2H)-one;

5-(2,6-dimethoxypyridin-3-yl)-2-methyl-6-(2-phenoxyphenyl)pyridazin-3(2H)-one;

methyl 2-[1-methyl-6-oxo-3-(2-phenoxyphenyl)-1,6-dihydropyridazin-4-yl]benzoate;

N-methyl-4-[1-methyl-6-oxo-3-(2-phenoxyphenyl)-1,6-dihydropyridazin-4-yl]benzamide;

N-methyl-3-[1-methyl-6-oxo-3-(2-phenoxyphenyl)-1,6-dihydropyridazin-4-yl]benzamide;

2-methyl-5-[1-(3-methylbutyl)-1H-pyrazol-4-yl]-6-(2-phenoxyphenyl)pyridazin-3(2H)-one;

2-methyl-6-(2-phenoxyphenyl)-5-[2-(propan-2-yloxy)pyridin-3-yl]pyridazin-3(2H)-one;

5-(1,3-benzothiazol-5-yl)-2-methyl-6-(2-phenoxyphenyl)pyridazin-3(2H)-one;

5-(5-acetyl-2-fluorophenyl)-2-methyl-6-(2-phenoxyphenyl)pyridazin-3(2H)-one;

5-(2,3-dihydro-1,4-benzodioxin-6-yl)-2-methyl-6-(2-phenoxyphenyl)pyridazin-3(2H)-one;

5-[3-(1-methoxyethyl)phenyl]-2-methyl-6-(2-phenoxyphenyl)pyridazin-3(2H)-one;

5-[4-(1-methoxyethyl)phenyl]-2-methyl-6-(2-phenoxyphenyl)pyridazin-3(2H)-one;

5-(3-ethoxy-2-fluorophenyl)-2-methyl-6-(2-phenoxyphenyl)pyridazin-3(2H)-one;

5-(2,1,3-benzothiadiazol-5-yl)-2-methyl-6-(2-phenoxyphenyl)pyridazin-3(2H)-one;

5-[5-(benzylamino)pyridin-3-yl]-2-methyl-6-(2-phenoxyphenyl)pyridazin-3(2H)-one;

2-methyl-5-[3-(morpholin-4-yl)phenyl]-6-(2-phenoxyphenyl)pyridazin-3(2H)-one;

2-methyl-6-(2-phenoxyphenyl)-5-[6-(2,2,2-trifluoroethoxy)pyridin-3-yl]pyridazin-3(2H)-one;

2-methyl-5-[3-(morpholin-4-ylmethyl)phenyl]-6-(2-phenoxyphenyl)pyridazin-3(2H)-one;

2-methyl-6-(2-phenoxyphenyl)-5-[3-(thiomorpholin-4-ylcarbonyl)phenyl]pyridazin-3(2H)-one;

5-[5-(cyclopentylamino)pyridin-3-yl]-2-methyl-6-(2-phenoxyphenyl)pyridazin-3(2H)-one;

N-cyclopropyl-5-[1-methyl-6-oxo-3-(2-phenoxyphenyl)-1,6-dihydropyridazin-4-yl]pyridine-3-carboxamide;

N-cyclopentyl-5-[1-methyl-6-oxo-3-(2-phenoxyphenyl)-1,6-dihydropyridazin-4-yl]pyridine-3-carboxamide;

N,N-diethyl-3-[1-methyl-6-oxo-3-(2-phenoxyphenyl)-1,6-dihydropyridazin-4-yl]benzenesulfonamide;

2-methyl-5-[4-(morpholin-4-ylcarbonyl)phenyl]-6-(2-phenoxyphenyl)pyridazin-3(2H)-one;

N-cyclohexyl-N-methyl-3-[1-methyl-6-oxo-3-(2-phenoxyphenyl)-1,6-dihydropyridazin-4-yl]benzamide;

2-methyl-5-[4-(morpholin-4-yl)phenyl]-6-(2-phenoxyphenyl)pyridazin-3(2H)-one;

N-[3-(dimethylamino)propyl]-4-[1-methyl-6-oxo-3-(2-phenoxyphenyl)-1,6-dihydropyridazin-4-yl]benzamide;

2-methyl-6-(2-phenoxyphenyl)-5-[6-(piperazin-1-yl)pyridin-3-yl]pyridazin-3(2H)-one;

3-fluoro-N,N-dimethyl-5-[1-methyl-6-oxo-3-(2-phenoxyphenyl)-1,6-dihydropyridazin-4-yl]benzamide;

2-methyl-5-[2-(morpholin-4-yl)pyridin-4-yl]-6-(2-phenoxyphenyl)pyridazin-3(2H)-one;

2-methyl-5-{3-[(4-methylpiperidin-1-yl)carbonyl]phenyl}-6-(2-phenoxyphenyl)pyridazin-3(2H)-one;

2-fluoro-N,N-dimethyl-5-[1-methyl-6-oxo-3-(2-phenoxyphenyl)-1,6-dihydropyridazin-4-yl]benzamide;

2-methyl-6-(2-phenoxyphenyl)-5-[3-(pyrrolidin-1-ylsulfonyl)phenyl]pyridazin-3(2H)-one;

2-methyl-6-(2-phenoxyphenyl)-5-[3-(piperidin-1-ylcarbonyl)phenyl]pyridazin-3(2H)-one;

N,N-diethyl-4-[1-methyl-6-oxo-3-(2-phenoxyphenyl)-1,6-dihydropyridazin-4-yl]benzamide;

N-methyl-4-[1-methyl-6-oxo-3-(2-phenoxyphenyl)-1,6-dihydropyridazin-4-yl]benzenesulfonamide;

N,N-diethyl-3-[1-methyl-6-oxo-3-(2-phenoxyphenyl)-1,6-dihydropyridazin-4-yl]benzamide;

2-methyl-5-[4-(4-methylpiperazin-1-yl)phenyl]-6-(2-phenoxyphenyl)pyridazin-3(2H)-one;

2-methyl-5-(6-{[2-(morpholin-4-yl)ethyl]amino}pyridin-3-yl)-6-(2-phenoxyphenyl)pyridazin-3(2H)-one;

N-[3-(dimethylamino)propyl]-3-[1-methyl-6-oxo-3-(2-phenoxyphenyl)-1,6-dihydropyridazin-4-yl]benzamide;

5-[6-(benzylamino)pyridin-3-yl]-2-methyl-6-(2-phenoxyphenyl)pyridazin-3(2H)-one;

N-(2-cyanoethyl)-4-[1-methyl-6-oxo-3-(2-phenoxyphenyl)-1,6-dihydropyridazin-4-yl]benzamide;

2-methyl-5-[5-methyl-6-(morpholin-4-yl)pyridin-3-yl]-6-(2-phenoxyphenyl)pyridazin-3(2H)-one;

N,N-diethyl-3-fluoro-5-[1-methyl-6-oxo-3-(2-phenoxyphenyl)-1,6-dihydropyridazin-4-yl]benzamide;

N-tert-butyl-4-[1-methyl-6-oxo-3-(2-phenoxyphenyl)-1,6-dihydropyridazin-4-yl]benzamide;

N-cyclopentyl-4-[1-methyl-6-oxo-3-(2-phenoxyphenyl)-1,6-dihydropyridazin-4-yl]benzamide;

4-[1-methyl-6-oxo-3-(2-phenoxyphenyl)-1,6-dihydropyridazin-4-yl]-N-(2-methylpropyl)benzamide;

N-(3-methoxypropyl)-4-[1-methyl-6-oxo-3-(2-phenoxyphenyl)-1,6-dihydropyridazin-4-yl]benzamide;

2-methyl-5-{1-[2-(morpholin-4-yl)ethyl]-1H-pyrazol-4-yl}-6-(2-phenoxyphenyl)pyridazin-3(2H)-one;

N-(2-methoxyethyl)-4-[1-methyl-6-oxo-3-(2-phenoxyphenyl)-1,6-dihydropyridazin-4-yl]benzamide;

2-methyl-5-[2-(4-methylpiperazin-1-yl)pyridin-4-yl]-6-(2-phenoxyphenyl)pyridazin-3(2H)-one;

2-methyl-5-[3-(morpholin-4-ylcarbonyl)phenyl]-6-(2-phenoxyphenyl)pyridazin-3(2H)-one;

2-methyl-5-[3-(5-methyl-1,3,4-oxadiazol-2-yl)phenyl]-6-(2-phenoxyphenyl)pyridazin-3(2H)-one;

N-cyclopropyl-3-[1-methyl-6-oxo-3-(2-phenoxyphenyl)-1,6-dihydropyridazin-4-yl]benzamide;
2-methyl-6-(2-phenoxyphenyl)-5-[4-(pyrrolidin-1-ylsulfonyl)phenyl]pyridazin-3(2H)-one;
2-methyl-5-[6-(morpholin-4-yl)pyridin-3-yl]-6-(2-phenoxyphenyl)pyridazin-3(2H)-one;
2-methyl-6-(2-phenoxyphenyl)-5-{4-[4-(propan-2-yl)piperazin-1-yl]phenyl}pyridazin-3(2H)-one;
N,N-diethyl-2-fluoro-5-[1-methyl-6-oxo-3-(2-phenoxyphenyl)-1,6-dihydropyridazin-4-yl]benzamide;
N-benzyl-4-[1-methyl-6-oxo-3-(2-phenoxyphenyl)-1,6-dihydropyridazin-4-yl]benzamide;
2-methyl-6-(2-phenoxyphenyl)-5-[4-(pyrrolidin-1-ylcarbonyl)phenyl]pyridazin-3(2H)-one;
2-methyl-6-(2-phenoxyphenyl)-5-[6-(piperidin-1-yl)pyridin-3-yl]pyridazin-3(2H)-one;
N-cyclohexyl-4-[1-methyl-6-oxo-3-(2-phenoxyphenyl)-1,6-dihydropyridazin-4-yl]benzamide;
N-[2-(dimethylamino)ethyl]-3-[1-methyl-6-oxo-3-(2-phenoxyphenyl)-1,6-dihydropyridazin-4-yl]benzamide;
2-methyl-6-(2-phenoxyphenyl)-5-{4-[(phenylamino)methyl]phenyl}pyridazin-3(2H)-one;
2-methyl-5-[2-(4-methylpiperazin-1-yl)pyrimidin-5-yl]-6-(2-phenoxyphenyl)pyridazin-3(2H)-one;
methyl{4-[1-methyl-6-oxo-3-(2-phenoxyphenyl)-1,6-dihydropyridazin-4-yl]phenyl}acetate;
5-(5-ethoxypyridin-3-yl)-2-methyl-6-(2-phenoxyphenyl)pyridazin-3(2H)-one;
2-methyl-5-[4-(methylamino)phenyl]-6-(2-phenoxyphenyl)pyridazin-3(2H)-one;
5-[2-(dimethylamino)pyrimidin-5-yl]-2-methyl-6-(2-phenoxyphenyl)pyridazin-3(2H)-one;
{3-[1-methyl-6-oxo-3-(2-phenoxyphenyl)-1,6-dihydropyridazin-4-yl]phenyl}acetonitrile;
2-methyl-5-(1-methyl-1H-pyrrol-2-yl)-6-(2-phenoxyphenyl)pyridazin-3(2H)-one;
2-methyl-6-(2-phenoxyphenyl)-5-(pyridin-3-yl)pyridazin-3(2H)-one;
2-methyl-5-(6-methylpyridin-3-yl)-6-(2-phenoxyphenyl)pyridazin-3(2H)-one;
5-(3-methoxyphenyl)-2-methyl-6-(2-phenoxyphenyl)pyridazin-3(2H)-one;
2-methyl-5-(4-methyl-3,4-dihydro-2H-pyrido[3,2-b][1,4]oxazin-7-yl)-6-(2-phenoxyphenyl)pyridazin-3(2H)-one;
5-(4-fluoro-3-methoxyphenyl)-2-methyl-6-(2-phenoxyphenyl)pyridazin-3(2H)-one;
5-(2-aminopyridin-4-yl)-2-methyl-6-(2-phenoxyphenyl)pyridazin-3(2H)-one;
5-(3-acetylphenyl)-2-methyl-6-(2-phenoxyphenyl)pyridazin-3(2H)-one;
N-ethyl-4-[1-methyl-6-oxo-3-(2-phenoxyphenyl)-1,6-dihydropyridazin-4-yl]benzamide;
5-(3-fluoro-4-methoxyphenyl)-2-methyl-6-(2-phenoxyphenyl)pyridazin-3(2H)-one;
5-(1,5-dimethyl-1H-pyrazol-4-yl)-2-methyl-6-(2-phenoxyphenyl)pyridazin-3(2H)-one;
2-methyl-5-(2-methylpyridin-4-yl)-6-(2-phenoxyphenyl)pyridazin-3(2H)-one;
2-methyl-5-[1-(2-methylpropyl)-1H-pyrazol-4-yl]-6-(2-phenoxyphenyl)pyridazin-3(2H)-one;
2-methyl-5-(4-methylpyridin-3-yl)-6-(2-phenoxyphenyl)pyridazin-3(2H)-one;
2-methyl-5-(1-methyl-1H-indol-5-yl)-6-(2-phenoxyphenyl)pyridazin-3(2H)-one;
5-[3-(dimethylamino)phenyl]-2-methyl-6-(2-phenoxyphenyl)pyridazin-3(2H)-one;
5-(2-fluoro-5-methoxyphenyl)-2-methyl-6-(2-phenoxyphenyl)pyridazin-3(2H)-one;
2-methyl-5-(5-methylfuran-2-yl)-6-(2-phenoxyphenyl)pyridazin-3(2H)-one;
5-(1-ethyl-1H-pyrazol-4-yl)-2-methyl-6-(2-phenoxyphenyl)pyridazin-3(2H)-one;
5-(3-methoxypyridin-4-yl)-2-methyl-6-(2-phenoxyphenyl)pyridazin-3(2H)-one;
2-methyl-5-(1-methyl-1H-indol-2-yl)-6-(2-phenoxyphenyl)pyridazin-3(2H)-one;
N,N-dimethyl-5-[1-methyl-6-oxo-3-(2-phenoxyphenyl)-1,6-dihydropyridazin-4-yl]pyridine-3-carboxamide;
5-[5-(dimethylamino)pyridin-3-yl]-2-methyl-6-(2-phenoxyphenyl)pyridazin-3(2H)-one;
5-butyl-2-methyl-6-(2-phenoxyphenyl)pyridazin-3(2H)-one;
methyl 1-methyl-6-oxo-3-(2-phenoxyphenyl)-1,6-dihydropyridazine-4-carboxylate;
methyl (2E)-3-[1-methyl-6-oxo-3-(2-phenoxyphenyl)-1,6-dihydropyridazin-4-yl]prop-2-enoate;
methyl 3-[1-methyl-6-oxo-3-(2-phenoxyphenyl)-1,6-dihydropyridazin-4-yl]propanoate;
5-acetyl-2-methyl-6-(2-phenoxyphenyl)pyridazin-3(2H)-one;
6-(2-benzylphenyl)-2-methylpyridazin-3(2H)-one;
N-[4-(2,4-difluorophenoxy)-3-(4-ethoxy-1-methyl-6-oxo-1,6-dihydropyridin-3-yl)phenyl]ethanesulfonamide;
N-[4-(2,4-difluorophenoxy)-3-{1-methyl-4-[2-(morpholin-4-yl)ethoxy]-6-oxo-1,6-dihydropyridin-3-yl}phenyl]ethanesulfonamide;
N-(3-(4-(cyclopropylmethoxy)-1-methyl-6-oxo-1,6-dihydropyridin-3-yl)-4-(2,4-difluorophenoxy)phenyl)ethanesulfonamide;
N-(4-(2,4-difluorophenoxy)-3-(4-(2-(dimethylamino)ethoxy)-1-methyl-6-oxo-1,6-dihydropyridin-3-yl)phenyl)ethanesulfonamide;
N-{4-(2,4-difluorophenoxy)-3-[1-methyl-6-oxo-4-(propan-2-yloxy)-1,6-dihydropyridin-3-yl]phenyl}ethanesulfonamide;
N-{4-(2,4-difluorophenoxy)-3-[1-methyl-4-(2-methylpropoxy)-6-oxo-1,6-dihydropyridin-3-yl]phenyl}ethanesulfonamide;
N-{4-(2,4-difluorophenoxy)-3-[1-methyl-6-oxo-4-(tetrahydrofuran-3-ylmethoxy)-1,6-dihydropyridin-3-yl]phenyl}ethanesulfonamide;
N-[4-(2,4-difluorophenoxy)-3-(1-methyl-6-oxo-4-propoxy-1,6-dihydropyridin-3-yl)phenyl]ethanesulfonamide; and
N-{4-(2,4-difluorophenoxy)-3-[1-methyl-6-oxo-4-(2,2,2-trifluoroethoxy)-1,6-dihydropyridin-3-yl]phenyl}ethanesulfonamide.

In certain embodiments, a compound of formula I is selected from the group consisting of:
3-methyl-5-(2-phenoxyphenyl)pyridin-2(1H)-one;
N-[3-(5-methyl-6-oxo-1,6-dihydropyridin-3-yl)-4-phenoxyphenyl]methanesulfonamide;
N-[3-(5-methyl-6-oxo-1,6-dihydropyridin-3-yl)-4-phenoxyphenyl]acetamide;
N-[4-(2,4-difluorophenoxy)-3-(5-methyl-6-oxo-1,6-dihydropyridin-3-yl)phenyl]methanesulfonamide;
N-[4-(2,4-difluorophenoxy)-3-(5-methyl-6-oxo-1,6-dihydropyridin-3-yl)phenyl]ethanesulfonamide;
N-[4-(2,4-difluorophenoxy)-3-(5-methyl-6-oxo-1,6-dihydropyridin-3-yl)phenyl]acetamide;
N-{4-[(4,4-difluorocyclohexyl)oxy]-3-(5-methyl-6-oxo-1,6-dihydropyridin-3-yl)phenyl}methanesulfonamide; and
N-{4-[(4,4-difluorocyclohexyl)oxy]-3-(5-methyl-6-oxo-1,6-dihydropyridin-3-yl)phenyl}ethanesulfonamide.

In another aspect, the present invention relates to pharmaceutical compositions comprising a pharmaceutically acceptable excipient and a therapeutically effective amount of a compound of formula I, or a pharmaceutically acceptable salt thereof.

In another aspect, the present invention relates to methods of treating cancer in a subject comprising administering a therapeutically effective amount of a compound of formula (I) or a pharmaceutically acceptable salt thereof, to a subject in need thereof. In certain embodiments, the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor. In certain embodiments, the methods further comprise administering a therapeutically effective amount of at least one additional therapeutic agent.

In another aspect, the present invention relates to methods of treating a disease or condition in a subject comprising administering a therapeutically effective amount of a compound of formula (I) or a pharmaceutically acceptable salt thereof, to a subject in need thereof, wherein said disease or condition is selected from the group consisting of: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis systemic lupus erythematosus, Takayasu's Arteritis, toxic shock, thyroiditis, type I diabetes, ulcerative colitis, uveitis, vitiligo, vasculitis, and Wegener's granulomatosis. In certain embodiments, the methods further comprise administering a therapeutically effective amount of at least one additional therapeutic agent. In certain embodiments, the methods further comprise administering a therapeutically effective amount of at least one additional therapeutic agent.

In another aspect, the present invention relates to methods of treating a chronic kidney disease or condition in a subject comprising administering a therapeutically effective amount of a compound of formula (I) or a pharmaceutically acceptable salt thereof, to a subject in need thereof, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis. In certain embodiments, the methods further comprise administering a therapeutically effective amount of at least one additional therapeutic agent. In certain embodiments, the methods further comprise administering a therapeutically effective amount of at least one additional therapeutic agent.

In another aspect, the present invention relates to methods of treating an acute kidney injury or disease or condition in a subject comprising administering a therapeutically effective amount of a compound of formula (I) or a pharmaceutically acceptable salt thereof, to a subject in need thereof, wherein said acute kidney injury or disease or condition is selected from the group consisting of: ischemia-reperfusion induced, cardiac and major surgery induced, percutaneous coronary intervention induced, radio-contrast agent induced, sepsis induced, pneumonia induced, and drug toxicity induced. In certain embodiments, the methods further comprise administering a therapeutically effective amount of at least one additional therapeutic agent. In certain embodiments, the methods further comprise administering a therapeutically effective amount of at least one additional therapeutic agent.

In another aspect, the present invention relates to methods of treating AIDS in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention relates to methods of treating obesity in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention relates to methods of treating type II diabetes in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention relates to methods of preventing conception by inhibiting spermatogenesis in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

A further aspect of the invention provides the use of a compound of formula (I), alone or in combination with a second active pharmaceutical agent, in the manufacture of a medicament for treating or preventing conditions and disorders disclosed herein, with or without a pharmaceutically acceptable carrier.

Pharmaceutical compositions comprising a compound of formula (I), or a pharmaceutically acceptable salt, alone or in combination with a second active pharmaceutical agent, are also provided.

DETAILED DESCRIPTION a). Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_4$ alkenyl" means an alkenyl group containing 2-4 carbon atoms. Non-limiting examples of alkenyl include buta-1,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon, for example, of 2 to 10 carbon atoms or of 2 to 6 carbon atoms ($C_2$-$C_6$ alkenylene) or of 2 to 4 carbon atoms ($C_2$-$C_4$ alkenylene), and contains at least one carbon-carbon double bond. Representative examples of alkenylene include, but are not limited to, —CH=CH— and —CH$_2$CH=CH—.

The term "alkyl" as used herein, means a saturated, straight or branched hydrocarbon chain radical. In some instances, the number of carbon atoms in an alkyl moiety is indicated by the prefix "$C_x$-$C_y$", wherein x is the minimum and y is the maximum number of carbon atoms in the substituent. Thus, for example, "$C_1$-$C_6$ alkyl" refers to an alkyl substituent containing from 1 to 6 carbon atoms and "$C_1$-$C_3$ alkyl" refers to an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylene) or of 1 to 4 carbon atoms or of 1 to 3 carbon atoms ($C_1$-$C_3$ alkylene). Examples of alkylene and alkylenyl include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "$C_2$-$C_4$ alkynyl" as used herein, means a straight or branched chain hydrocarbon radical containing from 2 to 4 carbon atoms and containing one carbon-carbon triple bond. Representative examples of $C_2$-$C_4$ alkynyl include, but are not limited, to acetylenyl, 1-propynyl, 2-propynyl, 3-butynyl, and 1-butynyl.

The term "$C_2$-$C_4$ alkynylene" means a divalent radical derived from a straight or branched chain hydrocarbon radical containing from 2 to 4 carbon atoms and containing one carbon-carbon triple bond.

The term "$C_3$-$C_{14}$ cycloalkyl" (alone or in combination with another term(s)) means a saturated cyclic hydrocarbyl substituent containing from 3 to 14 carbon ring atoms. The term cycloalkyl includes monocyclic cycloalkyl, bicyclic cycloalkyl, bridged cycloalkyl, and spiro cycloalkyl groups. Examples of monocyclic cycloalkyl groups include, but are not limited to, cyclopropyl (cyclopropanyl), cyclobutyl (cyclobutanyl), cyclopentyl (cyclopentanyl), cyclohexyl (cyclohexanyl), cycloheptyl, cyclooctyl, etc. Unless otherwise indicated, the term "$C_3$-$C_8$ monocyclic cycloalkyl" refers to monocylic cycloalkyl groups containing from 3 to 8 carbons. In certain embodiments, a "$C_3$-$C_{14}$ cycloalkyl" is a "$C_3$-$C_8$ monocyclic cycloalkyl" or a "$C_3$-$C_7$ monocyclic cycloalkyl."

In a spirocyclic cycloalkyl group, one atom is common to two different rings. Examples of spirocyclic cycloalkyls include spiro[2.2]pentanyl, spiro[2.4]heptanyl, and spiro [2.5]octanyl. Unless otherwise indicated, the term "$C_5$-$C_8$ spirocyclic cycloalkyl" refers to spirocyclic cycloalkyl groups containing from 5 to 8 carbons.

In a bridged cycloalkyl, the rings share at least two common non-adjacent atoms. Examples of bridged cycloalkyls include bicyclo[2.2.1]heptanyl, and adamantanyl. Unless otherwise indicated, the term "$C_7$-$C_{10}$ bridged cycloalkyl" refers to a bridged cycloalkyl groups containing from 5 to 10 carbons.

A bicyclic ring cycloalkyl is a $C_5$-$C_7$ monocyclic cycloalkyl fused to a monocyclic $C_5$-$C_7$ cycloalkyl ring. Non-limiting examples of bicyclic cycloalkyls include decahydronaphthalenyl, octahydro-1H-indenyl, octahydropentalenyl, and decahydroazulenyl. The bicyclic cycloalkyl groups may contain one or two alkylene bridges, each consisting of one, two, three, or four carbon atoms in length, and each bridge links two non-adjacent carbon atoms of the ring system. Non-limiting examples of bicyclic bridged groups include bicyclo[3.1.1]heptanyl, bicyclo[2.2.1]heptanyl, bicyclo[2.2.2]octanyl, bicyclo[3.2.2]nonanyl, bicyclo [3.3.1]nonanyl, and bicyclo[4.2.1]nonanyl, tricyclo[3.3.1.0$^{3,7}$]nonanyl(octahydro-2,5-methanopentalenyl or noradamantanyl), and tricyclo[3.3.1.1$^{3,7}$]decanyl(adamantanyl).

The term "cycloalkenyl" (alone or in combination with another term(s)) means a partially saturated cycloalkyl substituent containing from 3 to 14 carbon ring atoms. A cycloalkenyl may be a monocyclic carbon ring, which typically contains from 3 to 8 carbon ring atoms (i.e., a $C_3$-$C_8$ cycloalkenyl) and more typically from 4 to 6 carbon ring atoms (i.e., a $C_4$-$C_6$ cycloalkenyl). Examples of single-ring cycloalkenyls include cyclopentenyl, and cyclohexenyl. A cycloalkenyl may alternatively be bicyclic. Examples of bicyclic cycloalkenyls include bridged and spirocyclic cycloalkyls.

The term "heterocycloalkyl" as used herein, means a 3 to 15 membered non-aromatic monocylic or bicyclic ring radical containing carbon atoms and one to three heteroatoms independently selected from O, N, or S. The nitrogen and sulfur heteroatoms in the heterocycloalkyl rings may optionally be oxidized (e.g. 1,1-dioxidotetrahydrothienyl, 1,2-dioxido-1,2-thiazolidinyl, 1,1-dioxidothiomorpholinyl)) and the nitrogen atoms may optionally be quarternized. Unless otherwise indicated, the foregoing heterocycloalkyls can be C-attached or N-attached where such is possible and which results in the creation of a stable structure. For example, piperidinyl can be piperidin-1-yl (N-attached) or piperidin-4-yl (C-attached).

Examples of heterocycloalkyls include 3- to 8-membered monocyclic heterocycloalkyls, 8-12 membered bicyclic heterocycloalkyls, a spiro heterocycloalkyl, and 7-15 membered bridged bicyclic heterocycloalkyls.

The phrase "3- to 8-membered monocyclic heterocycloalkyl" means a non-aromatic cyclic group having carbon atoms and 1 to 3 heteroatoms independently selected from S, N or O, wherein when two O atoms or one O atom and one S atom are present, the two O atoms or one O atom and one S atom are not bonded to each other, respectively. Illustrative examples of 3- to 8-membered monocyclic heterocycloalkyl include aziridin-1-yl, 1-oxa-cyclobutan-2-yl, tetrahydrofuran-3-yl, morpholin-4-yl, 2-thiacyclohex-1-yl, 2-oxo-2-thiacyclohex-1-yl, 2,2-dioxo-2-thiacyclohex-1-yl, and 4-methyl-piperazin-2-yl.

A "3-membered monocyclic heterocycloalkyl" is a 3-membered, monocyclic cycloalkyl ring having 2 carbon atoms and 1 heteroatom selected from the group consisting of: 1 O; 1 S; and 1 N. Illustrative examples of 3-membered monocyclic heterocycloalkyls include oxiranyl, aziridinyl, and thiiranyl.

A "4-membered monocyclic heterocycloalkyl" is a 4-membered, monocyclic cycloalkyl ring having 3 carbon atoms and 1 heteroatom selected from the group consisting of: 1 O; 1 S; and 1 N. Illustrative examples of 4-membered monocyclic heterocycloalkyls include oxetanyl, azetidinyl, and thietanyl.

A "5-membered monocyclic heterocycloalkyl" is a 5-membered, monocyclic cycloalkyl ring having from 1 to 4 carbon atoms and from 1 to 3 heteroatoms selected from the group consisting of: 1 O; 1 S; 1 N; 2 N; 3 N; 1 S and 1 N; 1 S, and 2 N; 1 O and 1 N; and 1 O and 2 N. Illustrative examples of 5-membered monocyclic heterocycloalkyls include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl.

A "6-membered monocyclic heterocycloalkyl" is a 6-membered, monocyclic cycloalkyl ring having from 3 to 5 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Illustrative examples of 6-membered monocyclic heterocycloalkyls include 5,6-dihydro-4H-1,3-oxazinyl, tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, thiomorpholinyl, thioxanyl, and trithianyl.

A "7-membered monocyclic heterocycloalkyl" is a 7-membered, monocyclic cycloalkyl ring having from 5 or 6 carbon atoms and from 1 to 3 heteroatoms selected from the group consisting of: 1 O; 2 O; 1 S; 2 S; 1 N; 2 N; 1 S, 1 O, and 1 N; 1 S and 1 N; 1 S and 2 N; 1 S and 1 O; 1 S and 2 O; 1 O and 1 N; and 1 O and 2 N. Illustrative examples of 7-membered monocyclic heterocycloalkyls include azepanyl, 2,3,4,5-tetrahydro-1H-azepinyl, oxepanyl, 2,3,4,5-tetrahydro-1H-oxepinyl, thiepanyl, and 2,3,4,5-tetrahydro-1H-thiepinyl.

An "8-membered monocyclic heterocycloalkyl" is a 8-membered, monocyclic cycloalkyl ring having from 5 to 7 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Illustrative examples of 8-membered monocyclic heterocycloalkyls include azocanyl, thiocanyl, oxocanyl, 3,4,5,6-tetrahydro-2H-oxocinyl, etc.

A bicyclic 8-12 membered heterocycloalkyl is a monocyclic 5 to 7 membered heterocycloalkyl fused to a phenyl group, or a monocyclic 5 to 7 membered heterocycloalkyl fused to a monocyclic $C_5$-$C_7$ cycloalkyl, or a monocyclic 5 to 7 membered heterocycloalkyl fused to a monocyclic 5 to 7 membered heterocycloalkyl. Representative examples of bicyclic heterocycloalkyls include, but are not limited to, 2,3-dihydro-1,4-benzodioxin-6-yl, benzopyranyl, benzothiopyranyl, 2,3-dihydrobenzofuranyl, 2,3-dihydrobenzothienyl, 2,3-dihydro-1H-indolyl, 3,4-dihydroisoquinolin-2(1H)-yl, 2,3,4,6-tetrahydro-1H-pyrido[1,2-a]pyrazin-2-yl, hexahydropyrano[3,4-b][1,4]oxazin-1(5H)-yl.

The monocyclic heterocycloalkyl and the bicyclic heterocycloalkyl may contain one or two alkylene bridges or an alkenylene bridge, or mixture thereof, each consisting of no more than four carbon atoms and each linking two non adjacent atoms of the ring system. Examples of such bridged heterocycloalkyls include, but are not limited to, azabicyclo[2.2.1]heptyl (including 2-azabicyclo[2.2.1]hept-2-yl), 8-azabicyclo[3.2.1]oct-8-yl, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The term "6- to 9-membered bridged bicyclic heterocycloalkyl" refers to a ring radical which is either saturated or unsaturated, and which is the result of the fusion of 5-, 6-, or 7-membered monocyclic heterocycloalkyl to a 3-, 4-, or 5-membered monocyclic heterocycloalkyl; or a 5-, 6-, or 7-membered monocyclic heterocycloalkyl to a $C_5$-$C_7$-cycloalkyl, wherein the fusion junctions have 1 to 3 intervening ring atoms. The term "6- to 9-membered bridged bicyclic heterocycloalkyl" includes saturated and unsaturated "6- to 9-membered bridged bicyclic heterocycloalkyls." "6- to 9-membered bridged bicyclic heterocycloalkyls" may be substituted as set out above for alkyl. Examples of "6- to 9-membered bridged bicyclic heterocycloalkyls" include 3-azabicyclo[4.2.1]nonanyl and 7-azabicyclo[2.2.1]heptanyl.

A spiro heterocycloalkyl is a 7 to 15 membered heterocycloalkyl wherein two substituents on the same carbon atom of a monocyclic 5 to 7 membered heterocycloalkyl ring together with said carbon atom form a second ring system selected from a monocyclic cycloalkyl, a bicyclic cycloalkyl, a monocyclic heterocycloalkyl, or a bicyclic heterocycloalkyl. Examples of spiro heterocycloalkyls include, but not limited to, 2-azaspiro[3.3]hept-6-yl, 6-azaspiro[2.5]oct-6-yl, 1'H, 4H-spiro[1,3-benzodioxine-2, 4'-piperidin]-1'-yl, 1'H, 3H-spiro[2-benzofuran-1,4'-piperidin]-1'-yl, and 1,4-dioxa-8-azaspiro[4.5]dec-8-yl. The monocyclic, the bicyclic, and the spiro heterocycloalkyls can be unsubstituted or substituted. The monocyclic, the bicyclic and the spiro heterocycloalkyls are connected to the parent molecular moiety through any carbon atom or any nitrogen atom contained within the ring systems. The nitrogen and sulfur heteroatoms in the heterocycloalkyl rings may optionally be oxidized (e.g. 1,1-dioxidotetrahydrothienyl, 1,2-dioxido-1,2-thiazolidinyl, 1,1-dioxidothiomorpholinyl)) and the nitrogen atoms may optionally be quarternized.

An aryl group is an aromatic hydrocarbon radical. Furthermore, the term "aryl" includes multicyclic aryl groups, bicyclic, e.g., naphthyl. Typical aryl groups include phenyl, and naphthyl. The term "9- to 12-membered bicyclic aryl" is a ring structure formed by the fusion of a benzene ring to: (1) a $C_5$-$C_8$ monocyclic cycloalkyl (e.g., indanyl; 1,2,3,4-tetrahydro-naphthalenyl; 6,7,8,9-tetrahydro-5H-benzocycloheptenyl, etc.); or (2) another benzene ring (e.g., naphthalenyl); wherein the fusion junctions are at adjacent carbons on the benzene ring.

The term "heteroaryl" as used herein, means a monocyclic 5 or 6 membered heteroaryl and a bicyclic 8 to 12 membered heteroaryl.

A "5-membered heteroaryl" is a 5-membered, monocyclic, aromatic ring radical having from 1 to 4 carbon atoms and from 1 to 4 heteroatoms selected from the group consisting of: 1 O; 1 S; 1 N; 2 N; 3 N; 4 N; 1 S and 1 N; 1 S and 2 N; 1 O and 1 N; and 1 O and 2 N. Illustrative examples of 5-membered heteroaryls include, but are not limited to, furanyl, 2-furanyl, 3-furanyl, imidazolyl, isoxazolyl, isothiazolyl, oxadiazolyl, oxazolyl, pyrazolyl, pyrrolyl, 2- or 3-pyrrolyl, thienyl, 2-thienyl, 3-thienyl, tetrazolyl, thiazolyl, thiadiazolyl, and triazolyl.

A "6-membered heteroaryl" is a 6-membered, monocyclic, aromatic ring radical having from 3 to 5 carbon atoms and from 1 to 3 heteroatoms selected from the group consisting of: 1 N; 2 N; and 3 N. Illustrative examples of 6-membered heteroaryls include, but are not limited to, pyridinyl, 2-, 3-, or 4-pyridinyl, pyrimidinyl, 2-, 4-, or 5-pyrimidinyl, pyrazinyl, pyridazinyl, 3- or 4-pyridazinyl, 2-pyrazinyl, and triazinyl.

An "8- to 12-membered bicyclic heteroaryl" is a ring structure formed by the fusion of 5- or 6-membered heteroaryl to: (1) an independently selected 5-membered heteroaryl; (2) an independently selected 6-membered heteroaryl (e.g., naphthyridinyl, pteridinyl, phthalazinyl, purinyl, 3,4-dihydro-2H-pyrido[3,2-b][1,4]oxazin-7-yl, etc.); (3) a $C_5$-$C_8$ monocyclic cycloalkyl; (4) a 5- to 7-membered heterocycloalkyl; or (5) a benzene ring (e.g., benzimidazolyl, benzofuranyl, benzofurazanyl, 2H-1-benzopyranyl, benzothiadiazine, benzothiazinyl, 2,1,3-benzothiadiazol-5-yl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, and isoquinolinyl), wherein the fusion junctions are at adjacent ring atoms. The fusion junctions may be at nitrogen (e.g., indolizine) or carbon atoms in the 5- or 6-membered heteroaryl.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I). The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated). Examples of haloalkyl include $C_1$-$C_3$ haloalkyls, which is a halogenated alkyl containing from 1 to 3 carbons.

If a moiety is described as "substituted", a non-hydrogen radical is in the place of hydrogen radical of any substitutable atom of the moiety. Thus, for example, a substituted heteroaryl moiety is a heteroaryl moiety in which at least one non-hydrogen radical is in the place of a hydrogen radical on the heterocyclic ring. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another pharmaceutical agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, horses, dogs, cats, rabbits, rats, mice and the like. In preferred embodiments, the subject is a human.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl may also be designated as being of cis or trans configuration.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Compounds of formula (I) may contain one or more asymmetrically substituted atoms. Compounds of formula I may also exist as individual stereoisomers (including enantiomers and diastereomers) and mixtures thereof. Individual stereoisomers of compounds of formula I may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Compounds of formula I may also include the various geometric isomers and mixtures thereof resulting from the disposition of substituents around a carbon-carbon double bond, a carbon-nitrogen double bond, a cycloalkyl group, or a heterocycloalkyl group. Substituents around a carbon-carbon double bond or a carbon-nitrogen double bond are designated as being of Z or E configuration and substituents around a cycloalkyl or heterocycloalkyl are designated as being of cis or trans configuration.

Within the present invention it is to be understood that compounds disclosed herein may exhibit the phenomenon of tautomerism and all tautomeric isomers are included in the scope of the invention.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^{2}H$), tritium ($^{3}H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of BET bromodomain inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.,* 36(10):927-932 (1995); Kushner et al., *Can. J. Physiol. Pharmacol.,* 77, 79-88 (1999).

In addition, non-radio active isotope containing drugs, such as deuterated drugs called "heavy drugs," can be used for the treatment of diseases and conditions related to BET bromodomain activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

Schemes
General Synthesis

The compounds described herein, including compounds of general formula (I) and specific examples, can be prepared by methodologies in the reaction schemes depicted in schemes 1-8. The variables $A^1$, $A^2$, $A^3$, $A^4$, $R^{1a}$, $X^{1a}$, $X^{2a}$, $R^{1b}$, $X^{1b}$, $X^{2b}$, $Y^{1a}$, $Y^{1b}$, $X^3$, L, and G used in the following schemes have the meanings as set forth in the summary and detailed description sections, unless otherwise noted.

Abbreviations used in the descriptions of the schemes and the specific examples have the following meanings: Boc for tert-butoxycarbonyl; DME for 1,2-dimethoxyethane, DMF for dimethylformamide, DMSO for dimethyl sulfoxide, EtOH for ethanol; EtOAc for ethyl acetate; HATU for O-(7-azabenzotriazol-1-yl)-N,N,N',N'-tetramethyluronium hexafluorophosphate, HPLC for high performance liquid chromatography, MeOH for methanol; mCPBA for 3-chloroperbenzoic acid; $NH_4OAc$ for ammonium acetate; $Pd(PPh_3)_4$ for tetrakis(triphenylphosphine)palladium(0); $PdCl_2(PPh_3)_2$ for bis(triphenylphosphine)palladium(II)dichloride; $PdCl_2(dppf)$ for [1,1'-bis(diphenylphosphino)ferrocene]dichloropalladium(II); THF for tetrahydrofuran, TFA for trifluoroacetic acid, TLC for thin layer chromatography, and triflate for trifluoromethanesulfonate.

Compounds of general formula (I) wherein $X^3$ is L-G and J is IIa may be prepared using the general procedure as outlined in Scheme 1. Conversion of (1), wherein Z is Cl, Br, I, or triflate to compounds of general formula (3) may be achieved by reaction of (1) with a boronic acid of formula (2) or derivative thereof (e.g., pinacol ester) under Suzuki coupling conditions (N. Miyama and A. Suzuki, Chem. Rev. 1995, 95:2457-2483, J. Organomet. Chem. 1999, 576:147-148). For example, the coupling reaction may be conducted in the presence of a palladium catalyst and a base, and optionally in the presence of a ligand, and in a suitable solvent at elevated temperature (about 80° C. to about 150° C.). The reaction may be facilitated by microwave irradiation. Examples of the palladium catalyst include, but are not limited to, tetrakis(triphenylphosphine)palladium(0), tris (dibenzylideneacetone)dipalladium(0), bis(triphenylphosphine)palladium(II)dichloride, and palladium(II)acetate. Examples of suitable bases that may be employed include, but not limited to, carbonates or phosphates of sodium, potassium, and cesium, and cesium fluoride. Examples of suitable ligands include, but are not limited to, 1,3,5,7-tetramethyl-6-phenyl-2,4,8-trioxa-6-phosphaadamante, 2-dicyclohexylphosphino-2',4',6'-triisopropylbiphenyl (X-phos), and 1,1'-bis(diphenylphosphanyl)ferrocene. Non-limiting examples of suitable solvent include methanol, ethanol, dimethoxyethane, N,N-dimethylformamide, dimethylsulfoxide, dioxane, tetrahydropyran, and water, or a mixture thereof.

Alternatively, compounds of formula (3) may be synthesized by reaction of boronic acid (4) or a derivative thereof (e.g., pinacol ester) under Suzuki coupling conditions as described above with compounds of formula (5) wherein Z is Br, Cl, I, or triflate.

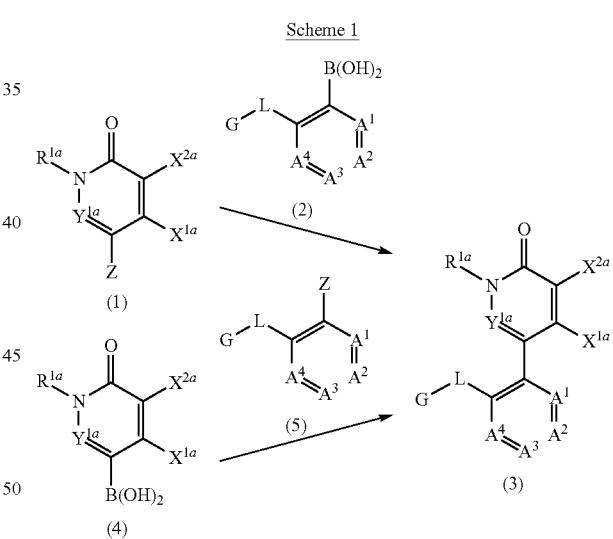

Scheme 1

Compounds of formula (1) wherein $R^{1a}$ is $C_1$-$C_3$ alkyl may be may be prepared using synthetic routes such as, but not limited to, those illustrated in Scheme 2. Reaction of compounds of formula (6), wherein Z is Br, Cl, I, with a $C_1$-$C_3$ alkyl halide, in the presence of a base such as carbonate of cesium, sodium, or potassium and in a solvent such as, but not limited to, dimethylformamide, tetrahydrofuran, or dimethylsulfoxide, provides intermediates of formula (1) wherein $R^{1a}$ is $C_1$-$C_3$ alkyl. The reaction may be conducted at temperature such as, but not limited to, about 25° C. to about 60° C.

Scheme 2

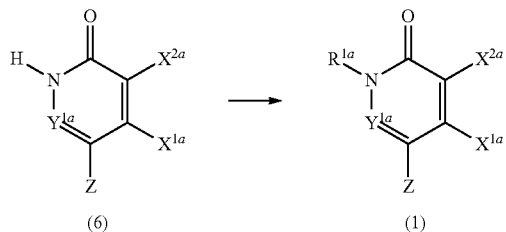

Compounds of formula (1) wherein $X^{1a}$ is —$C_2$-$C_4$ alkenylene-C(O)—O—$C_1$-$C_3$ alkyl, —O—$C_1$-$C_4$alkyl, an optionally substituted heterocycloalkyl or optionally substituted heterocycloalkenyl, wherein said heterocycloalkyl or heterocycloalkenyl is attached to the parent moiety through a nitrogen atom, or $X^{1a}$ is $NHR^{101}$ wherein $R^{101}$ is C(O)—$C_1$-$C_3$ alkyl, —$SO_2$—$C_1$-$C_3$ alkyl or —$C_1$-$C_3$ alkylene-C(O)—$C_1$-$C_3$ alkyl, may be prepared using general procedure as outlined in Scheme 3. Displacement of the chlorine atom of formula (7) with an alcohol of formula $R^{102}OH$ wherein $R^{102}$ is $C_1$-$C_4$alkyl provides compounds of formula (1a). Displacement of the chlorine atom may be accomplished in a solvent such as, but not limited to, methanol or ethanol, and in the presence of a base such as, but not limited to, sodium or sodium hydride, and at a temperature from about 40° C. to about 80° C. Displacement of the chlorine atom of formula (7) with an amine of formula $R^{101}R^{103}NH$ wherein $R^{101}$ is as defined above and $R^{103}$ is hydrogen, or $R^{101}$, $R^{103}$, and the nitrogen atom to which they are attached form a heterocycloalkyl or heterocycloalkenyl, provides compounds of formula (1b). Displacement of the chlorine atom by $R^{101}R^{103}NH$ may be accomplished in a solvent such as, but not limited to, methanol or ethanol, and in the presence of a base such as, but not limited to, triethylamine or diisopropylethylamine, and at a temperature from about 60° C. to about 100° C.

Utilizing reaction conditions such as those described in Scheme 1, intermediates (1a) and (1b) may be converted to target molecules (3a) and (3b) respectively by reacting with the appropriate boronic acids or derivatives thereof.

Alternatively, target molecules (3a) and (3b) may be synthesized from the reaction of (8) with $R^{102}OH$ and $R^{101}R^{103}NH$ using reaction conditions discussed above.

Scheme 3

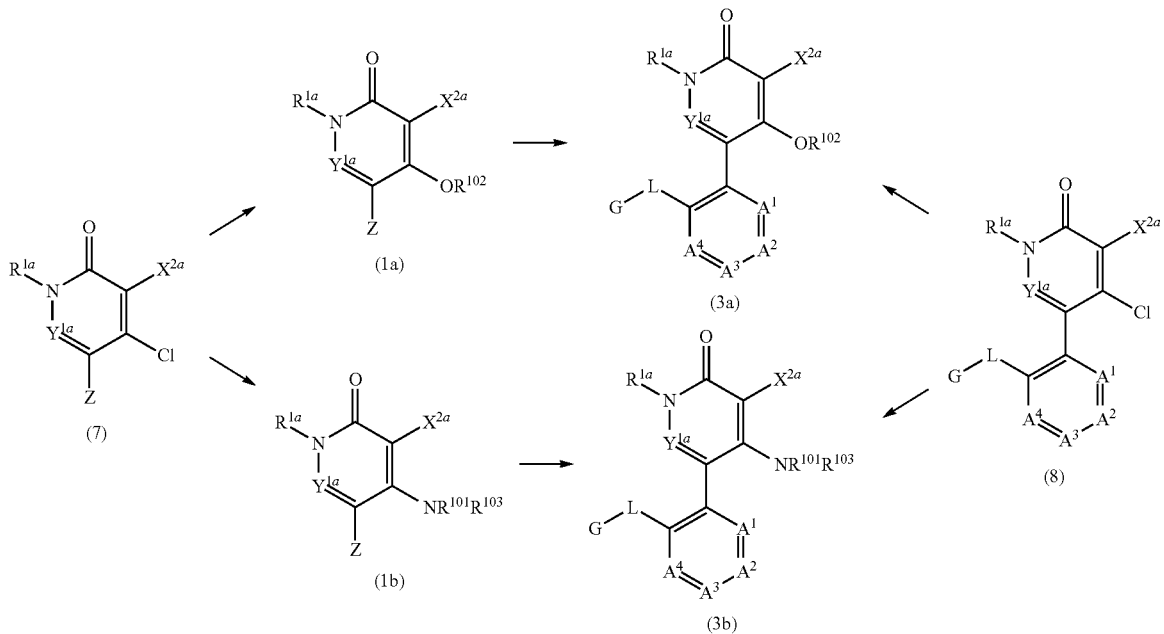

Compounds of formula (1) wherein $X^{1a}$ is aryl, heteroaryl, or heterocycloalkenyl may be prepared using reaction conditions described in Scheme 4. Reaction of 5,6-dichloropyridazin-3(2H)-ones (9) with boronic acids of formula (10) wherein $R^{104}$ is aryl, heteroaryl, or heterocycloalkenyl, or a derivative thereof (e.g., pinacol ester) under Suzuki coupling conditions as described in scheme 1 provides intermediates of formula (1c). Utilizing reaction conditions such as those described in Scheme 1, intermediates (1c) may be converted to target molecules (3c) by reacting with the appropriate boronic acids or derivatives thereof.

Alternatively, target molecules (3c) may be synthesized from the reaction of (8) with boronic acids of formula (10) wherein $R^{104}$ is aryl, heteroaryl, or heterocycloalkenyl, or a derivative thereof (e.g., pinacol ester) under Suzuki coupling conditions using reaction conditions discussed above.

Scheme 4

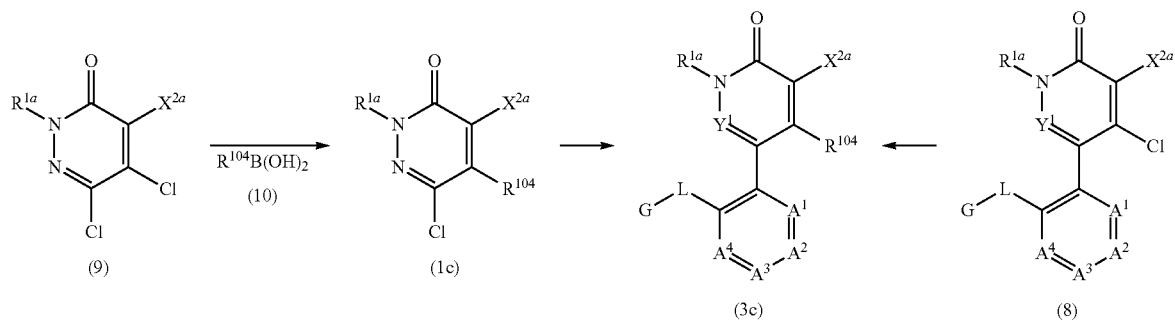

Compounds of formula (6) wherein $X^2$ is hydrogen may be prepared using general synthetic scheme as shown in Scheme 5. Hydrolysis of chloride (11) in an acid such as, but not limited to, acetic acid, and at a temperature from about 100° C. to about 150° C. provides compounds of formula (6a). Compounds of formula (6a) may also be prepared by reaction of compounds of formula (12) in the presence of sodium nitrite and an acid such as, but not limited to, sulfuric acid in a solvent such as water, and at a temperature from about 0° C. to about 25° C.

Scheme 5

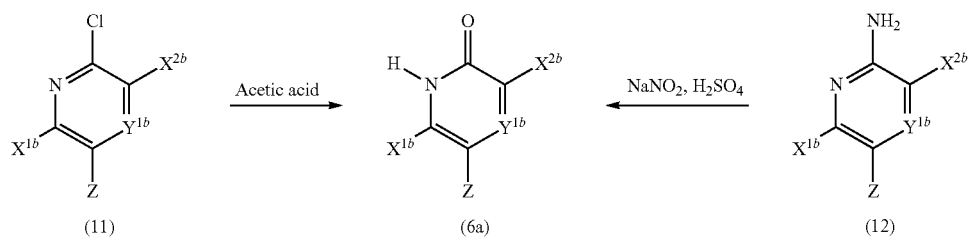

Compounds of general formula (I) wherein $X^3$ is L-G and J is IIb may be prepared using general procedure outlined in Scheme 6. Reaction of boronic acids (12), or a derivative thereof (e.g., pinacol ester) with compounds of formula (5) wherein Z is Br, Cl, I, or triflate under Suzuki coupling conditions as described in Scheme 1 provides compounds of formula (14). Hydrolysis of compounds of formula (14) in the presence of a base, such as, but not limited to, sodium hydroxide or potassium hydroxide, in a solvent such as water, dioxane, or tetrahydrofuran, or mixtures thereof, and at temperatures of 80° C. to about 140° C., provides compounds of formula (15). Hydrolysis of compounds of formula (14) may also be accomplished by reaction in an acid, such as but not limited to acetic acid, and water at temperatures of about 80° C. to about 120° C., to provide compounds of formula (15).

Scheme 6

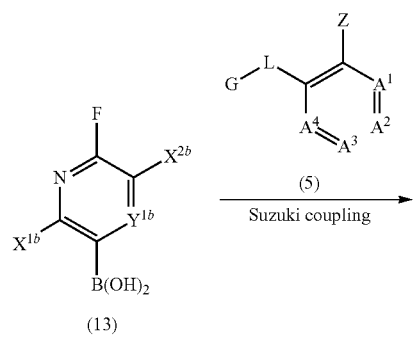

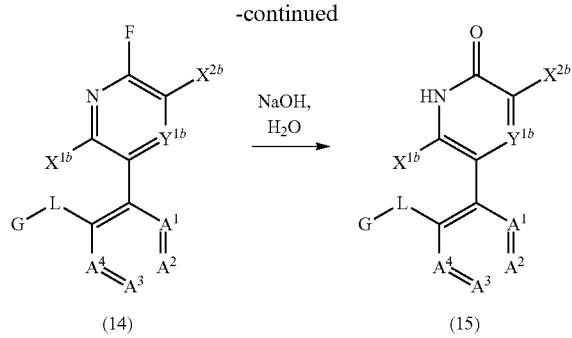

Compounds of general formula (I) wherein $X^3$ is L-G and L is —O— may be prepared as shown in Scheme 7.

Compounds of formula (17) may be prepared from reaction of (1) with a boronic acid of formula (16) or derivatives thereof (e.g. pinacol ester) using Suzuki coupling conditions as described in Scheme 1. Treatment of the resulting phenols of formula (17) with an appropriate halide of formula G-Z wherein Z is halogen such as Br, Cl, or F, in the presence of a base such as carbonate of cesium, potassium or sodium, in a solvent such as dimethylformamide or dimethylsulfoxide, and at temperatures ranging from about room temperature to about 100° C. provides compounds of formula (20). Alternatively, reaction of phenol (17) with an alcohol of formula G-OH in the presence of triphenylphosphine and in the presence of diisopropylazodicarboxylate or diethylazodicarboxylate, in a solvent such as tetrahydrofuran or dioxane, and at temperatures ranging from about room temperature to about 100° C. provides compounds of formula (20).

Alternatively, compounds of formula (20) may be obtained by (a) coupling of (1) wherein Z is triflate, Cl, Br, or I, with boronic acid (18) or derivative thereof using reaction conditions described in Scheme 1; and (b) displacement of the fluorine atom of the resulting intermediates (19) with an alcohol of formula G-OH. Displacement of the fluorine atom may be accomplished in a solvent such as, but not limited to, dimethylsulfoxide, dimethylformamide, dioxane, or tetrahydrofuran and in the presence of a base such as, but not limited to, carbonate of cesium, potassium, or sodium, or sodium hydride, and at a temperature from about 40° C. to about 120° C.

Scheme 7

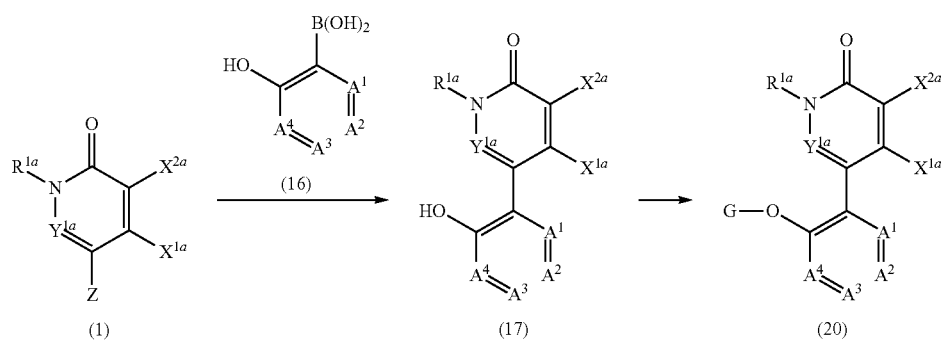

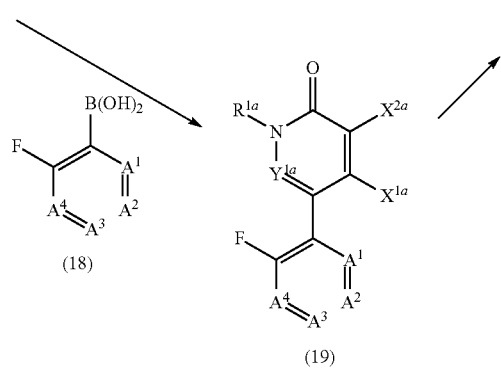

Compounds of general formula (I) wherein $A^2$ is $CR^{18}$ and $R^{18}$ is $NHC(O)R^{105}$ or $NHSO_2R^{106}$ wherein $R^{105}$ is $C_1$-$C_3$ alkyl, and $R^{106}$ is $C_1$-$C_3$ alkyl, $C_1$-$C_3$ haloalkyl, $C_3$-$C_7$ cycloalkyl, aryl, heteroaryl, $C_1$-$C_3$ alkylene-cycloalkyl, $C_1$-$C_3$ alkylene-heterocycloalkyl, $C_1$-$C_3$ alkylene-heteroaryl, or $C_1$-$C_3$ alkylene-aryl.

Reduction of the nitro compounds of formula (21) to the anilines of formula (22) may be achieved with iron powder in the presence of ammonium chloride in a solvent such as, but not limited to, tetrahydrofuran, ethanol, or water, or a mixture thereof, and at a temperature from about 80° C. to about 120° C. Alternatively the reduction may be carried out with tin chloride in hydrochloric acid at a temperature from about 80° C. to about 120° C. Transformation of (21) to (22) may also be conducted in the presence of a catalyst such as platinum oxide or palladium on charcoal, in a solvent such as ethanol or methanol and under hydrogen pressure. Treatment of aniline (22) with sulfonyl chlorides of formula $R^{106}SO_2Cl$, in the presence of a base such as triethylamine or diisopropylethylamine in a solvent such as dichloromethane or tetrahydrofuran and at a temperature from about 0° C. to about 40° C. provides sulfonamides (23).

Treatment of aniline (22) with carboxylic acids of formula $R^{105}COOH$ in the presence of a coupling agent such as HATU or EDAC and a base such as diisopropylethylaminde or triethylamine, and in a solvent such as tetrahydrofuran, dioxane, or dimethylformamide, at a temperature from about 0° C. to about 40° C. provides amides of formula (24).

Scheme 8

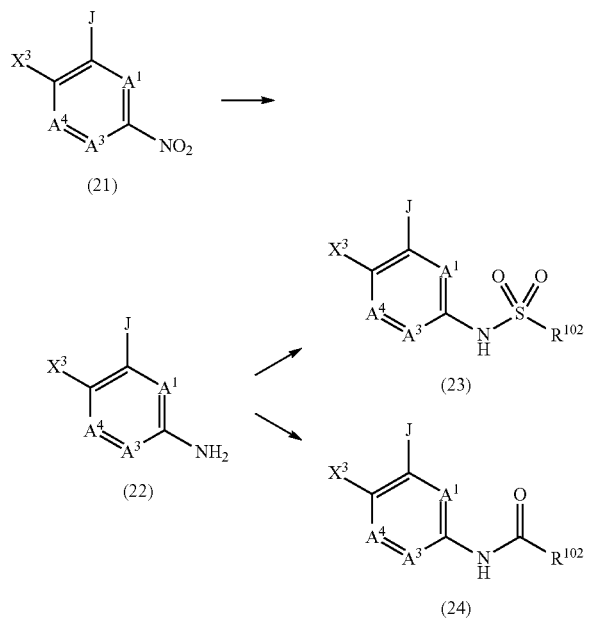

It can be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or typically can be prepared from commercially available materials.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it typically can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, precipitation, crystallization, or enzymatic resolution).

Similarly, when a pure geometric isomer of a compound is required, it typically can be prepared by carrying out one of the above procedures using a pure geometric isomer as a starting material, or by resolution of a mixture of the geometric isomers of the compound or intermediates using a standard procedure such as chromatographic separation.

Compounds of formula I can be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Pharmaceutical Compositions

This invention also provides for pharmaceutical compositions comprising a therapeutically effective amount of a compound of Formula I, or a pharmaceutically acceptable salt thereof together with a pharmaceutically acceptable carrier, diluent, or excipient therefor. The phrase "pharmaceutical composition" refers to a composition suitable for administration in medical or veterinary use.

The pharmaceutical compositions that comprise a compound of formula (I), alone or or in combination with a second active pharmaceutical agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula I. In certain embodiments, the compound of formula I may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 100 mg/kg for a typical subject.

For administration, compounds of the formula I can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of formula I may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of formula (I), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Methods of Use

The compounds of formula I, or pharmaceutically acceptable salts thereof, and pharmaceutical compositions comprising a compound of formula I, or a pharmaceutically acceptable salt thereof, can be administered to a subject suffering from a bromodomain-mediated disorder or condition. The term "administering" refers to the method of contacting a compound with a subject. Thus, the compounds of formula I can be administered by injection, that is, intravenously, intramuscularly, intracutaneously, subcutaneously, intraduodenally, parentally, or intraperitoneally. Also, the compounds described herein can be administered by inhalation, for example, intranasally. Additionally, the compounds of formula I can be administered transdermally, topically, via implantation, transdermally, topically, and via implantation. In certain embodiments, the compounds of the formula I may be delivered orally. The compounds can also be delivered rectally, bucally, intravaginally, ocularly, andially, or by insufflation. Bromodomain-mediated disorders and conditions can be treated prophylactically, acutely, and chronically using compounds of formula I, depending on the nature of the disorder or condition. Typically, the host or subject in each of these methods is human, although other mammals can also benefit from the administration of a compound of formula I.

A "bromodomain-mediated disorder or condition" is characterized by the participation of one or more bromodomains (e.g., BRD4) in the inception, manifestation of one or more symptoms or disease markers, severity, or progression of a disorder or condition. Accordingly, compounds of formula I may be used to treat cancer, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

Further, compounds of formula I may be used to treat inflammatory diseases, inflammatory conditions, and autoimmune diseases, including, but not limited to: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

Compounds of formula I, or pharmaceutically acceptable salts thereof, may be used to treat AIDS. In addition, compounds of formula I, or pharmaceutically acceptable salts thereof, may be used to treat obesity. Compounds of formula I, or pharmaceutically acceptable salts thereof, may be used to treat type II diabetes.

Compounds of formula I, or pharmaceutically acceptable salts thereof, may be used to treat a chronic kidney disease or condition including, but are not limited to: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis.

Compounds of formula I, or pharmaceutically acceptable salts thereof, may be used to treat acute kidney injury or disease or condition including, but are not limited to: ischemia-reperfusion induced kidney disease, cardiac and major surgery induced kidney disease, percutaneous coronary intervention induced kidney disease, radio-contrast agent induced kidney disease, sepsis induced kidney disease, pneumonia induced kidney disease, and drug toxicity induced kidney disease.

Compounds of formula I, or pharmaceutically acceptable salts thereof, may be used to treat obesity, dyslipidemia, hypercholesterolemia, Alzheimer's disease, metabolic syndrome, hepatic steatosis, type II diabetes, insulin resistance, diabetic retinopathy or diabetic neuropathy.

Compounds of formula I, or pharmaceutically acceptable salts thereof, may be used to prevent conception by inhibiting spermatogenesis in a subject comprising administering a therapeutically effective amount of a compound of formula (I) or a pharmaceutically acceptable salt thereof, to a subject in need thereof.

The compounds of formula I can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more pharmaceutical agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, J. of Immunology 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-(3-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-(2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax), ABT-199, and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 tri-functional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-0,1-vcMMAE, PSMA-ADC, MEDI-547, SGN-19 Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radio-sensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN®

(DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

The compounds of the invention can also be co-administered with a therapeutically effective amount of one or more agents to treat an inflammatory disease or condition, or autoimmune disease, where examples of the agents include, such as methotrexate, tofacitinib, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (etanercept) and p55TNFRIgG (Lenercept), sIL-1RI, sIL-1RII, sIL-6R), antiinflammatory cytokines (e.g. IL-4, IL-10, IL-11, IL-13 and TGFβ, celecoxib, folic acid, hydroxychloroquine sulfate, rofecoxib, etanercept, infliximab, adalimumab, certolizumab, tocilizumab, abatacept, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, cortisone, betamethasone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. In certain embodiments, combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (I) of the invention may be co-administered include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ. Preferred examples of therapeutic agents for Crohn's disease with which a compound of Formula (I) can be combined include the following: TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) may be co-administered include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ.

A compound of Formula (I) may also be co-administered with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be co-administered include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (HUMIRA®), CA2 (infliximab), CDP 571, TNFR-Ig constructs, (p75TNFRIgG (ENBREL®) and p55TNFRIgG (LENERCEPT®).

Non-limiting examples of therapeutic agents for asthma with which a compound of Formula (I) may be co-administered include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/ pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (I) may be co-administered include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for psoriasis with which a compound of Formula (I) may be co-administered include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) may be co-administered include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), and efalizumab.

Preferred examples of therapeutic agents for SLE (Lupus) with which a compound of Formula (I) may be co-administered include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with UP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™).

A compound of Formula (I) may also be co-administered with insulin for the treatment of type I diabetes.

The compounds of the invention can also be co-administered with a therapeutically effective amount of one or more agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, emtricitabine, lamivudine, nevirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir, ritonavir, saquinavir, and tipranavir. Examples of other retroviral drugs include, but are not limited to, elvitegravir, enfuvirtide, maraviroc and raltegravir.

The compounds of the invention can also be co-administered with a therapeutically effective amount of one or more agents used in the treatment of obesity, where examples of the agents include orlistat.

The compounds of the invention can also be co-administered with a therapeutically effective amount of one or more agents used in the treatment of type II diabetes, where examples of the agents include, alpha glucosidase inhibitors, insulin, metformin, sulfonylureas (e.g., carbutamide, acetohexamide, chlorpropamide, glibenclamide, glibornuride, gliclazide, glimepiride, glipizide, gliquidone, glisoxepide, glyclopyramide, tolbutamide, and tolazamide), nonsulfonylureas (e.g., nateglinide, and repaglinide), and thiazolidinediones (e.g., pioglitazone).

The compounds of the invention can be co-administered with a therapeutically effective amount of one or more agents to prevent or treat type II diabetes, hepatic steatosis, insulin resistance, metabolic syndrome and related disorders, where examples of the agents include, but are not limited to, insulin and insulins that have been modified to improve the duration of action in the body; agents that stimulate insulin secretion such as acetohexamide, chlorpropamide, glyburide, glimepiride, glipizide, glicazide, glycopyramide, gliquidone, rapaglinide, nataglinide, tolazamide and tolbutamide; agents that are glucagon-like peptide agonists such as exanatide, liraglutide and taspoglutide; agents that inhibit dipeptidyl-peptidase IV such as vildagliptin, sitagliptin, saxagliptin, linagliptin, alogliptin and septagliptin; agents that bind to the peroxisome proliferator-activated receptor gamma such as rosiglitazone and pioglitazone; agents that decrease insulin resistance such as metformin; agents that reduce glucose absorbance in the small intestine such as acarbose, miglitol and voglibose.

The compounds of the invention can be co-administered with a therapeutically effective amount of one or more agents to prevent or treat acute kidney disorders and chronic kidney diseases, where examples of the agents include, but are not limited to, dopamine, diuretics such as furosemide, bumetanide, thiazide and the like, mannitol, calcium gluconate, sodium bicarbonate, albuterol, paricalcitol, doxercalciferol, and cinacalcet.

The following Examples may be used for illustrative purposes and should not be deemed to narrow the scope of the invention.

EXAMPLES

Example 1

2-methyl-6-(2-phenoxyphenyl)pyridazin-3(2H)-one

Example 1A 6-chloro-2-methylpyridazin-3(2H)-one

A mixture of 6-chloropyridazin-3(2H)-one (5.04 g, 38.6 mmol) and iodomethane (2.88 mL, 46.3 mmol) in dimethylformamide (30 mL) was treated with $Cs_2CO_3$ (15.10 g, 46.3 mmol) at ambient temperature. The reaction mixture was stirred at ambient temperature for 4 hours. The reaction mixture was partitioned between water and ethyl acetate. The aqueous layer was extracted with additional ethyl acetate three times. The combined organic layers were washed with brine, dried over $MgSO_4$, filtered, and concentrated. The residue was purified by flash column chromatography on silica gel eluting with 20% ethyl acetate in hexanes to give 4.55 g (82%) of the title compound.

Example 1B 2-methyl-6-(2-phenoxyphenyl)pyridazin-3(2H)-one

A mixture of Example 1A (29 mg, 0.20 mmol), 2-phenoxyphenylboronic acid (0.056 g, 0.260 mmol, 1.3 equivalents), $Pd(PPh_3)_4$ (0.011 g, 5 mol %) and cesium fluoride (0.091 g, 0.6 mmol) in DME (2 mL) and methanol (1 mL) was heated under microwave condition (120° C., 40 minutes). The reaction mixture was partitioned between water and ethyl acetate. The aqueous layer was extracted with additional ethyl acetate three times. The combined organic layers were washed with brine, dried over $MgSO_4$, filtered, and concentrated. The residue was purified by flash column chromatography on silica gel eluting with 30% ethyl acetate in hexanes to give the title compound (0.041 g, 74% yield). $^1$H NMR (500 MHz, DMSO-$d_6$) δ 7.75 (d, J=9.77 Hz, 1H), 7.66 (dd, J=7.78, 1.68 hz, 1H), 7.45-7.49 (m, 1H), 7.35-7.40 (m, 2H), 7.26-7.30 (m, 2H), 7.11-7.15 (m, 1H), 6.97-7.01 (m, 3H), 6.94 (d, J=9.77 Hz, 1H), 3.68 (s, 3H). MS (ESI+) m/z 279.0 (M+H)$^+$.

Example 2

6-[2-(benzyloxy)phenyl]-2-methylpyridazin-3(2H)-one

Example 2 was prepared according to the procedure used for the preparation of Example 1B, substituting 2-(benzyloxy)phenylboronic acid for 2-phenoxyphenylboronic acid, to provide the title compound. $^1$H NMR (500 MHz, DMSO-$d_6$) δ 7.78 (d, J=9.77 Hz, 1H), 7.49 (dd, J=7.48, 1.68 hz, 1H), 7.30-7.46 (m, 6H), 7.25 (d, J=7.63 Hz, 1H), 7.06 (t, J=7.02 Hz, 1H), 6.92 (d, J=9.46 Hz, 1H), 5.19 (s, 2H), 3.70 (s, 3H). MS (ESI+) m/z 293.1 (M+H)$^+$.

Example 3

4-[2-(1-methyl-6-oxo-1,6-dihydropyridazin-3-yl)phenoxy]benzonitrile

A mixture of 6-(2-hydroxyphenyl)-2-methylpyridazin-3(2H)-one (0.100 g, 0.495 mmol) (prepared according to the procedure reported in *Synthetic Communications*, 2002, 32, 1675), 4-fluorobenzonitrile (0.072 g, 0.593 mmol), and sodium hydride (14.2 mg, 0.593 mmol) in N-methylpyrrolodone (4 mL) was heated at 130° C. for 16 hours. The reaction mixture was cooled to ambient temperature, taken up in ethyl acetate, and washed with 1 N aqueous sodium hydroxide solution followed by brine. The organic layer was separated, dried over anhydrous sodium sulfate, filtered, and evaporated under reduced pressure. The residue was purified by flash chromatography (silica gel, 30-100% ethyl acetate/hexane) to provide the title compound. $^1$H NMR (300 MHz, DMSO-$d_6$) δ 7.77-7.87 (m, 2H) 7.71-7.76 (m, 1H) 7.66-7.71 (m, 1H) 7.52-7.61 (m, 1H) 7.36-7.47 (m, 1H) 7.22 (d, J=7.93 Hz, 1H) 7.02-7.10 (m, 2H) 6.89-6.97 (m, 1H) 3.60 (s, 3H). MS (ESI+) m/z 304.3 (M+H)$^+$.

Example 4

6-[2-(cyclopentyloxy)phenyl]-2-methylpyridazin-3(2H)-one

A mixture of 6-(2-hydroxyphenyl)-2-methylpyridazin-3(2H)-one (0.120 g, 0.593 mmol) (prepared according to the procedure reported in *Synthetic Communications*, 2002, 32, 1675), 4-bromocyclopentane (0.097 g, 0.653 mmol), and sodium hydride (17.1 mg, 0.712 mmol) in N-methylpyrrolodone (4 mL) was stirred at ambient temperature for 72 h. The reaction mixture was taken up in ethyl acetate, and washed with 1 N aqueous sodium hydroxide solution followed by brine. The organic layer was separated, dried over anhydrous sodium sulfate, filtered, and evaporated under reduced pressure. The residue was purified by flash chromatography (silica gel, 10-30% ethyl acetate/hexane) to provide the title compound. $^1$H NMR (300 MHz, DMSO-$d_6$) δ 7.68 (d, J=9.49 Hz, 1H) 7.47 (dd, J=7.80, 1.70 Hz, 1H) 7.35-7.44 (m, 1H) 7.12 (d, J=7.80 Hz, 1H) 7.01 (t, J=6.95 Hz, 1H) 6.94 (d, J=9.49 Hz, 1H) 4.85-4.95 (m, 1H) 3.70 (s, 3H) 1.82-1.97 (m, 2H) 1.52-1.77 (m, 6H). MS (ESI+) m/z 271.3 (M+H)$^+$.

Example 5

N-{4-(2,4-difluorophenoxy)-3-[1-methyl-6-oxo-4-(trifluoromethyl)-1,6-dihydropyridin-3-yl]phenyl}methanesulfonamide

Example 5A

5-bromo-1-methyl-4-(trifluoromethyl)pyridin-2(1H)-one

Example 5A was prepared according to the procedure used for the preparation of Example 1A, substituting 5-bromo-4-(trifluoromethyl)-1,2-dihydropyridin-2-ol for 6-chloropyridazin-3(2H)-one, to provide the title compound.

Example 5B

2-bromo-1-(2,4-difluorophenoxy)-4-nitrobenzene

2-Bromo-1-fluoro-4-nitrobenzene (15 g, 68.2 mmol), 2,4-difluorophenol (7.82 ml, 82 mmol), and cesium carbonate (26.7 g, 82 mmol) were combined in DMSO (75 mL) then heated to 110° C. for 1 hour. After cooling, to the reaction mixture was added water (1000 mL) and brine (1000 mL), and the mixture was extracted with ethyl acetate (3×200 mL). The combined organics were washed with brine, dried (MgSO$_4$), filtered, and concentrated under reduced pressure to give a crude solid which was used in the next step without additional purification.

Example 5C

3-bromo-4-(2,4-difluorophenoxy)aniline

A mixture of Example 5B (22.5 g, 68.2 mmol), iron powder (19.0 g, 341 mmol), and ammonium chloride (7.30 g, 136 mmol) in tetrahydrofuran (117 ml), ethanol (117 ml), and water (39.0 ml) was refluxed at 100° C. for 2 hours. The mixture was cooled just below reflux, filtered through Celite. The filter cake was washed with warm MeOH (3×50 mL). The solution was concentrated under reduced pressure, neutralized to a pH of 8 with saturated NaHCO$_3$ (150 mL), and extracted with ethyl acetate (3×100 mL). The combined organics were washed with brine, dried (MgSO$_4$), filtered, concentrated, and purified by flash chromatography (silica gel, 0-15% ethyl acetate/hexane gradient) to provide the title compound (8.1 g, 85%).

Example 5D

4-(2,4-difluorophenoxy)-3-(4,4,5,5-tetramethyl-1,3,2-dioxaborolan-2-yl)aniline Example 5C (14.3 g, 47.7 mmol), 4,4,4',4',5,5,5',5'-octamethyl-2,2'-bi(1,3,2-dioxaborolane) (24 g, 95 mmol), potassium acetate (10.3 g, 105 mmol), 1,3,5,7-tetramethyl-6-phenyl-2,4,8-trioxa-6-phosphaadamantane (1.39 g, 4.77 mmol), and tris(dibenzylideneacetone)dipalladium(0) (1.31 g, 1.43 mmol) were degassed under argon for 30 minutes. Dioxane (200 mL), degassed with argon for 30 minutes, was then added by cannula transfer and the reaction mixture heated at 80° C. for 22 hours. The cooled mixture was vacuum filtered through Celite, rinsed with ethyl acetate (100 mL), and washed with brine (150 mL) and water (150 mL). The aqueous phase was extracted with ethyl acetate (3×150 mL). The combined organics were washed with brine, dried (MgSO$_4$), gravity filtered, then concentrated under reduced pressure. Purification by flash chromatography (silica gel, 0-25% ethyl acetate/hexane gradient) afforded the title compound (14.2 g, 88%).

Example 5E

5-(5-amino-2-(2,4-difluorophenoxy)phenyl)-1-methyl-4-(trifluoromethyl)pyridin-2(1H)-one Example 5E was prepared according to the procedure used for the preparation of Example 1B, substituting Example 5D for 2-phenoxyphenylboronic acid, and Example 5A for Example 1A, respectively, to provide the title compound.

Example 5F

N-{4-(2,4-difluorophenoxy)-3-[1-methyl-6-oxo-4-(trifluoromethyl)-1,6-dihydropyridin-3-yl]phenyl}methanesulfonamide Example 5F was prepared according to the procedure used for the preparation of Example 22, substituting Example 5E for Example 20C to provide the title compound. $^1$H NMR (300 MHz, DMSO-d$_6$) δ 9.74 (s, 1H), 7.93 (s, 1H), 7.46-7.31 (m, 1H), 7.31-7.00 (m, 4H), 6.89-6.75 (m, 2H), 3.47 (s, 3H), 2.96 (s, 3H). MS (ESI+) m/z 475.3 (M+H)$^+$.

Example 6

2-methyl-6-[2-(pyridin-2-yloxy)phenyl]pyridazin-3(2H)-one

Example 6 was prepared according to the procedure used for the preparation of Example 3, substituting 2-fluoropyridine for 4-fluorobenzonitrile, to provide the title compound. $^1$H NMR (300 MHz, DMSO-d$_6$) δ 8.08 (dd, J=5.35, 1.78 Hz, 1H) 7.79-7.88 (dd, J=6.74, 1.59 Hz, 1H) 7.63-7.68 (m, 1H) 7.63 (d, J=9.52 Hz, 1H) 7.47-7.55 (m, 1H) 7.32-7.39 (m, 1H) 7.20 (dd, J=8.33, 1.19 Hz, 1H) 7.07-7.12 dd, J=4.76, 0.79 Hz, 1H) 7.02 (d, J=8.33 Hz, 1H) 6.89 (d, J=9.52 Hz, 1H) 3.60 (s, 3H). MS (ESI+) m/z 280.2 (M+H)$^+$.

Example 7

2-methyl-6-{2-[4-(trifluoromethyl)phenoxy]phenyl}pyridazin-3(2H)-one

Example 7 was prepared according to the procedure used for the preparation of Example 3, substituting 1-fluoro-4-(trifluoromethyl)benzene for 4-fluorobenzonitrile, to provide the title compound. $^1$H NMR (300 MHz, DMSO-d$_6$) δ 7.66-7.76 (m, 4H) 7.51-7.59 (m, 1H) 7.36-7.43 (m, 1H) 7.19 (dd, J=8.13, 0.99 Hz, 1H) 7.11 (d, J=8.33 Hz, 2H) 6.94 (d, J=9.52 Hz, 1H) 3.62 (s, 3H). MS (ESI+) m/z 347.0 (M+H)$^+$.

Example 8

2-methyl-6-{2-[4-(methylsulfonyl)phenoxy]phenyl}pyridazin-3(2H)-one

Example 8 was prepared according to the procedure used for the preparation of Example 3, substituting 1-fluoro-4-(methylsulfonyl)benzene for 4-fluorobenzonitrile, to provide the title compound. $^1$H NMR (300 MHz, DMSO-d$_6$) δ 7.86-7.93 (m, 2H) 7.71-7.77 (m, 1H) 7.70 (d, J=9.49 Hz, 1H) 7.53-7.60 (m, 1H) 7.38-7.44 (m, 1H) 7.21 (dd, J=8.14, 1.02 Hz, 1H) 7.10-7.17 (m, 2H) 6.94 (d, J=9.49 Hz, 1H) 3.61 (s, 3H) 3.17 (s, 3H). MS (ESI+) m/z 357.2 (M+H)$^+$.

Example 9

2-methyl-6-(5-nitro-2-phenoxyphenyl)pyridazin-3(2H)-one

Example 9A

6-(2-fluoro-5-nitrophenyl)-2-methylpyridazin-3(2H)-one

Example 1A (0.145 g, 1 mmol), 2-fluoro-5-nitrophenylboronic acid (0.294 g, 1.1 mmol), Pd(PPh$_3$)$_4$ (0.058 g, 0.05 mmol) and sodium carbonate (0.212 g, 2.0 mmol) were combined in toluene (4 mL), ethanol (1 mL), and water (1 mL) and the mixture was degassed and left under nitrogen. The reaction mixture was heated at 90° C. overnight, and then cooled to room temperature. The mixture was partitioned between ethyl acetate and water. The organic layer was washed with brine, dried (MgSO$_4$), filtered and concentrated. The crude product was purified by flash chromatography (silica gel, 20-50% ethyl acetate in hexanes) to provide 0.19 g (76%) of the title compound.

Example 9B

2-methyl-6-(5-nitro-2-phenoxyphenyl)pyridazin-3(2H)-one

Phenol (0.045 g, 0.48 mmol), Example 9A (0.1 g, 0.4 mmol) and cesium carbonate (0.130 g, 0.4 mmol) were combined in DMSO (2 mL) and heated at 100° C. for 2 hours. The reaction mixture was partitioned between ethyl acetate and water and pH was adjusted to pH 7. The organic layer was washed with brine, dried (Na$_2$SO$_4$), filtered and concentrated. Purification by flash chromatography (silica gel, 60% ethyl acetate in hexanes) afforded 0.09 g (70%) of the title compound. $^1$H NMR (500 MHz, DMSO-d$_6$) δ 8.47 (d, J=2.75 Hz, 1H), 8.28 (dd, J=9.15, 2.75 Hz, 1H), 7.94 (d, J=9.46 Hz, 1H), 7.49-7.53 (m, 2H), 7.31 (t, J=7.48 Hz, 1H), 7.26 (d, J=7.63 Hz, 2H), 7.04 (d, J=9.46 HZ), 6.98 (d, J=9.16 Hz, 1H), 3.76 (s, 3H). MS (DCI+) m/z 324.1 (M+H)$^+$.

Example 10

6-(5-amino-2-phenoxyphenyl)-2-methylpyridazin-3(2H)-one

Example 9B (0.08 g, 0.247 mmol) and 10% palladium on carbon (0.023 g, 0.025 mmol) in ethyl acetate (10 mL) was treated with a balloon of hydrogen overnight. The solid was removed by filtration. The filtrate was concentrated under reduced pressure. The residue was purified by reverse phase HPLC (C18, CH$_3$CN/water (0.1% TFA), 0-100%) to afford the title compound (0.066 g, 90%). $^1$H NMR (500 MHz, DMSO-d$_6$) δ 7.72 (d, J=9.77 Hz, 1H), 7.31-7.36 (m, 2H), 7.23 (d, J=2.75 Hz, 1H), 7.31 (t, J=7.08 Hz, 1H), 7.03 (dd, J=8.85, 2.75 Hz, 1H), 6.92-6.94 (m, 4H), 3.67 (s, 3H). MS (DCI+) m/z 294.0 (M+H)$^+$.

Example 11

4-methyl-N-[3-(1-methyl-6-oxo-1,6-dihydropyridazin-3-yl)-4-phenoxyphenyl]benzenesulfonamide A mixture of Example 10 (0.03 g, 0.102 mmol), 4-methylbenzene-1-sulfonyl chloride (0.019 g, 0.102 mmol) and triethylamine (0.022 g, 0.204 mmol) in dichloromethane (2 mL) was stirred for 2 hours. The solvent was removed under reduced pressure. The residue was purified by reverse phase HPLC (C18, $CH_3CN$/water (0.1% TFA), 0-100%) to afford the title compound (0.037 g, 80%). $^1H$ NMR (500 MHz, DMSO-$d_6$) δ 10.30 (s, 1H), 7.66-7.69 (m, 3H), 7.31-7.36 (m, 2H), 7.31-7.39 (m, 5H), 7.16 (dd, J=8.85, 2.75 Hz, 1H), 7.09 (t, J=7.32 Hz, 1H), 6.89-6.92 (m, 4H), 3.66 (s, 3H), 2.35 (s, 3H). MS (DCI+) m/z 448.2 $(M+H)^+$.

Example 12

N-[3-(1-methyl-6-oxo-1,6-dihydropyridazin-3-yl)-4-phenoxyphenyl]acetamide

Example 12 was prepared according to the procedure used for the preparation of Example 10, substituting acetic chloride for 4-methylbenzene-1-sulfonyl chloride, to provide the title compound. $^1H$ NMR (500 MHz, DMSO-$d_6$) δ 10.11 (s, 1H), 7.89 (d, J=2.75 Hz, 1H), 7.67-7.72 (m, 2H), 7.32-7.36 (m, 2H), 7.08 (t, J=7.32 Hz, 1H), 7.00 (d, J=8.85 Hz, 1H), 6.92-6.95 (m, 3H), 3.67 (s, 3H), 2.05 (s, 3H). MS (ESI+) m/z 336.2 $(M+H)^+$.

Example 13

3-(1-methyl-6-oxo-1,6-dihydropyridazin-3-yl)-4-phenoxybenzonitrile

Example 13A

4-fluoro-3-(1-methyl-6-oxo-1,6-dihydropyridazin-3-yl)benzonitrile

Example 13A was prepared according to the procedure used for the preparation of Example 9A, substituting 4-fluoro-3-(4,4,5,5-tetramethyl-1,3,2-dioxaborolan-2-yl)benzonitrile for 2-fluoro-5-nitrophenylboronic acid, to provide the title compound.

Example 13B

3-(1-methyl-6-oxo-1,6-dihydropyridazin-3-yl)-4-phenoxybenzonitrile

Example 13B was prepared according to the procedure used for the preparation of Example 9B, substituting Example 13A for Example 9A, to provide the title compound. $^1H$ NMR (500 MHz, DMSO-$d_6$) δ 8.10 (d, J=2.14 Hz, 1H), 7.86-7.89 (m, 2H), 7.45-7.49 (m, 2H), 7.27 (t, J=7.48 Hz, 1H), 7.18-7.21 (m, 2H), 7.01 (d, J=9.46 Hz, 1H), 6.95 (d, J=8.85 Hz, 1H), 3.73 (s, 3H). MS (DCI+) m/z 304.1 $(M+H)^+$.

Example 14

3-(1-methyl-6-oxo-1,6-dihydropyridazin-3-yl)-4-phenoxybenzamide

A mixture of Example 13B (0.030 g, 0.1 mmol) and lithium hydroxide monohydrate (0.042 g, 1 mmol) in dioxane (3 mL) and water (1 mL) was heated at 90° C. for 2 hours. After cooling to room temperature, the reaction mixture was partitioned between water and ethyl acetate. The aqueous layer was neutralized to pH 5 using 10% HCl. It was then extracted with additional ethyl acetate three times. The combined organic layers were washed with brine, dried over $MgSO_4$, filtered, and concentrated. The residue was purified by reverse phase HPLC (C18, $CH_3CN$/water (0.1% TFA), 0-100%) to afford the title compound. $^1H$ NMR (500 MHz, DMSO-$d_6$) δ 8.17 (d, J=2.14 Hz, 1H), 8.03 (br s, 1H), 7.94 (dd, J=8.54, 2.44 Hz, 1H), 7.82 (d, J=9.77 Hz, 1H), 7.40-7.45 (m, 3H), 7.20 (t, J=7.32 Hz, 1H), 7.08-7.11 (m 2H), 6.98 (d, J=9.77 Hz, 1H), 6.94 (d, J=8.54 Hz, 1H), 3.72 (s, 3H). MS (DCI+) m/z 322.1 $(M+H)^+$.

Example 15

3-(1-methyl-6-oxo-1,6-dihydropyridazin-3-yl)-4-phenoxybenzoic acid

The title compound was isolated as a by-product during the preparation of Example 14. $^1H$ NMR (500 MHz, DMSO-$d_6$) δ 13.04 (br s, 1H), 8.20 (d, J=2.14 Hz, 1H), 7.98 (dd, J=8.7, 2.29 Hz, 1H), 7.86 (d, J=9.77 Hz, 1H), 7.44-7.48 (m, 2H), 7.24 (t, J=7.48 Hz, 1H), 7.13-7.17 (m 2H), 6.99 (d, J=9.77 Hz, 1H), 6.93 (d, J=8.54 Hz, 1H), 3.74 (s, 3H). MS (DCI+) m/z 323.1 $(M+H)^+$.

Example 16

N-[3-(1-methyl-6-oxo-1,6-dihydropyridazin-3-yl)-4-phenoxybenzyl]acetamide

Example 16A

6-(5-(aminomethyl)-2-phenoxyphenyl)-2-methylpyridazin-3(2H)-one

Example 13B (0.1 g, 0.330 mmol) and solvent 7M $NH_3$-methanol (10 mL) were added to Ra-Ni 2800, water slurry (0.200 g, 3.41 mmol) in a 50 mL pressure bottle and stirred for 16 hours at 30 psi and room temperature. The mixture was filtered through a nylon membrane and the filtrate was concentrated. The residue was purified by reverse phase HPLC (C18, $CH_3CN$/water (0.1% TFA), 0-100%) to afford the title compound.

Example 16B

N-[3-(1-methyl-6-oxo-1,6-dihydropyridazin-3-yl)-4-phenoxybenzyl]acetamide

Example 16B was prepared according to the procedure used for the preparation of Example 11, substituting acetic chloride for 4-methylbenzene-1-sulfonyl chloride, and Example 16A for Example 10, respectively, to provide the title compound. $^1H$ NMR (500 MHz, DMSO-$d_6$) δ 8.41 (t, J=5.65, 1H), 7.72 (d, J=9.77 Hz, 1H), 7.53 (d, J=2.14 Hz, 1H), 7.34-7.38 (m, 3H), 7.11 (t, J=7.32 Hz, 1H), 6.93-6.97 (m, 4H), 4.28 (d, J=6.1 Hz, 2H), 3.68 (s, 3H), 1.88 (s, 3H). MS (ESI+) m/z 350.1 $(M+H)^+$.

Example 17

2,2,2-trifluoro-N-[3-(1-methyl-6-oxo-1,6-dihydropyridazin-3-yl)-4-phenoxybenzyl]acetamide The title compound was isolated as a by-product during the preparation of Example 16B. $^1H$ NMR (500 MHz, DMSO-d$_6$) δ 10.5 (t, J=5.65, 1H), 7.75 (d, J=9.46 Hz, 1H), 7.59 (d, J=2.14 Hz, 1H), 7.35-7.39 (m, 3H), 7.13 (t, J=7.48 Hz, 1H), 6.94-7.01 (m, 4H), 4.43 (d, J=5.8 Hz, 2H), 3.69 (s, 3H). MS (ESI+) m/z 404.1 (M+H)$^+$.

Example 18

5-methoxy-2-methyl-6-(2-phenoxyphenyl)pyridazin-3(2H)-one

Example 18A 5,6-dichloropyridazin-3(2H)-one 3,4,6-Trichloropyridazine (12 g, 65.4 mmol) in acetic acid (45 mL) was heated at 130° C. for two hours. After cooling to room temperature, the reaction mixture was poured into ice water (200 mL). The solid was collected by filtration to give 3.7 g of the title compound.

Example 18B 5,6-dichloro-2-methylpyridazin-3(2H)-one

Example 18B was prepared according to the procedure used for the preparation of Example 1A, substituting Example 18A for 6-chloropyridazin-3(2H)-one, to provide the title compound.

Example 18C 6-chloro-5-methoxy-2-methylpyridazin-3(2H)-one

Methanol (80 mL) was cooled to 0° C. To this solvent was added sodium (0.804 g, 35.0 mmol). All sodium was dissolved completely within 1 hour. To this solution was added Example 18B (6.2 g, 34.5 mmol). The reaction mixture was stirred at 50° C. for 2 hours. The solvent was removed, and the residue was triturated with water. The solid was collected by filtration to give 5.41 g (89%) of the title compound.

Example 18D 5-methoxy-2-methyl-6-(2-phenoxyphenyl)pyridazin-3(2H)-one

Example 18D was prepared according to the procedure used for the preparation of Example 1B, substituting Example 18C for Example 1A, to provide the title compound. $^1$H NMR (500 MHz, DMSO-d$_6$) δ 7.60-7.64 (m, 1H), 7.40-7.47 (m, 2H), 7.32-7.38 (m, 2H), 7.21-7.25 (m, 1H), 7.10 (t, J=7.32 Hz, 1H), 6.91-6.98 (m, 3H), 6.29 (s, 1H), 3.61 (s, 3H), 3.57 (s, 3H). MS (DCI+) m/z 309.1 (M+H)$^+$.

Example 19

N-[3-(4-methoxy-1-methyl-6-oxo-1,6-dihydropyridazin-3-yl)phenyl]methanesulfonamide A mixture of the product from Example 18C (0.053 g, 0.30 mmol), 3-(methylsulfonylylamino)phenylboronic acid (Combi-Blocks 0.084 g, 0.390 mmol), tetrakis(triphenylphosphine)palladium(0) (0.017 g, 0.015 mmol) and sodium carbonate (2M, 0.300 mL, 0.600 mmol) in toluene (1.0 mL), ethanol (0.25 mL), and water (0.5 mL) was heated by microwave at 110° C. for 30 minutes. The reaction mixture was filtered through a 0.45 um Nylon filter disk to remove solids and the filtrate was partitioned between ethyl acetate and brine. The organic layer was separated and concentrated. Purification by reverse phase HPLC (C18, 0-100% CH$_3$CN/water (0.1% TFA)) afforded the title compound (0.048 g, 52%) $^1$H NMR (300 MHz, DMSO-d$_6$) δ 9.84 (s, 1H) 7.50 (s, 1H) 7.33-7.44 (m, 2H) 7.22-7.31 (m, 1H) 6.43 (s, 1H) 3.83 (s, 3H) 3.65 (s, 3H) 3.00 (s, 3H). MS (ESI+) m/z 310 (M+H)$^+$.

Example 20

6-(5-amino-2-phenoxyphenyl)-5-methoxy-2-methylpyridazin-3(2H)-one

Example 20A 6-(2-fluoro-5-nitrophenyl)-5-methoxy-2-methylpyridazin-3(2H)-one Example 20A was prepared according to the procedure used for the preparation of Example 9A, substituting Example 18C for Example 1A, to provide the title compound.

Example 20B 5-methoxy-2-methyl-6-(5-nitro-2-phenoxyphenyl)pyridazin-3(2H)-one Example 20B was prepared according to the procedure used for the preparation of Example 9B, substituting Example 20A for Example 9A, to provide the title compound.

Example 20C 6-(5-amino-2-phenoxyphenyl)-5-methoxy-2-methylpyridazin-3(2H)-one Example 20C was prepared according to the procedure used for the preparation of Example 10, substituting Example 20B for Example 9B, to provide the title compound. $^1$H NMR (500 MHz, DMSO-d$_6$) δ 7.23-7.26 (m, 2H), 6.95 (t, J=7.93 Hz, 1H), 6.76-6.81 (m, 3H), 6.64-6.67 (m, 1H), 6.56 (d, J=2.75 Hz, 1H), 6.21 (s, 1H), 5.11 (s, 2H), 3.51 (s, 3H), 3.50 (s, 3H). MS (DCI+) m/z 324.1 (M+H)$^+$.

Example 21

N-[3-(4-methoxy-1-methyl-6-oxo-1,6-dihydropyridazin-3-yl)-4-phenoxyphenyl]acetamide Example 21 was prepared according to the procedure used for the preparation of Example 11, substituting acetic chloride for 4-methylbenzene-1-sulfonyl chloride, and substituting Example 20C for Example 10, respectively, to provide the title compound. $^1$H NMR (500 MHz, DMSO-d$_6$) δ 10.05 (s, 1H), 7.67 (d, J=2.44 Hz, 1H), 7.59 (dd, J=8.85, 2.44 Hz, 1H), 7.29-7.34 (m, 2H), 7.06 (t, J=7.48 Hz, 1H), 6.97 (d, J=8.85 Hz, 1H), 6.86-6.92 (m, 2H), 6.28 (s, 1H), 3.58 (s, 3H), 3.56 (s, 3H), 2.04 (s, 3H). MS (DCI+) m/z 366.0 (M+H)$^+$.

Example 22

N-[3-(4-methoxy-1-methyl-6-oxo-1,6-dihydropyridazin-3-yl)-4-phenoxyphenyl]methanesulfonamide A mixture of Example 20C (0.03 g, 0.093 mmol), methanesulfonyl chloride (0.021 g, 0.186 mmol), and triethylamine (0.036 g, 0.36 mmol) in dichloromethane (1 mL) was stirred at room temperature for 1 hour. The solvent was removed, and the residue was taken up in dioxane (2 mL) and 1.0 N NaOH (1 mL). The reaction mixture was heated at 90° C. for 1 hour. The solvents were partially removed, and the residue was partitioned between water and ethyl acetate. The aqueous layer was neutralized with 10% HCl and extracted with additional ethyl acetate twice. The combined organic layers were washed with brine, dried over $MgSO_4$, filtered, and concentrated under reduced pressure. The residue was purified by reverse phase HPLC (C18, $CH_3CN$/water (0.1% TFA), 0-100%) to afford 0.025 g (68%) of the title compound. $^1H$ NMR (500 MHz, DMSO-$d_6$) δ 9.77 (s, 1H), 7.29-7.35 (m, 1H), 7.22 (d, J=2.75 Hz, 1H), 7.08 (t, J=7.32 Hz, 1H), 6.99 (d, J=8.85 Hz, 1H), 6.91-6.93 (m, 2H), 6.29 (s, 1H), 3.60 (s, 3H), 3.56 (s, 3H), 3.02 (s, 3H). MS (DCI+) m/z 402.2 $(M+H)^+$.

Example 23

N-[3-(4-methoxy-1-methyl-6-oxo-1,6-dihydropyridazin-3-yl)-4-phenoxyphenyl]-N-methylmethanesulfonamide The product from Example 22 (0.06 g, 0.149 mmol), potassium carbonate (0.027 g, 0.194 mmol) and methyl iodide (0.014 mL, 0.224 mmol) in dimethylformamide (0.7 mL) was stirred for 1 hour and partitioned between ethyl acetate and brine. The organic layer was separated and concentrated. Purification by reverse phase HPLC (C18, 0-100% $CH_3CN$/water (0.1% TFA)) afforded the title compound (0.030 g, 48%). $^1H$ NMR (300 MHz, DMSO-$d_6$) δ 7.43-7.51 (m, 2H) 7.30-7.41 (m, 2H) 7.13 (t, J=7.29 Hz, 1H) 6.89-7.04 (m, 3H) 6.32 (s, 1H) 3.64 (s, 3H) 3.58 (s, 3H) 3.24 (s, 3H) 2.98 (s, 3H). MS (ESI+) m/z 416 $(M+H)^+$.

Example 24

N-[3-(4-methoxy-1-methyl-6-oxo-1,6-dihydropyridazin-3-yl)-4-phenoxyphenyl]propane-1-sulfonamide The product from Example 20 (0.039 g, 0.12 mmol) and triethylamine (0.025 mL, 0.18 mmol) in dichloromethane (0.5 mL) were treated with propanesulfonyl chloride (0.015 mL, 0.13 mmol) stirred for 3 hours and partitioned between ethyl acetate and brine. The organic layer was separated and concentrated. Purification by reverse phase HPLC (C18, 0-100% $CH_3CN$/water (0.1% TFA)) afforded the title compound (0.023 g, 44%). $^1H$ NMR (300 MHz, DMSO-$d_6$) δ 9.84 (s, 1H) 7.26-7.41 (m, 3H) 7.21 (d, J=2.38 Hz, 1H) 7.08 (t, J=7.34 Hz, 1H) 6.98 (d, J=8.73 Hz, 1H) 6.91 (d, J=7.54 Hz, 2H) 6.30 (s, 1H) 3.59 (s, 3H) 3.56 (s, 3H) 3.02-3.13 (m, 2H) 1.63-1.81 (m, 2H) 0.96 (t, J=7.34 Hz, 3H). MS (ESI+) m/z 430 $(M+H)^+$.

Example 25

2,2,2-trifluoro-N-[3-(4-methoxy-1-methyl-6-oxo-1,6-dihydropyridazin-3-yl)-4-phenoxyphenyl]ethanesulfonamide Example 25 was prepared according to the procedure of Example 24 substituting 2,2,2-trifluoroethanesulfonyl chloride for propanesulfonyl chloride to afford the title compound (0.040 g, 71%). $^1H$ NMR (300 MHz, DMSO-$d_6$) δ 10.46 (s, 1H) 7.29-7.38 (m, 3H) 7.25 (d, J=2.38 Hz, 1H) 7.09 (t, J=7.34 Hz, 1H) 6.99 (d, J=8.73 Hz, 1H) 6.92 (d, J=7.54 Hz, 2H) 6.30 (s, 1H) 4.56 (q, J=9.78 Hz, 2H) 3.60 (s, 3H) 3.56 (s, 3H). MS (ESI+) m/z 470 $(M+H)^+$.

Example 26

N-[3-(4-methoxy-1-methyl-6-oxo-1,6-dihydropyridazin-3-yl)-4-phenoxyphenyl]cyclopentanesulfonamide A mixture of the product from Example 20 (0.049 g, 0.15 mmol) cyclopentanesulfonyl chloride (0.03 g, 0.18 mmol) and cesium carbonate (0.073 g, 0.225 mmol) in dimethylformamide (0.75 mL) was heated at 80° C. for 30 minutes and partitioned between ethyl acetate and brine adjusting the pH to 2 with 1M HCl. The organic layer was separated and concentrated. Purification by reverse phase HPLC (C18, 0-100% $CH_3CN$/water (0.1% TFA)) afforded the title compound (0.006 g, 8%). $^1H$ NMR (300 MHz, DMSO-$d_6$) δ 9.77 (s, 1H) 7.26-7.37 (m, 3H) 7.22 (d, J=2.78 Hz, 1H) 7.07 (t, J=7.34 Hz, 1H) 6.98 (d, J=9.12 Hz, 1H) 6.90 (d, J=7.54 Hz, 2H) 6.29 (s, 1H) 3.59 (s, 3H) 3.55 (s, 3H) 1.81-1.98 (m, 4H) 1.48-1.75 (m, 4H). MS (ESI+) m/z 456 $(M+H)^+$.

Example 27

N-[3-(4-methoxy-1-methyl-6-oxo-1,6-dihydropyridazin-3-yl)-4-phenoxyphenyl]-1-phenylmethanesulfonamide Example 27 was prepared according to the procedure of Example 26 substituting alpha-toluenesulfonyl chloride for cyclopentanesulfonyl chloride to afford the title compound (0.025 g, 43%). $^1H$ NMR (300 MHz, DMSO-$d_6$) δ 9.88 (s, 1H) 7.30-7.40 (m, 7H) 7.26 (dd, J=8.73, 2.78 Hz, 1H) 7.13 (d, J=2.78 Hz, 1H) 7.08 (t, J=7.34 Hz, 1H) 6.95 (d, J=8.73 Hz, 1H) 6.91 (d, J=7.54 Hz, 2H) 6.29 (s, 1H) 4.49 (s, 2H) 3.61 (s, 3H) 3.57 (s, 3H). MS (ESI+) m/z 478 $(M+H)^+$.

Example 28

3,3,3-trifluoro-N-[3-(4-methoxy-1-methyl-6-oxo-1,6-dihydropyridazin-3-yl)-4-phenoxyphenyl]propane-1-sulfonamide Example 28 was prepared according to the procedure of Example 24 substituting 3,3,3-trifluoropropane-1-sulfonyl chloride for propanesulfonyl chloride. Purification by chromatography (silica gel, 0-100% ethyl acetate in hexane) afforded the title compound (0.30 g, 41%). to afford the title compound (0.040 g, 71%). $^1H$ NMR (300 MHz, DMSO-$d_6$) δ 10.04 (s, 1H) 7.29-7.38 (m, 3H) 7.25 (d, J=2.71 Hz, 1H) 7.09 (t, J=7.46 Hz, 1H) 6.99 (d, J=8.82 Hz, 1H) 6.91 (d, J=7.80 Hz, 2H) 6.29 (s, 1H) 3.60 (s, 3H) 3.56 (s, 3H) 3.33-3.40 (m, 2H) 2.67-2.85 (m, 2H). MS (ESI+) m/z 484 $(M+H)^+$.

Example 29 ethyl[3-(4-methoxy-1-methyl-6-oxo-1,6-dihydropyridazin-3-yl)-4-phenoxyphenyl]carbamate A mixture of Example 20C (0.03 g, 0.093 mmol), ethyl carbonochloridate (0.015 g, 0.139 mmol), and triethylamine (0.028 g, 0.278 mmol) in dichloromethane (1 mL) was stirred at room temperature for 1 hour. The solvent was removed, and the residue was purified by reverse phase HPLC (C18, CH$_3$CN/water (0.1% TFA), 0-100%) to afford 0.030 g (81%) of the title compound. $^1$H NMR (500 MHz, DMSO-d$_6$) δ 9.71 (s, 1H), 7.48-7.51 (m, 2H), 7.29-7.33 (m, 2H), 7.05 (t, J=7.48 Hz, 1H), 6.96 (d, J=8.85 Hz, 1H), 6.88 (d, J=7.63 Hz, 2H), 6.27 (s, 1H), 4.12 (q, J=7.02 Hz, 2H), 3.57 (s, 3H), 3.55 (s, 3H), 1.24 (t, J=7.02 Hz, 3H). MS (DCI+) m/z 396.2 (M+H)$^+$.

Example 30

1-ethyl-3-[3-(4-methoxy-1-methyl-6-oxo-1,6-dihydropyridazin-3-yl)-4-phenoxyphenyl]urea A mixture of Example 20C (0.03 g, 0.093 mmol), isocyanatoethane (0.019 g, 0.269 mmol), and triethylamine (0.027 g, 0.269 mmol) in dichloromethane (1 mL) was stirred at 43° C. overnight. The solvent was removed, and the residue was purified by reverse phase HPLC (C18, CH$_3$CN/water (0.1% TFA), 0-100%) to afford 0.019 g (51%) of the title compound. $^1$H NMR (500 MHz, DMSO-d$_6$) δ 8.54 (s, 1H), 7.52 (d, J=2.44 Hz, 1H), 7.38 (dd, J=8.85, 2.75 Hz, 1H), 7.28-7.31 (m, 2H), 7.03 (t, J=7.32 Hz, 1H), 6.90 (d, J=8.54 Hz, 1H), 6.87 (d, J=7.63 Hz, 2H), 6.26 (s, 1H), 3.56 (s, 3H), 3.55 (s, 3H), 3.10 (q, J=7.22 Hz, 2H), 1.05 (t, J=7.17 Hz, 3H). MS (DCI+) m/z 395.2 (M+H)$^+$.

Example 31

N'-[3-(4-methoxy-1-methyl-6-oxo-1,6-dihydropyridazin-3-yl)-4-phenoxyphenyl]-N,N-dimethylsulfuric diamide Example 31 was prepared according to the procedure of Example 26 substituting dimethylsulfamoyl chloride for cyclopentanesulfonyl chloride to afford the title compound (0.013 g, 25%). $^1$H NMR (300 MHz, DMSO-d$_6$) δ 9.92 (s, 1H) 7.26-7.35 (m, 3H) 7.20 (d, J=2.78 Hz, 1H) 7.06 (t, J=7.34 Hz, 1H) 6.97 (d, J=8.72 Hz, 1H) 6.89 (d, J=7.54 Hz, 2H) 6.28 (s, 1H) 3.59 (s, 3H) 3.55 (s, 3H) 2.73 (s, 6H). MS (ESI+) m/z 432 (M+H)$^+$.

Example 32

4-[2-(4-methoxy-1-methyl-6-oxo-1,6-dihydropyridazin-3-yl)phenoxy]benzonitrile

Example 32A 6-(2-hydroxyphenyl)-5-methoxy-2-methylpyridazin-3(2H)-one

Example 32A was prepared according to the procedure used for the preparation of Example 9A, substituting Example 18C for Example 1A, and substituting 2-(4,4,5,5-tetramethyl-1,3,2-dioxaborolan-2-yl)phenol for 2-fluoro-5-nitrophenylboronic acid, respectively, to provide the title compound.

Example 32B

4-[2-(4-methoxy-1-methyl-6-oxo-1,6-dihydropyridazin-3-yl)phenoxy]benzonitrile

Example 32B was prepared according to the procedure used for the preparation of Example 9B, substituting Example 32A for phenol, and substituting 4-fluorobenzonitrile for Example 9A, respectively, to provide crude material. The crude mixture was purified by reverse phase HPLC (C18, CH$_3$CN/water (0.1% TFA), 0-100%) to afford the title compound. $^1$H NMR (500 MHz, DMSO-d$_6$) δ 7.79-7.82 (m, 2H), 7.54-7.58 (m, 1H), 7.50 (dd, J=7.78, 1.68 Hz, 1H), 7.35-7.38 (m, 1H), 7.20 (d, J=8.24 Hz, 1H), 7.03-7.06 (m, 2H), 6.28 (s, 1H), 3.53 (s, 3H), 3.51 (s, 3H). MS (ESI+) m/z 334.2 (M+H)$^+$.

Example 33

6-[2-(4-fluorophenoxy)phenyl]-5-methoxy-2-methylpyridazin-3(2H)-one

A mixture of Example 32A (0.035 g, 0.015 mmol), 4-fluorophenylboronic acid (0.042 g, 0.03 mmol), copper (II) acetate (0.027 g, 0.015 mmol), triethylamine (0.076 g, 0.750 mmol) and molecular sieves 4 Å (0.05 g) in dichloromethane (2 mL) was stirred overnight. The solid was removed by filtration, and the filtrate was concentrated. The residue was purified by reverse phase HPLC (C18, CH$_3$CN/water (0.1% TFA), 0-100%) to afford 0.019 g (31%) of the title compound. $^1$H NMR (500 MHz, DMSO-d$_6$) δ 7.40-7.47 (m, 2H), 7.17-7.24 (m, 3H), 6.97-7.00 (m, 2H), 6.92 (d, J=7.32 Hz, 1H), 6.31 (s, 1H), 3.64 (s, 3H), 3.58 (s, 3H). MS (ESI+) m/z 327.1 (M+H)$^+$.

Example 34

6-[2-(3-chloro-4-fluorophenoxy)phenyl]-5-methoxy-2-methylpyridazin-3(2H)-one

Example 34 was prepared according to the procedure used for the preparation of Example 33, substituting 4-fluoro3-chlorophenylboronic acid for 4-fluorophenylboronic acid, to provide the title compound. $^1$H NMR (500 MHz, DMSO-d$_6$) δ 7.37-7.52 (m, 3H), 7.26-7.30 (m, 1H), 7.14 (dd, J=6.26, 2.9 Hz, 1H), 7.06 (d, J=7.32 Hz, 1H), 6.93-6.97 (m, 1H), 6.31 (s, 1H), 3.62 (s, 3H), 3.57 (s, 3H). MS (ESI+) m/z 361.1 (M+H)$^+$.

Example 35

5-methoxy-6-[2-(4-methoxyphenoxy)phenyl]-2-methylpyridazin-3(2H)-one

Example 35 was prepared according to the procedure used for the preparation of Example 33, substituting 4-methoxyphenylboronic acid for 4-fluorophenylboronic acid, to provide the title compound. $^1$H NMR (500 MHz, DMSO-d$_6$) δ 7.36-7.42 (m, 3H), 7.13-7.17 (m, 1H), 6.93 (s, 4H), 6.80 (d, J=8.24 Hz, 1H), 6.32 (s, 1H), 3.73 (s, 3H), 3.69 (s, 3H), 3.60 (s, 3H). MS (ESI+) m/z 339.1 (M+H)$^+$.

Example 36

6-[2-(3-fluorophenoxy)phenyl]-5-methoxy-2-methylpyridazin-3(2H)-one

Example 36 was prepared according to the procedure used for the preparation of Example 33, substituting 3-fluorophenylboronic acid for 4-fluorophenylboronic acid, to provide the title compound. $^1$H NMR (500 MHz, DMSO-d$_6$) δ 7.44-7.52 (m, 2H), 7.34-7.40 (m, 1H), 7.29 (t, J=7.48 Hz, 1H), 7.08 (d, J=8.24 Hz, 1H), 6.91-6.95 (m, 1H), 6.76 (dd, J=9, 1.37 Hz, 2H), 6.32 (s, 1H), 3.59 (s, 3H), 3.56 (s, 3H). MS (DCI+) m/z 327.2 (M+H)+.

Example 37

6-[2-(4-chlorophenoxy)phenyl]-5-methoxy-2-methylpyridazin-3(2H)-one

A mixture of Example 32A (0.035 g, 0.15 mmol), 1-chloro-4-iodobenzene (0.054 g, 0.225 mmol), copper(I) iodide (0.00714 g, 0.0038 mmol), picolinic acid (0.00923 g, 0.075 mmol) and tripotassium phosphate (0.064 g, 0.30 mmol) in toluene (1 mL) was degassed and back-filled with nitrogen three times. The reaction mixture was heated at 110° C. overnight. After cooling, the reaction mixture was partitioned between water and ethyl acetate. The aqueous layer was extracted with additional ethyl acetate twice. The combined organic layers were washed with brine, dried over MgSO$_4$, filtered, and concentrated under reduced pressure. The residue was purified by reverse phase HPLC (C18, CH$_3$CN/water (0.1% TFA), 0-100%) to afford 0.038 g (75%) of the title compound. $^1$H NMR (500 MHz, DMSO-d$_6$) δ 7.37-7.50 (m, 1H), 7.24-7.28 (m, 1H), 7.04 (d, J=8.24 Hz, 1H), 6.94-6.98 (m, 2H), 6.30 (s, 1H), 3.60 (s, 3H), 3.57 (s, 3H). MS (DCI+) m/z 343.2 (M+H)+.

Example 38 methyl{[1-methyl-6-oxo-3-(2-phenoxyphenyl)-1,6-dihydropyridazin-4-yl]oxy}acetate

Example 38A ethyl 2-(3-chloro-1-methyl-6-oxo-1,6-dihydropyridazin-4-yloxy)acetate

Ethyl 2-hydroxyacetate (0.208 g, 2.0 mmol) in tetrahydrofuran (5 mL) was treated with sodium hydride (0.080 g, 2.0 mmol, 60% dispersion in mineral oil) for 5 minutes. To this solution was added Example 18B (0.179 g, 1.0 mmol). The reaction mixture was stirred at room temperature overnight. The reaction mixture was partitioned between water and ethyl acetate. The aqueous layer was extracted with additional ethyl acetate twice. The combined organic layers were washed with brine, dried over MgSO$_4$, filtered, and concentrated under reduced pressure. The residue was purified by flash column chromatography on silica gel eluting with 70% ethyl acetate in hexanes to afford 0.128 g (52%) of the title compound.

Example 38B methyl{[1-methyl-6-oxo-3-(2-phenoxyphenyl)-1,6-dihydropyridazin-4-yl]oxy}acetate Example 38B was prepared according to the procedure used for the preparation of Example 1B, substituting Example 38A for Example 1A, to provide the title compound. $^1$H NMR (500 MHz, DMSO-d$_6$) δ 7.60-7.64 (m, 1H), 7.40-7.47 (m, 2H), 7.32-7.38 (m, 2H), 7.21-7.25 (m, 1H), 7.10 (t, J=7.32 Hz, 1H), 6.91-6.98 (m, 3H), 6.39 (s, 1H), 4.82 (s, 2H), 3.66 (s, 3H), 3.53 (s, 3H). MS (ESI+) m/z 367.1 (M+H)+.

Example 39

6-[2-(cyclohexyloxy)phenyl]-5-methoxy-2-methylpyridazin-3(2H)-one

A mixture of the product from Example 32A (0.046 g, 0.2 mmol), cyclohexanol (0.022 mL, 0.210 mmol) and triphenylphosphine (0.055 g, 0.210 mmol) in tetrahydrofuran (0.1 mL) was sonicated until the solids dissolved. With continued sonication, diisopropyl azodicarboxylate (0.041 mL, 0.210 mmol) was added and sonication continued for 20 minutes. Purification by chromatography (silica gel, 0-70% ethyl acetate in hexane) afforded the title compound (0.030 g, 48%). $^1$H NMR (300 MHz, DMSO-d$_6$) δ 7.33-7.41 (m, 1H) 7.21 (dd, J=7.54, 1.59 Hz, 1H) 7.06 (d, J=8.33 Hz, 1H) 6.95 (t, J=6.94 Hz, 1H) 6.33 (s, 1H) 4.28-4.44 (m, 1H) 3.72 (s, 3H) 3.60 (s, 3H) 1.69-1.86 (m, 2H) 1.49-1.62 (m, J=8.93, 6.15 Hz, 2H) 1.16-1.49 (m, 6H). MS (ESI+) m/z 315 (M+H)+.

Example 40

5-methoxy-2-methyl-6-[2-(pyridin-2-ylmethoxy)phenyl]pyridazin-3(2H)-one

The product from Example 32A (0.046 g, 0.2 mmol), 2-(bromomethyl)pyridine hydrobromide (0.066 g, 0.260 mmol), and potassium carbonate (0.069 g, 0.500 mmol) were combined in dimethylformamide (1.0 mL) and stirred for 16 hours. The reaction mix was partitioned between ethyl acetate and water. The organic layer was separated and concentrated. Purification by chromatography (silica gel, 0-4% methanol in dichloromethane) afforded the title compound (0.030 g, 46%). $^1$H NMR (300 MHz, DMSO-d$_6$) δ 8.55 (d, J=3.97 Hz, 1H) 7.78-7.87 (m, 1H) 7.37-7.45 (m, 1H) 7.22-7.35 (m, 3H) 7.14 (d, J=7.93 Hz, 1H) 7.04 (t, J=7.54 Hz, 1H) 6.36 (s, 1H) 5.18 (s, 2H) 3.69 (s, 3H) 3.61 (s, 3H). MS (ESI+) m/z 324 (M+H)+.

Example 41

6-[2-(1H-indazol-5-ylmethoxy)phenyl]-5-methoxy-2-methylpyridazin-3(2H)-one

Example 41 was prepared according to the procedure of Example 40 substituting 5-(bromomethyl)-1H-indazole hydrobromide for 2-(bromomethyl)pyridine hydrobromide. Purification by reverse phase HPLC (C18, 0-100% CH$_3$CN/water (0.1% TFA)) afforded the title compound (0.007 g, 10%). $^1$H NMR (300 MHz, DMSO-d$_6$) δ 13.07 (s, 1H) 8.05 (s, 1H) 7.70 (s, 1H) 7.53 (d, J=8.72 Hz, 1H) 7.37-7.46 (m, 1H) 7.18-7.30 (m, 3H) 7.01 (t, J=6.94 Hz, 1H) 6.32 (s, 1H) 5.19 (s, 2H) 3.72 (s, 3H) 3.58 (s, 3H). MS (ESI+) m/z 363 (M+H)+.

Example 42

6-[2-(2-cyclohexylethoxy)phenyl]-5-methoxy-2-methylpyridazin-3(2H)-one

Example 42 was prepared according to the procedure of Example 40, substituting (2-bromoethyl)cyclohexane for 2-(bromomethyl)pyridine hydrobromide and heating the reaction mixture at 50° C. for 6 hours. Purification by chromatography (silica gel, 0-100% ethyl acetate in hexane) afforded the title compound (0.038 g, 63%). $^1$H NMR (300 MHz, DMSO-d$_6$) δ 7.35-7.45 (m, 1H) 7.21 (dd, J=7.54, 1.59

Hz, 1H) 7.07 (d, J=7.54 Hz, 1H) 6.98 (t, J=7.93 Hz, 1H) 6.36 (s, 1H) 3.97 (t, J=6.35 Hz, 2H) 3.71 (s, 3H) 3.60 (s, 3H) 1.56-1.67 (m, 5H) 1.46 (q, J=6.61 Hz, 2H) 1.03-1.36 (m, 4H) 0.72-0.98 (m, J=11.11 Hz, 2H). MS (ESI+) m/z 343 (M+H)$^+$.

Example 43 tert-butyl 4-{[2-(4-methoxy-1-methyl-6-oxo-1,6-dihydropyridazin-3-yl)phenoxy]methyl}piperidine-1-carboxylate Example 43 was prepared according to the procedure of Example 40 substituting 4-bromomethyl-piperidine-1-carboxylic acid tert-butyl ester for 2-(bromomethyl)pyridine hydrobromide and heating the reaction mixture at 50° C. for 6 hours. Purification by chromatography (silica gel, 0-100% ethyl acetate in hexane) afforded the title compound (0.030 g, 31%). $^1$H NMR (300 MHz, DMSO-d$_6$) δ 7.35-7.44 (m, 1H) 7.21 (dd, J=7.54, 1.98 Hz, 1H) 7.07 (d, J=8.33 Hz, 1H) 6.99 (t, J=7.34 Hz, 1H) 6.33 (s, 1H) 3.91 (d, J=12.69 Hz, 2H) 3.83 (d, J=5.95 Hz, 2H) 3.71 (s, 3H) 3.60 (s, 3H) 2.62-2.75 (m, 2H) 1.70-1.87 (m, 1H) 1.53-1.60 (m, 2H) 1.38 (s, 9H) 0.96-1.13 (m, 2H). MS (ESI+) m/z 430 (M+H)$^+$.

Example 44

5-methoxy-2-methyl-6-[2-(piperidin-4-ylmethoxy)phenyl]pyridazin-3(2H)-one

The product from Example 43 (0.028 g, 0.065 mmol) in dichloromethane (1 mL) was treated with trifluoroacetic acid (0.3 mL, 3.89 mmol), stirred for 1 hour and concentrated. Purification by reverse phase HPLC (C18, 0-100% CH$_3$CN/water (0.1% TFA)) afforded the TFA salt of the title compound (0.015 g, 51%). $^1$H NMR (300 MHz, DMSO-d$_6$) δ 8.47 (d, J=9.52 Hz, 1H) 8.15 (d, J=7.54 Hz, 1H) 7.38-7.46 (m, 1H) 7.23 (dd, J=7.54, 1.59 Hz, 1H) 7.10 (d, J=7.93 Hz, 1H) 7.01 (t, J=7.14 Hz, 1H) 6.34 (s, 1H) 3.85 (d, J=6.35 Hz, 2H) 3.61 (s, 3H) 3.73 (s, 3H) 3.24-3.31 (m, 2H) 2.87 (q, J=11.24 Hz, 2H) 1.87-2.02 (m, 1H) 1.75 (d, J=12.70 Hz, 2H) 1.23-1.41 (m, 2H). MS (ESI+) m/z 330 (M+H)$^+$.

Example 45

5-methoxy-2-methyl-6-[2-(pyridin-4-ylmethoxy)phenyl]pyridazin-3(2H)-one

Example 45 was prepared according to the procedure of Example 40 substituting 4-(bromomethyl)pyridine hydrobromide for 2-(bromomethyl)pyridine hydrobromide. Purification by chromatography (silica gel, 0-6% methanol in dichloromethane) afforded the title compound (0.022 g, 38%). $^1$H NMR (300 MHz, DMSO-d$_6$) δ 8.51-8.59 (m, 2H) 7.37-7.46 (m, 1H) 7.21-7.32 (m, 3H) 6.99-7.14 (m, 2H) 6.37 (s, 1H) 5.20 (s, 2H) 3.70 (s, 3H) 3.62 (s, 3H). MS (ESI+) m/z 324 (M+H)$^+$.

Example 46

6-[2-(cyclopentylmethoxy)phenyl]-5-methoxy-2-methylpyridazin-3(2H)-one

Example 46 was prepared according to the procedure of Example 40 substituting iodomethylcyclopentane for 2-(bromomethyl)pyridine hydrobromide and heating the reaction mixture at 50° C. for 6 hours. Purification by reverse phase HPLC (C18, 0-100% CH$_3$CN/water (0.1% TFA)) afforded the title compound (0.008 g, 14%). $^1$H NMR (300 MHz, DMSO-d$_6$) δ 7.35-7.44 (m, 1H) 7.21 (dd, J=7.54, 1.59 Hz, 1H) 7.05 (d, J=7.54 Hz, 1H) 6.98 (t, J=7.93 Hz, 1H) 6.34 (s, 1H) 3.83 (d, J=6.35 Hz, 2H) 3.71 (s, 3H) 3.60 (s, 3H) 2.08-2.23 (m, 1H) 1.56-1.69 (m, 2H) 1.42-1.52 (m, 4H) 1.11-1.29 (m, 2H). MS (ESI+) m/z 315 (M+H)$^+$.

Example 47

5-methoxy-2-methyl-6-[2-(tetrahydro-2H-pyran-4-ylmethoxy)phenyl]pyridazin-3(2H)-one Example 47 was prepared according to the procedure of Example 40 substituting 4-(bromomethyl)tetrahydropyran for 2-(bromomethyl)pyridine hydrobromide and heating the reaction mixture at 50° C. for 6 hours. Purification by reverse phase HPLC (C18, 0-100% CH$_3$CN/water (0.1% TFA)) afforded the title compound (0.025 g, 43%). $^1$H NMR (300 MHz, DMSO-d$_6$) δ 7.36-7.44 (m, 1H) 7.21 (dd, J=7.46, 2.03 Hz, 1H) 7.07 (d, J=7.80 Hz, 1H) 6.99 (t, J=7.46 Hz, 1H) 3.79-3.86 (m, 2H) 6.34 (s, 1H) 3.82 (d, J=6.44 Hz, 2H) 3.71 (s, 3H) 3.60 (s, 3H) 3.21-3.31 (m, 2H) 1.74-1.96 (m, 1H) 1.49 (dd, J=12.72, 1.86 Hz, 2H) 1.13-1.30 (m, 2H). MS (ESI+) m/z 331 (M+H)$^+$.

Example 48 methyl 1-[1-methyl-6-oxo-3-(2-phenoxyphenyl)-1,6-dihydropyridazin-4-yl]pyrrolidine-3-carboxylate Example 48A methyl 1-(3-chloro-1-methyl-6-oxo-1,6-dihydropyridazin-4-yl)pyrrolidine-3-carboxylate A mixture of Example 18B (0.179 g, 1.0 mmol), methyl pyrrolidine-3-carboxylate, hydrochloric acid (0.364 g, 2.2 mmol), and triethylamine (0.405 g. 4.0 mmol) in ethanol (5 mL) was heated under reflux for 16 hours. The solvent was removed, and the crude product was used directly for the next reaction.

Example 48B methyl 1-[1-methyl-6-oxo-3-(2-phenoxyphenyl)-1,6-dihydropyridazin-4-yl]pyrrolidine-3-carboxylate Example 48B was prepared according to the procedure used for the preparation of Example 9A, substituting Example 48A for Example 1A, and substituting 2-phenoxyphenylboronic acid for 2-fluoro-5-nitrophenylboronic acid, respectively, to provide the title compound. $^1$H NMR (500 MHz, DMSO-d$_6$) δ 7.43-7.48 (m, 2H), 7.33-7.36 (m, 2H), 7.32-7.38 (m, 1H), 7.11 (t, J=7.32 Hz, 1H), 6.92-6.93 (m, 3H), 5.64 (s, 1H), 4.82 (s, 2H), 3.59 (s, 3H), 3.46 (s, 3H) 3.00-3.15 (m, 5H), 1.99-2.06 (m, 2H). MS (DCI+) m/z 406.1 (M+H)$^+$.

Example 49 ethyl 1-[1-methyl-6-oxo-3-(2-phenoxyphenyl)-1,6-dihydropyridazin-4-yl]pyrrolidine-3-carboxylate Example 49 was isolated as a by-product during the formation of Example 48B. $^1$H NMR (500 MHz, DMSO-d$_6$) δ 7.42-7.48 (m, 2H), 7.33-7.36 (m, 2H), 7.22 (t, J=7.48 Hz, 1H), 7.12 (t, J=7.32 Hz, 1H), 6.91-6.92 (m, 3H), 5.64 (s, 1H), 4.02-4.07 (s, 2H), 3.46 (s, 3H), 3.02-3.17 (m, 5H), 1.84-2.08 (m, 2H), 1.13 (t, J=7.02 Hz, 3H). MS (DCI+) m/z 420.2 (M+H)+.

Example 50 methyl N-[1-methyl-6-oxo-3-(2-phenoxyphenyl)-1,6-dihydropyridazin-4-yl]glycinate

Example 50A methyl 2-(3-chloro-1-methyl-6-oxo-1,6-dihydropyridazin-4-ylamino)acetate A mixture of Example 18B (0.179 g, 1.0 mmol), 2-amino-N-methylacetamide, hydrochloric acid (0.374 g, 3 mmol), and triethylamine (0.506 g. 5.0 mmol) in ethanol (10 mL) was heated under reflux for 16 hours. After cooling, more 2-amino-N-methylacetamide, hydrochloric acid (0.374 g, 3 mmol), and triethylamine (0.506 g. 5.0 mmol) were added. The reaction mixture was heated under reflux overnight. The solvent was removed, and the residue was taken up to ethyl acetate. It was washed with water. The aqueous layer was extracted with additional ethyl acetate three times. The combined organic layers were washed with brine, dried over $MgSO_4$, filtered, and concentrated. The residue was purified by flash column chromatography on silica gel eluting with 40-80% ethyl acetate in hexanes to afford 0.135 g (55%) of the title compound.

Example 50B methyl N-[1-methyl-6-oxo-3-(2-phenoxyphenyl)-1,6-dihydropyridazin-4-yl]glycinate Example 50B was prepared according to the procedure used for the preparation of Example 1B, substituting Example 50A for Example 1A, to provide the title compound. $^1$H NMR (500 MHz, DMSO-$d_6$) δ 7.47-7.50 (m, 2H), 7.40 (dd, J=7.63, 1.83 Hz, 1H), 7.33-7.36 (m, 2H), 7.24-7.27 (m, 1H), 7.12 (t, J=7.32 Hz, 1H), 7.05-7.06 (m, 3H), 6.92 (d, J=7.63 Hz, 1H), 5.96 (t, J=6.26, Hz, 1H), 5.62 (s, 1H), 3.90 (d, J=5.8 Hz, 1H), 3.59 (s, 3H), 3.47 (s, 3H). MS (DCI+) m/z 366.2 (M+H)+.

Example 51

2-methyl-5-(4-methyl-3-oxopiperazin-1-yl)-6-(2-phenoxyphenyl)pyridazin-3(2H)-one

Example 51A 6-chloro-2-methyl-5-(4-methyl-3-oxopiperazin-1-yl)pyridazin-3(2H)-one A mixture of Example 18B (0.179 g, 1.0 mmol), 1-methylpiperazin-2-one, hydrochloric acid (0.301 g, 2 mmol), and triethylamine (0.405 g 4.0 mmol) in ethanol (10 mL) was heated under reflux for 16 hours. The solvent was removed, and the residue was purified by flash column chromatography on silica gel eluting with 1-5% methanol in ethyl acetate to afford 0.21 g (82%) of the title compound.

Example 51B 2-methyl-5-(4-methyl-3-oxopiperazin-1-yl)-6-(2-phenoxyphenyl)pyridazin-3(2H)-one Example 50B was prepared according to the procedure used for the preparation of Example 1B, substituting Example 51A for Example 1A, to provide the title compound. $^1$H NMR (500 MHz, DMSO-$d_6$) δ 7.54 (dd, J=7.63, 1.83 Hz, 1H), 7.46-7.49 (m, 1H), 7.31-7.35 (m, 2H), 7.28 (t, J=7.63 Hz, 1H), 7.1 (t, J=7.32 Hz, 1H), 7.01 (d, J=8.24 Hz, 1H), 6.98-6.91 (m, 2H), 6.14 (s, 1H), 3.51 (s, 3H), 3.34 (br s, 2H), 3.09 (br 2, 2H), 2.93 (br s, 2H), 2.78 (s, 3H). MS (ESI+) m/z 391.1 (M+H)+.

Example 52

6-(biphenyl-2-yl)-2-methylpyridazin-3(2H)-one

Example 52A 2-(1-methyl-6-oxo-1,6-dihydropyridazin-3-yl)phenyl trifluoromethanesulfonate A mixture of 6-(2-hydroxyphenyl)-2-methylpyridazin-3 (2H)-one (1.24 g, 6.13 mmol), 1,1,1-trifluoro-N-phenyl-N-(trifluoromethylsulfonyl)methanesulfonamide (2.41 g, 6.75 mmol), and triethylamine (0.745 g, 7.36 mmol) in dichloromethane (35 mL) was stirred at ambient temperature for 16 h. The reaction mixture was concentrated under reduced pressure, and the residue purified by flash chromatography (silica gel, 10-30% ethyl acetate/hexane gradient) to provide the title compound.

Example 52B 6-(biphenyl-2-yl)-2-methylpyridazin-3(2H)-one

A mixture of Example 52A (0.232 g, 0.694 mmol), phenylboronic acid (0.102 g, 0.833 mmol) and $PdCl_2$(dppf) (0.025 g, 0.035 mmol) in dioxane (4 mL) and 2M aqueous sodium carbonate (2 mL) was heated at 70° C. for 4 hours. The reaction mixture was cooled to ambient temperature, partitioned between ethyl acetate and brine, and the organic layer separated, dried (anhydrous sodium sulfate), filtered, and concentrated. The residue was purified by flash chromatography (silica gel, 10-50% ethyl acetate/hexane gradient) to provide the title compound. $^1$H NMR (300 MHz, DMSO-$d_6$) δ 7.43-7.63 (m, 4H) 7.30-7.39 (m, 3H) 7.18-7.26 (m, 2H) 6.83 (d, J=9.51 Hz, 1H) 6.67 (d, J=9.51 Hz, 1H) 3.64 (s, 3H). MS (ESI+) m/z 263.1 (M+H)+.

Example 53

2'-(1-methyl-6-oxo-1,6-dihydropyridazin-3-yl)biphenyl-3-carbonitrile

Example 53 was prepared according to the procedure used for the preparation of Example 52B, substituting 3-cyanophenylboronic acid for phenylboronic acid, to provide the title compound. $^1$H NMR (300 MHz, DMSO-$d_6$) δ 7.78-7.83 (m, 1H) 7.75 (t, J=1.53 Hz, 1H) 7.43-7.66 (m, 6H) 7.04 (d, J=9.49 Hz, 1H) 6.76 (d, J=9.49 Hz, 1H) 3.57 (s, 3H). MS (ESI+) m/z 288.3 (M+H)+.

Example 54

5-(2-fluoropyridin-4-yl)-2-methyl-6-(2-phenoxyphenyl)pyridazin-3(2H)-one

Example 54A 6-chloro-5-(2-fluoropyridin-4-yl)-2-methylpyridazin-3(2H)-one

Example 54A was prepared according to the procedure used for the preparation of Example 9A, substituting Example 18B for Example 1A, and substituting 2-fluoropyridin-4-ylboronic acid for 2-fluoro-5-nitrophenylboronic acid, respectively, to provide the title compound.

Example 54B 5-(2-fluoropyridin-4-yl)-2-methyl-6-(2-phenoxyphenyl)pyridazin-3(2H)-one Example 54B was prepared according to the procedure used for the preparation of Example 9A, substituting Example 54A for Example 1A, and substituting 2-phenoxyphenylboronic acid for 2-fluoro-5-nitrophenylboronic acid, respectively, to provide the title compound. $^1$H NMR (500 MHz, DMSO-$d_6$) δ 8.13 (d, J=5.13 Hz, 1H), 7.64 (dd, J=7.51, 1.65 Hz, 1H), 7.37-7.41 (m, 2H), 7.24-7.27 (m, 3H), 7.07-7.10 (m, 2H), 6.99 (s, 1H), 6.63 (d, J=8.43 Hz, 1H), 6.38-6.39 (m, 2H), 3.73 (s, 3H). MS (ESI+) m/z 374.1 (M+H)$^+$.

Example 55

2-methyl-5-(2-oxo-1,2-dihydropyridin-4-yl)-6-(2-phenoxyphenyl)pyridazin-3(2H)-one Example 54B (0.032 g, 0.086 mmol) in acetic acid (4 mL) and water (1 mL) was heated at 100° C. overnight. The solvents were removed under reduced pressure. The residue was purified by reverse phase HPLC (C18, CH$_3$CN/water (0.1% TFA), 0-100%) to afford 0.028 g (88%) of the title compound. $^1$H NMR (500 MHz, DMSO-$d_6$) δ 7.56 (dd, J=7.63, 1.53 Hz, 1H), 7.37-7.41 (m, 1H), 7.27-7.29 (m, 2H), 7.21-7.25 (m, 2H), 7.10 (t, J=7.48 Hz, 1H), 6.98 (s, 1H), 6.70 (d, J=7.32 Hz, 1H), 6.93-6.95 (m, 2H), 6.07 (d, J=1.22 Hz, 1H), 5.92 (dd, J=6.71, 1.83 Hz, 1H), 3.69 (s, 3H). MS (DCI+) m/z 372.2 (M+H)$^+$.

Example 56

2-methyl-5-(1-methyl-2-oxo-1,2-dihydropyridin-4-yl)-6-(2-phenoxyphenyl)pyridazin-3(2H)-one Example 56 was prepared according to the procedure used for the preparation of Example 1A, substituting Example 55 for 6-chloropyridazin-3(2H)-one, except that the crude product was purified by reverse phase HPLC (C18, CH$_3$CN/water (0.1% TFA), 0-100%) to provide the title compound. $^1$H NMR (500 MHz, DMSO-$d_6$) δ 7.58 (dd, J=7.63, 1.53 Hz, 1H), 7.51 (d, J=7.02 Hz, 1H), 7.38-7.41 (m, 1H), 7.23-7.30 (m, 3H), 7.08 (t, J=7.32 Hz, 1H), 6.98 (s, 1H), 6.74 (d, J=7.32 Hz, 1H), 6.59-6.61 (m, 2H), 6.10 (d, J=1.83 Hz, 1H), 5.94 (dd, J=6.71, 1.83 Hz, 1H), 3.70 (s, 3H), 3.35 (s, 3H). MS (DCI+) m/z 386.2 (M+H)$^+$.

Example 57

5-(2-methoxypyridin-4-yl)-2-methyl-6-(2-phenoxyphenyl)pyridazin-3(2H)-one

Methanol (2 mL) was cooled to 0° C. To this solvent was added sodium (0.0248 g, 1.08 mmol). All sodium was dissolved completely within 10 minutes. To this solution was added Example 54B (0.08 g, 0.216 mmol). The reaction mixture was stirred at 60° C. for 10 hours. The solvent was removed, and the residue was purified by reverse phase HPLC (C18, CH$_3$CN/water (0.1% TFA), 0-100%) to provide the title compound. $^1$H NMR (500 MHz, DMSO-$d_6$) δ 8.03 (d, J=5.19 Hz, 1H), 7.61 (dd, J=7.63, 1.83 Hz, 1H), 7.35-7.39 (m, 1H), 7.21-7.27 (m, 3H), 7.08 (t, J=7.32 Hz, 1H), 7.03 (s, 1H), 6.70 (dd, J=5.19, 1.53 Hz, 1H), 6.56-6.62 (m, 2H), 6.36-6.40 (m, 2H), 3.76 (s, 3H), 3.72 (s, 3H). MS (DCI+) m/z 386.2 (M+H)$^+$.

Example 58

N-{3-[4-(2-methoxypyridin-4-yl)-1-methyl-6-oxo-1,6-dihydropyridazin-3-yl]-4-phenoxyphenyl}methanesulfonamide Example 58A 6-chloro-5-(2-methoxypyridin-4-yl)-2-methylpyridazin-3(2H)-one Example 58A was prepared according to the procedure used for the preparation of Example 57, substituting Example 54A for Example 54B, to provide the title compound.

Example 58B 6-(2-fluoro-5-nitrophenyl)-5-(2-methoxypyridin-4-yl)-2-methylpyridazin-3(2H)-one Example 54B was prepared according to the procedure used for the preparation of Example 9A, substituting Example 58A for Example 1A, to provide the title compound.

Example 58C 5-(2-methoxypyridin-4-yl)-2-methyl-6-(5-nitro-2-phenoxyphenyl)pyridazin-3(2H)-one Example 54B was prepared according to the procedure used for the preparation of Example 9B, substituting Example 58B for Example 9A, to provide the title compound.

Example 58D 6-(5-amino-2-phenoxyphenyl)-5-(2-methoxypyridin-4-yl)-2-methylpyridazin-3(2H)-one Example 58D was prepared according to the procedure used for the preparation of Example 10, substituting Example 58D for Example 9B, to provide the title compound.

Example 58E

N-{3-[4-(2-methoxypyridin-4-yl)-1-methyl-6-oxo-1,6-dihydropyridazin-3-yl]-4-phenoxyphenyl}methanesulfonamide Example 58D was prepared according to the procedure used for the preparation of Example 22, substituting Example 58E for Example 20C, to provide the title compound. $^1$H NMR (500 MHz, DMSO-$d_6$) δ 9.76 (s, 1H), 8.04 (d, J=5.19 Hz, 1H), 7.43 (d, J=2.75 Hz, 1H), 7.19-7.24 (m, 3H), 7.05 (t, J=7.32 Hz, 1H), 7.02 (s, 1H), 6.72 (dd, J=5.34, 1.37 Hz, 1H), 6.68 (d, J=8.85 Hz, 1H), 6.57 (s, 1H), 6.40 (d, J=7.63 Hz, 2H), 3.77 (s, 3H), 3.70 (s, 3H), 2.99 (s, 3H). MS (ESI+) m/z 479.0 (M+H)$^+$.

Example 59 ethyl 3-[1-methyl-6-oxo-3-(2-phenoxyphenyl)-1,6-dihydropyridazin-4-yl]benzoate

Example 18B (0.090 g, 0.5 mmol), 3-(ethoxycarbonyl)phenylboronic acid (0.107 g, 0.55 mmol), Pd(PPh$_3$)$_4$ (0.058 g, 0.05 mmol) and sodium carbonate (0.106 g, 1.0 mmol) were combined in toluene (4 mL), ethanol (1 mL) and water (1 mL) and the mixture was degassed and left under nitrogen. The reaction mixture was heated at 90° C. for 2 hours, and then cooled to room temperature. To this solution was he added 2-phenoxyphenylboronic acid (0.150 g, 1.4 mmol). The reaction mixture was heated under reflux overnight. After cooling to room temperature, the mixture was partitioned between ethyl acetate and water. The aqueous layer was extracted with additional ethyl acetate twice. The combined organic layers were washed with brine, dried (MgSO$_4$), filtered and concentrated. The crude product was purified by flash chromatography (silica gel, 20-50% ethyl acetate in hexanes) to provide crude material, which was further purified by reverse HPLC (C18, CH$_3$CN/water (0.1% TFA), 0-100%) to afford 0.11 g (52%) of the title compound. $^1$H NMR (500 MHz, DMSO-d$_6$) δ 7.90-7.92 (m, 1H), 7.67 (s, 1H), 7.61 (dd, J=7.63, 1.83 Hz, 1H), 7.40-7.46 (m, 2H), 7.19-7.24 (m, 3H), 7.32-7.35 (m, 1H), 7.17-7.23 (m, 3H), 7.03 (t, J=7.32 Hz, 1H), 7.00 (s, 1H), 6.56 (d, J=8.24 Hz, 1H), 6.32 (d, J=7.63 Hz, 2H), 4.21 (q, J=7.12 Hz, 2H), 3.73 (s, 3H), 1.23 (t, J=7.02 Hz, 3H). MS (DCI+) m/z 427.1 (M+H)$^+$.

Example 60

2-methyl-5-{3-[(4-methylpiperazin-1-yl)methyl]phenyl}-6-(2-phenoxyphenyl)pyridazin-3(2H)-one Syntheses were performed using a Personal Chemistry Ermy's optimizer microwave. Each microwave tube was charged with a stir bar and 0.1 equivalent of PdCl$_2$(PPh$_3$)$_2$ (15 mg). In the microwave tube, a solution of Example 18B (39 mg, 0.22 mmol) dissolved in dioxane (1.0 mL) was added, followed by the addition of 1-methyl-4-(3-(4,4,5,5-tetramethyl-1,3,2-dioxaborolan-2-yl)benzyl)piperazine (82 mg, 0.26 mmol) in dioxane (0.7 mL). Then, 434 μL of 1M aqueous solution of Cs$_2$CO$_3$ was added. The resulting mixture was heated in the microwave for 1800 seconds at 150° C. In the microwave vial with the previous mixture a solution of 2-phenoxyphenylboronic acid (26 mg, 0.12 mmol) in dioxane (0.5 mL), was added, along with 0.1 equivalent of PdCl$_2$(PPh$_3$)$_2$ (9 mg) and 246 μL of 1M aqueous solution of Cs$_2$CO$_3$. This was capped and placed back in the microwave to heat for 1800 seconds at 150° C. The reaction mixture was filtered, and concentrated to dryness. The residues were dissolved in 1:1 DMSO/MeOH. Purification by reverse phase HPLC (C18, CH$_3$CN/water (0.1% TFA), 0-100% gradient) provided the title compound as TFA salt. $^1$H NMR (500 MHz, DMSO-d$_6$) δ 7.67 (dd, J=7.63, 1.53 Hz, 1H), 7.29-7.39 (m, 4H), 7.22-7.26 (m, 3H), 7.01-7.15 (m, 3H), 6.94 (s, 1H), 6.91 (s, 1H), 6.54 (d, J=7.93 Hz, 1H), 6.32 (d, J=7.63 Hz, 1H), 3.73 (s, 3H), 3.52 (s, 2H), 2.77 (s, 3H). MS (ESI) m/z 467 (M+H)$^+$.

Example 61

2-methyl-5-{4-[(4-methylpiperazin-1-yl)methyl]phenyl}-6-(2-phenoxyphenyl)pyridazin-3(2H)-one Example 61 was prepared according to the procedure used for the preparation of Example 60, substituting 1-methyl-4-(4-(4,4,5,5-tetramethyl-1,3,2-dioxaborolan-2-yl)benzyl)piperazine for 1-methyl-3-(4-(4,4,5,5-tetramethyl-1,3,2-dioxaborolan-2-yl)benzyl)piperazine, to provide the title compound as TFA salt. $^1$H NMR (500 MHz, DMSO-d$_6$) δ 7.59 (dd, J=7.63, 1.83 Hz, 1H), 7.31-7.35 (m, 1H), 7.14-7.24 (m, 7H), 7.07 (t, J=7.48 Hz, 1H), 6.91 (s, 1H), 6.51 (d, J=8.24 Hz, 1H), 6.31 (d, J=8.54 Hz, 2H), 3.71 (s, 3H), 3.40 (br s, 2H), 2.96 (br s, 4H), 2.77 (s, 3H). MS (ESI) m/z 467.1 (M+H)$^+$.

Example 62

N-[3-(1-methyl-4-{4-[(4-methylpiperazin-1-yl)methyl]phenyl}-6-oxo-1,6-dihydropyridazin-3-yl)-4-phenoxyphenyl]methanesulfonamide

Example 62A 6-chloro-2-methyl-5-(4-((4-methylpiperazin-1-yl)methyl)phenyl)pyridazin-3(2H)-one Example 62A was prepared according to the procedure used for the preparation of Example 9A, substituting Example 18B for Example 1A, and substituting 1-methyl-4-(4-(4,4,5,5-tetramethyl-1,3,2-dioxaborolan-2-yl)benzyl)piperazine for 2-fluoro-5-nitrophenylboronic acid, respectively, to provide the title compound.

Example 62B 6-(2-fluoro-5-nitrophenyl)-2-methyl-5-(4-((4-methylpiperazin-1-yl)methyl)phenyl)pyridazin-3(2H)-one Example 62B was prepared according to the procedure used for the preparation of Example 9A, substituting Example 62A for Example 1A, to provide the title compound.

Example 62C 2-methyl-5-(4-((4-methylpiperazin-1-yl)methyl)phenyl)-6-(5-nitro-2-phenoxyphenyl)pyridazin-3(2H)-one Example 62C was prepared according to the procedure used for the preparation of Example 9B, substituting Example 62B for Example 9A, to provide the title compound.

Example 62D 6-(5-amino-2-phenoxyphenyl)-2-methyl-5-(4-((4-methylpiperazin-1-yl)methyl)phenyl)pyridazin-3(2H)-one Example 58D was prepared according to the procedure used for the preparation of Example 10, substituting Example 62D for Example 9B, to provide the title compound.

Example 62E

N-[3-(1-methyl-4-{4-[(4-methylpiperazin-1-yl)methyl]phenyl}-6-oxo-1,6-dihydropyridazin-3-yl)-4-phenoxyphenyl]methanesulfonamide Example 62E was prepared according to the procedure used for the preparation of Example 22, substituting Example 62D for Example 20C, to provide the title compound. $^1$H NMR (500 MHz, DMSO-$d_6$) δ 9.74 (s, 1H), 7.38 (d, J=2.75 Hz, 1H), 7.14-7.25 (m, 7H), 7.05 (t, J=7.32 Hz, 1H), 6.91 (s, 1H), 6.59 (d, J=8.85 Hz, 1H), 6.36 (d, J=7.63 Hz, 2H), 4.21 (q, J=7.12 Hz, 2H), 3.69 (s, 3H), 3.64 (s, 2H), 2.97 (br s, 4H), 2.77 (s, 3H). MS (ESI+) m/z 560.2 (M+H)$^+$.

Example 63

N-{3-[1-methyl-4-(4-methylphenyl)-6-oxo-1,6-dihydropyridazin-3-yl]-4-phenoxyphenyl}methanesulfonamide Example 63A 6-(5-amino-2-phenoxyphenyl)-2-methyl-5-p-tolylpyridazin-3(2H)-one The title compound was isolated as a by-product in preparation of Example 62D.

Example 63B

N-{3-[1-methyl-4-(4-methylphenyl)-6-oxo-1,6-dihydropyridazin-3-yl]-4-phenoxyphenyl}methanesulfonamide Example 63B was prepared according to the procedure used for the preparation of Example 22, substituting Example 63A for Example 20C, to provide the title compound. $^1$H NMR (500 MHz, DMSO-$d_6$) δ 9.72 (s, 1H), 7.36 (d, J=2.75 Hz, 1H), 7.16-7.22 (m, 3H), 7.02-7.08 (m, 5H), 6.87 (s, 1H), 6.61 (d, J=8.85 Hz, 1H), 6.35 (d, J=7.63 Hz, 2H), 3.86 (s, 3H), 2.95 (s, 2H), 2.29 (s, 3H). MS (ESI+) m/z 462.1 (M+H)$^+$.

Example 64

5-(3-amino-4-methylphenyl)-2-methyl-6-(2-phenoxyphenyl)pyridazin-3(2H)-one

Example 64 was prepared according to the procedure used for the preparation of Example 60, substituting 3-amino-4-methylphenylboronic acid for 1-methyl-3-(4-(4,4,5,5-tetramethyl-1,3,2-dioxaborolan-2-yl)benzyl)piperazine, to provide the title compound as TFA salt. $^1$H NMR (500 MHz, DMSO-$d_6$) δ 7.57 (dd, J=7.63, 1.53 Hz, 1H) 7.33-7.40 (m, 1H) 7.20-7.26 (m, 3H) 7.00-7.11 (m, 2H) 6.90 (d, J=1.53 Hz, 1H) 6.86 (s, 1H) 6.68 (dd, J=7.93, 1.53 Hz, 1H) 6.59 (d, J=7.63 Hz, 1H) 6.38 (d, J=7.63 Hz, 2H) 3.70 (s, 3H) 2.19 (s, 3H). MS (ESI) m/z 384 (M+H)$^+$.

Example 65

4-[1-methyl-6-oxo-3-(2-phenoxyphenyl)-1,6-dihydropyridazin-4-yl]benzaldehyde

Example 65A 4-(3-chloro-1-methyl-6-oxo-1,6-dihydropyridazin-4-yl)benzaldehyde 4-formylphenylboronic acid (1.18 g, 7.88 mmol), Example 18B (1.34 g, 7.5 mmol), bis(triphenylphosphine)palladium(II)chloride (0.26 g, 0.375 mmol) and sodium carbonate (7.50 mL, 15.00 mmol) were combined in 1,2-dimethoxyethane (18 mL) and water (12 mL), sparged with nitrogen for 15 minutes and heated at 90° C. for 16 hours under nitrogen. The reaction mixture was partitioned between ethyl acetate and water. The ethyl acetate layer was washed with brine, dried (Na$_2$SO$_4$), treated with mercaptopropyl silica gel for 30 minutes, filtered and concentrated. Purification by chromatography (silica gel, 20-70% ethyl acetate in hexane) afforded the title compound (1.2 g, 64%). MS (APCI+) m/z 249 (M+H)$^+$.

Example 65B

4-[1-methyl-6-oxo-3-(2-phenoxyphenyl)-1,6-dihydropyridazin-4-yl]benzaldehyde

The product from Example 65A (0.249 g, 1.0 mmol), 2-phenoxyphenylboronic acid (0.257 g, 1.2 mmol), bis(triphenylphosphine)palladium(II)chloride (0.035 g, 0.05 mmol) and sodium carbonate (1.0 mL, 2.0 mmol) were combined in 1,2-dimethoxyethane (4.0 mL), sparged with argon for 15 minutes and heated at 120° C. for 60 minutes under argon. The mixture was cooled and partitioned between ethyl acetate and water. The organic layer was washed with brine, dried (Na$_2$SO$_4$), treated with mercaptopropyl silica gel for twenty minutes, filtered and concentrated. Purification by chromatography (silica gel, 0-70% ethyl acetate in hexane) afforded the title compound (0.38 g, 94%). $^1$H NMR (300 MHz, DMSO-$d_6$) δ 9.98 (d, 1H) 7.76 (d, J=8.48 Hz, 2H) 7.62 (dd, J=7.46, 1.70 Hz, 1H) 7.34-7.39 (m, 3H) 7.15-7.26 (m, 3H) 7.05 (d, J=7.12 Hz, 1H) 7.01 (s, 1H) 6.56 (d, J=8.14 Hz, 1H) 6.32 (d, J=7.80 Hz, 2H) 3.71-3.73 (m, 3H). MS (ESI+) m/z 383 (M+H)$^+$.

Example 66

2-methyl-5-[4-(morpholin-4-ylmethyl)phenyl]-6-(2-phenoxyphenyl)pyridazin-3(2H)-one A mixture of the product from Example 65B (0.048 g, 0.125 mmol), morpholine (0.016 mL, 0.188 mmol) and acetic acid (7.16 µl, 0.125 mmol) in dichloroethane (0.625 mL) was treated with sodium triacetoxyborohydride (0.034 g, 0.163 mmol) and stirred for two hours. The reaction mixture was partitioned between ethyl acetate and 5% aqueous sodium bicarbonate. The organic layer was separated, dried (Na$_2$SO$_4$) and concentrated. Purification by reverse phase HPLC (C18, 0-100% CH$_3$CN/water (0.1% TFA)) afforded the title compound as the trifluoroacetic acid salt (0.050 g, 70%). $^1$H NMR (300 MHz, DMSO-$d_6$) δ 9.87 (s, 1H) 7.61 (dd, J=7.46, 1.70 Hz, 1H) 7.34-7.40 (m, 3H) 7.17-7.29 (m, 5H) 7.07 (t, J=7.46 Hz, 1H) 6.94 (s, 1H) 6.55 (d, J=8.14 Hz, 1H) 6.35 (d, J=7.80 Hz, 2H) 4.33 (s, 2H) 3.90-4.04 (m, 2H) 3.71 (s, 3H) 3.55-3.67 (m, 2H) 3.02-3.27 (m, 4H). MS (ESI+) m/z 454 (M+H)$^+$.

Example 67

2-methyl-6-(2-phenoxyphenyl)-5-[4-(piperidin-1-ylmethyl)phenyl]pyridazin-3(2H)-one Example 67 was prepared according to the procedure of Example 66 substituting piperidine for morpholine. Purification by reverse phase HPLC (C18, 0-100% CH$_3$CN/water (0.1% TFA)) afforded the title compound as the trifluoroacetic acid salt (0.050 g, 71%). $^1$H NMR (300 MHz, DMSO-$d_6$) δ 9.30 (s, 1H) 7.61 (dd, J=7.80, 1.70 Hz, 1H) 7.31-7.40 (m, 3H) 7.18-7.28 (m, 5H) 7.08 (t, J=7.46 Hz, 1H) 6.95 (s, 1H) 6.53 (d, J=8.14 Hz, 1H) 6.36 (d, J=7.46 Hz, 2H)

4.27 (d, J=5.09 Hz, 2H) 3.75-3.77 (s, 3H) 3.28 (d, J=11.87 Hz, 2H) 2.81-2.95 (m, 2H) 1.75-1.90 (m, 2H) 1.50-1.74 (m, 3H) 1.26-1.45 (m, 1H). MS (ESI+) m/z 452 (M+H)+.

Example 68

2-methyl-5-{4-[(4-methylpiperidin-1-yl)methyl]phenyl}-6-(2-phenoxyphenyl)pyridazin-3(2H)-one Example 68 was prepared according to the procedure of Example 66 substituting 4-methylpiperidine for morpholine. Purification by reverse phase HPLC (C18, 0-100% CH$_3$CN/water (0.1% TFA)) afforded the title compound as the trifluoroacetic acid salt (0.050 g, 69%). $^1$H NMR (300 MHz, DMSO-d$_6$) δ 9.24 (s, 1H) 7.61 (dd, J=7.54, 1.59 Hz, 1H) 7.31-7.42 (m, 3H) 7.18-7.28 (m, 5H) 7.08 (t, J=7.34 Hz, 1H) 6.95 (s, 1H) 6.53 (d, J=8.33 Hz, 1H) 6.35 (d, J=7.54 Hz, 2H) 4.26 (d, J=4.76 Hz, 2H) 3.72 (s, 3H) 3.29 (d, J=11.90 Hz, 2H) 2.83-3.00 (m, 2H) 1.18-1.87 (m, 5H) 0.91 (d, J=6.35 Hz, 3H). MS (ESI+) m/z 466 (M+H)+.

Example 69

5-{4-[(diethylamino)methyl]phenyl}-2-methyl-6-(2-phenoxyphenyl)pyridazin-3(2H)-one Example 69 was prepared according to the procedure of Example 66 substituting diethylamine for morpholine. Purification by reverse phase HPLC (C18, 0-100% CH$_3$CN/water (0.1% TFA)) afforded the title compound as the trifluoroacetic acid salt (0.048 g, 69%). $^1$H NMR (300 MHz, DMSO-d$_6$) δ 9.27 (s, 1H) 7.60 (dd, J=7.54, 1.98 Hz, 1H) 7.30-7.44 (m, 3H) 7.18-7.29 (m, 5H) 7.08 (t, J=7.34 Hz, 1H) 6.96 (s, 1H) 6.54 (d, J=7.93 Hz, 1H) 6.37 (d, J=7.54 Hz, 2H) 4.30 (d, J=5.16 Hz, 2H) 3.71 (s, 3H) 3.00-3.09 (m, 4H) 1.21 (t, J=7.14 Hz, 6H). MS (ESI+) m/z 440 (M+H)+.

Example 70

2-methyl-6-(2-phenoxyphenyl)-5-[4-(piperazin-1-ylmethyl)phenyl]pyridazin-3(2H)-one Example 70A tert-butyl 4-(4-(1-methyl-6-oxo-3-(2-phenoxyphenyl)-1,6-dihydropyridazin-4-yl)benzyl)piperazine-1-carboxylate Example 70A was prepared according to the procedure of Example 66 substituting 1-Boc-piperazine for morpholine and used in the next step without further purification (0.052 g, 75%).

Example 70B 2-methyl-6-(2-phenoxyphenyl)-5-[4-(piperazin-1-ylmethyl)phenyl]pyridazin-3(2H)-one The product from Example 70A (0.052 g, 0.094 mmol) and trifluoroacetic acid (0.5 mL) in dichloromethane (1 mL) was stirred for 1 h and concentrated. Purification by reverse phase HPLC (C18, 0-100% CH$_3$CN/water (0.1% TFA)) afforded the title compound as the bis-trifluoroacetic acid salt (0.024 g, 37%). $^1$H NMR (300 MHz, DMSO-d$_6$) δ 8.70 (s, 2H) 7.59 (dd, J=7.54, 1.59 Hz, 1H) 7.14-7.38 (m, 8H) 7.06 (t, J=7.34 Hz, 1H) 6.90 (s, 1H) 6.53 (d, J=8.33 Hz, 1H) 6.32 (d, J=7.54 Hz, 2H) 3.82 (s, 1H) 3.71 (s, 3H) 3.19 (s, 4H) 2.80 (s, 4H). MS (ESI+) m/z 453 (M+H)+.

Example 71

2-methyl-6-(2-phenoxyphenyl)-5-[4-(pyrrolidin-1-ylmethyl)phenyl]pyridazin-3(2H)-one Example 71 was prepared according to the procedure of Example 66 substituting pyrrolidine for morpholine. Purification by reverse phase HPLC (C18, 0-100% CH$_3$CN/water (0.1% ammonium acetate)) afforded the title compound (0.048 g, 87%). $^1$H NMR (300 MHz, DMSO-d$_6$) δ 9.27 (s, 1H) 7.58 (dd, J=7.46, 1.70 Hz, 1H) 7.27-7.37 (m, 1H) 7.15-7.23 (m, 5H) 7.04-7.12 (m, 3H) 6.90 (s, 1H) 6.46 (d, J=7.46 Hz, 1H) 6.28 (d, J=7.46 Hz, 2H, 3.71 (s, 2H) 3.55 (s, 3H) 2.42 (s, 4H) 1.67-1.74 (m, 4H). MS (ESI+) m/z 438 (M+H)+.

Example 72

5-[4-(1-hydroxyethyl)phenyl]-2-methyl-6-(2-phenoxyphenyl)pyridazin-3(2H)-one

To a solution of the product of Example 65B (0.09 g, 0.235 mmol) in tetrahydrofuran (10 mL) was added dropwise methylmagnesium bromide (0.26 mL of a 1M solution in tetrahydrofuran, 0.26 mmol). The reaction mixture was stirred at ambient temperature for 3 hours under nitrogen gas. The reaction mixture was quenched by the addition of ethyl acetate and then washed with saturated aqueous sodium chloride solution. The organic phase was dried with anhydrous Na$_2$SO$_4$ and filtered. The solvent was evaporated under reduced pressure, and the resulting residue was purified by flash chromatography (silica gel. 0-100% ethyl acetate/hexane gradient) to provide the title compound (0.030 g, 18% yield). $^1$H NMR (400 MHz, DMSO-d$_6$) δ 7.53 (d, J=7.6 Hz, 1H), 7.26-7.01 (m, 9H), 6.88 (s, 1H), 6.53 (d, J=7.6 Hz, 1H), 6.29 (d, J=7.6 Hz, 2H), 4.88 (q, J=6.4 Hz, 1H), 3.87 (s, 3H), 1.50 (d, J=6.4 Hz, 3H). MS (ESI+): m/z 399.2 (M+H).

Example 73

5-[4-(1-hydroxy-2-methylpropyl)phenyl]-2-methyl-6-(2-phenoxyphenyl)pyridazin-3(2H)-one Example 73 was prepared according to the procedure used for the preparation of Example 72, substituting isopropylmagnesium bromide for methylmagnesium bromide, to provide the title compound. $^1$H NMR (400 MHz, DMSO-d$_6$) δ 7.57 (dd, J=7.6, 1.6, Hz, 1H), 7.30 (t, J=6.4 Hz, 1H), 7.23-7.16 (m, 5H), 7.11-7.08 (m, 3H), 6.90 (s, 1H), 6.44 (d, J=8.4 Hz, 1H), 6.31 (d, J=7.6 Hz, 2H), 5.14 (d, J=4.8 Hz, 1H), 4.24 (t, J=4.2 Hz, 1H), 3.71 (s, 3H), 1.79 (q, J=6.4 Hz, 1H), 0.83 (d, J=6.4 Hz, 3H), 0.77 (d, J=6.8 Hz, 3H). MS (ESI+) m/z 427.1 (M+H).

Example 74

5-{4-[cyclopentyl(hydroxy)methyl]phenyl}-2-methyl-6-(2-phenoxyphenyl)pyridazin-3(2H)-one Example 74 was prepared according to the procedure used for the preparation of Example 72, substituting cyclopentylmagnesium bromide for methylmagnesium bromide, to provide the title compound. $^1$H NMR (400 MHz, CDCl$_3$) δ

7.51 (dd, J=7.6, 1.6 Hz, 1H), 7.26-7.02 (m, 8H), 6.90 (s, 1H), 6.52 (d, J=7.6 Hz, 1H), 6.35 (d, J=7.6 Hz, 2H), 4.39 (d, J=7.6 Hz, 1H), 3.86 (s, 3H), 2.22-2.16 (m, 1H), 1.87-1.82 (m, 2H), 1.65-1.41 (m, 5H), 1.19-1.14 (m, 1H). MS (ESI) m/z 453.1 (M+H).

Example 75

5-[4-(1-hydroxypropyl)phenyl]-2-methyl-6-(2-phenoxyphenyl)pyridazin-3(2H)-one Example 75 was prepared according to the procedure used for the preparation of Example 72, substituting ethylmagnesium bromide for methylmagnesium bromide, to provide the title compound. $^1$H NMR (400 MHz, DMSO-$d_6$) δ 7.58 (dd, J=7.6, 1.9 Hz, 1H), 7.29 (dd, J=7.6, 1.6 Hz, 1H), 7.22-7.18 (m, 5H), 7.10-7.07 (m, 3H), 6.90 (s, 1H), 6.43 (d, J=8.0 Hz, 1H), 6.26 (d, J=8.0 Hz, 2H). 5.15 (brs, 1H), 4.43 (t, J=6.4 Hz, 1H), 3.71 (s, 3H), 1.63-1.56 (dt, J=7.2, 14.0 Hz, 2H), 0.85 (t, J=7.2 Hz, 3H). MS (ESI+) m/z 412.9 (M).

Example 76

5-{4-[hydroxy(phenyl)methyl]phenyl}-2-methyl-6-(2-phenoxyphenyl)pyridazin-3(2H)-one Example 76 was prepared according to the procedure used for the preparation of Example 72, substituting phenylmagnesium bromide for methylmagnesium bromide, to provide the title compound. $^1$H NMR (400 MHz, DMSO-$d_6$) δ 7.57 (d, J=6.0 Hz, 1H), 7.39 (d, J=7.2 Hz, 2H), 7.35-7.16 (m, 7H), 7.07 (d, J=8.0 Hz, 2H), 7.02-7.00 (m, 3H), 6.87 (s, 1H), 6.39 (d, J=7.6 Hz, 1H), 6.16 (dd, J=6.4, 2.4 Hz, 2H), 5.92 (d, J=4.4 Hz, 1H), 5.68 (d, J=4.0 Hz, 1H), 3.70 (s, 3H). MS (ESI) m/z 461.2 (M+H).

Example 77

5-[4-(1-hydroxybut-3-en-1-yl)phenyl]-2-methyl-6-(2-phenoxyphenyl)pyridazin-3(2H)-one To a solution of the product of Example 65B (0.2 g, 0.523 mmol) in dimethylformamide (10 mL) was added indium (0.523 mmol, 0.060 g), and to the mixture was added dropwise 3-bromoprop-1-ene (0.070 g, 0.575 mmol). The reaction mixture was stirred at ambient temperature for 2 days under nitrogen gas. The reaction mixture was quenched by the addition of ethyl acetate and then washed with saturated aqueous sodium chloride solution. The organic phase was dried with anhydrous $Na_2SO_4$ and filtered. The solvent was evaporated under reduced pressure, and the resulting residue was purified by reverse phase HPLC (C18, $CH_3CN$/water (10 mM $NH_4CO_3$), 35-75%) to provide the title compound (0.30 g, 39% yield). $^1$H NMR (400 MHz, DMSO-$d_6$) δ 7.57 (d, J=5.6 Hz, 1H), 7.32 (t, J=6.8 Hz, 1H), 7.22-7.13 (m, 5H), 7.11-7.06 (m, 3H), 6.89 (s, 1H), 6.47 (d, J=5.6 Hz, 1H), 6.27 (d, J=8.0 Hz, 2H), 5.78-5.74 (m, 1H), 5.29 (d, J=4.8 Hz, 1H), 5.04-5.00 (m, 2H), 4.58-4.56 (m, 1H), 3.71 (s, 3H), 2.38-2.35 (m, 2H). MS (ESI) m/z 425.2 (M+H).

Example 78

5-[4-(methoxymethyl)phenyl]-2-methyl-6-(2-phenoxyphenyl)pyridazin-3(2H)-one

Example 78A

6-chloro-5-(4-(methoxymethyl)phenyl)-2-methylpyridazin-3(2H)-one

A mixture of Example 18B (121 mg, 0.726 mmol), 4-(methoxymethyl)phenylboronic acid, (100 mg, 0.559 mmol), Pd(Ph$_3$P)$_4$ (32 mg, 0.028 mmol) and sodium carbonate (118 mg, 1.12 mmol) in toluene (4 mL), ethanol (1 mL) and water (1 mL) was stirred at 85° C. for 16 hours. The reaction mixture was concentrated and purified by preparatory-thin layer chromatography (silica, 3:1 petroleum ether/ethyl acetate) to afford the title compound (107 mg, 0.404 mmol, 72.4% yield). MS (ESI+) m/z 265 (M+H)$^+$.

Example 78B

5-[4-(methoxymethyl)phenyl]-2-methyl-6-(2-phenoxyphenyl)pyridazin-3(2H)-one

A mixture of 2-phenoxyphenylboronic acid (323 mg, 1.511 mmol), Example 78A (100 mg, 0.378 mmol), potassium carbonate (157 mg, 1.133 mmol) and Pd(dppf)Cl$_2$ (30.9 mg, 0.038 mmol) in 1,4-dioxane (2 mL) and water (0.5 mL) was heated in a microwave reactor at 100° C. for 1 hour. The mixture was diluted with ethyl acetate (100 mL) and washed with brine (4×30 mL). The organic layer was dried over anhydrous $Na_2SO_4$, filtered, and concentrated in vacuo. The residue was purified by preparative-TLC (silica, 100/1 dichloromethane/methanol) followed by preparative HPLC (C18, water (10 mM $NH_4HCO_3$)/acetonitrile, 35-75% gradient) to afford the title compound (73 mg, 49% yield). $^1$H NMR (400 MHz, DMSO-$d_6$) δ 11.80 (s, 1H), 8.64 (s, 1H), 8.63 (d, J=4.4 Hz, 1H), 7.76-7.80 (m, 2H), 7.34-7.43 (m, 2H), 6.70 (br s, 1H), 6.25-6.28 (m, 1H), 3.46 (s, 3H), 2.25 (s, 3H), 2.04 (s, 3H), 2.03 (s, 3H). MS (ESI+) m/z 399 (M+H)$^+$.

Example 79

5-[4-(hydroxymethyl)phenyl]-2-methyl-6-(2-phenoxyphenyl)pyridazin-3(2H)-one

Example 79A

6-chloro-5-(4-(hydroxymethyl)phenyl)-2-methylpyridazin-3(2H)-one

Example 79A was prepared according to the procedure used for the preparation of Example 78A, substituting 4-(hydroxymethyl)phenylboronic acid for 4-(methoxymethyl)phenylboronic acid, to provide the title compound.

Example 79B

5-[4-(hydroxymethyl)phenyl]-2-methyl-6-(2-phenoxyphenyl)pyridazin-3(2H)-one

Example 79B was prepared according to the procedure used for the preparation of Example 78B, substituting Example 79A for Example 78A, to provide the title compound. $^1$H NMR (400 MHz, DMSO-$d_6$) δ 11.80 (s, 1H), 8.64

(s, 1H), 8.63 (d, J=4.4 Hz, 1H), 7.76-7.80 (m, 2H), 7.34-7.43 (m, 2H), 6.70 (br s, 1H), 6.25-6.28 (m, 1H), 3.46 (s, 3H), 2.25 (s, 3H), 2.04 (s, 3H), 2.03 (s, 3H). MS (ESI+) m/z 385 (M+H)$^+$.

Example 80

4-[1-methyl-6-oxo-3-(2-phenoxyphenyl)-1,6-dihydropyridazin-4-yl]benzyl acetate

Example 80A 4-(3-chloro-1-methyl-6-oxo-1,6-dihydropyridazin-4-yl)benzyl acetate

Example 80A was prepared according to the procedure used for the preparation of Example 78A, substituting 4-(acetoxymethyl)phenylboronic acid for 4-(methoxymethyl)phenylboronic acid, to provide the title compound.

Example 80B

4-[1-methyl-6-oxo-3-(2-phenoxyphenyl)-1,6-dihydropyridazin-4-yl]benzyl acetate

Example 80B was prepared according to the procedure used for the preparation of Example 78B, substituting Example 80A for Example 78A, to provide the title compound. $^1$H NMR (400 MHz, DMSO-d$_6$) δ 11.80 (s, 1H), 8.64 (s, 1H), 8.63 (d, J=4.4 Hz, 1H), 7.76-7.80 (m, 2H), 7.34-7.43 (m, 2H), 6.70 (br s, 1H), 6.25-6.28 (m, 1H), 3.46 (s, 3H), 2.25 (s, 3H), 2.04 (s, 3H), 2.03 (s, 3H). MS (ESI+) m/z 427 (M+H)$^+$.

Example 81 tert-butyl 4-[1-methyl-6-oxo-3-(2-phenoxyphenyl)-1,6-dihydropyridazin-4-yl]-3,6-dihydropyridine-1(2H)-carboxylate Example 81A tert-butyl 4-(3-chloro-1-methyl-6-oxo-1,6-dihydropyridazin-4-yl)-5,6-dihydropyridine-1(2H)-carboxylate A mixture of tert-butyl 4-(4,4,5,5-tetramethyl-1,3,2-dioxaborolan-2-yl)-5,6-dihydropyridine-1(2H)-carboxylate (1.73 g, 5.59 mmol), 5,6-dichloro-2-methylpyridazin-3(2H)-one (1.00 g, 5.59 mmol), Pd(Ph$_3$P)$_4$ (0.323 g, 0.279 mmol), and sodium carbonate (1.18 g, 11.2 mmol) in toluene (40 mL), ethanol (10 mL) and water (10 mL) was stirred at 85° C. for 16 hours. The reaction mixture was diluted with ethyl acetate (10 mL), filtered through Celite and concentrated under reduced pressure. The resulting residue was purified by flash chromatography (silica gel, 2:1, petroleum ether/ethyl acetate) to afford the title compound (1.4 g, 74% yield).

Example 81B tert-butyl 4-[1-methyl-6-oxo-3-(2-phenoxyphenyl)-1,6-dihydropyridazin-4-yl]-3,6-dihydropyridine-1(2H)-carboxylate A mixture of 2-phenoxyphenylboronic acid (197 mg, 0.921 mmol), Example 81A (100 mg, 0.307 mmol), potassium carbonate (127 mg, 0.921 mmol) and Pd(dppf)Cl$_2$ (25.1 mg, 0.031 mmol) in dioxane (3 mL) and water (0.75 mL) was heated under microwave conditions at 130° C. for 2 hours. The reaction mixture was diluted with ethyl acetate (20 mL) and washed with brine (2×10 mL). The organic layer was dried over anhydrous Na$_2$SO$_4$, filtered, and concentrated under reduced pressure. The residue was purified by flash chromatography (silica gel, 6:1 to 3:1 gradient, petroleum ether/ethyl acetate) to afford the title compound (0.070 g, 47% yield). $^1$H NMR (400 MHz, CDCl$_3$) δ 7.42 (d, J=7.2 Hz, 1H), 7.37-7.27 (m, 3H), 7.18 (t, J=7.2 Hz, 1H), 7.08 (t, J=7.2 Hz, 1H), 6.87 (t, J=7.2 Hz, 3H), 6.73 (s, 1H), 5.56 (s, 1H), 3.81-3.77 (m, 5H), 3.38 (s, 2H), 2.09 (s, 2H), 1.46 (s, 9H). MS (ESI+) m/z 460.0 (M+H)$^+$.

Example 82

2-methyl-6-(2-phenoxyphenyl)-5-(1,2,3,6-tetrahydropyridin-4-yl)pyridazin-3(2H)-one Example 81B (0.3 g, 0.650 mmol) was dissolved in the solution of HCl in dioxane (2M, 10 mL) and the mixture was stirred at room temperature for 2 hours. The solvent was evaporated under reduced pressure. The crude material was purified via flash chromatography (Redi-Sep C-18 column, 0-100% acetonitrile/Water (NH$_4$OAc buffer) to provide the title compound. $^1$H NMR (400 MHz, CD$_3$OD) δ 7.51-7.44 (m, 2H), 7.33-7.26 (m, 3H), 7.08 (t, J=7.2 Hz, 1H), 7.01 (d, J=8.4 Hz, 1H), 6.91-6.89 (m, 2H), 6.81 (s, 1H), 5.69 (s, 1H), 3.72 (s, 3H), 3.39-3.38 (m, 2H), 2.94 (t, J=5.6 Hz, 2H), 2.24-2.23 (m, 2H). MS (ESI+) m/z 360.1 (M+H)$^+$.

Example 83

2-methyl-5-(1-methyl-1,2,3,6-tetrahydropyridin-4-yl)-6-(2-phenoxyphenyl)pyridazin-3(2H)-one Sodium cyanoborohydride (0.027 g, 0.422 mmol) was added to a solution of Example 82 (0.070 g, 0.18 mmol), formaldehyde (37% solution) (0.131 mL, 1.759 mmol) and acetic acid (0.013 mL, 0.229 mmol) in methanol (2 mL) and the reaction mixture was stirred at ambient temperature for 16 hours. The reaction mixture was neutralized with aqueous saturated aqueous sodium bicarbonate solution, and methanol was evaporated under reduced pressure. The residue was diluted with water and extracted with ethyl acetate (2×25 mL). The combined organic layers were combined, dried over anhydrous Na$_2$SO$_4$, filtered, and concentrated under reduced pressure. The crude product was purified by preparative-TLC (silica, 15:1 CH$_2$Cl$_2$/MeOH) to provide the title compound. $^1$H NMR (400 MHz, CD$_3$OD) δ 7.37-7.31 (m, 2H), 7.21-7.12 (m, 3H), 6.96 (t, J=7.2 Hz, 1H), 6.85 (d, J=8.4 Hz, 1H), 6.80-6.77 (m, 2H), 6.68 (s, 1H), 5.52-5.51 (m, 1H), 3.61 (s, 3H), 2.82-2.81 (m, 2H), 2.38 (t, J=5.6 Hz, 2H), 2.19 (s, 3H), 2.15-2.14 (m, 2H). MS (ESI+) m/z 373.9 (M+H)$^+$.

Example 84

5-(1-acetyl-1,2,3,6-tetrahydropyridin-4-yl)-2-methyl-6-(2-phenoxyphenyl)pyridazin-3(2H)-one Acetyl chloride (0.021 g, 0.264 mmol) was added to a solution of Example 82 (0.070 g, 0.18 mmol) and triethylamine (0.049 mL, 0.35 mmol) in tetrahydrofuran (2 mL). The reaction mixture was stirred at ambient temperature for 16 hours. The crude reaction mixture was diluted with ethyl acetate (20 mL) and washed with water (15 mL) and brine (15 mL), filtered and concentrated. The crude residue was purified by preparative-TLC (silica gel, 20:1 dichloromethane/methanol) to afford the title compound. $^1$H NMR (400 MHz, CDCl$_3$) δ 7.45-7.27 (m, 4H), 7.20 (t, J=7.2 Hz, 1H), 7.08 (d, J=7.2 Hz, 1H), 6.92-6.83 (m, 3H), 6.74 (s, 1H), 5.60-5.55 (m, 1H), 3.99-3.98 (m, 1H), 3.86-3.85 (m, 1H), 3.78-3.77 (m, 3H), 3.60-3.57 (m, 1H), 3.40 (t, J=5.6 Hz, 1H), 2.15-2.13 (m, 2H), 2.06-2.05 (m, 3H). MS (ESI+) m/z 462.0 (M+H)$^+$.

Example 85

2-methyl-5-[1-(methylsulfonyl)-1,2,3,6-tetrahydropyridin-4-yl]-6-(2-phenoxyphenyl)pyridazin-3(2H)-one Methanesulfonyl chloride (0.026 g, 0.226 mmol) was added to a solution of Example 82 (0.06 g, 0.15 mmol) and triethylamine (0.042 mL, 0.30 mmol) in tetrahydrofuran (2 mL). The reaction mixture was stirred at ambient temperature for 16 h. The crude reaction mixture was diluted with ethyl acetate (20 mL), washed with water (15 mL) and brine (15 mL), filtered and concentrated. The crude material was purified by preparative TLC (silica gel, 20:1 dichloromethane/methanol) to afford the title compound. $^1$H NMR (400 MHz, CDCl$_3$) δ 7.43-7.27 (m, 4H), 7.21-7.17 (m, 1H, 7.09 (t, J=7.6 Hz, 1H), 6.92-6.89 (m, 3H), 6.73 (s, 1H), 5.60-5.59 (m, 1H), 3.78 (s, 3H), 3.70-3.69 (m, 2H), 3.27 (t, J=5.6 Hz, 2H), 2.76 (s, 3H), 2.23-2.22 (m, 2H). MS (ESI+) m/z 438.0 (M+H)$^+$.

Example 86 tert-butyl 4-[1-methyl-6-oxo-3-(2-phenoxyphenyl)-1,6-dihydropyridazin-4-yl]piperidine-1-carboxylate To a solution of Example 81B (0.090 g, 0.20 mmol) in methanol (4 mL) was added Pd/C (0.021 g, 0.020 mmol) under argon, and the reaction was degassed with hydrogen three times and stirred under an atmosphere of hydrogen at 20° C. for 6 hours. The reaction mixture was filtered through Celite and concentrated to afford the title compound (0.09 g, 100% yield). $^1$H NMR (400 MHz, CDCl$_3$) δ 7.43-7.27 (m, 4H), 7.24-7.21 (m, 1H), 7.09 (t, J=7.6 Hz, 1H), 6.98 (d, J=7.6 Hz, 1H), 6.91-6.89 (m, 2H), 6.76 (s, 1H), 4.15-4.07 (m, 2H), 3.74 (s, 3H), 2.58-2.45 (m, 3H), 1.77-1.47 (m, 4H), 1.44 (s, 9H). MS (ESI+) m/z 406.0 (M+H)$^+$.

Example 87

2-methyl-6-(2-phenoxyphenyl)-5-(piperidin-4-yl)pyridazin-3(2H)-one

Example 86 (0.3 g, 0.650 mmol) was dissolved in the solution of HCl in dioxane (2M, 10 mL) and the reaction mixture was stirred at ambient temperature for 2 hours. The solvent was evaporated under reduced pressure and the residue was purified by flash chromatography (Redi-Sep C-18 column, 0-100% acetonitrile/water (NH$_4$OAc buffer) to provide the title compound. $^1$H NMR (400 MHz, CDCl$_3$) δ 7.52-7.43 (m, 2H), 7.35-7.27 (m, 3H), 7.10 (t, J=7.2 Hz, 1H), 7.04 (d, J=8.4 Hz, 1H), 6.93-6.91 (m, 2H), 6.87 (s, 1H), 3.71 (s, 3H), 3.35-3.32 (m, 1H), 3.16-3.06 (m, 2H), 2.64-2.44 (m, 3H), 1.77-1.67 (m, 3H), 1.45-1.41 (m, 1H). MS (ESI+) m/z 362.0 (M+H)$^+$.

Example 88

2-methyl-5-(1-methylpiperidin-4-yl)-6-(2-phenoxyphenyl)pyridazin-3(2H)-one

Sodium cyanoborohydride (0.027 g, 0.422 mmol) was added to a solution of Example 87 (0.070 g, 0.18 mmol), formaldehyde (37% solution) (0.131 mL, 1.759 mmol) and acetic acid (0.013 mL, 0.229 mmol) in methanol (2 mL) and the reaction mixture was stirred at ambient temperature for 16 hours. The reaction mixture was neutralized with aqueous saturated sodium bicarbonate solution, and methanol was evaporated under reduced pressure. The residue was diluted with water and extracted with ethyl acetate (2×25 mL). The combined organic layers were dried over anhydrous Na$_2$SO$_4$, filtered, and concentrated under reduced pressure. The crude product was purified by preparative TLC (silica, 15:1 dichloromethane/methanol) to afford the title compound (38 mg, 57.5% yield). $^1$H NMR (400 MHz, CD$_3$OD) δ 7.52-7.42 (m, 2H), 7.35-7.27 (m, 3H), 7.12-7.08 (m, 1H), 7.05-7.03 (m, 1H), 6.92-6.88 (m, 2H), 6.87 (s, 1H), 3.71 (s, 3H), 2.99-2.87 (m, 2H), 2.48-2.41 (m, 1H), 2.29 (s, 3H), 2.00-1.48 (m, 6H). MS (ESI+) m/z 376.0 (M+H)$^+$.

Example 89

5-(1-acetylpiperidin-4-yl)-2-methyl-6-(2-phenoxyphenyl)pyridazin-3(2H)-one

Acetyl chloride (0.021 g, 0.264 mmol) was added to a solution of Example 87 (0.070 g, 0.18 mmol) and Et$_3$N (0.049 mL, 0.352 mmol) in tetrahydrofuran (2 mL). The reaction mixture was stirred at ambient temperature for 16 hours. The crude material was diluted with ethyl acetate (20 mL), washed with water (15 mL) and brine (15 mL), filtered and concentrated. The crude residue was purified by preparative TLC (silica gel, 20:1 dichloromethane/1methanol) to afford the title compound. (49 mg, 0.121 mmol, 69.0% yield). $^1$HNMR (400 MHz, CD$_3$OD) δ 7.45-7.25 (m, 5H), 7.11-7.08 (m, 1H), 7.01 (d, J=8.0 Hz, 1H), 6.91-6.89 (m, 2H), 6.74 (s, 1H), 4.74-4.61 (m, 1H), 3.88-3.79 (m, 1H), 3.74 (s, 3H), 2.96-2.81 (m, 1H), 2.62-2.55 (m, 1H), 2.43-2.25 (m, 1H), 2.07 (d, J=5.2 Hz, 3H), 1.93-1.83 (m, 1H), 1.63-1.53 (m, 2H), 1.32-1.24 (m, 1H). MS (ESI+) m/z 404.0 (M+H)$^+$.

Example 90

2-methyl-5-[1-(methylsulfonyl)piperidin-4-yl]-6-(2-phenoxyphenyl)pyridazin-3(2H)-one Methanesulfonyl chloride (0.026 g, 0.226 mmol) was added to a solution of Example 87 (0.060 g, 0.15 mmol) and triethylamine (0.042 mL, 0.302 mmol) in tetrahydrofuran (2 mL). The reaction mixture was stirred at ambient temperature for 16 hours. The crude material was diluted with ethyl acetate (20 mL), washed with water (15 mL) and brine (15 mL), filtered and concentrated. The crude material was purified by preparative TLC (silica gel, 20:1 dichloromethane/methanol) to afford the title compound (46 mg, 69.4% yield). $^1$H NMR (400 MHz, CD$_3$OD) δ 7.46-7.44 (m, 1H), 7.38-7.36 (m, 1H), 7.32-7.23 (m, 3H), 7.09 (t, J=7.6 Hz, 1H), 7.02 (d, J=8.0 Hz, 1H), 6.89-6.87 (m, 2H), 6.79 (s, 1H), 3.91-3.76 (m, 2H), 3.73 (s, 3H), 2.76 (s, 3H), 2.50-2.42 (m, 2H), 1.94-1.48 (m, 5H). MS (ESI+) m/z 440.0 (M+H)$^+$.

Example 91

2-methyl-5-[4-(5-methyl-1,3,4-oxadiazol-2-yl)phenyl]-6-(2-phenoxyphenyl)pyridazin-3(2H)-one

Example 91A 6-chloro-2-methyl-5-(4-(5-methyl-1,3,4-oxadiazol-2-yl)phenyl)pyridazin-3(2H)-one Example 91A was prepared according to the procedure used for the preparation of Example 78A, substituting 4-(5-methyl-1,3,4-oxadiazol-2-yl)phenylboronic acid for 4-(methoxymethyl)phenylboronic acid, to provide the title compound.

Example 91B 2-methyl-5-[4-(5-methyl-1,3,4-oxadiazol-2-yl)phenyl]-6-(2-phenoxyphenyl)pyridazin-3(2H)-one Example 91B was prepared according to the procedure used for the preparation of Example 78B, substituting Example 91A for Example 78A, to provide the title compound. $^1$H NMR (400 MHz, DMSO-$d_6$) δ 11.80 (s, 1H), 8.64 (s, 1H), 8.63 (d, J=4.4 Hz, 1H), 7.76-7.80 (m, 2H), 7.34-7.43 (m, 2H), 6.70 (br s, 1H), 6.25-6.28 (m, 1H), 3.46 (s, 3H), 2.25 (s, 3H), 2.04 (s, 3H), 2.03 (s, 3H). MS (ESI+) m/z 437 (M+H)$^+$.

Example 92 methyl 3-{4-[1-methyl-6-oxo-3-(2-phenoxyphenyl)-1,6-dihydropyridazin-4-yl]phenyl}propanoate

Example 92A methyl 3-(4-(3-chloro-1-methyl-6-oxo-1,6-dihydropyridazin-4-yl)phenyl)propanoate Example 92A was prepared according to the procedure used for the preparation of Example 78A, substituting 4-(3-methoxy-3-oxopropyl)phenylboronic acid for 4-(methoxymethyl)phenylboronic acid, to provide the title compound.

Example 92B methyl 3-{4-[1-methyl-6-oxo-3-(2-phenoxyphenyl)-1,6-dihydropyridazin-4-yl]phenyl}propanoate Example 92B was prepared according to the procedure used for the preparation of Example 78B, substituting Example 92A for Example 78A, to provide the title compound. $^1$H NMR (400 MHz, DMSO-$d_6$) δ 11.80 (s, 1H), 8.64 (s, 1H), 8.63 (d, J=4.4 Hz, 1H), 7.76-7.80 (m, 2H), 7.34-7.43 (m, 2H), 6.70 (br s, 1H), 6.25-6.28 (m, 1H), 3.46 (s, 3H), 2.25 (s, 3H), 2.04 (s, 3H), 2.03 (s, 3H). MS (ESI+) m/z 441 (M+H)$^+$.

Example 93

5-(4-benzylphenyl)-2-methyl-6-(2-phenoxyphenyl)pyridazin-3(2H)-one

Example 93A 5-(4-benzylphenyl)-6-chloro-2-methylpyridazin-3(2H)-one

Example 93A was prepared according to the procedure used for the preparation of Example 78A, substituting 4-benzylphenylboronic acid for 4-(methoxymethyl)phenylboronic acid, to provide the title compound.

Example 93B 5-(4-benzylphenyl)-2-methyl-6-(2-phenoxyphenyl)pyridazin-3(2H)-one Example 93B was prepared according to the procedure used for the preparation of Example 78B, substituting Example 93A for Example 78A, to provide the title compound. $^1$H NMR (400 MHz, DMSO-$d_6$) δ 11.80 (s, 1H), 8.64 (s, 1H), 8.63 (d, J=4.4 Hz, 1H), 7.76-7.80 (m, 2H), 7.34-7.43 (m, 2H), 6.70 (br s, 1H), 6.25-6.28 (m, 1H), 3.46 (s, 3H), 2.25 (s, 3H), 2.04 (s, 3H), 2.03 (s, 3H). MS (ESI+) m/z 445 (M+H)$^+$.

Example 94

{4-[1-methyl-6-oxo-3-(2-phenoxyphenyl)-1,6-dihydropyridazin-4-yl]phenyl}acetonitrile

Example 94A 2-(4-(3-chloro-1-methyl-6-oxo-1,6-dihydropyridazin-4-yl)phenyl)acetonitrile Example 94A was prepared according to the procedure used for the preparation of Example 78A, substituting 4-(cyanomethyl)phenylboronic acid for 4-(methoxymethyl)phenylboronic acid, to provide the title compound.

Example 94B

{4-[1-methyl-6-oxo-3-(2-phenoxyphenyl)-1,6-dihydropyridazin-4-yl]phenyl}acetonitrile Example 94B was prepared according to the procedure used for the preparation of Example 78B, substituting Example 94A for Example 78A, to provide the title compound. $^1$H NMR (400 MHz, DMSO-$d_6$) δ 11.80 (s, 1H), 8.64 (s, 1H), 8.63 (d, J=4.4 Hz, 1H), 7.76-7.80 (m, 2H), 7.34-7.43 (m, 2H), 6.70 (br s, 1H), 6.25-6.28 (m, 1H), 3.46 (s, 3H), 2.25 (s, 3H), 2.04 (s, 3H), 2.03 (s, 3H). MS (ESI+) m/z 394 (M+H)$^+$.

Example 95

5-[4-(5,6-dihydro-4H-1,3-oxazin-2-yl)phenyl]-2-methyl-6-(2-phenoxyphenyl)pyridazin-3(2H)-one

Example 95A 6-chloro-5-(4-(5,6-dihydro-4H-1,3-oxazin-2-yl)phenyl)-2-methylpyridazin-3(2H)-one Example 95A was prepared according to the procedure used for the preparation of Example 78A, substituting 4-(5,6-dihydro-4H-1,3-oxazin-2-yl)phenylboronic acid for 4-(methoxymethyl)phenylboronic acid, to provide the title compound.

Example 95B

5-[4-(5,6-dihydro-4H-1,3-oxazin-2-yl)phenyl]-2-methyl-6-(2-phenoxyphenyl)pyridazin-3(2H)-one Example 95B was prepared according to the procedure used for the preparation of Example 78B, substituting Example 95A for Example 78A, to provide the title compound. $^1$H NMR (400 MHz, DMSO-$d_6$) δ 11.80 (s, 1H), 8.64 (s, 1H), 8.63 (d, J=4.4 Hz, 1H), 7.76-7.80 (m, 2H), 7.34-7.43 (m, 2H), 6.70 (br s, 1H), 6.25-6.28 (m, 1H), 3.46 (s, 3H), 2.25 (s, 3H), 2.04 (s, 3H), 2.03 (s, 3H). MS (ESI+) m/z 438 (M+H)$^+$.

Example 96

2-methyl-5-[4-(2-methylpropyl)phenyl]-6-(2-phenoxyphenyl)pyridazin-3(2H)-one

Example 96A 6-chloro-5-(4-isobutylphenyl)-2-methylpyridazin-3(2H)-one

Example 96A was prepared according to the procedure used for the preparation of Example 78A, substituting 4-isobutylphenylboronic acid for 4-(methoxymethyl)phenylboronic acid, to provide the title compound.

Example 96B 2-methyl-5-[4-(2-methylpropyl)phenyl]-6-(2-phenoxyphenyl)pyridazin-3(2H)-one Example 96B was prepared according to the procedure used for the preparation of Example 78B, substituting Example 96A for Example 78A, to provide the title compound. $^1$H NMR (400 MHz, DMSO-$d_6$) δ 11.80 (s, 1H), 8.64 (s, 1H), 8.63 (d, J=4.4 Hz, 1H), 7.76-7.80 (m, 2H), 7.34-7.43 (m, 2H), 6.70 (br s, 1H), 6.25-6.28 (m, 1H), 3.46 (s, 3H), 2.25 (s, 3H), 2.04 (s, 3H), 2.03 (s, 3H). MS (ESI+) m/z 411 (M+H)$^+$.

Example 97 ethyl{4-[1-methyl-6-oxo-3-(2-phenoxyphenyl)-1,6-dihydropyridazin-4-yl]phenyl}acetate Example 97A ethyl 2-(4-(3-chloro-1-methyl-6-oxo-1,6-dihydropyridazin-4-yl)phenyl)acetate Example 97A was prepared according to the procedure used for the preparation of Example 78A, substituting 4-(2-ethoxy-2-oxoethyl)phenylboronic acid for 4-(methoxymethyl)phenylboronic acid, to provide the title compound.

Example 97B ethyl{4-[1-methyl-6-oxo-3-(2-phenoxyphenyl)-1,6-dihydropyridazin-4-yl]phenyl}acetate Example 97B was prepared according to the procedure used for the preparation of Example 78B, substituting Example 97A for Example 78A, to provide the title compound. $^1$H NMR (400 MHz, DMSO-$d_6$) δ 11.80 (s, 1H), 8.64 (s, 1H), 8.63 (d, J=4.4 Hz, 1H), 7.76-7.80 (m, 2H), 7.34-7.43 (m, 2H), 6.70 (br s, 1H), 6.25-6.28 (m, 1H), 3.46 (s, 3H), 2.25 (s, 3H), 2.04 (s, 3H), 2.03 (s, 3H). MS (ESI+) m/z 441 (M+H)$^+$.

Example 98

N-{4-[1-methyl-6-oxo-3-(2-phenoxyphenyl)-1,6-dihydropyridazin-4-yl]benzyl}methanesulfonamide Example 98A N-(4-(3-chloro-1-methyl-6-oxo-1,6-dihydropyridazin-4-yl)benzyl)ethanesulfonamide Example 98A was prepared according to the procedure used for the preparation of Example 78A, substituting 4-(ethylsulfonamidomethyl)phenylboronic acid for 4-(methoxymethyl)phenylboronic acid, to provide the title compound.

Example 98B

N-{4-[1-methyl-6-oxo-3-(2-phenoxyphenyl)-1,6-dihydropyridazin-4-yl]benzyl}methanesulfonamide Example 98B was prepared according to the procedure used for the preparation of Example 78B, substituting Example 98A for Example 78A, to provide the title compound. $^1$H NMR (400 MHz, DMSO-$d_6$) δ 11.80 (s, 1H), 8.64 (s, 1H), 8.63 (d, J=4.4 Hz, 1H), 7.76-7.80 (m, 2H), 7.34-7.43 (m, 2H), 6.70 (br s, 1H), 6.25-6.28 (m, 1H), 3.46 (s, 3H), 2.25 (s, 3H), 2.04 (s, 3H), 2.03 (s, 3H). MS (ESI+) m/z 462 (M+H)$^+$.

Example 99

N-{4-[1-methyl-6-oxo-3-(2-phenoxyphenyl)-1,6-dihydropyridazin-4-yl]benzyl}acetamide Example 99A N-(4-(3-chloro-1-methyl-6-oxo-1,6-dihydropyridazin-4-yl)benzyl)acetamide Example 99A was prepared according to the procedure used for the preparation of Example 78A, substituting 4-(acetamidomethyl)phenylboronic acid for 4-(methoxymethyl)phenylboronic acid, to provide the title compound.

Example 99B

N-{4-[1-methyl-6-oxo-3-(2-phenoxyphenyl)-1,6-dihydropyridazin-4-yl]benzyl}acetamide Example 99B was prepared according to the procedure used for the preparation of Example 78B, substituting Example 99A for Example 78A, to provide the title compound. $^1$H NMR (400 MHz, DMSO-$d_6$) δ 11.80 (s, 1H), 8.64 (s, 1H), 8.63 (d, J=4.4 Hz, 1H), 7.76-7.80 (m, 2H), 7.34-7.43

(m, 2H), 6.70 (br s, 1H), 6.25-6.28 (m, 1H), 3.46 (s, 3H), 2.25 (s, 3H), 2.04 (s, 3H), 2.03 (s, 3H). MS (ESI+) m/z 426 (M+H)$^+$.

Example 100

N-(2-{4-[1-methyl-6-oxo-3-(2-phenoxyphenyl)-1,6-dihydropyridazin-4-yl]phenyl}ethyl)acetamide

Example 100A

N-(4-(3-chloro-1-methyl-6-oxo-1,6-dihydropyridazin-4-yl)phenethyl)acetamide

Example 100A was prepared according to the procedure used for the preparation of Example 78A, substituting 4-(2-acetamidoethyl)phenylboronic acid for 4-(methoxymethyl)phenylboronic acid, to provide the title compound.

Example 100B

N-(2-{4-[1-methyl-6-oxo-3-(2-phenoxyphenyl)-1,6-dihydropyridazin-4-yl]phenyl}ethyl)acetamide Example 100B was prepared according to the procedure used for the preparation of Example 78B, substituting Example 100A for Example 78A, to provide the title compound. $^1$H NMR (400 MHz, DMSO-d$_6$) δ 1.80 (s, 1H), 8.64 (s, 1H), 8.63 (d, J=4.4 Hz, 1H), 7.76-7.80 (m, 2H), 7.34-7.43 (m, 2H), 6.70 (br s, 1H), 6.25-6.28 (m, 1H), 3.46 (s, 3H), 2.25 (s, 3H), 2.04 (s, 3H), 2.03 (s, 3H). MS (ESI+) m/z 440 (M+H)$^+$.

Example 101

5-[4-(3-hydroxypropyl)phenyl]-2-methyl-6-(2-phenoxyphenyl)pyridazin-3(2H)-one

Example 101A 6-chloro-5-(4-(3-hydroxypropyl)phenyl)-2-methyl-pyridazin-3(2H)-one Example 101A was prepared according to the procedure used for the preparation of Example 78A, substituting 4-(3-hydroxypropyl)phenylboronic acid for 4-(methoxymethyl)phenylboronic acid, to provide the title compound.

Example 101B

5-[4-(3-hydroxypropyl)phenyl]-2-methyl-6-(2-phenoxyphenyl)pyridazin-3(2H)-one

Example 101B was prepared according to the procedure used for the preparation of Example 78B, substituting Example 101A for Example 78A, to provide the title compound. $^1$H NMR (400 MHz, DMSO-d$_6$) δ 11.80 (s, 1H), 8.64 (s, 1H), 8.63 (d, J=4.4 Hz, 1H), 7.76-7.80 (m, 2H), 7.34-7.43 (m, 2H), 6.70 (br s, 1H), 6.25-6.28 (m, 1H), 3.46 (s, 3H), 2.25 (s, 3H), 2.04 (s, 3H), 2.03 (s, 3H). MS (ESI+) m/z 413 (M+H)$^+$.

Example 102 methyl 4-[1-methyl-6-oxo-3-(2-phenoxyphenyl)-1,6-dihydropyridazin-4-yl]benzoate

Example 102 was prepared according to the procedure used for the preparation of Example 105, substituting 4-(methoxycarbonyl)phenylboronic acid in 1,4-dioxane for N-(4-(4,4,5,5-tetramethyl-1,3,2-dioxaborolan-2-yl)phenyl)acetamide, to provide the title compound. %). $^1$H NMR (500 MHz, DMSO-d$_6$/D$_2$O) δ 7.81 (d, J=8.24 Hz, 2H) 7.62 (dd, J=7.63, 1.53 Hz, 1H) 7.36-7.40 (m, 1H) 7.24-7.32 (m, 3H) 7.20 (t, J=7.93 Hz, 2H) 7.06 (t, J=7.48 Hz, 1H) 7.01 (s, 1H) 6.58 (d, J=8.24 Hz, 1H) 6.32 (d, J=7.63 Hz, 2H) 3.86 (s, 3H) 3.74 (s, 3H) MS (ESI+) m/z 413.3 (M+H)$^+$.

Example 103

2-methyl-5-(1-methyl-1H-pyrazol-4-yl)-6-(2-phenoxyphenyl)pyridazin-3(2H)-one

Example 103 was prepared according to the procedure used for the preparation of Example 105, substituting 1-methyl-4-(4,4,5,5-tetramethyl-1,3,2-dioxaborolan-2-yl)-1H-pyrazole for N-(4-(4,4,5,5-tetramethyl-1,3,2-dioxaborolan-2-yl)phenyl)acetamide, to provide the title compound. $^1$H NMR (500 MHz, DMSO-d$_6$/D$_2$O) δ 7.58 (s, 1H) 7.44-7.54 (m, 2H) 7.26-7.33 (m, 3H) 7.08-7.13 (m, 1H) 7.00 (s, 1H) 6.96 (s, 1H) 6.79 (d, J=8.24 Hz, 1H) 6.49-6.59 (m, 2H) 3.75 (s, 3H) 3.65 (s, 3H). MS (ESI+) m/z 359.2 (M+H)$^+$.

Example 104

2-methyl-6-(2-phenoxyphenyl)-5-(pyridin-4-yl)pyridazin-3(2H)-one

Example 104 was prepared according to the procedure used for the preparation of Example 105, substituting pyridin-4-yl-boronic acid for N-(4-(4,4,5,5-tetramethyl-1,3,2-dioxaborolan-2-yl)phenyl)acetamide, to provide the title compound. $^1$H NMR (500 MHz, DMSO-d$_6$/D$_2$O) δ 7.67 (dd, J=7.48, 1.68 Hz, 1H) 7.52 (d, J=6.10 Hz, 1H) 7.43 (d, J=6.41 Hz, 3H) 7.23-7.34 (m, 4H) 7.12 (s, 1H) 7.07-7.11 (m, 1H) 6.63 (d, J=8.24 Hz, 1H) 6.38 (d, J=7.93 Hz, 2H) 3.75 (s, 3H) MS (ESI+) m/z 356.2 (M+H)$^+$.

Example 105

N-{4-[1-methyl-6-oxo-3-(2-phenoxyphenyl)-1,6-dihydropyridazin-4-yl]phenyl}acetamide A 4 mL microwave vial was charged with a stir bar, a solution of Example 18B (40 mg, 0.22 mmol) in dioxane (1 mL), a solution of N-(4-(4,4,5,5-tetramethyl-1,3,2-dioxaborolan-2-yl)phenyl)acetamide monomer (87 mg, 1.5 equivalents, 0.34 mmol) in dioxane (1 mL), cesium carbonate (145 mg, 2 eq, 0.44 mmol) in water (0.45 mL) with Silicat resin (82 mg, 0.1 eq, 0.27 loading). This was placed in parallel dual model microwave system Anton Parr and was allowed to heat at 135° C. for 30 minutes. Upon completion, the crude material was filtered, dried, and purified by reverse phase HPLC (C18, 0-100% CH$_3$CN/water (0.1% TFA)) to afford N-(4-(3-chloro-1-methyl-6-oxo-1,6-dihydropyridazin-4-yl)phenyl)acetamide intermediate (35 mg, 0.13 mmol) which was then dissolved in dioxane (1 mL) to which was added excess 2-pheoxyphenyl boronic acid (45 mg, 1.6 equivalents, 0.20 mmol) in dioxane, cesium carbonate (41 mg, 1 equivalent, 0.12 mmol) in water (0.130 mL) and with Silicat resin (93 mg, 0.2 eq, 0.27 loading). This was again placed in parallel dual model microwave system Anton Parr and was allowed to heat at 135° C. for 30 minutes. Upon completion, the crude material was filtered, dried, and purified by reverse phase HPLC (C18, 0-100% CH$_3$CN/water (0.1% TFA)) to afford the title compound. ¹H NMR (400 MHz, DMSO-d$_6$/D$_2$O) δ 7.58 (dd, J=7.5, 1.7 Hz, 1H), 7.48-7.32 (m, 3H), 7.25-7.16 (m, 3H), 7.06 (t, J=7.9 Hz, 3H), 6.89 (s, 1H), 6.57 (d, J=7.7 Hz, 1H), 6.36 (d, J=7.7 Hz, 2H), 3.70 (s, 3H), 2.06 (s, 3H). MS (ESI+) m/z 412 (M+H)$^+$.

Example 106

N-{3-[1-methyl-6-oxo-3-(2-phenoxyphenyl)-1,6-dihydropyridazin-4-yl]phenyl}acetamide Example 106 was prepared according to the procedure used for the preparation of Example 105, substituting N-(3-(4,4,5,5-tetramethyl-1,3,2-dioxaborolan-2-yl)phenyl)acetamide for N-(4-(4,4,5,5-tetramethyl-1,3,2-dioxaborolan-2-yl)phenyl)acetamide, to provide the title compound. ¹H NMR (400 MHz, DMSO-d$_6$/D$_2$O) δ 7.65-7.52 (m, 2H), 7.47 (s, 1H), 7.40-7.28 (m, 1H), 7.22 (dd, J=11.0, 4.5 Hz, 3H), 7.15 (t, J=7.9 Hz, 1H), 7.06 (t, J=7.4 Hz, 1H), 6.85 (s, 1H), 6.72 (d, J=7.9 Hz, 1H), 6.56 (d, J=7.6 Hz, 1H), 6.42-6.29 (m, 2H), 3.71 (s, 3H), 1.99 (s, 3H). MS (ESI+) m/z 412 (M+H)$^+$.

Example 107

5-(4-ethoxy-3-fluorophenyl)-2-methyl-6-(2-phenoxyphenyl)pyridazin-3(2H)-one

Example 107 was prepared according to the procedure used for the preparation of Example 105, substituting 4-ethoxy-3-fluorophenylboronic acid for N-(4-(4,4,5,5-tetramethyl-1,3,2-dioxaborolan-2-yl)phenyl)acetamide, to provide the title compound. ¹H NMR (400 MHz, DMSO-d$_6$/D$_2$O) δ 7.60 (dd, J=7.5, 1.7 Hz, 1H), 7.44-7.31 (m, 1H), 7.24 (dd, J=15.9, 8.1 Hz, 3H), 7.13-6.96 (m, 2H), 6.96-6.80 (m, 3H), 6.64 (t, J=8.7 Hz, 1H), 6.42 (dd, J=25.2, 7.7 Hz, 2H), 4.10 (q, J=7.0 Hz, 2H), 3.70-3.69 (m, 3H), 1.34 (t, J=7.0 Hz, 3H). MS (ESI+) m/z 417 (M+H)$^+$.

Example 108

N,N-dimethyl-4-[1-methyl-6-oxo-3-(2-phenoxyphenyl)-1,6-dihydropyridazin-4-yl]benzamide Example 108 was prepared according to the procedure used for the preparation of Example 105, substituting 4-(dimethylcarbamoyl)phenylboronic acid for N-(4-(4,4,5,5-tetramethyl-1,3,2-dioxaborolan-2-yl)phenyl)acetamide, to provide the title compound. ¹H NMR (400 MHz, DMSO-d$_6$/D$_2$O) δ 7.68-7.51 (m, 1H), 7.42-7.33 (m, 1H), 7.33-7.24 (m, 3H), 7.24-7.17 (m, 4H), 7.08 (t, J=7.4 Hz, 1H), 6.98 (d, J=2.5 Hz, 1H), 6.59-6.46 (m, 1H), 6.39-6.26 (m, 2H), 3.75 (d, J=9.9 Hz, 3H), 2.98 (s, 3H), 2.90 (s, 3H). MS (ESI+) m/z 426 (M+H)$^+$.

Example 109

N,N-dimethyl-3-[1-methyl-6-oxo-3-(2-phenoxyphenyl)-1,6-dihydropyridazin-4-yl]benzamide Example 109 was prepared according to the procedure used for the preparation of Example 105, substituting 3-(dimethylcarbamoyl)phenylboronic acid for N-(4-(4,4,5,5-tetramethyl-1,3,2-dioxaborolan-2-yl)phenyl)acetamide, to provide the title compound. ¹H NMR (400 MHz, DMSO-d$_6$/D$_2$O) δ 7.60 (dd, J=7.5, 1.7 Hz, 1H), 7.44-7.32 (m, 2H), 7.32-7.18 (m, 3H), 7.10 (dd, J=18.1, 10.7 Hz, 1H), 6.96 (s, 1H), 6.54 (d, J=7.8 Hz, 1H), 6.41 (d, J=7.7 Hz, 1H), 3.72 (d, J=2.4 Hz, 3H), 2.54 (dd, J=9.3, 7.5 Hz, 6H). MS (ESI+) m/z 426 (M+H)$^+$.

Example 110

2-methyl-5-[3-(2-methylpropoxy)phenyl]-6-(2-phenoxyphenyl)pyridazin-3(2H)-one

Example 110 was prepared according to the procedure used for the preparation of Example 105, substituting 3-isobutoxyphenylboronic acid for N-(4-(4,4,5,5-tetramethyl-1,3,2-dioxaborolan-2-yl)phenyl)acetamide, to provide the title compound. ¹H NMR (400 MHz, DMSO-d$_6$/D$_2$O) δ 7.59 (dd, J=7.5, 1.7 Hz, 1H), 7.44-7.29 (m, 1H), 7.29-7.12 (m, 4H), 7.07 (t, J=7.4 Hz, 1H), 7.00-6.84 (m, 2H), 6.74 (t, J=12.2 Hz, 1H), 6.68-6.59 (m, 1H), 6.55 (t, J=9.7 Hz, 1H), 6.44-6.27 (m, 2H), 3.73 (s, 3H), 3.42 (d, J=6.6 Hz, 2H), 1.81 (td, J=13.3, 6.7 Hz, 1H), 0.91-0.81 (m, 6H). MS (ESI+) m/z 427 (M+H)$^+$.

Example 111

5-[3-fluoro-4-(propan-2-yloxy)phenyl]-2-methyl-6-(2-phenoxyphenyl)pyridazin-3(2H)-one Example 111 was prepared according to the procedure used for the preparation of Example 105, substituting 3-fluoro-4-isopropoxyphenylboronic acid for N-(4-(4,4,5,5-tetramethyl-1,3,2-dioxaborolan-2-yl)phenyl)acetamide, to provide the title compound. ¹H NMR (400 MHz, DMSO-d$_6$/D$_2$O) δ 7.66-7.56 (m, 1H), 7.49-7.33 (m, 1H), 7.31-7.15 (m, 3H), 7.14-6.86 (m, 6H), 6.60 (t, J=8.3 Hz, 1H), 6.42-6.32 (m, 2H), 4.71-4.55 (m, 1H), 3.73 (d, J=10.4 Hz, 3H), 1.29 (d, J=6.0 Hz, 6H). MS (ESI+) m/z 430 (M+H)$^+$.

Example 112

4-[1-methyl-6-oxo-3-(2-phenoxyphenyl)-1,6-dihydropyridazin-4-yl]benzenesulfonamide Example 112 was prepared according to the procedure used for the preparation of Example 105, substituting 4-sulfamoylphenylboronic acid for N-(4-(4,4,5,5-tetramethyl-1,3,2-dioxaborolan-2-yl)phenyl)acetamide, to provide the title compound. ¹H NMR (400 MHz, DMSO-d$_6$/D$_2$O) δ 7.72-7.59 (m, 3H), 7.49-7.30 (m, 3H), 7.32-7.19 (m, 4H), 7.18-7.05 (m, 1H), 7.06-6.91 (m, 1H), 6.53 (dd, J=8.2, 0.6 Hz, 1H), 6.32-6.17 (m, 2H), 3.73 (d, J=10.4 Hz, 3H). MS (ESI+) m/z 434 (M+H)$^+$.

Example 113

5-(1-benzyl-1H-pyrazol-4-yl)-2-methyl-6-(2-phenoxyphenyl)pyridazin-3(2H)-one

Example 113 was prepared according to the procedure used for the preparation of Example 105, substituting 1-benzyl-4-(4,4,5,5-tetramethyl-1,3,2-dioxaborolan-2-yl)-1H-pyrazole for N-(4-(4,4,5,5-tetramethyl-1,3,2-dioxaborolan-2-yl)phenyl)acetamide, to provide the title compound. ¹H NMR (400 MHz, DMSO-d$_6$/D$_2$O) δ 7.58-7.40 (m, 3H), 7.35-7.27 (m, 3H), 7.26-7.22 (m, 1H), 7.22-7.10 (m, 4H), 7.10-7.00 (m, 2H), 6.70-6.56 (m, 1H), 6.44-6.28 (m, 2H), 5.21 (s, 2H), 3.66 (s, 3H). MS (ESI+) m/z 435 (M+H)$^+$.

Example 114

N-cyclopropyl-4-[1-methyl-6-oxo-3-(2-phenoxyphenyl)-1,6-dihydropyridazin-4-yl]benzamide Example 114 was prepared according to the procedure used for the preparation of Example 105, substituting 4-(cyclopropylcarbamoyl)phenylboronic acid for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 7.72-7.51 (m, 3H), 7.42-7.30 (m, 1H), 7.23 (dt, J=10.8, 4.5 Hz, 3H), 7.06 (t, J=7.4 Hz, 1H), 6.97 (d, J=6.2 Hz, 1H), 6.57 (d, J=7.8 Hz, 1H), 6.32 (d, J=7.7 Hz, 2H), 3.72 (s, 3H), 2.94-2.74 (m, 1H), 0.84-0.66 (m, 2H), 0.63-0.45 (m, 2H). MS (ESI+) m/z 438 (M+H)$^+$.

Example 115

5-(3,5-dimethyl-1H-pyrazol-4-yl)-2-methyl-6-(2-phenoxyphenyl)pyridazin-3(2H)-one Example 115 was prepared according to the procedure used for the preparation of Example 105, substituting 3,5-dimethyl-4-(4,4,5,5-tetramethyl-1,3,2-dioxaborolan-2-yl)-1H-pyrazole for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 7.54 (dd, J=7.6, 1.7 Hz, 1H), 7.43-7.27 (m, 3H), 7.27-7.08 (m, 2H), 6.76 (s, 1H), 6.57 (d, J=8.3 Hz, 1H), 6.49 (dd, J=8.5, 0.9 Hz, 2H), 3.72-3.71 (m, 3H), 1.72 (s, 6H). MS (ESI+) m/z 373 (M+H)$^+$.

Example 116

5-(6-methoxypyridin-3-yl)-2-methyl-6-(2-phenoxyphenyl)pyridazin-3(2H)-one

Example 116 was prepared according to the procedure used for the preparation of Example 105, substituting 6-methoxypyridin-3-ylboronic acid for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 8.04-7.90 (m, 1H), 7.62 (dd, J=7.5, 1.7 Hz, 1H), 7.47-7.37 (m, 2H), 7.33-7.20 (m, 3H), 7.08 (dd, J=10.6, 4.2 Hz, 1H), 6.98 (s, 1H), 6.80-6.63 (m, 2H), 6.48-6.28 (m, 2H), 3.83 (s, 3H), 3.71-3.71 (m, 3H). MS (ESI+) m/z 386 (M+H)$^+$.

Example 117

5-(4-ethoxyphenyl)-2-methyl-6-(2-phenoxyphenyl)pyridazin-3(2H)-one

Example 117 was prepared according to the procedure used for the preparation of Example 105, substituting 4-ethoxyphenylboronic acid for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 7.68-7.48 (m, 1H), 7.42-7.27 (m, 1H), 7.28-7.14 (m, 3H), 7.07 (t, J=8.1 Hz, 3H), 6.86 (s, 1H), 6.83-6.72 (m, 2H), 6.57 (d, J=7.7 Hz, 1H), 6.36 (d, J=7.7 Hz, 2H), 4.01 (q, J=7.0 Hz, 2H), 3.70 (s, 3H), 1.32 (t, J=7.0 Hz, 3H). MS (ESI+) m/z 399 (M+H)$^+$.

Example 118

5-(isoquinolin-4-yl)-2-methyl-6-(2-phenoxyphenyl)pyridazin-3(2H)-one

Example 118 was prepared according to the procedure used for the preparation of Example 105, substituting isoquinolin-4-ylboronic acid for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 9.48-9.17 (m, 1H), 8.34-8.22 (m, 1H), 8.22-8.09 (m, 1H), 7.86-7.77 (m, 1H), 7.77-7.64 (m, 2H), 7.63-7.49 (m, 1H), 7.25-7.14 (m, 3H), 7.14-7.08 (m, 1H), 7.08-6.90 (m, 2H), 6.51-6.35 (m, 1H), 6.32-6.09 (m, 2H), 3.80 (s, 3H). MS (ESI+) m/z 406 (M+H)+.

Example 119

N-{4-[1-methyl-6-oxo-3-(2-phenoxyphenyl)-1,6-dihydropyridazin-4-yl]phenyl}methanesulfonamide Example 119 was prepared according to the procedure used for the preparation of Example 105, substituting 4-(methylsulfonamido)phenylboronic acid for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 7.63-7.55 (m, 1H), 7.43-7.31 (m, 2H), 7.30-7.19 (m, 2H), 7.19-7.10 (m, 2H), 7.10-7.03 (m, 2H), 7.04 (d, J=2.1 Hz, 1H), 6.91 (s, 1H), 6.63-6.46 (m, 1H), 6.40-6.19 (m, 1H), 3.71 (d, J=3.1 Hz, 3H), 3.03 (s, 3H). MS (ESI+) m/z 448 (M+H)+.

Example 120

N-{3-[1-methyl-6-oxo-3-(2-phenoxyphenyl)-1,6-dihydropyridazin-4-yl]phenyl}methanesulfonamide Example 120 was prepared according to the procedure used for the preparation of Example 105, substituting 3-(methylsulfonamido)phenylboronic acid for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 7.57 (dd, J=7.5, 1.7 Hz, 1H), 7.40-7.31 (m, 1H), 7.31-7.21 (m, 4H), 7.18 (t, J=8.4 Hz, 1H), 7.15-7.02 (m, 2H), 6.90 (d, J=5.3 Hz, 2H), 6.55 (d, J=8.3 Hz, 1H), 6.39 (d, J=7.6 Hz, 2H), 3.72 (s, 3H), 2.69 (s, 3H). MS (ESI+) m/z 448 (M+H)+.

Example 121

N-{5-[1-methyl-6-oxo-3-(2-phenoxyphenyl)-1,6-dihydropyridazin-4-yl]pyridin-3-yl}acetamide Example 121 was prepared according to the procedure used for the preparation of Example 105, substituting 5-acetamidopyridin-3-ylboronic acid for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 8.69 (d, J=2.2 Hz, 1H), 8.00 (d, J=1.9 Hz, 1H), 7.90 (t, J=2.1 Hz, 1H), 7.61 (dd, J=7.6, 1.7 Hz, 1H), 7.45-7.34 (m, 1H), 7.34-7.18 (m, 3H), 7.16-7.03 (m, 1H), 7.01 (s, 1H), 6.64 (d, J=7.6 Hz, 1H), 6.40 (d, J=0.8 Hz, 1H), 3.73 (s, 3H), 2.03 (s, 3H). MS (ESI+) m/z 413 (M+H)+.

Example 122

N-methyl-5-[1-methyl-6-oxo-3-(2-phenoxyphenyl)-1,6-dihydropyridazin-4-yl]pyridine-3-carboxamide Example 122 was prepared according to the procedure used for the preparation of Example 105, substituting 5-(methylcarbamoyl)pyridin-3-ylboronic acid for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 8.91 (d, J=2.0 Hz, 1H), 8.40 (d, J=2.2 Hz, 1H), 8.02 (t, J=2.1 Hz, 1H), 7.65 (dd, J=7.6, 1.7 Hz, 1H), 7.49-7.34 (m, 1H), 7.33-7.16 (m, 3H), 7.12 (s, 1H), 7.06 (dd, J=10.6, 4.1 Hz, 1H), 6.64-6.52 (m, 1H), 6.38-6.24 (m, 2H), 3.74 (d, J=2.8 Hz, 3H), 2.77 (s, 3H). MS (ESI+) m/z 413 (M+H)+.

Example 123

2-methyl-6-(2-phenoxyphenyl)-5-[6-(propan-2-yloxy)pyridin-3-yl]pyridazin-3(2H)-one Example 123 was prepared according to the procedure used for the preparation of Example 105, substituting 6-isopropoxypyridin-3-ylboronic acid for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 7.92 (d, J=2.3 Hz, 1H), 7.62 (dd, J=7.5, 1.7 Hz, 1H), 7.48-7.32 (m, 2H), 7.32-7.17 (m, 3H), 7.08 (t, J=7.4 Hz, 1H), 7.02-6.84 (m, 1H), 6.59 (dd, J=12.5, 4.3 Hz, 2H), 6.52-6.29 (m, 2H), 5.32-5.02 (m, 1H), 3.72 (d, J=1.5 Hz, 3H), 1.28 (d, J=6.2 Hz, 6H). MS (ESI+) m/z 414 (M+H)+.

Example 124

5-(3-acetyl-2-fluorophenyl)-2-methyl-6-(2-phenoxyphenyl)pyridazin-3(2H)-one

Example 124 was prepared according to the procedure used for the preparation of Example 105, substituting 3-acetyl-2-fluorophenylboronic acid for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 7.74 (dd, J=10.3, 4.5 Hz, 1H), 7.60 (dd, J=7.6, 1.7 Hz, 1H), 7.40-7.29 (m, 2H), 7.30-7.17 (m, 4H), 7.14-7.00 (m, 2H), 6.60 (d, J=7.7 Hz, 1H), 6.41 (d, J=7.7 Hz, 2H), 3.76 (s, 3H), 2.24 (d, J=4.5 Hz, 3H). MS (ESI+) m/z 415 (M+H)+.

Example 125

5-(2,6-dimethoxypyridin-3-yl)-2-methyl-6-(2-phenoxyphenyl)pyridazin-3(2H)-one

Example 125 was prepared according to the procedure used for the preparation of Example 105, substituting 2,6-dimethoxypyridin-3-ylboronic acid for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 7.59-7.45 (m, 1H), 7.37-7.30 (m, 2H), 7.30-7.22 (m, 3H), 7.22-7.15 (m, 1H), 7.09 (q, J=7.0 Hz, 1H), 6.89 (d, J=7.6 Hz, 1H), 6.67 (dd, J=12.5, 4.9 Hz, 1H), 6.47 (dd, J=8.5, 0.9 Hz, 2H), 6.26 (d, J=8.1 Hz, 1H), 3.81 (s, 3H), 3.69 (s, 3H), 3.44 (d, J=6.9 Hz, 3H). MS (ESI+) m/z 416 (M+H)+.

Example 126 methyl 2-[1-methyl-6-oxo-3-(2-phenoxyphenyl)-1,6-dihydropyridazin-4-yl]benzoate

Example 126 was prepared according to the procedure used for the preparation of Example 105, substituting methyl 2-(4,4,5,5-tetramethyl-1,3,2-dioxaborolan-2-yl)benzoate for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 7.77-7.67 (m, 1H), 7.63-7.46 (m, 2H), 7.41-7.32 (m, 1H), 7.33-7.21 (m, 4H), 7.20-7.03 (m, 2H), 6.85 (s, 1H), 6.50-6.44 (m, 1H), 6.43 (d, J=7.7 Hz, 2H), 3.72 (s, 3H), 3.63 (s, 3H). MS (ESI+) m/z 413 (M+H)+.

Example 127

N-methyl-4-[1-methyl-6-oxo-3-(2-phenoxyphenyl)-1,6-dihydropyridazin-4-yl]benzamide Example 127 was prepared according to the procedure used for the preparation of Example 105, substituting N-methyl-4-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 7.67 (d, J=8.4 Hz, 2H), 7.61 (dd, J=7.5, 1.7 Hz, 1H), 7.47-7.32 (m, 1H), 7.27-7.21 (m, 4H), 7.18 (d, J=8.4 Hz, 2H), 7.06 (t, J=7.4 Hz, 1H), 6.97 (s, 1H), 6.56 (d, J=7.7 Hz, 1H), 6.42-6.22 (m, 2H), 3.73 (s, 3H), 2.79 (s, 3H). MS (ESI+) m/z 412 (M+H)+.

Example 128

N-methyl-3-[1-methyl-6-oxo-3-(2-phenoxyphenyl)-1,6-dihydropyridazin-4-yl]benzamide Example 128 was prepared according to the procedure used for the preparation of Example 105, substituting N-methyl-3-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 7.90-7.76 (m, 1H), 7.71 (t, J=1.6 Hz, 1H), 7.59 (dd, J=7.5, 1.7 Hz, 1H), 7.39-7.24 (m, 2H), 7.26-7.14 (m, 4H), 7.09-7.02 (m, 1H), 7.01 (s, 1H), 6.52 (dd, J=8.2, 0.7 Hz, 1H), 6.31 (dd, J=8.6, 0.9 Hz, 2H), 3.74 (s, 3H), 2.74 (s, 3H). MS (ESI+) m/z 412 (M+H)+.

Example 129

2-methyl-5-[1-(3-methylbutyl)-1H-pyrazol-4-yl]-6-(2-phenoxyphenyl)pyridazin-3(2H)-one Example 129 was prepared according to the procedure used for the preparation of Example 105, substituting 1-isopentyl-4-(4,4,5,5-tetramethyl-1,3,2-dioxaborolan-2-yl)-1H-pyrazole for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 7.57-7.44 (m, 3H), 7.37-7.22 (m, 3H), 7.23-7.08 (m, 2H), 7.03 (s, 1H), 6.72 (d, J=7.8 Hz, 1H), 6.54 (dd, J=11.9, 10.8 Hz, 2H), 4.02 (t, J=7.0 Hz, 2H), 3.66 (s, 3H), 1.54 (q, J=6.9 Hz, 2H), 1.42-1.23 (m, 1H), 0.82 (d, J=6.6 Hz, 6H). MS (ESI+) m/z 415 (M+H)+.

Example 130

2-methyl-6-(2-phenoxyphenyl)-5-[2-(propan-2-yloxy)pyridin-3-yl]pyridazin-3(2H)-one Example 130 was prepared according to the procedure used for the preparation of Example 105, substituting 2-isopropoxy-3-(4,4,5,5-tetramethyl-1,3,2-dioxaborolan-2-yl)pyridine for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 8.21-8.03 (m, 1H), 7.63-7.47 (m, 1H), 7.42-7.24 (m, 4H), 7.24-7.15 (m, 1H), 7.15-7.04 (m, 1H), 6.97-6.89 (m, 1H), 6.89-6.80 (m, 1H), 6.66-6.49 (m, 1H), 6.44 (dd, J=8.6, 1.0 Hz, 2H), 5.10-4.80 (m, 1H), 3.71 (t, J=2.2 Hz, 3H), 0.99 (d, J=6.1 Hz, 6H). MS (ESI+) m/z 414 (M+H)$^+$.

Example 131

5-(1,3-benzothiazol-5-yl)-2-methyl-6-(2-phenoxyphenyl)pyridazin-3(2H)-one

Example 131 was prepared according to the procedure used for the preparation of Example 105, substituting 5-(4,4,5,5-tetramethyl-1,3,2-dioxaborolan-2-yl)benzo[d]thiazole for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 8.03 (d, J=8.4 Hz, 1H), 7.83 (d, J=1.5 Hz, 1H), 7.72-7.53 (m, 1H), 7.37-7.25 (m, 4H), 6.98 (ddd, J=15.3, 10.8, 4.4 Hz, 3H), 6.90-6.71 (m, 2H), 6.53 (d, J=7.5 Hz, 1H), 6.34-6.01 (m, 2H), 3.75 (s, 3H). MS (ESI+) m/z 412 (M+H)$^+$.

Example 132

5-(5-acetyl-2-fluorophenyl)-2-methyl-6-(2-phenoxyphenyl)pyridazin-3(2H)-one

Example 132 was prepared according to the procedure used for the preparation of Example 105, substituting 1-(4-fluoro-3-(4,4,5,5-tetramethyl-1,3,2-dioxaborolan-2-yl)phenyl)ethanone for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 8.05-7.90 (m, 1H), 7.72 (dd, J=7.2, 2.2 Hz, 1H), 7.59 (dd, J=7.6, 1.6 Hz, 1H), 7.38-7.29 (m, 1H), 7.29-7.17 (m, 4H), 7.14-7.00 (m, 2H), 6.60 (d, J=7.7 Hz, 1H), 6.40 (s, 1H), 3.76 (s, 3H), 2.34 (d, J=24.6 Hz, 3H). MS (ESI+) m/z 415 (M+H)$^+$.

Example 133

5-(2,3-dihydro-1,4-benzodioxin-6-yl)-2-methyl-6-(2-phenoxyphenyl)pyridazin-3(2H)-one Example 133 was prepared according to the procedure used for the preparation of Example 105, substituting 2-(2,3-dihydrobenzo[b][1,4]dioxin-6-yl)-4,4,5,5-tetramethyl-1,3,2-dioxaborolane for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.57 (dd, J=7.6, 1.7 Hz, 1H), 7.43-7.32 (m, 1H), 7.29-7.20 (m, 3H), 7.09 (dd, J=10.6, 4.1 Hz, 1H), 6.84 (s, 1H), 6.69 (t, J=7.6 Hz, 1H), 6.64-6.54 (m, 3H), 6.44-6.26 (m, 2H), 4.30-4.20 (m, 2H), 4.16 (d, J=2.5 Hz, 2H), 3.71 (s, 3H). MS (ESI+) m/z 413 (M+H)$^+$.

Example 134

5-[3-(1-methoxyethyl)phenyl]-2-methyl-6-(2-phenoxyphenyl)pyridazin-3(2H)-one

Example 134 was prepared according to the procedure used for the preparation of Example 105, substituting 2-(3-(1-methoxyethyl)phenyl)-4,4,5,5-tetramethyl-1,3,2-dioxaborolane for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.59 (dd, J=7.5, 1.7 Hz, 1H), 7.38-7.30 (m, 3H), 7.24-7.16 (m, 3H), 7.07 (t, J=7.4 Hz, 1H), 7.00 (s, 1H), 6.95 (s, 1H), 6.57-6.37 (m, 1H), 6.30 (dd, J=8.5, 0.9 Hz, 2H), 4.14 (q, J=6.4 Hz, 1H), 3.74 (s, 3H), 2.89 (s, 3H), 1.07 (d, J=6.4 Hz, 3H). MS (ESI+) m/z 413 (M+H)$^+$.

Example 135

5-[4-(1-methoxyethyl)phenyl]-2-methyl-6-(2-phenoxyphenyl)pyridazin-3(2H)-one

Example 135 was prepared according to the procedure used for the preparation of Example 105, substituting 2-(4-(1-methoxyethyl)phenyl)-4,4,5,5-tetramethyl-1,3,2-dioxaborolane for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.61 (dd, J=7.5, 1.7 Hz, 1H), 7.42-7.27 (m, 1H), 7.28-7.18 (m, 4H), 7.18-7.04 (m, 4H), 6.94 (s, 1H), 6.42 (d, J=8.2 Hz, 1H), 6.24 (d, J=7.7 Hz, 2H), 4.33 (q, J=6.4 Hz, 1H), 3.74 (s, 3H), 3.16 (d, J=11.7 Hz, 3H), 1.33 (d, J=6.4 Hz, 3H). MS (ESI+) m/z 469 (M+H)$^+$.

Example 136

5-(3-ethoxy-2-fluorophenyl)-2-methyl-6-(2-phenoxyphenyl)pyridazin-3(2H)-one

Example 136 was prepared according to the procedure used for the preparation of Example 105, substituting 2-(3-ethoxy-2-fluorophenyl)-4,4,5,5-tetramethyl-1,3,2-dioxaborolane for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.53 (dd, J=7.6, 1.7 Hz, 1H), 7.38-7.31 (m, 1H), 7.31-7.23 (m, 2H), 7.19 (dt, J=7.5, 3.7 Hz, 1H), 7.11 (dd, J=11.6, 4.3 Hz, 2H), 7.03-6.93 (m, 2H), 6.62-6.52 (m, 2H), 6.50-6.33 (m, 2H), 4.09-3.88 (m, 2H), 3.73 (s, 3H), 1.26 (t, J=7.0 Hz, 3H). MS (ESI+) m/z 413 (M+H)$^+$.

Example 137

5-(2,1,3-benzothiadiazol-5-yl)-2-methyl-6-(2-phenoxyphenyl)pyridazin-3(2H)-one

Example 137 was prepared according to the procedure used for the preparation of Example 105, substituting 5-(4,4,5,5-tetramethyl-1,3,2-dioxaborolan-2-yl)benzo[c][1,2,5]thiadiazole for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.99-7.88 (m, 1H), 7.86-7.82 (m, 1H), 7.77-7.59 (m, 1H), 7.50-7.42 (m, 1H), 7.41-7.33 (m, 1H), 7.32-7.26 (m, 1H), 7.14 (s, 1H), 7.00-6.87 (m, 3H), 6.70-6.52 (m, 1H), 6.30-6.06 (m, 2H), 3.77 (s, 3H). MS (ESI+) m/z 413 (M+H)$^+$.

Example 138

5-[5-(benzylamino)pyridin-3-yl]-2-methyl-6-(2-phenoxyphenyl)pyridazin-3(2H)-one

Example 138 was prepared according to the procedure used for the preparation of Example 105, substituting N-benzyl-5-(4,4,5,5-tetramethyl-1,3,2-dioxaborolan-2-yl)pyridin-3-amine for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 7.99-7.87 (m, 1H), 7.66-7.58 (m, 1H), 7.55-7.47 (m, 1H), 7.43-7.36 (m, 1H), 7.36-7.28 (m, 2H), 7.28-7.20 (m, 6H), 7.17-7.03 (m, 1H), 6.98-6.85 (m, 2H), 6.74-6.62 (m, 1H), 6.52-6.22 (m, 2H), 4.14 (s, 2H), 3.71 (d, J=17.5 Hz, 3H). MS (ESI+) m/z 461 (M+H)$^+$.

Example 139

2-methyl-5-[3-(morpholin-4-yl)phenyl]-6-(2-phenoxyphenyl)pyridazin-3(2H)-one

Example 139 was prepared according to the procedure used for the preparation of Example 105, substituting 4-(3-(4,4,5,5-tetramethyl-1,3,2-dioxaborolan-2-yl)phenyl)morpholine for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 7.58-7.42 (m, 1H), 7.39-7.30 (m, 1H), 7.28-7.18 (m, 3H), 7.16-7.10 (m, 1H), 7.10-7.03 (m, 1H), 6.96-6.89 (m, 1H), 6.86 (s, 1H), 6.69-6.55 (m, 3H), 6.51-6.31 (m, 2H), 3.70 (s, 3H), 3.65 (dd, J=13.7, 8.9 Hz, 4H), 2.96-2.73 (m, 4H). MS (ESI+) m/z 440 (M+H)$^+$.

Example 140

2-methyl-6-(2-phenoxyphenyl)-5-[6-(2,2,2-trifluoroethoxy)pyridin-3-yl]pyridazin-3(2H)-one Example 140 was prepared according to the procedure used for the preparation of Example 105, substituting 5-(4,4,5,5-tetramethyl-1,3,2-dioxaborolan-2-yl)-2-(2,2,2-trifluoroethoxy)pyridine for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 8.02-7.91 (m, 1H), 7.60-7.45 (m, 2H), 7.41-7.33 (m, 1H), 7.32-7.16 (m, 3H), 7.13-6.97 (m, 1H), 6.93 (s, 1H), 6.84-6.76 (m, 1H), 6.75-6.63 (m, 1H), 6.55-6.32 (m, 2H), 4.92 (q, J=9.0 Hz, 2H), 3.70 (s, 3H). MS (ESI+) m/z 453 (M+H)$^+$.

Example 141

2-methyl-5-[3-(morpholin-4-ylmethyl)phenyl]-6-(2-phenoxyphenyl)pyridazin-3(2H)-one Example 141 was prepared according to the procedure used for the preparation of Example 105, substituting 4-(3-(4,4,5,5-tetramethyl-1,3,2-dioxaborolan-2-yl)benzyl)morpholine for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 7.59-7.52 (m, 1H), 7.50-7.43 (m, 1H), 7.43-7.33 (m, 2H), 7.31-7.27 (m, 1H), 7.27-7.18 (m, 4H), 7.12-7.02 (m, 1H), 6.93 (d, J=3.4 Hz, 1H), 6.68-6.59 (m, 1H), 6.52-6.42 (m, 2H), 4.30-4.07 (m, 2H), 3.76-3.71 (m, 4H), 3.70 (s, 3H), 3.00-2.81 (m, 4H). MS (ESI+) m/z 454 (M+H)$^+$.

Example 142

2-methyl-6-(2-phenoxyphenyl)-5-[3-(thiomorpholin-4-ylcarbonyl)phenyl]pyridazin-3(2H)-one Example 142 was prepared according to the procedure used for the preparation of Example 105, substituting (3-(4,4,5,5-tetramethyl-1,3,2-dioxaborolan-2-yl)phenyl)(thiomorpholino)methanone for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 7.54-7.44 (m, 1H), 7.42-7.31 (m, 3H), 7.31-7.23 (m, 3H), 7.23-7.15 (m, 2H), 7.16-7.09 (m, 1H), 7.09-7.00 (m, 2H), 6.97-6.85 (m, 2H), 6.65 (t, J=7.1 Hz, 1H), 6.51 (d, J=7.9 Hz, 2H), 3.70 (s, 3H), 3.61-3.42 (m, 4H), 3.26 (s, 4H). MS (ESI+) m/z 484 (M+H)$^+$.

Example 143

5-[5-(cyclopentylamino)pyridin-3-yl]-2-methyl-6-(2-phenoxyphenyl)pyridazin-3(2H)-one Example 143 was prepared according to the procedure used for the preparation of Example 105, substituting N-cyclopentyl-5-(4,4,5,5-tetramethyl-1,3,2-dioxaborolan-2-yl)pyridin-3-amine for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 8.04-7.90 (m, 1H), 7.74-7.61 (m, 1H), 7.61-7.48 (m, 1H), 7.46-7.32 (m, 1H), 7.36-7.19 (m, 3H), 7.15-7.04 (m, 1H), 6.99 (s, 1H), 6.96-6.88 (m, 1H), 6.81-6.64 (m, 1H), 6.59-6.28 (m, 2H), 3.71 (s, 3H), 3.55-3.40 (m, 1H), 1.95-1.72 (m, 2H), 1.71-1.40 (m, 4H), 1.44-1.21 (m, 2H). MS (ESI+) m/z 439 (M+H)$^+$.

Example 144

N-cyclopropyl-5-[1-methyl-6-oxo-3-(2-phenoxyphenyl)-1,6-dihydropyridazin-4-yl]pyridine-3-carboxamide Example 144 was prepared according to the procedure used for the preparation of Example 105, substituting N-cyclopropyl-5-(4,4,5,5-tetramethyl-1,3,2-dioxaborolan-2-yl)nicotinamide for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 8.96-8.76 (m, 1H), 8.56-8.26 (m, 1H), 7.97 (t, J=2.1 Hz, 1H), 7.65-7.48 (m, 1H), 7.48-7.33 (m, 1H), 7.23 (dd, J=10.9, 4.4 Hz, 3H), 7.12-6.93 (m, 2H), 6.77-6.58 (m, 1H), 6.50-6.33 (m, 2H), 3.72 (s, 3H), 2.97-2.74 (m, 1H), 0.87-0.67 (m, 2H), 0.62-0.46 (m, 2H). MS (ESI+) m/z 439 (M+H)$^+$.

Example 145

N-cyclopentyl-5-[1-methyl-6-oxo-3-(2-phenoxyphenyl)-1,6-dihydropyridazin-4-yl]pyridine-3-carboxamide Example 145 was prepared according to the procedure used for the preparation of Example 105, substituting N-cyclopentyl-5-(4,4,5,5-tetramethyl-1,3,2-dioxaborolan-2-yl)nicotinamide for N-(4-(4,4,5,5-tetramethyl-1,3,2-dioxaborolan-2-yl)phenyl)acetamide, to provide the title compound. $^1$H NMR (400 MHz, DMSO-$d_6$/$D_2O$) δ 8.89 (d, J=2.0 Hz, 1H), 8.38 (d, J=2.2 Hz, 1H), 8.00 (t, J=2.1 Hz, 1H), 7.57 (dd, J=7.5, 1.7 Hz, 1H), 7.42-7.32 (m, 2H), 7.28-7.17 (m, 3H), 6.98 (d, J=7.7 Hz, 1H), 6.65 (d, J=8.2 Hz, 1H), 6.54-6.37 (m, 2H), 4.19 (dd, J=13.4, 6.7 Hz, 1H), 3.73 (s, 3H), 2.07-1.80 (m, 2H), 1.78-1.61 (m, 2H), 1.61-1.38 (m, 4H). MS (ESI+) m/z 467 (M+H)+.

Example 146

N,N-diethyl-3-[1-methyl-6-oxo-3-(2-phenoxyphenyl)-1,6-dihydropyridazin-4-yl]benzenesulfonamide Example 146 was prepared according to the procedure used for the preparation of Example 105, substituting N,N-diethyl-3-(4,4,5,5-tetramethyl-1,3,2-dioxaborolan-2-yl)benzenesulfonamide for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.85-7.70 (m, 1H), 7.60-7.51 (m, 3H), 7.49 (d, J=10.8 Hz, 1H), 7.39-7.31 (m, 1H), 7.29-7.18 (m, 3H), 7.16-6.99 (m, 1H), 6.92 (s, 1H), 6.73-6.59 (m, 1H), 6.50 (dd, J=9.8, 4.2 Hz, 2H), 3.71 (s, 3H), 2.94 (q, J=7.1 Hz, 4H), 0.99 (t, J=7.1 Hz, 6H). MS (ESI+) m/z 490 (M+H)+.

Example 147

2-methyl-5-[4-(morpholin-4-ylcarbonyl)phenyl]-6-(2-phenoxyphenyl)pyridazin-3(2H)-one Example 147 was prepared according to the procedure used for the preparation of Example 105, substituting morpholino(4-(4,4,5,5-tetramethyl-1,3,2-dioxaborolan-2-yl)phenyl)methanone for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.57-7.47 (m, 1H), 7.39-7.32 (m, 1H), 7.30-7.26 (m, 2H), 7.26-7.19 (m, 5H), 7.15-7.00 (m, 1H), 6.90 (s, 1H), 6.62 (dd, J=8.3, 5.2 Hz, 1H), 6.49-6.40 (m, 2H), 3.71 (s, 3H), 3.65-3.55 (m, 4H), 3.51-3.35 (m, 4H). MS (ESI+) m/z 468 (M+H)+.

Example 148

N-cyclohexyl-N-methyl-3-[1-methyl-6-oxo-3-(2-phenoxyphenyl)-1,6-dihydropyridazin-4-yl]benzamide Example 148 was prepared according to the procedure used for the preparation of Example 105, substituting N-cyclohexyl-N-methyl-3-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.56-7.43 (m, 1H), 7.36 (dd, J=9.2, 5.7 Hz, 1H), 7.32-7.28 (m, 2H), 7.27-7.21 (m, 2H), 7.20-7.12 (m, 1H), 7.12-7.02 (m, 2H), 6.88 (s, 1H), 6.62 (d, J=8.2 Hz, 1H), 6.52 (t, J=5.5 Hz, 1H), 3.69 (s, 3H), 2.58-2.43 (m, 1H), 1.87-1.65 (m, 2H), 1.64-1.33 (m, 4H), 1.26-0.76 (m, 3H). MS (ESI+) m/z 494 (M+H)+.

Example 149

2-methyl-5-[4-(morpholin-4-yl)phenyl]-6-(2-phenoxyphenyl)pyridazin-3(2H)-one

Example 149 was prepared according to the procedure used for the preparation of Example 105, substituting 4-(4-(4,4,5,5-tetramethyl-1,3,2-dioxaborolan-2-yl)phenyl)morpholine for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.64-7.39 (m, 1H), 7.39-7.30 (m, 1H), 7.25-7.13 (m, 4H), 7.09-6.96 (m, 3H), 6.80-6.72 (m, 3H), 6.69-6.56 (m, 1H), 6.51-6.32 (m, 2H), 3.77-3.70 (m, 4H), 3.70-3.62 (s, 3H), 3.19-3.03 (m, 4H). MS (ESI+) m/z 440 (M+H)+.

Example 150

N-[3-(dimethylamino)propyl]-4-[1-methyl-6-oxo-3-(2-phenoxyphenyl)-1,6-dihydropyridazin-4-yl]benzamide Example 150 was prepared according to the procedure used for the preparation of Example 105, substituting N-(3-(dimethylamino)propyl)-4-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.75-7.63 (m, 2H), 7.58-7.45 (m, 1H), 7.42-7.30 (m, 1H), 7.30-7.15 (m, 5H), 7.08-6.98 (m, 1H), 6.96-6.82 (m, 1H), 6.69-6.60 (m, 1H), 6.55-6.43 (m, 2H), 3.78-3.65 (m, 3H), 3.45-3.32 (m, 2H), 3.17-3.06 (m, 2H), 2.81 (s, 6H), 2.06-1.79 (m, 2H). MS (ESI+) m/z 483 (M+H)+.

Example 151

2-methyl-6-(2-phenoxyphenyl)-5-[6-(piperazin-1-yl)pyridin-3-yl]pyridazin-3(2H)-one Example 151 was prepared according to the procedure used for the preparation of Example 105, substituting 1-(5-(4,4,5,5-tetramethyl-1,3,2-dioxaborolan-2-yl)pyridin-2-yl)piperazine for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.98-7.86 (m, 1H), 7.59-7.46 (m, 1H), 7.42-7.36 (m, 1H), 7.36-7.29 (m, 1H), 7.28-7.16 (m, 3H), 7.12-6.97 (m, 1H), 6.85 (s, 1H), 6.81-6.66 (m, 2H), 6.59-6.42 (m, 2H), 3.77-3.70 (m, 4H), 3.67 (s, 3H), 3.23-3.12 (m, 4H). MS (ESI+) m/z 440 (M+H)+.

Example 152

3-fluoro-N,N-dimethyl-5-[1-methyl-6-oxo-3-(2-phenoxyphenyl)-1,6-dihydropyridazin-4-yl]benzamide Example 152 was prepared according to the procedure used for the preparation of Example 105, substituting 3-fluoro-N,N-dimethyl-5-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.64-7.46 (m, 1H), 7.42-7.31 (m, 1H), 7.28-7.21 (m, 2H), 7.21-7.14 (m, 2H), 7.14-7.04 (m, 2H), 6.96 (dd, J=4.3, 3.0 Hz, 2H), 6.75-6.64 (m, 1H), 6.54 (t, J=5.4 Hz, 2H), 3.70 (s, 3H), 2.90-2.64 (m, 6H). MS (ESI+) m/z 444 (M+H)+.

Example 153

2-methyl-5-[2-(morpholin-4-yl)pyridin-4-yl]-6-(2-phenoxyphenyl)pyridazin-3(2H)-one Example 153 was prepared according to the procedure used for the preparation of Example 105, substituting 4-(4-(4,4,5,5-tetramethyl-1,3,2-dioxaborolan-2-yl)pyridin-2-yl)morpholine for N-(4-(4,4,5,5-tetramethyl-1,3,2-dioxaborolan-2-yl)phenyl)acetamide, to provide the title compound.

$^1$H NMR (400 MHz, DMSO-d$_6$/D$_2$O) δ 8.01-7.81 (m, 1H), 7.64-7.49 (m, 1H), 7.43-7.31 (m, 1H), 7.27-7.14 (m, 3H), 7.11-7.02 (m, 1H), 6.97 (s, 1H), 6.81-6.65 (m, 1H), 6.55-6.41 (m, 4H), 3.71 (s, 3H), 3.63-3.55 (m, 4H), 3.25 (s, 4H). MS (ESI+) m/z 441 (M+H)$^+$.

Example 154

2-methyl-5-{3-[(4-methylpiperidin-1-yl)carbonyl] phenyl}-6-(2-phenoxyphenyl)pyridazin-3(2H)-one Example 154 was prepared according to the procedure used for the preparation of Example 105, substituting (4-methylpiperidin-1-yl)(3-(4,4,5,5-tetramethyl-1,3,2-dioxaborolan-2-yl)phenyl)methanone for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.52-7.46 (m, 1H), 7.39-7.30 (m, 2H), 7.30-7.25 (m, 2H), 7.25-7.21 (m, 1H), 7.21-7.15 (m, 1H), 7.10-7.01 (m, 2H), 6.89 (s, 1H), 6.66-6.59 (m, 1H), 6.55-6.46 (m, 2H), 3.70 (s, 3H), 2.88-2.67 (m, 2H), 1.66-1.48 (m, 2H), 0.98-0.78 (m, 4H). MS (ESI+) m/z 480 (M+H)$^+$.

Example 155

2-fluoro-N,N-dimethyl-5-[1-methyl-6-oxo-3-(2-phenoxyphenyl)-1,6-dihydropyridazin-4-yl]benzamide Example 155 was prepared according to the procedure used for the preparation of Example 105, substituting 2-fluoro-N,N-dimethyl-5-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.54-7.46 (m, 1H), 7.40-7.33 (m, 1H), 7.33-7.27 (m, 1H), 7.28-7.23 (m, 2H), 7.23-7.18 (m, 1H), 7.18-7.12 (m, 1H), 7.11-7.03 (m, 2H), 6.93-6.87 (m, 1H), 6.74-6.66 (m, 1H), 6.63-6.54 (m, 2H), 3.68 (s, 3H), 3.09-2.81 (m, 3H), 2.78-2.55 (m, 3H). MS (ESI+) m/z 444 (M+H)$^+$.

Example 156

2-methyl-6-(2-phenoxyphenyl)-5-[3-(pyrrolidin-1-ylsulfonyl)phenyl]pyridazin-3(2H)-one Example 156 was prepared according to the procedure used for the preparation of Example 105, substituting 1-(3-(4,4,5,5-tetramethyl-1,3,2-dioxaborolan-2-yl)phenylsulfonyl)pyrrolidine for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.86-7.68 (m, 1H), 7.66-7.44 (m, 4H), 7.44-7.29 (m, 1H), 7.30-7.15 (m, 3H), 7.13-6.97 (m, 1H), 6.99-6.89 (m, 1H), 6.72-6.61 (m, 1H), 6.57-6.40 (m, 2H), 3.71 (d, J=4.0 Hz, 3H), 3.07-2.78 (m, 4H), 1.71-1.47 (m, 4H). MS (ESI+) m/z 488 (M+H)$^+$.

Example 157

2-methyl-6-(2-phenoxyphenyl)-5-[3-(piperidin-1-ylcarbonyl)phenyl]pyridazin-3(2H)-one Example 157 was prepared according to the procedure used for the preparation of Example 105, substituting piperidin-1-yl(3-(4,4,5,5-tetramethyl-1,3,2-dioxaborolan-2-yl)phenyl)methanone for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.53-7.46 (m, 1H), 7.40-7.31 (m, 3H), 7.31-7.25 (m, 2H), 7.25-7.15 (m, 3H), 7.11-7.01 (m, 2H), 6.89 (d, J=3.9 Hz, 1H), 6.67-6.57 (m, 1H), 6.55-6.43 (m, 2H), 3.70 (s, 3H), 3.25-3.18 (m, 4H), 1.73-1.46 (m, 2H), 1.48-1.23 (m, 4H). MS (ESI+) m/z 466 (M+H)$^+$.

Example 158

N,N-diethyl-4-[1-methyl-6-oxo-3-(2-phenoxyphenyl)-1,6-dihydropyridazin-4-yl]benzamide Example 158 was prepared according to the procedure used for the preparation of Example 105, substituting N,N-diethyl-4-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.55-7.45 (m, 1H), 7.38-7.32 (m, 1H), 7.30-7.18 (m, 7H), 7.12-7.00 (m, 1H), 6.96-6.80 (m, 1H), 6.71-6.59 (m, 1H), 6.47 (s, 1H), 3.70 (s, 3H), 3.35-3.29 (m, 4H), 1.21-0.92 (m, 6H). MS (ESI+) m/z 454 (M+H)$^+$.

Example 159

N-methyl-4-[1-methyl-6-oxo-3-(2-phenoxyphenyl)-1,6-dihydropyridazin-4-yl]benzenesulfonamide Example 159 was prepared according to the procedure used for the preparation of Example 105, substituting N-methyl-4-(4,4,5,5-tetramethyl-1,3,2-dioxaborolan-2-yl)benzenesulfonamide for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.75-7.61 (m, 2H), 7.58-7.47 (m, 1H), 7.40-7.32 (m, 3H), 7.27-7.15 (m, 3H), 7.12-6.98 (m, 1H), 6.96-6.84 (m, 1H), 6.65-6.58 (m, 1H), 6.46-6.35 (m, 2H), 3.72 (s, 3H), 2.47-2.44 (m, 3H). MS (ESI+) m/z 448 (M+H)$^+$.

Example 160

N,N-diethyl-3-[1-methyl-6-oxo-3-(2-phenoxyphenyl)-1,6-dihydropyridazin-4-yl]benzamide Example 160 was prepared according to the procedure used for the preparation of Example 105, substituting N,N-diethyl-3-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.48 (dd, J=7.6, 1.7 Hz, 1H), 7.36-7.28 (m, 4H), 7.29-7.20 (m, 3H), 7.17 (t, J=7.0 Hz, 1H), 7.03-6.92 (m, 1H), 6.98-6.86 (m, 2H), 6.63 (d, J=8.3 Hz, 1H), 6.52 (d, J=8.3 Hz, 2H), 3.70 (s, 3H), 3.14 (s, 4H), 0.98 (t, J=6.9 Hz, 6H). MS (ESI+) m/z 454 (M+H)$^+$.

Example 161

2-methyl-5-[4-(4-methylpiperazin-1-yl)phenyl]-6-(2-phenoxyphenyl)pyridazin-3(2H)-one Example 161 was prepared according to the procedure used for the preparation of Example 105, substituting 1-methyl-4-(4-(4,4,5,5-tetramethyl-1,3,2-dioxaborolan-2-yl)phenyl)piperazine for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.62-7.43 (m, 1H), 7.41-7.29 (m, 1H), 7.28-7.14 (m, 3H), 7.04 (dd, J=8.0, 5.8 Hz, 3H), 6.84 (d, J=8.8 Hz, 2H), 6.78 (s, 1H), 6.66 (d, J=8.2 Hz, 1H), 6.46 (d, J=8.4 Hz, 2H), 3.67 (s, 3H), 3.31 (d, J=20.1 Hz, 8H), 2.88 (s, 3H). MS (ESI+) m/z 453 (M+H)$^+$.

Example 162

2-methyl-5-(6-{[2-(morpholin-4-yl)ethyl] amino}pyridin-3-yl)-6-(2-phenoxyphenyl)pyridazin-3(2H)-one Example 162 was prepared according to the procedure used for the preparation of Example 105, substituting N-(2-morpholinoethyl)-5-(4,4,5,5-tetramethyl-1,3,2-dioxaborolan-2-yl)pyridin-2-amine for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.83 (d, J=2.3 Hz, 1H), 7.57-7.45 (m, 1H), 7.45-7.31 (m, 1H), 7.27-7.16 (m, 4H), 7.06 (td, J=7.2, 3.5 Hz, 1H), 6.84 (d, J=3.5 Hz, 1H), 6.76 (d, J=8.1 Hz, 1H), 6.62-6.51 (m, 2H), 6.51-6.39 (m, 1H), 3.86-3.76 (m, 4H), 3.66 (s, 3H), 3.63 (t, J=6.1 Hz, 2H), 3.27 (dd, J=6.8, 3.6 Hz, 6H). MS (ESI+) m/z 484 (M+H)$^+$.

Example 163

N-[3-(dimethylamino)propyl]-3-[1-methyl-6-oxo-3-(2-phenoxyphenyl)-1,6-dihydropyridazin-4-yl]benzamide Example 163 was prepared according to the procedure used for the preparation of Example 105, substituting N-(3-(dimethylamino)propyl)-3-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.89-7.76 (m, 1H), 7.71-7.65 (m, 1H), 7.57-7.43 (m, 1H), 7.39-7.30 (m, 2H), 7.29-7.17 (m, 4H), 7.09-7.00 (m, 1H), 6.93 (s, 1H), 6.68-6.55 (m, 1H), 6.54-6.32 (m, 2H), 3.71 (s, 3H), 3.35-3.27 (m, 2H), 3.13-2.99 (m, 2H), 2.52 (dt, J=3.6, 1.8 Hz, 6H), 2.01-1.81 (m, 2H). MS (ESI+) m/z 483 (M+H)$^+$.

Example 164

5-[6-(benzylamino)pyridin-3-yl]-2-methyl-6-(2-phenoxyphenyl)pyridazin-3(2H)-one

Example 164 was prepared according to the procedure used for the preparation of Example 105, substituting N-benzyl-5-(4,4,5,5-tetramethyl-1,3,2-dioxaborolan-2-yl)pyridin-2-amine for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.70 (t, J=12.0 Hz, 1H), 7.53 (dd, J=7.5, 1.7 Hz, 1H), 7.44-7.35 (m, 1H), 7.37-7.30 (m, 5H), 7.30-7.17 (m, 4H), 7.05 (t, J=7.4 Hz, 1H), 6.87 (d, J=4.4 Hz, 1H), 6.81-6.68 (m, 1H), 6.62 (d, J=9.0 Hz, 1H), 6.53 (s, 1H), 4.51 (d, J=5.4 Hz, 2H), 3.70 (d, J=21.2 Hz, 3H). MS (ESI+) m/z 461 (M+H)$^+$.

Example 165

N-(2-cyanoethyl)-4-[1-methyl-6-oxo-3-(2-phenoxyphenyl)-1,6-dihydropyridazin-4-yl]benzamide Example 165 was prepared according to the procedure used for the preparation of Example 105, substituting N-(2-cyanoethyl)-4-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.75-7.63 (m, 2H), 7.61-7.46 (m, 1H), 7.43-7.31 (m, 1H), 7.30-7.15 (m, 5H), 7.13-6.95 (m, 1H), 6.89 (d, J=9.4 Hz, 1H), 6.75-6.53 (m, 1H), 6.53-6.27 (m, 2H), 3.71 (s, 3H), 3.58-3.42 (m, 2H), 2.76 (t, J=6.5 Hz, 2H) MS (ESI+) m/z 451 (M+H)$^+$.

Example 166

2-methyl-5-[5-methyl-6-(morpholin-4-yl)pyridin-3-yl]-6-(2-phenoxyphenyl)pyridazin-3(2H)-one Example 166 was prepared according to the procedure used for the preparation of Example 105, substituting 4-(3-methyl-5-(4,4,5,5-tetramethyl-1,3,2-dioxaborolan-2-yl)pyridin-2-yl)morpholine for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.94-7.77 (m, 1H), 7.66-7.49 (m, 1H), 7.49-7.33 (m, 1H), 7.29-7.16 (m, 5H), 7.14-7.02 (m, 1H), 6.89 (d, J=3.7 Hz, 1H), 6.68 (d, J=7.8 Hz, 1H), 6.54-6.35 (m, 2H), 3.74-3.70 (m, 3H), 3.70 (s, 3H), 3.17-3.00 (m, 4H), 2.04 (s, 3H). MS (ESI+) m/z 455 (M+H)$^+$.

Example 167

N,N-diethyl-3-fluoro-5-[1-methyl-6-oxo-3-(2-phenoxyphenyl)-1,6-dihydropyridazin-4-yl]benzamide Example 167 was prepared according to the procedure used for the preparation of Example 105, substituting N,N-diethyl-3-fluoro-5-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.55-7.47 (m, 1H), 7.43-7.31 (m, 1H), 7.30-7.22 (m, 2H), 7.19 (tt, J=7.2, 2.4 Hz, 1H), 7.15-7.10 (m, 1H), 7.10-7.03 (m, 2H), 6.95 (d, J=3.9 Hz, 1H), 6.89 (d, J=5.9 Hz, 1H), 6.72-6.64 (m, 1H), 6.61-6.52 (m, 2H), 3.70 (s, 3H), 3.24-3.04 (m, 4H), 1.21-0.82 (m, 6H). MS (ESI+) m/z 472 (M+H)$^+$.

Example 168

N-tert-butyl-4-[1-methyl-6-oxo-3-(2-phenoxyphenyl)-1,6-dihydropyridazin-4-yl]benzamide Example 168 was prepared according to the procedure used for the preparation of Example 105, substituting N-tert-butyl-4-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.71-7.59 (m, 2H), 7.57-7.47 (m, 1H), 7.44-7.27 (m, 1H), 7.20 (t, J=7.7 Hz, 5H), 7.07-6.98 (m, 1H), 6.89-6.80 (m, 1H), 6.71-6.56 (m, 1H), 6.53-6.25 (m, 2H), 3.69 (s, 3H), 1.39 (s, 9H). MS (ESI+) m/z 454 (M+H)$^+$.

Example 169

N-cyclopentyl-4-[1-methyl-6-oxo-3-(2-phenoxyphenyl)-1,6-dihydropyridazin-4-yl]benzamide Example 169 was prepared according to the procedure used for the preparation of Example 105, substituting N-cyclopentyl-4-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-$d_6$/D$_2$O) δ 7.69 (d, J=8.3 Hz, 2H), 7.52 (dd, J=7.5, 1.7 Hz, 1H), 7.44-7.28 (m, 1H), 7.20 (dd, J=11.6, 5.3 Hz, 5H), 7.04 (t, J=7.4 Hz, 1H), 6.88 (s, 1H), 6.66 (d, J=8.2 Hz, 1H), 6.45 (d, J=7.8 Hz, 2H), 4.37-4.08 (m, 1H), 3.70 (s, 3H), 1.90 (dd, J=8.0, 4.9 Hz, 2H), 1.65 (d, J=40.3 Hz, 2H), 1.60-1.37 (m, 4H) MS (ESI+) m/z 466 (M+H)$^+$.

Example 170

4-[1-methyl-6-oxo-3-(2-phenoxyphenyl)-1,6-dihydropyridazin-4-yl]-N-(2-methylpropyl)benzamide Example 170 was prepared according to the procedure used for the preparation of Example 105, substituting N-isobutyl-4-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-$d_6$/D$_2$O) δ 7.77-7.60 (m, 2H), 7.56-7.48 (m, 1H), 7.39-7.30 (m, 1H), 7.27-7.13 (m, 5H), 7.13-6.96 (m, 1H), 6.89 (s, 1H), 6.66 (dd, J=11.3, 4.7 Hz, 1H), 6.52-6.32 (m, 2H), 3.70 (s, 3H), 3.11 (d, J=6.9 Hz, 2H), 2.05-1.74 (m, 1H), 0.90 (d, J=6.7 Hz, 6H). MS (ESI+) m/z 454 (M+H)$^+$.

Example 171

N-(3-methoxypropyl)-4-[1-methyl-6-oxo-3-(2-phenoxyphenyl)-1,6-dihydropyridazin-4-yl]benzamide Example 171 was prepared according to the procedure used for the preparation of Example 105, substituting N-(3-methoxypropyl)-4-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-$d_6$/D$_2$O) δ 7.67 (d, J=8.3 Hz, 2H), 7.52 (dd, J=7.6, 1.7 Hz, 1H), 7.43-7.30 (m, 1H), 7.32-7.17 (m, 5H), 7.04 (t, J=7.4 Hz, 1H), 6.89 (s, 1H), 6.65 (d, J=8.2 Hz, 1H), 6.44 (d, J=7.8 Hz, 2H), 3.70 (s, 3H), 3.40 (t, J=6.4 Hz, 2H), 3.32 (t, J=6.7 Hz, 2H), 3.25 (s, 3H), 1.78 (p, J=6.6 Hz, 2H). MS (ESI+) m/z 470 (M+H)$^+$.

Example 172

2-methyl-5-{1-[2-(morpholin-4-yl)ethyl]-1H-pyrazol-4-yl}-6-(2-phenoxyphenyl)pyridazin-3(2H)-one Example 172 was prepared according to the procedure used for the preparation of Example 105, substituting 4-(2-(4-(4,4,5,5-tetramethyl-1,3,2-dioxaborolan-2-yl)-1H-pyrazol-1-yl)ethyl)morpholine for N-(4-(4,4,5,5-tetramethyl-1,3,2-dioxaborolan-2-yl)phenyl)acetamide, to provide the title compound. $^1$H NMR (400 MHz, DMSO-$d_6$/D$_2$O) δ 7.66 (s, 1H), 7.56-7.39 (m, 2H), 7.35-7.21 (m, 3H), 7.14 (s, 1H), 7.07 (t, J=7.4 Hz, 1H), 6.97 (s, 1H), 6.90 (d, J=8.2 Hz, 1H), 6.68-6.53 (m, 2H), 4.45 (t, J=6.5 Hz, 2H), 3.86-3.74 (m, 4H), 3.62 (s, 3H), 3.50 (t, J=6.5 Hz, 2H), 3.18 (dd, J=9.3, 4.3 Hz, 4H). MS (ESI+) m/z 458 (M+H)$^+$.

Example 173

N-(2-methoxyethyl)-4-[1-methyl-6-oxo-3-(2-phenoxyphenyl)-1,6-dihydropyridazin-4-yl]benzamide Example 173 was prepared according to the procedure used for the preparation of Example 105, substituting N-(2-methoxyethyl)-4-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-$d_6$/D$_2$O) δ 7.68 (d, J=8.3 Hz, 2H), 7.52 (dd, J=7.6, 1.7 Hz, 1H), 7.41-7.28 (m, 1H), 7.26-7.14 (m, 5H), 7.04 (t, J=7.4 Hz, 1H), 6.89 (s, 1H), 6.65 (d, J=8.2 Hz, 1H), 6.44 (d, J=8.2 Hz, 2H), 3.70 (s, 3H), 3.54-3.40 (m, 4H), 3.29 (s, 3H). MS (ESI+) m/z 456 (M+H)$^+$.

Example 174

2-methyl-5-[2-(4-methylpiperazin-1-yl)pyridin-4-yl]-6-(2-phenoxyphenyl)pyridazin-3(2H)-one Example 174 was prepared according to the procedure used for the preparation of Example 105, substituting 1-methyl-4-(4-(4,4,5,5-tetramethyl-1,3,2-dioxaborolan-2-yl)pyridin-2-yl)piperazine for N-(4-(4,4,5,5-tetramethyl-1,3,2-dioxaborolan-2-yl)phenyl)acetamide, to provide the title compound. $^1$H NMR (400 MHz, DMSO-$d_6$/D$_2$O) δ 8.02 (d, J=5.2 Hz, 1H), 7.55 (dd, J=7.6, 1.7 Hz, 1H), 7.45-7.32 (m, 1H), 7.23 (q, J=8.3 Hz, 3H), 7.08 (t, J=7.4 Hz, 1H), 6.96 (s, 1H), 6.69 (d, J=8.2 Hz, 1H), 6.62 (s, 1H), 6.53-6.42 (m, 3H), 3.71 (s, 3H), 3.26-3.24 (m, 4H), 3.20 (s, 4H), 2.84 (s, 3H). MS (ESI+) m/z 454 (M+H)$^+$.

Example 175

2-methyl-5-[3-(morpholin-4-ylcarbonyl)phenyl]-6-(2-phenoxyphenyl)pyridazin-3(2H)-one Example 175 was prepared according to the procedure used for the preparation of Example 105, substituting morpholino(3-(4,4,5,5-tetramethyl-1,3,2-dioxaborolan-2-yl)phenyl)methanone for N-(4-(4,4,5,5-tetramethyl-1,3,2-dioxaborolan-2-yl)phenyl)acetamide, to provide the title compound. $^1$H NMR (400 MHz, DMSO-$d_6$/D$_2$O) δ 7.51 (dd, J=7.5, 1.7 Hz, 1H), 7.44-7.29 (m, 4H), 7.26-7.19 (m, 2H), 7.13 (s, 1H), 7.06 (t, J=7.4 Hz, 1H), 6.90 (s, 1H), 6.63 (d, J=8.3 Hz, 1H), 6.50 (d, J=7.9 Hz, 2H), 3.70 (s, 3H), 3.55-3.44 (m, 4H), 3.27 (s, 4H). MS (ESI+) m/z 468 (M+H)$^+$.

Example 176

2-methyl-5-[3-(5-methyl-1,3,4-oxadiazol-2-yl)phenyl]-6-(2-phenoxyphenyl)pyridazin-3(2H)-one Example 176 was prepared according to the procedure used for the preparation of Example 105, substituting 2-methyl-5-(3-(4,4,5,5-tetramethyl-1,3,2-dioxaborolan-2-yl)phenyl)-1,3,4-oxadiazole for N-(4-(4,4,5,5-tetramethyl-1,3,2-dioxaborolan-2-yl)phenyl)acetamide, to provide the title compound. $^1$H NMR (400 MHz, DMSO-$d_6$/D$_2$O) δ 7.98-7.85 (m, 1H), 7.73-7.64 (m, 1H), 7.59-7.52 (m, 1H), 7.46 (t, J=7.8 Hz, 1H), 7.39-7.29 (m, 3H), 7.28-7.12 (m, 4H), 7.03-6.90 (m, 2H), 6.64 (dd, J=13.1, 8.2 Hz, 1H), 6.47 (d, J=8.3 Hz, 2H), 3.71 (d, J=8.3 Hz, 3H), 2.53 (s, 3H). MS (ESI+) m/z 437 (M+H)$^+$.

Example 177

N-cyclopropyl-3-[1-methyl-6-oxo-3-(2-phenoxyphenyl)-1,6-dihydropyridazin-4-yl]benzamide Example 177 was prepared according to the procedure used for the preparation of Example 105, substituting N-cyclopropyl-3-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.85-7.73 (m, 1H), 7.66 (t, J=1.6 Hz, 1H), 7.50 (dd, J=7.6, 1.7 Hz, 1H), 7.39-7.26 (m, 2H), 7.26-7.13 (m, 4H), 7.04 (t, J=7.4 Hz, 1H), 6.93 (s, 1H), 6.61 (d, J=8.2 Hz, 1H), 6.52-6.27 (m, 2H), 3.71 (s, 3H), 2.92-2.75 (m, 1H), 0.78-0.61 (m, 2H), 0.60-0.44 (m, 2H). MS (ESI+) m/z 438 (M+H)$^+$.

Example 178

2-methyl-6-(2-phenoxyphenyl)-5-[4-(pyrrolidin-1-ylsulfonyl)phenyl]pyridazin-3(2H)-one Example 178 was prepared according to the procedure used for the preparation of Example 105, substituting 1-(4-(4,4,5,5-tetramethyl-1,3,2-dioxaborolan-2-yl)phenylsulfonyl)pyrrolidine for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.74-7.58 (m, 2H), 7.52 (dd, J=7.6, 1.7 Hz, 1H), 7.44-7.29 (m, 3H), 7.27-7.16 (m, 3H), 7.06 (t, J=7.4 Hz, 1H), 6.95 (s, 1H), 6.63 (d, J=8.3 Hz, 1H), 6.49 (d, J=7.8 Hz, 2H), 3.71 (s, 3H), 3.14 (t, J=6.8 Hz, 4H), 1.80-1.56 (m, 4H). MS (ESI+) m/z 488 (M+H)$^+$.

Example 179

2-methyl-5-[6-(morpholin-4-yl)pyridin-3-yl]-6-(2-phenoxyphenyl)pyridazin-3(2H)-one Example 179 was prepared according to the procedure used for the preparation of Example 105, substituting 4-(5-(4,4,5,5-tetramethyl-1,3,2-dioxaborolan-2-yl)pyridin-2-yl)morpholine for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.87 (d, J=2.5 Hz, 1H), 7.53 (dd, J=7.5, 1.7 Hz, 1H), 7.44-7.35 (m, 1H), 7.32 (dd, J=9.0, 2.5 Hz, 1H), 7.24 (ddd, J=11.6, 6.2, 3.0 Hz, 3H), 7.05 (t, J=7.4 Hz, 1H), 6.85 (s, 1H), 6.74 (d, J=8.2 Hz, 1H), 6.68 (d, J=9.0 Hz, 1H), 6.52 (d, J=7.9 Hz, 2H), 3.69 (s, J=4.0 Hz, 3H), 3.68 (d, J=1.8 Hz, 4H), 3.56-3.37 (m, 4H). MS (ESI+) m/z 441 (M+H)$^+$.

Example 180

2-methyl-6-(2-phenoxyphenyl)-5-{4-[4-(propan-2-yl)piperazin-1-yl]phenyl}pyridazin-3(2H)-one Example 180 was prepared according to the procedure used for the preparation of Example 105, substituting 1-isopropyl-4-(4-(4,4,5,5-tetramethyl-1,3,2-dioxaborolan-2-yl)phenyl)piperazine for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.50 (dd, J=7.6, 1.7 Hz, 1H), 7.42-7.30 (m, 1H), 7.26-7.15 (m, 4H), 7.05 (t, J=7.4 Hz, 3H), 6.86 (t, J=13.8 Hz, 2H), 6.78 (s, 1H), 6.66 (d, J=7.7 Hz, 1H), 6.46 (d, J=7.8 Hz, 2H), 3.68 (d, J=4.7 Hz, 4H), 3.53 (dt, J=13.2, 6.5 Hz, 4H), 3.33 (s, 2H), 3.20 (s, 2H), 1.32 (d, J=6.6 Hz, 6H). MS (ESI+) m/z 481 (M+H)$^+$.

Example 181

N,N-diethyl-2-fluoro-5-[1-methyl-6-oxo-3-(2-phenoxyphenyl)-1,6-dihydropyridazin-4-yl]benzamide Example 181 was prepared according to the procedure used for the preparation of Example 105, substituting N,N-diethyl-2-fluoro-5-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.53-7.45 (m, 1H), 7.39-7.29 (m, 3H), 7.29-7.22 (m, 2H), 7.22-7.13 (m, 2H), 7.06 (dd, J=14.2, 6.8 Hz, 1H), 7.04-6.98 (m, 1H), 6.90 (s, 1H), 6.69 (d, J=8.2 Hz, 1H), 6.58 (d, J=8.2 Hz, 2H), 3.68 (s, 3H), 3.38 (s, 2H), 2.91 (s, 2H), 1.07 (s, 3H), 0.88 (s, 3H). MS (ESI+) m/z 472 (M+H)$^+$.

Example 182

N-benzyl-4-[1-methyl-6-oxo-3-(2-phenoxyphenyl)-1,6-dihydropyridazin-4-yl]benzamide Example 182 was prepared according to the procedure used for the preparation of Example 105, substituting N-benzyl-4-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.73 (d, J=8.3 Hz, 2H), 7.53 (dd, J=7.5, 1.7 Hz, 1H), 7.38-7.30 (m, 4H), 7.29-7.13 (m, 6H), 7.02 (t, J=7.4 Hz, 1H), 6.90 (s, 1H), 6.64 (d, J=8.2 Hz, 1H), 6.43 (d, J=7.7 Hz, 2H), 4.48 (s, 2H), 3.70 (s, 3H). MS (ESI+) m/z 488 (M+H)$^+$.

Example 183

2-methyl-6-(2-phenoxyphenyl)-5-[4-(pyrrolidin-1-ylcarbonyl)phenyl]pyridazin-3(2H)-one Example 183 was prepared according to the procedure used for the preparation of Example 105, substituting pyrrolidin-1-yl(4-(4,4,5,5-tetramethyl-1,3,2-dioxaborolan-2-yl)phenyl)methanone for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.52 (dd, J=7.5, 1.7 Hz, 1H), 7.41-7.28 (m, 3H), 7.25-7.14 (m, 5H), 7.06 (t, J=7.4 Hz, 1H), 6.90 (s, 1H), 6.61 (d, J=8.3 Hz, 1H), 6.46 (d, J=7.7 Hz, 2H), 3.71 (s, 3H), 3.40 (s, 4H), 1.85 (t, J=6.7 Hz, 4H). MS (ESI+) m/z 452 (M+H)$^+$.

Example 184

2-methyl-6-(2-phenoxyphenyl)-5-[6-(piperidin-1-yl)pyridin-3-yl]pyridazin-3(2H)-one Example 184 was prepared according to the procedure used for the preparation of Example 105, substituting 2-(piperidin-1-yl)-5-(4,4,5,5-tetramethyl-1,3,2-dioxaborolan-2-yl)pyridine for N-(4-(4,4,5,5-tetramethyl-1,3,2-dioxaborolan-2-yl)phenyl)acetamide, to provide the title compound. $^1$H NMR (400 MHz, DMSO-d$_6$/D$_2$O) δ 7.82 (d, J=2.5 Hz, 1H), 7.56-7.45 (m, 1H), 7.38 (d, J=7.6 Hz, 1H), 7.31-7.16 (m, 4H), 7.05 (t, J=7.3 Hz, 1H), 6.83 (s, 1H), 6.72 (d, J=8.2 Hz, 1H), 6.65 (d, J=9.1 Hz, 1H), 6.52 (d, J=8.3 Hz, 2H), 3.67 (s, 3H), 3.63-3.40 (m, 4H), 1.63 (d, J=5.1 Hz, 2H), 1.56 (d, J=5.3 Hz, 4H). MS (ESI+) m/z 439 (M+H)$^+$.

Example 185

N-cyclohexyl-4-[1-methyl-6-oxo-3-(2-phenoxyphenyl)-1,6-dihydropyridazin-4-yl]benzamide Example 185 was prepared according to the procedure used for the preparation of Example 105, substituting N-cyclohexyl-4-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. ¹H NMR (400 MHz, DMSO-d₆/D₂O) δ 7.68 (d, J=8.3 Hz, 2H), 7.52 (dd, J=7.6, 1.7 Hz, 1H), 7.40-7.29 (m, 1H), 7.29-7.15 (m, 5H), 7.04 (t, J=7.4 Hz, 1H), 6.88 (s, 1H), 6.66 (d, J=8.2 Hz, 1H), 6.45 (d, J=7.9 Hz, 2H), 3.75 (d, J=4.0 Hz, 1H), 3.70 (s, 3H), 1.91-1.69 (m, 4H), 1.60 (d, J=12.5 Hz, 1H), 1.42-1.26 (m, 4H), 1.16 (d, J=8.0 Hz, 1H). MS (ESI+) m/z 480 (M+H)⁺.

Example 186

N-[2-(dimethylamino)ethyl]-3-[1-methyl-6-oxo-3-(2-phenoxyphenyl)-1,6-dihydropyridazin-4-yl]benzamide Example 186 was prepared according to the procedure used for the preparation of Example 105, substituting N-(2-(dimethylamino)ethyl)-3-(4,4,5,5-tetramethyl-1,3,2-dioxaborolan-2-yl)benzamide for N-(4-(4,4,5,5-tetramethyl-1,3,2-dioxaborolan-2-yl)phenyl)acetamide, to provide the title compound. ¹H NMR (400 MHz, DMSO-d₆/D₂O) δ 7.81 (d, J=7.7 Hz, 1H), 7.72 (s, 1H), 7.51 (dd, J=7.5, 1.7 Hz, 1H), 7.40-7.29 (m, 2H), 7.29-7.14 (m, 4H), 7.04 (t, J=7.4 Hz, 1H), 6.92 (s, 1H), 6.63 (d, J=8.2 Hz, 1H), 6.46 (d, J=7.8 Hz, 2H), 3.71 (s, 3H), 3.57 (dt, J=23.4, 5.9 Hz, 2H), 3.27 (d, J=5.9 Hz, 2H), 2.56-2.40 (m, 5H). MS (ESI+) m/z 469 (M+H)⁺.

Example 187

2-methyl-6-(2-phenoxyphenyl)-5-{4-[(phenylamino)methyl]phenyl}pyridazin-3(2H)-one Example 187 was prepared according to the procedure used for the preparation of Example 105, substituting N-(4-(4,4,5,5-tetramethyl-1,3,2-dioxaborolan-2-yl)benzyl)aniline for N-(4-(4,4,5,5-tetramethyl-1,3,2-dioxaborolan-2-yl)phenyl)acetamide, to provide the title compound. ¹H NMR (400 MHz, DMSO-d₆/D₂O) δ 7.49 (dd, J=7.6, 1.7 Hz, 1H), 7.39-7.26 (m, 1H), 7.23 (d, J=8.2 Hz, 2H), 7.21-7.13 (m, 3H), 7.12-7.00 (m, 5H), 6.82 (s, 1H), 6.58 (dd, J=16.0, 7.6 Hz, 4H), 6.42 (t, J=11.7 Hz, 2H), 4.27 (s, 2H), 3.70 (d, J=8.9 Hz, 3H). MS (ESI+) m/z 460 (M+H)⁺.

Example 188

2-methyl-5-[2-(4-methylpiperazin-1-yl)pyrimidin-5-yl]-6-(2-phenoxyphenyl)pyridazin-3(2H)-one Example 188 was prepared according to the procedure used for the preparation of Example 105, substituting 2-(4-methylpiperazin-1-yl)-5-(4,4,5,5-tetramethyl-1,3,2-dioxaborolan-2-yl)pyrimidine for N-(4-(4,4,5,5-tetramethyl-1,3,2-dioxaborolan-2-yl)phenyl)acetamide, to provide the title compound. ¹H NMR (400 MHz, DMSO-d₆/D₂O) δ 8.17 (s, 2H), 7.57 (dd, J=7.6, 1.7 Hz, 1H), 7.43 (td, J=8.1, 1.7 Hz, 1H), 7.26 (dd, J=15.8, 8.1 Hz, 3H), 7.06 (t, J=7.4 Hz, 1H), 6.93 (s, 1H), 6.81 (d, J=8.3 Hz, 1H), 6.55 (d, J=8.4 Hz, 2H), 3.98 (s, 4H), 3.67 (s, 3H), 3.26 (s, 4H), 2.87 (s, 3H). MS (ESI+) m/z 455 (M+H)⁺.

Example 189 methyl{4-[1-methyl-6-oxo-3-(2-phenoxyphenyl)-1,6-dihydropyridazin-4-yl]phenyl}acetate Example 189 was prepared according to the procedure used for the preparation of Example 105, substituting methyl 2-(4-(4,4,5,5-tetramethyl-1,3,2-dioxaborolan-2-yl)phenyl)acetate for N-(4-(4,4,5,5-tetramethyl-1,3,2-dioxaborolan-2-yl)phenyl)acetamide, to provide the title compound. ¹H NMR (500 MHz, DMSO-d₆/D₂O) δ 7.61 (dd, J=7.5, 1.6 Hz, 1H), 7.42-7.30 (m, 1H), 7.22 (t, J=7.6 Hz, 3H), 7.15 (d, J=8.2 Hz, 2H), 7.13-7.03 (m, 3H), 6.92 (s, 1H), 6.45 (d, J=8.3 Hz, 1H), 6.28-6.15 (m, 2H), 3.73 (d, J=2.8 Hz, 3H), 3.69 (s, 2H), 3.64 (s, 3H). MS (ESI+) m/z 427 (M+H)⁺.

Example 190

5-(5-ethoxypyridin-3-yl)-2-methyl-6-(2-phenoxyphenyl)pyridazin-3(2H)-one

Example 190 was prepared according to the procedure used for the preparation of Example 105, substituting 3-ethoxy-5-(4,4,5,5-tetramethyl-1,3,2-dioxaborolan-2-yl)pyridine for N-(4-(4,4,5,5-tetramethyl-1,3,2-dioxaborolan-2-yl)phenyl)acetamide, to provide the title compound. ¹H NMR (500 MHz, DMSO-d₆/D₂O) δ 8.26 (d, J=2.7 Hz, 1H), 7.98 (d, J=1.5 Hz, 1H), 7.66 (dd, J=7.6, 1.6 Hz, 1H), 7.45-7.35 (m, 1H), 7.33-7.16 (m, 4H), 7.14-7.04 (m, 2H), 6.63 (d, J=8.3 Hz, 1H), 6.40-6.31 (m, 2H), 3.83 (q, J=7.0 Hz, 2H), 3.75 (s, 3H), 1.19 (t, J=7.0 Hz, 3H). MS (ESI+) m/z 400 (M+H)⁺.

Example 191

2-methyl-5-[4-(methylamino)phenyl]-6-(2-phenoxyphenyl)pyridazin-3(2H)-one

Example 191 was prepared according to the procedure used for the preparation of Example 105, substituting N-methyl-4-(4,4,5,5-tetramethyl-1,3,2-dioxaborolan-2-yl)aniline for N-(4-(4,4,5,5-tetramethyl-1,3,2-dioxaborolan-2-yl)phenyl)acetamide, to provide the title compound. ¹H NMR (500 MHz, DMSO-d₆/D₂O) δ 7.55 (dd, J=7.5, 1.6 Hz, 1H), 7.40-7.30 (m, 1H), 7.22 (dd, J=15.1, 7.8 Hz, 3H), 7.11-7.00 (m, 1H), 6.93 (t, J=19.3 Hz, 2H), 6.80 (s, 1H), 6.66-6.51 (m, 3H), 6.50-6.31 (m, 2H), 3.69 (d, J=9.5 Hz, 3H), 2.71 (s, 3H). MS (ESI+) m/z 384 (M+H)⁺.

Example 192

5-[2-(dimethylamino)pyrimidin-5-yl]-2-methyl-6-(2-phenoxyphenyl)pyridazin-3(2H)-one Example 192 was prepared according to the procedure used for the preparation of Example 105, substituting N,N-dimethyl-5-(4,4,5,5-tetramethyl-1,3,2-dioxaborolan-2-yl)pyrimidin-2-amine for N-(4-(4,4,5,5-tetramethyl-1,3,2-dioxaborolan-2-yl)phenyl)acetamide, to provide the title compound. ¹H NMR (500 MHz, DMSO-d₆/D₂O) δ 8.04 (s, 2H), 7.70-7.57 (m, 1H), 7.44 (dt, J=31.2, 11.8 Hz, 1H), 7.36-7.30 (m, 1H), 7.25 (dd, J=22.7, 15.2 Hz, 2H), 7.12-7.05 (m, 1H), 6.97 (d, J=10.5 Hz, 1H), 6.78 (t, J=7.4 Hz, 1H), 6.57-6.41 (m, 2H), 3.69 (s, 3H), 3.08 (s, 6H). MS (ESI+) m/z 400 (M+H)⁺.

Example 193

{3-[1-methyl-6-oxo-3-(2-phenoxyphenyl)-1,6-dihydropyridazin-4-yl]phenyl}acetonitrile Example 193 was prepared according to the procedure used for the preparation of Example 105, substituting 2-(3-(4,4,5,5-tetramethyl-1,3,2-dioxaborolan-2-yl)phenyl)acetonitrile for N-(4-(4,4,5,5-tetramethyl-1,3,2-dioxaborolan-2-yl)phenyl)acetamide, to provide the title compound. $^1$H NMR (500 MHz, DMSO-d$_6$/D$_2$O) δ 7.60 (dd, J=7.5, 1.6 Hz, 1H), 7.60 (dd, J=7.5, 1.6 Hz, 1H), 7.36 (dd, J=10.6, 4.8 Hz, 2H), 7.36 (dd, J=10.6, 4.8 Hz, 2H), 7.32-7.15 (m, 5H), 7.30-7.17 (m, 5H), 7.14-7.01 (m, 2H), 7.11-7.02 (m, 2H), 6.93 (s, 1H), 6.93 (s, 1H), 6.56 (d, J=8.2 Hz, 1H), 6.56 (d, J=8.2 Hz, 1H), 6.35-6.32 (m, 2H), 6.41-6.20 (m, 2H), 3.84 (s, 2H), 3.84 (s, 2H), 3.73-3.73 (m, 3H). MS (ESI+) m/z 394 (M+H)$^+$.

Example 194

2-methyl-5-(1-methyl-1H-pyrrol-2-yl)-6-(2-phenoxyphenyl)pyridazin-3(2H)-one

Example 194 was prepared according to the procedure used for the preparation of Example 105, substituting 1-methyl-2-(4,4,5,5-tetramethyl-1,3,2-dioxaborolan-2-yl)-1H-pyrrole for N-(4-(4,4,5,5-tetramethyl-1,3,2-dioxaborolan-2-yl)phenyl)acetamide, to provide the title compound. $^1$H NMR (500 MHz, DMSO-d$_6$/D$_2$O) δ 7.54 (dd, J=7.5, 1.6 Hz, 1H), 7.41-7.32 (m, 1H), 7.27 (t, J=7.9 Hz, 2H), 7.22 (t, J=7.5 Hz, 1H), 7.11 (t, J=7.4 Hz, 1H), 6.81 (dd, J=4.5, 2.6 Hz, 2H), 6.56 (d, J=8.2 Hz, 1H), 6.39 (d, J=7.7 Hz, 2H), 5.95 (dd, J=3.6, 2.8 Hz, 1H), 5.55 (dd, J=3.7, 1.7 Hz, 1H), 3.71 (s, 3H), 3.28 (s, 3H). MS (ESI+) m/z 358 (M+H)$^+$.

Example 195

2-methyl-6-(2-phenoxyphenyl)-5-(pyridin-3-yl)pyridazin-3(2H)-one

Example 195 was prepared according to the procedure used for the preparation of Example 105, substituting 3-(4,4,5,5-tetramethyl-1,3,2-dioxaborolan-2-yl)pyridine for N-(4-(4,4,5,5-tetramethyl-1,3,2-dioxaborolan-2-yl)phenyl)acetamide, to provide the title compound. $^1$H NMR (500 MHz, DMSO-d$_6$/D$_2$O) δ 8.73-8.64 (m, 1H), 8.54 (d, J=1.6 Hz, 1H), 7.96-7.79 (m, 1H), 7.66 (dd, J=7.6, 1.6 Hz, 1H), 7.57 (dd, J=8.0, 5.2 Hz, 1H), 7.47-7.34 (m, 1H), 7.34-7.19 (m, 3H), 7.12-7.03 (m, 1H), 6.61 (d, J=8.3 Hz, 1H), 6.44-6.29 (m, 2H), 3.75 (s, 3H). MS (ESI+) m/z 356 (M+H)$^+$.

Example 196

2-methyl-5-(6-methylpyridin-3-yl)-6-(2-phenoxyphenyl)pyridazin-3(2H)-one

Example 196 was prepared according to the procedure used for the preparation of Example 105, substituting 2-methyl-5-(4,4,5,5-tetramethyl-1,3,2-dioxaborolan-2-yl)pyridine for N-(4-(4,4,5,5-tetramethyl-1,3,2-dioxaborolan-2-yl)phenyl)acetamide, to provide the title compound. $^1$H NMR (500 MHz, DMSO-d$_6$/D$_2$O) δ 8.51 (d, J=1.9 Hz, 1H), 7.92 (t, J=2.8 Hz, 1H), 7.68 (dd, J=7.6, 1.5 Hz, 1H), 7.57 (d, J=8.3 Hz, 1H), 7.44 (td, J=8.3, 1.7 Hz, 1H), 7.35-7.20 (m, 3H), 7.14 (s, 1H), 7.09 (t, J=7.4 Hz, 1H), 6.70 (d, J=8.2 Hz, 1H), 6.52-6.37 (m, 2H), 3.75 (s, 3H), 2.61 (s, 3H). MS (ESI+) m/z 370 (M+H)$^+$.

Example 197

5-(3-methoxyphenyl)-2-methyl-6-(2-phenoxyphenyl)pyridazin-3(2H)-one

Example 197 was prepared according to the procedure used for the preparation of Example 105, substituting 2-(3-methoxyphenyl)-4,4,5,5-tetramethyl-1,3,2-dioxaborolane for N-(4-(4,4,5,5-tetramethyl-1,3,2-dioxaborolan-2-yl)phenyl)acetamide, to provide the title compound. $^1$H NMR (500 MHz, DMSO-d$_6$/D$_2$O) δ 7.60 (dd, J=7.5, 1.6 Hz, 1H), 7.42-7.32 (m, 1H), 7.28-7.15 (m, 4H), 7.15-7.03 (m, 1H), 7.00-6.85 (m, 2H), 6.75 (t, J=10.4 Hz, 1H), 6.69-6.61 (m, 1H), 6.55 (d, J=8.3 Hz, 1H), 6.44-6.21 (m, 2H), 3.73 (s, 3H), 3.50 (s, 3H). MS (ESI+) m/z 385 (M+H)$^+$.

Example 198

2-methyl-5-(4-methyl-3,4-dihydro-2H-pyrido[3,2-13][1,4]oxazin-7-yl)-6-(2-phenoxyphenyl)pyridazin-3(2H)-one Example 198 was prepared according to the procedure used for the preparation of Example 105, substituting 4-methyl-7-(4,4,5,5-tetramethyl-1,3,2-dioxaborolan-2-yl)-3,4-dihydro-2H-pyrido[3,2-b][1,4]oxazine for N-(4-(4,4,5,5-tetramethyl-1,3,2-dioxaborolan-2-yl)phenyl)acetamide, to provide the title compound. $^1$H NMR (500 MHz, DMSO-d$_6$/D$_2$O) δ 7.63 (dd, J=7.6, 1.6 Hz, 1H), 7.50-7.42 (m, 1H), 7.35 (d, J=2.0 Hz, 1H), 7.33-7.23 (m, 3H), 7.08 (t, J=7.4 Hz, 1H), 6.93 (s, 1H), 6.81 (dd, J=18.5, 5.1 Hz, 2H), 6.58-6.44 (m, 2H), 4.14 (s, 2H), 3.71 (s, 3H), 3.55 (t, J=4.2 Hz, 2H), 3.07 (s, 3H). MS (ESI+) m/z 403 (M+H)$^+$.

Example 199

5-(4-fluoro-3-methoxyphenyl)-2-methyl-6-(2-phenoxyphenyl)pyridazin-3(2H)-one

Example 199 was prepared according to the procedure used for the preparation of Example 105, substituting 2-(4-fluoro-3-methoxyphenyl)-4,4,5,5-tetramethyl-1,3,2-dioxaborolane for N-(4-(4,4,5,5-tetramethyl-1,3,2-dioxaborolan-2-yl)phenyl)acetamide, to provide the title compound. $^1$H NMR (500 MHz, DMSO-d$_6$/D$_2$O) δ 7.63 (dd, J=7.6, 1.6 Hz, 1H), 7.48-7.34 (m, 1H), 7.31-7.17 (m, 3H), 7.10 (dt, J=14.6, 7.9 Hz, 2H), 6.98 (s, 1H), 6.82-6.72 (m, 2H), 6.64 (d, J=8.3 Hz, 1H), 6.51-6.34 (m, 2H), 3.73 (s, 3H), 3.45 (s, 3H). MS (ESI+) m/z 403 (M+H)$^+$.

Example 200

5-(2-aminopyridin-4-yl)-2-methyl-6-(2-phenoxyphenyl)pyridazin-3(2H)-one

Example 200 was prepared according to the procedure used for the preparation of Example 105, substituting 4-(4,4,5,5-tetramethyl-1,3,2-dioxaborolan-2-yl)pyridin-2-amine for N-(4-(4,4,5,5-tetramethyl-1,3,2-dioxaborolan-2-yl)phenyl)acetamide, to provide the title compound. $^1$H NMR (500 MHz, DMSO-d$_6$/D$_2$O) δ 7.75 (dd, J=8.9, 3.5 Hz, 1H), 7.69-7.62 (m, 1H), 7.50-7.40 (m, 1H), 7.37-7.25 (m, 3H), 7.14-7.07 (m, 2H), 6.83-6.76 (m, 1H), 6.76-6.71 (m, 1H), 6.64-6.52 (m, 3H), 3.74 (d, J=1.6 Hz, 5H). MS (ESI+) m/z 371 (M+H)$^+$.

Example 201

5-(3-acetylphenyl)-2-methyl-6-(2-phenoxyphenyl)pyridazin-3(2H)-one

Example 201 was prepared according to the procedure used for the preparation of Example 105, substituting 1-(3-(4,4,5,5-tetramethyl-1,3,2-dioxaborolan-2-yl)phenyl)ethanone for N-(4-(4,4,5,5-tetramethyl-1,3,2-dioxaborolan-2-yl)

phenyl)acetamide, to provide the title compound. $^1$H NMR (500 MHz, DMSO-$d_6$/D$_2$O) δ 7.99-7.83 (m, 1H), 7.74-7.60 (m, 2H), 7.47-7.39 (m, 2H), 7.36 (td, J=8.0, 1.7 Hz, 1H), 7.26 (dd, J=7.5, 0.7 Hz, 1H), 7.19 (dd, J=10.7, 5.2 Hz, 2H), 7.10-6.99 (m, 2H), 6.57 (d, J=8.2 Hz, 1H), 6.28 (d, J=7.7 Hz, 2H), 3.74 (d, J=9.2 Hz, 3H), 2.33 (s, 3H). MS (ESI+) m/z 397 (M+H)$^+$.

Example 202

N-ethyl-4-[1-methyl-6-oxo-3-(2-phenoxyphenyl)-1,6-dihydropyridazin-4-yl]-benzamide Example 202 was prepared according to the procedure used for the preparation of Example 105, substituting N-ethyl-4-(4,4,5,5-tetramethyl-1,3,2-dioxaborolan-2-yl) benzamide for N-(4-(4,4,5,5-tetramethyl-1,3,2-dioxaborolan-2-yl)phenyl)acetamide, to provide the title compound. $^1$H NMR (500 MHz, DMSO-$d_6$/D$_2$O) δ 7.68 (d, J=8.4 Hz, 2H), 7.61 (dt, J=9.5, 4.7 Hz, 1H), 7.38 (ddd, J=9.1, 6.7, 1.8 Hz, 1H), 7.26-7.18 (m, 4H), 7.13-7.03 (m, 1H), 6.97 (d, J=5.9 Hz, 1H), 6.57 (d, J=8.2 Hz, 1H), 6.41-6.21 (m, 2H), 3.73 (s, 3H), 3.29 (q, J=7.2 Hz, 2H), 1.12 (t, J=7.2 Hz, 3H). MS (ESI+) m/z 426 (M+H)$^+$.

Example 203

5-(3-fluoro-4-methoxyphenyl)-2-methyl-6-(2-phenoxyphenyl)pyridazin-3(2H)-one

Example 203 was prepared according to the procedure used for the preparation of Example 105, substituting 2-(3-fluoro-4-methoxyphenyl)-4,4,5,5-tetramethyl-1,3,2-dioxaborolane for N-(4-(4,4,5,5-tetramethyl-1,3,2-dioxaborolan-2-yl)phenyl)acetamide, to provide the title compound. $^1$H NMR (500 MHz, DMSO-$d_6$/D$_2$O) δ 7.60 (dd, J=7.5, 1.6 Hz, 1H), 7.47-7.36 (m, 1H), 7.25 (ddd, J=15.1, 11.1, 8.0 Hz, 3H), 7.06 (dt, J=17.8, 8.3 Hz, 2H), 6.99-6.86 (m, 3H), 6.64 (d, J=8.3 Hz, 1H), 6.43-6.30 (m, 2H), 3.83 (s, 3H), 3.71 (s, 3H). MS (ESI+) m/z 403 (M+H)$^+$.

Example 204

5-(1,5-dimethyl-1H-pyrazol-4-yl)-2-methyl-6-(2-phenoxyphenyl)pyridazin-3(2H)-one Example 204 was prepared according to the procedure used for the preparation of Example 105, substituting 1,5-dimethyl-4-(4,4,5,5-tetramethyl-1,3,2-dioxaborolan-2-yl)-1H-pyrazole for N-(4-(4,4,5,5-tetramethyl-1,3,2-dioxaborolan-2-yl)phenyl)acetamide, to provide the title compound. $^1$H NMR (500 MHz, DMSO-$d_6$/D$_2$O) δ 7.62-7.53 (m, 1H), 7.48-7.35 (m, 1H), 7.32-7.24 (m, 4H), 7.10 (q, J=7.5 Hz, 1H), 6.77-6.69 (m, 2H), 6.67 (s, 1H), 6.49-6.31 (m, 3H), 3.71 (d, J=2.0 Hz, 3H), 3.59 (d, J=9.4 Hz, 3H), 1.83 (s, 3H). MS (ESI+) m/z 373 (M+H)$^+$.

Example 205

2-methyl-5-(2-methylpyridin-4-yl)-6-(2-phenoxyphenyl)pyridazin-3(2H)-one

Example 205 was prepared according to the procedure used for the preparation of Example 105, substituting 2-methyl-4-(4,4,5,5-tetramethyl-1,3,2-dioxaborolan-2-yl) pyridine for N-(4-(4,4,5,5-tetramethyl-1,3,2-dioxaborolan-2-yl)phenyl)acetamide, to provide the title compound. $^1$H NMR (500 MHz, DMSO-$d_6$/D$_2$O) δ 8.62-8.45 (m, 1H), 7.83-7.62 (m, 1H), 7.57-7.49 (m, 1H), 7.48-7.38 (m, 1H), 7.36-7.30 (m, 2H), 7.30-7.22 (m, 3H), 7.18-7.07 (m, 2H), 6.73-6.66 (m, 1H), 6.49-6.33 (m, 2H), 3.79-3.74 (m, 3H), 2.40 (s, 3H). MS (ESI+) m/z 370 (M+H)$^+$.

Example 206

2-methyl-5-[1-(2-methylpropyl)-1H-pyrazol-4-yl]-6-(2-phenoxyphenyl)pyridazin-3(2H)-one Example 206 was prepared according to the procedure used for the preparation of Example 105, substituting 1-isobutyl-4-(4,4,5,5-tetramethyl-1,3,2-dioxaborolan-2-yl)-1H-pyrazole for N-(4-(4,4,5,5-tetramethyl-1,3,2-dioxaborolan-2-yl)phenyl)acetamide, to provide the title compound. $^1$H NMR (500 MHz, DMSO-$d_6$/D$_2$O) δ 7.65-7.44 (m, 3H), 7.40-7.21 (m, 3H), 7.11 (dd, J=13.6, 6.2 Hz, 2H), 7.02 (d, J=9.8 Hz, 1H), 6.77 (t, J=9.9 Hz, 1H), 6.66-6.51 (m, 2H), 3.81 (d, J=7.0 Hz, 2H), 3.65 (s, 3H), 2.09-1.88 (m, 1H), 0.76 (d, J=6.7 Hz, 6H). MS (ESI+) m/z 401 (M+H)$^+$.

Example 207

2-methyl-5-(4-methylpyridin-3-yl)-6-(2-phenoxyphenyl)pyridazin-3(2H)-one

Example 207 was prepared according to the procedure used for the preparation of Example 105, substituting 4-methyl-3-(4,4,5,5-tetramethyl-1,3,2-dioxaborolan-2-yl) pyridine for N-(4-(4,4,5,5-tetramethyl-1,3,2-dioxaborolan-2-yl)phenyl)acetamide, to provide the title compound. $^1$H NMR (500 MHz, DMSO-$d_6$/D$_2$O) δ 8.54 (d, J=5.6 Hz, 1H), 8.45 (s, 1H), 7.69-7.51 (m, 2H), 7.39-7.28 (m, 3H), 7.20 (dd, J=18.3, 10.8 Hz, 1H), 7.16-7.08 (m, 2H), 6.56 (dd, J=12.3, 8.1 Hz, 3H), 3.76 (d, J=7.5 Hz, 3H), 2.19 (s, 3H). MS (ESI+) m/z 370 (M+H)$^+$.

Example 208

2-methyl-5-(1-methyl-1H-indol-5-yl)-6-(2-phenoxyphenyl)pyridazin-3(2H)-one

Example 208 was prepared according to the procedure used for the preparation of Example 105, substituting 1-methyl-5-(4,4,5,5-tetramethyl-1,3,2-dioxaborolan-2-yl)-1H-indole for N-(4-(4,4,5,5-tetramethyl-1,3,2-dioxaborolan-2-yl)phenyl)acetamide, to provide the title compound. $^1$H NMR (500 MHz, DMSO-$d_6$/D$_2$O) δ 7.58 (dd, J=7.5, 1.6 Hz, 1H), 7.46 (dd, J=7.6, 1.6 Hz, 1H), 7.38-7.18 (m, 4H), 7.15-7.03 (m, 2H), 7.03-6.94 (m, 1H), 6.95-6.87 (m, 1H), 6.55 (dd, J=21.5, 8.2 Hz, 1H), 6.39-6.28 (m, 1H), 6.28-6.17 (m, 1H), 3.81-3.74 (m, 3H), 3.71 (s, 3H). MS (ESI+) m/z 408 (M+H)$^+$.

Example 209

5-[3-(dimethylamino)phenyl]-2-methyl-6-(2-phenoxyphenyl)pyridazin-3(2H)-one

Example 209 was prepared according to the procedure used for the preparation of Example 105, substituting N,N-dimethyl-3-(4,4,5,5-tetramethyl-1,3,2-dioxaborolan-2-yl) aniline for N-(4-(4,4,5,5-tetramethyl-1,3,2-dioxaborolan-2-yl)phenyl)acetamide, to provide the title compound. $^1$H NMR (500 MHz, DMSO-$d_6$/D$_2$O) δ 7.60 (dd, J=7.5, 1.6 Hz, 1H), 7.44-7.30 (m, 1H), 7.27-7.13 (m, 4H), 7.07 (t, J=7.4 Hz, 1H), 6.94 (d, J=12.7 Hz, 1H), 6.91 (dd, J=8.3, 2.2 Hz, 1H), 6.63 (d, J=7.8 Hz, 1H), 6.58 (s, 1H), 6.53 (d, J=8.2 Hz, 1H), 6.34-6.15 (m, 2H), 3.73 (s, 3H), 2.70 (s, 6H). MS (ESI+) m/z 398 (M+H)$^+$.

Example 210

5-(2-fluoro-5-methoxyphenyl)-2-methyl-6-(2-phenoxyphenyl)pyridazin-3(2H)-one

Example 210 was prepared according to the procedure used for the preparation of Example 105, substituting 2-(2-fluoro-5-methoxyphenyl)-4,4,5,5-tetramethyl-1,3,2-dioxaborolane for N-(4-(4,4,5,5-tetramethyl-1,3,2-dioxaborolan-2-yl)phenyl)acetamide, to provide the title compound. $^1$H NMR (500 MHz, DMSO-d$_6$/D$_2$O) δ 7.63-7.46 (m, 1H), 7.43-7.31 (m, 1H), 7.31-7.24 (m, 2H), 7.19 (dd, J=11.6, 4.1 Hz, 1H), 7.10 (t, J=7.4 Hz, 1H), 7.04 (t, J=9.3 Hz, 1H), 7.00 (d, J=5.2 Hz, 1H), 6.94-6.84 (m, 1H), 6.69-6.54 (m, 2H), 6.46 (dd, J=9.4, 8.5 Hz, 2H), 3.73 (s, 3H), 3.47 (s, 3H). MS (ESI+) m/z 403 (M+H)$^+$.

Example 211

2-methyl-5-(5-methylfuran-2-yl)-6-(2-phenoxyphenyl)pyridazin-3(2H)-one

Example 211 was prepared according to the procedure used for the preparation of Example 105, substituting 4,4,5,5-tetramethyl-2-(5-methylfuran-2-yl)-1,3,2-dioxaborolane for N-(4-(4,4,5,5-tetramethyl-1,3,2-dioxaborolan-2-yl)phenyl)acetamide, to provide the title compound. $^1$H NMR (500 MHz, DMSO-d$_6$/D$_2$O) δ 7.61-7.42 (m, 2H), 7.37-7.21 (m, 3H), 7.11 (t, J=7.4 Hz, 1H), 7.03 (s, 1H), 6.89 (d, J=8.3 Hz, 1H), 6.84-6.65 (m, 2H), 6.26-6.10 (m, 1H), 5.72 (d, J=3.4 Hz, 1H), 3.63 (s, 3H), 2.27 (s, 3H). MS (ESI+) m/z 359 (M+H)$^+$.

Example 212

5-(1-ethyl-1H-pyrazol-4-yl)-2-methyl-6-(2-phenoxyphenyl)pyridazin-3(2H)-one

Example 212 was prepared according to the procedure used for the preparation of Example 105, substituting 1-ethyl-4-(4,4,5,5-tetramethyl-1,3,2-dioxaborolan-2-yl)-1H-pyrazole for N-(4-(4,4,5,5-tetramethyl-1,3,2-dioxaborolan-2-yl)phenyl)acetamide, to provide the title compound. $^1$H NMR (500 MHz, DMSO-d$_6$/D$_2$O) δ 7.62-7.56 (m, 1H), 7.57-7.45 (m, 2H), 7.35-7.21 (m, 3H), 7.19-7.02 (m, 2H), 7.04-6.93 (m, 2H), 6.79-6.66 (m, 1H), 6.56-6.30 (m, 2H), 4.15-3.97 (m, 2H), 3.66 (s, 3H), 1.28 (t, J=7.3 Hz, 3H). MS (ESI+) m/z 373 (M+H)$^+$.

Example 213

5-(3-methoxypyridin-4-yl)-2-methyl-6-(2-phenoxyphenyl)pyridazin-3(2H)-one

Example 213 was prepared according to the procedure used for the preparation of Example 105, substituting 3-methoxy-4-(4,4,5,5-tetramethyl-1,3,2-dioxaborolan-2-yl)pyridine for N-(4-(4,4,5,5-tetramethyl-1,3,2-dioxaborolan-2-yl)phenyl)acetamide, to provide the title compound. $^1$H NMR (500 MHz, DMSO-d$_6$/D$_2$O) δ 8.37-8.24 (m, 2H), 7.55 (d, J=5.1 Hz, 1H), 7.48-7.27 (m, 4H), 7.27-7.08 (m, 2H), 7.01 (s, 1H), 6.67 (d, J=8.3 Hz, 1H), 6.61 (d, J=8.0 Hz, 2H), 3.74 (s, 3H), 3.48 (s, 3H). MS (ESI+) m/z 386 (M+H)$^+$.

Example 214

2-methyl-5-(1-methyl-1H-indol-2-yl)-6-(2-phenoxyphenyl)pyridazin-3(2H)-one

Example 214 was prepared according to the procedure used for the preparation of Example 105, substituting 1-methyl-2-(4,4,5,5-tetramethyl-1,3,2-dioxaborolan-2-yl)-1H-indole for N-(4-(4,4,5,5-tetramethyl-1,3,2-dioxaborolan-2-yl)phenyl)acetamide, to provide the title compound. $^1$H NMR (500 MHz, DMSO-d$_6$/D$_2$O) δ 7.74-7.56 (m, 1H), 7.44 (d, J=7.9 Hz, 1H), 7.42-7.33 (m, 1H), 7.28-7.19 (m, 2H), 7.12-7.05 (m, 1H), 7.03-6.92 (m, 3H), 6.51 (d, J=8.2 Hz, 1H), 6.25-6.11 (m, 2H), 6.07 (s, 1H), 3.77 (s, 3H), 3.34 (s, 3H). MS (ESI+) m/z 408 (M+H)$^+$.

Example 215

N,N-dimethyl-5-[1-methyl-6-oxo-3-(2-phenoxyphenyl)-1,6-dihydropyridazin-4-yl]pyridine-3-carboxamide Example 215 was prepared according to the procedure used for the preparation of Example 105, substituting N,N-dimethyl-5-(4,4,5,5-tetramethyl-1,3,2-dioxaborolan-2-yl)nicotinamide for N-(4-(4,4,5,5-tetramethyl-1,3,2-dioxaborolan-2-yl)phenyl)acetamide, to provide the title compound. $^1$H NMR (500 MHz, DMSO-d$_6$/D$_2$O) δ 8.60 (d, J=1.9 Hz, 1H), 8.48 (d, J=2.1 Hz, 1H), 7.70-7.59 (m, 3H), 7.43-7.33 (m, 1H), 7.27 (td, J=7.5, 2.7 Hz, 4H), 7.16-7.03 (m, 3H), 6.57 (d, J=8.3 Hz, 1H), 6.46-6.30 (m, 3H), 3.74 (s, 3H), 3.05 (d, J=124.7 Hz, 6H). MS (ESI+) m/z 427 (M+H)$^+$.

Example 216

5-[5-(dimethylamino)pyridin-3-yl]-2-methyl-6-(2-phenoxyphenyl)pyridazin-3(2H)-one Example 216 was prepared according to the procedure used for the preparation of Example 105, substituting N,N-dimethyl-5-(4,4,5,5-tetramethyl-1,3,2-dioxaborolan-2-yl)pyridin-3-amine for N-(4-(4,4,5,5-tetramethyl-1,3,2-dioxaborolan-2-yl)phenyl)acetamide, to provide the title compound. $^1$H NMR (500 MHz, DMSO-d$_6$/D$_2$O) δ 8.06 (t, J=5.6 Hz, 1H), 7.84 (d, J=7.4 Hz, 1H), 7.73-7.65 (m, 1H), 7.55-7.43 (m, 1H), 7.32 (t, J=6.3 Hz, 1H), 7.31-7.24 (m, 3H), 7.21 (s, 1H), 7.15-7.01 (m, 1H), 6.76 (dd, J=9.6, 5.6 Hz, 1H), 6.45-6.27 (m, 2H), 3.76 (d, J=3.2 Hz, 3H), 2.79 (s, 6H). MS (ESI+) m/z 399 (M+H)$^+$.

Example 217

5-butyl-2-methyl-6-(2-phenoxyphenyl)pyridazin-3(2H)-one

Example 217A 5-butyl-6-chloro-2-methylpyridazin-3(2H)-one

A mixture of Example 18B (0.537 g, 3 mmol), (E)-ethyl 3-(tributylstannyl)acrylate (1.226 g, 3.15 mmol), and tetrakis (0.173 g, 0.150 mmol) in dioxane (20 mL) was heated at 80° C. overnight. The solvent was removed under reduced pressure, and the residue was purified by flash chromatography on silica gel eluting with 10% ethyl acetate in hexanes to give 0.15 g (25%) of the title compound.

Example 217B 5-butyl-2-methyl-6-(2-phenoxyphenyl)pyridazin-3 (2H)-one

Example 217B was prepared according to the procedure used for the preparation of Example 1B, substituting Example 217A for Example 1A, to provide the title compound. $^1$H NMR (500 MHz, DMSO-$d_6$) δ 7.32-7.50 (m, 4H), 7.24-7.28 (m, 1H), 7.11 (t, J=7.32 Hz, 1H), 6.98 (d, J=7.32 Hz, 1H), 6.92 (d, J=7.63 Hz, 2H), 6.77 (s, 1H), 3.57 (s, 3H), 2.23-2.26 (m, 2H), 1.33-1.38 (m, 2H), 0.72 (t, J=7.32 Hz, 3H). MS (DCI+) m/z 355.2 (M+H)$^+$.

Example 218 methyl 1-methyl-6-oxo-3-(2-phenoxyphenyl)-1,6-dihydropyridazine-4-carboxylate

Example 218A methyl 3-chloro-6-oxo-1,6-dihydropyridazine-4-carboxylate

Methyl 3,6-dichloropyridazine-4-carboxylate (12 g, 58.0 mmol) in acetic acid (45 mL) was heated at 130° C. for two hours. After cooling to room temperature, the solvent was removed under reduced pressure to give a white solid (10 g), which contained 45% of the desired product. The crude product was used directly for the next step.

Example 218B methyl 3-chloro-1-methyl-6-oxo-1,6-dihydropyridazine-4-carboxylate Example 218B was prepared according to the procedure used for the preparation of Example 1A, substituting Example 218A for 6-chloropyridazin-3(2H)-one, to provide the title compound.

Example 218C methyl 1-methyl-6-oxo-3-(2-phenoxyphenyl)-1,6-dihydropyridazine-4-carboxylate Example 218C was prepared according to the procedure used for the preparation of Example 1B, substituting Example 218B for Example 1A, to provide the title compound. $^1$H NMR (500 MHz, DMSO-$d_6$) δ 7.56 (dd, J=7.63, 1.83 Hz, 1H), 7.42-7.46 (m, 1H), 7.33-7.38 (m, 2H), 7.24-7.28 (m, 1H), 7.23 (s, 1H), 7.13 (t, J=7.48 Hz, 1H), 6.87-6.89 (m, 3H), 3.71 (s, 3H), 3.63 (s, 3H). MS (DCI+) m/z 337.1 (M+H)$^+$.

Example 219 methyl (2E)-3-[1-methyl-6-oxo-3-(2-phenoxyphenyl)-1,6-dihydropyridazin-4-yl]prop-2-enoate

Example 219A (E)-ethyl 3-(3-chloro-1-methyl-6-oxo-1,6-dihydropyridazin-4-yl)acrylate Example 219A was prepared according to the procedure used for the preparation of Example 9A, substituting Example 18B for Example 1A, and substituting (E)-ethyl 3-(4,4,5,5-tetramethyl-1,3,2-dioxaborolan-2-yl)acrylate for 2-fluoro-5-nitrophenylboronic acid, respectively, to provide the title compound.

Example 219B methyl (2E)-3-[1-methyl-6-oxo-3-(2-phenoxyphenyl)-1,6-dihydropyridazin-4-yl]prop-2-enoate Example 219B was prepared according to the procedure used for the preparation of Example 1B, substituting Example 219A for Example 1A, to provide the title compound. $^1$H NMR (500 MHz, DMSO-$d_6$) δ 7.44-7.53 (m, 3H), 7.26-7.36 (m, 3H), 7.11-7.15 (m, 2H), 6.89-6.92 (m, 3H), 6.73 (d, J=16.17 Hz, 1H), 3.69 (s, 3H), 3.67 (s, 3H). MS (DCI+) m/z 363.1 (M+H)$^+$.

Example 220 methyl 3-[1-methyl-6-oxo-3-(2-phenoxyphenyl)-1,6-dihydropyridazin-4-yl]propanoate Example 219B was prepared according to the procedure used for the preparation of Example 10, substituting Example 219B for Example 9B, to provide the title compound. $^1$H NMR (500 MHz, DMSO-$d_6$) δ 7.46-7.50 (m, 1H), 7.43 (dd, J=7.48, 1.68 Hz, 1H), 7.34-7.37 (m, 2H), 7.26 (t, J=7.48 Hz, 1H), 7.13 (t, J=7.48 hz, 1H), 6.93-6.97 (m, 3H), 6.80 (s, 1H), 3.58 (s, 3H), 3.54 (s, 3H), 2.55-2.63 (m 4H). MS (DCI+) m/z 365.1 (M+H)$^+$.

Example 221

5-acetyl-2-methyl-6-(2-phenoxyphenyl)pyridazin-3 (2H)-one

Example 221A 6-chloro-5-(1-ethoxyvinyl)-2-methylpyridazin-3 (2H)-one

Example 218C was prepared according to the procedure used for the preparation of Example 217A, substituting tributyl(1-ethoxyvinyl)stannane for (E)-ethyl 3-(tributylstannyl)acrylate, to provide the title compound.

Example 221B 5-(1-ethoxyvinyl)-2-methyl-6-(2-phenoxyphenyl) pyridazin-3(2H)-one Example 221B was prepared according to the procedure used for the preparation of Example 1B, substituting Example 221A for Example 1A, to provide the title compound.

Example 221C 5-acetyl-2-methyl-6-(2-phenoxyphenyl)pyridazin-3 (2H)-one

Example 221B (0.11 g, 0.316 mmol) in tetrahydrofuran (5 mL) was treated with 1.0 N HCl (1.3 mL, 1.3 mmol). The reaction mixture was heated at 60° C. for one hour. The solvent was removed, and the residue was purified by reverse phase HPLC (C18, CH$_3$CN/water (0.1% TFA), 0-100%) to provide 0.085 g (84%) of the title compound. ¹H NMR (500 MHz, DMSO-d₆) δ 7.54 (dd, J=7.63, 1.83 Hz, 1H), 7.36-7.42 (m, 4H), 7.22-7.26 (m, 1H), 7.16 (t, J=7.32 Hz, 1H), 6.90 (d, J=7.63 Hz, 2H), 6.75 (d, J=8.24 Hz, 1H), 3.71 (s, 3H), 2.41 (s, 3H). MS (DCI+) m/z 321.0 (M+H)⁺.

Example 222

6-(2-benzylphenyl)-2-methylpyridazin-3(2H)-one

A mixture of 2-(1-methyl-6-oxo-1,6-dihydropyridazin-3-yl)phenyl trifluoromethanesulfonate (0.232 g, 0.694 mmol), 2-benzyl-4,4,5,5-tetramethyl-1,3,2-dioxaborolane (0.182 g, 0.833 mmol), cesium fluoride (0.211, 1.39 mmol) and PdCl₂(dppf) (0.025 g, 0.035 mmol) in dioxane (5 mL) was heated at 75° C. for 16 hours. The reaction mixture was cooled to ambient temperature and concentrated under reduced pressure. The residue was purified by flash chromatography (silica gel, 10-50% ethyl acetate/hexane gradient) to provide the title compound. ¹H NMR (300 MHz, DMSO-d₆) δ 7.29-7.46 (m, 5H) 7.15-7.23 (m, 2H) 7.07-7.15 (m, 1H) 6.94-7.00 (m, 2H) 6.89 (d, J=9.49 Hz, 1H) 4.09 (s, 2H) 3.65 (s, 3H). MS (ESI+) m/z 277.3 (M+H)⁺.

Example 223

1-methyl-5-(2-phenoxyphenyl)pyridin-2(1H)-one

Example 223 was prepared according to the procedure used for the preparation of Example 1B, substituting 5-bromo-1-methylpyridin-2(1H)-one for Example 1A, to provide the title compound. ¹H NMR (500 MHz, DMSO-d₆) δ 7.91 (d, J=2.44 Hz, 1H), 7.63 (dd, J=9.31, 2.59 Hz, 1H), 7.48 (dd, J=7.63, 1.83 Hz, 1H), 7.232-7.37 (m, 3H), 7.23-7.27 (m, 1H), 7.08 (t, J=7.48 Hz, 1H), 6.92-6.98 (m, 3H), 3.44 (s, 3H). MS (DCI+) m/z 278.1 (M+H)⁺.

Example 224

N-[3-(1-methyl-6-oxo-1,6-dihydropyridin-3-yl)-4-phenoxyphenyl]methanesulfonamide A mixture of 1-methyl-5-(4,4,5,5-tetramethyl-[1,3,2]dioxaborolan-2-yl)-1H-pyridine-2-one (Synchem Inc. 0.056 g, 0.24 mmol), the product from Example 261C (0.068 g, 0.2 mmol), tetrakis(tiriphenylphosphine)palladium(0) (0.012 g, 0.01 mmol) and sodium carbonate 2M (0.2 mL, 0.40 mmol) in toluene (1 mL), ethanol (0.25 mL) and water (0.5 mL) was heated by microwave at 110° C. for 30 minutes. The reaction mixture was filtered through a 0.45 μm Nylon filter disk to remove solids and the filtrate was partitioned between ethyl acetate and brine. The organic layer was separated and concentrated. Purification by reverse phase HPLC (C18, 0-100% CH₃CN/water (0.1% TFA)) afforded the title compound (0.028 g, 37%). ¹H NMR (300 MHz, DMSO-d₆) δ 9.73 (s, 1H) 7.88 (d, J=2.38 Hz, 1H) 7.56 (dd, J=9.52, 2.78 Hz, 1H) 7.28-7.36 (m, 2H) 7.26 (d, J=2.78 Hz, 1H) 7.16-7.22 (m, 1H) 7.05 (t, J=7.34 Hz, 1H) 7.00 (d, J=8.73 Hz, 1H) 6.90 (d, J=7.93 Hz, 2H) 6.35-6.40 (m, 1H) 3.44 (s, 3H) 3.03 (s, 3H). MS (ESI+) m/z 371 (M+H)⁺.

Example 225 methyl {[3-(1-methyl-6-oxo-1,6-dihydropyridin-3-yl)-4-phenoxyphenyl]sulfamoyl}acetate Example 225A 5-(2-fluoro-5-nitrophenyl)-1-methylpyridin-2(1H)-one Example 225A was prepared according to the procedure used for the preparation of Example 9A, substituting 5-bromo-1-methylpyridin-2(1H)-one for Example 1A, to provide the title compound.

Example 225B 1-methyl-5-(5-nitro-2-phenoxyphenyl)pyridin-2(1H)-one

Example 225B was prepared according to the procedure used for the preparation of Example 9B, substituting Example 225A for Example 9A, to provide the title compound.

Example 225C 5-(5-amino-2-phenoxyphenyl)-1-methylpyridin-2(1H)-one

Example 225B was prepared according to the procedure used for the preparation of Example 10, substituting Example 225B for Example 9B, to provide the title compound.

Example 225D methyl {[3-(1-methyl-6-oxo-1,6-dihydropyridin-3-yl)-4-phenoxyphenyl]sulfamoyl}acetate A mixture of Example 225C (0.04 g, 0.137 mmol), 2,2,2-trifluoroethanesulfonyl chloride (0.062 g, 0.342 mmol), and triethylamine (0.055 g, 0.4 mmol) in dichloromethane (3 mL) was stirred at room temperature for 1 hour. The solvent was removed, and the residue was taken up in dioxane (1 mL), methanol (1 mL) and 1.0 N NaOH (1 mL). The reaction mixture was heated at 90° C. for 1 hour. The solvents were partially removed under reduced pressure, and the residue was partitioned between water and ethyl acetate. The aqueous layer was neutralized with 10% HCl and extracted with additional ethyl acetate twice. The combined organic layers were washed with brine, dried over MgSO₄, filtered, and concentrated under reduced pressure. The residue was purified by reverse phase HPLC (C18, CH₃CN/water (0.1% TFA), 0-100%) to afford 0.026 g (19%) of the title compound. ¹H NMR (500 MHz, DMSO-d₆) δ 10.18 (s, 1H), 7.88 (d, J=2.44 Hz, 1H), 7.56 (dd, J=9.31, 2.59 Hz, 1H), 7.29-7.36 (m, 3H), 7.20 (dd, J=8.7, 2.59 Hz, 1H), 7.06 (t, J=7.32 Hz, 1H), 7.01 (d, J=8.54 Hz, 1H), 6.91 (d, J=7.93 Hz, 2H), 6.39 (d, J=9.46 Hz, 1H), 4.30 (s, 2H), 3.67 (s, 3H), 3.44 (s, 3H). MS (ESI+) m/z 429.1 (M+H)⁺.

Example 226

{[3-(1-methyl-6-oxo-1,6-dihydropyridin-3-yl)-4-phenoxyphenyl]sulfamoyl}acetic acid Example 226 was obtained as a by-product in the synthesis of Example 225D. ¹H NMR (500 MHz, DMSO-d₆) δ

10.06 (s, 1H), 7.87 (d, J=2.44 Hz, 1H), 7.56 (dd, J=9.31, 2.59 Hz, 1H), 7.29-7.34 (m, 3H), 7.20 (dd, J=8.7, 2.59 Hz, 1H), 7.06 (t, J=7.32 Hz, 1H), 7.00 (d, J=8.85 Hz, 1H), 6.91 (d, J=7.93 Hz, 2H), 6.39 (d, J=9.46 Hz, 1H), 4.15 (s, 2H), 3.44 (s, 3H). MS (ESI+) m/z 415.0 (M+H)$^+$.

Example 227

1-methyl-N-[3-(1-methyl-6-oxo-1,6-dihydropyridin-3-yl)-4-phenoxyphenyl]-1H-imidazole-4-sulfonamide The product from Example 225C (0.044 g, 0.15 mmol), 1-methyl-1H-imidazole-4-sulfonyl chloride (0.033 g, 0.180 mmol) and triethylamine (0.042 mL, 0.30 mmol) were combined in dichloromethane (0.75 mL), heated at 60° C. for 2 hours and concentrated. Purification by chromatography (silica gel, 0-3% methanol in dichloromethane) afforded the title compound (0.038 g, 56%). $^1$H NMR (300 MHz, DMSO-d$_6$) δ 10.21 (s, 1H) 7.84 (d, J=1.36 Hz, 1H) 7.75-7.78 (m, 2H) 7.48 (dd, J=9.49, 2.71 Hz, 1H) 7.25-7.35 (m, 2H) 7.21 (d, J=2.71 Hz, 1H) 7.09 (dd, J=8.82, 2.71 Hz, 1H) 7.03 (t, J=7.46 Hz, 1H) 6.89 (d, J=8.82 Hz, 1H) 6.83 (d, J=7.80 Hz, 2H) 6.37 (d, J=9.49 Hz, 1H) 3.67 (s, 3H) 3.43 (s, 3H). MS (ESI+) m/z 437 (M+H)$^+$.

Example 228

N-[3-(1-methyl-6-oxo-1,6-dihydropyridin-3-yl)-4-phenoxyphenyl]-1H-imidazole-4-sulfonamide The product from Example 225C (0.044 g, 0.15 mmol), 1H-imidazole-4-sulfonyl chloride (0.03 g, 0.180 mmol) and triethylamine (0.042 mL, 0.30 mmol) were combined in dimethylformamide (0.75 mL) and heated at 60° C. for 24 hours. The reaction mix was partitioned between ethyl acetate and brine. The organic layer was separated and concentrated. Purification by reverse phase HPLC (C18, 0-100% CH$_3$CN/water (0.1% TFA)) afforded the title compound as the trifluoroacetic acid salt (0.004 g, 4%). $^1$H NMR (300 MHz, DMSO-d$_6$) δ 12.66-12.79 (m, 1H) 10.18-10.21 (m, 1H) 7.83 (d, J=6.35 Hz, 2H) 7.76 (d, J=2.38 Hz, 1H) 7.47 (dd, J=9.32, 2.58 Hz, 1H) 7.26-7.32 (m, 2H) 7.20 (d, J=2.78 Hz, 1H) 7.09 (dd, J=8.73, 2.38 Hz, 1H) 7.02 (t, J=7.34 Hz, 1H) 6.88 (d, J=8.73 Hz, 1H) 6.82 (d, J=7.54 Hz, 2H) 6.36 (d, J=9.52 Hz, 1H) 3.30-3.57 (m, 3H). MS (ESI+) m/z 423 (M+H)$^+$.

Example 229

2,2,2-trifluoro-N-[3-(1-methyl-6-oxo-1,6-dihydropyridin-3-yl)-4-phenoxyphenyl]ethanesulfonamide A mixture of Example 225C (0.04 g, 0.137 mmol), 2,2,2-trifluoroethanesulfonyl chloride (0.037 g, 0.205 mmol), and triethylamine (0.042 g, 0.41 mmol) in dichloromethane (3 mL) was stirred at room temperature for 1 hour. The solvent was removed, and the residue was purified by reverse phase HPLC (C18, CH$_3$CN/water (0.1% TFA), 0-100%) to afford 0.035 g (59%) of the title compound. $^1$H NMR (500 MHz, DMSO-d$_6$) δ 10.46 (s, 1H), 7.89 (d, J=2.44 Hz, 1H), 7.58 (dd, J=9.46, 2.44 Hz, 1H), 7.28-7.35 (m, 3H), 7.19 (dd, J=8.7, 2.59 Hz, 1H), 7.07 (t, J=7.32 Hz, 1H), 7.01 (d, J=8.85 Hz, 1H), 6.91 (d, J=7.63 Hz, 2H), 6.39 (d, J=9.46 Hz, 1H), 4.58 (q, J=9.97 Hz, 2H), 3.44 (s, 3H). MS (ESI+) m/z 439.1 (M+H)$^+$.

Example 230

N-methyl-N'-[3-(1-methyl-6-oxo-1,6-dihydropyridin-3-yl)-4-phenoxyphenyl]sulfuric diamide Example 230 was prepared according to the procedure used for the preparation of Example 229, substituting methylsulfamoyl chloride for 2,2,2-trifluoroethanesulfonyl chloride, to provide the title compound. $^1$H NMR (500 MHz, DMSO-d$_6$) δ 9.72 (s, 1H), 7.85 (d, J=2.44 Hz, 1H), 7.55 (dd, J=9.46, 2.75 Hz, 1H), 7.28-7.36 (m, 3H), 7.22 (d, J=2.75 Hz, 1H), 7.13 (dd, J=8.7, 2.59 Hz, 1H), 7.03 (t, J=7.32 Hz, 1H), 6.99 (d, J=8.54 Hz, 1H), 6.86 (d, J=7.63 Hz, 2H), 6.37 (d, J=9.16 Hz, 1H), 3.43 (s, 6H). MS (ESI+) m/z 386.1 (M+H)$^+$.

Example 231

N-{3-(1-methyl-6-oxo-1,6-dihydropyridin-3-yl)-4-[4-(trifluoromethyl)phenoxy]phenyl}methanesulfonamide Example 231A 1-methyl-5-(5-nitro-2-(4-(trifluoromethyl)phenoxy)phenyl)pyridin-2(1H)-one Example 231A was prepared according to the procedure used for the preparation of Example 9B, substituting 4-(trifluoromethyl)phenol for phenol, and substituting Example 225A for Example 9A, respectively, to provide the title compound.

Example 231B 5-(5-amino-2-(4-(trifluoromethyl)phenoxy)phenyl)-1-methylpyridin-2(1H)-one Example 231B was prepared according to the procedure used for the preparation of Example 10, substituting Example 231A for Example 9B, to provide the title compound.

Example 231C

N-{3-(1-methyl-6-oxo-1,6-dihydropyridin-3-yl)-4-[4-(trifluoromethyl)phenoxy]phenyl}methanesulfonamide Example 231C was prepared according to the procedure used for the preparation of Example 22, substituting Example 231B for Example 20C, to provide the title compound. $^1$H NMR (300 MHz, DMSO-d$_6$) δ9.84 (s, 1H), 7.87 (d, J=2.6 Hz, 1H), 7.69-7.62 (m, 2H), 7.51 (dd, J=9.4, 2.6 Hz, 1H), 7.29 (d, J=2.5 Hz, 1H), 7.28-7.20 (m, 1H), 7.17 (d, J=8.6 Hz, 1H), 7.07-6.99 (m, 2H), 6.37 (dd, J=9.4, 0.6 Hz, 1H), 3.42 (s, 3H), 3.06 (s, 3H). MS (ESI+) m/z 439.0 (M+H)$^+$ Example 232

N-[4-(4-fluorophenoxy)-3-(1-methyl-6-oxo-1,6-dihydropyridin-3-yl)phenyl]methanesulfonamide Example 232A 5-(2-(4-fluorophenoxy)-5-nitrophenyl)-1-methylpyridin-2(1H)-one Example 232A was prepared according to the procedure used for the preparation of Example 9B, substituting 4-fluorophenol for phenol, and substituting Example 225A for Example 9A, respectively, to provide the title compound.

Example 232B 5-(5-amino-2-(4-fluorophenoxy)phenyl)-1-methyl-pyridin-2(1H)-one Example 232B was prepared according to the procedure used for the preparation of Example 10, substituting Example 232A for Example 9B, to provide the title compound.

Example 232C

N-[4-(4-fluorophenoxy)-3-(1-methyl-6-oxo-1,6-dihydropyridin-3-yl)phenyl]methanesulfonamide Example 232C was prepared according to the procedure used for the preparation of Example 22, substituting Example 232B for Example 20C, to provide the title compound. $^1$H NMR (300 MHz, DMSO-$d_6$) δ 9.72 (s, 1H), 7.89 (d, J=2.6 Hz, 1H), 7.57 (dd, J=9.4, 2.6 Hz, 1H), 7.29-7.06 (m, 4H), 7.00-6.91 (m, 3H), 6.39 (d, J=9.3 Hz, 1H), 3.45 (s, 3H) 3.02 (s, 3H). MS (ESI+) m/z 389.1 (M+H)$^+$

Example 233

N-[4-(4-chlorophenoxy)-3-(1-methyl-6-oxo-1,6-dihydropyridin-3-yl)phenyl]methanesulfonamide

Example 233A 5-(2-(4-chlorophenoxy)-5-nitrophenyl)-1-methyl-pyridin-2(1H)-one Example 233A was prepared according to the procedure used for the preparation of Example 9B, substituting 4-chlorophenol for phenol, and substituting Example 225A for Example 9A, respectively, to provide the title compound.

Example 233B 5-(5-amino-2-(4-chlorophenoxy)phenyl)-1-methyl-pyridin-2(1H)-one Example 233B was prepared according to the procedure used for the preparation of Example 10, substituting Example 233A for Example 9B, to provide the title compound.

Example 233C

N-[4-(4-chlorophenoxy)-3-(1-methyl-6-oxo-1,6-dihydropyridin-3-yl)phenyl]methanesulfonamide Example 233C was prepared according to the procedure used for the preparation of Example 22, substituting Example 233B for Example 20C, to provide the title compound. $^1$H NMR (300 MHz, DMSO-$d_6$) δ 9.76 (s, 1H), 7.87 (d, J=2.6 Hz, 1H), 7.45 (dd, 1H), 7.39-7.32 (m, 2H), 7.26 (d, J=2.6 Hz, 1H), 7.20 (dd, J=8.7, 2.7 Hz, 1H), 7.05 (d, J=8.7 Hz, 1H), 6.95-6.88 (m, 2H), 6.38 (d, J=9.4 Hz, 1H), 3.44 (s, 3H), 3.04 (s, 3H). MS (ESI+) m/z 405.0 (M+H)$^+$

Example 234

N-[3-(1-methyl-6-oxo-1,6-dihydropyridin-3-yl)-4-(pyridin-3-yloxy)phenyl]methanesulfonamide

Example 234A 1-methyl-5-(5-nitro-2-(pyridin-3-yloxy)phenyl)pyridin-2(1H)-one Example 234A was prepared according to the procedure used for the preparation of Example 9B, substituting pyrindin-3-ol for phenol, and substituting Example 225A for Example 9A, respectively, to provide the title compound.

Example 234B 5-(5-amino-2-(pyridin-3-yloxy)phenyl)-1-methyl-pyridin-2(1H)-one Example 234A (340.4 mg, 1.053 mmol), iron (294 mg, 5.26 mmol), and ammonium chloride (113 mg, 2.106 mmol) were combined in ethanol (12 mL), tetrahydrofuran (12 mL), and water (4 mL), then allowed to reflux at 100° C. for 2 hours. The mixture was cooled just below reflux, vacuum filtered through diatomaceous earth, the filter cake was washed with warm methanol (3×35 mL). The filtrate was concentrated under reduced pressure and the residue was partitioned between saturated aqueous NaHCO$_3$ and ethyl acetate. The combined organics were washed with brine, dried (MgSO$_4$), gravity filtered, and concentrated to give the title compound.

Example 234C

N-[3-(1-methyl-6-oxo-1,6-dihydropyridin-3-yl)-4-(pyridin-3-yloxy)phenyl]methanesulfonamide Example 234C was prepared according to the procedure used for the preparation of Example 22, substituting Example 234B for Example 20C, to provide the title compound. $^1$H NMR (300 MHz, DMSO-$d_6$) δ 9.79 (s, 1H), 8.37-8.24 (m, 2H), 7.89 (d, J=2.6 Hz, 1H), 7.56 (dd, J=9.4, 2.6 Hz, 1H), 7.43-7.17 (m, 4H), 7.10 (d, J=8.6 Hz, 1H), 6.38 (d, J=9.6 Hz, 1H), 3.44 (s, 3H), 3.05 (s, 3H). MS (ESI+) m/z 372.1 (M+H)$^+$

Example 235

N-[4-(2-chlorophenoxy)-3-(1-methyl-6-oxo-1,6-dihydropyridin-3-yl)phenyl]methanesulfonamide

Example 235A 5-(2-(2-chlorophenoxy)-5-nitrophenyl)-1-methyl-pyridin-2(1H)-one Example 235A was prepared according to the procedure used for the preparation of Example 9B, substituting 2-chlorophenol for phenol, and substituting Example 225A for Example 9A, respectively, to provide the title compound.

Example 235B 5-(5-amino-2-(2-chlorophenoxy)phenyl)-1-methyl-pyridin-2(1H)-one Example 235B was prepared according to the procedure used for the preparation of Example 234B, substituting Example 235A for Example 234A, to provide the title compound.

Example 235C

N-[4-(2-chlorophenoxy)-3-(1-methyl-6-oxo-1,6-dihydropyridin-3-yl)phenyl]methanesulfonamide Example 235C was prepared according to the procedure used for the preparation of Example 22, substituting Example 235B for Example 20C, to provide the title compound. $^1$H NMR (300 MHz, DMSO-$d_6$) δ 9.75 (s, 1H), 7.91 (d, J=2.6 Hz, 1H), 7.59 (dd, J=9.4, 2.6 Hz, 1H), 7.53 (dd, J=7.9, 1.6 Hz, 1H), 7.31-7.21 (m, 2H), 7.19 (dd, J=8.7, 2.7 Hz, 1H), 7.16-7.06 (m, 1H), 6.94 (d, J=8.7 Hz, 1H), 6.88 (dd, J=8.1, 1.5 Hz, 1H), 6.39 (d, J=9.4 Hz, 1H), 3.45 (s, 3H), 3.03 (s, 3H). MS (ESI+) m/z 405.1 (M+H)$^+$

Example 236

N-{3-(1-methyl-6-oxo-1,6-dihydropyridin-3-yl)-4-[2-(trifluoromethyl)phenoxy]phenyl}methanesulfonamide

Example 236A 1-methyl-5-(5-nitro-2-(2-(trifluoromethyl)phenoxy)phenyl)pyridin-2(1H)-one Example 236A was prepared according to the procedure used for the preparation of Example 9B, substituting 2-(trifluoromethyl)phenol for phenol, and substituting Example 225A for Example 9A, respectively, to provide the title compound.

Example 236B 5-(5-amino-2-(2-(trifluoromethyl)phenoxy)phenyl)-1-methylpyridin-2(1H)-one Example 236B was prepared according to the procedure used for the preparation of Example 234B, substituting Example 236A for Example 234A, to provide the title compound.

Example 236C

N-{3-(1-methyl-6-oxo-1,6-dihydropyridin-3-yl)-4-[2-(trifluoromethyl)phenoxy]phenyl}methanesulfonamide Example 236C was prepared according to the procedure used for the preparation of Example 22, substituting Example 236B for Example 20C, to provide the title compound. $^1$H NMR (300 MHz, DMSO-$d_6$) δ 9.83 (s, 1H), 7.84 (d, J=2.6 Hz, 1H), 7.72 (dd, J=7.8, 1.6 Hz, 1H), 7.56 (dd, J=8.0, 1.6 Hz, 1H), 7.50 (dd, J=9.4, 2.6 Hz, 1H), 7.32-7.17 (m, 3H), 7.07 (d, J=8.7 Hz, 1H), 6.80 (d, J=8.4 Hz, 1H), 6.36 (d, J=9.3 Hz, 1H), 3.41 (s, 3H), 3.06 (s, 3H). MS (ESI+) m/z 439.1 (M+H)$^+$

Example 237

N-[4-(2-cyanophenoxy)-3-(1-methyl-6-oxo-1,6-dihydropyridin-3-yl)phenyl]methanesulfonamide

Example 237A 2-(2-(1-methyl-6-oxo-1,6-dihydropyridin-3-yl)-4-nitrophenoxy)benzonitrile Example 237A was prepared according to the procedure used for the preparation of Example 9B, substituting 2-hydroxybenzonitrile for phenol, and substituting Example 225A for Example 9A, respectively, to provide the title compound.

Example 237B 2-(4-amino-2-(1-methyl-6-oxo-1,6-dihydropyridin-3-yl)phenoxy)benzonitrile Example 237B was prepared according to the procedure used for the preparation of Example 234B, substituting Example 237A for Example 234A, to provide the title compound.

Example 237C

N-[4-(2-cyanophenoxy)-3-(1-methyl-6-oxo-1,6-dihydropyridin-3-yl)phenyl]methanesulfonamide Example 237C was prepared according to the procedure used for the preparation of Example 22, substituting Example 237B for Example 20C, to provide the title compound. $^1$H NMR (300 MHz, DMSO-$d_6$) δ 9.89 (s, 1H), 7.88 (d, J=2.6 Hz, 1H), 7.82 (dd, J=7.7, 1.7 Hz, 1H), 7.61-7.45 (m, 2H), 7.30 (dd, J=2.2, 0.9 Hz, 1H), 7.27-7.06 (m, 3H), 6.78 (d, J=8.0 Hz, 1H), 6.36 (d, J=9.3 Hz, 1H), 3.43 (s, 3H), 3.07 (s, 3H). MS (ESI+) m/z 396.1 (M+H)$^+$.

Example 238

N-[4-(2-methoxyphenoxy)-3-(1-methyl-6-oxo-1,6-dihydropyridin-3-yl)phenyl]methanesulfonamide

Example 238A 5-(2-(2-methoxyphenoxy)-5-nitrophenyl)-1-methyl-pyridin-2(1H)-one Example 238A was prepared according to the procedure used for the preparation of Example 9B, substituting 2-methoxyphenol for phenol, and substituting Example 225A for Example 9A, respectively, to provide the title compound.

Example 238B 5-(5-amino-2-(2-methoxyphenoxy)phenyl)-1-methylpyridin-2(1H)-one Example 238B was prepared according to the procedure used for the preparation of Example 234B, substituting Example 238A for Example 234A, to provide the title compound.

Example 238C

N-[4-(2-methoxyphenoxy)-3-(1-methyl-6-oxo-1,6-dihydropyridin-3-yl)phenyl]methanesulfonamide Example 238C was prepared according to the procedure used for the preparation of Example 22, substituting Example 238B for Example 20C, to provide the title compound. $^1$H NMR (300 MHz, DMSO-$d_6$) δ 9.58 (s, 1H), 7.93 (d, J=2.6 Hz, 1H), 7.69 (dd, J=9.4, 2.6 Hz, 1H), 7.21 (d, J=2.6 Hz, 1H), 7.18-7.05 (m, 3H), 6.99-6.88 (m, 2H), 6.67 (d, J=8.7 Hz, 1H), 6.42 (d, J=9.3 Hz, 1H), 3.76 (s, 3H), 3.47 (s, 3H), 2.99 (s, 3H). MS (ESI+) m/z 401.1 (M+H)$^+$

Example 239

N-[4-(2-fluorophenoxy)-3-(1-methyl-6-oxo-1,6-dihydropyridin-3-yl)phenyl]methanesulfonamide

Example 239A 5-(2-(2-fluorophenoxy)-5-nitrophenyl)-1-methylpyridin-2(1H)-one

Example 239A was prepared according to the procedure used for the preparation of Example 9B, substituting 2-fluorophenol for phenol, and substituting Example 225A for Example 9A, respectively, to provide the title compound.

Example 239B 5-(5-amino-2-(2-fluorophenoxy)phenyl)-1-methylpyridin-2(1H)-one

Example 239B was prepared according to the procedure used for the preparation of Example 234B, substituting Example 239A for Example 234A, to provide the title compound.

Example 239C

N-[4-(2-fluorophenoxy)-3-(1-methyl-6-oxo-1,6-dihydropyridin-3-yl)phenyl]methanesulfonamide Example 239C was prepared according to the procedure used for the preparation of Example 22, substituting Example 239B for Example 20C, to provide the title compound. $^1$H NMR (300 MHz, DMSO-$d_6$) δ 9.71 (s, 1H), 7.90 (d, J=2.6 Hz, 1H), 7.59 (dd, J=9.4, 2.6 Hz, 1H), 7.38-7.23 (m, 2H), 7.20-7.09 (m, 3H), 7.06-6.96 (m, 1H), 6.92 (d, J=8.7 Hz, 1H), 6.41 (d, J=9.3 Hz, 1H), 3.46 (s, 3H), 3.02 (s, 3H). MS (ESI+) m/z 389.1 (M+H)$^+$.

Example 240

N-[4-(2,4-difluorophenoxy)-3-(1-methyl-6-oxo-1,6-dihydropyridin-3-yl)phenyl]methanesulfonamide

Example 240A 5-(2-(2,4-difluorophenoxy)-5-nitrophenyl)-1-methylpyridin-2(1H)-one Example 239A was prepared according to the procedure used for the preparation of Example 9B, substituting 2,4-difluorophenol for phenol, and substituting Example 225A for Example 9A, respectively, to provide the title compound.

Example 240B 5-(5-amino-2-(2,4-difluorophenoxy)phenyl)-1-methylpyridin-2(1H)-one Example 240B was prepared according to the procedure used for the preparation of Example 234B, substituting Example 240A for Example 234A, to provide the title compound.

Example 240C

N-[4-(2,4-difluorophenoxy)-3-(1-methyl-6-oxo-1,6-dihydropyridin-3-yl)phenyl]methanesulfonamide Example 240C was prepared according to the procedure used for the preparation of Example 22, substituting Example 240B for Example 20C, to provide the title compound. $^1$H NMR (300 MHz, DMSO-$d_6$) δ 9.69 (s, 1H), 7.90 (d, J=2.6 Hz, 1H), 7.60 (dd, J=9.4, 2.6 Hz, 1H), 7.49-7.38 (m, 1H), 7.24 (d, J=2.6 Hz, 1H), 7.19-7.01 (m, 3H), 6.88 (d, J=8.7 Hz, 1H), 6.43 (d, J=9.3 Hz, 1H), 3.47 (s, 3H) 3.01 (s, 3H). MS (ESI+) m/z 407.1 (M+H)$^+$

Example 241

N-[4-(2,4-difluorophenoxy)-3-(1-methyl-6-oxo-1,6-dihydropyridin-3-yl)phenyl]ethanesulfonamide Example 241 was prepared according to the procedure used for the preparation of Example 22, substituting ethanesulfonyl chloride for methanesulfonyl chloride, and substituting Example 240B for Example 20C, respectively, to provide the title compound. $^1$H NMR (300 MHz, DMSO-$d_6$) δ 9.77 (s, 1H), 7.89 (d, J=2.6 Hz, 1H), 7.59 (dd, J=9.3, 2.6 Hz, 1H), 7.43 (ddd, J=11.3, 8.7, 2.8 Hz, 1H), 7.24 (d, J=2.7 Hz, 1H), 7.19-7.01 (m, 3H), 6.87 (d, J=8.7 Hz, 1H), 6.43 (d, J=9.3 Hz, 1H), 3.46 (s, 3H), 3.11 (q, J=7.3 Hz, 2H), 1.22 (t, J=7.3 Hz, 3H). MS (ESI+) m/z 421.1 (M+H)$^+$.

Example 242

N-[4-(3,5-difluorophenoxy)-3-(1-methyl-6-oxo-1,6-dihydropyridin-3-yl)phenyl]methanesulfonamide

Example 242A 5-(2-(3,5-difluorophenoxy)-5-nitrophenyl)-1-methylpyridin-2(1H)-one Example 242A was prepared according to the procedure used for the preparation of Example 9B, substituting 3,5- difluorophenol for phenol, and substituting Example 225A for Example 9A, respectively, to provide the title compound.

Example 242B 5-(5-amino-2-(3,5-difluorophenoxy)phenyl)-1-methylpyridin-2(1H)-one Example 242B was prepared according to the procedure used for the preparation of Example 234B, substituting Example 242A for Example 234A, to provide the title compound.

Example 242C

N-[4-(3,5-difluorophenoxy)-3-(1-methyl-6-oxo-1,6-dihydropyridin-3-yl)phenyl]methanesulfonamide Example 242C was prepared according to the procedure used for the preparation of Example 22, substituting Example 242B for Example 20C, to provide the title compound. $^1$H NMR (300 MHz, DMSO-$d_6$) δ 9.83 (s, 1H), 7.87 (d, J=2.6 Hz, 1H), 7.52 (dd, J=9.4, 2.6 Hz, 1H), 7.30-7.19 (m, 2H), 7.16 (d, J=8.6 Hz, 1H), 6.91 (tt, J=9.3, 2.3 Hz, 1H), 6.67-6.57 (m, 2H), 6.39 (d, J=9.3 Hz, 1H), 3.44 (s, 3H), 3.06 (s, 3H). MS (ESI+) m/z 407.1 (M+H)$^+$

Example 243

N-[4-(3-chlorophenoxy)-3-(1-methyl-6-oxo-1,6-dihydropyridin-3-yl)phenyl]methanesulfonamide

Example 243A 5-(2-(3-chlorophenoxy)-5-nitrophenyl)-1-methylpyridin-2(1H)-one Example 243A was prepared according to the procedure used for the preparation of Example 9B, substituting 3-chlorophenol for phenol, and substituting Example 225A for Example 9A, respectively, to provide the title compound.

Example 243B 5-(5-amino-2-(3-chlorophenoxy)phenyl)-1-methylpyridin-2(1H)-one Example 243B was prepared according to the procedure used for the preparation of Example 234B, substituting Example 243A for Example 234A, to provide the title compound.

Example 243C

N-[4-(3-chlorophenoxy)-3-(1-methyl-6-oxo-1,6-dihydropyridin-3-yl)phenyl]methanesulfonamide Example 243C was prepared according to the procedure used for the preparation of Example 22, substituting Example 243B for Example 20C, to provide the title compound. $^1$H NMR (300 MHz, DMSO-$d_6$) δ 9.80 (s, 1H), 7.89 (d, J=2.6 Hz, 1H), 7.54 (dd, J=9.4, 2.7 Hz, 1H), 7.33 (t, J=8.1 Hz, 1H), 7.27 (d, J=2.6 Hz, 1H), 7.21 (dd, J=8.6, 2.7 Hz, 1H), 7.14-7.05 (m, 2H), 6.97 (t, J=2.2 Hz, 1H), 6.85 (ddd, J=8.3, 2.4, 0.9 Hz, 1H), 6.38 (d, J=9.3 Hz, 1H), 3.44 (s, 3H), 3.05 (s, 3H). MS (ESI+) m/z 405.1 (M+H)$^+$

Example 244

N-{3-(1-methyl-6-oxo-1,6-dihydropyridin-3-yl)-4-[3-(trifluoromethyl)phenoxy]phenyl}methanesulfonamide

Example 244A 1-methyl-5-(5-nitro-2-(3-(trifluoromethyl)phenoxy)phenyl)pyridin-2(1H)-one Example 244A was prepared according to the procedure used for the preparation of Example 9B, substituting 3-(trifluoromethyl)phenol for phenol, and substituting Example 225A for Example 9A, respectively, to provide the title compound.

Example 244B 5-(5-amino-2-(3-(trifluoromethyl)phenoxy)phenyl)-1-methylpyridin-2(1H)-one Example 244B was prepared according to the procedure used for the preparation of Example 234B, substituting Example 244A for Example 234A, to provide the title compound.

Example 244C

N-{3-(1-methyl-6-oxo-1,6-dihydropyridin-3-yl)-4-[3-(trifluoromethyl)phenoxy]phenyl}methanesulfonamide Example 244C was prepared according to the procedure used for the preparation of Example 22, substituting Example 244B for Example 20C, to provide the title compound. $^1$H NMR (300 MHz, DMSO-$d_6$) δ 9.82 (s, 1H), 7.90 (d, J=2.6 Hz, 1H), 7.58-7.48 (m, 2H), 7.44-7.36 (m, 1H), 7.28 (d, J=2.6 Hz, 1H), 7.26-7.08 (m, 4H), 6.37 (d, J=9.3 Hz, 1H), 3.44 (s, 3H), 3.05 (s, 3H). MS (ESI+) m/z 439.1 (M+H)$^+$.

Example 245

N-[4-(3-cyanophenoxy)-3-(1-methyl-6-oxo-1,6-dihydropyridin-3-yl)phenyl]methanesulfonamide

Example 245A 3-(2-(1-methyl-6-oxo-1,6-dihydropyridin-3-yl)-4-nitrophenoxy)benzonitrile Example 245A was prepared according to the procedure used for the preparation of Example 9B, substituting 3-hydroxybenzonitrile for phenol, and substituting Example 225A for Example 9A, respectively, to provide the title compound.

Example 245B 3-(4-amino-2-(1-methyl-6-oxo-1,6-dihydropyridin-3-yl)phenoxy)benzonitrile Example 245B was prepared according to the procedure used for the preparation of Example 234B, substituting Example 245A for Example 234A, to provide the title compound.

Example 245C

N-[4-(3-cyanophenoxy)-3-(1-methyl-6-oxo-1,6-dihydropyridin-3-yl)phenyl]methanesulfonamide Example 245C was prepared according to the procedure used for the preparation of Example 22, substituting Example 245B for Example 20C, o provide the title compound. $^1$H NMR (300 MHz, DMSO-d$_6$) δ 9.81 (s, 1H), 7.88 (d, J=2.6 Hz, 1H), 7.57-7.46 (m, 3H), 7.39-7.34 (m, 1H), 7.30-7.18 (m, 3H), 7.10 (d, J=8.6 Hz, 1H), 6.37 (d, J=9.3 Hz, 1H), 3.44 (s, 3H), 3.05 (s, 3H). MS (ESI+) m/z 396.1 (M+H)$^+$.

Example 246

N-[4-(3-fluorophenoxy)-3-(1-methyl-6-oxo-1,6-dihydropyridin-3-yl)phenyl]methanesulfonamide

Example 246A

5-(2-(3-fluorophenoxy)-5-nitrophenyl)-1-methylpyridin-2(1H)-one

Example 246A was prepared according to the procedure used for the preparation of Example 9B, substituting 3-fluorophenol for phenol, and substituting Example 225A for Example 9A, respectively, to provide the title compound.

Example 246B

5-(5-amino-2-(3-fluorophenoxy)phenyl)-1-methylpyridin-2(1H)-one

Example 246B was prepared according to the procedure used for the preparation of Example 234B, substituting Example 246A for Example 234A, to provide the title compound.

Example 246C

N-[4-(3-fluorophenoxy)-3-(1-methyl-6-oxo-1,6-dihydropyridin-3-yl)phenyl]methanesulfonamide Example 246C was prepared according to the procedure used for the preparation of Example 22, substituting Example 246B for Example 20C, to provide the title compound. $^1$H NMR (300 MHz, DMSO-d$_6$) 9.79 (s, 1H), 7.88 (d, J=2.6 Hz, 1H), 7.54 (dd, J=9.4, 2.6 Hz, 1H), 7.34 (td, J=8.1, 6.8 Hz, 1H), 7.27 (d, J=2.6 Hz, 1H), 7.21 (dd, J=8.6, 2.6 Hz, 1H), 7.10 (d, J=8.6 Hz, 1H), 6.88 (tdd, J=8.5, 2.4, 0.9 Hz, 1H), 6.79-6.67 (m, 2H), 6.38 (d, J=9.3 Hz, 1H), 3.43 (s, 3H) 3.05 (s, 3H). MS (ESI+) m/z 389.1 (M+H)$^+$.

Example 247

N-[4-(cyclohexyloxy)-3-(1-methyl-6-oxo-1,6-dihydropyridin-3-yl)phenyl]methanesulfonamide

Example 247A

5-(2-(cyclohexyloxy)-5-nitrophenyl)-1-methylpyridin-2(1H)-one

Cyclohexanol (48.4 mg, 0.483 mmol) and sodium hydride (56.4 mg, 1.410 mmol) were combined in anhydrous tetrahydrofuran (5 mL). Bubbling occurred and the opaque mixture was stirred at ambient temperature for 1 hour. Example 225A (100 mg, 0.403 mmol) was added and the mixture heated to 50° C. for 2 hours. Cold water (10 mL) was added and the aqueous extracted with ethyl acetate. The combined organics were washed with brine, dried (MgSO$_4$), filtered, and concentrated to give the title compound.

Example 247B

5-(5-amino-2-(cyclohexyloxy)phenyl)-1-methylpyridin-2(1H)-one

Example 247B was prepared according to the procedure used for the preparation of Example 234B, substituting Example 247A for Example 234A, to provide the title compound.

Example 247C

N-[4-(cyclohexyloxy)-3-(1-methyl-6-oxo-1,6-dihydropyridin-3-yl)phenyl]methanesulfonamide Example 247C was prepared according to the procedure used for the preparation of Example 22, substituting Example 247B for Example 20C, to provide the title compound. $^1$H NMR (300 MHz, DMSO-d$_6$) $^1$H NMR 9.40 (s, 1H), 7.83 (d, J=2.6 Hz, 1H), 7.61 (dd, J=9.3, 2.6 Hz, 1H), 7.15-7.04 (m, 3H), 6.42 (d, J=9.3 Hz, 1H), 4.39-4.27 (m, 1H), 3.48 (s, 3H), 2.94 (s, 3H), 1.96-1.20 (m, 10H). MS (ESI+) m/z 377.1 (M+H)$^+$.

Example 248

N-[4-(cyclopentyloxy)-3-(1-methyl-6-oxo-1,6-dihydropyridin-3-yl)phenyl]methanesulfonamide

Example 248A

5-(2-(cyclopentyloxy)-5-nitrophenyl)-1-methylpyridin-2(1H)-one

Example 248A was prepared according to the procedure used for the preparation of Example 247A, substituting cyclopentanol for cyclohexanol, to provide the title compound.

Example 248B

5-(5-amino-2-(cyclopentyloxy)phenyl)-1-methylpyridin-2(1H)-one

Example 248B was prepared according to the procedure used for the preparation of Example 234B, substituting Example 248A for Example 234A, to provide the title compound.

Example 248C

N-[4-(cyclopentyloxy)-3-(1-methyl-6-oxo-1,6-dihydropyridin-3-yl)phenyl]methanesulfonamide Example 248C was prepared according to the procedure used for the preparation of Example 22, substituting Example 248B for Example 20C, to provide the title compound. $^1$H NMR (300 MHz, DMSO-d$_6$) 9.39 (s, 1H), 7.80 (d, J=2.6 Hz, 1H), 7.55 (dd, J=9.3, 2.6 Hz, 1H), 7.16-7.09 (m, 2H), 7.08-7.01 (m, 1H), 6.41 (d, J=9.3 Hz, 1H), 4.83-

4.75 (m, 1H), 3.47 (s, 3H), 2.93 (s, 3H), 1.90-1.75 (m, 2H), 1.76-1.35 (m, 6H). MS (ESI+) m/z 363.1 (M+H)+.

Example 249

N-[3-(1-methyl-6-oxo-1,6-dihydropyridin-3-yl)-4-(tetrahydrofuran-3-yloxy)phenyl]methanesulfonamide

Example 249A 1-methyl-5-(5-nitro-2-(tetrahydrofuran-3-yloxy)phenyl)pyridin-2(1H)-one Example 249A was prepared according to the procedure used for the preparation of Example 247A, substituting tetrahydrofuran-3-ol for cyclohexanol, to provide the title compound.

Example 249B 5-(5-amino-2-(tetrahydrofuran-3-yloxy)phenyl)-1-methylpyridin-2(1H)-one Example 249B was prepared according to the procedure used for the preparation of Example 234B, substituting Example 249A for Example 234A, to provide the title compound.

Example 249C

N-[3-(1-methyl-6-oxo-1,6-dihydropyridin-3-yl)-4-(tetrahydrofuran-3-yloxy)phenyl]methanesulfonamide Example 249C was prepared according to the procedure used for the preparation of Example 22, substituting Example 249B for Example 20C, to provide the title compound. $^1$H NMR (300 MHz, DMSO-$d_6$) 9.43 (s, 1H), 7.82 (d, J=2.6 Hz, 1H), 7.57 (dd, J=9.4, 2.6 Hz, 1H), 7.21-7.09 (m, 2H), 7.09-7.02 (m, 1H), 6.42 (d, J=9.3 Hz, 1H), 5.06-4.98 (m, 1H), 3.89-3.76 (m, 4H), 3.47 (s, 3H), 2.95 (s, 3H), 2.30-2.10 (m, 1H), 2.00-1.87 (m, 1H). MS (ESI+) m/z 365.1 (M+H)+.

Example 250

N-[3-(1-methyl-6-oxo-1,6-dihydropyridin-3-yl)-4-(tetrahydro-2H-pyran-4-ylmethoxy)phenyl]methanesulfonamide

Example 250A 1-methyl-5-(5-nitro-2-((tetrahydro-2H-pyran-4-yl)methoxy)phenyl)pyridin-2(1H)-one Example 250A was prepared according to the procedure used for the preparation of Example 247A, substituting (tetrahydro-2H-pyran-4-yl)methanol for cyclohexanol, to provide the title compound.

Example 250B 5-(5-amino-2-((tetrahydro-2H-pyran-4-yl)methoxy)phenyl)-1-methylpyridin-2(1H)-one Example 250B was prepared according to the procedure used for the preparation of Example 234B, substituting Example 250A for Example 234A, to provide the title compound.

Example 250C

N-[3-(1-methyl-6-oxo-1,6-dihydropyridin-3-yl)-4-(tetrahydro-2H-pyran-4-ylmethoxy)phenyl]methanesulfonamide Example 250C was prepared according to the procedure used for the preparation of Example 22, substituting Example 250B for Example 20C, to provide the title compound. $^1$H NMR (300 MHz, DMSO-$d_6$) 9.41 (s, 1H), 7.83 (d, J=2.6 Hz, 1H), 7.57 (dd, J=9.3, 2.6 Hz, 1H), 7.17-7.03 (m, 3H), 6.42 (d, J=9.3 Hz, 1H), 3.87 (d, J=4.0 Hz, 2H), 3.83 (d, J=6.1 Hz, 2H), 3.47 (s, 3H), 3.41-3.17 (m, 2H), 2.93 (s, 3H), 2.04-1.86 (m, 1H), 1.64-1.54 (m, 2H), 1.39-1.20 (m, 2H). MS (ESI+) m/z 393.1 (M+H)+.

Example 251

N-[3-(1-methyl-6-oxo-1,6-dihydropyridin-3-yl)-4-phenoxyphenyl]-1H-pyrrole-2-carboxamide A mixture of 1H-pyrrole-2-carboxylic acid (0.018 g, 0.164 mmol), oxalyl chloride (0.035 g, 0.274 mmol) and dimethylformamide (1 drop) in dichloromethane (3 mL) was stirred at ambient temperature for 1 hour. The solvent was evaporated under reduced pressure and the residue treated with toluene (2 mL) and then evaporated under reduced pressure. The residue was dissolved in dichloromethane (2 mL) and was then added to a solution of Example 225C (0.040 g, 0.137 mmol) and triethylamine (0.055 g, 0.547 mmol) in dichloromethane (3 mL). The reaction mixture was stirred at ambient temperature for 2 hours. The reaction mixture was concentrated under reduced pressure. The residue was purified by reverse phase HPLC (C18, CH$_3$CN/water (0.1% TFA), 0-100%) to afford the title compound (0.035 g, 66%). $^1$H NMR (500 MHz, DMSO-$d_6$) δ 10.64 (s, 1H), 9.85 (s, 1H), 7.90 (d, J=2.75 Hz, 1H), 7.82 (d, J=2.75 Hz, 1H), 7.76 (dd, J=8.85, 2.75 Hz, 1H), 7.60 (dd, J=9.31, 2.59 Hz, 1H), 7.29-7.33 (m, 2H), 6.97-7.01 (m, 3H), 6.97-6.98 (m, 1H), 6.89 (d, J=7.63 Hz, 2H), 6.38 (d, J=9.46 Hz, 1H), 6.17-6.19 (m, 1H), 3.44 (s, 3H). MS (ESI+) m/z 386.1 (M+H)+.

Example 252 tert-butyl (2-{[3-(1-methyl-6-oxo-1,6-dihydropyridin-3-yl)-4-phenoxyphenyl]amino}-2-oxoethyl)carbamate The product from Example 225C (0.058 g, 0.2 mmol), Boc-glycine (0.042 g, 0.240 mmol), triethylamine (0.098 mL, 0.70 mmol) and HATU (0.091 g, 0.240 mmol) were combined in DMSO (1.2 mL), stirred for 1 hour and partitioned between ethyl acetate and brine. The organic layer was separated and concentrated. Purification by chromatography (silica gel, 1-4% methanol in dichloromethane) afforded the title compound (0.071 g, 79%). $^1$H NMR (300

MHz, DMSO-d$_6$) δ 10.00 (s, 1H) 7.86 (d, J=2.71 Hz, 1H) 7.70 (d, J=2.37 Hz, 1H) 7.48-7.59 (m, 2H) 7.27-7.34 (m, 2H) 6.97-7.08 (m, 3H) 6.87 (d, J=7.80 Hz, 2H) 6.37 (d, J=9.49 Hz, 1H) 3.72 (d, J=6.10 Hz, 2H) 3.43 (s, 3H) 1.40 (s, 9H). MS (ESI+) m/z 448 (M+H)$^+$.

Example 253

N-[3-(1-methyl-6-oxo-1,6-dihydropyridin-3-yl)-4-phenoxyphenyl]glycinamide

The product from Example 252 (0.071 g, 0.158 mmol) and trifluoroacetic acid (0.5 mL) in dichloromethane (1 mL) was stirred for 1 h and concentrated. Purification by reverse phase HPLC (C18, 0-100% CH$_3$CN/water (0.1% TFA)) afforded the title compound as the trifluoroacetic acid salt (0.060 g, 81%). $^1$H NMR (300 MHz, DMSO-d$_6$) δ 10.49 (s, 1H) 8.08 (s, 2H) 7.86 (d, J=2.37 Hz, 1H) 7.63 (d, J=2.37 Hz, 1H) 7.51-7.58 (m, 2H) 7.29-7.36 (m, 2H) 6.99-7.10 (m, 2H) 6.89 (d, J=7.46 Hz, 2H) 6.39 (d, J=9.49 Hz, 1H) 3.79 (q, J=5.54 Hz, 2H) 3.44 (s, 3H). MS (ESI+) m/z 350 (M+H)$^+$.

Example 254

1-methyl-5-[2-phenoxy-5-(pyridin-2-ylamino)phenyl]pyridin-2(1H)-one

A mixture of Example 225C (0.035 g, 0.120 mmol), 2-bromopyridine (0.023 g, 0.144 mmol), 2'-(dicyclohexylphosphino)-N,N-dimethylbiphenyl-2-amine (0.0071 g, 0.018 mmol), tris(dibenzylideneacetone)dipalladium(0) (0.0055 g, 0.006 mmol), and Cs$_2$CO$_3$ (0.055 g, 0.168 mmol) in dioxane (1 mL) was degassed and back-filled with nitrogen several times. The reaction mixture was heated at 100° C. overnight. After cooling to room temperature, the reaction mixture was partitioned between ethyl acetate and water. The aqueous layer was extracted with additional ethyl acetate twice. The combined organic layers were washed with brine, dried over MgSO$_4$, filtered, and concentrated. The residue was purified by reverse phase HPLC (C18, CH$_3$CN/water (0.1% TFA), 0-100%) to afford 0.019 g (33%) of the title compound as a TFA salt. $^1$H NMR (500 MHz, DMSO-d$_6$) δ 10.46 (s, 1H), 9.86 (br s, 1H), 8.08 (dd, J=5.49, 1.22 Hz, 1H), 7.91 (d, J=2.44 Hz, 1H), 7.75 (t, J=7.02 Hz, 1H), 7.67 (d, J=2.75 Hz, 1H), 7.61 (dd, J=9.46, 2.75 Hz, 1H), 7.57 (dd, J=8.7, 2.59 Hz, 1H), 7.30-7.35 (m, 2H), 7.02-7.07 (m, 2H), 6.98 (d, J=8.54 Hz, 1H), 6.90 (d, J=7.93 Hz, 2H), 6.84-6.87 (m, 1H), 6.38 (d, J=9.46 Hz, 1H), 3.43 (s, 3H). MS (ESI+) m/z 370.2 (M+H)$^+$.

Example 255

N-ethyl-3-(1-methyl-6-oxo-1,6-dihydropyridin-3-yl)-4-phenoxybenzenesulfonamide

Example 255A 3-(1-methyl-6-oxo-1,6-dihydropyridin-3-yl)-4-phenoxybenzene-1-sulfonyl chloride Under ice-cooling, thionyl chloride (2 mL) was added dropwise over 20 minutes to water (8 mL). The mixture was stirred overnight for 12 hours to give a SO$_2$ containing solution. Separately, Example 225C (0.3 g, 1.026 mmol) was added to concentrated HCl (8 mL) and dioxane (6 mL) at 0° C. The solution was stirred for 5 minutes. To this suspension/solution was added sodium nitrite (0.078 g, 1.129 mmol) in water (2 mL) dropwise at 0° C. The solution was stirred at 0° C. for three hours. To the SO$_2$ containing solution was added copper(I)chloride (0.020 g, 0.205 mmol). Then, to this solution was added the diazotized Example 225C at 0° C. The solution was stirred for 30 minutes. The reaction mixture was extracted with ethyl acetate. The solvent was removed, and the residue was taken up into tetrahydrofuran which was used directly for the next reaction.

Example 255B

N-ethyl-3-(1-methyl-6-oxo-1,6-dihydropyridin-3-yl)-4-phenoxybenzenesulfonamide

A quater of tetrahydrofuran solution containing Example 255A was treated with excess ethyl amine in tetrahydrofuran. The solution was stirred at ambient temperature for three hours. The solvent was removed, and the residue was purified by reverse phase HPLC (C18, CH$_3$CN/water (0.1% TFA), 0-100%) to afford 0.010 g of the title compound. $^1$H NMR (500 MHz, DMSO-d$_6$) δ 8.00 (d, J=2.44 Hz, 1H), 7.82 (d, J=2.44 Hz, 1H), 7.71 (dd, J=2.59, 1.37 Hz, 1H), 7.69 (d, J=2.14 Hz, 1H), 7.51 (t, J=5.8 Hz, 1H), 7.41-7.45 (m, 3H), 7.21 (t, J=7.32 Hz, 1H), 7.11 (d, J=7.63 Hz, 2H), 6.99 (d, J=8.54 Hz, 1H), 6.44 (d, J=9.46 Hz, 1H), 3.49 (s, 3H), 2.77-2.84 (m, 2H), 1.00 (t, J=7.17 Hz, 3H). MS (ESI+) m/z 385.2 (M+H)$^+$.

Example 256

3-(1-methyl-6-oxo-1,6-dihydropyridin-3-yl)-4-phenoxybenzenesulfonamide

A quarter of tetrahydrofuran solution containing Example 255A was treated with excess concentrated ammonium hydroxide. The solution was stirred at for three hours. The solvent was removed, and the residue was purified by reverse phase HPLC (C18, CH$_3$CN/water (0.1% TFA), 0-100%) to afford 0.010 g of the title compound. $^1$H NMR (500 MHz, DMSO-d$_6$) δ 7.98 (d, J=2.75 Hz, 1H), 7.88 (d, J=2.44 Hz, 1H), 7.74 (dd, J=8.7, 2.29 Hz, 1H), 7.6 (dd, J=9.46, 2.75 Hz, 1H), 7.40-7.44 (m, 2H), 7.34 (s, 2H), 7.20 (t, J=7.32 Hz, 1H), 7.08 (d, J=7.63 Hz, 2H), 7.00 (d, J=8.54 Hz, 1H), 6.45 (d, J=9.46 Hz, 1H), 3.49 (s, 3H). MS (ESI+) m/z 357.2 (M+H)$^+$.

Example 257

N-[2-methyl-5-(1-methyl-6-oxo-1,6-dihydropyridin-3-yl)-4-phenoxyphenyl]methanesulfonamide Example 257A 5-(2-fluoro-4-methyl-5-nitrophenyl)-1-methylpyridin-2(1H)-one 4-bromo-5-fluoro-2-nitrotoluene (Aldrich, 0.234 g, 1.0 mmol), 1-methyl-5-(4,4,5,5-tetramethyl-[1,3,2]dioxaboralan-2-yl)-1H-pyridin-2-one (Synchem, Inc. 0.235 g, 1.0 mmol), bis(triphenylphosphine)palladium(II)chloride (0.035 g, 0.05 mmol) and sodium carbonate 2M (1.5 mL, 3.0 mmol) were combined in DME (4 mL) and water (4.0 mL), sparged with nitrogen and heated by microwave at 120° C. for 30 minutes. The reaction mixture was partitioned between ethyl acetate and water. The ethyl acetate layer was washed with brine, dried (Na$_2$SO$_4$), treated with mercaptopropyl silica gel for 30 minutes, filtered and concentrated to afford the title compound (0.262 g, 99%).

Example 257B 1-methyl-5-(4-methyl-5-nitro-2-phenoxyphenyl) pyridin-2(1H)-one The product from Example 257A (0.262 g, 1.0 mmol), phenol (0.104 g, 1.1 mmol) and cesium carbonate (0.358 g, 1.1 mmol) were combined in DMSO (5 mL) and heated at 100° C. for 30 minutes under nitrogen. The reaction mixture was partitioned between ethyl acetate and water. The organic layer was washed with brine, dried ($Na_2SO_4$), filtered and concentrated to afford the title compound (0.31 g, 92%).

Example 257C 5-(5-amino-4-methyl-2-phenoxyphenyl)-1-methyl-pyridin-2(1H)-one The product from Example 257B (0.336 g, 1.0 mmol), iron (0.279 g, 5.0 mmol), and ammonium chloride (0.080 g, 1.5 mmol) were combined in a solvent mixture of ethanol (9 mL), tetrahydrofuran (9 mL) and water (3 mL) and heated at 95° C. with vigorous stirring for 1.5 hours. The mixture was cooled, filtered through Celite and the Celite was rinsed repeatedly with methanol and tetrahydrofuran. The filtrate was concentrated and the residue partitioned between ethyl acetate and water. The ethyl acetate layer was washed with brine, dried ($Na_2SO_4$), filtered and concentrated. Purification by chromatography (silica gel, 0-4% methanol in dichloromethane) afforded the title compound (0.186 g, 61%).

Example 257D

N-[2-methyl-5-(1-methyl-6-oxo-1,6-dihydropyridin-3-yl)-4-phenoxyphenyl]methanesulfonamide A solution of the product from Example 257C (0.060 g, 0.196 mmol) and triethylamine (0.068 mL, 0.49 mmol) in dichloromethane (3 mL) was treated with methanesulfonyl chloride (0.035 mL, 0.45 mmol), stirred for 2 hours and concentrated. The residue was dissolved in a mixture of dioxane (2 mL) and 1M sodium hydroxide (2 mL) and heated for 1 hour at 90° C. The mixture was cooled, diluted with ethyl acetate, brought to pH 7 with 1 M HCl and the organic layer was separated, dried ($Na_2SO_4$), filtered and concentrated. Purification by chromatography (silica gel, 0-4% methanol in dichloromethane) afforded the title compound (0.039 g, 52%). $^1$H NMR (300 MHz, DMSO-$d_6$) δ 9.11 (s, 1H) 7.86 (d, J=2.78 Hz, 1H) 7.58 (dd, J=9.52, 2.78 Hz, 1H) 7.29-7.39 (m, 3H) 7.08 (t, J=7.34 Hz, 1H) 6.93 (d, J=7.93 Hz, 2H) 6.87 (s, 1H) 6.37 (d, J=9.52 Hz, 1H) 3.44 (s, 3H) 3.03 (s, 3H) 2.27 (s, 3H). MS (ESI+) m/z 385 (M+H)$^+$.

Example 258

4-methoxy-1-methyl-5-(2-phenoxyphenyl)pyridin-2(1H)-one

Example 258A 5-chloro-4-methoxy-1-methylpyridin-2(1H)-one

5-Chloro-4-hydroxypyridin-2(1H)-one (1.27 g, 8.73 mmol) in dimethylformamide was cooled to 0° C. To this solution was added sodium hydride (0.254 g, 21.81 mmol). After the end of bubbling, iodomethane (3.1 g, 21.81 mmol) was added to the solution. The solution was stirred for 6 hours at room temperature. The reaction mixture was partitioned between water and ethyl acetate. The aqueous layer was extracted with additional ethyl acetate three times. The combined organic layers were washed with brine, dried over $MgSO_4$, filtered, and concentrated. The residue was purified by flash chromatography on silica gel eluting with 40% ethyl acetate in hexanes to afford 0.2 g (6.6%) of the title compound.

Example 258B 4-methoxy-1-methyl-5-(2-phenoxyphenyl)pyridin-2 (1H)-one

A mixture of Example 258A (0.035 g, 0.2 mmol), 2-phenoxyphenylboronic acid (0.064 g, 0.30 mmol), 2'-(dicyclohexylphosphino)-N,N-dimethylbiphenyl-2-amine (0.016 g, 0.040 mmol), palladium(II)acetate (0.0045 g, 0.02 mmol) and CsF (0.091 g, 0.6 mmol) in dioxane (1 mL) in a 4 mL vial was degassed and back-filled with nitrogen four times. The reaction mixture was heated at 90° C. overnight. The mixture was filtered through a pad of filtering agent. The filtrate was concentrated. The residue was then purified by reverse HPLC (C18, $CH_3CN$/water (0.1% TFA), 0-100%) to afford 0.030 g (48%) of the title compound. $^1$H NMR (500 MHz, DMSO-$d_6$) δ 7.57 (m, 1H), 7.30-7.37 (m, 4H), 7.16-7.20 (m, 1H), 7.07 (t, J=7.32 Hz, 1H), 6.90-6.92. (m, 3H), 5.79 (s, 1H), 3.54 (s, 3H), 3.34 (s, 3H). MS (ESI+) m/z 308.1 (M+H)$^+$.

Example 259

N-[3-(4-methoxy-1-methyl-6-oxo-1,6-dihydropyridin-3-yl)-4-phenoxyphenyl]methanesulfonamide

Example 259A 5-(2-fluoro-5-nitrophenyl)-4-methoxy-1-methylpyridin-2(1H)-one

Example 259A was prepared according to the procedure used for the preparation of Example 258B, substituting 2-fluoro-5-nitrophenylboronic acid for 2-phenoxyphenylboronic acid, to provide the title compound.

Example 259B 4-methoxy-1-methyl-5-(5-nitro-2-phenoxyphenyl) pyridin-2(1H)-one Example 259B was prepared according to the procedure used for the preparation of Example 9B, substituting Example 259A for Example 9A, to provide the title compound.

Example 259C 5-(5-amino-2-phenoxyphenyl)-4-methoxy-1-methylpyridin-2(1H)-one Example 259C was prepared according to the procedure used for the preparation of Example 10, substituting Example 259B for Example 9B, to provide the title compound.

Example 259D

N-[3-(4-methoxy-1-methyl-6-oxo-1,6-dihydropyridin-3-yl)-4-phenoxyphenyl]methanesulfonamide Example 259D was prepared according to the procedure used for the preparation of Example 22, substituting Example 259C for Example 20C, to provide the title compound. $^1$H NMR (500 MHz, DMSO-$d_6$) δ 9.70 (s, 1H), 7.58 (s, 1H), 7.29-7.33 (m, 2H), 7.20 (dd, J=8.85, 2.75 Hz, 1H), 7.13 (d, J=2.75 Hz, 1H), 7.04 (t, J=7.48 Hz, 1H), 6.94 (d, J=8.85 Hz, 1H), 6.88 (d, J=7.63 Hz, 2H), 5.79 (s, 1H), 3.53 (s, 3H), 3.33 (s, 3H), 3.02 (s, 3H). MS (ESI+) m/z 401.0 (M+H)$^+$.

Example 260

3-methyl-5-(2-phenoxyphenyl)pyridin-2(1H)-one

2-Phenoxylphenylboronic acid (0.072 g, 0.335 mmol), 5-bromo-3-methylpyridin-2(1H)-one (0.060 g, 0.319 mmol), bis(triphenylphosphine)palladium(II)chloride (0.009 g, 0.013 mmol) and 2M sodium carbonate (0.64 mL, 1.28 mmol) were combined in 1,2-dimethoxyethane (1.6 mL) and ethanol (1.6 mL), sparged with nitrogen for 15 minutes and heated by microwave at 120° C. for 30 minutes. The reaction mixture was partitioned between ethyl acetate and water. The ethyl acetate layer was washed with brine, dried (Na$_2$SO$_4$), filtered and concentrated. Purification by reverse phase HPLC (C18, 0-100% CH$_3$CN/water (0.1% TFA)) afforded the title compound as the trifluoroacetic acid salt (0.020 g, 23%). $^1$H NMR (300 MHz, DMSO-$d_6$) δ 11.60 (s, 1H) 6.75-7.63 (m, 11H) 1.97 (m, 3H) MS (APCI+) m/z 278 (M+H)$^+$.

Example 261

N-[3-(5-methyl-6-oxo-1,6-dihydropyridin-3-yl)-4-phenoxyphenyl]methanesulfonamide

Example 261A 2-bromo-4-nitro-1-phenoxybenzene

2-Bromo-1-fluoro-4-nitrobenzene (2.5 g, 11.4 mmol), phenol (1.28 g, 13.6 mmol), and cesium carbonate (4.44 g, 13.6 mmol) were combined in dimethylsulfoxide (140 mL) and heated to 110° C. for 1 hour. The reaction mixture was partitioned between ethyl acetate and brine. The combined organics were washed with brine, dried (MgSO$_4$), filtered and concentrated to afford the title compound (3.43 g, quantitative yield).

Example 261B 3-bromo-4-phenoxyaniline

Example 261A (3.43 g, 11.7 mmol), iron powder (3.26 g, 58.4 mmol), and ammonium chloride (1.25 g, 23.4 mmol) were combined in ethanol (50 mL), tetrahydrofuran (50 mL), and water (16.7 mL), and heated at 100° C. for 2 hours. The reaction mixture was cooled to just below reflux, vacuum filtered through diatomaceous earth, the filter cake washed with warm methanol (3×35 mL), and the filtrate concentrated under reduced pressure. The residue was partitioned between saturated aqueous NaHCO$_3$ and ethyl acetate (3×125 mL). The combined organics were washed with brine, dried (MgSO$_4$), gravity filtered then concentrated to afford the title compound (2.86, 93%).

Example 261C

N-(3-bromo-4-phenoxyphenyl)methanesulfonamide

Example 261B (2.86 g, 10.8 mmol) and triethylamine (6.03 mL, 43.3 mmol) were stirred in dichloromethane (48.1 mL) at ambient temperature. Methanesulfonyl chloride (2.53 mL, 32.4 mmol) was added dropwise and the solution stirred at ambient temperature for 1 hour. The reaction mixture was concentrated under reduced pressure, dioxane (24 mL) and sodium hydroxide (10% w/v, 12 mL, 0.427 mmol) were added, and the solution was heated to 70° C. for 1 hour. The solution was neutralized to a pH of 7 with saturated aqueous NH$_4$Cl (200 mL). The aqueous phase was extracted with ethyl acetate (3×125 mL). The combined organics were washed with brine, dried (MgSO$_4$), filtered, then concentrated. The residue was purified by flash chromatography (silica gel, 0-25% ethyl acetate/hexane gradient) to afford the title compound (2.79 g, 75%).

Example 261D

N-(3-(6-fluoro-5-methylpyridin-3-yl)-4-phenoxyphenyl)methanesulfonamide

A mixture of 2-fluoro-3-methylpyridine-5-boronic acid (Combi-Blocks 0.088 g, 0.566 mmol), the product from Example 261C (0.149 g, 0.435 mmol), tetrakis(tiriphenylphosphine)palladium(0) (0.025 g, 0.022 mmol) and sodium carbonate (0.435 mL, 0.871 mmol) in toluene (2.4 mL), ethanol (0.62 mL) and water (1.24 mL) was heated by microwave at 110° C. for 30 minutes. The reaction mixture was filtered through a 0.45 um Nylon filter disk to remove solids and the filtrate was partitioned between ethyl acetate and brine. The organic layer was separated and concentrated. Purification by chromatography (silica gel, 0-60% ethyl acetate in hexane) afforded the title compound (0.133 g, 82%). MS (ESI+) m/z 373 (M+H)$^+$.

Example 261E

N-[3-(5-methyl-6-oxo-1,6-dihydropyridin-3-yl)-4-phenoxyphenyl]methanesulfonamide The product from Example 261D (0.12 g, 0.322 mmol) and sodium hydroxide (1M, 6.0 mL, 6.00 mmol) were combined in dioxane (1.611 mL) and heated at 140° C. for 3 hours. The reaction mixture was partitioned into ethyl acetate and water adjusting the pH to 6. The ethyl acetate layer was washed with brine, dried (Na$_2$SO$_4$), filtered and concentrated. Purification by reverse phase HPLC (C18, 0-100% CH$_3$CN/water (0.1% TFA)) afforded the title compound (0.027 g, 22%). $^1$H NMR (300 MHz, DMSO-$d_6$) δ 11.60 (s, 1H) 9.70 (s, 1H) 7.48 (s, 1H) 7.36 (s, 1H) 7.31 (t, J=7.93 Hz, 2H) 7.25 (d, J=2.38 Hz, 1H) 7.14-7.20 (m, 1H) 7.04 (t, J=7.34 Hz, 1H) 6.99 (d, J=8.73 Hz, 1H) 6.88 (d, J=7.93 Hz, 2H) 3.02 (s, 3H) 1.95 (s, 3H). MS (ESI+) m/z 371 (M+H)$^+$.

Example 262

N-[3-(5-methyl-6-oxo-1,6-dihydropyridin-3-yl)-4-phenoxyphenyl]acetamide

Example 262A 3-(6-fluoro-5-methylpyridin-3-yl)-4-phenoxyaniline

The product from Example 261B (0.792 g, 3.0 mmol), 2-fluoro-3-methylpyridine-5-boronic acid (Combi-Blocks 0.604 g, 3.9 mmol), tetrakis(triphenylphosphine)palladium (0) (0.173 g, 0.15 mmol) and sodium carbonate (4.50 mL, 9.0 mmol) were combined in toluene (10 mL), ethanol (2.5 mL) and water (2.5 mL), sparged with nitrogen for 10 minutes and heated by microwave at 120° C. for 60 minutes. The reaction mixture was partitioned between ethyl acetate and brine. The organic layer was separated, dried ($Na_2SO_4$), filtered and concentrated. Purification by chromatography (silica gel, 0-60% ethyl acetate in hexane) afforded the title compound (0.742 g, 84%).

Example 262B

N-(3-(6-fluoro-5-methylpyridin-3-yl)-4-phenoxyphenyl)acetamide

The product from Example 262A (0.059 g, 0.2 mmol) in acetic anhydride (0.5 mL) was heated by microwave at 100° C. for 20 minutes and concentrated. Purification by chromatography (silica gel, 0-4% methanol in dichloromethane) afforded the title compound (0.050 g, 72%).

Example 262C

N-[3-(5-methyl-6-oxo-1,6-dihydropyridin-3-yl)-4-phenoxyphenyl]acetamide

The product from Example 262B (0.045 g, 0.134 mmol) in acetic acid (1.4 mL)/water (0.35 mL) was heated at 100° C. for 16 hours and concentrated. Purification by reverse phase HPLC (C18, 0-100% $CH_3CN$/water (0.1% TFA)) afforded the title compound (0.030 g, 66%). $^1$H NMR (300 MHz, DMSO-$d_6$) δ 11.56 (s, 1H) 10.01 (s, 1H) 7.67 (d, J=2.78 Hz, 1H) 7.52 (dd, J=8.73, 2.78 Hz, 1H) 7.44-7.48 (m, J=1.59 Hz, 1H) 7.26-7.35 (m, 3H) 7.02 (t, J=7.34 Hz, 1H) 6.96 (d, J=8.73 Hz, 1H) 6.84 (d, J=7.54 Hz, 2H) 2.05 (s, 3H) 1.95 (s, 3H). MS (ESI+) m/z 335 (M+H)$^+$.

Example 263

N-[4-(2,4-difluorophenoxy)-3-(5-methyl-6-oxo-1,6-dihydropyridin-3-yl)phenyl]methanesulfonamide

Example 263A 2-bromo-1-(2,4-difluorophenoxy)-4-nitrobenzene

Example 263A was prepared according to the procedure used for the preparation of Example 9B, substituting 2-bromo-1-fluoro-4-nitrobenzene for Example 9A, and substituting 2,4-difluorophenol for phenol, respectively, to provide the title compound.

Example 263B 3-bromo-4-(2,4-difluorophenoxy)aniline

Example 263B was prepared according to the procedure used for the preparation of Example 234B, substituting Example 263A for Example 234A, to provide the title compound.

Example 263C 4-(2,4-difluorophenoxy)-3-(6-fluoro-5-methylpyridin-3-yl)aniline Example 263C was prepared according to the procedure used for the preparation of Example 9A, substituting Example 263B for Example 1A, and substituting 6-fluoro-5-methylpyridin-3-ylboronic acid for 2-fluoro-5-nitrophenylboronic acid, respectively, to provide the title compound.

Example 263D

N-(4-(2,4-difluorophenoxy)-3-(6-fluoro-5-methylpyridin-3-yl)phenyl)methanesulfonamide Example 263C was prepared according to the procedure used for the preparation of Example 22, substituting Example 263C for Example 20C, to provide the title compound.

Example 263E

N-[4-(2,4-difluorophenoxy)-3-(5-methyl-6-oxo-1,6-dihydropyridin-3-yl)phenyl]methanesulfonamide Example 263E was prepared according to the procedure used for the preparation of Example 55, substituting Example 263D for Example 54B, to provide the title compound. $^1$H NMR (500 MHz, DMSO-$d_6$) δ 11.63 (br s, 1H), 9.68 (s, 1H), 7.51-7.53 (m, 1H), 7.40-7.46 (m, 2H), 7.24 (d, J=2.75 Hz, 1H), 7.01-7.15 (m, 3H), 6.89 (d, J=8.54 Hz, 1H), 3.01 (s, 3H), 1.99 (s, 3H). MS (DCI+) m/z 407.0 (M+H)$^+$.

Example 264

N-[4-(2,4-difluorophenoxy)-3-(5-methyl-6-oxo-1,6-dihydropyridin-3-yl)phenyl]ethanesulfonamide

Example 264A

N-(4-(2,4-difluorophenoxy)-3-(6-fluoro-5-methylpyridin-3-yl)phenyl)ethanesulfonamide Example 264A was prepared according to the procedure used for the preparation of Example 22, substituting Example 263C for Example 20C, and substituting ethanesulfonyl chloride for methanesulfonyl chloride, respectively, to provide the title compound.

Example 264B

N-[4-(2,4-difluorophenoxy)-3-(5-methyl-6-oxo-1,6-dihydropyridin-3-yl)phenyl]ethanesulfonamide Example 264B was prepared according to the procedure used for the preparation of Example 55, substituting Example 264A for Example 54B, to provide the title compound. $^1$H NMR (500 MHz, DMSO-$d_6$) δ 11.67 (br s, 1H), 9.75 (s, 1H), 7.49-7.51 (m, 1H), 7.41-7.46 (m, 1H), 7.38 (d, J=2.44 Hz, 1H), 7.23 (d, J=2.44 Hz, 1H), 7.14 (dd, J=8.85, 2.75 Hz, 1H), 7.01-7.10 (m, 2H), 6.88 (d, J=8.85 Hz, 1H), 3.11 (q, J=7.32 Hz, 2H), 1.21 (t, J=7.32 Hz, 3H). MS (DCI+) m/z 421.0 (M+H)$^+$.

Example 265

N-[4-(2,4-difluorophenoxy)-3-(5-methyl-6-oxo-1,6-dihydropyridin-3-yl)phenyl]acetamide Example 265 was prepared according to the procedure used for the preparation of Example 55, substituting Example 263C for Example 54B, to provide the title compound. $^1$H NMR (500 MHz, DMSO-$d_6$) δ 11.63 (br s, 1H), 10.00 (s, 1H), 7.65 (d, J=2.44 Hz, 1H), 7.46-7.50 (m, 2H), 7.39-7.44 (m, 1H), 7.36 (d, J=2.44 Hz, 1H), 7.01-7.04 (m, 2H), 6.87 (d, J=8.85 Hz, 1H), 2.04 (s, 3H), 1.98 (s, 3H). MS (DCI+) m/z 371.1 (M+H)$^+$.

Example 266

N-{4-[(4,4-difluorocyclohexyl)oxy]-3-(5-methyl-6-oxo-1,6-dihydropyridin-3-yl)phenyl}methanesulfonamide Example 266A 2-bromo-1-(4,4-difluorocyclohexyloxy)-4-nitrobenzene Example 266A was prepared according to the procedure used for the preparation of Example 247A, substituting 2-bromo-1-fluoro-4-nitrobenzene for Example 225A, and substituting 4,4-difluorocyclohexanol for cyclohexanol, respectively, to provide the title compound.

Example 266B 3-bromo-4-(4,4-difluorocyclohexyloxy)aniline

Example 266B was prepared according to the procedure used for the preparation of Example 10, substituting Example 266A for Example 9B, and substituting platinum on carbon for palladium on carbon, respectively, to provide the title compound.

Example 266C 4-(4,4-difluorocyclohexyloxy)-3-(6-fluoro-5-methylpyridin-3-yl)aniline Example 266C was prepared according to the procedure used for the preparation of Example 9A, substituting Example 266B for Example 1A, and substituting 6-fluoro-5-methylpyridin-3-ylboronic acid for 2-fluoro-5-nitrophenylboronic acid, respectively, to provide the title compound.

Example 266D

N-(4-(4,4-difluorocyclohexyloxy)-3-(6-fluoro-5-methylpyridin-3-yl)phenyl)methanesulfonamide Example 266D was prepared according to the procedure used for the preparation of Example 22, substituting Example 266C for Example 20C, to provide the title compound.

Example 266E

N-{4-[(4,4-difluorocyclohexyl)oxy]-3-(5-methyl-6-oxo-1,6-dihydropyridin-3-yl)phenyl}methanesulfonamide Example 266E was prepared according to the procedure used for the preparation of Example 55, substituting Example 266D for Example 54B, to provide the title compound. $^1$H NMR (300 MHz, DMSO-$d_6$) δ 11.63 (bs, 1H), 9.42 (s, 1H), 7.52 (dd, J=2.6, 1.1 Hz, 1H), 7.34 (d, J=2.2 Hz, 1H), 7.25 7.00 (m, 3H), 4.57 (d, J=3.3 Hz, 1H), 2.94 (s, 3H), 2.00 (s, 3H), 1.98-1.74 (m, 8H). MS (ESI+) m/z 413.1 (M+H)$^+$.

Example 267

N-{4-[(4,4-difluorocyclohexyl)oxy]-3-(5-methyl-6-oxo-1,6-dihydropyridin-3-yl)phenyl}ethanesulfonamide Example 267A N-(4-(4,4-difluorocyclohexyloxy)-3-(6-fluoro-5-methylpyridin-3-yl)phenyl)ethanesulfonamide Example 267A was prepared according to the procedure used for the preparation of Example 22, substituting Example 266C for Example 20C, and substituting ethanesulfonyl chloride for methanesulfonyl chloride, respectively, to provide the title compound.

Example 267B

N-{4-[(4,4-difluorocyclohexyl)oxy]-3-(5-methyl-6-oxo-1,6-dihydropyridin-3-yl)phenyl}ethanesulfonamide Example 267B was prepared according to the procedure used for the preparation of Example 55, substituting Example 267A for Example 54B, to provide the title compound. $^1$H NMR (300 MHz, DMSO-$d_6$) δ 11.62 (bs, 1H), 9.51 (s, 1H), 7.50 (dd, J=2.5, 1.1 Hz, 1H), 7.33 (d, J=2.1 Hz, 1H), 7.12 (s, 3H), 4.56 (d, J=3.2 Hz, 1H), 3.04 (q, J=7.4 Hz, 2H), 2.00 (s, 3H), 1.95 1.70 (m, 8H), 1.20 (t, J=7.3 Hz, 3H). MS (ESI+) m/z 427.1 (M+H)$^+$.

Example 268

N-{4-(2,4-difluorophenoxy)-3-[1-methyl-6-oxo-4-(trifluoromethyl)-1,6-dihydropyridin-3-yl]phenyl}ethanesulfonamide Example 268 was prepared according to the procedure used for the preparation of Example 22, substituting ethanesulfonyl chloride for methanesulfonyl chloride, and substituting Example 5E for Example 20C, respectively, to provide the title compound. $^1$H NMR (300 MHz, DMSO-$d_6$) δ1H, 9.82 (s, 1H), 7.93 (s, 1H), 7.46-7.34 (m, 1H), 7.34-7.12 (m, 2H), 7.13-6.95 (m, 2H), 6.85 (d, J=8.8 Hz, 2H), 3.47 (s, 3H), 3.06 (q, J=7.4 Hz, 2H), 1.19 (t, J=7.3 Hz, 3H). MS (ESI+) m/z 489.1 (M+H)$^+$.

Example 269

N-[3-(4-chloro-1-methyl-6-oxo-1,6-dihydropyridin-3-yl)-4-(2,4-difluorophenoxy)phenyl]methanesulfonamide

Example 269A 5-bromo-4-chloropyridin-2-ol

5-Bromo-4-chloropyridin-2-amine (2.01 g, 9.69 mmol) was dissolved in 75% (v/v) sulfuric acid (40.2 ml, 566 mmol) and then chilled in an ice bath. Sodium nitrite (2.21 g, 32.0 mmol) dissolved in water (20.1 ml, 1116 mmol) was added dropwise and the reaction mixture was then stirred for 3 hours. The mixture was concentrated under reduced pressure and aqueous ammonia (15 mL) was added dropwise. The resulting white precipitate was collected via vacuum filtration and the filter cake washed with cold water (100 mL) then dried in a vacuum oven for 24 hours to give 1.94 g (95%) of the title compound.

Example 269B 5-bromo-4-chloro-1-methylpyridin-2(1H)-one

Example 269B was prepared according to the procedure used for the preparation of Example 1A, substituting Example 269A for 6-chloropyridazin-3(2H)-one, to provide the title compound.

Example 269C 5-(5-amino-2-(2,4-difluorophenoxy)phenyl)-4-chloro-1-methylpyridin-2(1H)-one Example 269C was prepared according to the procedure used for the preparation of Example 1B, substituting Example 5D for 2-phenoxyphenylboronic acid, and Example 269B for Example 1A, respectively, to provide the title compound.

Example 269D

N-[3-(4-chloro-1-methyl-6-oxo-1,6-dihydropyridin-3-yl)-4-(2,4-difluorophenoxy)phenyl]methanesulfonamide Example 269D was prepared according to the procedure used for the preparation of Example 22, substituting Example 269C for Example 20C, to provide the title compound. $^1$H NMR (300 MHz, DMSO-d$_6$) δ 9.82-9.74 (m, 1H), 7.93 (s, 1H), 7.48-7.35 (m, 1H), 7.27-7.01 (m, 4H), 6.90 (d, J=8.8 Hz, 1H), 6.65-6.44 (m, 1H), 3.46-3.41 (m, 3H), 3.01 (s, 3H). MS (ESI+) m/z 441.1 (M+H)$^+$.

Example 270

N-[4-(2,4-difluorophenoxy)-3-(4-methoxy-1-methyl-6-oxo-1,6-dihydropyridin-3-yl)phenyl]methanesulfonamide

Example 270A 5-bromo-4-methoxy-1-methylpyridin-2(1H)-one

Example 270A was prepared according to the procedure used for the preparation of Example 18C, substituting Example 269B for Example 18B, to provide the title compound.

Example 270B 5-(5-amino-2-(2,4-difluorophenoxy)phenyl)-4-methoxy-1-methylpyridin-2(1H)-one Example 270B was prepared according to the procedure used for the preparation of Example 1B, substituting Example 5D for 2-phenoxyphenylboronic acid, and Example 270A for Example 1A, respectively, to provide the title compound.

Example 270C

N-[4-(2,4-difluorophenoxy)-3-(4-methoxy-1-methyl-6-oxo-1,6-dihydropyridin-3-yl)phenyl]methanesulfonamide Example 270C was prepared according to the procedure used for the preparation of Example 22, substituting 270B for Example 20C. $^1$H NMR (300 MHz, DMSO-d$_6$) δ 9.69 (s, 1H), 7.62 (s, 1H), 7.43-7.32 (m, 1H), 7.18 (dd, J=8.7, 2.7 Hz, 1H), 7.15-6.97 (m, 3H), 6.88 (d, J=8.7 Hz, 1H), 5.82 (s, 1H), 3.60 (s, 3H), 3.36 (s, 3H), 3.01 (s, 3H).
MS (ESI+) m/z 437.1 (M+H)$^+$.

Example 271

N-[4-(2,4-difluorophenoxy)-3-(4-methoxy-1-methyl-6-oxo-1,6-dihydropyridin-3-yl)phenyl]ethanesulfonamide Example 271 was prepared according to the procedure used for the preparation of Example 22, substituting Example 270B for Example 20C and substituting ethanesulfonyl chloride for methanesulfonyl chloride, respectively to provide the title compound. $^1$H NMR (300 MHz, DMSO-d$_6$) δ 9.76 (s, 1H), 7.62 (s, 1H), 7.43-7.32 (m, 1H), 7.18 (dd, J=8.7, 2.7 Hz, 1H), 7.14-6.96 (m, 3H), 6.87 (d, J=8.7 Hz, 1H), 5.81 (s, 1H), 3.60 (s, 3H), 3.36 (s, 3H), 3.10 (q, J=7.3 Hz, 2H), 1.22 (t, J=7.3 Hz, 3H). MS (ESI+) m/z 451.1 (M+H)$^+$.

Example 272

N-[4-(2,4-difluorophenoxy)-3-{4-[4-(hydroxymethyl)phenyl]-1-methyl-6-oxo-1,6-dihydropyridin-3-yl}phenyl]methanesulfonamide Example 272 was prepared according to the procedure used for the preparation of Example 1B, substituting 4-(hydroxymethyl)phenylboronic acid for 2-phenoxyphenylboronic acid, and Example 269D for Example 1A, respectively.

The reaction mixture was heated at 140° C., instead of 120° C., to provide the title compound. ¹H NMR (300 MHz, DMSO-d₆) δ 9.62 (s, 1H), 7.87-7.76 (m, 1H), 7.43-7.29 (m, 1H), 7.21-6.94 (m, 6H), 6.96-6.85 (m, 1H), 6.63-6.54 (m, 1H), 6.45-6.25 (m, 1H), 6.14 (td, J=9.2, 5.6 Hz, 1H), 4.48-4.42 (m, 2H), 3.49 (s, 3H), 2.87-2.76 (m, 3H). MS (ESI+) m/z 513.1 (M+H)⁺.

Example 273

N-[4-(2,4-difluorophenoxy)-3-(1-methyl-4-{4-[(4-methylpiperazin-1-yl)methyl]phenyl}-6-oxo-1,6-dihydropyridin-3-yl)phenyl]methanesulfonamide Example 273 was prepared according to the procedure used for the preparation of Example 1B, substituting 1-methyl-4-(4-(4,4,5,5-tetramethyl-1,3,2-dioxaborolan-2-yl)benzyl)piperazine for 2-phenoxyphenylboronic acid, and substituting Example 269D for Example 1A, respectively. The reaction mixture was heated at 140° C., instead of 120° C., to provide the title compound. ¹H NMR (300 MHz, DMSO-d₆) δ 9.66 (s, 1H), 7.83 (s, 1H), 7.41-7.28 (m, 1H), 7.20 (d, J=8.3 Hz, 2H), 7.13 (d, J=2.8 Hz, 1H), 7.09 (d, J=8.7 Hz, 2H), 7.06 (dd, J=8.9, 3.0 Hz, 1H), 6.99-6.87 (m, 1H), 6.57 (d, J=8.7 Hz, 1H), 6.37 (s, 1H), 6.31 (td, J=9.2, 5.8 Hz, 1H), 3.58 (m, 2H), 3.49 (s, 3H), 3.45-3.21 (m, 4H), 2.87 (s, 3H), 2.74 (s, 3H), 2.43-2.27 (m, 4H). MS (ESI+) m/z 595.1 (M+H)⁺

Example 274

N-[4-(2,4-difluorophenoxy)-3-{1-methyl-4-[4-(morpholin-4-yl)phenyl]-6-oxo-1,6-dihydropyridin-3-yl]phenyl}methanesulfonamide Example 274 was prepared according to the procedure used for the preparation of Example 1B, substituting 4-morpholinophenyl boronic acid for 2-phenoxyphenylboronic acid, and substituting Example 269D for Example 1A, respectively. The reaction mixture was heated at 140° C. instead of 120° C., to provide the title compound. ¹H NMR (300 MHz, DMSO-d₆) δ 9.62 (s, 1H), 7.75 (s, 1H), 7.40-7.28 (m, 1H), 7.13 (d, J=2.7 Hz, 1H), 7.07 (dd, J=8.7, 2.7 Hz, 1H), 6.97 (s, 1H), 6.96-6.86 (m, 2H), 6.88-6.74 (m, 2H), 6.62 (d, J=8.7 Hz, 1H), 6.34-6.24 (m, 2H), 3.75-3.66 (m, 4H), 3.47 (s, 3H), 3.13-3.06 (m, 4H), 2.86 (s, 3H). MS (ESI+) m/z 568.2 (M+H)⁺

Example 275

5-[2-(cyclopropylmethoxy)-5-(ethylsulfonyl)phenyl]-4-methoxy-1-methylpyridin-2(1H)-one Example 275A (3-bromo-4-fluorophenyl)(ethyl)sulfane A mixture of 3-bromo-4-fluorobenzenethiol (3.89 g, 18.8 mmol) and 5.0 M sodium hydroxide (3.95 mL, 19.7 mmol) in methanol (50 mL) was stirred at 0° C. for 10 minutes. To this solution was added iodoethane (1.80 mL, 22.5 mmol). The reaction mixture was stirred at ambient temperature for 6 hours. The solvent was removed under reduced pressure, and the residue was partitioned between water and ethyl acetate. The aqueous layer was extracted with additional ethyl acetate three times. The combined organic layers were washed with brine, dried over MgSO₄, filtered, and concentrated to provide the title compound (4.35 g, 98% yield).

Example 275B 2-bromo-4-(ethylsulfonyl)-1-fluorobenzene

Example 275A (4.4 g, 18.7 mmol) in dichloromethane (300 mL) was treated with mCPBA (10.2 g, 41.2 mmol). The reaction was stirred at ambient temperature for 6 hours. The solvent was removed under reduced pressure, and the residue was taken up into ethyl acetate and was washed with saturated aqueous NaHCO₃ solution (150 mL). The aqueous layer was then extracted with additional ethyl acetate three times. The combined organic layers were washed with brine, dried over MgSO₄, filtered, and concentrated. The residue was purified by flash chromatography (silica gel, 15% ethyl acetate in hexane to afford the title compound (4.4 g, 88% yield).

Example 275C 2-bromo-1-(cyclopropylmethoxy)-4-(ethylsulfonyl)benzene

Example 275C was prepared according to the procedure used for the preparation of Example 247A, substituting Example 275B for Example 225A, and substituting cyclopropylmethanol for cyclohexanol, respectively, to provide the title compound.

Example 275D 2-(2-(cyclopropylmethoxy)-5-(ethylsulfonyl)phenyl)-4,4,5,5-tetramethyl-1,3,2-dioxaborolane Example 275D was prepared according to the procedure used for the preparation of Example 5D, substituting Example 275C for Example 5C, to provide the title compound.

Example 275E

5-[2-(cyclopropylmethoxy)-5-(ethylsulfonyl)phenyl]-4-methoxy-1-methylpyridin-2(1H)-one Example 275E was prepared according to the procedure used for the preparation of Example 1B, substituting Example 275D for 2-phenoxyphenylboronic acid, and substituting Example 270A for Example 1A, respectively, to provide the title compound. ¹H NMR (300 MHz, DMSO-d₆) δ 7.79 (dd, J=8.6, 2.4 Hz, 1H), 7.61 (d, J=2.4 Hz, 2H), 7.23 (d, J=8.7 Hz, 1H), 5.89 (s, 1H), 3.93 (d, J=6.7 Hz, 2H), 3.67 (s, 3H), 3.39 (s, 3H), 3.25 (q, J=7.3 Hz, 2H), 1.20-1.06 (m, 4H), 0.61-0.44 (m, 2H), 0.37-0.24 (m, 2H). MS (ESI+) m/z 378.1 (M+H)⁺.

Example 276

5-{2-(2,4-difluorophenoxy)-5-[(methylsulfonyl)amino]phenyl}-N,1-dimethyl-2-oxo-1,2-dihydropyridine-4-carboxamide Example 276A methyl 5-bromo-1-methyl-2-oxo-1,2-dihydropyridine-4-carboxylate Example 276A was prepared according to the procedure used for the preparation of Example 1A, substituting methyl 5-bromo-2-hydroxyisonicotinate for 6-chloropyridazin-3 (2H)-one, to provide the title compound.

Example 276B

Methyl 5-(5-amino-2-(2,4-difluorophenoxy)phenyl)-1-methyl-2-oxo-1,2-dihydropyridine-4-carboxylate Example 276B was prepared according to the procedure used for the preparation of Example 1B, substituting Example 5D for 2-phenoxyphenylboronic acid, and Example 276A for Example 1A, respectively, to provide the title compound.

Example 276C 5-(2-(2,4-difluorophenoxy)-5-(methylsulfonamido)phenyl)-1-methyl-2-oxo-1,2-dihydropyridine-4-carboxylic acid Example 276C was prepared according to the procedure used for the preparation of Example 22, substituting Example 276B for Example 20C to provide the title compound.

Example 276D

5-{2-(2,4-difluorophenoxy)-5-[(methylsulfonyl)amino]phenyl}-N,1-dimethyl-2-oxo-1,2-dihydropyridine-4-carboxamide Example 276C (23 mg, 0.051 mmol) and oxalyl chloride (8.94 µL, 0.102 mmol) were combined in dichloromethane (5 mL) and 1 drop of dimethylformamide. After stirring at ambient temperature for 2 hours, the solution was concentrated under reduced pressure. The residue was treated with 2.0 N methylamine in tetrahydrofuran (0.383 mL, 0.766 mmol) and stirred at ambient temperature for 1 hour. To this mixture was added 1:1 brine/water (20 mL) and the mixture was extracted with ethyl acetate. The combined organics were washed with brine, dried (MgSO$_4$), filtered, and concentrated. Purification by reverse phase chromatography (C18, CH$_3$CN/water 0.1% TFA) afforded 18.8 mg (79%) of the title compound. $^1$H NMR (300 MHz, DMSO-d$_6$) δ 9.67 (s, 1H), 8.39-8.32 (m, 1H), 7.78 (s, 1H), 7.46-7.34 (m, 1H), 7.17-7.00 (m, 4H), 6.73 (d, J=8.6 Hz, 1H), 6.45 (s, 1H), 3.47 (s, 3H), 2.99 (s, 3H). MS (ESI+) m/z 464.1 (M+H)$^+$.

Example 277

N-[4-(2,4-difluorophenoxy)-3-(4-ethoxy-1-methyl-6-oxo-1,6-dihydropyridin-3-yl)phenyl]methanesulfonamide Example 277 was prepared according to the procedure used for the preparation of Example 18C, substituting Example 269D for Example 18B, and substituting ethanol for methanol, respectively. Purification by flash chromatography (SiO$_2$, 0-2% methanol/dichloromethane gradient) afforded 25 mg (49%) of the title compound. $^1$H NMR (300 MHz, DMSO-d$_6$) δ 9.69 (s, 1H), 7.61 (s, 1H), 7.43-7.31 (m, 1H), 7.21-7.11 (m, 2H), 7.08-6.96 (m, 2H), 6.90 (d, J=8.6 Hz, 1H), 5.79 (s, 1H), 3.92 (q, J=7.0 Hz, 2H), 3.35 (s, 3H), 3.00 (s, 3H), 1.14 (t, J=6.9 Hz, 3H). MS (ESI+) m/z 451.1 (M+H)$^+$

Example 278

N-[4-(2,4-difluorophenoxy)-3-{4-[4-(hydroxymethyl)phenyl]-1-methyl-6-oxo-1,6-dihydropyridin-3-yl]phenyl}ethanesulfonamide

Example 278A

N-(3-(4-chloro-1-methyl-6-oxo-1,6-dihydropyridin-3-yl)-4-(2,4-difluorophenoxy)phenyl)ethanesulfonamide Example 278A was prepared according to the procedure used for the preparation of Example 22, substituting ethanesulfonyl chloride for methanesulfonyl chloride, and Example 269C for Example 20C, respectively to provide the title compound.

Example 278B

N-[4-(2,4-difluorophenoxy)-3-{4-[4-(hydroxymethyl)phenyl]-1-methyl-6-oxo-1,6-dihydropyridin-3-yl]phenyl}ethanesulfonamide Example 278B was prepared according to the procedure used for the preparation of Example 1B, substituting 4-(hydroxymethyl)phenylboronic acid for 2-phenoxyphenylboronic acid, and substituting Example 278A for Example 1A, respectively. The reaction mixture was heated at 140° C. instead of 120° C., to provide the title compound. $^1$H NMR (300 MHz, DMSO-d$_6$) δ 9.72-9.65 (m, 1H), 7.82-7.76 (m, 1H), 7.43-7.29 (m, 1H), 7.21-7.11 (m, 2H), 7.12-6.82 (m, 5H), 6.59 (d, J=8.6 Hz, 1H), 6.44-6.34 (m, 1H), 6.25 (td, J=9.3, −5.6 Hz, 1H), 4.49-4.42 (m, 2H), 3.49 (s, 3H), 2.88 (q, J=7.3 Hz, 2H), 1.13 (t, J=7.3 Hz, 3H). MS (ESI+) m/z 527.1 (M+H)$^+$.

Example 279

N-[4-(2,4-difluorophenoxy)-3-(1-methyl-4-{4-[(4-methylpiperazin-1-yl)methyl]phenyl}-6-oxo-1,6-dihydropyridin-3-yl)phenyl]ethanesulfonamide Example 279 was prepared according to the procedure used for the preparation of Example 1B, substituting 1-methyl-4-(4-(4,4,5,5-tetramethyl-1,3,2-dioxaborolan-2-yl)benzyl)piperazine for 2-phenoxyphenylboronic acid, and substituting Example 278A for Example 1A, respectively. The reaction mixture was heated at 140° C. instead of 120° C., to provide the title compound. $^1$H NMR (400 MHz, pyridine-d$_5$) δ 7.51 (d, J=1.6 Hz, 1H) 7.43 (dd, J=8.7, 2.7 Hz, 1H), 7.33-7.25 (m, 4H), 7.05 (ddd, J=11.0, 8.3, 2.8 Hz, 1H), 6.90-6.81 (m, 1H), 6.73 (t, J=4.4 Hz, 2H), 6.68 (td, J=5.5 Hz, 2H), 3.51 (s, 3H), 3.47 (s, 2H), 3.18 (q, J=7.3 Hz, 2H), 2.72 (m, 4H), 2.59 (m, 4H), 2.42 (s, 3H), 1.35 (t, J=7.3 Hz, 3H). MS (ESI+) m/z 609.1 (M+H)$^+$.

Example 280

N-[4-(2,4-difluorophenoxy)-3-(4-{4-[(dimethylamino)methyl]phenyl}-1-methyl-6-oxo-1,6-dihydropyridin-3-yl)phenyl]ethanesulfonamide Example 280 was prepared according to the procedure used for the preparation of Example 1B, substituting 4-((dimethylamino)methyl)phenylboronic acid for 2-phenoxyphenylboronic acid, and substituting Example 278A for Example 1A, respectively. The reaction mixture was heated at 140° C. instead of 120° C., to provide the title compound. $^1$H NMR (300 MHz, DMSO-$d_6$) δ 9.68 (s, 1H), 9.54 (bs, 1H), 7.81 (s, 1H), 7.40-7.26 (m, 3H), 7.21-7.14 (m, 2H), 7.12 (d, J=2.6 Hz, 1H), 7.04 (dd, J=8.7, 2.7 Hz, 1H), 6.97-6.86 (m, 1H), 6.55 (d, J=8.7 Hz, 1H), 6.48-6.31 (m, 2H), 4.25-4.18 (m, 2H), 3.47 (s, 3H), 2.96 (q, J=7.3 Hz, 2H), 2.69 (d, J=4.3 Hz, 6H), 1.14 (t, J=7.3 Hz, 3H). MS (ESI+) m/z 554.0 (M+H)$^+$.

Example 281

3-chloro-1-methyl-5-(2-phenoxyphenyl)pyridin-2(1H)-one

Example 281A 5-bromo-3-chloro-1-methylpyridin-2(1H)-one

Example 281A was prepared according to the procedure used for the preparation of Example 1A, substituting 5-bromo-3-chloropyridin-2(1H)-one for 6-chloropyridazin-3(2H)-one, to provide the title compound.

Example 281B 3-chloro-5-(2-phenoxyphenyl)pyridin-2(1H)-one

Example 281B was prepared according to the procedure used for the preparation of Example 1B, substituting Example 281A for Example 1A to provide the title compound. $^1$H NMR (300 MHz, DMSO-$d_6$) δ 7.98 (d, J=2.4 Hz, 1H), 7.93 (d, J=2.4 Hz, 1H), 7.51 (dd, J=7.6, 1.8 Hz, 1H), 7.43-7.29 (m, 3H), 7.25 (td, J=7.5, 1.3 Hz, 1H), 7.15-7.05 (m, 1H), 7.01-6.91 (m, 3H), 3.54 (s, 3H). MS (ESI+) m/z 312.3 (M+H)$^+$.

Example 282

N-[3-(5-chloro-1-methyl-6-oxo-1,6-dihydropyridin-3-yl)-4-(2,4-difluorophenoxy)phenyl]methanesulfonamide Example 282A 5-(5-amino-2-(2,4-difluorophenoxy)phenyl)-3-chloro-1-methylpyridin-2(1H)-one Example 282A was prepared according to the procedure used for the preparation of Example 1B, substituting Example 5D for 2-phenoxyphenylboronic acid, and substituting Example 281A for Example 1A, respectively, to provide the title compound.

Example 282B

N-(3-(5-chloro-1-methyl-6-oxo-1,6-dihydropyridin-3-yl)-4-(2,4-difluorophenoxy)phenyl)methanesulfonamide Example 282B was prepared according to the procedure used for the preparation of Example 22, substituting Example 282A for Example 20C, to provide the title compound. $^1$H NMR (300 MHz, DMSO-$d_6$) δ 9.70 (s, 1H), 7.97 (d, J=2.4 Hz, 1H), 7.92 (d, J=2.4 Hz, 1H), 7.50-7.39 (m, 1H), 7.31-7.12 (m, 3H), 7.13-7.02 (m, 1H), 6.88 (d, J=8.7 Hz, 1H), 3.56 (s, 3H), 3.02 (s, 3H). MS (ESI+) m/z 441.1 (M+H)$^+$.

Example 283

N-[3-(5-chloro-1-methyl-6-oxo-1,6-dihydropyridin-3-yl)-4-(2,4-difluorophenoxy)phenyl]ethanesulfonamide Example 283 was prepared according to the procedure used for the preparation of Example 22, substituting Example 282A for Example 20C and substituting ethanesulfonyl chloride for methanesulfonyl chloride, respectively, to provide the title compound. $^1$H NMR (300 MHz, DMSO-$d_6$) δ 9.78 (s, 1H), 7.98-7.88 (m, 2H), 7.50-7.39 (m, 1H), 7.28-7.12 (m, 3H), 7.13-7.02 (m, 1H), 6.87 (d, J=8.7 Hz, 1H), 3.56 (s, 3H), 3.12 (q, J=7.3 Hz, 2H), 1.22 (t, J=7.3 Hz, 3H). MS (ESI+) m/z 455.1 (M+H)$^+$.

Example 284

N-[4-(2,4-difluorophenoxy)-3-{1-methyl-4-[4-(morpholin-4-yl)phenyl]-6-oxo-1,6-dihydropyridin-3-yl]phenyl}ethanesulfonamide Example 284 was prepared according to the procedure used for the preparation of Example 1B, substituting 4-morpholinophenyl boronic acid for 2-phenoxyphenylboronic acid, and substituting Example 278A for Example 1A, respectively. The reaction mixture was heated at 140° C. instead of 120° C., to provide the title compound. $^1$H NMR (300 MHz, DMSO-$d_6$) δ 9.67 (s, 1H), 7.75 (s, 1H), 7.40-7.28 (m, 1H), 7.13 (d, J=2.7 Hz, 1H), 7.07 (dd, J=8.7, 2.7 Hz, 1H), 6.97 (s, 1H), 6.96-6.86 (m, 2H), 6.88-6.74 (m, 2H), 6.62 (d, J=8.7 Hz, 1H), 6.34-6.24 (m, 2H), 3.75-3.66 (m, 4H), 3.46 (s, 3H), 3.13-3.06 (m, 4H), 2.88 (q, J=7.46 Hz, 2H), 1.12 (t, J=7.46 Hz, 3H). MS (ESI+) m/z 582.2 (M+H)$^+$.

Example 285

N-[4-(2,4-difluorophenoxy)-3-(4-ethoxy-1-methyl-6-oxo-1,6-dihydropyridin-3-yl)phenyl]ethanesulfonamide A mixture of Example 278a (0.050 g, 0.110 mmol) and sodium ethoxide (0.187 g, 2.75 mmol) in ethanol (2 mL) was heated at 65° C. for 72 hours. The reaction mixture was cooled to ambient temperature and quenched with water. The mixture was extracted with ethyl acetate, and the organic layer was washed with saturated aqueous sodium chloride, dried over anhydrous magnesium sulfate, filtered, and evaporated. The residue was purified by flash chromatography (silica gel, 0-2% methanol/dichloromethan gradient) to provide the title compound (0.025 g, 49% yield). $^1$H NMR (300 MHz, DMSO-$d_6$) δ 9.75 (s, 1H), 7.60 (s, 1H), 7.36 (ddd, J=11.2, 8.7, 2.7 Hz, 1H), 7.17 (dd, J=8.7, 2.7 Hz, 1H), 7.12 (d, J=2.7 Hz, 1H), 7.05-6.94 (m, 2H), 6.88 (d, J=8.7 Hz, 1H), 5.78 (s, 1H), 3.90 (q, J=7.0 Hz, 2H), 3.34 (s, 1H), 3.10 (q, J=7.0 Hz, 2H), 1.21 (t, J=7.3 Hz, 3H), 1.13 (t, J=6.9 Hz, 3H). MS (ESI+) m/z 465.1 (M+H)$^+$.

Example 286

N-[4-(2,4-difluorophenoxy)-3-{1-methyl-4-[2-(morpholin-4-yl)ethoxy]-6-oxo-1,6-dihydropyridin-3-yl]phenyl}ethanesulfonamide To a slurry of sodium hydride (16.23 mg, 0.440 mmol) in anhydrous dioxane (2 mL) was added portion-wise 2-morpholinoethanol (0.040 mL, 0.327 mmol), and the suspension was stirred for 30 minutes. Example 278a (50 mg, 0.110 mmol) was added and the mixture was stirred for 2 hours at 75° C. The mixture was cooled to ambient temperature, cold water (10 mL) was added and the reaction mixture was extracted with ethyl acetate. The combined organic phase was washed with brine, dried (anhydrous MgSO$_4$), filtered, and concentrated under reduced pressure. Purification by reverse phase HPLC (C18, CH$_3$CN/water (0.1% TFA), 0-100%) afforded the title compound (17 mg, 28% yield). $^1$H NMR (300 MHz, DMSO-d$_6$) δ 9.81 (s, 1H), 7.65 (s, 1H), 7.39-7.31 (m, 1H), 7.21 7.10 (m, 2H), 7.04-6.91 (m, 3H), 5.93 (s, 1H), 4.26 (t, J=4.6 Hz, 2H), 4.21-3.55 (m, 6H), 3.34 (s, 3H), 3.28 2.85 (m, 6H), 1.22 (t, J=7.3 Hz, 3H). MS (ESI+) m/z 550.1 (M+H)$^+$.

Example 287

N-(3-(4-(cyclopropylmethoxy)-1-methyl-6-oxo-1,6-dihydropyridin-3-yl)-4-(2,4-difluorophenoxy)phenyl)ethanesulfonamide Example 287 was prepared according to the procedure used for the preparation of Example 286, substituting cyclopropylmethanol for 2-morpholinoethanol. $^1$H NMR (300 MHz, DMSO-d$_6$) δ 9.78 (s, 1H), 7.60 (s, 1H), 7.41-7.32 (m, 1H), 7.19 (dd, J=8.7, 2.7 Hz, 1H), 7.15 (d, J=2.7 Hz, 1H), 7.12-6.94 (m, 2H), 6.91 (d, J=8.7 Hz, 1H), 5.77 (s, 1H), 3.73 (d, J=6.8 Hz, 2H), 3.34 (s, 3H), 3.11 (q, J=7.3 Hz, 2H), 1.22 (t, J=7.3 Hz, 3H), 1.17-1.00 (m, 1H), 0.50-0.39 (m, 2H), 0.27-0.15 (m, 2H). MS (ESI+) m/z 491.0 (M+H)$^+$.

Example 288

N-(4-(2,4-difluorophenoxy)-3-(4-(2-(dimethylamino)ethoxy)-1-methyl-6-oxo-1,6-dihydropyridin-3-yl)phenyl)ethanesulfonamide Example 288 was prepared according to the procedure used for the preparation of Example 286, substituting 2-(dimethylamino)ethanol for 2-morpholinoethanol. $^1$H NMR (300 MHz, DMSO-d$_6$) δ 9.78 (s, 1H), 7.66 (s, 1H), 7.22 7.12 (m, 2H), 7.07-6.92 (m, 3H), 6.92 (s, 1H), 5.95 (s, 1H), 4.25 (t, J=4.8 Hz, 2H), 3.35 (s, 3H), 3.11 (q, J=7.3 Hz, 2H), 2.71-2.65 (m, 6H), 1.23 (t, J=7.3 Hz, 3H). MS (ESI+) m/z 508.0 (M+H)$^+$.

Example 289

N-{4-(2,4-difluorophenoxy)-3-[1-methyl-6-oxo-4-(propan-2-yloxy)-1,6-dihydropyridin-3-yl]phenyl}ethanesulfonamide Example 289 was prepared according to the procedure used for the preparation of Example 286, substituting propan-2-ol for 2-morpholinoethanol. $^1$H NMR (300 MHz, DMSO-d$_6$) δ 9.76 (s, 1H), 7.59 (s, 1H), 7.37 (ddd, J=11.4, 8.7, 2.7 Hz, 1H), 7.20 7.11 (m, 2H), 7.07-6.93 (m, 2H), 6.91 (d, J=8.5 Hz, 1H), 5.80 (s, 1H), 4.59 4.51 (m, J=6 Hz, 1H), 3.34 (s, 3H), 3.11 (q, J=7.3 Hz, 2H), 1.21 (d, J=7.3 Hz, 3H), 1.18-1.05 (d, J=6 Hz, 6H). MS (ESI+) m/z 479.0 (M+H)$^+$.

Example 290

N-{4-(2,4-difluorophenoxy)-3-[1-methyl-4-(2-methylpropoxy)-6-oxo-1,6-dihydropyridin-3-yl]phenyl}ethanesulfonamide Example 290 was prepared according to the procedure used for the preparation of Example 286, substituting 2-methylpropan-1-ol for 2-morpholinoethanol. $^1$H NMR (300 MHz, DMSO-d$_6$) δ 9.77 (s, 1H), 7.58 (s, 1H), 7.38-7.17 (m, 2H), 7.13 (d, J=2.7 Hz, 1H), 7.03-6.92 (m, 2H), 6.87 (td, J=9.1, 5.6 Hz, 1H), 5.76 (s, 1H), 3.62 (d, J=6.4 Hz, 2H), 3.33 (s, 3H), 3.07 (q, J=7.3 Hz, 2H), 1.93-1.76 (m, 1H), 1.20 (t, J=7.3 Hz, 3H), 0.81 (d, J=6.7 Hz, 6H). MS (ESI+) m/z 493.0 (M+H)$^+$.

Example 291

N-{4-(2,4-difluorophenoxy)-3-[1-methyl-6-oxo-4-(tetrahydrofuran-3-ylmethoxy)-1,6-dihydropyridin-3-yl]phenyl}ethanesulfonamide Example 291 was prepared according to the procedure used for the preparation of Example 286, substituting (tetrahydrofuran-3-yl)methanol for 2-morpholinoethanol. $^1$H NMR (300 MHz, DMSO-d$_6$) δ 9.78 (s, 1H), 7.59 (s, 1H), 7.39-7.28 (m, 1H), 7.21 (dd, J=8.7, 2.7 Hz, 1H), 7.12 (d, J=2.7 Hz, 1H), 7.03-6.84 (m, 3H), 5.82 (s, 1H), 3.89-3.74 (m, 2H), 3.65 3.53 (m, 4H), 3.33 (s, 3H), 3.09 (q, J=7.3 Hz, 2H), 2.50 (m, 1H), 1.93 1.78 (m, 1H), 1.61 1.47 (m, 1H), 1.21 (t, J=7.3 Hz, 3H). MS (ESI+) m/z 521.0 (M+H)$^+$.

Example 292

N-[4-(2,4-difluorophenoxy)-3-(1-methyl-6-oxo-4-propoxy-1,6-dihydropyridin-3-yl)phenyl]ethanesulfonamide Example 292 was prepared according to the procedure used for the preparation of Example 286, substituting propan-1-ol for 2-morpholinoethanol. $^1$H NMR (300 MHz, DMSO-d$_6$) δ 9.76 (s, 1H), 7.59 (s, 1H), 7.40-7.26 (m, 1H), 7.19 (dd, J=8.7, 2.7 Hz, 1H), 7.13 (d, J=2.7 Hz, 1H), 7.04-6.83 (m, 3H), 5.78 (s, 1H), 3.89-3.72 (t, J=7.3 Hz, 2H), 3.46 (s, 3H), 3.24-2.97 (q, J=7.3 Hz, 2H), 1.69-1.41 (sextet, J=7.3 Hz, 2H), 1.30-1.12 (t, J=7.3 Hz, 3H), 0.90-0.72 (t, J=7.3 Hz, 3H). MS (ESI+) m/z 479.0 (M+H)$^+$.

Example 293

N-{4-(2,4-difluorophenoxy)-3-[1-methyl-6-oxo-4-(2,2,2-trifluoroethoxy)-1,6-dihydropyridin-3-yl]phenyl}ethanesulfonamide Example 293 was prepared according to the procedure used for the preparation of Example 286, substituting 2,2,2-trifluoroethanol for 2-morpholinoethanol. $^1$H NMR (300 MHz, DMSO-d$_6$) δ 9.77 (s, 1H), 7.69 (s, 1H), 7.41-7.30 (m, 1H), 7.20 (dd, J=8.7, 2.7 Hz, 1H), 7.13 (d, J=2.7 Hz, 1H), 7.05-6.86 (m, 3H), 6.03 (s, 1H), 4.70 (q, J=8.8 Hz, 2H), 3.37 (s, 3H), 3.07 (q, J=7.3 Hz, 2H), 1.20 (t, J=7.3 Hz, 3H). MS (ESI+) m/z 519.0 (M+H)$^+$.

Example 294

4-{4-[(ethylsulfonyl)amino]-2-[1-methyl-6-oxo-4-(2,2,2-trifluoroethoxy)-1,6-dihydropyridin-3-yl]phenoxy}benzamide Example 294A 5-bromo-1-methyl-4-(2,2,2-trifluoroethoxy)pyridin-2(1H)-one 2,2,2-Trifluoroethanol (3.37 g, 33.7 mmol) in dioxane (40 mL) was treated with sodium hydride (1.348 g, 33.7 mmol, 60% in oil). The solution was stirred at ambient temperature for 10 minutes. To this solution was added Example 269B (2.5 g, 11.24 mmol). The reaction mixture was heated at 90° C. for three hours. The solvent was evaporated, and the residue was subjected re-dissolved in ethyl acetate, washed with water, and partitioned. The aqueous layer was extracted with additional ethyl acetate three times. The combined organic layers were washed with saturated aqueous sodium chloride, dried over anhydrous magnesium sulfate, filtered and concentrated. The residue was purified by flash column chromatography on silica gel eluting with 60% ethyl acetate in hexanes to afford the title compound (3.06 g, 10.70 mmol, 95% yield).

Example 294B 4-(2-bromo-4-nitrophenoxy)benzonitrile

A mixture of 2-bromo-1-fluoro-4-nitrobenzene (2.20 g, 10 mmol), 4-hydroxybenzonitrile (1.31 g, 11 mmol), and cesium carbonate (3.58 g, 11 mmol) in dimethyl sulfoxide (20 mL) was heated at 90° C. for 2 hours. After cooling, the reaction mixture was partitioned between water and ethyl acetate. The aqueous layer was extracted three times with ethyl acetate. The combined organic layers were washed with saturated aqueous sodium chloride, dried over anhydrous magnesium sulfate, filtered, and concentrated to give 3.19 g (110%) of the title compound.

Example 294C 4-(4-amino-2-bromophenoxy)benzonitrile

Example 294B (3.21 g, 10.06 mmol) and tetrahydrofuran (70 mL) were added to platinum(IV)oxide (0.642 g, 2.83 mmol) in a 250 mL stainless steel pressure bottle and stirred for 45 minutes at 30 psi of hydrogen at ambient temperature. The solid was filtered off, and the filtrate was concentrated. The residue was purified by flash chromatography on silica gel eluting with 30% ethyl acetate in hexanes to give 1.75 g (60%) of the title compound.

Example 294D 4-(4-amino-2-(4,4,5,5-tetramethyl-1,3,2-dioxaborolan-2-yl)phenoxy)benzonitrile A mixture of Example 294C (1.75 g, 6.05 mmol), 4,4,4',4',5,5,5',5'-octamethyl-2,2'-bi(1,3,2-dioxaborolane) (3.07 g, 12.11 mmol), 1,3,5,7-tetramethyl-6-phenyl-2,4,8-trioxa-6-phosphaadamantane (0.159 g, 0.545 mmol), tris(dibenzylideneacetone)dipalladium(0) (0.166 g, 0.182 mmol), and potassium acetate (1.307 g, 13.32 mmol) in dioxane (30 mL) was degassed and back-filled with nitrogen several times. The reaction mixture was heated at 80° C. for 20 hours. The solvent was evaporated, and the residue was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated. The crude product was purified by flash chromatography (silica gel, 40-70% ethyl acetate in hexanes) to provide 2.0 g (98%) of the title compound.

Example 294E 4-(4-amino-2-(1-methyl-6-oxo-4-(2,2,2-trifluoroethoxy)-1,6-dihydropyridin-3-yl)phenoxy)benzonitrile Example 294E was prepared according to the procedure used for the preparation of Example 1B, substituting Example 294D for 2-phenoxyphenylboronic acid, and Example 294A for Example 1A, respectively, to provide the title compound.

Example 294F

4-{4-[(ethylsulfonyl)amino]-2-[1-methyl-6-oxo-4-(2,2,2-trifluoroethoxy)-1,6-dihydropyridin-3-yl]phenoxy}benzamide Example 294F was prepared according to the procedure used for the preparation of Example 22, substituting Example 294D for Example 20C, and ethanesulfonyl chloride for methanesulfonyl chloride, respectively, to provide the title compound. The title product was isolated as a minor product. $^1$H NMR (500 MHz, DMSO-$d_6$) δ 9.87 (s, 1H), 7.85 (s, 1H), 7.78 (d, J=8.54 Hz, 2H), 7.65 (s, 1H), 7.24-7.27 (m, 2H), 7.17 (d, J=2.44 Hz, 1H), 7.07 (d, J=8.85 Hz, 1H), 6.79 (d, J=8.85 Hz, 2H), 5.99 (s, 1H), 4.69 (q, J=8.65 Hz, 2H), 3.32 (s, 3H), 3.11 (q, J=7.32 Hz, 2H), 1.22 (t, J=7.32 Hz, 3H). MS (ESI+) m/z 526.1 (M+H)$^+$.

Example 295

N-[4-(2,4-difluorophenoxy)-3-(4-ethoxy-1-methyl-6-oxo-1,6-dihydropyridin-3-yl)phenyl]-2-oxo-1-phenylpyrrolidine-3-carboxamide A solution of Example 406B and diisopropylethylamine (0.182 M and 0.52 M in dimethyl acetamide, respectively, 221 μL, 0.40 mmol Example 406B (1.0 equivalent) and 1.21 mmol diisopropylethylamine (3.0 equivalents)), O-(7-azabenzotriazol-1-yl)-N,N,N',N'-tetramethyluronium hexafluorophosphate (HATU) (0.182 M in dimethyl acetamide, 221 μL, 0.40 mmol, 1 equivalent) and 2-oxo-1-phenylpyrrolidine-3-carboxylic acid (0.40 M in dimethyl acetamide, 151 μL, 0.60 mmol, 1.5 equivalents) were mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 μL per minute (10 minute residence time). Upon exiting the reactor, the solution was loaded directly into an injection loop and purified by preparative HPLC on a Phenomenex Luna C8(2) 5 μm 100 Å AXIA column (50 mm×21.2 mm) eluting with a gradient of acetonitrile (A) and 0.1% trifluoroacetic acid in water (B) at a flow rate of 30 mL/min (0-0.5 min 5% A, 0.5-6.5 min linear gradient 5-100% A, 6.5-8.5 min 100% A, 8.5-9.0 min linear gradient 100-5% A, 9.0-10 min 5% A) to provide the title compound. $^1$H NMR (400 MHz, DMSO-$d_6$/D$_2$O) δ 7.71-7.55 (m, 5H), 7.47-7.28 (m, 3H), 7.24-7.16 (m, 1H), 7.07-6.96 (m, 2H), 6.92 (d, J=8.7 Hz, 1H), 5.83 (s, 1H), 4.03-3.85 (m, 4H), 3.37 (s, 3H), 2.46-2.32 (m, 2H), 1.15 (t, J=6.9 Hz, 3H). MS (APCI+) m/z 560.0 (M+H)$^+$.

Example 296

N-[4-(2,4-difluorophenoxy)-3-(4-ethoxy-1-methyl-6-oxo-1,6-dihydropyridin-3-yl)phenyl]-3,3-dimethylbutanamide Example 296 was prepared according to the procedure used for the preparation of Example 295, substituting 3,3- dimethylbutanoic acid for 2-oxo-1-phenylpyrrolidine-3-carboxylic acid. $^1$H NMR (400 MHz, DMSO-d$_6$/D$_2$O) δ 7.68-7.49 (m, 1H), 7.37-7.27 (m, 1H), 7.10-6.94 (m, 1H), 6.88 (d, J=8.7 Hz, 1H), 5.83 (s, 1H), 3.93 (q, J=7.0 Hz, 1H), 3.37 (s, 3H), 1.15 (t, J=6.9 Hz, 3H), 1.02 (s, 9H). MS (APCI+) m/z 471.1 (M+H)$^+$.

Example 297

N-[4-(2,4-difluorophenoxy)-3-(4-ethoxy-1-methyl-6-oxo-1,6-dihydropyridin-3-yl)phenyl]-4-(phenoxymethyl)benzamide Example 297 was prepared according to the procedure used for the preparation of Example 295, substituting 4-phenoxymethylbenzoic acid for 2-oxo-1-phenylpyrrolidine-3-carboxylic acid. $^1$H NMR (400 MHz, DMSO-d$_6$/D$_2$O) δ 10.36 (s, 1H), 8.00-7.93 (m, 2H), 7.76-7.69 (m, 2H), 7.64-7.57 (m, 3H), 7.38-7.27 (m, 3H), 7.12-6.90 (m, 6H), 5.84 (s, 1H), 5.23-5.17 (m, 2H), 3.95 (q, J=7.0 Hz, 2H), 3.38 (s, 3H), 1.16 (t, J=6.9 Hz, 3H). MS (APCI+) m/z 582.9 (M+H)$^+$.

Example 298

N-[4-(2,4-difluorophenoxy)-3-(4-ethoxy-1-methyl-6-oxo-1,6-dihydropyridin-3-yl)phenyl]-4-methylpentanamide Example 298 was prepared according to the procedure used for the preparation of Example 295, substituting 4-methylpentanoic acid for 2-oxo-1-phenylpyrrolidine-3-carboxylic acid. $^1$H NMR (400 MHz, DMSO-d$_6$/D$_2$O) δ 7.59-7.49 (m, 3H), 7.32 (ddd, J=11.2, 8.6, 2.7 Hz, 1H), 7.06-6.92 (m, 2H), 6.88 (d, J=8.6 Hz, 1H), 5.82 (s, 1H), 3.92 (q, J=6.9 Hz, 2H), 3.37 (s, 3H), 2.30 (t, J=7.5 Hz, 2H), 1.62-1.38 (m, 3H), 1.14 (t, J=6.9 Hz, 3H), 0.89 (d, J=6.3 Hz, 6H). MS (APCI+) m/z 471.1 (M+H)$^+$.

Example 299

N-[4-(2,4-difluorophenoxy)-3-(4-ethoxy-1-methyl-6-oxo-1,6-dihydropyridin-3-yl)phenyl]-1-phenylcyclopropanecarboxamide Example 299 was prepared according to the procedure used for the preparation of Example 295, substituting 1-phenylcyclopropanecarboxylic acid for 2-oxo-1-phenylpyrrolidine-3-carboxylic acid. $^1$H NMR (400 MHz, DMSO-d$_6$/D$_2$O) δ 7.55-7.47 (m, 2H), 7.46 (d, J=2.6 Hz, 1H), 7.45-7.24 (m, 6H), 7.06-6.92 (m, 2H), 6.84 (d, J=8.7 Hz, 1H), 5.81 (s, 1H), 3.91 (q, J=6.9 Hz, 2H), 3.35 (s, 3H), 1.47-1.40 (m, 2H), 1.18-1.07 (m, 5H). MS (APCI+) m/z 517.0 (M+H)$^+$.

Example 300

4-(acetylamino)-N-[4-(2,4-difluorophenoxy)-3-(4-ethoxy-1-methyl-6-oxo-1,6-dihydropyridin-3-yl)phenyl]benzamide Example 300 was prepared according to the procedure used for the preparation of Example 295, substituting 4-(acetylamino)benzoic acid for 2-oxo-1-phenylpyrrolidine-3-carboxylic acid. $^1$H NMR (400 MHz, DMSO-d$_6$/D$_2$O) δ 7.95-7.86 (m, 2H), 7.74-7.68 (m, 4H), 7.62-7.51 (m, 1H), 7.38-7.29 (m, 1H), 7.09-6.95 (m, 2H), 6.96-6.86 (m, 1H), 5.84 (s, 1H), 3.95 (q, J=7.0 Hz, 2H), 3.38 (s, 3H), 2.12-1.95 (m, 3H), 1.16 (t, J=6.9 Hz, 3H). MS (APCI+) m/z 534.0 (M+H)$^+$.

Example 301

N-[4-(2,4-difluorophenoxy)-3-(4-ethoxy-1-methyl-6-oxo-1,6-dihydropyridin-3-yl)phenyl]-4-(propan-2-yloxy)benzamide Example 301 was prepared according to the procedure used for the preparation of Example 295, substituting 4-(propan-2-yloxy)benzoic acid for 2-oxo-1-phenylpyrrolidine-3-carboxylic acid. $^1$H NMR (400 MHz, DMSO-d$_6$/D$_2$O) δ 7.95-7.85 (m, 2H), 7.74-7.68 (m, 1H), 7.62-7.50 (m, 1H), 7.38-7.29 (m, 1H), 7.08-6.89 (m, 4H), 5.84 (s, 1H), 4.78-4.67 (m, 1H), 3.94 (q, J=6.9 Hz, 1H), 3.38 (s, 2H), 1.38-1.26 (m, 6H), 1.15 (t, J=6.9 Hz, 3H). MS (APCI+) m/z 535.0 (M+H)$^+$.

Example 302

N-[4-(2,4-difluorophenoxy)-3-(4-ethoxy-1-methyl-6-oxo-1,6-dihydropyridin-3-yl)phenyl]-2-(2-phenylethyl)benzamide Example 302 was prepared according to the procedure used for the preparation of Example 295, substituting 2-(2-phenylethyl)benzoic acid for 2-oxo-1-phenylpyrrolidine-3-carboxylic acid. $^1$H NMR (400 MHz, DMSO-d$_6$/D$_2$O) δ 7.84-7.65 (m, 2H), 7.61 (s, 1H), 7.53-7.38 (m, 3H), 7.39-7.19 (m, 6H), 7.21-7.15 (m, 3H), 7.08-6.97 (m, 2H), 6.95 (d, J=8.7 Hz, 1H), 5.84 (s, 1H), 3.94 (q, J=7.0 Hz, 2H), 3.38 (s, 3H), 3.04 (d, J=6.8 Hz, 1H), 3.01 (d, J=5.3 Hz, 2H), 2.92-2.78 (m, 2H), 1.14 (t, J=6.9 Hz, 3H). MS (APCI+) m/z 581.0 (M+H)$^+$.

Example 303

4-(diethylamino)-N-[4-(2,4-difluorophenoxy)-3-(4-ethoxy-1-methyl-6-oxo-1,6-dihydropyridin-3-yl)phenyl]benzamide Example 303 was prepared according to the procedure used for the preparation of Example 295, substituting 4-(diethylamino)benzoic acid for 2-oxo-1-phenylpyrrolidine-3-carboxylic acid to provide the compound as the trifluoroacetic acid salt. $^1$H NMR (400 MHz, DMSO-d$_6$/D$_2$O) δ 7.86-7.79 (m, 2H), 7.74-7.68 (m, 2H), 7.60 (s, 1H), 7.37-7.26 (m, 1H), 7.07-6.96 (m, 2H), 6.94-6.88 (m, 1H), 6.75 (d, J=8.7 Hz, 2H), 5.84 (s, 1H), 3.94 (q, J=6.9 Hz, 2H), 3.42 (d, J=7.1 Hz, 3H), 3.38 (s, 3H), 2.96 (s, 1H), 2.80 (s, 1H), 1.98 (s, 1H), 1.17 (s, 1H), 1.17-1.07 (m, 8H). MS (APCI+) m/z 548.1 (M+H)$^+$.

Example 304

N-[4-(2,4-difluorophenoxy)-3-(4-ethoxy-1-methyl-6-oxo-1,6-dihydropyridin-3-yl)phenyl]biphenyl-4-carboxamide Example 304 was prepared according to the procedure used for the preparation of Example 295, substituting 4-phenylbenzoic acid for 2-oxo-1-phenylpyrrolidine-3-carboxylic acid. $^1$H NMR (400 MHz, DMSO-d$_6$/D$_2$O) δ 8.08-8.01 (m, 2H), 7.88-7.78 (m, 2H), 7.79-7.71 (m, 4H), 7.62 (s, 1H), 7.57-7.48 (m, 3H), 7.48-7.40 (m, 1H), 7.39-7.30 (m, 1H), 7.10-6.99 (m, 2H), 6.95 (d, J=8.5 Hz, 1H), 5.85 (s, 1H), 3.96 (q, J=6.9 Hz, 2H), 3.39 (s, 3H), 1.17 (t, J=6.9 Hz, 3H). MS (APCI+) m/z 552.9 (M+H)+.

Example 305

5-{2-(2,4-difluorophenoxy)-5-[(2,2-dimethylpropyl)amino]phenyl}-4-ethoxy-1-methylpyridin-2(1H)-one A solution of Example 406B and acetic acid (0.152 M and 1.4 M in methanol, respectively, 265 μL, 0.40 mmol Example 406B (1.0 equivalent) and 4 mmol acetic acid (10 equivalents)), sodium cyanoborohydride (0.2 M in methanol, 294 μL, 0.6 mmol, 1.5 equivalents) and 2,2-dimethylpropanal (0.40 M in dimethyl acetamide, 121 μL, 0.48 mmol, 1.2 equivalents) were mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 μL per minute (10 minute residence time). Upon exiting the reactor, the reaction mixture was loaded directly into an injection loop and purified by preparative HPLC on a Phenomenex Luna C8(2) 5 μm 100 Å AXIA column (50 mm×21.2 mm) eluting with a gradient of acetonitrile (A) and 0.1% trifluoroacetic acid in water (B) at a flow rate of 30 mL/min (0-0.5 min 5% A, 0.5-6.5 min linear gradient 5-100% A, 6.5-8.5 min 100% A, 8.5-9.0 min linear gradient 100-5% A, 9.0-10 min 5% A) to provide the title compound as the trifluoroacetate salt. $^1$H NMR (400 MHz, DMSO-d$_6$/D$_2$O) δ 7.48 (s, 1H), 7.23 (ddd, J=11.4, 8.6, 2.9 Hz, 1H), 6.98-6.88 (m, 1H), 6.85-6.76 (m, 2H), 6.65 (dd, J=8.7, 2.9 Hz, 1H), 6.55 (d, J=2.9 Hz, 1H), 5.76 (s, 1H), 3.87 (q, J=7.0 Hz, 2H), 3.33 (s, 3H), 2.80 (s, 2H), 1.10 (t, J=6.9 Hz, 3H), 0.96 (s, 9H). MS (APCI+) m/z 443.1 (M+H)+.

Example 306

5-{2-(2,4-difluorophenoxy)-5-[(3,3-dimethylbutyl)amino]phenyl}-4-ethoxy-1-methylpyridin-2(1H)-one Example 306 was prepared according to the procedure used for the preparation of Example 305, substituting 3,3-dimethylbutanal for 2,2-dimethylpropanal. $^1$H NMR (400 MHz, DMSO-d$_6$/D$_2$O) δ 7.48 (s, 1H), 7.23 (ddd, J=11.4, 8.6, 2.9 Hz, 1H), 6.98-6.89 (m, 1H), 6.85-6.76 (m, 2H), 6.58 (dd, J=8.7, 2.9 Hz, 1H), 6.47 (d, J=2.8 Hz, 1H), 5.77 (s, 1H), 3.87 (q, J=7.0 Hz, 2H), 3.33 (s, 3H), 3.02-2.94 (m, 2H), 1.52-1.44 (m, 2H), 1.12 (t, J=6.9 Hz, 3H), 0.94 (s, 9H) MS (APCI+) m/z 457.1 (M+H)+.

Example 307

N-[4-(2,4-difluorophenoxy)-3-(4-ethoxy-1-methyl-6-oxo-1,6-dihydropyridin-3-yl)phenyl]-4-(methylsulfonyl)benzenesulfonamide A stock solution of Example 406B and diisopropylethylamine (0.11 M and 0.2 M in dimethyl acetamide, respectively, 375 μL, 0.40 mmol Example 406B (1.0 equivalent) and 0.80 mmol diisopropylethylamine (2 equivalents)) and 4-(methylsulfonyl)benzenesulfonyl chloride (0.40 M in dimethyl acetamide, 232 μL, 0.92 mmol, 2.3 equivalents) were mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 50° C., and passed through the reactor at 180 μL per minute (10 minute residence time). Upon exiting the reactor, the reaction mixture was loaded directly into an injection loop and purified by preparative HPLC on a Phenomenex Luna C8(2) 5 μm 100 Å AXIA column (50 mm×21.2 mm) eluting with a gradient of acetonitrile (A) and 0.1% trifluoroacetic acid in water (B) at a flow rate of 30 mL/min (0-0.5 min 5% A, 0.5-6.5 min linear gradient 5-100% A, 6.5-8.5 min 100% A, 8.5-9.0 min linear gradient 100-5% A, 9.0-10 min 5% A) to provide the title compound. $^1$H NMR (400 MHz, DMSO-d$_6$/D$_2$O) δ 8.16-8.09 (m, 2H), 8.02-7.96 (m, 2H), 7.45 (s, 1H), 7.36-7.27 (m, 1H), 7.07 (dd, J=8.7, 2.7 Hz, 1H), 7.06-6.91 (m, 3H), 6.85-6.79 (m, 1H), 5.80 (s, 1H), 3.89 (q, J=7.0 Hz, 2H), 3.35 (s, 3H), 3.27 (s, 3H), 1.26-1.06 (m, 3H). MS (APCI+) m/z 590.9 (M+H)+.

Example 308

N-[4-(2,4-difluorophenoxy)-3-(4-ethoxy-1-methyl-6-oxo-1,6-dihydropyridin-3-yl)phenyl]-4-(trifluoromethoxy)benzenesulfonamide Example 308 was prepared according to the procedure used for the preparation of Example 307, substituting 4-(trifluoromethoxy)benzenesulfonyl chloride for 4-(methylsulfonyl)benzenesulfonyl chloride. $^1$H NMR (400 MHz, DMSO-d$_6$/D$_2$O) δ 7.91-7.85 (m, 2H), 7.60-7.54 (m, 2H), 7.46 (s, 1H), 7.38-7.27 (m, 1H), 7.11-6.89 (m, 4H), 6.82 (d, J=8.7 Hz, 1H), 5.80 (s, 1H), 3.89 (q, J=7.0 Hz, 2H), 3.35 (s, 3H), 1.09 (t, J=6.9 Hz, 3H). MS (APCI+) m/z 596.9 (M+H)+.

Example 309

N-[4-(2,4-difluorophenoxy)-3-(4-ethoxy-1-methyl-6-oxo-1,6-dihydropyridin-3-yl)phenyl]biphenyl-4-sulfonamide Example 309 was prepared according to the procedure used for the preparation of Example 307, substituting 4-phenylbenzenesulfonyl chloride for 4-(methylsulfonyl)benzenesulfonyl chloride. $^1$H NMR (400 MHz, DMSO-d$_6$/D$_2$O) δ 7.91-7.85 (m, 2H), 7.87-7.80 (m, 2H), 7.73 (d, J=1.6 Hz, 1H), 7.52 (t, J=7.5 Hz, 2H), 7.46 (d, J=7.2 Hz, 2H), 7.46-7.42 (m, 2H), 7.30 (ddd, J=11.2, 8.6, 2.8 Hz, 1H), 7.11 (dd, J=8.7, 2.7 Hz, 1H), 7.05-6.89 (m, 3H), 6.83 (d, J=8.7 Hz, 1H), 5.79 (s, 1H), 3.87 (q, J=7.0 Hz, 2H), 3.31 (s, 3H), 1.06 (t, J=6.9 Hz, 3H). MS (APCI+) m/z 588.9 (M+H)+.

Example 310

N-[4-(2,4-difluorophenoxy)-3-(4-ethoxy-1-methyl-6-oxo-1,6-dihydropyridin-3-yl)phenyl]-1-[(1S,4R)-7,7-dimethyl-2-oxobicyclo[2.2.1]hept-1-yl]methanesulfonamide Example 310 was prepared according to the procedure used for the preparation of Example 307, substituting 1-[(1S,4R)-7,7-dimethyl-2-oxobicyclo[2.2.1]hept-1-yl]methanesulfonyl chloride for 4-(methylsulfonyl)benzenesulfonyl chloride. $^1$H NMR (400 MHz, DMSO-d$_6$/D$_2$O) δ 7.57 (s, 1H), 7.37-7.27 (m, 1H), 7.20-7.12 (m, 2H), 7.06-6.96 (m, 2H), 6.92-6.86 (m, 1H), 5.82 (s, 1H), 3.96-3.88 (m, 2H), 3.37 (s, 4H), 3.20-2.93 (m, 1H), 2.43-2.29 (m, 3H), 2.09-2.03 (m, 1H), 1.99-1.87 (m, 2H), 1.66 (s, 4H), 1.57-1.47 (m, 1H), 1.45-1.35 (m, 1H), 1.19-1.13 (m, 2H), 1.13 (d, J=6.9 Hz, 3H), 1.00 (s, 3H), 0.77 (s, 3H). MS (APCI+) m/z 587.0 (M+H)+.

Example 311

N-[4-(2,4-difluorophenoxy)-3-(4-ethoxy-1-methyl-6-oxo-1,6-dihydropyridin-3-yl)phenyl]-1-phenylmethanesulfonamide A flask with stirbar was charged with Example 406B (0.173 g, 0.465 mmol), phenylmethanesulfonyl chloride (0.23 g, 1.206 mmol) and triethylamine (0.30 mL, 2.152 mmol) in dichloromethane (6.00 mL) and the solution was stirred at ambient temperature for 18 hours. The mixture was stripped down by rotovap, then 1 M sodium hydroxide (2 mL, 2.000 mmol) and tetrahydrofuran (4.00 mL) were added and the mixture was heated at 60° C. for 1 hour. The mixture was cooled and partitioned between 60 mL each of ethyl acetate and aqueous ammonium chloride. The organics were dried over anhydrous sodium sulfate, filtered, and concentrated. The residues chromatographed on a 12 g silica cartridge eluting with 0-10% methanol/dichloromethane to provide the title compound. 1H NMR (400 MHz, DMSO-$d_6$) δ 12.04 (s, 1H), 9.85 (s, 1H), 7.40-7.24 (m, 9H), 7.17 (dd, J=8.8, 2.7 Hz, 1H), 7.09-6.95 (m, 2H), 6.91 (d, J=8.8 Hz, 1H), 6.26 (t, J=2.2 Hz, 1H), 4.50 (s, 2H), 3.54 (s, 3H). MS (ESI) 522.1 (M+H+).

Example 312

5-[2-(cyclopropylmethoxy)-4-(3-methyl-1H-pyrazol-5-yl)phenyl]-1-methylpyridin-2(1H)-one

Example 312A 1-(4-bromo-3-(cyclopropylmethoxy)phenyl)ethanone 1-(4-bromo-3-hydroxyphenyl)ethanone (2.04 g, 9.50 mmol), (bromomethyl)cyclopropane (1.01 mL, 10.5 mmol) and potassium carbonate (1.58 g, 11.4 mmol) were combined in dimethylsulfoxide (10 mL). The reaction mixture was heated at 50° C. for 3 hours. The reaction mixture was partitioned with ethyl acetate and water. The organic layer was washed with saturated aqueous sodium chloride, dried with anhydrous sodium sulfate, filtered, and concentrated. The residue was purified by flash chromatography (silica gel, 10-20% ethyl acetate in heptanes) to provide the title compound (2.05 g, 80%).

Example 312B (Z)-1-(4-bromo-3-(cyclopropylmethoxy)phenyl)-3-hydroxybut-2-en-1-one Example 312A (1.66 g, 6.17 mmol), sodium ethoxide (0.504 g, 7.40 mmol) and anhydrous ethyl acetate (2.42 mL, 24.7 mmol) were combined and stirred at ambient temperature for 18 hours. To this reaction mixture was added sodium ethoxide (0.840 mg, 1.23 mmol) again and stirred at ambient temperature for another 4 hours. The reaction mixture was partitioned with ethyl acetate and 1M HCl. The organic layer was washed with saturated aqueous sodium chloride, dried with anhydrous sodium sulfate, filtered, and concentrated. The residue was purified by flash chromatography (silica gel, 0-10% ethyl acetate in heptanes) to provide the title compound (1.57 g, 82%).

Example 312C 5-(4-bromo-3-(cyclopropylmethoxy)phenyl)-3-methyl-1H-pyrazole

Example 312B (1.50 g, 4.82 mmol) and hydrazine (0.159 mL, 5.06 mmol) were combined in ethanol (20 mL). The reaction mixture was stirred at ambient temperature for 1 hour and concentrated to provide the title compound (1.48 g, 100%).

Example 312D

5-[2-(cyclopropylmethoxy)-4-(3-methyl-1H-pyrazol-5-yl)phenyl]-1-methylpyridin-2(1H)-one Example 312C (61.4 mg, 0.200 mmol), 1-methyl-5-(4,4,5,5-tetramethyl-1,3,2-dioxaborolan-2-yl)pyridin-2(1H)-one (47.0 mg, 0.200 mmol), cesium fluoride (91 mg, 0.60 mmol) and tetrakis(triphenylphosphine)palladium(0) (11.6 mg, 10.0 μmol) were combined in the mixture of dimethoxyethane (2 mL) and methanol (1 mL). The reaction mixture was purged with nitrogen for 15 minutes and heated in a microwave reactor at 130° C. for 80 minutes. The reaction mixture was partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 2-6% methanol in dichloromethane) to provide the title compound (36 mg, 54%). $^1$H NMR (300 MHz, DMSO-$d_6$) δ 12.53 (s, 1H) 7.93 (s, 1H) 7.71 (dd, J=9.49, 2.71 Hz, 1H) 7.09-7.45 (m, 3H) 6.35-6.57 (m, 2H) 3.93 (d, J=6.44 Hz, 2H) 3.49 (s, 3H) 2.27 (s, 3H) 1.13-1.31 (m, 1H) 0.48-0.60 (m, 2H) 0.27-0.40 (m, 2H). MS (ESI+) m/z 336 (M+H)+.

Example 313

5-{2-[2-(but-3-en-1-yn-1-yl)phenoxy]-5-(ethylsulfonyl)phenyl}-4-hydroxy-1-methylpyridin-2(1H)-one

Example 313A 2-(5-(ethylsulfonyl)-2-fluorophenyl)-4,4,5,5-tetramethyl-1,3,2-dioxaborolane Example 313A was prepared according to the procedure used for the preparation of Example 5D, substituting Example 275B for Example 5C, to provide the title compound.

Example 313B 4-chloro-5-(5-(ethylsulfonyl)-2-fluorophenyl)-1-methylpyridin-2(1H)-one A mixture of Example 269B (1.112 g, 5 mmol), Example 313A (1.571 g, 5 mmol), 1,3,5,7-tetramethyl-6-phenyl-2,4,8-trioxa-6-phosphaadamantane (0.171 g, 0.585 mmol), tris(dibenzylideneacetone)dipalladium(0) (0.137 g, 0.150 mmol), and potassium phosphate (2.65 g, 12.50 mmol) in dioxane (16 mL) and water (4.00 mL) was degassed and back-filled with nitrogen several times. The reaction mixture was heated at 60° C. for 16 hours. The reaction mixture was partitioned between water and ethyl acetate. The aqueous layer was extracted with additional ethyl acetate three times.

The combined organic layers were washed with saturated aqueous sodium chloride, dried over anhydrous magnesium sulfate, filtered, and concentrated. The residue was purified by flash column chromatography on silica gel eluting with 60% ethyl acetate in hexanes to give the title compound (0.72 g, 2.183 mmol, 43.7% yield).

Example 313C 4-chloro-5-(5-(ethylsulfonyl)-2-(2-iodophenoxy)phenyl)-1-methylpyridin-2(1H)-one A mixture of Example 313B (0.46 g, 1.395 mmol), 2-iodophenol (0.307 g, 1.395 mmol), and cesium carbonate (0.454 g, 1.395 mmol) in dimethyl sulfoxide (10 mL) was heated at 100° C. overnight. After cooling, the reaction mixture was partitioned between water and ethyl acetate. The aqueous layer was separarred and extracted with additional ethyl acetate twice. The combined organic layers were washed with saturated aqueous sodium chloride, dried over anhydrous magnesium sulfate, filtered, and concentrated. The residue was purified by flash chromatography on silica gel eluting 1:1 ethyl acetate/hexanes to give the title compound (0.46 g, 0.868 mmol, 62.2% yield).

Example 313D 4-chloro-5-(5-(ethylsulfonyl)-2-(2-(4-hydroxybut-1-yn-1-yl)phenoxy)phenyl)-1-methylpyridin-2(1H)-one A mixture of Example 313C (0.106 g, 0.2 mmol), but-3-yn-1-ol (0.028 g, 0.400 mmol), copper(I)iodide (7.62 mg, 0.040 mmol), bis(triphenylphosphine)palladium(II)chloride (0.014 g, 0.020 mmol), and triethylamine (0.573 mL, 4.00 mmol) in dimethylformamide (2 mL) was heated at 80° C. for 2 hours. After cooling, the reaction mixture was partitioned between water and ethyl acetate. The aqueous layer was separarred and extracted with additional ethyl acetate twice. The combined organic layers were washed with saturated aqueous sodium chloride, dried over anhydrous magnesium sulfate, filtered, and concentrated. The residue was purified by flash chromatography on silica gel eluting 4:1 ethyl acetate/hexanes to give the title compound (0.078 g, 0.165 mmol, 83% yield).

Example 313E

5-{2-[2-(but-3-en-1-yn-1-yl)phenoxy]-5-(ethylsulfonyl)phenyl}-4-hydroxy-1-methylpyridin-2(1H)-one A mixture of Example 313D (0.078 g, 0.165 mmol) and sodium hydride (0.043 g, 0.662 mmol, 60% in oil) in dioxane (5 mL) was heated at 85° C. overnight. After cooling, the reaction mixture was partitioned between water and ethyl acetate. The aqueous layer was separated and extracted with additional ethyl acetate twice. The combined organic layers were washed with saturated aqueous sodium chloride, dried over anhydrous magnesium sulfate, filtered, and concentrated. The residue was purified by reverse phase HPLC (C18, $CH_3CN$/water (0.1% TFA), 0-100%) to give (0.036 g, 0.083 mmol, 50.0% yield). $^1H$ NMR (500 MHz, DMSO-$d_6$) δ 10.89 (s, 1H), 7.81 (d, J=2.14 Hz, 1H), 7.78 (dd, J=8.54, 2.44 Hz, 1H), 7.73 (s, 1H), 7.53 (dd, J=7.78, 1.68 Hz, 1H), 7.42-7.45 (m, 1H), 7.23 (t, J=7.48 Hz, 1H), 7.10 (d, J=7.63 Hz, 1H), 6.93 (d, J=8.54 Hz, 1H), 6.00 (dd, J=17.39, 11.29 Hz, 1H), 5.22 (s, 1H), 5.50-5.57 (m, 2H), 3.34 (s, 3H), 3.28 (q, J=7.32 Hz, 2H), 1.11 (t, J=7.32 Hz, 3H). MS (ESI+) m/z 436.1 (M+H)$^+$.

Example 314

4-chloro-5-{5-(ethylsulfonyl)-2-[2-(3-hydroxyprop-1-yn-1-yl)phenoxy]phenyl}-1-methylpyridin-2(1H)-one Example 314 was prepared according to the procedure used for the preparation of Example 313D, substituting prop-2-yn-1-ol for but-3-yn-1-ol, to provide the title compound. $^1H$ NMR (500 MHz, DMSO-$d_6$) δ 7.99 (s, 1H), 7.87-7.89 (m, 1H), 7.86 (d, J=2.44 Hz, 1H), 7.52 (dd, J=7.78, 1.68 Hz, 1H), 7.42-7.46 (m, 1H), 7.24-7.28 (m, 1H), 7.11 (d, J=7.32 Hz, 1H), 6.93 (d, J=8.85 Hz, 1H), 6.86 (s, 1H), 4.17 (s, 1H), 3.46 (s, 3H), 3.32 (q, J=7.32 Hz, 2H), 1.13 (t, J=7.32 Hz, 3H). MS (ESI+) m/z 457.9 (M+H)$^+$.

Example 315

N-[4-(2,4-difluorophenoxy)-3-(1-methyl-4-{[4-(morpholin-4-ylmethyl)benzyl]oxy}-6-oxo-1,6-dihydropyridin-3-yl)phenyl]ethanesulfonamide The trifluoroacetic acid salt of Example 315 was prepared according to the procedure used for the preparation of Example 286, substituting (4-(morpholinomethyl)phenyl)methanol for 2-morpholinoethanol. $^1H$ NMR (300 MHz, DMSO-$d_6$) δ 9.82 (s, 1H), 7.66 (s, 1H), 7.34-7.46 (m, 5H), 7.17-7.20 (m, 2H), 6.90-6.95 (m, 3H), 5.85 (s, 1H), 5.12 (s, 2H), 4.33 (s, 2H), 3.94 (s, 2H), 3.34 (s, 3H), 3.05-3.24 (m, 10H), 1.19 (t, J=7.32 Hz, 3H). MS (ESI+) m/z 626.1 (M+H)$^+$.

Example 316

N-{4-(2,4-difluorophenoxy)-3-[1-methyl-4-(oxetan-3-yloxy)-6-oxo-1,6-dihydropyridin-3-yl]phenyl}ethanesulfonamide Example 316 was prepared according to the procedure used for the preparation of Example 286, substituting oxetan-3-ol for 2-morpholinoethanol. $^1H$ NMR (500 MHz, DMSO-$d_6$) δ 9.80 (s, 1H), 7.70 (s, 1H), 7.36-7.42 (m, 1H), 7.18-7.22 (m, 2H), 7.01-7.11 (m, 2H), 6.91 (d, J=8.54 Hz, 1H), 5.48 (s, 1H), 5.15-5.21 (m, 1H), 4.80 (t, J=6.87 Hz, 2H), 4.33 (dd, J=7.63, 4.88 Hz, 2H), 3.36 (s, 3H), 3.12 (q, J=7.32 Hz, 2H), 1.23 (t, J=7.32 Hz, 3H). MS (ESI+) m/z 493.1 (M+H)$^+$.

Example 317

4-(2,4-difluorophenoxy)-5-[2-(2,4-difluorophenoxy)-5-(ethylsulfonyl)phenyl]-1-methylpyridin-2(1H)-one A mixture of Example 313B (0.330 g, 1 mmol), 2,4-difluorophenol (0.195 g, 1.500 mmol), and cesium carbonate (0.489 g, 1.500 mmol) in dimethyl sulfoxide (8 mL) was heated at 100° C. overnight. After cooling, the reaction mixture was partitioned between water and ethyl acetate. The aqueous layer was separarred and extracted with additional ethyl acetate twice. The combined organic layers were washed with saturated aqueous sodium chloride, dried over anhydrous magnesium sulfate, filtered, and concentrated. The residue was purified by reverse phase HPLC (C18, $CH_3CN$/water (0.1% TFA), 0-100%) to give the title compound (0.115 g, 0.216 mmol, 21.56% yield). $^1$H NMR (500 MHz, DMSO-$d_6$) δ 8.01 (s, 1H), 7.95 (d, J=2.44 Hz, 1H), 7.85 (d, J=8.7, 2.29 Hz, 1H), 7.45-7.54 (m, 2H), 7.26-7.32 (m, 2H), 7.13-7.18 (m, 2H), 6.96 (d, J=8.54 Hz, 1H), 5.36 (s, 1H), 3.45 (s, 3H), 3.33 (q, J=7.32 Hz, 2H), 1.15 (t, J=7.32 Hz, 3H). MS (ESI+) m/z 543.4 (M+H)$^+$.

Example 318

5-[2-(2,4-difluorophenoxy)-5-(ethylsulfonyl)phenyl]-1-methyl-4-(oxetan-3-yloxy)pyridin-2(1H)-one

Example 318A 4-chloro-5-(2-(2,4-difluorophenoxy)-5-(ethylsulfonyl)phenyl)-1-methylpyridin-2(1H)-one The title compound was isolated as a major product from preparation of Example 317.

Example 318B

5-[2-(2,4-difluorophenoxy)-5-(ethylsulfonyl)phenyl]-1-methyl-4-(oxetan-3-yloxy)pyridin-2(1H)-one Example 318B was prepared according to the procedure used for the preparation of Example 286, substituting oxetan-3-ol for 2-morpholinoethanol, and Example 318A for Example 278A. $^1$H NMR (500 MHz, DMSO-$d_6$) δ 7.82-7.85 (m, 3H), 7.50-7.56 (m, 1H), 7.33-7.39 (m, 1H), 7.15-7.21 (m, 2H), 6.99 (d, J=9.77 Hz, 1H), 5.56 (s, 1H), 5.23-5.29 (m, 1H), 4.80 (t, J=6.87 Hz, 2H), 4.38 (dd, J=7.63, 4.88 Hz, 2H), 3.40 (s, 3H), 3.33 (q, J=7.32 Hz, 2H), 1.14 (t, J=7.32 Hz, 3H). MS (ESI+) m/z 478.1 (M+H)$^+$.

Example 319 tert-butyl 4-[(5-{2-(2,4-difluorophenoxy)-5-[(ethylsulfonyl)amino]phenyl}-1-methyl-2-oxo-1,2-dihydropyridin-4-yl)oxy]piperidine-1-carboxylate Example 319 was prepared according to the procedure used for the preparation of Example 286, substituting tert-butyl 4-hydroxypiperidine-1-carboxylate for 2-morpholinoethanol. $^1$H NMR (500 MHz, DMSO-$d_6$) δ 9.80 (s, 1H), 7.63 (s, 1H), 7.32-7.38 (m, 1H), 7.18-7.21 (m, 1H), 7.14 (d, J=2.75 Hz, 1H), 6.90-7.02 (m, 3H), 5.91 (s, 1H), 4.54-4.57 (m, 1H), 3.34-3.39 (m, 5H), 3.07 (q, J=7.43 Hz, 2H), 1.73-1.78 (m, 2H), 1.38-1.42 (m, 1H), 1.20 (t, J=7.32 Hz, 3H). MS (ESI+) m/z 619.8 (M+H)$^+$.

Example 320 tert-butyl 4-[(5-{2-(4-{[1-(tert-butoxycarbonyl)piperidin-4-yl]oxy}-2-fluorophenoxy)-5-[(ethylsulfonyl)amino]phenyl}-1-methyl-2-oxo-1,2-dihydropyridin-4-yl)oxy]piperidine-1-carboxylate The title compound was isolated as a minor product from preparation of Example 319. $^1$H NMR (500 MHz, DMSO-$d_6$) δ 9.69 (s, 1H), 7.64 (s, 1H), 7.10-7.15 (m, 3H), 6.92-6.95 (m, 1H), 6.71-6.76 (m, 1H), 6.69 (d, J=8.85 Hz, 1H), 5.96 (s, 1H), 4.50-4.54 (m, 2H), 3.43 (s, 3H), 2.96-3.24 (m, 8H), 1.68-1.72 (m, 4H), 1.34-1.53 (m, 24H), 1.17 (t, J=7.32 Hz, 3H). MS (ESI+) m/z 801.0 (M+H)$^+$.

Example 321

N-[4-(2,4-difluorophenoxy)-3-(4-{[trans-4-(dimethylamino)cyclohexyl]oxy}-1-methyl-6-oxo-1,6-dihydropyridin-3-yl)phenyl]ethanesulfonamide The trifluoroacetic acid salt of Example 321 was prepared according to the procedure used for the preparation of Example 286, substituting (1r,4r)-4-(dimethylamino)cyclohexanol for 2-morpholinoethanol. $^1$H NMR (500 MHz, DMSO-$d_6$) δ 9.79 (s, 1H), 9.49 (br s, 1H), 7.62 (s, 1H), 7.34-7.40 (m, 1H), 7.13-7.18 (m, 2H), 6.93-7.04 (m, 2H), 6.90 (d, J=8.54 Hz, 1H), 5.93 (s, 1H), 4.28-4.35 (m, 1H), 3.34 (s, 2H), 3.010 (q, J=7.43 Hz, 2H), 2.71-2.73 (d, J=4.48 Hz, 6H), 1.94-2.03 (m, 4H), 1.56-1.63 (m, 2H), 1.20-1.28 (m, 5H). MS (ESI+) m/z 562.1 (M+H)$^+$.

Example 322

N-{4-(2,4-difluorophenoxy)-3-[1-methyl-6-oxo-4-(piperidin-4-yloxy)-1,6-dihydropyridin-3-yl]phenyl}ethanesulfonamide A mixture of Example 319 (0.062 g, 0.100 mmol), and 2,2,2-trifluoroacetic acid (1.71 g, 15.00 mmol) in dichloromethane (2 mL) was stirred at ambient temperature for 4 hours. The solvent was evaporated, and the residue was purified by reverse phase HPLC (C18, CH$_3$CN/water (0.1% TFA), 0-100%) to give the trifluoroacetic acid salt of the title compound (0.038 g, 0.073 mmol, 73.1% yield). $^1$H NMR (500 MHz, DMSO-$d_6$) δ 9.82 (s, 1H), 8.52 (br s, 1H), 8.38 (br s, 1H), 7.64 (s, 1H), 7.33-7.38 (m, 1H), 7.16-7.21 (m, 2H), 6.90-7.02 (m, 3H), 5.98 (s, 1H), 4.62-4.66 (m, 1H), 3.34 (s, 2H), 3.03-3.16 (m, 6H), 1.97-2.02 (m, 2H), 1.66-1.71 (m, 2H), 1.22 (t, J=7.32 Hz, 2H). MS (ESI+) m/z 520.0 (M+H)$^+$.

Example 323

N-[4-(2,4-difluorophenoxy)-3-{1-methyl-4-[(1-methylpyrrolidin-3-yl)methoxy]-6-oxo-1,6-dihydropyridin-3-yl]phenyl}ethanesulfonamide The trifluoroacetic acid salt of Example 323 was prepared according to the procedure used for the preparation of Example 286, substituting (1-methylpyrrolidin-3-yl)methanol for 2-morpholinoethanol. $^1$H NMR (500 MHz, DMSO-$d_6$) δ 9.78-9.83 (m, 2H), 7.62 (s, 1H), 7.32-7.38 (m, 1H), 7.18-7.23 (m, 1H), 7.14 (d, J=2.75 Hz, 1H), 6.97-7.02 (m, 2H), 5.85 (s, 1H), 3.87-3.96 (m, 2H), 3.34 (s, 2H), 3.47-3.58 (m, 2H), 3.10-3.15 (m, 3H), 2.67-2.81 (m, 5H), 1.61-2.02 (m, 2H), 1.22 (t, J=7.32 Hz, 3H). MS (ESI+) m/z 534.2 (M+H)$^+$.

Example 324 tert-butyl 4-{[(5-{2-(2,4-difluorophenoxy)-5-[(ethylsulfonyl)amino]phenyl}-1-methyl-2-oxo-1,2-dihydropyridin-4-yl)oxy]methyl}piperidine-1-carboxylate Example 324 was prepared according to the procedure used for the preparation of Example 286, substituting tert-butyl 4-(hydroxymethyl)piperidine-1-carboxylate for 2-morpholinoethanol. $^1$H NMR (500 MHz, DMSO-$d_6$) δ 9.80 (s, 1H), 7.59 (s, 1H), 7.32-7.37 (m, 1H), 7.20 (dd, J=8.7, 2.59 Hz, 1H), 7.12 (d, J=2.75 Hz, 1H), 6.87-7.03 (m, 3H), 5.80 (s, 1H), 3.87 (d, J=11.9 Hz, 2H), 3.74 (d, J=6.41 Hz, 2H), 3.33 (s, 3H), 3.07 (q, J=7.32 Hz, 2H), 2.46 (br s, 2H), 1.73-1.77 (m, 1H), 1.54 (d, J=10.99 Hz, 2H), 1.37 (s, 9H), 1.22 (t, J=7.32 Hz, 3H), 0.95-1.05 (m, 2H). MS (ESI+) m/z 633.9 (M+H)$^+$.

Example 325 tert-butyl 6-[(5-{2-(2,4-difluorophenoxy)-5-[(ethylsulfonyl)amino]phenyl}-1-methyl-2-oxo-1,2-dihydropyridin-4-yl)oxy]-2-azaspiro[3.3]heptane-2-carboxylate Example 325 was prepared according to the procedure used for the preparation of Example 286, substituting tert-butyl 6-hydroxy-2-azaspiro[3.3]heptane-2-carboxylate for 2-morpholinoethanol. $^1$H NMR (500 MHz, DMSO-d$_6$) δ 9.79 (s, 1H), 7.62 (s, 1H), 7.38-7.43 (m, 1H), 7.17-7.20 (m, 1H), 7.12 (d, J=2.75 Hz, 1H), 6.99-7.08 (m, 2H), 6.93 (d, J=8.85 Hz, 1H), 5.67 (s, 1H), 4.49-4.56 (m, 1H), 3.83 (s, 2H), 3.65 (s, 2H), 3.36 (s, 3H), 3.17 (q, J=7.32 Hz, 2H), 2.56-2.60 (m, 2H), 1.89-1.94 (m, 2H), 1.35 (s, 9H), 1.23 (t, J=7.32 Hz, 3H). MS (APCI+) m/z 632.2 (M+H)$^+$.

Example 326

N-{3-[4-(2-azaspiro[3.3]hept-6-yloxy)-1-methyl-6-oxo-1,6-dihydropyridin-3-yl]-4-(2,4-difluorophenoxy)phenyl}ethanesulfonamide The trifluoroacetic acid salt of Example 326 was prepared according to the procedure used for the preparation of Example 322, substituting Example 325 for Example 319. $^1$H NMR (500 MHz, DMSO-d$_6$) δ 9.80 (s, 1H), 8.62 (s, 2H), 7.64 (s, 1H), 7.38-7.43 (m, 1H), 7.17-7.20 (m, 1H), 7.13 (d, J=2.44 Hz, 1H), 6.99-7.07 (m, 2H), 6.92 (d, J=8.54 Hz, 1H), 5.69 (s, 1H), 4.49-4.56 (m, 1H), 3.98 (t, J=5.95 Hz, 2H), 3.81 (t, J=6.1 Hz, 2H), 3.35 (s, 3H), 3.12 (q, J=7.43 Hz, 2H), 2.64-2.69 (m, 2H), 1.97-2.02 (m, 2H), 1.23 (t, J=7.32 Hz, 3H). MS (ESI+) m/z 532.3 (M+H)$^+$.

Example 327

5-{2-[(cyclopropylmethyl)amino]-5-(methylsulfonyl)phenyl}-4-[(E)-2-ethoxyethenyl]-1-methylpyridin-2(1H)-one Example 327A 2-bromo-1-fluoro-4-(methylsulfonyl)benzene To a solution of 1-fluoro-4-(methylsulfonyl)benzene (25.04 g, 144 mmol) in sulfuric acid (140 mL) was added N-bromosuccinimide (28.48 g, 160 mmol). The mixture was stirred for 16 hours and then poured into ice water. A white finely divided solid was collected by decanting and filtration, washed repeatedly with water and dried to constant mass providing the title compound.

Example 327B 2-bromo-N-(cyclopropylmethyl)-4-(methylsulfonyl)aniline

A mixture of Example 327A (1.28 g, 5.06 mmol) and cyclopropylmethanamine (1.10 g, 15.47 mmol) in dioxane (12 mL) was heated at 100° C. overnight. The crude reaction mixture was adsorbed on silica gel and chromatographed on a 40 g silica cartridge eluting with 0-100% ethyl acetate/heptane to give the title compound.

Example 327C

N-(cyclopropylmethyl)-4-(methylsulfonyl)-2-(4,4,5,5-tetramethyl-1,3,2-dioxaborolan-2-yl)aniline Example 327C was prepared according to the procedure used for the preparation of Example 5D, substituting Example 327B for Example 5C.

Example 327D 4-chloro-5-(2-((cyclopropylmethyl)amino)-5-(methylsulfonyl)phenyl)-1-methylpyridin-2(1H)-one Example 327C (0.793 g, 2.258 mmol), Example 269B (0.521 g, 2.342 mmol), tris(dibenzylidineacetone)dipalladium(0) (0.089 g, 0.097 mmol), 1,3,5,7-tetramethyl-6-phenyl-2,4,8-trioxa-6-phosphaadamantane (0.079 g, 0.270 mmol) and tris-potassium phosphate (1.41 g, 6.64 mmol) were combined in a sealed 20 mL microwave tube with stir bar and sparged with nitrogen for 15 minutes. A degassed mixture of 4:1 dioxane/water (12.5 mL) was added by syringe into the reaction vessel which was heated to 100° C. for 30 minutes, then cooled to ambient temperature. The reaction mixture was shaken in a separatory funnel with 150 mL ethyl acetate and 100 mL saturated aqueous sodium chloride. The organics were washed with saturated aqueous sodium chloride and dried over anhydrous sodium sulfate. After filtration and solvent removal the residues were chromatographed on a 40 g silica cartridge eluting with 0-100% ethyl acetate/heptane to provide the title compound.

Example 327E

5-{2-[(cyclopropylmethyl)amino]-5-(methylsulfonyl)phenyl}-4-[(E)-2-ethoxyethenyl]-1-methylpyridin-2(1H)-one A 5 mL microwave vessel with stirbar was charged with Example 327D (0.199 g, 0.542 mmol), tris-potassium phosphate (1.17 g, 5.51 mmol), tris(dibenzylidineacetone)dipalladium(0) (0.0315 g, 0.034 mmol), and 1,3,5,7-tetramethyl-6-phenyl-2,4,8-trioxa-6-phosphaadamantane (0.0314 g, 0.107 mmol), sealed and swept with nitrogen for 15 minutes. A solution of (E)-2-(2-ethoxyvinyl)-4,4,5,5-tetramethyl-1,3,2-dioxaborolane (1.0 g, 5.05 mmol) in degassed dioxane (2.000 mL)/water (0.5 mL) was added and the mixture stirred in a 90° C. oil bath for 22 hours. The mixture was cooled and partitioned between ethyl acetate and saturated aqueous sodium chloride. The organics were dried over anhydrous sodium sulfate, filtered and concentrated, then the residues were chromatographed on a 40 g silica cartridge eluting with 0-7% methanol/dichloromethane to provide the title compound. $^1$H NMR (300 MHz, DMSO-d$_6$) δ 7.91 (s, 1H), 7.66 (m, 1H), 7.52 (s, 1H), 7.34 (d, J=2.4 Hz, 1H), 7.27 (d, J=12.6 Hz, 1H), 6.82 (d, J=8.8 Hz, 1H), 6.55 (s, 1H), 5.56 (m, 1H), 5.07 (d, J=12.6 Hz, 1H), 3.74 (q, J=7.1 Hz, 2H), 3.40 (s, 3H), 3.08 (s, 3H), 3.03 (d, J=2.4 Hz, 2H), 1.17 (t, J=7.0 Hz, 3H), 1.05 (m, 1H), 0.39 (dd, J=2.0, 8.5 Hz, 2H), 0.16 (dd, J=1.7, 4.8 Hz, 2H). MS (ESI+) 403.2.

Example 328

N-[3-(4-{[4-(diethylamino)but-2-yn-1-yl]oxy}-1-methyl-6-oxo-1,6-dihydropyridin-3-yl)-4-(2,4-difluorophenoxy)phenyl]ethanesulfonamide The trifluoroacetic acid salt of Example 328 was prepared according to the procedure used for the preparation of Example 286, substituting 4-(diethylamino)but-2-yn-1-ol for 2-morpholinoethanol. $^1$H NMR (500 MHz, DMSO-d$_6$) δ 9.90 (br s, 1H), 9.79 (s, 1H), 8.62 (s, 2H), 7.69 (s, 1H), 7.38-7.44 (m, 1H), 7.15-7.18 (m, 1H), 7.13 (d, J=2.75 Hz, 1H), 7.03-7.10 (m, 2H), 6.83 (d, J=8.85 Hz, 1H), 5.99 (s, 1H), 4.87 (s, 2H), 4.15 (s, 2H), 3.38 (s, 3H), 3.06-3.14 (m, 6H), 1.23 (t, J=7.32 Hz, 3H), 1.14 (t, J=7.32H, 6H). MS (ESI+) m/z 560.1 (M+H)$^+$.

Example 329

N-[4-(2,4-difluorophenoxy)-3-{1-methyl-6-oxo-4-[(1E)-prop-1-en-1-yl]-1,6-dihydropyridin-3-yl]phenyl}ethanesulfonamide Example 329 was prepared according to the procedure used for the preparation of Example 1B, substituting (E)-prop-1-enylboronic acid for 2-phenoxyphenylboronic acid, and Example 278A for Example 1A, respectively. The reaction mixture was heated at 140° C. instead of 120° C., to provide the title compound. $^1$H NMR (300 MHz, DMSO-d$_6$) δ 9.78 (s, 1H), 7.62 (s, 1H), 7.32-7.4324 (m, 1H), 7.21 (dd, J=8.8, 2.7 Hz, 1H), 6.97-7.12 (m, 3H), 6.87 (d, J=8.7 Hz, 1H), 6.49 (s, 1H), 6.20-6.39 (m, 1H), 5.95 (dd, J=15.7, 2.0 Hz, 1H), 3.40 (s, 3H), 3.11 (q, J=7.3 Hz, 2H), 1.71 (dd, J=6.6, 1.7 Hz, 3H), 1.22 (t, J=7.3 Hz, 3H). MS (ESI+) m/z 461.0 (M+H)$^+$.

Example 330

N-[4-(2,4-difluorophenoxy)-3-{1-methyl-4-[4-(4-methylpiperazin-1-yl)phenyl]-6-oxo-1,6-dihydropyridin-3-yl}phenyl]ethanesulfonamide Example 330 was prepared according to the procedure used for the preparation of Example 1B, substituting 1-methyl-4-(4-(4,4,5,5-tetramethyl-1,3,2-dioxaborolan-2-yl)phenyl)piperazine for 2-phenoxyphenylboronic acid, and Example 278A for Example 1A, respectively. The reaction mixture was heated at 140° C. instead of 120° C., to provide the trifluoroacetic acid salt of the title compound. $^1$H NMR (500 MHz, DMSO-d$_6$) δ 9.87-9.93 (m, 1H), 7.55-7.63 (m, 2H), 7.32-7.46 (m, 1H), 7.03-7.14 (m, 2H), 6.86-7.05 (m, 2H), 6.81-6.87 (m, 1H), 6.31-6.51 (m, 1H), 3.55-4.43 (m, 4H), 2.83-2.88 (m, 3H), 2.81 (d, J=7.3 Hz, 1H), 1.08-1.16 (m, 1H), 1.08 (d, J=7.3 Hz, 1H). MS (ESI+) m/z 595.1 (M+H)$^+$.

Example 331

N-{4-(2,4-difluorophenoxy)-3-[4-(2-hydroxyphenyl)-1-methyl-6-oxo-1,6-dihydropyridin-3-yl]phenyl}ethanesulfonamide Example 331 was prepared according to the procedure used for the preparation of Example 1B, substituting 2-hydroxyphenylboronic acid for 2-phenoxyphenylboronic acid, and Example 278A for Example 1A, respectively. The reaction mixture was heated at 140° C. instead of 120° C., to provide the title compound. $^1$H NMR (300 MHz, DMSO-d$_6$) δ 9.53-9.60 (m, 1H), 9.34 (s, 1H), 7.65-7.75 (m, 1H), 7.32-7.46 (m, 1H), 6.88-7.11 (m, 4H), 6.75-6.89 (m, 1H), 6.58-6.77 (m, 3H), 6.55 (d, J=8.8 Hz, 1H), 6.28-6.41 (m, 1H), 3.48 (s, 3H), 2.66-2.83 (q, J=7.3 Hz, 2H), 1.04-1.15 (t, J=7.3 Hz, 3H). MS (ESI+) m/z 513.1 (M+H)$^+$.

Example 332

N-{4-(2,4-difluorophenoxy)-3-[4-(4-formylthiophen-3-yl)-1-methyl-6-oxo-1,6-dihydropyridin-3-yl]phenyl}ethanesulfonamide A mixture of 4-formylthiophen-3-ylboronic acid (206 mg, 1.319 mmol), Example 278A (200 mg, 0.440 mmol), PdCl$_2$ (dppf)-CH$_2$Cl$_2$ Adduct (35.9 mg, 0.044 mmol), tetrabutylammonium tetrahydroborate (113 mg, 0.440 mmol) and K$_2$CO$_3$ (182 mg, 1.319 mmol) in water (4 mL) was heated in a Biotage microwave apparatus at 140° C. under N$_2$ for 6 hours. The reaction mixture was cooled to ambient temperature, concentrated, and purified by reverse phase HPLC (C18, CH$_3$CN/water (10 mM ammonium carbonate), 25-55% gradient) to provide the title compound (15 mg, 6.43% yield). $^1$H NMR (400 MHz, CDCl$_3$) 9.58 (s, 1H), 8.01 (d, J=3.2 Hz, 1H), 7.42 (s, 1H), 7.24-7.23 (m, 1H), 7.03-6.98 (m, 2H), 6.89-6.46 (s, 4H), 6.47 (d, J=8.8 Hz, 1H), 3.63 (s, 3H), 3.01 (q, J=7.2 Hz, 2H), 1.35 (t, J=7.2 Hz, 3H). MS (ESI+) m/z 531.2 (M+H)$^+$.

Example 333

N-[4-(2,4-difluorophenoxy)-3-{4-[(1,1-$^2$H$_2$)ethyloxy]-1-methyl-6-oxo-1,6-dihydropyridin-3-yl}phenyl]ethanesulfonamide Example 333 was prepared according to the procedure used for the preparation of Example 286, substituting ethanol-1,1-d$_2$ for 2-morpholinoethanol. $^1$H NMR (300 MHz, DMSO-d$_6$) δ 9.75 (s, 1H), 7.60 (s, 1H), 7.36 (ddd, J=11.2, 8.7, 2.7 Hz, 1H), 7.17 (dd, J=8.7, 2.7 Hz, 1H), 7.12 (d, J=2.7 Hz, 1H), 7.05-6.94 (m, 2H), 6.88 (d, J=8.7 Hz, 1H), 5.78 (s, 1H), 3.34 (s, 1H), 3.10 (q, J=7.0 Hz, 2H), 1.21 (t, J=7.3 Hz, 3H), 1.13 (s, 3H). MS (ESI) 467.1 (M+H+).

Example 334

N-[4-(2,4-difluorophenoxy)-3-{4-[($^2$H$_5$)ethyloxy]-1-methyl-6-oxo-1,6-dihydropyridin-3-yl}phenyl]ethanesulfonamide Example 334 was prepared according to the procedure used for the preparation of Example 286, substituting ethanol-1,1,2,2,2-d$_5$ for 2-morpholinoethanol. $^1$H NMR (300 MHz, DMSO-d$_6$) δ 9.75 (s, 1H), 7.60 (s, 1H), 7.37 (m, 1H), 7.18 (dd, J=8.7, 2.7 Hz, 1H), 7.13 (d, J=2.7 Hz, 1H), 7.05-6.94 (m, 2H), 6.88 (d, J=8.7 Hz, 1H), 5.79 (s, 1H), 3.34 (s, 3H), 3.10 (q, J=7.0 Hz, 2H), 1.21 (t, J=7.3 Hz, 3H). MS (ESI) 470.1 (M+H+).

Example 335

N-[3-{4-[(2,2-difluoro-1-methylcyclopropyl)methoxy]-1-methyl-6-oxo-1,6-dihydropyridin-3-yl}-4-(2,4-difluorophenoxy)phenyl]ethanesulfonamide

Example 335A 5-bromo-4-((2,2-difluoro-1-methylcyclopropyl)methoxy)-1-methylpyridin-2(1H)-one (2,2-Difluoro-1-methylcyclopropyl)methanol (0.165 g, 1.349 mmol) in dioxane (3 mL) was treated with NaH (0.108 g, 2.70 mmol, 60% in oil) at ambient temperature. The reaction mixture was stirred for 10 minutes. To this solution was added Example 269B (0.2 g, 0.899 mmol). The reaction mixture was then heated at 85° C. for 4 hours. After cooling, the reaction mixture was partitioned between water and ethyl acetate. The aqueous layer was separarred and extracted with additional ethyl acetate three times. The combined organic layers were washed with saturated aqueous sodium chloride, dried over anhydrous magnesium sulfate, filtered, and concentrated. The residue was purified by flash chromatography on silical ge eluting with 4:1 ethyl acetate/hexanes to give the title compound (0.195 g, 0.633 mmol, 70.4% yield).

Example 335B 5-(5-amino-2-(2,4-difluorophenoxy)phenyl)-4-((2,2-difluoro-1-methylcyclopropyl)methoxy)-1-methyl-pyridin-2(1H)-one Example 335B was prepared according to the procedure used for the preparation of Example 1B, substituting Example 5D for 2-phenoxyphenylboronic acid, and Example 335A for Example 1A, respectively, to provide the title compound.

Example 335C

N-[3-{4-[(2,2-difluoro-1-methylcyclopropyl)methoxy]-1-methyl-6-oxo-1,6-dihydropyridin-3-yl}-4-(2,4-difluorophenoxy)phenyl]ethanesulfonamide Example 335C was prepared according to the procedure used for the preparation of Example 22, substituting Example 335B for Example 20C, and ethanesulfonyl chloride for methanesulfonyl chloride, respectively, to provide the title compound. $^1$H NMR (500 MHz, DMSO-$d_6$) δ 9.80 (s, 1H), 7.61 (s, 1H), 7.30-7.36 (m, 1H), 7.22 (dd, J=8.85, 2.75 Hz, 1H), 7.14 (d, J=2.75 Hz, 1H), 6.93-6.98 (m, 2H), 6.83-6.90 (m, 1H), 5.80 (s, 1H), 3.96 (d, J=10.38 Hz, 1H), 3.84 (d, J=10.68 Hz, 1H), 3.34 (s, 3H), 3.08 (q, J=7.32 Hz, 2H), 1.42-1.47 (m, 1H), 1.27-1.31 (m, 1H), 1.20 (t, J=7.32 Hz, 3H), 1.11 (s, 3H). MS (ESI+) m/z 541.0 (M+H)$^+$.

Example 336

N-{4-[2-fluoro-4-(oxetan-3-yloxy)phenoxy]-3-[1-methyl-4-(oxetan-3-yloxy)-6-oxo-1,6-dihydropyridin-3-yl]phenyl}ethanesulfonamide The title compound was isolated as a minor product during the preparation of Example 318B. $^1$H NMR (500 MHz, DMSO-$d_6$) δ 9.72 (s, 1H), 7.73 (s, 1H), 7.15-7.20 (m, 2H), 6.93 (dd, J=8.85, 5.8 Hz, 1H), 6.81 (d, J=8.85 Hz, 1H), 6.69-6.78 (m, 2H), 6.83-6.90 (m, 1H), 5.49 (s, 1H), 5.18-5.27 (m, 1H), 4.81-4.86 (m, 4H), 4.36-4.41 (m, 4H), 3.36 (s, 3H), 3.08 (q, J=7.32 Hz, 2H), 1.22 (t, J=7.32 Hz, 3H). MS (ESI+) m/z 547.2 (M+H)$^+$.

Example 337

5-{2-[(cyclopropylmethyl)amino]-5-(methylsulfonyl)phenyl}-4-[(Z)-2-ethoxyethenyl]-1-methylpyridin-2(1H)-one Example 337 was prepared according to the procedure used for the preparation of Example 327E, substituting (Z)-2-(2-ethoxyvinyl)-4,4,5,5-tetramethyl-1,3,2-dioxaborolane for (E)-2-(2-ethoxyvinyl)-4,4,5,5-tetramethyl-1,3,2-dioxaborolane. $^1$H NMR (300 MHz, DMSO-$d_6$) δ 7.66 (dd, J=2.4, 8.8 Hz, 1H), 7.49 (s, 1H), 7.32 (d, J=2.4 Hz, 1H), 7.06 (s, 1H), 6.82 (d, J=8.8 Hz, 1H), 6.52 (d, J=7.0 Hz, 1H), 5.52 (t, J=6.1 Hz, 1H), 4.48 (d, J=7.0 Hz, 1H), 4.03 (m, 2H), 3.39 (s, 3H), 3.08 (s, 3H), 3.04 (m, 2H), 1.26 (t, J=7.1 Hz, 3H), 1.13 (m, 1H), 0.41 (m, 2H), 0.17 (m, 2H). MS (ESI+) 403.1.

Example 338 ethyl{5-[2-(cyclopropylmethoxy)-5-(ethylsulfonyl)phenyl]-1-methyl-2-oxo-1,2-dihydropyridin-3-yl}carbamate Example 338 was prepared according to the procedure used for the preparation of Example 11, substituting ethyl carbonochloridate for 4-methylbenzene-1-sulfonyl chloride, and Example 357 for Example 10, to provide the title compound. $^1$H NMR (300 MHz, DMSO-$d_6$) δ 8.19 (d, J=2.3 Hz, 1H), 8.16 (s, 1H), 7.79 (dd, J=8.6, 2.4 Hz, 1H), 7.74 (d, J=2.3 Hz, 1H), 7.69 (d, J=2.4 Hz, 1H), 7.30 (d, J=8.7 Hz, 1H), 4.14 (q, J=7.1 Hz, 2H), 4.02 (d, J=6.9 Hz, 2H), 3.58 (s, 3H), 3.27 (q, J=7.3 Hz, 2H), 1.23 (t, J=7.1 Hz, 4H), 1.11 (t, J=7.3 Hz, 3H), 0.58 (m, 2H), 0.36 (m, 2H). MS (ESI+) m/z 435.0 (M+H)$^+$.

Example 339

N-{5-[2-(cyclopropylmethoxy)-5-(ethylsulfonyl)phenyl]-1-methyl-2-oxo-1,2-dihydropyridin-3-yl}methanesulfonamide Example 339 was prepared according to the procedure used for the preparation of Example 11, substituting methanesulfonyl chloride for 4-methylbenzene-1-sulfonyl chloride, and Example 357 for Example 10, to provide the title compound. $^1$H NMR (300 MHz, DMSO-$d_6$) δ 8.80 (s, 1H), 7.73-7.83 (m, 3H), 7.71 (d, J=2.4 Hz, 1H), 7.29 (d, J=8.6 Hz, 1H), 4.00 (d, J=7.0 Hz, 2H), 3.59 (s, 3H), 3.27 (q, J=7.3 Hz, 2H), 3.09 (s, 3H), 1.26 (m, 1H), 1.12 (t, J=7.3 Hz, 3H), 0.56 (m, 2H), 0.35 (m, 2H). MS (ESI+) m/z 440.9 (M+H)$^+$.

Example 340

5-{2-[(cyclopropylmethyl)amino]-5-(methylsulfonyl)phenyl}-4-ethoxy-1-methylpyridin-2(1H)-one Example 340 was prepared according to the procedure used for the preparation of Example 327D, substituting Example 368B for Example 327C and Example 327B for Example 269B, respectively. Purification by reverse phase HPLC (C18, CH$_3$CN/water (0.1% TFA), 10-100%) afforded the title compound as the trifluoroacetic acid salt. $^1$H NMR (300 MHz, DMSO-$d_6$) δ 7.62 (dd, J=2.3, 8.8 Hz, 1H), 7.57 (s, 1H), 7.35 (d, J=2.3 Hz, 1H), 6.76 (d, J=8.8 Hz, 1H), 5.90 (s, 1H), 3.99 (q, J=7.0 Hz, 2H), 3.38 (s, 3H), 3.07 (s, 3H), 3.04 (d, J=6.1 Hz, 2H), 1.18 (t, J=7.0 Hz, 3H), 1.05 (m, 1H), 0.42 (dd, J=2.1, 6.0 Hz, 2H), 0.19 (m, 2H). MS (ESI+) 377.1.

Example 341

5-{2-[(cyclopropylmethyl)amino]-5-(methylsulfonyl)phenyl}-4-[(3-hydroxy-2,3-dimethylbutan-2-yl)oxy]-1-methylpyridin-2(1H)-one Example 341 is prepared according to the procedure used for the preparation of Example 286, substituting 1,1,2,2- tetramethylethane-1-2-diol for 2-morpholinoethanol, and Example 327D for Example 278A, respectively. $^1$H NMR (300 MHz, CDCl$_3$) δ 7.83 (dd, J=2.4, 8.8 Hz, 1H), 7.62 (d, J=2.0 Hz, 1H), 7.54 (s, 1H), 6.76 (m, 2H), 4.24 (bds, 1H), 3.52 (s, 3H), 3.06 (s, 3H), 3.03 (d, J=6.1 Hz, 2H), 1.55 (s, 12H), 0.96 (m, 1H), 0.52 (m, 2H), 0.19 (m, 2H). MS (ESI+) 449.0.

Example 342

N-{4-(2,4-difluorophenoxy)-3-[1-methyl-4-(1-methyl-1H-pyrazol-4-yl)-6-oxo-1,6-dihydropyridin-3-yl]phenyl}ethanesulfonamide Example 342 was prepared according to the procedure used for the preparation of Example 1B, substituting 1-methyl-4-(4,4,5,5-tetramethyl-1,3,2-dioxaborolan-2-yl)-1H-pyrazole for 2-phenoxyphenylboronic acid, and Example 278A for Example 1A, respectively. The reaction mixture was heated at 140° C. instead of 120° C., to provide the trifluoroacetic acid salt of the title compound. $^1$H NMR (500 MHz, DMSO-d$_6$) δ 9.76 (d, J=2.7 Hz, 1H), 7.81 (s, 1H), 7.67 (s, 1H), 7.30-7.41 (m, 1H), 7.26 (s, 1H), 7.19 (ddd, J=13.8, 8.8, 2.7 Hz, 1H), 6.93-7.07 (m, 2H), 6.88 (s, 1H), 6.76 (dd, J=21.7, 8.8 Hz, 1H), 6.46-6.66 (m, 1H), 6.35 (s, 1H), 3.70 (s, 3H), 3.47 (s, 3H), 3.04 (q, J=7.3 Hz, 2H), 1.13 (d, J=7.3 Hz, 3H). MS (ESI+) m/z 501.1 (M+H)$^+$.

Example 343

N-[4-(2,4-difluorophenoxy)-3-(4-ethoxy-1-methyl-6-oxo-1,6-dihydropyridin-3-yl)phenyl]naphthalene-1-sulfonamide Example 343 was prepared according to the procedure used for the preparation of Example 307, substituting naphthalene-1-sulfonyl chloride for 4-(methylsulfonyl)benzenesulfonyl chloride. $^1$H NMR (400 MHz, DMSO-d$_6$/D$_2$O) δ 8.69-8.63 (m, 1H), 8.25 (d, J=8.2 Hz, 1H), 8.21 (d, J=7.3 Hz, 1H), 8.10 (d, J=7.2 Hz, 1H), 7.77-7.61 (m, 3H), 7.30-7.23 (m, 2H), 7.00-6.94 (m, 2H), 6.91-6.80 (m, 2H), 6.72 (d, J=8.7 Hz, 1H), 5.77 (s, 1H), 3.84 (q, J=7.0 Hz, 2H), 3.32 (s, 3H), 1.03 (t, J=6.9 Hz, 3H). MS (APCI+) m/z 563.0 (M+H)$^+$.

Example 344

N-[4-(2,4-difluorophenoxy)-3-(4-ethoxy-1-methyl-6-oxo-1,6-dihydropyridin-3-yl)phenyl]benzenesulfonamide Example 344 was prepared according to the procedure used for the preparation of Example 307, substituting benzenesulfonyl chloride for 4-(methylsulfonyl)benzenesulfonyl chloride. $^1$H NMR (400 MHz, DMSO-d$_6$/D$_2$O) δ 7.75 (d, J=8.9 Hz, 2H), 7.76-7.72 (m, 2H), 7.70-7.60 (m, 1H), 7.58 (t, J=7.6 Hz, 2H), 7.43 (s, 1H), 7.39-7.26 (m, 1H), 7.10-6.88 (m, 4H), 6.80 (d, J=8.7 Hz, 1H), 5.80 (s, 1H), 3.89 (q, J=7.0 Hz, 2H), 3.35 (s, 3H), 1.11 (t, J=6.9 Hz, 3H). MS (APCI+) m/z 513.0 (M+H)$^+$.

Example 345

N-[4-(2,4-difluorophenoxy)-3-(1-methyl-4-{1-[2-(morpholin-4-yl)ethyl]-1H-pyrazol-4-yl}-6-oxo-1,6-dihydropyridin-3-yl)phenyl]ethanesulfonamide Example 345 was prepared according to the procedure used for the preparation of Example 1B, substituting 4-(2-(4-(4,4,5,5-tetramethyl-1,3,2-dioxaborolan-2-yl)-1H-pyrazol-1-yl)ethyl)morpholine for 2-phenoxyphenylboronic acid, and Example 278A for Example 1A, respectively. The reaction mixture was heated at 140° C. instead of 120° C., to provide the trifluoroacetic acid salt of the title compound. $^1$H NMR (300 MHz, DMSO-d$_6$) δ 9.79 (s, 1H), 7.84-7.67 (m, 1H), 7.44-7.32 (m, 1H), 7.26-7.12 (m, 1H), 7.10-6.94 (m, 2H), 6.85-6.52 (m, 2H), 4.44-4.36 (m, 1H), 3.67 (bs, 2H), 3.32-2.90 (m, 9H), 1.25-1.14 (m, 3H). MS (ESI+) m/z 600.2 (M+H)$^+$.

Example 346

N-{4-(2,4-difluorophenoxy)-3-[1-methyl-6-oxo-4-(1H-pyrazol-1-yl)-1,6-dihydropyridin-3-yl]phenyl}ethanesulfonamide The trifluoroacetic acid salt of Example 346 was prepared according to the procedure used for the preparation of Example 286, substituting imidazole for 2-morpholinoethanol. $^1$H NMR (500 MHz, DMSO-d$_6$) δ 9.75 (s, 1H), 7.94 (s, 1H), 7.65 (d, J=2.6 Hz, 1H), 7.62 (d, J=1.7 Hz, 1H), 7.36 (ddd, J=11.2, 8.6, 2.8 Hz, 1H), 7.17-7.10 (m, 2H), 7.05-6.94 (m, 1H), 6.67-6.55 (m, 3H), 6.42-6.38 (m, 1H), 3.50 (s, 3H), 3.06 (q, J=7.3 Hz, 2H), 1.19 (t, J=7.3 Hz, 3H). MS (ESI+) m/z 487.1 (M+H)$^+$.

Example 347

N-[4-(2,4-difluorophenoxy)-3-(4-ethoxy-1-methyl-6-oxo-1,6-dihydropyridin-3-yl)phenyl]-4-(propan-2-yl)benzenesulfonamide Example 347 was prepared according to the procedure used for the preparation of Example 307, substituting 4-(propan-2-yl)benzenesulfonyl chloride for 4-(methylsulfonyl)benzenesulfonyl chloride. $^1$H NMR (400 MHz, DMSO-d$_6$/D$_2$O) δ 7.71-7.65 (m, 2H), 7.48-7.43 (m, 2H), 7.43 (s, 1H), 7.31 (ddd, J=11.2, 8.6, 2.8 Hz, 1H), 7.10-6.77 (m, 5H), 5.80 (s, 1H), 3.89 (q, J=7.0 Hz, 2H), 3.35 (s, 3H), 3.01-2.90 (m, 1H), 1.19 (d, J=6.9 Hz, 6H), 1.10 (t, J=6.9 Hz, 3H). MS (APCI+) m/z 555.0 (M+H)$^+$.

Example 348

4-chloro-N-[4-(2,4-difluorophenoxy)-3-(4-ethoxy-1-methyl-6-oxo-1,6-dihydropyridin-3-yl)phenyl]-2-fluorobenzenesulfonamide Example 348 was prepared according to the procedure used for the preparation of Example 307, substituting 4-chloro-2-fluorobenzenesulfonyl chloride for 4-(methylsulfonyl)benzenesulfonyl chloride. $^1$H NMR (400 MHz, DMSO-d$_6$/D$_2$O) δ 7.81 (t, J=8.1 Hz, 1H), 7.71-7.63 (m, 1H), 7.49-7.42 (m, 2H), 7.35-7.26 (m, 1H), 7.08-6.88 (m, 5H), 6.80 (d, J=8.9 Hz, 1H), 5.80 (s, 1H), 3.89 (q, J=6.9 Hz, 2H), 3.35 (s, 4H), 1.09 (t, J=6.9 Hz, 3H). MS (APCI+) m/z 564.9 (M+H)$^+$.

Example 349

N-[4-(2,4-difluorophenoxy)-3-(4-ethoxy-1-methyl-6-oxo-1,6-dihydropyridin-3-yl)phenyl]propane-1-sulfonamide Example 349 was prepared according to the procedure used for the preparation of Example 307, substituting 1-propylsulfonyl chloride for 4-(methylsulfonyl)benzenesulfonyl chloride. $^1$H NMR (400 MHz, DMSO-d$_6$/D$_2$O) δ 7.59 (s, 1H), 7.37-7.28 (m, 1H), 7.20-7.09 (m, 2H), 7.07-6.95 (m, 2H), 6.90 (d, J=8.7 Hz, 1H), 5.82 (s, 1H), 3.93 (q, J=7.0 Hz, 2H), 3.37 (s, 3H), 3.09-3.02 (m, 2H), 1.75-1.65 (m, 3H), 1.15 (t, J=6.9 Hz, 3H), 0.96 (t, J=7.4 Hz, 3H). MS (APCI+) m/z 479.0 (M+H)$^+$.

Example 350

1-(2-chloro-5-fluorophenyl)-N-[4-(2,4-difluorophenoxy)-3-(4-ethoxy-1-methyl-6-oxo-1,6-dihydropyridin-3-yl)phenyl]methanesulfonamide Example 350 was prepared according to the procedure used for the preparation of Example 311, substituting 2-chloro-5-fluorophenylmethanesulfonyl chloride for phenylmethanesulfonyl chloride. $^1$H NMR (300 MHz, DMSO-d$_6$) δ 10.96 (m, 1H), 9.79 (bds, 1H), 7.50 (s, 1H), 7.44-7.25 (m, 7H), 7.12-6.99 (m, 3H), 6.91 (dd, J=7.0, 5.7 Hz, 1H), 6.85 (d, J=8.7 Hz, 1H), 6.55 (dd, J=7.0, 1.2 Hz, 1H), 4.47 (s, 2H), 4.09 (s, 3H). MS (ESI) 522.1 (M+H+).

Example 351

N-[4-(2,4-difluorophenoxy)-3-(4-ethoxy-1-methyl-6-oxo-1,6-dihydropyridin-3-yl)phenyl]-1-(2-fluorophenyl)methanesulfonamide Example 351 was prepared according to the procedure used for the preparation of Example 311, substituting 2-fluorophenylmethanesulfonyl chloride for phenylmethanesulfonyl chloride. $^1$H NMR (500 MHz, DMSO-d$_6$) δ 10.00 (s, 1H), 7.56 (s, 1H), 7.45-7.35 (m, 3H), 7.25-7.17 (m, 2H), 7.14 (dd, J=8.7, 2.7 Hz, 1H), 7.10 (d, J=2.7 Hz, 1H), 7.05 (m, 1H), 6.98 (td, J=9.1, 5.5 Hz, 1H), 6.89 (d, J=8.8 Hz, 1H), 5.80 (s, 1H), 4.53 (s, 2H), 3.93 (q, J=6.9 Hz, 2H), 3.36 (s, 3H), 1.15 (t, J=6.9 Hz, 3H). MS (ESI) 545.1 (M+H+).

Example 352

N-[4-(2,4-difluorophenoxy)-3-(5-fluoro-1-methyl-6-oxo-1,6-dihydropyridin-3-yl)phenyl]ethanesulfonamide Example 352A Example 352A was prepared according to the procedure used for the preparation of Example 1A, substituting 5-bromo-3-fluoropyridin-2-ol for 6-chloropyridazin-3(2H)-one, to provide the title compound.

Example 352B 5-(5-amino-2-(2,4-difluorophenoxy)phenyl)-3-fluoro-1-methylpyridin-2(1H)-one Example 352B was prepared according to the procedure used for the preparation of Example 1B, substituting Example 5D for 2-phenoxyphenylboronic acid, and Example 352A for Example 1A, respectively, to provide the title compound.

Example 352C

N-[4-(2,4-difluorophenoxy)-3-(5-fluoro-1-methyl-6-oxo-1,6-dihydropyridin-3-yl)phenyl]ethanesulfonamide Example 352C was prepared according to the procedure used for the preparation of Example 22, substituting Example 352B for Example 20C, and ethanesulfonyl chloride for methanesulfonyl chloride, respectively, to provide the title compound. $^1$H NMR (500 MHz, DMSO-d$_6$) δ 9.79 (s, 1H), 7.79 (d, J=2.2 Hz, 1H), 7.60 (dd, J=11.1, 2.3 Hz, 1H), 7.45 (ddd, J=11.2, 8.6, 2.8 Hz, 1H), 7.26 (d, J=2.7 Hz, 1H), 7.13-7.24 (m, 2H), 7.04-7.12 (m, 1H), 6.86 (d, J=8.7 Hz, 1H), 3.55 (s, 3H), 3.12 (q, J=7.3 Hz, 2H), 1.22 (t, J=7.3 Hz, 3H). MS (ESI+) m/z 439.1 (M+H)$^+$.

Example 353

N-[3-{4-[(cyclopropylmethyl)amino]-1-methyl-6-oxo-1,6-dihydropyridin-3-yl}-4-(2,4-difluorophenoxy)phenyl]ethanesulfonamide Example 353A 5-bromo-4-((cyclopropylmethyl)amino)-1-methylpyridin-2(1H)-one A mixture of Example 269B (0.044 g, 0.2 mmol) and cyclopropylmethanamine (0.043 g, 0.600 mmol) in dioxane (1 mL) was heated at 100° C. for 2 days. The solvent was evaporated, and the residue was purified by flash chromatography on silica gel to give the title compound (0.042 g, 0.163 mmol, 82% yield).

Example 353B 5-(5-amino-2-(2,4-difluorophenoxy)phenyl)-4-((cyclopropylmethyl)amino)-1-methylpyridin-2(1H)-one Example 353B was prepared according to the procedure used for the preparation of Example 1B, substituting Example 5D for 2-phenoxyphenylboronic acid, and Example 353A for Example 1A, respectively, to provide the title compound.

Example 353C

N-[3-{4-[(cyclopropylmethyl)amino]-1-methyl-6-oxo-1,6-dihydropyridin-3-yl}-4-(2,4-difluorophenoxy)phenyl]ethanesulfonamide Example 353C was prepared according to the procedure used for the preparation of Example 22, substituting Example 353B for Example 20C, and ethanesulfonyl chloride for methanesulfonyl chloride, respectively, to provide the title compound. $^1$H NMR (500 MHz, DMSO-d$_6$) δ 9.68 (s, 1H), 7.37 (s, 1H), 7.22-7.26 (m, 1H), 7.06-7.11 (m, 1H), 6.94 (d, J=2.75 Hz, 1H), 6.89-6.93 (m, 1H), 6.83-6.90 (m, 1H), 6.75 (d, J=8.85 Hz, 1H), 5.74 (s, 1H), 5.42 (s, 3H), 3.23 (s, 3H), 2.97 (q, J=7.32 Hz, 2H), 2.77 (d, J=5.96 Hz, 2H), 1.07 (t, J=7.32 Hz, 3H), 0.78-0.83 (m, 1H), 0.22 (t, J=7.32 Hz, 3H). MS (ESI+) m/z 490.1 (M+H)⁺.

Example 354

N-[4-(2,4-difluorophenoxy)-3-(1-methyl-6-oxo-4-propoxy-1,6-dihydropyridin-3-yl)phenyl]ethanesulfonamide Example 354 was prepared according to the procedure used for the preparation of Example 286, substituting propan-1-ol for 2-morpholinoethanol, to provide the title compound ¹H NMR (300 MHz, DMSO-d₆) δ 9.76 (s, 1H), 7.59 (s, 1H), 7.26-7.40 (m, 1H), 7.19 (dd, J=8.7, 2.7 Hz, 1H), 7.13 (d, J=2.7 Hz, 1H), 6.83-7.04 (m, 3H), 5.78 (s, 1H), 3.72-3.89 (t, J=7.3 Hz, 2H), 3.46 (s, 3H), 2.97-3.24 (q, J=7.3 Hz, 2H), 1.41-1.69 (sextet, J=7.3 Hz, 2H), 1.12-1.30 (t, J=7.3 Hz, 3H), 0.72-0.90 (t, J=7.3 Hz, 3H). MS (ESI+) m/z 479.0 (M+H)⁺.

Example 355

N-{4-(2,4-difluorophenoxy)-3-[1-methyl-6-oxo-4-(2,2,2-trifluoroethoxy)-1,6-dihydropyridin-3-yl]phenyl}ethanesulfonamide Example 355 was prepared according to the procedure used for the preparation of Example 286, substituting 2,2,2-trifluoroethanol for 2-morpholinoethanol, to provide the title compound ¹H NMR (300 MHz, DMSO-d₆) δ 9.77 (s, 1H), 7.69 (s, 1H), 7.30-7.41 (m, 1H), 7.20 (dd, J=8.7, 2.7 Hz, 1H), 7.13 (d, J=2.7 Hz, 1H), 6.86-7.05 (m, 3H), 6.03 (s, 1H), 4.70 (q, J=8.8 Hz, 2H), 3.37 (s, 3H), 3.07 (q, J=7.3 Hz, 2H), 1.20 (t, J=7.3 Hz, 3H). MS (ESI+) m/z 519.0 (M+H)⁺.

Example 356

5-[2-(cyclopropylmethoxy)-6-methylphenyl]-1-methylpyridin-2(1H)-one

Example 356A. 2-bromo-1-(cyclopropylmethoxy)-3-methyl-4-nitrobenzene. A flask with stirbar was charged with 2-bromo-3-methyl-4-nitrophenol (1.15 g, 4.96 mmol), (bromomethyl)cyclopropane (0.60 mL, 6.19 mmol) and cesium carbonate (2.65 g, 8.13 mmol) in dimethylformamide (16 mL). The mixture was stirred overnight at ambient temperature. The mixture was then heated to 50° C. in an oil bath for 3 hours, cooled and shaken in a separatory funnel with 100 mL each of ethyl acetate and saturated aqueous sodium chloride. The organics were washed twice with saturated aqueous sodium chloride and dried over anhydrous sodium sulfate. Filtration and solvent removal provided the title compound.

Example 356B

5-[2-(cyclopropylmethoxy)-6-methylphenyl]-1-methylpyridin-2(1H)-one

Example 356B was prepared according to the procedure used for the preparation of Example 327D, substituting 1-methyl-5-(4,4,5,5-tetramethyl-1,3,2-dioxaborolan-2-yl)pyridin-2(1H)-one for Example 327C and Example 356A for Example 269B, respectively, to provide the title compound. ¹H NMR (300 MHz, DMSO-d₆) δ ppm 7.59 (d, J=2.0 Hz, 1H), 7.29 (dd, J=9.2, 2.4 Hz, 1H), 7.16 (m, 1H), 6.87 (d, J=8.5 Hz, 1H), 6.41 (d, J=9.8 Hz, 1H), 3.77 (m, 2H), 3.46 (s, 3H), 2.14 (m, 3H), 1.08 (m, 1H), 0.46 (m, 2H), 0.22 (m, 2H). MS (DCI+) m/z 270.0 (M+H)⁺.

Example 357

3-amino-5-[2-(cyclopropylmethoxy)-5-(ethylsulfonyl)phenyl]-1-methylpyridin-2(1H)-one The trifluoroacetic acid salt of Example 357 was prepared according to the procedure used for the preparation of Example 1B, substituting Example 275D for 2-phenoxyphenylboronic acid, and 3-amino-5-bromo-1-methylpyridin-2(1H)-one for Example 1A, respectively. ¹H NMR (400 MHz, DMSO-d₆) δ 7.75 (dd, J=2.4, 6 Hz, 1H) 7.71 (d, J=2 Hz, 1H), 7.42 (d, J=1.6 Hz, 1H), 7.28 (d, J=8.8 Hz, 1H), 6.93 (d, J=2.4 Hz, 1H), 3.95 (d, J=6.8 Hz, 2H), 3.46 (s, 3H), 3.66 (q, J=7.3 Hz, 2H), 1.19-1.35 (m, 1H), 1.04 (t, J=7.3 Hz, 3H), 0.47-0.66 (m, 2H), 0.24-0.46 (m, 2H). MS (ESI+) m/z 363.1 (M+H)⁺.

Example 358

N-[4-(4-cyanophenoxy)-3-(4-ethoxy-1-methyl-6-oxo-1,6-dihydropyridin-3-yl)phenyl]ethanesulfonamide Example 358A 4-(4-amino-2-(4-ethoxy-1-methyl-6-oxo-1,6-dihydropyridin-3-yl)phenoxy)benzonitrile Example 358A was prepared according to the procedure used for the preparation of Example 1B, substituting Example 294D for 2-phenoxyphenylboronic acid, and Example 368A for Example 1A, respectively, to provide the title compound.

Example 358B

N-[4-(4-cyanophenoxy)-3-(4-ethoxy-1-methyl-6-oxo-1,6-dihydropyridin-3-yl)phenyl]ethanesulfonamide Example 358B was prepared according to the procedure used for the preparation of Example 22, substituting Example 358A for Example 20C, and ethanesulfonyl chloride for methanesulfonyl chloride, respectively, to provide the title compound. ¹H NMR (300 MHz, DMSO-d₆) δ 9.88 (s, 1H), 7.71-7.78 (m, 2H), 7.55 (s, 1H), 7.26 (dd, J=8.7, 2.7 Hz, 1H), 7.18 (d, J=2.6 Hz, 1H), 7.15 (d, J=8.7 Hz, 1H), 6.92-6.99 (m, 2H), 5.74 (s, 1H), 3.84 (q, J=7.0 Hz, 2H), 3.30 (s, 3H), 3.15 (q, J=7.3 Hz, 2H), 1.24 (t, J=7.3 Hz, 3H), 1.06 (t, J=6.9 Hz, 3H). MS (ESI+) m/z 454.0 (M+H)⁺.

Example 359

N-[4-(2,4-difluorophenoxy)-3-(1-methyl-6-oxo-4-propyl-1,6-dihydropyridin-3-yl)phenyl]ethanesulfonamide Example 329 (0.056 g, 0.122 mmol) and palladium on carbon (0.013 g, 0.122 mmol) were stirred in ethyl acetate (10 mL) then subjected to hydrogen gas for 22 hours. The mixture was filtered through diatomaceous earth then concentrated under reduced pressure. The residue was purified by reverse phase HPLC (C18, CH₃CN/water (0.1% TFA), 0-100%) to afford 4.1 mg (7%) of the title compound. ¹H NMR (300 MHz, DMSO-d₆) δ 9.77 (s, 1H), 7.55 (s, 1H), 7.32-7.44 (m, 1H), 7.21 (dd, J=8.8, 2.7 Hz, 1H), 6.99-7.13 (m, 3H), 6.88 (d, J=8.7 Hz, 1H), 6.24 (s, 1H), 3.43 (s, 3H), 3.08 (q, J=7.3 Hz, 2H), 2.26 (t, J=7.8 Hz, 2H), 1.35 (sextet, J=7.5 Hz, 2H), 1.19 (t, J=7.3 Hz, 3H), 0.74 (t, J=7.3 Hz, 3H). MS (ESI+) m/z 463.0 (M+H)⁺.

Example 360

5-{5-(ethylsulfonyl)-2-[(cis-4-methoxy-4-methylcyclohexyl)oxy]phenyl}-1-methylpyridin-2(1H)-one Example 360A 8-(2-bromo-4-(ethylsulfonyl)phenoxy)-1,4-dioxaspiro[4.5]decane Example 360A was prepared according to the procedure used for the preparation of Example 247A, substituting Example 275B for Example 225A, and 1,4-dioxaspiro[4.5]decan-8-ol for cyclohexanol, respectively, to provide the title compound.

Example 360B 4-(2-bromo-4-(ethylsulfonyl)phenoxy)cyclohexanone

Example 360A (1.2 g, 2.96 mmol) in tetrahydrofuran (15 mL) was treated with hydrogen chloride (5.92 mL, 29.6 mmol). The reaction mixture was heated at 60° C. for 2 hours. The solvent was evaporated, and the residue was taken into ethyl acetate. It was washed with saturated aqueous sodium chloride, dried over anhydrous magnesium sulfate, filtered, and concentrated. The residue was purified by flash chromatography on silica gel eluting with 1:1 ethyl acetate/hexanes to give the title compound (0.95 g, 2.63 mmol, 89% yield).

Example 360C (cis)-4-(2-bromo-4-(ethylsulfonyl)phenoxy)-1-methylcyclohexanol

Example 360B (0.95 g, 2.63 mmol) in tetrahydrofuran (15 mL) was cooled to 0° C. This solution was treated with 3.0 M methylmagnesium bromide (2.63 mL, 7.89 mmol). The reaction mixture was stirred at room temperature. overnight. The reaction mixture was quenched with saturated NH₄Cl solution and partitioned between water and ethyl acetate. Aqueous layer was separated and extracted with additional ethyl acetate twice. The combined organic layers were washed with saturated aqueous sodium chloride, dried over anhydrous magnesium sulfate, filtered and concentrated. The residue was purified by flash column chromatography on silica gel eluting with 1:1 ethyl acetate/hexanes to give two fractions. Example 360C was the first fraction from the column.

Example 360D 2-bromo-4-(ethylsulfonyl)-1-((cis)-4-methoxy-4-methylcyclohexyloxy)benzene Example 360C (0.43 g, 1.140 mmol) in tetrahydrofuran (5 mL) was treated with 60% sodium hydride (0.182 g, 4.5 mmol). The reaction mixture was stirred at ambient temperature for 10 minutes. To this solution was added iodomethane (0.65 g, 4.5 mmol). The reaction mixture was heated at 40° C. for 16 ours. The reaction mixture was partitioned between water and ethyl acetate. The aqueous layer was extracted with additional ethyl acetate two more times. The combined organic layers were washed with saturated aqueous sodium chloride, dried over anhydrous magnesium sulfate, filtered, and concentrated. The residue was purified by flash chromatography on silica gel to give the title compound (0.356 g, 0.910 mmol, 80% yield).

Example 360E

5-{5-(ethylsulfonyl)-2-[(cis-4-methoxy-4-methylcyclohexyl)oxy]phenyl}-1-methylpyridin-2(1H)-one Example 360E was prepared according to the procedure used for the preparation of Example 1B, substituting 1-methyl-5-(4,4,5,5-tetramethyl-1,3,2-dioxaborolan-2-yl)pyridin-2(1H)-one for 2-phenoxyphenylboronic acid, and Example 360D for Example 1A, respectively, to provide the title compound. ¹H NMR (500 MHz, DMSO-d₆) δ 7.92 (s, 1H), 7.73-7.77 (m, 2H), 7.66 (dd, J=9.31, 2.59 Hz, 1H), 7.36 (d, J=8.85 Hz, 1H), 6.43 (d, J=9.46 Hz, 1H), 4.51-4.56 (m, 1H), 3.49 (s, 3H), 3.28 (q, J=7.32 Hz, 2H), 3.07 (s, 3H), 1.75-1.83 (m, 4H), 1.56-1.63 (m 2H), 1.37-1.43 (m, 2H), 1.12 (t, J=7.32 Hz, 3H), 1.09 (s, 3H). MS (ESI+) m/z 420.1 (M+H)⁺.

Example 361

N-{5-[2-(cyclopropylmethoxy)-5-(ethylsulfonyl)phenyl]-1-methyl-2-oxo-1,2-dihydropyridin-3-yl}acetamide Example 361 was prepared according to the procedure used for the preparation of Example 11, substituting acetic chloride for 4-methylbenzene-1-sulfonyl chloride, and Example 357 for Example 10, to provide the title compound. ¹H NMR (300 MHz, DMSO-d₆) δ 9.28 (s, 1H), 8.56 (d, J=2.4 Hz, 1H), 7.78 (dd, J=8.6, 2.4 Hz, 1H), 7.72 (d, J=2.4 Hz, 1H), 7.69 (d, J=2.4 Hz, 1H), 7.30 (d, J=8.7 Hz, 1H), 4.01 (d, J=6.8 Hz, 2H), 3.58 (s, 3H), 3.27 (q, J=7.5 Hz, 2H), 2.14 (s, 3H), 1.25 (m, 1H), 1.11 (t, J=7.5 Hz, 3H), 0.52 (m, 2H), 0.35 (m, 2H). MS (ESI+) m/z 404.9 (M+H)⁺.

Example 362

N-{3-[4-(cyclopropylamino)-1-methyl-6-oxo-1,6-dihydropyridin-3-yl]-4-(2,4-difluorophenoxy)phenyl}ethanesulfonamide Example 362A 5-bromo-4-(cyclopropylamino)-1-methylpyridin-2(1H)-one Example 362A was prepared according to the procedure used for the preparation of Example 353A, substituting cyclopropanamine for cyclopropylmethanamine, to provide the title compound.

Example 362B 5-(5-amino-2-(2,4-difluorophenoxy)phenyl)-4-(cyclopropylamino)-1-methylpyridin-2(1H)-one Example 362B was prepared according to the procedure used for the preparation of Example 1B, substituting Example 5D for 2-phenoxyphenylboronic acid, and Example 362A for Example 1A, respectively, to provide the title compound.

Example 362C

N-{3-[4-(cyclopropylamino)-1-methyl-6-oxo-1,6-dihydropyridin-3-yl]-4-(2,4-difluorophenoxy)phenyl}ethanesulfonamide Example 362C was prepared according to the procedure used for the preparation of Example 22, substituting Example 362B for Example 20C, and ethanesulfonyl chloride for methanesulfonyl chloride, respectively, to provide the title compound. $^1$H NMR (500 MHz, DMSO-$d_6$) δ 9.81 (s, 1H), 7.48 (s, 1H), 7.35-7.41 (m, 1H), 7.19-7.26 (m, 2H), 7.11 (d, J=2.75 Hz, 1H), 7.02-7.07 (m, 1H), 6.91 (d, J=8.85 Hz, 1H), 6.16 (s, 1H), 5.64 (s, 1H), 3.36 (s, 3H), 3.07 (q, J=7.32 Hz, 2H), 2.32-2.34 (m, 1H), 1.22 (t, J=7.32 Hz, 3H), 0.72-0.76 (m, 2H), 0.50-0.53 (m, 2H). MS (LC/MS, APCI+) m/z 476.4 (M+H)$^+$.

Example 363

N-{4-(2,4-difluorophenoxy)-3-[4-(ethylamino)-1-methyl-6-oxo-1,6-dihydropyridin-3-yl]phenyl}ethanesulfonamide

Example 363A 5-bromo-4-(ethylamino)-1-methylpyridin-2(1H)-one

Example 363A was prepared according to the procedure used for the preparation of Example 353A, substituting ethylamine for cyclopropylmethanamine, to provide the title compound.

Example 363B 5-(5-amino-2-(2,4-difluorophenoxy)phenyl)-4-(ethylamino)-1-methylpyridin-2(1H)-one Example 363B was prepared according to the procedure used for the preparation of Example 1B, substituting Example 5D for 2-phenoxyphenylboronic acid, and Example 363A for Example 1A, respectively, to provide the title compound.

Example 363C

N-{4-(2,4-difluorophenoxy)-3-[4-(ethylamino)-1-methyl-6-oxo-1,6-dihydropyridin-3-yl]phenyl}ethanesulfonamide Example 363C was prepared according to the procedure used for the preparation of Example 22, substituting Example 363B for Example 20C, and ethanesulfonyl chloride for methanesulfonyl chloride, respectively, to provide the title compound. $^1$H NMR (500 MHz, DMSO-$d_6$) δ 9.84 (s, 1H), 7.49 (s, 1H), 7.36-7.42 (m, 1H), 7.19-7.26 (m, 2H), 7.11 (d, J=2.75 Hz, 1H), 7.02-7.07 (m, 1H), 6.91 (d, J=8.85 Hz, 1H), 5.81 (s, 1H), 5.46 (s, 3H), 3.36 (s, 3H), 3.02-3.06 (m, 4H), 1.22 (t, J=7.32 Hz, 3H), 1.01 (t, J=7.17 Hz, 3H). MS (ESI+) m/z 460.0 (M+H)$^+$.

Example 364

5-[2-(2,4-difluorophenoxy)-5-(propan-2-ylsulfonyl)phenyl]-1-methylpyridin-2(1H)-one

Example 364A

Example 364A was prepared according to the procedure used for the preparation of Example 275A, substituting 2-iodopropane for iodoethane, to provide the title compound.

Example 364B 2-bromo-1-fluoro-4-(isopropylsulfonyl)benzene

Example 364B was prepared according to the procedure used for the preparation of Example 275B, substituting Example 364A for Example 275A, to provide the title compound.

Example 364C 2-bromo-1-(2,4-difluorophenoxy)-4-(isopropylsulfonyl)benzene

A mixture of Example 364B (0.562 g, 2 mmol), 2,4-difluorophenol (0.260 g, 2.000 mmol), and cesium carbonate (0.652 g, 2.000 mmol) in dimethyl sulfoxide (10 mL) was heated at 110° C. overnight. After cooling, the reaction mixture was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated. The residue was purified by flash chromatography on silica gel eluting 3:1 hexanes/ethyl acetate to give the title compound (0.73 g, 1.866 mmol, 93% yield).

Example 364D

5-[2-(2,4-difluorophenoxy)-5-(propan-2-ylsulfonyl)phenyl]-1-methylpyridin-2(1H)-one Example 364D was prepared according to the procedure used for the preparation of Example 1B, substituting 1-methyl-5-(4,4,5,5-tetramethyl-1,3,2-dioxaborolan-2-yl)pyridin-2(1H)-one for 2-phenoxyphenylboronic acid, and Example 364C for Example 1A, respectively, to provide the title compound. $^1$H NMR (500 MHz, DMSO-$d_6$) δ 8.05 (d, J=2.44 Hz, 1H), 7.88 (d, J=2.44 Hz, 1H), 7.73-7.79 (m, 2H), 7.47-7.58 (m, 2H), 7.19-7.24 (m, 1H), 6.96 (d, J=8.54 Hz, 1H), 6.48 (d, J=9.46 Hz, 1H), 3.52 (s, 3H), 1.18 (d, J=6.71 Hz, 6H). MS (ESI+) m/z 420.1 (M+H)$^+$.

Example 365

N-[4-(cyclopropylmethoxy)-2-methyl-3-(1-methyl-6-oxo-1,6-dihydropyridin-3-yl)phenyl]ethanesulfonamide

Example 365A 2-bromo-1-(cyclopropylmethoxy)-3-methyl-4-nitrobenzene

A flask with stirbar was charged with 2-bromo-3-methyl-4-nitrophenol (Parkway Scientific, 1.15 g, 4.96 mmol), (bromomethyl)cyclopropane (0.60 mL, 6.19 mmol) and cesium carbonate (2.65 g, 8.13 mmol) in dimethylformamide (16 mL). The mixture was stirred overnight at ambient temperature. The mixture was then heated to 50° C. in an oil bath. After 3 hours, the mixture was cooled and shaken in a separatory funnel with 100 mL each of ethyl acetate and saturated aqueous sodium chloride. The organics were washed twice with saturated aqueous sodium chloride, dried over anhydrous sodium sulfate, filtered and concentrated. The crude product was purified by flash chromatography (silica gel, 0-30% ethyl acetate in hexanes) to provide 1.24 g (87%) of the title compound

Example 365B 5-(6-(cyclopropylmethoxy)-2-methyl-3-nitrophenyl)-1-methylpyridin-2(1H)-one Example 365B was prepared according to the procedure used for the preparation of Example 327D, substituting 1-methyl-5-(4,4,5,5-tetramethyl-1,3,2-dioxaborolan-2-yl)pyridin-2(1H)-one for Example 327C and Example 365A for Example 269B, respectively, to provide the title compound.

Example 365C 5-(3-amino-6-(cyclopropylmethoxy)-2-methylphenyl)-1-methylpyridin-2(1H)-one Example 365C was prepared according to the procedure used for the preparation of Example 10, substituting Example 365B for Example 9B, to provide the title compound.

Example 365D

N-[4-(cyclopropylmethoxy)-2-methyl-3-(1-methyl-6-oxo-1,6-dihydropyridin-3-yl)phenyl]ethanesulfonamide Example 365D was prepared according to the procedure used for the preparation of Example 311, substituting ethanesulfonyl chloride for phenylmethanesulfonyl chloride and Example 365C for Example 406B, respectively, to provide the title compound. $^1$H NMR (300 MHz, CD$_3$OD) δ ppm 7.55 (d, J=2.4 Hz, 1H), 7.43 (dd, J=9.2, 2.4 Hz, 1H), 7.27 (d, J=8.8 Hz, 1H), 6.87 (d, J=8.8 Hz, 1H), 6.64 (d, J=9.2 Hz, 1H), 3.80 (d, J=6.4 Hz, 2H), 3.64 (s, 3H), 3.11 (q, J=7.5 Hz, 2H), 2.20 (s, 3H), 1.39 (m, 3H), 1.10 (m, 1H), 0.50 (m, 2H), 0.22 (m, 2H). MS (ESI+) m/z 377.0 (M+H)+.

Example 366

N-[4-(cyclopropylmethoxy)-2-methyl-5-(1-methyl-6-oxo-1,6-dihydropyridin-3-yl)phenyl]ethanesulfonamide

Example 366A 2-bromo-1-(cyclopropylmethoxy)-5-methyl-4-nitrobenzene

Example 366A was prepared according to the procedure used for the preparation of Example 365A, substituting 2-bromo-5-methyl-4-nitrophenol for 2-bromo-3-methyl-4-nitrophenol, to provide the title compound.

Example 366B 5-(6-(cyclopropylmethoxy)-4-methyl-3-nitrophenyl)-1-methylpyridin-2(1H)-one Example 366B was prepared according to the procedure used for the preparation of Example 327D, substituting 1-methyl-5-(4,4,5,5-tetramethyl-1,3,2-dioxaborolan-2-yl)pyridin-2(1H)-one for Example 327C and Example 366A for Example 269B, respectively, to provide the title compound.

Example 366C 5-(3-amino-6-(cyclopropylmethoxy)-4-methylphenyl)-1-methylpyridin-2(1H)-one Example 366C was prepared according to the procedure used for the preparation of Example 10, substituting Example 366B for Example 9B, to provide the title compound.

Example 366D

N-[4-(cyclopropylmethoxy)-2-methyl-5-(1-methyl-6-oxo-1,6-dihydropyridin-3-yl)phenyl]ethanesulfonamide Example 366D was prepared according to the procedure used for the preparation of Example 311, substituting ethanesulfonyl chloride for phenylmethanesulfonyl chloride and Example 366C for Example 406B, respectively, to provide the title compound. $^1$H NMR (300 MHz, DMSO-d$_6$) δ ppm 8.89 (s, 1H), 7.84 (d, J=2.7 Hz, 1H), 7.61 (dd, J=9.5, 2.7 Hz, 1H), 7.10 (s, 1H), 6.93 (s, 1H), 6.42 (d, J=9.5 Hz, 1H), 3.85 (d, J=6.8 Hz, 2H), 3.48 (s, 3H), 3.06 (q, J=7.4 Hz, 2H), 2.31 (s, 3H), 1.26 (t, J=7.4 Hz, 3H), 1.22 (m, 1H), 0.55 (m, 2H), 0.30 (m, 2H). MS (ESI+) m/z 377.1 (M+H)+.

Example 367

N-{3-[4-(cyclobutyloxy)-1-methyl-6-oxo-1,6-dihydropyridin-3-yl]-4-(2,4-difluorophenoxy)phenyl}ethanesulfonamide Example 367 was prepared according to the procedure used for the preparation of Example 286, substituting cyclobutanol for 2-morpholinoethanol, to provide the title compound $^1$H NMR (300 MHz, DMSO-d$_6$) δ 9.77 (s, 1H), 7.62 (s, 1H), 7.33-7.45 (m, 1H), 7.12-7.22 (m, 2H), 6.99-7.10 (m, 2H), 6.91 (d, J=8.7 Hz, 1H), 5.62 (s, 1H), 4.60 (p, J=7.1 Hz, 1H), 3.34 (s, 3H), 3.12 (q, J=7.3 Hz, 2H), 2.20-2.38 (m, 2H), 1.73-1.92 (m, 2H), 1.43-1.72 (m, 2H), 1.23 (t, J=7.3 Hz, 3H). MS (ESI+) m/z 491.0 (M+H)$^+$.

Example 368

5-{2-[(2,2-difluorocyclopropyl)methoxy]-5-(ethylsulfonyl)phenyl}-4-ethoxy-1-methylpyridin-2(1H)-one

Example 368A 5-bromo-4-ethoxy-1-methylpyridin-2(1H)-one

Example 269B (10 g, 45.0 mmol) was combined with 2.0 N potassium ethoxide in ethanol (67.4 mL, 135 mmol) then heated at 80° C. for 1 hour. The solution was cooled to ambient temperature, water (150 mL) added, then the aqueous extracted with ethyl acetate. The combined organics were washed with saturated aqueous sodium chloride, dried (anhydrous magnesium sulfate), filtered, and concentrated. The residue was purified by flash chromatography on silica gel eluting with 0→2% methanol/CH$_2$Cl$_2$ to afford 9.25 g (89%) of the title compound.

Example 368B 4-ethoxy-1-methyl-5-(4,4,5,5-tetramethyl-1,3,2-dioxaborolan-2-yl)pyridin-2(1H)-one A mixture of Example 368A (2.5 g, 10.77 mmol), bis(pinacolato)diboron (4.10 g, 16.16 mmol), 2-(dicyclohexylphosphino)-2',4',6'-triisopropylbiphenyl (0.514 g, 1.077 mmol), tris(dibenzylideneacetone)dipalladium(0) (0.247 g, 0.269 mmol), and potassium acetate (2.326 g, 23.70 mmol) in dioxane (25 mL) was degassed and back-filled with nitrogen 10 time. The reaction mixture was heated at 80° C. overnight. After cooling, the reaction mixture was filtered through a pad of filtrating agent. The solvents were evaporated, and the residue was loaded onto a silica column and eluted with 2% methanol in ethyl acetate to give the title compound (1.75 g, 6.27 mmol, 58.2% yield).

Example 368C 2-bromo-1-((2,2-difluorocyclopropyl)methoxy)-4-(ethylsulfonyl)benzene Example 368C was prepared according to the procedure used for the preparation of Example 247A, substituting Example 275B for Example 225A, and substituting (2,2-difluorocyclopropyl)methanol for cyclohexanol, respectively, to provide the title compound.

Example 368D

5-{2-[(2,2-difluorocyclopropyl)methoxy]-5-(ethylsulfonyl)phenyl}-4-ethoxy-1-methylpyridin-2(1H)-one Example 368D was prepared according to the procedure used for the preparation of Example 1B, substituting Example 368B for 2-phenoxyphenylboronic acid, and Example 368C for Example 1A, respectively, to provide the title compound. $^1$H NMR (500 MHz, DMSO-d$_6$) δ 7.81 (dd, J=8.54, 2.44 Hz, 1H), 7.66-7.67 (m, 2H), 7.30 (d, J=8.54 Hz, 1H), 5.88 (s, 1H), 4.20-4.24 (1H), 4.07-4.14 (m, 1H), 3.94-3.98 (m, 4H), 3.39 (s, 3H), 2.10-2.22 (m, 1H), 1.67-1.77 (m, 1H), 1.14-1.50 (m, 1H), 1.17 (t, J=7.02 Hz, 3H), 1.11 (t, J=7.32 Hz, 3H). MS (ESI+) m/z 428.0 (M+H)$^+$.

Example 369

5-[2-(2,4-difluorophenoxy)-5-(propan-2-ylsulfonyl)phenyl]-4-ethoxy-1-methylpyridin-2(1H)-one Example 369 was prepared according to the procedure used for the preparation of Example 1B, substituting Example 368B for 2-phenoxyphenylboronic acid, and Example 364C for Example 1A, respectively, to provide the title compound. $^1$H NMR (500 MHz, DMSO-d$_6$) δ 7.74-7.79 (m, 3H), 7.48-7.54 (m, 1H), 7.27-7.33 (m, 1H), 7.14-7.19 (m, 1H), 6.99 (d, J=8.54 Hz, 1H), 5.87 (s, 1H), 3.99 (q, J=6.82 Hz, 2H), 3.39 (s, 3H), 1.15-1.19 (m, 9H). MS (ESI+) m/z 464.0 (M+H)$^+$.

Example 370

5-{2-(2,4-difluorophenoxy)-5-[(methylsulfonyl)methyl]phenyl}-4-ethoxy-1-methylpyridin-2(1H)-one Example 370A 3-bromo-4-(2,4-difluorophenoxy)benzaldehyde A mixture of 3-bromo-4-fluorobenzaldehyde (4.06 g, 20.0 mmol), 2,4-difluorophenol (2.60 g, 20.0 mmol) and cesium carbonate (7.17 g, 22.0 mmol) in dimethyl sulfoxide (20 mL) was heated at 100° C. for 1 hour. The reaction mixture was partitioned with ethyl acetate and water. The organic layer was washed with saturated aqueous sodium chloride twice, dried with anhydrous sodium sulfate, filtered, and concentrated. The residue was purified by flash chromatography (silica gel, 20% ethyl acetate in heptanes) to provide the title compound (5.94 g, 95%).

Example 370B (3-bromo-4-(2,4-difluorophenoxy)phenyl)methanol

To Example 370A (3.76 g, 12.0 mmol) in the mixture of ethanol (10 mL) and tetrahydrofuran (10 mL) was added sodium borohydride (0.136 g, 3.60 mmol). The reaction mixture was stirred at ambient temperature for 1 hour. The solvent was evaporated and the residue was partitioned with ethyl acetate and water. The organic layer was washed with saturated aqueous sodium chloride, dried with anhydrous sodium sulfate, filtered, and concentrated to provide the title compound (3.72 g, 98%).

Example 370C 2-bromo-4-(bromomethyl)-1-(2,4-difluorophenoxy)benzene

To Example 370B (3.700 g, 11.74 mmol) in dichloromethane (20 mL) was added phosphorus tribromide (1.107 mL, 11.74 mmol) dropwise. The reaction mixture was stirred at ambient temperature for 3 hours and poured into ice water. The pH was adjusted to basic by addition of saturated aqueous sodium bicarbonate slowly, and the mixture was extracted with dichloromethane. The organic layer was washed with saturated aqueous sodium chloride, dried with anhydrous sodium sulfate, filtered, and concentrated to provide the title compound (4.15 g, 93%).

Example 370D (3-bromo-4-(2,4-difluorophenoxy)benzyl)(methyl)sulfane

A mixture of Example 370C (1.51 g, 4.00 mmol) and sodium thiomethoxide (0.280 g, 4.00 mmol) in dimethylformamide (8 mL) was stirred at ambient temperature for 6 hours. The reaction mixture was partitioned with ethyl acetate and water. The organic layer was washed with saturated aqueous sodium chloride twice, dried with anhydrous sodium sulfate, filtered, and concentrated to provide the title compound (1.38 g, 100%).

Example 370E 2-bromo-1-(2,4-difluorophenoxy)-4-(methylsulfonylmethyl)benzene To Example 370D (1.38 g, 4.00 mmol) in methanol (15 mL) was added oxone (5.16 g, 8.40 mmol) in water (15 mL) at 0° C. The reaction mixture was stirred at ambient temperature for 1 hour. The reaction mixture was partitioned with ethyl acetate and water. The organic layer was washed with saturated aqueous sodium chloride, dried with anhydrous sodium sulfate, filtered, and concentrated. The residue was purified by flash chromatography (silica gel, 20-40% ethyl acetate in heptanes) to provide the title compound (1.485 g, 98%).

Example 370F

5-{2-(2,4-difluorophenoxy)-5-[(methylsulfonyl)methyl]phenyl}-4-ethoxy-1-methylpyridin-2(1H)-one Example 370E (75.0 mg, 0.200 mmol), Example 368B (55.8 mg, 0.200 mmol), potassium phosphate (149 mg, 0.700 mmol), tris(dibenzylideneacetone)dipalladium (5.5 mg, 6.0 µmol) and 1,3,5,7-tetramethyl-6-phenyl-2,4,8-trioxa-6-phosphaadamantane (5.3 mg, 0.018 mmol) were combined in a microwave tube and purged with nitrogen for 15 minutes. A mixture of dioxane (2 mL) and water (0.5 mL) was purged with nitrogen for 15 minutes and transferred to the microwave tube. The reaction mixture was heated at 60° C. for 1 hour. The reaction mixture was partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 1-4% methanol in dichloromethane) to provide the title compound (7 mg, 8%). $^1$H NMR (500 MHz, DMSO-d$_6$) δ 7.62 (s, 1H) 7.26-7.48 (m, 3H) 7.00-7.19 (m, 2H) 6.87 (d, J=8.85 Hz, 1H) 5.82 (s, 1H) 4.47 (s, 2H) 3.94 (q, J=7.02 Hz, 2H) 3.37 (s, 3H) 2.93 (s, 3H) 1.15 (t, J=6.87 Hz, 3H). MS (ESI+) m/z 450 (M+H)$^+$.

Example 371

5-[5-(cyclopropylsulfonyl)-2-(2,4-difluorophenoxy)phenyl]-4-ethoxy-1-methylpyridin-2(1H)-one

Example 371A (3-bromo-4-fluorophenyl)(cyclopropyl)sulfane

Example 371A was prepared according to the procedure used for the preparation of Example 275a, substituting bromocyclopropane for iodoethane, to provide the title compound.

Example 371B

Example 371B was prepared according to the procedure used for the preparation of Example 275B, substituting Example 371A for Example 275A, to provide the title compound.

Example 371C

Example 371C was prepared according to the procedure used for the preparation of Example 364C, substituting Example 371B for Example 364B, to provide the title compound.

Example 371D

5-[5-(cyclopropylsulfonyl)-2-(2,4-difluorophenoxy)phenyl]-4-ethoxy-1-methylpyridin-2(1H)-one Example 371D was prepared according to the procedure used for the preparation of Example 1B, substituting Example 368B for 2-phenoxyphenylboronic acid, and Example 371C for Example 1A, respectively, to provide the title compound. $^1$H NMR (500 MHz, DMSO-d$_6$) δ 7.81-7.83 (m, 2H), 7.76 (s, 1H), 7.49-7.54 (m, 1H), 7.27-7.33 (m, 1H), 7.14-7.20 (m, 1H), 6.96 (d, J=9.77 Hz, 1H), 5.88 (s, 1H), 4.01 (q, J=7.02 Hz, 2H), 3.40 (s, 3H), 2.85-2.93 (m, 1H), 1.18 (t, J=7.02 Hz, 3H), 1.03-1.15 (m 4H). MS (ESI+) m/z 462.0 (M+H)$^+$.

Example 372

N-{4-(2,4-difluorophenoxy)-3-[4-(3-hydroxy-3-methylbutoxy)-1-methyl-6-oxo-1,6-dihydropyridin-3-yl]phenyl}ethanesulfonamide Example 372 was prepared according to the procedure used for the preparation of Example 286, substituting 3-methylbutane-1,3-diol for 2-morpholinoethanol. $^1$H NMR (300 MHz, DMSO-d$_6$) δ 9.75 (s, 1H), 7.59 (s, 1H), 7.36 (ddd, J=11.4, 8.8, 2.5 Hz, 1H), 7.18 (dd, J=8.7, 2.9 Hz, 1H), 7.12 (d, J=2.4 Hz, 1H), 7.04-6.94 (m, 2H), 6.92 (d, J=8.8 Hz, 1H), 5.81 (s, 1H), 3.95 (t, J=7.0 Hz, 2H), 3.08 (q, J=7.1 Hz, 2H), 2.50 (s, 3H), 1.63 (t, J=7.1 Hz, 2H), 1.21 (t, J=7.3 Hz, 3H), 1.00 (s, 6H). MS (ESI) 523.0 (M+H+).

Example 373

5-[2-(cyclopropylamino)-5-(ethylsulfonyl)phenyl]-4-ethoxy-1-methylpyridin-2(1H)-one

Example 373A 2-bromo-N-cyclopropyl-4-(ethylsulfonyl)aniline

Example 373A was prepared according to the procedure used for the preparation of Example 353A, substituting cyclopropanamine for cyclopropylmethanamine, and Example 275B for Example 269B, to provide the title compound.

Example 373B

5-[2-(cyclopropylamino)-5-(ethylsulfonyl)phenyl]-4-ethoxy-1-methylpyridin-2(1H)-one Example 373B was prepared according to the procedure used for the preparation of Example 1B, substituting Example 368B for 2-phenoxyphenylboronic acid, and Example 373A for Example 1A, respectively, to provide the title compound. $^1$H NMR (500 MHz, DMSO-d$_6$) δ 7.62 (dd, J=8.7, 2.29 Hz, 1H), 7.54 (s, 1H), 7.29 (d, J=2.14, 1H), 7.07 (d, J=8.54 Hz, 1H), 6.06 (br s, 1H), 5.86 (s, 1H), 3.95 (q, J=7.02 Hz, 2H), 3.36 (s, 3H), 3.14 (q, J=7.32 Hz, 2H), 2.35-2.40 (m, 1H), 1.13 (t, J=6.87 Hz, 3H), 1.09 (t, J=7.32 Hz, 3H), 0.75 (dd, J=6.41, 1.83 Hz, 2H), 0.44-0.46 (m, 2H). MS (ESI+) m/z 377.1 (M+H)$^+$.

Example 374

N-{4-(4-cyanophenoxy)-3-[1-methyl-6-oxo-4-(2,2,2-trifluoroethoxy)-1,6-dihydropyridin-3-yl]phenyl}ethanesulfonamide The title compound was isolated as a major product from the preparation of Example 294F. $^1$H NMR (500 MHz, DMSO-$d_6$) δ 7.62 (dd, J=8.7, 2.29 Hz, 1H), 7.54 (s, 1H), 7.29 (d, J=2.14, 1H), 7.07 (d, J=8.54 Hz, 1H), 6.06 (br s, 1H), 5.86 (s, 1H), 3.95 (q, J=7.02 Hz, 2H), 3.36 (s, 3H), 3.14 (q, J=7.32 Hz, 2H), 2.35-2.40 (m, 1H), 1.13 (t, J=6.87 Hz, 3H), 1.09 (t, J=7.32 Hz, 3H), 0.75 (dd, J=6.41, 1.83 Hz, 2H), 0.44-0.46 (m, 2H). MS (ESI+) m/z 377.1 (M+H)$^+$.

Example 375

5-[2-(2,4-difluorophenoxy)-5-(ethylsulfonyl)phenyl]-4-ethoxy-1-methylpyridin-2(1H)-one

Example 375A 4-ethoxy-5-(5-(ethylsulfonyl)-2-fluorophenyl)-1-methylpyridin-2(1H)-one A mixture of Example 368B (0.837 g, 3 mmol), Example 275B (0.801 g, 3.00 mmol), 1,3,5,7-tetramethyl-6-phenyl-2,4,8-trioxa-6-phosphaadamantane (0.103 g, 0.351 mmol), tris(dibenzylideneacetone)dipalladium (0.082 g, 0.090 mmol), and potassium phosphate (1.592 g, 7.50 mmol) in dioxane (12 ml) and water (3.00 ml) was degassed and back-filled with nitrogen several times. The reaction was heated at 60° C. for 16 hours. After cooling, the reaction mixture was partitioned between water and ethyl acetate. The aqueous layer was extracted with additional ethyl acetate three times. The combined organic layers were washed with brine, dried over MgSO$_4$, filtered, and concentrated. The residue was purified by flash column chromatography on silica gel eluting with 60% ethyl acetate in hexanes to give the title compound (0.67 g, 1.974 mmol, 65.8% yield).

Example 375B

5-[2-(2,4-difluorophenoxy)-5-(ethylsulfonyl)phenyl]-4-ethoxy-1-methylpyridin-2(1H)-one A mixture of Example 375A (0.051 g, 0.15 mmol), 2,4-difluorophenol (0.023 g, 0.180 mmol), and cesium carbonate (0.059 g, 0.180 mmol) in dimethyl sulfoxide was heated at 100° C. overnight. After cooling to ambient temperature, the reaction mixture was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated. The residue was purified by reverse phase HPLC (C18, CH$_3$CN/water (0.1% TFA), 0-100%) to afford the title compound (0.045 g, 0.100 mmol, 66.7% yield). $^1$H NMR (500 MHz, DMSO-$d_6$) δ 7.80-7.83 (m, 2H), 7.77 (s, 1H), 7.49-7.54 (m, 1H), 7.27-7.33 (m, 1H), 7.15-7.20 (m, 2H), 6.98 (d, J=7.93 Hz, 1H), 5.88 (s, 1H), 4.00 (q, J=7.02 Hz, 2H), 3.40 (s, 3H), 3.32 (q, J=7.32 Hz, 2H), 1.17 (t, J=7.02 Hz, 3H), 1.13 (t, J=7.48 Hz, 3H). MS (ESI+) m/z 450.0 (M+H)$^+$.

Example 376

N-{4-(2,4-difluorophenoxy)-3-[4-(2-hydroxy-2-methylpropoxy)-1-methyl-6-oxo-1,6-dihydropyridin-3-yl]phenyl}ethanesulfonamide Example 376 was prepared according to the procedure used for the preparation of Example 286, substituting 2-methylpropane-1,2-diol for 2-morpholinoethanol. $^1$H NMR (400 MHz, DMSO-$d_6$) δ 9.78 (s, 1H), 7.59 (s, 1H), 7.31 (m, 1H), 7.22 (dd, J=8.7, 2.6 Hz, 1H), 7.13 (d, J=2.8 Hz, 1H), 6.97 (d, J=8.9 Hz, 1H), 6.95-6.87 (m, 2H), 5.74 (s, 1H), 3.58 (s, 2H), 3.08 (q, J=7.3 Hz, 2H), 2.50 (s, 3H), 1.21 (t, J=7.3 Hz, 3H), 1.01 (s, 6H). MS (ESI) 509.1 (M+H+).

Example 377

4-ethoxy-5-{5-(ethylsulfonyl)-2-[4-(trifluoromethoxy)phenoxy]phenyl}-1-methylpyridin-2(1H)-one Example 377 was prepared according to the procedure used for the preparation of Example 364C, substituting Example 375A for Example 364B, and 4-(trifluoromethoxy)phenol for 2,4-difluorophenol, respectively, to provide the title compound. $^1$H NMR (500 MHz, DMSO-$d_6$) δ 7.81-7.86 (m, 2H), 7.74 (s, 1H), 7.43 (d, J=8.54 Hz, 1H), 7.16-7.19 (m, 2H), 7.13 (d, J=8.54 Hz, 1H), 5.84 (s, 1H), 3.94 (q, J=7.02 Hz, 2H), 3.38 (s, 3H), 3.32 (q, J=7.32 Hz, 2H), 1.14 (t, J=7.32 Hz, 3H), 1.11 (t, J=7.02 Hz, 3H). MS (ESI+) m/z 498.1 (M+H)$^+$.

Example 378

4-[2-(4-ethoxy-1-methyl-6-oxo-1,6-dihydropyridin-3-yl)-4-(ethylsulfonyl)phenoxy]benzonitrile Example 378 was prepared according to the procedure used for the preparation of Example 364C, substituting Example 375A for Example 364B, and 4-cyanophenol for 2,4-difluororphenol, respectively, to provide the title compound. $^1$H NMR (500 MHz, DMSO-$d_6$) δ 7.85-7.91 (m, 4H), 7.72 (s, 1H), 7.32 (d, J=8.54 Hz, 1H), 7.15-7.17 (m, 2H), 5.81 (s, 1H), 3.90 (q, J=6.82 Hz, 2H), 3.33-3.38 (m, 5H), 1.15 (t, J=7.32 Hz, 3H), 1.06 (t, J=7.02 Hz, 3H). MS (ESI+) m/z 439.1 (M+H)$^+$.

Example 379

5-{2-(2,4-difluorophenoxy)-5-[(ethylsulfonyl)methyl]phenyl}-4-ethoxy-1-methylpyridin-2(1H)-one

Example 379A (3-bromo-4-(2,4-difluorophenoxy)benzyl)(ethyl)sulfane

Example 379A was prepared according to the procedure used for the preparation of Example 370D, substituting sodium ethanethiolate for sodium thiomethoxide, to provide the title compound (1.04 g, 99%).

Example 379B 2-bromo-1-(2,4-difluorophenoxy)-4-(ethylsulfonyl-methyl)benzene Example 379B was prepared according to the procedure used for the preparation of Example 370E, substituting Example 379A for Example 370D, to provide the title compound (1.01 g, 89%).

Example 379C

5-{2-(2,4-difluorophenoxy)-5-[(ethylsulfonyl)methyl]phenyl}-4-ethoxy-1-methylpyridin-2(1H)-one Example 379B (46.9 mg, 0.120 mmol), Example 368B (40.2 mg, 0.144 mmol), cesium fluoride (54.7 mg, 0.360 mmol) and tetrakis(triphenylphosphine)palladium(0) (6.9 mg, 6.0 µmol) were combined in a microwave tube and purged with nitrogen for 15 minutes. A mixture of dimethoxyethane (2 mL) and methanol (1 mL) was purged with nitrogen for 15 minutes and transferred to the microwave tube. The reaction mixture was heated in a microwave reactor at 120° C. for 30 minutes. The reaction mixture was partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by reverse phase HPLC (C18, CH$_3$CN/water (0.1% TFA), 0-100%) to afford the title compound (23 mg, 41%). $^1$H NMR (300 MHz, DMSO-d$_6$) δ 7.60 (s, 1H) 7.30-7.47 (m, 3H) 7.01-7.17 (m, 2H) 6.86 (d, J=7.80 Hz, 1H) 5.82 (s, 1H) 4.45 (s, 2H) 3.94 (q, J=7.12 Hz, 2H) 3.37 (s, 3H) 3.05 (q, J=7.46 Hz, 2H) 1.22 (t, J=7.46 Hz, 3H) 1.15 (t, J=6.95 Hz, 3H). MS (ESI+) m/z 464 (M+H)$^+$.

Example 380

5-{2-(2,4-difluorophenoxy)-5-[2-(ethylsulfonyl)propan-2-yl]phenyl}-4-ethoxy-1-methylpyridin-2(1H)-one

Example 380A 2-bromo-1-(2,4-difluorophenoxy)-4-(2-(ethylsulfonyl)propan-2-yl)benzene To Example 379B (469 mg, 1.20 mmol) in tetrahydrofuran (10 mL) was added 60% sodium hydride in mineral oil (240 mg, 6.00 mmol) at 0° C. The reaction mixture was stirred at ambient temperature under nitrogen for 10 minutes. Iodomethane (0.750 mL, 12.00 mmol) was added. The reaction mixture was stirred at ambient temperature for 20 hours. The reaction mixture was partitioned with ethyl acetate and water. The organic layer was washed with saturated aqueous sodium chloride, dried with anhydrous sodium sulfate, filtered, and concentrated. The residue was purified by flash chromatography (silica gel, 20-40% ethyl acetate in heptanes) to provide the title compound (442 mg, 88%).

Example 380B

5-{2-(2,4-difluorophenoxy)-5-[2-(ethylsulfonyl)propan-2-yl]phenyl}-4-ethoxy-1-methylpyridin-2(1H)-one Example 380B was prepared according to the procedure used for the preparation of Example 379C, substituting Example 380A for Example 379B, to provide the title compound (24 mg, 41%). $^1$H NMR (300 MHz, DMSO-d$_6$) δ 7.60 (s, 1H) 7.54-7.57 (m, 1H) 7.53 (s, 1H) 7.36-7.47 (m, 1H) 7.01-7.18 (m, 2H) 6.85 (d, J=8.48 Hz, 1H) 5.82 (s, 1H) 3.94 (q, J=6.78 Hz, 2H) 2.86 (q, J=7.46 Hz, 2H) 1.75 (s, 6H) 1.15 (t, J=6.95 Hz, 3H) 1.03 (t, J=7.46 Hz, 3H). MS (ESI+) m/z 492 (M+H)$^+$.

Example 381

N-[4-(cyclopropylmethoxy)-3-(4-ethoxy-1-methyl-6-oxo-1,6-dihydropyridin-3-yl)phenyl]ethanesulfonamide

Example 381A 4-ethoxy-5-(2-fluoro-5-nitrophenyl)-1-methylpyridin-2(1H)-one

Example 381A was prepared according to the procedure used for the preparation of Example 313B, substituting 2-(2-fluoro-5-nitrophenyl)-4,4,5,5-tetramethyl-1,3,2-dioxaborolane for Example 313A, and Example 368A for Example 269B, respectively, to provide the title compound.

Example 381B 5-(2-(cyclopropylmethoxy)-5-nitrophenyl)-4-ethoxy-1-methylpyridin-2(1H)-one Example 381B was prepared according to the procedure used for the preparation of Example 247A, substituting cyclopropylmethanol for cyclohexanol, and Example 381A for Example 225A, respectively, to provide the title compound.

Example 381C 5-(5-amino-2-(cyclopropylmethoxy)phenyl)-4-ethoxy-1-methylpyridin-2(1H)-one Example 381B was prepared according to the procedure used for the preparation of Example 10, substituting Example 381B for Example 9B, to provide the title compound.

Example 381D

N-[4-(cyclopropylmethoxy)-3-(4-ethoxy-1-methyl-6-oxo-1,6-dihydropyridin-3-yl)phenyl]ethanesulfonamide Example 381D was prepared according to the procedure used for the preparation of Example 22, substituting Example 381C for Example 20C, and ethanesulfonyl chloride for methanesulfonyl chloride, respectively, to provide the title compound. $^1$H NMR (400 MHz, CDCl$_3$) δ 7.24 (s, 1H), 7.19-7.10 (m, 2H), 6.86 (d, J=8.5 Hz, 1H), 6.16 (s, 1H), 6.02 (s, 1H), 3.98 (t, J=7.0 Hz, 2H), 3.77 (d, J=6.6 Hz, 2H), 3.53 (s, 3H), 3.10 (q, J=7.4 Hz, 2H), 1.40 (t, J=7.4 Hz, 3H), 1.30 (t, J=7.0 Hz, 3H), 1.13 (m, 1H), 0.56 (d, J=6.9 Hz, 2H), 0.25 (d, J=5.8 Hz, 2H). MS (ESI+) m/z 407.2 (M+H)$^+$.

Example 382

4-chloro-5-[2-(2,4-difluorophenoxy)-5-(ethylsulfonyl)phenyl]-1-methylpyridin-2(1H)-one The title compound was isolated as a major product from the preparation of Example 317. $^1$H NMR (500 MHz, DMSO-d$_6$) δ 8.04 (s, 1H), 7.85-7.90 (m, 2H), 7.50-7.55 (m, 1H), 7.34-7.41 (m, 1H), 7.16-7.21 (M, 1H), 6.99 (d, J=8.54 Hz, 1H), 6.69 (s, 1H), 3.48 (s, 3H), 3.32 (q, J=7.32 Hz, 2H), 1.13 (t, J=7.32 Hz, 3H). MS (ESI+) m/z 440.1 (M+H)$^+$.

Example 383

N-[4-(2-cyclopropylethoxy)-3-(4-ethoxy-1-methyl-6-oxo-1,6-dihydropyridin-3-yl)phenyl]ethanesulfonamide

Example 383A 5-(2-(2-cyclopropylethoxy)-5-nitrophenyl)-4-ethoxy-1-methylpyridin-2(1H)-one Example 383A was prepared according to the procedure used for the preparation of Example 247A, substituting 2-cyclopropylethanol for cyclohexanol, and Example 381A for Example 225A, respectively, to provide the title compound.

Example 383B 5-(5-amino-2-(2-cyclopropylethoxy)phenyl)-4-ethoxy-1-methylpyridin-2(1H)-one Example 383B was prepared according to the procedure used for the preparation of Example 10, substituting Example 383A for Example 9B, to provide the title compound.

Example 383C

N-[4-(2-cyclopropylethoxy)-3-(4-ethoxy-1-methyl-6-oxo-1,6-dihydropyridin-3-yl)phenyl]ethanesulfonamide Example 383C was prepared according to the procedure used for the preparation of Example 22, substituting Example 383B for Example 20C, and ethanesulfonyl chloride for methanesulfonyl chloride, respectively, to provide the title compound. $^1$H NMR (400 MHz, CDCl$_3$) δ 7.18 (dd, J=8.6, 2.8 Hz, 2H), 7.12 (d, J=2.7 Hz, 1H), 6.90 (d, J=8.8 Hz, 1H), 6.15 (s, 1H), 5.98 (s, 1H), 4.04-3.87 (m, 4H), 3.51 (s, 3H), 3.10 (q, J=7.4 Hz, 2H), 1.50 (d, J=10.2 Hz, 2H), 1.40 (t, J=7.4 Hz, 3H), 1.28 (t, J=6.9 Hz, 3H), 0.71 (s, 1H), 0.46-0.40 (m, 2H), 0.05 (d, J=5.3 Hz, 2H). MS (ESI+) m/z 421.1 (M+H)$^+$.

Example 384

N-[4-(cyclobutyloxy)-3-(4-ethoxy-1-methyl-6-oxo-1,6-dihydropyridin-3-yl)phenyl]ethanesulfonamide

Example 384A 5-(2-cyclobutoxy-5-nitrophenyl)-4-ethoxy-1-methylpyridin-2(1H)-one Example 384A was prepared according to the procedure used for the preparation of Example 247A, substituting cyclobutanol for cyclohexanol, and Example 381A for Example 225A, respectively, to provide the title compound.

Example 384B 5-(5-amino-2-cyclobutoxyphenyl)-4-ethoxy-1-methylpyridin-2(1H)-one Example 384B was prepared according to the procedure used for the preparation of Example 10, substituting Example 384A for Example 9B, to provide the title compound.

Example 384C

N-[4-(cyclobutyloxy)-3-(4-ethoxy-1-methyl-6-oxo-1,6-dihydropyridin-3-yl)phenyl]ethanesulfonamide Example 384C was prepared according to the procedure used for the preparation of Example 22, substituting Example 384B for Example 20C, and ethanesulfonyl chloride for methanesulfonyl chloride, respectively, to provide the title compound. $^1$H NMR (400 MHz, CDCl$_3$) δ 7.21-7.15 (m, 2H), 7.13 (d, J=2.7 Hz, 1H), 6.91 (s, 1H), 6.71 (d, J=8.7 Hz, 1H), 5.99 (s, 1H), 4.62-4.49 (m, 1H), 3.99 (q, J=7.0 Hz, 2H), 3.51 (s, 3H), 3.10 (q, J=7.4 Hz, 2H), 2.45-2.33 (m, 2H), 2.13-1.99 (m, 2H), 1.89-1.80 (m, 1H), 1.67 (m, 1H), 1.39 (t, J=7.4 Hz, 3H), 1.30 (t, J=7.0 Hz, 3H). MS (ESI+) m/z 407.2 (M+H)$^+$.

Example 385

N-{4-[(4,4-difluorocyclohexyl)oxy]-3-(4-ethoxy-1-methyl-6-oxo-1,6-dihydropyridin-3-yl)phenyl}ethanesulfonamide

Example 385A 5-(2-((4,4-difluorocyclohexyl)oxy)-5-nitrophenyl)-4-ethoxy-1-methylpyridin-2(1H)-one Example 385A was prepared according to the procedure used for the preparation of Example 247A, substituting 4,4-difluorocyclohexanol for cyclohexanol, and Example 381A for Example 225A, respectively, to provide the title compound.

Example 385B 5-(5-amino-2-((4,4-difluorocyclohexyl)oxy)phenyl)-4-ethoxy-1-methylpyridin-2(1H)-one Example 385B was prepared according to the procedure used for the preparation of Example 10, substituting Example 385A for Example 9B, to provide the title compound.

Example 385C

N-{4-[(4,4-difluorocyclohexyl)oxy]-3-(4-ethoxy-1-methyl-6-oxo-1,6-dihydropyridin-3-yl)phenyl}ethanesulfonamide Example 385C was prepared according to the procedure used for the preparation of Example 22, substituting Example 385B for Example 20C, and ethanesulfonyl chloride for methanesulfonyl chloride, respectively, to provide the title compound. ¹H NMR (400 MHz, CDCl₃) δ 7.20 (dd, J=8.7, 2.7 Hz, 1H), 7.16-7.10 (m, 2H), 6.88 (d, J=8.8 Hz, 1H), 6.59 (s, 1H), 5.99 (s, 1H), 4.39 (s, 1H), 3.98 (q, J=7.0 Hz, 2H), 3.51 (s, 3H), 3.11 (q, J=7.3 Hz, 2H), 1.98-1.77 (m, 8H), 1.40 (t, J=7.4 Hz, 3H), 1.28 (t, J=7.0 Hz, 3H). MS (ESI+) m/z 471.4 (M+H)⁺.

Example 386

N-{3-(4-ethoxy-1-methyl-6-oxo-1,6-dihydropyridin-3-yl)-4-[4-(trifluoromethyl)phenoxy]phenyl}ethanesulfonamide Example 386A 4-ethoxy-1-methyl-5-(5-nitro-2-(4-(trifluoromethyl)phenoxy)phenyl)pyridin-2(1H)-one Example 386A was prepared according to the procedure used for the preparation of Example 9B, substituting 4-trifluoromethylphenol for phenol, and Example 381A for Example 9A, respectively, to provide the title compound.

Example 386B 5-(5-amino-2-(4-(trifluoromethyl)phenoxy)phenyl)-4-ethoxy-1-methylpyridin-2(1H)-one Example 386B was prepared according to the procedure used for the preparation of Example 10, substituting Example 386A for Example 9B, to provide the title compound.

Example 386C

N-{3-(4-ethoxy-1-methyl-6-oxo-1,6-dihydropyridin-3-yl)-4-[4-(trifluoromethyl)phenoxy]phenyl}ethanesulfonamide Example 386C was prepared according to the procedure used for the preparation of Example 22, substituting Example 386B for Example 20C, and ethanesulfonyl chloride for methanesulfonyl chloride, respectively, to provide the title compound. ¹H NMR (400 MHz, CDCl₃) δ 7.47 (d, J=8.7 Hz, 2H), 7.20 (dd, J=8.7, 2.8 Hz, 1H), 7.16 (s, 1H), 7.13 (d, J=2.7 Hz, 1H), 6.91 (t, J=8.4 Hz, 3H), 6.44 (s, 1H), 5.97 (s, 1H), 4.41-4.38 (m, 1H), 3.95 (q, J=7.0 Hz, 2H), 3.47 (s, 3H), 3.40-3.34 (m, 2H), 3.23-3.15 (m, 2H), 3.12 (q, J=7.4 Hz, 2H), 2.06-1.92 (m, 2H), 1.85-1.79 (m, 2H), 1.41 (t, J=7.4 Hz, 3H), 1.27 (t, J=7.0 Hz, 3H). MS (ESI+) m/z 560.0 (M+H)⁺.

Example 387

N-{3-(4-ethoxy-1-methyl-6-oxo-1,6-dihydropyridin-3-yl)-4-[4-(trifluoromethoxy)phenoxy]phenyl}ethanesulfonamide Example 387A 4-ethoxy-1-methyl-5-(5-nitro-2-(4-(trifluoromethoxy)phenoxy)phenyl)pyridin-2(1H)-one Example 387A was prepared according to the procedure used for the preparation of Example 9B, substituting 4-(trifluoromethoxy)phenol for phenol, and Example 381A for Example 9A, respectively, to provide the title compound.

Example 387B

Example 387B was prepared according to the procedure used for the preparation of Example 10, substituting Example 387A for Example 9B, to provide the title compound.

Example 387C

N-{3-(4-ethoxy-1-methyl-6-oxo-1,6-dihydropyridin-3-yl)-4-[4-(trifluoromethoxy)phenoxy]phenyl}ethanesulfonamide Example 387C was prepared according to the procedure used for the preparation of Example 22, substituting Example 387B for Example 20C, and ethanesulfonyl chloride for methanesulfonyl chloride, respectively, to provide the title compound. ¹H NMR (400 MHz, CDCl₃) δ 7.52 (d, J=8.4 Hz, 2H), 7.26-7.23 (m, 2H), 7.13-7.01 (m, 3H), 6.94 (d, J=9.6 Hz, 2H), 5.95 (s, 1H), 3.89 (q, J=7.0 Hz, 2H), 3.46 (s, 3H), 3.17 (q, J=7.2 Hz, 2H), 1.43 (t, J=7.2 Hz, 3H), 1.19 (t, J=7.0 Hz, 3H). MS (ESI+) m/z 513.2 (M+H)⁺.

Example 388 ethyl 4-{2-(4-ethoxy-1-methyl-6-oxo-1,6-dihydropyridin-3-yl)-4-[(ethylsulfonyl)amino]phenoxy}piperidine-1-carboxylate Example 388A ethyl 4-(2-(4-ethoxy-1-methyl-6-oxo-1,6-dihydropyridin-3-yl)-4-nitrophenoxy)piperidine-1-carboxylate Example 388A was prepared according to the procedure used for the preparation of Example 247A, substituting ethyl 4-hydroxypiperidine-1-carboxylate for cyclohexanol, and Example 381A for Example 225A, respectively, to provide the title compound.

Example 388B ethyl 4-(4-amino-2-(4-ethoxy-1-methyl-6-oxo-1,6-dihydropyridin-3-yl)phenoxy)piperidine-1-carboxylate Example 388B was prepared according to the procedure used for the preparation of Example 10, substituting Example 388A for Example 9B, to provide the title compound.

Example 388C ethyl 4-{2-(4-ethoxy-1-methyl-6-oxo-1,6-dihydropyridin-3-yl)-4-[(ethylsulfonyl)amino]phenoxy}piperidine-1-carboxylate Example 388C was prepared according to the procedure used for the preparation of Example 22, substituting Example 388B for Example 20C, and ethanesulfonyl chloride for methanesulfonyl chloride, respectively, to provide the title compound. ¹H NMR (400 MHz, CDCl₃) δ 7.20-7.16 (m, 2H), 7.13 (d, J=2.7 Hz, 1H), 6.90 (d, J=8.7 Hz, 1H), 6.17

(s, 1H), 6.14 (s, 1H), 4.39 (m, 1H), 4.13 (q, J=7.1 Hz, 2H), 4.01 (q, J=7.0 Hz, 2H), 3.54 (s, 3H), 3.50-3.32 (m, 4H), 3.11 (q, J=7.4 Hz, 2H), 1.86-1.79 (m, 2H), 1.41 (t, J=7.4 Hz, 3H), 1.31-1.24 (m, 6H). MS (ESI+) m/z 508.3 (M+H)$^+$.

Example 389

N-{4-[(1-acetylpiperidin-4-yl)oxy]-3-(4-ethoxy-1-methyl-6-oxo-1,6-dihydropyridin-3-yl)phenyl}ethanesulfonamide

Example 389A 5-(2-((1-acetylpiperidin-4-yl)oxy)-5-nitrophenyl)-4-ethoxy-1-methylpyridin-2(1H)-one Example 389A was prepared according to the procedure used for the preparation of Example 247A, substituting 1-(4-hydroxypiperidin-1-yl)ethanone for cyclohexanol, and Example 381A for Example 225A, respectively, to provide the title compound.

Example 389B 5-(2-((1-acetylpiperidin-4-yl)oxy)-5-aminophenyl)-4-ethoxy-1-methylpyridin-2(1H)-one Example 389B was prepared according to the procedure used for the preparation of Example 10, substituting Example 389A for Example 9B, to provide the title compound.

Example 389C

N-{4-[(1-acetylpiperidin-4-yl)oxy]-3-(4-ethoxy-1-methyl-6-oxo-1,6-dihydropyridin-3-yl)phenyl}ethanesulfonamide Example 389C was prepared according to the procedure used for the preparation of Example 22, substituting Example 389B for Example 20C, and ethanesulfonyl chloride for methanesulfonyl chloride, respectively, to provide the title compound. $^1$H NMR (400 MHz, CDCl$_3$) δ 7.21-7.16 (m, 2H), 7.13 (d, J=2.8 Hz, 1H), 6.90 (d, J=8.8 Hz, 1H), 6.21 (s, 1H), 6.10 (s, 1H), 4.44 (m, 1H), 4.00 (q, J=7.0 Hz, 2H), 3.62-3.36 (m, 7H), 3.11 (t, J=7.4 Hz, 2H), 2.08 (s, 3H), 1.82-1.62 (m, 4H), 1.41 (t, J=7.4 Hz, 3H), 1.29 (t, J=7.0 Hz, 3H). MS (ESI+) m/z 478.3 (M+H)$^+$.

Example 390

N-{3-[4-(1-benzyl-1H-pyrazol-4-yl)-1-methyl-6-oxo-1,6-dihydropyridin-3-yl]-4-(2,4-difluorophenoxy)phenyl}ethanesulfonamide A mixture of Example 278A (100 mg, 0.220 mmol), 1-benzyl-4-(4,4,5,5-tetra methyl-1,3,2-dioxaborolan-2-yl)-1H-pyrazole (250 mg, 0.879 mmol), PdCl$_2$(dppf) (16.1 mg, 0.022 mmol) and K$_2$CO$_3$ (91 mg, 0.660 mmol) in water (1 mL) and dioxane (4 mL) were heated in a Biotage microwave apparatus at 130° C. under nitrogen for 2 hours. The reaction mixture was concentrated and purified by reverse phase HPLC (C18, CH$_3$CN/water (10 mM ammonium carbonate), 30-60% gradient) to provide the title compound (60 mg, 47% yield). $^1$H NMR (400 MHz, CDCl$_3$) δ 7.30 (m, 3H), 7.27 (s, 1H), 7.24 (s, 1H), 7.22 (s, 1H), 7.16-7.11 (m, 4H), 7.05 (s, 1H), 6.85-6.80 (m, 1H), 6.67 (s, 1H), 6.64-6.60 (m, 1H), 6.53 (d, J=8 Hz, 1H), 6.40-6.34 (m, 1H), 5.15 (s, 2H), 3.55 (s, 3H), 3.02 (q, J=7.2 Hz, 2H), 1.33 (t, J=7.2 Hz, 3H). MS (ESI+) m/z 577.2 (M+H)$^+$.

Example 391

N-[4-(2,4-difluorophenoxy)-3-{1-methyl-4-[1-(2-methylpropyl)-1H-pyrazol-4-yl]-6-oxo-1,6-dihydropyridin-3-yl]phenyl}ethanesulfonamide Example 391 was prepared according to the procedure utilized for the preparation of Example 390, replacing 1-benzyl-4-(4,4,5,5-tetra methyl-1,3,2-dioxaborolan-2-yl)-1H-pyrazole with 1-isobutyl-4-(4,4,5,5-tetramethyl-1,3,2-dioxaborolan-2-yl)-1H-pyrazole to provide the title compound. $^1$H NMR (400 MHz, CDCl$_3$) δ 7.46 (s, 1H), 7.29 (s, 1H), 7.19-7.15 (m, 3H), 7.11 (s, 1H), 6.88-6.83 (m, 1H), 6.77-6.73 (m, 1H), 6.70 (s, 1H), 6.64-6.57 (m, 1H), 3.78 (d, J=7.2 Hz, 2H), 3.57 (s, 3H), 3.07 (q, J=7.2 Hz, 2H), 2.09-2.06 (m, 1H), 1.37 (t, J=7.2 Hz, 3H), 0.84 (s, 3H), 0.82 (s, 3H). MS (ESI+) m/z 543.2 (M+H)$^+$.

Example 392

N-{4-(2,4-difluorophenoxy)-3-[4-(furan-2-yl)-1-methyl-6-oxo-1,6-dihydropyridin-3-yl]phenyl}ethanesulfonamide Example 392 was prepared according to the procedure utilized for the preparation of Example 390, replacing 1-benzyl-4-(4,4,5,5-tetra methyl-1,3,2-dioxaborolan-2-yl)-1H-pyrazole with 2-(furan-2-yl)-4,4,5,5-tetramethyl-1,3,2-dioxaborolane to provide the title compound. $^1$H NMR (400 MHz, CDCl$_3$) δ 7.33 (s, 1H), 7.19-7.16 (m, 3H), 7.10 (d, J=2.4 Hz, 1H), 6.91 (s, 1H), 6.78-6.59 (m, 4H), 6.24 (t, J=1.6 Hz, 1H), 5.77 (d, J=3.2 Hz, 1H), 3.49 (s, 3H), 3.04 (q, J=7.6 Hz, 2H), 1.31 (t, J=7.2 Hz, 3H). MS (ESI+) m/z 487.1 (M+H)$^+$.

Example 393

N-{4-(2,4-difluorophenoxy)-3-[4-(furan-3-yl)-1-methyl-6-oxo-1,6-dihydropyridin-3-yl]phenyl}ethanesulfonamide Example 393 was prepared according to the procedure utilized for the preparation of Example 390, replacing 1-benzyl-4-(4,4,5,5-tetra methyl-1,3,2-dioxaborolan-2-yl)-1H-pyrazole with 2-(furan-3-yl)-4,4,5,5-tetramethyl-1,3,2-dioxaborolane to provide the title compound. $^1$HNMR (400 MHz, CDCl$_3$) δ 7.31 (s, 2H), 7.19-7.14 (m, 3H), 7.19-7.15 (m, 3H), 7.04 (s, 1H), 6.90-6.58-6.83 (m, 5H), 6.25 (d, J=0.8 Hz, 1H), 6.70 (s, 1H), 3.58 (s, 3H), 3.06 (q, J=7.2 Hz, 2H), 1.36 (t, J=7.2 Hz, 3H). MS (ESI+) m/z 487.1 (M+H)$^+$.

Example 394

N-[4-(2,3-dihydro-1H-inden-2-yloxy)-3-(4-ethoxy-1-methyl-6-oxo-1,6-dihydropyridin-3-yl)phenyl]ethanesulfonamide

Example 394A

Example 394A was prepared according to the procedure used for the preparation of Example 247A, substituting 2,3-dihydro-1H-inden-2-ol for cyclohexanol, and Example 381A for Example 225A, respectively, to provide the title compound.

Example 394B 5-(5-amino-2-((2,3-dihydro-1H-inden-2-yl)oxy)phenyl)-4-ethoxy-1-methylpyridin-2(1H)-one Example 394B was prepared according to the procedure used for the preparation of Example 10, substituting Example 394A for Example 9B, to provide the title compound.

Example 394C

N-[4-(2,3-dihydro-1H-inden-2-yloxy)-3-(4-ethoxy-1-methyl-6-oxo-1,6-dihydropyridin-3-yl)phenyl]ethanesulfonamide Example 394C was prepared according to the procedure used for the preparation of Example 22, substituting Example 394B for Example 20C, and ethanesulfonyl chloride for methanesulfonyl chloride, respectively, to provide the title compound. $^1$H NMR (400 MHz, CDCl$_3$) δ 7.24-7.12 (m, 6H), 6.97 (d, J=8.7 Hz, 1H), 6.86 (s, 1H), 6.35 (s, 1H), 5.88 (s, 1H), 5.10 (m, 1H), 3.82 (q, J=7.0 Hz, 2H), 3.30 (d, J=5.7 Hz, 1H), 3.26 (d, J=5.7 Hz, 1H), 3.19-3.03 (m, 7H), 1.40 (t, J=7.4 Hz, 3H), 1.21 (t, J=7.0 Hz, 3H). MS (ESI+) m/z 469.2 (M+H)$^+$.

Example 395 tert-butyl(trans-4-{2-(4-ethoxy-1-methyl-6-oxo-1,6-dihydropyridin-3-yl)-4-[(ethylsulfonyl)amino]phenoxy}cyclohexyl)carbamate

Example 395A tert-butyl((trans)-4-(2-(4-ethoxy-1-methyl-6-oxo-1,6-dihydropyridin-3-yl)-4-nitrophenoxy)cyclohexyl)carbamate Example 395A was prepared according to the procedure used for the preparation of Example 247A, substituting tert-butyl((1r,4r)-4-hydroxycyclohexyl)carbamate for cyclohexanol, and Example 381A for Example 225A, respectively, to provide the title compound.

Example 395B tert-butyl((trans)-4-(4-amino-2-(4-ethoxy-1-methyl-6-oxo-1,6-dihydropyridin-3-yl)phenoxy)cyclohexyl)carbamate Example 395B was prepared according to the procedure used for the preparation of Example 10, substituting Example 395A for Example 9B, to provide the title compound.

Example 395C tert-butyl(trans-4-{2-(4-ethoxy-1-methyl-6-oxo-1,6-dihydropyridin-3-yl)-4-[(ethylsulfonyl)amino]phenoxy}cyclohexyl)carbamate Example 395C was prepared according to the procedure used for the preparation of Example 22, substituting Example 395B for Example 20C, and ethanesulfonyl chloride for methanesulfonyl chloride, respectively, to provide the title compound. $^1$H NMR (400 MHz, CDCl$_3$) δ 7.16 (dd, J=8.5, 2.7 Hz, 2H), 7.10 (d, J=2.7 Hz, 1H), 6.88 (d, J=8.8 Hz, 1H), 6.24 (s, 1H), 6.00 (s, 1H), 4.38 (m, 1H), 4.10-3.91 (m, 3H), 3.51-3.40 (m, 4H), 3.10 (q, J=7.4 Hz, 2H), 2.01-1.99 (m, 4H), 1.48-1.35 (m, 14H), 1.28 (t, J=7.0 Hz, 3H), 1.26-1.14 (m, 2H). MS (ESI+) m/z 550.2 (M+H)$^+$.

Example 396

N-[3-(4-ethoxy-1-methyl-6-oxo-1,6-dihydropyridin-3-yl)-4-(4-fluorophenoxy)phenyl]ethanesulfonamide

Example 396A

Example 396A was prepared according to the procedure used for the preparation of Example 9B, substituting 4-fluorophenol for phenol, and Example 381A for Example 9A, respectively, to provide the title compound.

Example 396B

Example 396B was prepared according to the procedure used for the preparation of Example 10, substituting Example 396A for Example 9B, to provide the title compound.

Example 396C

N-[3-(4-ethoxy-1-methyl-6-oxo-1,6-dihydropyridin-3-yl)-4-(4-fluorophenoxy)phenyl]ethanesulfonamide Example 396C was prepared according to the procedure used for the preparation of Example 22, substituting Example 396B for Example 20C, and ethanesulfonyl chloride for methanesulfonyl chloride, respectively, to provide the title compound. $^1$HMR (400 MHz, CDCl$_3$) δ 7.20 (d, J=2.7 Hz, 1H), 7.15 (dd, J=9.2, 2.2 Hz, 2H), 7.03-6.94 (m, 2H), 6.91-6.82 (m, 3H), 6.42 (s, 1H), 5.96 (s, 1H), 3.93 (q, J=7.0 Hz, 2H), 3.48 (s, 3H), 3.15 (q, J=7.4 Hz, 2H), 1.43 (t, J=7.4 Hz, 3H), 1.24 (t, J=7.0 Hz, 3H). MS (ESI+) m/z 447.1 (M+H)$^+$.

Example 397

5-[2-(cyclopropylmethoxy)-5-(2,3-dihydro-1H-indol-1-ylsulfonyl)phenyl]-4-ethoxy-1-methylpyridin-2(1H)-one

Example 397A 1-(3-bromo-4-fluorophenylsulfonyl)indoline

A solution of 3-bromo-4-fluorobenzene-1-sulfonyl chloride (2.53 g, 8.33 mmol), indoline (0.99 g, 8.33 mmol), N,N-diisopropylethylamine (1.60 mL, 9.16 mmol) and tetrahydrofuran (20 mL) was stirred at ambient temperature for overnight. The reaction mixture was partitioned between water and ethyl acetate. The aqueous layer was extracted twice with additional ethyl acetate. The combined organic layers were washed with saturated aqueous sodium chloride, dried over anhydrous magnesium sulfate, filtered, and concentrated to afford a brown oil which solidified upon standing. The crude product was recrystallized from ether/heptane to afford the title compound (1.99 g, 5.59 mmol, 67% yield).

Examples 397B 1-(3-bromo-4-(cyclopropylmethoxy)phenylsulfonyl) indoline

A mixture of cyclopropylmethanol (118 mg, 1.63 mmol) in dioxane (10 mL) was treated with 60% sodium hydride (87 mg, 2.18 mmol) at ambient temperature. The reaction mixture was stirred at ambient temperature for 20 minutes then treated with Example 397A (388 mg, 1.09 mmol). The reaction mixture was stirred at 60° C. for 18 hours. The reaction mixture was partitioned between dilute aqueous sodium chloride and ethyl acetate. The aqueous layer was extracted with additional ethyl acetate. The combined organic layers were dried over anhydrous magnesium sulfate, filtered, and concentrated. The residue was purified by flash column chromatography on silica gel eluting with 10% ethyl acetate in heptanes to give 0.40 g (90%) of the title compound.

Example 397C

5-[2-(cyclopropylmethoxy)-5-(2,3-dihydro-1H-indol-1-ylsulfonyl)phenyl]-4-ethoxy-1-methylpyridin-2(1H)-one A mixture of Example 397B (67 mg, 0.164 mmol), Example 368B (46 mg, 0.164 mmol), Pd(PPh$_3$)$_4$ (19 mg, 10 mol %) and cesium fluoride (75 mg, 0.492 mmol) in dimethoxyethane (2 mL) and methanol (1 mL) was heated under microwave condition (120° C., 50 min). The reaction mixture was partitioned between saturated aqueous sodium chloride and ethyl acetate. The aqueous layer was extracted with additional ethyl acetate. The combined organic layers were dried over anhydrous magnesium sulfate, filtered, and concentrated. The residue was purified by reverse phase HPLC (C18, CH$_3$CN/water (0.1% TFA), 0-100%) to give the title compound (0.025 g, 32% yield). $^1$H NMR (400 MHz, DMSO-d$_6$) δ 7.69 (dd, J=8.7, 2.5 Hz, 1H), 7.54 (d, J=2.4 Hz, 1H), 7.44-7.51 (m, 2H), 7.14-7.24 (m, 2H), 7.12 (d, J=8.8 Hz, 1H), 7.00 (t, J=7.4 Hz, 1H), 5.85 (s, 1H), 3.81-4.01 (m, 6H), 3.37 (s, 3H), 2.88 (t, J=8.4 Hz, 2H), 1.14 (t, J=6.9 Hz, 3H), 1.05-1.12 (m, 1H), 0.44-0.53 (m, 2H), 0.21-0.31 (m, 2H). MS (ESI+) m/z 481.1 (M+H)$^+$.

Example 398

4-[2-(2,4-difluorophenoxy)-5-(ethylsulfonyl)phenyl]-1-methyl-5-(2,2,2-trifluoroethoxy)pyridin-2(1H)-one

Example 398A 5-(5-(ethylsulfonyl)-2-fluorophenyl)-1-methyl-4-(2,2,2-trifluoroethoxy)pyridin-2(1H)-one Example 398A was prepared according to the procedure used for the preparation of Example 313B, substituting Example 294A for Example 269B, to provide the title compound.

Example 398B

4-[2-(2,4-difluorophenoxy)-5-(ethylsulfonyl)phenyl]-1-methyl-5-(2,2,2-trifluoroethoxy)pyridin-2(1H)-one Example 398B was prepared according to the procedure used for the preparation of Example 364C, substituting Example 398A for Example 364B, to provide the title compound. $^1$H NMR (500 MHz, DMSO-d$_6$) δ 7.79-7.86 (m, 3H), 7.48-7.53 (m, 1H), 7.23-7.29 (m, 1H), 7.15-7.21 (m, 1H), 6.98 (d, J=8.54 Hz, 1H), 6.11 (s, 1H), 4.78 (q, J=8.75 Hz, 3H), 3.42 (s, 3H), 3.30 (q, J=7.32 Hz, 2H), 1.10 (t, J=7.32 Hz, 3H). MS (ESI+) m/z 504.1 (M+H)$^+$.

Example 399

N-{4-(2,4-difluorophenoxy)-3-[1-methyl-6-oxo-4-(piperidin-4-ylmethoxy)-1,6-dihydropyridin-3-yl] phenyl}ethanesulfonamide The trifluoroacetic acid salt of Example 399 was prepared according to the procedure used for the preparation of Example 322, substituting Example 324 for Example 319. $^1$H NMR (500 MHz, DMSO-d$_6$) δ 9.78 (s, 1H), 8.56 (d, J=9.77 Hz, 1H), 8.26 (dd, J=9.77 Hz, 1H), 7.58 (s, 1H), 7.30-7.35 (m, 1H), 7.19 (dd, J=8.85, 2.75 Hz, 1H), 7.12 (d, J=2.75 Hz, 1H), 6.85-7.00 (m, 3H), 5.84 (s, 1H), 3.76 (d, J=6.71 Hz, 12H), 3.32 (s, 3H), 3.22 (d, J=12.21 Hz, 2H), 3.09 (q, J=7.32 Hz, 2H), 2.77-2.86 (m, 2H), 1.88-1.94 (m, 1H), 1.74 (d, J=12.21 Hz, 2H), 1.25-1.33 (m, 2H), 1.21 (t, J=7.32 Hz, 3H). MS (ESI+) m/z 534.1 (M+H)$^+$.

Example 400

N-[4-(4-chlorophenoxy)-3-(4-ethoxy-1-methyl-6-oxo-1,6-dihydropyridin-3-yl)phenyl]ethanesulfonamide

Example 400A 5-(2-(4-chlorophenoxy)-5-nitrophenyl)-4-ethoxy-1-methylpyridin-2(1H)-one A mixture of Example 381A (150 mg, 0.513 mmol), 4-chlorophenol (99 mg, 0.770 mmol), and cesium carbonate (251 mg, 0.770 mmol) in dimethyl sulfoxide (5 ml) was heated at 110° C. for 3 hours. After cooling to ambient temperature, the mixture was partitioned between ethyl acetate and water. The aqueous layer was extracted with additional ethyl acetate twice. The combined organic layers were washed with brine, dried over anhydrous magnesium sulfate, filtered and concentrated to give the title compound (198 mg, 0.469 mmol, 91% yield).

Example 400B 5-(5-amino-2-(4-chlorophenoxy)phenyl)-4-ethoxy-1-methylpyridin-2(1H)-one A mixture of Example 400A (198 mg, 0.494 mmol), iron (27.6 mg, 0.494 mmol), and ammonium chloride (26.4 mg, 0.494 mmol) in ethanol (10 mL), tetrahydrofuran (10.00 mL), and water (3 mL) was heated under reflux at 100° C. for 4 hours. The mixture was cooled just below reflux, vacuum filtered through celite, the filter cake washed with warm methanol (3×35 mL), then concentrated under reduced pressure. The residue was partitioned between saturated NaHCO$_3$ and ethyl acetate (3×75 mL). The combined organics were washed with saturated aqueous sodium chloride, dried over anhydrous magnesium sulfate, filtered, and concentrated to give the title compound (162 mg, 0.288 mmol, 58.4% yield, 66% pure).

Example 400C

N-[4-(4-chlorophenoxy)-3-(4-ethoxy-1-methyl-6-oxo-1,6-dihydropyridin-3-yl)phenyl]ethanesulfonamide A mixture of Example 400B (162 mg, 0.437 mmol, 66% pure), ethanesulfonyl chloride (169 mg, 1.311 mmol), and triethylamine (0.244 ml, 1.747 mmol) in dichloromethane (5 mL) was stirred at ambient temperature for 2 hours. The solvent was removed under reduced pressure. The residue was treated with 2.0M sodium hydroxide (3 mL) and dioxane (5 mL). The reaction mixture was heated at 80° C. for three hours. After cooling, the reaction mixture was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated under reduced pressure. The residue was purified by reverse phase HPLC (C18, $CH_3CN$/water (0.1% TFA), 0-100%) to give the title compound (106 mg, 0.229 mmol, 52% yield). $^1$H NMR (400 MHz, $CDCl_3$) δ 7.25-7.19 (m, 3H), 7.15 (s, 2H), 6.96 (s, 1H), 6.83 (d, J=9.0 Hz, 2H), 6.36 (s, 1H), 5.98 (s, 1H), 3.93 (q, J=7.0 Hz, 2H), 3.48 (s, 3H), 3.16 (q, J=7.4 Hz, 2H), 1.43 (t, J=7.4 Hz, 3H), 1.23 (t, J=7.0 Hz, 3H). MS (ESI+) m/z 463.1 (M+H)$^+$.

Example 401

N-[4-(3,4-difluorophenoxy)-3-(4-ethoxy-1-methyl-6-oxo-1,6-dihydropyridin-3-yl)phenyl]ethanesulfonamide

Example 401A 5-(2-(3,4-difluorophenoxy)-5-nitrophenyl)-4-ethoxy-1-methylpyridin-2(1H)-one Example 401A was prepared according to the procedure used for the preparation of Example 9B, substituting 3,4-difluorophenol for phenol, and Example 381A for Example 9A, respectively, to provide the title compound.

Example 401B 5-(5-amino-2-(3,4-difluorophenoxy)phenyl)-4-ethoxy-1-methylpyridin-2(1H)-one Example 401B was prepared according to the procedure used for the preparation of Example 10, substituting Example 401A for Example 9B, to provide the title compound.

Example 401C

N-[4-(3,4-difluorophenoxy)-3-(4-ethoxy-1-methyl-6-oxo-1,6-dihydropyridin-3-yl)phenyl]ethanesulfonamide Example 401C was prepared according to the procedure used for the preparation of Example 22, substituting Example 401B for Example 20C, and ethanesulfonyl chloride for methanesulfonyl chloride, respectively, to provide the title compound. $^1$H NMR (400 MHz, $CDCl_3$) δ 7.23-7.13 (m, 3H), 7.07 (m, 1H), 6.96 (d, J=8.6 Hz, 1H), 6.73-6.55 (m, 2H), 6.33 (s, 1H), 5.98 (s, 1H), 3.94 (q, J=7.0 Hz, 2H), 3.49 (s, 3H), 3.17 (q, J=7.4 Hz, 2H), 1.43 (t, J=7.4 Hz, 3H), 1.24 (t, J=7.0 Hz, 3H). MS (ESI+) m/z 465.1 (M+H)$^+$.

Example 402

N-[3-(4-ethoxy-1-methyl-6-oxo-1,6-dihydropyridin-3-yl)-4-(3,4,5-trifluorophenoxy)phenyl]ethanesulfonamide

Example 402A 4-ethoxy-1-methyl-5-(5-nitro-2-(3,4,5-trifluorophenoxy)phenyl)pyridin-2(1H)-one Example 402A was prepared according to the procedure used for the preparation of Example 9B, substituting 3,4,5-trifluorophenol for phenol, and Example 381A for Example 9A, respectively, to provide the title compound.

Example 402B 5-(5-amino-2-(3,4,5-trifluorophenoxy)phenyl)-4-ethoxy-1-methylpyridin-2(1H)-one Example 402B was prepared according to the procedure used for the preparation of Example 10, substituting Example 402A for Example 9B, to provide the title compound.

Example 402C

N-[3-(4-ethoxy-1-methyl-6-oxo-1,6-dihydropyridin-3-yl)-4-(3,4,5-trifluorophenoxy)phenyl]ethanesulfonamide Example 402C was prepared according to the procedure used for the preparation of Example 22, substituting Example 402B for Example 20C, and ethanesulfonyl chloride for methanesulfonyl chloride, respectively, to provide the title compound. $^1$H NMR (400 MHz, $CDCl_3$) δ 7.24-7.19 (m, 2H), 7.13 (s, 1H), 7.00 (d, J=9.2 Hz, 1H), 6.56 (s, 1H), 6.48 (dd, J=8.7, 5.7 Hz, 2H), 5.93 (s, 1H), 3.92 (q, J=7.0 Hz, 2H), 3.48 (s, 3H), 3.18 (q, J=7.4 Hz, 2H), 1.43 (t, J=7.4 Hz, 3H), 1.24 (t, J=7.0 Hz, 3H). MS (ESI+) m/z 483.2 (M+H)$^+$.

Example 403

N-[4-(4-chloro-2-fluorophenoxy)-3-(4-ethoxy-1-methyl-6-oxo-1,6-dihydropyridin-3-yl)phenyl]ethanesulfonamide

Example 403A 5-(2-(4-chloro-2-fluorophenoxy)-5-nitrophenyl)-4-ethoxy-1-methylpyridin-2(1H)-one Example 402A was prepared according to the procedure used for the preparation of Example 9B, substituting 2-fluoro-4-chlorophenol for phenol, and Example 381A for Example 9A, respectively, to provide the title compound.

Example 403B

Example 403B was prepared according to the procedure used for the preparation of Example 234B, substituting Example 403A for Example 234A, to provide the title compound.

Example 403C

N-[4-(4-chloro-2-fluorophenoxy)-3-(4-ethoxy-1-methyl-6-oxo-1,6-dihydropyridin-3-yl)phenyl]ethanesulfonamide Example 403C was prepared according to the procedure used for the preparation of Example 22, substituting Example 403B for Example 20C, and ethanesulfonyl chloride for methanesulfonyl chloride, respectively, to provide the title compound. $^1$H NMR (400 MHz, CDCl$_3$) δ 7.23 (d, J=4.2 Hz, 2H), 7.20-7.10 (m, 2H), 7.06-6.96 (m, 1H), 6.88 (d, J=8.7 Hz, 1H), 6.82 (t, J=8.7 Hz, 1H), 6.61 (s, 1H), 5.92 (s, 1H), 3.94 (q, J=7.0 Hz, 2H), 3.49 (s, 3H), 3.15 (q, J=7.4 Hz, 2H), 1.41 (t, J=7.4 Hz, 3H), 1.27 (t, J=7.0 Hz, 3H). MS (ESI+) m/z 481.2 (M+H)$^+$.

Example 404

N-[4-(4-chloro-2,6-difluorophenoxy)-3-(4-ethoxy-1-methyl-6-oxo-1,6-dihydropyridin-3-yl)phenyl]ethanesulfonamide

Example 404A 5-(2-(4-chloro-2,6-difluorophenoxy)-5-nitrophenyl)-4-ethoxy-1-methylpyridin-2(1H)-one Example 404A was prepared according to the procedure used for the preparation of Example 9B, substituting 2,6-difluoro-4-chlorophenol for phenol, and Example 381A for Example 9A, respectively, to provide the title compound.

Example 404B 5-(5-amino-2-(4-chloro-2,6-difluorophenoxy)phenyl)-4-ethoxy-1-methylpyridin-2(1H)-one Example 404B was prepared according to the procedure used for the preparation of Example 234B, substituting Example 404A for Example 234A, to provide the title compound.

Example 404C

N-[4-(4-chloro-2,6-difluorophenoxy)-3-(4-ethoxy-1-methyl-6-oxo-1,6-dihydropyridin-3-yl)phenyl]ethanesulfonamide Example 404C was prepared according to the procedure used for the preparation of Example 22, substituting Example 404B for Example 20C, and ethanesulfonyl chloride for methanesulfonyl chloride, respectively, to provide the title compound. $^1$H NMR (400 MHz, CDCl$_3$) δ 7.27 (s, 1H), 7.19 (d, J=2.7 Hz, 1H), 7.11 (dd, J=8.8, 2.7 Hz, 1H), 7.02 (d, J=7.3 Hz, 2H), 6.68 (d, J=8.7 Hz, 1H), 6.35 (s, 1H), 5.96 (s, 1H), 3.98 (d, J=7.0 Hz, 2H), 3.53 (s, 3H), 3.12 (d, J=7.4 Hz, 3H), 1.40 (t, J=7.4 Hz, 3H), 1.30 (t, J=7.0 Hz, 3H). MS (ESI+) m/z 499.2 (M+H)$^+$.

Example 405

N-[3-(4-ethoxy-1-methyl-6-oxo-1,6-dihydropyridin-3-yl)-4-(pyridin-3-yloxy)phenyl]ethanesulfonamide

Example 405A 4-ethoxy-1-methyl-5-(5-nitro-2-(pyridin-3-yloxy)phenyl)pyridin-2(1H)-one Example 405A was prepared according to the procedure used for the preparation of Example 9B, substituting pyridin-3-ol for phenol, and Example 381A for Example 9A, respectively, to provide the title compound.

Example 405B 5-(5-amino-2-(pyridin-3-yloxy)phenyl)-4-ethoxy-1-methylpyridin-2(1H)-one Example 405B was prepared according to the procedure used for the preparation of Example 10, substituting Example 405A for Example 9B, to provide the title compound.

Example 405C

N-[3-(4-ethoxy-1-methyl-6-oxo-1,6-dihydropyridin-3-yl)-4-(pyridin-3-yloxy)phenyl]ethanesulfonamide Example 405C was prepared according to the procedure used for the preparation of Example 22, substituting Example 405B for Example 20C, and ethanesulfonyl chloride for methanesulfonyl chloride, respectively, to provide the title compound. $^1$H NMR (400 MHz, CDCl$_3$) δ 8.32 (s, 1H), 7.28-7.20 (m, 5H), 6.98 (d, J=8.7 Hz, 1H), 6.46 (s, 1H), 5.90 (s, 1H), 3.90 (d, J=7.0 Hz, 2H), 3.48 (s, 3H), 3.17 (d, J=7.4 Hz, 2H), 1.43 (t, J=7.4 Hz, 3H), 1.21 (t, J=7.0 Hz, 3H). MS (ESI+) m/z 430.2 (M+H)$^+$.

Example 406

5-[5-amino-2-(2,4-difluorophenoxy)phenyl]-4-ethoxy-1-methylpyridin-2(1H)-one

Example 406A 5-bromo-4-ethoxy-1-methylpyridin-2(1H)-one

A flask with stirbar was charged with Example 269B (3.29 g, 14.79 mmol) in ethanol (80 mL). Sodium ethoxide, 21 wt % (9.65 g, 29.8 mmol) was added and the solution was heated at 80° C. for 70 minutes. The solution was cooled, reduced in volume by rotovap, then shaken in a separatory funnel with 200 mL each of ethyl acetate and saturated aqueous sodium chloride. The organics were dried over anhydrous sodium sulfate. After filtration and solvent removal the residues were chromatographed on a 40 g silica cartridge eluting with 0-100% ethyl acetate/heptane to provide the title compound.

Example 406B

5-[5-amino-2-(2,4-difluorophenoxy)phenyl]-4-ethoxy-1-methylpyridin-2(1H)-one

Example 406B was prepared according to the procedure used for the preparation of Example 1B, substituting Example 5D for 2-phenoxyphenylboronic acid, and Example 406A for Example 1A, respectively, to provide the title compound. $^1$H NMR (300 MHz, DMSO-d$_6$) δ 7.47 (s, 1H), 7.32-7.16 (m, 1H), 6.92 (dddd, J=9.7, 8.2, 3.0, 1.6 Hz, 1H), 6.80 (dt, J=9.2, 4.6 Hz, 1H), 6.76-6.71 (m, 1H), 6.56 (dd, J=8.6, 2.8 Hz, 1H), 6.48 (d, J=2.7 Hz, 1H), 5.71 (s, 1H), 5.02 (s, 2H), 4.08 (q, J=5.3 Hz, 2H), 3.31 (s, 3H), 1.11 (t, J=7.0 Hz, 3H). MS (ESI) m/z 373.1 (M+H+).

Example 407

N-{4-(2,4-difluorophenoxy)-3-[1-methyl-4-(5-methylthiophen-2-yl)-6-oxo-1,6-dihydropyridin-3-yl]phenyl}ethanesulfonamide Example 407 was prepared according to the procedure utilized for the preparation of Example 390, replacing 1-benzyl-4-(4,4,5,5-tetra methyl-1,3,2-dioxaborolan-2-yl)-1H-pyrazole with 4,4,5,5-tetramethyl-2-(5-methylthiophen-2-yl)-1,3,2-dioxaborolane to provide the title compound $^1$H NMR (400 MHz, CDCl$_3$) δ 7.68 (s, 1H), 7.26-7.24 (m, 2H), 7.07-7.01 (m, 1H), 6.86-6.80 (m, 1H), 6.73-6.70 (m, 2H), 6.67-6.66 (m, 2H), 6.59-6.53 (m, 1H), 3.61 (s, 3H), 3.07 (q, J=7.2 Hz, 2H), 1.32 (t, J=7.2 Hz, 3H). MS (ESI+) m/z 517.2 (M+H)$^+$.

Example 408

N-[4-(4-cyano-2-fluorophenoxy)-3-(4-ethoxy-1-methyl-6-oxo-1,6-dihydropyridin-3-yl)phenyl]ethanesulfonamide Example 408A 4-(2-(4-ethoxy-1-methyl-6-oxo-1,6-dihydropyridin-3-yl)-4-nitrophenoxy)-3-fluorobenzonitrile Example 408A was prepared according to the procedure used for the preparation of Example 9B, substituting 2-fluoro-4-cyanophenol for phenol, and Example 381A for Example 9A, respectively, to provide the title compound.

Example 408B 4-(4-amino-2-(4-ethoxy-1-methyl-6-oxo-1,6-dihydropyridin-3-yl)phenoxy)-3-fluorobenzonitrile Example 408B was prepared according to the procedure used for the preparation of Example 10, substituting Example 408A for Example 9B, to provide the title compound.

Example 408C

N-[4-(4-cyano-2-fluorophenoxy)-3-(4-ethoxy-1-methyl-6-oxo-1,6-dihydropyridin-3-yl)phenyl]ethanesulfonamide Example 408C was prepared according to the procedure used for the preparation of Example 22, substituting Example 408B for Example 20C, and ethanesulfonyl chloride for methanesulfonyl chloride, respectively, to provide the title compound. $^1$H NMR (400 MHz, CDCl$_3$) δ 7.42 (d, J=1.9 Hz, 1H), 7.39-7.20 (m, 4H), 7.05 (d, J=8.6 Hz, 1H), 6.83 (t, J=8.3 Hz, 1H), 6.52 (s, 1H), 5.88 (s, 1H), 3.91 (q, J=7.0 Hz, 2H), 3.47 (s, 3H), 3.19 (q, J=7.4 Hz, 2H), 1.43 (t, J=7.4 Hz, 3H), 1.24 (t, J=7.0 Hz, 3H). MS (ESI+) m/z 472.3 (M+H)$^+$.

Example 409

5-{2-[(2,4-difluorobenzyl)amino]-5-(methylsulfonyl)phenyl}-4-ethoxy-1-methylpyridin-2(1H)-one 5-[2-(cyclopropylmethoxy)-5-(2,3-dihydro-1H-indol-1-ylsulfonyl)phenyl]-4-ethoxy-1-methylpyridin-2(1H)-one Example 409A was prepared according to the procedure used for the preparation of Example 327B, substituting 2,4-difluorobenzylamine for cyclopropylmethylamine.

Example 409B

5-{2-[(2,4-difluorobenzyl)amino]-5-(methylsulfonyl)phenyl}-4-ethoxy-1-methylpyridin-2(1H)-one Example 409B was prepared according to the procedure used for the preparation of Example 327D, substituting Example 368B for Example 327C and Example 409AB for Example 269B, respectively. Purification by reverse phase HPLC (C18, CH$_3$CN/water (0.1% TFA), 10-100%) afforded the title compound as the trifluoroacetic acid salt. $^1$H NMR (300 MHz, DMSO-d$_6$) δ 7.63 (s, 1H), 7.56 (dd, J=2.2, 8.7 Hz, 1H), 7.39 (d, J=2.3 Hz, 1H), 7.34-7.20 (m, 2H), 7.03 (td, J=2.4, 8.7 Hz, 1H), 6.52 (d, J=8.8 Hz, 1H), 6.34 (t, J=6.3 Hz, 1H), 5.92 (s, 1H), 4.39 (d, J=5.8 Hz, 2H), 4.01 (q, J=6.8 Hz, 2H), 3.39 (s, 3H), 3.07 (s, 3H), 1.16 (t, J=7.0 Hz, 3H). MS (ESI+) 449.1.

Example 410

N-[3-(4-ethoxy-1-methyl-6-oxo-1,6-dihydropyridin-3-yl)-4-({1-[4-(trifluoromethyl)phenyl]piperidin-4-yl}oxy)phenyl]ethanesulfonamide Example 410A Example 410A was prepared according to the procedure used for the preparation of Example 247A, substituting 1-(4-(trifluoromethyl)phenyl)piperidin-4-ol for cyclohexanol, and Example 381A for Example 225A, respectively, to provide the title compound.

Example 410B 5-(5-amino-2-((1-(4-(trifluoromethyl)phenyl)piperidin-4-yl)oxy)phenyl)-4-ethoxy-1-methylpyridin-2(1H)-one Example 410B was prepared according to the procedure used for the preparation of Example 10, substituting Example 410A for Example 9B.

Example 410C

N-[3-(4-ethoxy-1-methyl-6-oxo-1,6-dihydropyridin-3-yl)-4-({1-[4-(trifluoromethyl)phenyl]piperidin-4-yl}oxy)phenyl]ethanesulfonamide Example 410C was prepared according to the procedure used for the preparation of Example 22, substituting Example 410B for Example 20C, and ethanesulfonyl chloride for methanesulfonyl chloride, respectively, to provide the title compound. $^1$H NMR (400 MHz, CDCl$_3$) δ 7.47 (d, J=8.7 Hz, 2H), 7.20 (dd, J=8.7, 2.8 Hz, 1H), 7.16 (s, 1H), 7.13 (d, J=2.7 Hz, 1H), 6.91 (t, J=8.4 Hz, 3H), 6.44 (s, 1H), 5.97 (s, 1H), 4.41-4.38 (m, 1H), 3.95 (q, J=7.0 Hz, 2H), 3.47 (s, 3H), 3.40-3.34 (m, 2H), 3.23-3.15 (m, 2H), 3.12 (q, J=7.4 Hz, 2H), 2.06-1.92 (m, 2H), 1.85-1.79 (m, 2H), 1.41 (t, J=7.4 Hz, 3H), 1.27 (t, J=7.0 Hz, 3H). MS (ESI+) m/z 560.0 (M+H)+.

Example 411

N-[4-(2,4-difluorophenoxy)-3-(4-ethoxy-1-methyl-6-oxo-1,6-dihydropyridin-3-yl)phenyl]-1,3-thiazole-5-carboxamide Example 411 was prepared according to the procedure used for the preparation of Example 295, substituting 1,3-thiazole-5-carboxylic acid for 2-oxo-1-phenylpyrrolidine-3-carboxylic acid to provide the title compound as the trifluoroacetic acid salt. $^1$H NMR (400 MHz, DMSO-$d_6$/$D_2O$) δ 9.28 (s, 1H), 8.66 (s, 1H), 7.71-7.64 (m, 2H), 7.61 (s, 1H), 7.39-7.30 (m, 1H), 7.10-6.99 (m, 2H), 6.94 (d, J=8.8 Hz, 1H), 5.85 (s, 1H), 4.00-3.90 (m, 2H), 3.39 (s, 3H), 1.16 (t, J=6.9 Hz, 3H). MS (APCI+) m/z 484.0 (M+H)+.

Example 412

2,5-dichloro-N-[4-(2,4-difluorophenoxy)-3-(4-ethoxy-1-methyl-6-oxo-1,6-dihydropyridin-3-yl)phenyl]benzamide Example 412 was prepared according to the procedure used for the preparation of Example 295, substituting 2,5-dichlorobenzoic acid for 2-oxo-1-phenylpyrrolidine-3-carboxylic acid. $^1$H NMR (400 MHz, DMSO-$d_6$/$D_2O$) δ 7.71-7.65 (m, 2H), 7.67-7.56 (m, 4H), 7.39-7.29 (m, 1H), 7.10-6.92 (m, 3H), 5.84 (s, 1H), 3.95 (q, J=6.9 Hz, 2H), 3.38 (s, 3H), 1.16 (t, J=6.9 Hz, 3H). MS (APCI+) m/z 544.9 (M+H)+.

Example 413

N-[4-(2,4-difluorophenoxy)-3-(4-ethoxy-1-methyl-6-oxo-1,6-dihydropyridin-3-yl)phenyl]-4-(propan-2-yl)benzamide Example 413 was prepared according to the procedure used for the preparation of Example 295, substituting 4-(propan-2-yl)benzoic acid for 2-oxo-1-phenylpyrrolidine-3-carboxylic acid. $^1$H NMR (400 MHz, DMSO-$d_6$/$D_2O$) δ 10.27 (s, 1H), 7.88 (d, J=6.5 Hz, 2H), 7.88-7.84 (m, 1H), 7.76-7.68 (m, 2H), 7.61 (s, 1H), 7.45-7.29 (m, 3H), 7.09-6.98 (m, 2H), 6.93 (d, J=8.6 Hz, 1H), 5.84 (s, 1H), 3.95 (q, J=7.0 Hz, 2H), 3.38 (s, 2H), 3.03-2.91 (m, 1H), 1.27-1.10 (m, 9H). MS (APCI+) m/z 519.0 (M+H)+.

Example 414

N-[4-(2,4-difluorophenoxy)-3-(4-ethoxy-1-methyl-6-oxo-1,6-dihydropyridin-3-yl)phenyl]-5-methylpyrazine-2-carboxamide Example 414 was prepared according to the procedure used for the preparation of Example 295, substituting 5-methylpyrazine-2-carboxylic acid for 2-oxo-1-phenylpyrrolidine-3-carboxylic acid to provide the title compound as the trifluoroacetic acid salt. $^1$H NMR (400 MHz, DMSO-$d_6$/$D_2O$) δ 9.14 (d, J=1.4 Hz, 1H), 8.72-8.67 (m, 1H), 7.87-7.79 (m, 2H), 7.62 (s, 1H), 7.39-7.30 (m, 1H), 7.09-7.00 (m, 2H), 6.94 (d, J=8.7 Hz, 1H), 5.85 (s, 1H), 3.95 (q, J=6.9 Hz, 2H), 3.39 (s, 3H), 2.64 (s, 3H), 1.16 (t, J=6.9 Hz, 3H). MS (APCI+) m/z 493.0 (M+H)+.

Example 415

N-[4-(2,4-difluorophenoxy)-3-(4-ethoxy-1-methyl-6-oxo-1,6-dihydropyridin-3-yl)phenyl]pyridine-2-carboxamide Example 415 was prepared according to the procedure used for the preparation of Example 295, substituting pyridine-2-carboxylic acid for 2-oxo-1-phenylpyrrolidine-3-carboxylic acid to provide the title compound as a trifluoroacetic acid salt. $^1$H NMR (400 MHz, DMSO-$d_6$/$D_2O$) δ 8.78-8.72 (m, 1H), 8.16 (d, J=7.8 Hz, 1H), 8.08 (td, J=7.6, 1.7 Hz, 1H), 7.92-7.80 (m, 2H), 7.69 (ddd, J=7.5, 4.7, 1.3 Hz, 1H), 7.62 (s, 1H), 7.39-7.30 (m, 1H), 7.10-7.00 (m, 2H), 6.94 (d, J=8.7 Hz, 1H), 5.85 (s, 1H), 3.95 (q, J=6.9 Hz, 2H), 3.39 (s, 3H), 1.16 (t, J=6.9 Hz, 3H). MS (APCI+) m/z 478.0 (M+H)+.

Example 416

4-tert-butyl-N-[4-(2,4-difluorophenoxy)-3-(4-ethoxy-1-methyl-6-oxo-1,6-dihydropyridin-3-yl)phenyl]benzenesulfonamide Example 416 was prepared according to the procedure used for the preparation of Example 307, substituting 4-(2,2-dimethylethyl)benzenesulfonyl chloride for 4-(methylsulfonyl)benzenesulfonyl chloride. $^1$H NMR (400 MHz, DMSO-$d_6$/$D_2O$) δ 7.73-7.66 (m, 2H), 7.62-7.56 (m, 2H), 7.47 (s, 1H), 7.31 (ddd, J=11.2, 8.6, 2.8 Hz, 1H), 7.08 (dd, J=8.7, 2.7 Hz, 1H), 7.06-6.87 (m, 3H), 6.81 (d, J=8.7 Hz, 1H), 5.80 (s, 1H), 3.89 (q, J=7.0 Hz, 2H), 3.35 (s, 3H), 1.27 (s, 9H), 1.10 (t, J=6.9 Hz, 3H). MS (APCI+) m/z 568.9 (M+H)+.

Example 417

2,4-dichloro-N-[4-(2,4-difluorophenoxy)-3-(4-ethoxy-1-methyl-6-oxo-1,6-dihydropyridin-3-yl)phenyl]benzenesulfonamide Example 417 was prepared according to the procedure used for the preparation of Example 307, substituting 2,4-dichlorobenzenesulfonyl chloride for 4-(methylsulfonyl)benzenesulfonyl chloride. $^1$H NMR (400 MHz, DMSO-$d_6$/$D_2O$) δ 8.01 (d, J=8.5 Hz, 1H), 7.87 (d, J=2.0 Hz, 1H), 7.62 (dd, J=8.5, 2.1 Hz, 1H), 7.45 (s, 1H), 7.31 (ddd, J=11.2, 8.6, 2.8 Hz, 1H), 7.10-6.96 (m, 3H), 6.93 (td, J=9.1, 5.5 Hz, 1H), 6.80 (d, J=8.7 Hz, 1H), 5.81 (s, 1H), 3.89 (q, J=7.0 Hz, 2H), 3.35 (s, 3H), 1.09 (t, J=6.9 Hz, 3H). MS (APCI+) m/z 580.9 (M+H)+.

Example 418

N-[4-(2,4-difluorophenoxy)-3-(4-ethoxy-1-methyl-6-oxo-1,6-dihydropyridin-3-yl)phenyl]naphthalene-2-sulfonamide Example 418 was prepared according to the procedure used for the preparation of Example 307, substituting naphthalene-2-sulfonyl chloride for 4-(methylsulfonyl)benzenesulfonyl chloride. $^1$H NMR (400 MHz, DMSO-$d_6$/$D_2O$) δ 8.37 (s, 1H), 8.15-8.07 (m, 2H), 8.07-8.01 (m, 1H), 7.81-

7.65 (m, 3H), 7.33-7.26 (m, 2H), 7.08 (dd, J=8.7, 2.7 Hz, 1H), 7.01-6.92 (m, 2H), 6.92-6.82 (m, 1H), 6.78 (d, J=8.7 Hz, 1H), 5.77 (s, 1H), 3.86-3.78 (m, 2H), 3.29 (s, 3H), 0.98 (t, J=6.9 Hz, 3H). MS (APCI+) m/z 562.9 (M+H)$^+$.

Example 419

5-[2-(2,4-difluorophenoxy)-5-(2,3-dihydro-1H-indol-1-ylsulfonyl)phenyl]-4-ethoxy-1-methylpyridin-2(1H)-one Example 419A A mixture of 2,4-difluorophenol (0.260 g, 1.98 mmol) and Example 397A (0.705 g, 1.98 mmol) in dimethylformamide (10 mL) was treated with potassium carbonate (0.684 g, 4.95 mmol). The mixture was stirred at 75° C. for 3 hours. The reaction mixture was partitioned between dilute saturated aqueous sodium chloride and ethyl acetate. The aqueous layer was extracted with additional ethyl acetate. The combined organic layers were dried over anhydrous magnesium sulfate, filtered, and concentrated to give title compound.

Example 419B

5-[2-(2,4-difluorophenoxy)-5-(2,3-dihydro-1H-indol-1-ylsulfonyl)phenyl]-4-ethoxy-1-methylpyridin-2(1H)-one A mixture of Example 419A (92 mg, 0.197 mmol), Example 368B (55 mg, 0.197 mmol), tetrakis(tiriphenylphosphine)palladium(0) (23 mg, 10 mol %) and cesium fluoride (90 mg, 0.591 mmol) in dimethoxyethane (2 mL) and methanol (1 mL) was heated under microwave conditions (120° C., 50 minutes). The reaction mixture was partitioned between saturated aqueous sodium chloride and ethyl acetate. The aqueous layer was extracted with additional ethyl acetate. The combined organic layers were dried over anhydrous magnesium sulfate, filtered, and concentrated. The residue was purified by reverse phase HPLC (C18, CH$_3$CN/water (0.1% TFA), 0-100%) to give the title compound (0.021 g, 20% yield). $^1$H NMR (400 MHz, DMSO-d$_6$) δ ppm 7.72 (dd, J=8.6, 2.4 Hz, 1H), 7.68 (d, J=2.4 Hz, 1H), 7.56 (s, 1H), 7.42-7.52 (m, 2H), 7.08-7.34 (m, 4H), 7.01 (td, J=7.4, 1.0 Hz, 1H), 6.87 (d, J=8.6 Hz, 1H), 5.85 (s, 1H), 3.89-4.01 (m, 4H), 3.35 (s, 3H), 2.91 (t, J=8.3 Hz, 2H), 1.13 (t, J=6.9 Hz, 3H). MS (ESI+) m/z 539.1 (M+H)$^+$.

Example 420

N-[4-(2,4-difluorophenoxy)-3-(4-ethoxy-1-methyl-6-oxo-1,6-dihydropyridin-3-yl)phenyl]-N-methyl-1-phenylmethanesulfonamide A vial with stirbar was charged with Example 311 (0.098 g, 0.186 mmol), powdered sodium hydroxide (15.3 mg, 0.383 mmol), tetrabutylammonium bromide (4.9 mg, 0.015 mmol) and tetrahydrofuran (2 mL), and then placed in an ice bath. After stirring for 10 minutes at 0° C., iodomethane (0.015 mL, 0.240 mmol) was added by syringe. The mixture was stirred at 0° C. for 1 hour, then at ambient temperature for an additional 2 hours. The mixture was partitioned between 30 mL each of ethyl acetate and 1 M HCl. The organics were dried over anhydrous sodium sulfate. After filtration and solvent removal, the residues were chromatographed on a 4 g silica cartridge eluting with 0-10% methanol/dichloromethane to provide the title compound. $^1$H NMR (400 MHz, DMSO-d$_6$) δ 7.63 (s, 1H), 7.54-7.31 (m, 6H), 7.22 (dd, J=8.7, 2.8 Hz, 1H), 7.21-6.96 (m, 3H), 6.82 (d, J=8.7 Hz, 1H), 5.87 (s, 1H), 4.59 (s, 2H), 4.00 (q, J=7.0 Hz, 2H), 3.42 (s, 3H), 3.26 (s, 3H), 1.20 (t, J=7.0 Hz, 3H). MS (ESI) 541.1 (M+H+).

BIOLOGICAL EXAMPLES

Bromodomain Domain Binding Assay

A time-resolved fluorescence resonance energy transfer (TR-FRET) assay was used to determine the affinities of compounds of the Examples listed in Table 1 for each bromodomain of BRD4. His-tagged first (BD1: amino acids K57-E168) and second (BD2: amino acids E352-E168) bromodomains of BRD4 were expressed and purified. An Alexa647-labeled BET-inhibitor was used as the fluorescent probe in the assay.

Synthesis of Alexa647-labeled bromodomain inhibitor compound 2-((6S,Z)-4-(4-chlorophenyl)-2,3,9-trimethyl-6H-thieno[3,2-f][1,2,4]triazolo[4,3-a][1,4]diazepin-6-yl)acetic acid Methyl 2-((6S,Z)-4-(4-chlorophenyl)-2,3,9-trimethyl-6H-thieno[3,2-f][1,2,4]triazolo[4,3-a][1,4]diazepin-6-yl)acetate (see e.g., WO 2006129623) (100.95 mg, 0.243 mmol was suspended in 1 mL methanol to which was added a freshly prepared solution of lithium hydroxide monohydrate (0.973 mL, 0.5 M, 0.487 mmol) and shaken at ambient temperature for 3 hours. The methanol was evaporated and the pH adjusted with aqueous hydrochloric acid (1 M, 0.5 mL, 0.5 mmol) and extracted four times with ethyl acetate. The combined ethyl acetate layers were dried over magnesium sulfate and evaporated to afford 2-((6S,Z)-4-(4-chlorophenyl)-2,3,9-trimethyl-6H-thieno[3,2-f][1,2,4]triazolo[4,3-a][1,4]diazepin-6-yl)acetic acid (85.3 mg, 87.0%); ESI-MS m/z=401.1 [(M+H)$^+$] which was used directly in the next reaction.

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate)

2-((6S,Z)-4-(4-chlorophenyl)-2,3,9-trimethyl-6H-thieno[3,2-f][1,2,4]triazolo[4,3-a][1,4]diazepin-6-yl)acetic acid) (85.3 mg, 0.213 mmol) was combined with 2,2'-(ethane-1,2-diylbis(oxy))diethanamine (Sigma-Aldrich, 0.315 mg, 2.13 mmol) were combined in 5 mL anhydrous dimethylformamide. (1H-benzo[d][1,2,3]triazol-1-yloxy)tripyrrolidin-1-ylphosphonium hexafluorophosphate(V) (PyBOB, CSBio, Menlo Park Calif.; 332 mg, 0.638 mmol) was added and the reaction shaken at ambient temperature for 16 hours. The reaction was diluted to 6 mL with dimethylsulfoxide: water (9:1, v:v) and purified in two injections with time collection Waters Deltapak C18 200×25 mm column eluted with a gradient of 0.1% trifluoroacetic acid (v/v) in water and acetonitrile. The fractions containing the two purified products were lyophilized to afford N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (134.4 mg, 82.3%); ESI-MS m/z=531.1 [(M+H)$^+$]; 529.1 [(M−H)$^-$] and (S,Z)—N,N'-(2,2'-(ethane-1,2-diylbis(oxy))bis(ethane-2,1-diyl))bis(2-((6S,Z)-4-(4-chlorophenyl)-2,3,9-trimethyl-6H-thieno[3, 2-f][1,2,4]triazolo[4,3-a][1,4]diazepin-6-yl)acetamide)bis(2,2,2-trifluoroacetate) (3.0 mg, 1.5%); ESI-MS m/z=913.2 [(M+H)$^+$]; 911.0 [(M−H)$^−$].

N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide(2,2,2-trifluoroacetate)

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (5.4 mg, 0.0071 mmol) was combined with Alexa Fluor® 647 carboxylic Acid, succinimidyl ester (Life Technologies, Grand Island, N.Y.; 3 mg, 0.0024 mmol) were combined in 1 mL anhydrous dimethylsulfoxide containing diisopropylethylamine (1% v/v) and shaken at ambient temperature for 16 hours. The reaction was diluted to 3 mL with dimethylsulfoxide:water (9:1, v:v) and purified in one injection with time collection Waters Deltapak C18 200×25 mm column eluted with a gradient of 0.1% trifluoroacetic acid (v/v) in water and acetonitrile. The fractions containing the purified product were lyophilized to afford N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide(2,2,2-trifluoroacetate) (1.8 mg); MALDI-MS m/z=1371.1, 1373.1 [(M+H)$^+$] as a dark blue powder.

Assay

Compound dilution series were prepared in DMSO via an approximately 3-fold serial dilution from one of the following:
Assay method C: 1250 µM-21 nM
Assay method D: 500 µM-8.5 nM
Assay method E: 0.47 mM to 7.8 nM
Assay method F: 250 µM-4.2 nM
Assay method G: 0.047 mM to 0.78 nM
or 5-fold serial dilution from one of the following:
Assay method A: 2.5 mM-800 nM
Assay method B: 2.5 mM-797 nM For Assay methods A, C, D, and F: Compounds were then diluted 6:100 in assay buffer (20 mM Sodium Phosphate, pH 6.0, 50 mM NaCl, 1 mM Ethylenediaminetetraacetic acid, 0.01% Triton X-100, 1 mM DL-Dithiothreitol) to yield 3× working solutions. Six microliters (µL) of the working solution was then transferred to white, low-volume assay plates (Costar #3673). A 1.5× assay mixture containing His-tagged bromodomain, Europium-conjugated anti-His antibody (Invitrogen PV5596) and the Alexa-647-conjugated probe molecule was also prepared. Twelve µL of this solution were added to the assay plate to reach a final volume of 18 µL.

For Assay methods B, E, and G: Compound dilutions were added directly into white, low-volume assay plates (Perkin Elmer Proxiplate 384 Plus#6008280) using a Labcyte Echo in conjunction with Labcyte Access and Thermo Multidrop CombinL robotics. Compounds were then suspended in eight microliters (µL) of assay buffer (20 mM Sodium Phosphate, pH 6.0, 50 mM NaCl, 1 mM Ethylenediaminetetraacetic acid disodium salt dihydrate, 0.01% Triton X-100, 1 mM DL-Dithiothreitol) containing His-tagged bromodomain, Europium-conjugated anti-His antibody (Invitrogen PV5596) and Alexa-647-conjugated probe.

The final concentration of 1× assay mixture for assay methods A, B, C, D, E, F, and G contains 2% DMSO, 8 nM His-tagged bromodomain, 1 nM Europium-conjugated anti-His-tag antibody and 100 nM or 30 nM probe (for BDI or BDII, respectively) and compound concentration in the range of: 50 µM-16 nM for method A, 49.02 µM-15.63 nM for method B, 25 µM-423 µM for method C, 10 µM-169 µM for method D, 9.19 µM-150 µM for method E, 5 µM-85 µM for method F, and 0.92 µM-15 µM for method G.

After a one-hour equilibration at room temperature, TR-FRET ratios were determined using an Envision multilabel plate reader (Ex 340, Em 495/520).

TR-FRET data were normalized to the means of 24 no-compound controls ("high") and 8 controls containing 1 µM un-labeled probe ("low"). Percent inhibition was plotted as a function of compound concentration and the data were fit with the 4 parameter logistic equation to obtain IC$_{50}$s. Inhibition constants (K$_i$) were calculated from the IC$_{50}$s, probe K$_d$ and probe concentration. Typical Z' values were between 0.65 and 0.75. The minimum significant ratio was determined to evaluate assay reproducibility (Eastwood et al., (2006) J Biomol Screen, 11: 253-261). The MSR was determined to be 2.03 for BDI and 1.93 for BDII, and a moving MSR (last six run MSR overtime) for both BDI and BDII was typically <3. The K$_i$ values are reported in Table 1.

MX-1 Cell Line Proliferation Assay

The impact of compounds of the Examples on cancer cell proliferation was determined using the breast cancer cell line MX-1 (ATCC) in a 3-day proliferation assay. MX-1 cells were maintained in RPMI supplemented with 10% FBS at 37° C. and an atmosphere of 5% CO$_2$. For compound testing, MX-1 cells were plated in 96-well black bottom plates at a density of 5000 cells/well in 90 µL of culture media and incubated at 37° overnight to allow cell adhesion and spreading. Compound dilution series were prepared in DMSO via a 3-fold serial dilution from 3 mM to 0.1 µM. The DMSO dilution series were then diluted 1:100 in phosphate buffered saline, and 10 µL of the resulted solution were added to the appropriate wells of the MX-1 cell plate. The final compound concentrations in the wells were 3, 1, 0.3, 0.1, 0.03, 0.01, 0.003, 0.001, 0.0003 and 0.0001 µM. After the addition of compounds, the cells were incubated for 72 more hours and the amounts of viable cells were determined using the Cell Titer Glo assay kit (Promega) according to manufacturer suggested protocol.

Luminescence readings from the Cell Titer Glo assay were normalized to the DMSO treated cells and analyzed using the GraphPad Prism software with sigmoidal curve fitting to obtain EC$_{50}$s. The minimum significant ratio (MSR) was determined to evaluate assay reproducibility (Eastwood et al., (2006) J Biomol Screen, 11: 253-261). The overall MSR was determined to be 2.1 and a moving MSR (last six run MSR overtime) has been <2. The EC$_{50}$ values are reported in Table 1 for the indicated compounds.

TABLE 1

| Compounds of Example # | TR-FRET assay protocol | TR-FRET Binding Ki: BRD4 (BDI_K57-E168) (µM) | TR-FRET Binding Ki: BRD4 (BDII_E352-M457) (µM) | Cellular proliferation: EC$_{50}$ (µM) |
|---|---|---|---|---|
| 1 | A | 1.87 | 2.05 | 20.0 |
| 2 | A | 11.7 | 2.86 | 13.5 |
| 3 | A | 0.851 | 3.43 | ND |
| 4 | E | 1.34 | >4.08 | ND |
| 5 | F | 0.922 | 0.688 | >3 |
| 6 | A | 4.08 | 3.17 | ND |
| 7 | A | 1.97 | 10.4 | ND |
| 8 | A | 8.59 | 17.8 | ND |
| 9 | A | 10.5 | 9.26 | ND |

TABLE 1-continued

| Compounds of Example # | TR-FRET assay protocol | TR-FRET Binding Ki: BRD4 (BDI_K57-E168) (μM) | TR-FRET Binding Ki: BRD4 (BDII_E352-M457) (μM) | Cellular proliferation: EC$_{50}$ (μM) |
|---|---|---|---|---|
| 10 | A | 2.44 | 1.5 | 3.7 |
| 11 | A | 4.04 | 4.37 | 9.46 |
| 12 | A | 0.575 | 0.696 | 2.66 |
| 13 | A | 13.1 | 10.2 | ND |
| 14 | A | 2.55 | 1.22 | 11.5 |
| 15 | A | 17.8 | 16.3 | ND |
| 16 | A | 1.11 | 8.42 | 5.9 |
| 17 | A | 0.513 | 4.52 | 2.63 |
| 18 | A | 1.65 | 0.523 | 4.3 |
| 19 | A | 8.85 | 8.58 | ND |
| 20 | A | 2.7 | 0.524 | 7.16 |
| 21 | E | 0.147 | 0.103 | 1.34 |
| 22 | E | 0.258 | 0.0519 | 0.73 |
| 23 | E | 0.48 | 0.214 | 3.8 |
| 24 | A | 0.326 | 0.108 | 1.01 |
| 25 | A | 0.0974 | 0.0125 | 0.45 |
| 26 | A | 0.569 | 0.104 | 0.80 |
| 27 | E | 0.296 | 0.0789 | 0.72 |
| 28 | E | 0.71 | 0.227 | 7.62 |
| 29 | E | 1.37 | 0.95 | 4.53 |
| 30 | E | >2.38 | 1.33 | 12.9 |
| 31 | A | 0.238 | 0.0465 | 0.42 |
| 32 | A | 5.32 | 12.2 | ND |
| 33 | A | 3 | 2.29 | 4.1 |
| 34 | A | 8.17 | 3.19 | ND |
| 35 | A | 2.39 | 1.08 | ND |
| 36 | A | 5.06 | 4.43 | ND |
| 37 | A | 1.73 | 1.79 | 10.0 |
| 38 | A | 6.35 | 6.83 | ND |
| 39 | A | 3.54 | 14.6 | ND |
| 40 | A | 9.48 | 20.1 | ND |
| 41 | A | >12.9 | >20.3 | ND |
| 42 | A | >12.6 | >22.2 | ND |
| 43 | A | >5.82 | >22.2 | ND |
| 44 | A | 2.71 | 5.11 | ND |
| 45 | C | >5.67 | >11.1 | ND |
| 46 | A | 4.39 | 18 | ND |
| 47 | A | 5.28 | >22.2 | ND |
| 48 | A | 9.44 | 1.08 | ND |
| 49 | A | 6.68 | 0.748 | 7.11 |
| 50 | A | 2.1 | 2.42 | 9.52 |
| 51 | A | 11.6 | 6.6 | ND |
| 52 | A | 9 | 10.5 | ND |
| 53 | A | >11.5 | >14.3 | ND |
| 54 | A | 4.12 | 0.356 | 4.24 |
| 55 | A | 6.89 | 0.778 | 13.7 |
| 56 | A | 2.9 | 0.341 | 10.4 |
| 57 | A | 0.598 | 0.25 | 1.86 |
| 58 | A | 0.264 | 0.0635 | 0.444 |
| 59 | A | 9.79 | 2.11 | >30 |
| 60 | A | 0.17 | 0.413 | >3 |
| 61 | E | 0.0331 | 0.0489 | 0.911 |
| 62 | F | 0.00749 | 0.00513 | 0.281 |
| 63 | A | 0.0852 | 0.0239 | 0.739 |
| 64 | A | 0.448 | 0.507 | ND |
| 65 | A | 0.797 | 0.14 | ND |
| 66 | A | 0.141 | 0.159 | 2.48 |
| 67 | E | 0.0708 | 0.0925 | 1.73 |
| 68 | A | 0.0631 | 0.0719 | 1.11 |
| 69 | A | 0.098 | 0.225 | >3 |
| 70 | A | 0.0891 | 0.062 | 0.815 |
| 71 | A | 0.0622 | 0.133 | 0.398 |
| 72 | A | 0.225 | 0.128 | 3.75 |
| 73 | A | 0.462 | 0.307 | 1.13 |
| 74 | A | 0.632 | 1.05 | ND |
| 75 | A | 0.264 | 0.195 | 1.39 |
| 76 | A | 0.755 | 1.28 | ND |
| 77 | A | 0.511 | 0.38 | ND |
| 78 | A | 0.435 | 0.211 | >3 |
| 79 | A | 0.126 | 0.0875 | 1.87 |
| 80 | A | 0.708 | 0.439 | ND |
| 81 | A | 1.12 | 0.733 | >3 |
| 82 | A | 4.07 | 2.48 | ND |
| 83 | A | 3.61 | 6.83 | ND |
| 84 | A | 1.02 | 1.01 | ND |
| 85 | A | 1.61 | 0.791 | ND |
| 86 | A | >13 | 2.74 | ND |
| 87 | A | 2.01 | 3.09 | ND |
| 88 | A | 6.79 | 4.44 | ND |
| 89 | A | 8.1 | 3.89 | ND |
| 90 | A | 4.55 | 2.33 | ND |
| 91 | G | >0.238 | 0.238 | ND |
| 92 | A | 0.77 | 0.455 | 1.13 |
| 93 | A | >13 | 3.24 | ND |
| 94 | A | 0.402 | 0.154 | ND |
| 95 | A | 0.172 | 0.145 | >3 |
| 96 | A | 8.33 | 13.4 | ND |
| 97 | A | 0.561 | 0.176 | ND |
| 98 | A | 0.216 | 0.0712 | 0.639 |
| 99 | A | 0.142 | 0.0587 | 0.558 |
| 100 | A | 0.143 | 0.0722 | >3 |
| 101 | E | 0.233 | 0.147 | 1.13 |
| 102 | A | 2.6 | 0.96 | ND |
| 103 | A | 0.253 | 0.109 | >3 |
| 104 | A | 1.6 | 0.562 | ND |
| 105 | E | 0.516 | 0.0847 | >3 |
| 106 | A | 0.176 | 0.925 | ND |
| 107 | A | 1.76 | 2.58 | ND |
| 108 | A | 0.41 | 0.327 | ND |
| 109 | A | 1.26 | 1.53 | ND |
| 110 | A | >13 | 13.5 | ND |
| 111 | A | 2.47 | 1.97 | ND |
| 112 | E | 0.138 | 0.181 | 1.28 |
| 113 | A | 0.407 | 0.317 | ND |
| 114 | E | 0.328 | 0.184 | ND |
| 115 | A | 11.1 | 6.94 | ND |
| 116 | A | 1.05 | 0.553 | ND |
| 117 | A | 1.49 | 0.619 | ND |
| 118 | A | >13 | 17.2 | ND |
| 119 | A | 0.135 | 0.0636 | 0.615 |
| 120 | A | 0.611 | 1.19 | ND |
| 121 | A | 1.12 | 2.96 | ND |
| 122 | A | 8.56 | 4.52 | ND |
| 123 | A | 7.26 | 1.17 | ND |
| 124 | A | 8.12 | 17.7 | ND |
| 125 | A | >13 | 16 | ND |
| 126 | A | 9.34 | >22.2 | ND |
| 127 | A | 0.249 | 0.139 | >3 |
| 128 | A | 1.64 | 0.376 | ND |
| 129 | A | 0.52 | 0.264 | ND |
| 130 | A | >13 | 17.1 | ND |
| 131 | A | 6.39 | 0.41 | ND |
| 132 | A | >13 | 8.05 | ND |
| 133 | A | 0.782 | 0.159 | ND |
| 134 | A | 4.32 | 4.06 | ND |
| 135 | A | 0.604 | 0.411 | ND |
| 136 | A | 4.33 | 6.7 | ND |
| 137 | A | 3.26 | 1.17 | ND |
| 138 | A | 7.43 | 3.18 | ND |
| 139 | E | >1.52 | 0.879 | ND |
| 140 | A | >13 | 8.21 | ND |
| 141 | A | 0.526 | 0.297 | ND |
| 142 | A | 2.4 | 1.73 | ND |
| 143 | A | 3.2 | 5.47 | ND |
| 144 | E | >2.38 | >3.37 | ND |
| 145 | A | >13 | 10.2 | ND |
| 146 | A | >13 | 12.2 | ND |
| 147 | A | 0.26 | 0.168 | ND |
| 148 | A | >13 | 19.7 | ND |
| 149 | A | 0.213 | 0.259 | 0.384 |
| 150 | A | 0.471 | 0.411 | ND |
| 151 | A | 0.4 | 0.258 | ND |
| 152 | A | 6.62 | 7.27 | ND |
| 153 | A | 5.96 | 3.09 | ND |
| 154 | A | 11.9 | 5.94 | ND |
| 155 | A | 5.52 | 6.9 | ND |
| 156 | A | >13 | 13.1 | ND |
| 157 | A | 5.51 | 4.75 | ND |

TABLE 1-continued

| Compounds of Example # | TR-FRET assay protocol | TR-FRET Binding Ki: BRD4 (BDI_K57-E168) (μM) | TR-FRET Binding Ki: BRD4 (BDII_E352-M457) (μM) | Cellular proliferation: EC$_{50}$ (μM) |
|---|---|---|---|---|
| 158 | A | 0.604 | 0.529 | ND |
| 159 | A | 5.45 | 8.42 | ND |
| 160 | A | 8.54 | 10.2 | ND |
| 161 | A | 0.0263 | 0.0249 | 0.244 |
| 162 | A | 0.109 | 0.0751 | ND |
| 163 | A | 1.99 | 0.366 | ND |
| 164 | E | 1.51 | 0.245 | ND |
| 165 | A | 0.567 | 0.492 | ND |
| 166 | A | 0.705 | 1.01 | ND |
| 167 | A | 5.43 | 7.37 | ND |
| 168 | A | 1.07 | 0.993 | ND |
| 169 | A | 0.599 | 0.562 | ND |
| 170 | A | 1.67 | 1.62 | ND |
| 171 | A | 0.253 | 0.215 | ND |
| 172 | A | 0.572 | 0.593 | ND |
| 173 | A | 0.805 | 0.545 | ND |
| 174 | A | 0.854 | 0.764 | ND |
| 175 | A | 2.95 | 2.49 | ND |
| 176 | A | 3.66 | 2.08 | ND |
| 177 | A | 4.17 | 1.07 | ND |
| 178 | A | 3.34 | 4.54 | ND |
| 179 | A | 0.923 | 0.488 | ND |
| 180 | A | 0.0445 | 0.0677 | 0.372 |
| 181 | A | 3.95 | 6.16 | ND |
| 182 | E | 0.531 | 0.174 | ND |
| 183 | A | 0.256 | 0.166 | ND |
| 184 | A | 2.14 | 1.96 | ND |
| 185 | E | 0.832 | 0.324 | ND |
| 186 | A | 1.32 | 0.854 | ND |
| 187 | A | 4.95 | 2.25 | ND |
| 188 | A | 0.67 | 1.13 | ND |
| 189 | A | 3.14 | 1.48 | ND |
| 190 | A | 6.56 | 2.42 | ND |
| 191 | A | 0.324 | 0.162 | 1.43 |
| 192 | A | 1.04 | 0.395 | ND |
| 193 | A | 0.167 | 1.01 | 1.29 |
| 194 | A | 1.52 | 1.43 | ND |
| 195 | A | 0.664 | 0.317 | ND |
| 196 | A | 1.08 | 0.67 | ND |
| 197 | A | 1.06 | 0.725 | ND |
| 198 | A | 0.282 | 0.0923 | ND |
| 199 | A | >13 | 5.66 | ND |
| 200 | A | 0.344 | 0.971 | ND |
| 201 | A | 2.41 | 1.71 | ND |
| 202 | A | 0.227 | 0.251 | ND |
| 203 | A | 3.51 | 1.52 | ND |
| 204 | A | 1.02 | 1.96 | ND |
| 205 | A | 2.83 | 2.97 | ND |
| 206 | A | 0.412 | 0.672 | ND |
| 207 | A | 7.02 | 11.8 | ND |
| 208 | A | 0.901 | 1.51 | ND |
| 209 | A | >5.49 | 8.48 | ND |
| 210 | A | 9.87 | 15.2 | ND |
| 211 | A | 2.15 | 1.52 | ND |
| 212 | A | 0.0898 | 0.117 | ND |
| 213 | A | >13 | 15.2 | ND |
| 214 | A | >13 | 10.4 | ND |
| 215 | A | 11.5 | 11.8 | ND |
| 216 | A | 0.719 | 0.462 | ND |
| 217 | A | 4.22 | 2.03 | ND |
| 218 | A | 0.778 | 1.14 | 9.7 |
| 219 | A | 7.25 | 0.308 | 5.5 |
| 220 | A | 24.3 | 1.91 | 16.4 |
| 221 | A | 0.976 | 0.517 | 7.2 |
| 222 | A | 6.84 | 1.36 | ND |
| 223 | A | 0.635 | 0.872 | 4.81 |
| 224 | E | 0.0482 | 0.113 | 0.208 |
| 225 | A | 0.152 | 0.107 | 10.0 |
| 226 | A | 0.271 | 1.13 | 10.0 |
| 227 | A | 0.157 | 0.42 | >3 |
| 228 | A | 0.142 | 0.154 | >3 |
| 229 | E | 0.0318 | 0.0218 | 0.507 |
| 230 | A | 0.056 | 0.048 | 0.395 |
| 231 | E | 0.0446 | 0.539 | 0.911 |
| 232 | E | 0.0278 | 0.101 | 0.357 |
| 233 | A | 0.0192 | 0.11 | 0.423 |
| 234 | A | 0.0213 | 0.216 | 1.29 |
| 235 | A | 0.0476 | 0.017 | 0.238 |
| 236 | E | 0.0142 | 0.0816 | 0.501 |
| 237 | E | 0.0162 | 0.227 | 1.38 |
| 238 | E | 0.0292 | 0.0499 | 0.643 |
| 239 | A | 0.0326 | 0.0398 | 0.138 |
| 240 | F | 0.0282 | 0.107 | 0.285 |
| 241 | F | 0.0346 | 0.0271 | 0.181 |
| 242 | A | 0.045 | 0.338 | 0.556 |
| 243 | E | 0.115 | 0.257 | 0.279 |
| 244 | A | 0.116 | 0.282 | 0.481 |
| 245 | A | 0.0786 | 0.439 | 1.01 |
| 246 | A | 0.0431 | 0.132 | 0.238 |
| 247 | A | 0.0224 | 0.194 | 0.425 |
| 248 | A | 0.156 | 4.57 | 0.488 |
| 249 | E | 0.0862 | 0.701 | >3 |
| 250 | A | 0.143 | 12.5 | >3 |
| 251 | A | 0.197 | 0.26 | 1.1 |
| 252 | A | 0.297 | 0.695 | >3 |
| 253 | A | 0.942 | 3.29 | >3 |
| 254 | A | 0.324 | 3.27 | ND |
| 255 | A | 0.635 | 0.142 | >3 |
| 256 | A | 0.219 | 0.0936 | 1.06 |
| 257 | A | 0.0181 | 0.0316 | 0.173 |
| 258 | A | 0.73 | 0.382 | 1.51 |
| 259 | E | 0.0286 | 0.00941 | 0.13 |
| 260 | E | 0.216 | 0.406 | 2.35 |
| 261 | E | 0.0259 | 0.0664 | 0.387 |
| 262 | A | 0.0779 | 0.29 | 0.783 |
| 263 | F | 0.0488 | 0.121 | 0.304 |
| 264 | F | 0.0335 | 0.0553 | 0.176 |
| 265 | A | 0.132 | 0.172 | 1.72 |
| 266 | F | 0.0583 | 0.341 | >3 |
| 267 | F | 0.0478 | 0.101 | >3 |
| 268 | F | 0.483 | 0.0951 | 0.579 |
| 269 | F | 0.246 | 0.204 | ND |
| 270 | F | 0.0256 | 0.0109 | 0.138 |
| 271 | F | 0.00976 | 0.00155 | 0.0473 |
| 272 | F | 0.0169 | 0.00462 | 0.167 |
| 273 | F | 0.00458 | 0.00245 | 0.107 |
| 274 | F | 0.0245 | 0.0055 | 0.0774 |
| 275 | F | 0.0559 | 0.119 | 0.223 |
| 276 | F | 0.916 | 0.57 | ND |
| 277 | F | 0.0107 | 0.00529 | 0.0481 |
| 278 | F | 0.00753 | 0.00139 | 0.0634 |
| 279 | F | 0.00273 | 0.0013 | 0.0454 |
| 280 | F | 0.0038 | 0.00173 | 0.0381 |
| 281 | A | 0.15 | 0.509 | 1.65 |
| 282 | F | 0.0204 | 0.0997 | ND |
| 283 | F | 0.0174 | 0.0394 | 0.194 |
| 284 | F | 0.00575 | 0.00184 | 0.0443 |
| 285 | F | 0.0049 | 0.00103 | 0.024 |
| 286 | F | 0.0826 | 0.0759 | >3 |
| 287 | D | 0.00662 | 0.00215 | 0.0596 |
| 288 | D | 0.19 | 0.551 | ND |
| 289 | D | 0.00631 | 0.000639 | 0.077 |
| 290 | D | 0.012 | 0.00322 | 0.138 |
| 291 | E | 0.0162 | 0.00627 | 0.112 |
| 292 | D | 0.00497 | 0.00173 | 0.045 |
| 293 | D | 0.0371 | 0.00599 | 0.115 |
| 294 | D | 0.0278 | 0.0083 | >3 |
| 295 | E | 0.275 | 0.093 | ND |
| 296 | E | 0.195 | 0.104 | ND |
| 297 | G | >0.238 | 0.256 | 2.42 |
| 298 | E | 0.143 | 0.0545 | 0.637 |
| 299 | E | 0.149 | 0.0352 | ND |
| 300 | E | 0.0256 | 0.0246 | 0.291 |
| 301 | E | 0.0618 | 0.0556 | ND |
| 302 | E | 0.209 | 0.0472 | ND |
| 303 | E | 0.233 | 0.201 | ND |
| 304 | E | 0.195 | 0.359 | ND |
| 305 | E | 0.557 | 0.271 | ND |

TABLE 1-continued

| Compounds of Example # | TR-FRET assay protocol | TR-FRET Binding Ki: BRD4 (BDI_K57-E168) (μM) | TR-FRET Binding Ki: BRD4 (BDII_E352-M457) (μM) | Cellular proliferation: EC$_{50}$ (μM) |
|---|---|---|---|---|
| 306 | E | 0.542 | 0.349 | ND |
| 307 | E | 0.0949 | 0.0416 | ND |
| 308 | E | 0.318 | 0.0659 | ND |
| 309 | E | 0.359 | 0.151 | ND |
| 310 | E | 0.2 | 0.0389 | ND |
| 311 | G | 0.0238 | 0.00514 | 1.0 |
| 312 | F | 0.353 | 2.15 | ND |
| 313 | E | 0.754 | 0.0552 | 1.33 |
| 314 | E | 0.642 | 0.229 | ND |
| 315 | D | 0.00251 | 0.00039 | 0.0556 |
| 316 | D | 0.0039 | 0.000809 | 0.0247 |
| 317 | E | 0.377 | 0.182 | ND |
| 318 | E | 0.156 | 0.0153 | 0.0427 |
| 319 | E | 0.316 | 0.104 | 0.322 |
| 320 | E | >2.38 | 0.275 | ND |
| 321 | E | 0.05 | 0.00915 | 0.423 |
| 322 | E | 0.437 | 0.0909 | >3 |
| 323 | E | 0.15 | 0.101 | 1.14 |
| 324 | E | 0.045 | 0.0181 | 0.436 |
| 325 | E | 0.0306 | 0.0214 | 0.101 |
| 326 | E | 0.00261 | 0.0175 | 2.98 |
| 327 | E | 0.68 | 1.11 | ND |
| 328 | D | 0.0071 | 0.0146 | 0.0727 |
| 329 | D | 0.00298 | 0.00171 | 0.0227 |
| 330 | F | 0.00196 | 0.000584 | 0.0497 |
| 331 | D | 0.164 | 0.551 | ND |
| 332 | E | 1.01 | 0.205 | ND |
| 333 | D | 0.00441 | 0.00183 | 0.0277 |
| 334 | D | 0.0276 | 0.00408 | 0.0152 |
| 335 | D | 0.0953 | 0.0151 | 0.239 |
| 336 | E | 0.0214 | 0.00167 | 0.165 |
| 337 | E | 0.611 | 1.83 | ND |
| 338 | D | 0.114 | 0.702 | ND |
| 339 | D | 0.172 | 0.971 | ND |
| 340 | E | 0.225 | 0.251 | 0.384 |
| 341 | E | >2.38 | >4.08 | ND |
| 342 | F | 0.00221 | 0.000609 | 0.0912 |
| 343 | E | 0.0698 | 0.0127 | 0.504 |
| 344 | E | 0.0231 | 0.00507 | 0.271 |
| 345 | E | 0.0102 | 0.00544 | 0.126 |
| 346 | D | 0.0415 | 0.013 | 0.264 |
| 347 | E | 0.169 | 0.0534 | 1.56 |
| 348 | E | 0.196 | 0.0631 | ND |
| 349 | E | 0.0438 | 0.00871 | 0.151 |
| 350 | G | 0.036 | 0.0195 | 1.0 |
| 351 | G | 0.0257 | 0.0298 | 0.36 |
| 352 | D | 0.0268 | 0.0779 | 0.256 |
| 353 | D | 0.00441 | 0.0023 | 0.0569 |
| 354 | D | 0.00497 | 0.00173 | 0.045 |
| 355 | D | 0.0371 | 0.00599 | 0.115 |
| 356 | D | 1.39 | 0.752 | ND |
| 357 | D | 0.159 | 1.42 | ND |
| 358 | D | 0.0078 | 0.00761 | 0.0526 |
| 359 | D | 0.0126 | 0.0051 | 0.112 |
| 360 | D | 0.127 | 0.7 | ND |
| 361 | D | 0.6 | 1.17 | ND |
| 362 | D | 0.00581 | 0.00276 | 0.0336 |
| 363 | D | 0.00494 | 0.00153 | 0.0296 |
| 364 | D | 0.0844 | 0.153 | 0.878 |
| 365 | D | 1.35 | >4.44 | ND |
| 366 | D | 0.629 | 0.57 | ND |
| 367 | D | 0.00211 | 0.000528 | 0.0189 |
| 368 | D | 0.0196 | 0.0286 | 0.0962 |
| 369 | D | 0.00529 | 0.00242 | 0.0281 |
| 370 | D | 0.0527 | 0.0395 | 0.135 |
| 371 | D | 0.00873 | 0.00229 | 0.0409 |
| 372 | D | 0.0335 | 0.0143 | 0.205 |
| 373 | D | 0.118 | 0.167 | 0.859 |
| 374 | D | 0.0123 | 0.0172 | 0.0761 |
| 375 | D | 0.0129 | 0.00322 | 0.0402 |
| 376 | G | 0.123 | 0.0171 | 0.708 |
| 377 | D | 0.0534 | 0.00641 | 0.0924 |
| 378 | D | 0.113 | 0.0317 | 0.103 |
| 379 | D | 0.0621 | 0.0161 | 0.126 |
| 380 | D | 0.0143 | 0.00388 | 0.0384 |
| 381 | D | 0.0334 | 0.0561 | 0.115 |
| 382 | E | 0.317 | 0.276 | ND |
| 383 | E | 0.0432 | 0.0828 | 0.0836 |
| 384 | E | 0.0653 | 0.146 | 0.237 |
| 385 | E | 0.0553 | 0.14 | 0.254 |
| 386 | E | 0.0818 | 0.0102 | 0.0541 |
| 387 | E | 0.0691 | 0.00787 | 0.0618 |
| 388 | E | 0.766 | 1.42 | ND |
| 389 | E | 1.26 | 3.99 | ND |
| 390 | E | 0.0365 | 0.0135 | 0.0798 |
| 391 | E | 0.00905 | 0.00459 | 0.0573 |
| 392 | E | 0.022 | 0.00429 | 0.0692 |
| 393 | E | 0.0119 | 0.00249 | 0.0707 |
| 394 | E | 0.272 | 0.516 | ND |
| 395 | E | 0.105 | 0.221 | 0.479 |
| 396 | E | 0.00954 | 0.00317 | 0.0156 |
| 397 | E | 0.0752 | 0.00884 | 0.0866 |
| 398 | E | 0.203 | 0.0309 | 0.45 |
| 399 | E | 0.0311 | 0.0201 | >3 |
| 400 | E | 0.00721 | 0.00181 | 0.0181 |
| 401 | E | 0.0198 | 0.00499 | 0.0251 |
| 402 | E | 0.0323 | 0.0166 | 0.0552 |
| 403 | E | 0.0147 | 0.00138 | 0.0239 |
| 404 | E | 0.0118 | 0.00143 | 0.0247 |
| 405 | E | 0.0363 | 0.00499 | 0.0502 |
| 406 | E | 1.55 | 0.567 | ND |
| 407 | E | 0.00692 | 0.00206 | 0.0723 |
| 408 | E | 0.0451 | 0.0191 | 0.115 |
| 409 | E | 2.01 | 1.1 | ND |
| 410 | E | 0.59 | 0.56 | ND |
| 411 | E | 0.0613 | 0.047 | 0.254 |
| 412 | E | 0.0289 | 0.0119 | 0.251 |
| 413 | E | 0.181 | 0.148 | ND |
| 414 | E | 0.0614 | 0.0389 | ND |
| 415 | E | 0.0405 | 0.0333 | 0.279 |
| 416 | E | 0.493 | 0.281 | ND |
| 417 | E | 0.259 | 0.0571 | ND |
| 418 | E | 0.362 | 0.165 | ND |
| 419 | G | 0.0253 | 0.00284 | 1.0 |
| 420 | G | >0.238 | 0.0221 | 0.832 |

ND = not determined

Proliferation Panel Assay

The compounds of Examples 224 and 261 were tested for their impact on proliferation of a panel of cancer cell lines types (with specific cell line tested) as set out in Table 2. Cells were plated in 96-well plates at 1500 cells/well in the appropriate culture media. Series dilution of compounds were prepared and added to the wells as in the MX-1 proliferation assay. After the addition of compounds, cells were incubated for another 5 days and the amounts of viable cells were determined using the Cell Titer Glo assay kit (Promega) according to manufacturer suggested protocol. Cell proliferation data were analyzed as described above in the MX-1 proliferation assay to obtain the EC$_{50}$ for the compounds of Examples 224 and 261 and reported in Table 2.

TABLE 2

| Cell line Type | Cell Line | Compound of Example 224 Cellular Proliferation EC$_{50}$ (μM) | Compound of Example 261 Cellular Proliferation EC$_{50}$ (μM) |
|---|---|---|---|
| AML | Raji | 0.129 | 0.134 |
| AML | SKM1 | 0.116 | 0.135 |

TABLE 2-continued

| Cell line Type | Cell Line | Compound of Example 224 Cellular Proliferation $EC_{50}$ (μM) | Compound of Example 261 Cellular Proliferation $EC_{50}$ (μM) |
|---|---|---|---|
| Bladder | EJ-1 | 1.593 | 1.159 |
| Breast | MDAMB231 | 0.72 | 0.46 |
| Breast | MDAMB453 | 0.32 | 0.34 |
| Colon | DLD-1 | 0.85 | 0.62 |
| Colon | GEO | 0.55 | 0.67 |
| Glioblastoma | D54MG | 0.423 | 0.338 |
| Head & Neck | FaDu | 0.28 | 0.27 |
| Hepatocellular | HepG2 | 0.486 | 0.51 |
| Melanoma | A-375 | 0.430 | 0.498 |
| Multiple Myeloma | NCI-H929 | 0.109 | 0.098 |
| Multiple Myeloma | OPM2 | 0.050 | 0.055 |
| Multiple Myeloma | RPMI-8226 | 0.279 | 0.305 |
| NHL | Ly18 | 0.52 | 0.51 |
| NHL | Ramos | 0.37 | 0.39 |
| NSCLC | H1299 | 0.75 | 0.74 |
| NSCLC | H1975 | 0.38 | 0.47 |
| NSCLC | H460 | 0.11 | 0.31 |
| Pancreas | BxPC3FP5 | 0.23 | 0.23 |
| Pancreas | HPAC | 0.38 | 0.50 |
| Prostate | PC3M | 1.45 | 1.40 |
| RCC | 786-0 | 0.273 | 0.250 |
| Sarcoma | SK-LMS-1 | 0.448 | 0.348 |

LPS (Lipopolysaccharide) Induced IL-6 Production Mouse Assay

Compounds of the Examples listed in Table 3 were assayed for their ability to inhibit LPS (lipopolysaccharide) induced IL-6 production in mice. Severe combined immunodeficient female mice (5 per group) received an intraperitoneal challenge of lipopolysaccharide (2.5 mg/kg, L2630 E. coli 0111:B4) one hour after oral administration of compounds. Mice were euthanized 2 hours after lipopolysaccharide injection, blood was removed by cardiac puncture, and then the serum harvested from the blood samples was frozen at −80° C. On the day of the assay the serum samples were brought to room temperature and then diluted 1:20 in phosphate-buffered saline containing 2% bovine serum albumin. Interleukin-6 measurements were performed using a cytokine assay from Meso Scale Discovery (Gaithersburg, Md.) for mouse serum analysis according to the manufacturer's protocol and read on a SECTOR Imager 6000 (Meso Scale Discovery, Gaithersburg, Md.) instrument. Statistical analysis was performed using Prism software (version 5.0) incorporating Dunnett's one way ANOVA. The IL-6 mean and standard deviation of the group of vehicle treated animals were compared with the IL-6 mean and standard deviation of the group treated with drug. A p value <0.05 means that there is less than a 5% probability that the mean values in the two groups are equal. The % inhibition values in Table 3 all exhibited a p value less than 0.05.

TABLE 3

Inhibition of LPS induced IL-6 production

| Compound of Example # | % inhibition |
|---|---|
| 22 | 53.9 @ 50 mg/kg |
| 233 | 75.9 @ 30 mg/kg |
| 235 | 58.7 @ 30 mg/kg |
| 240 | 72.6 @ 30 mg/kg |
| 241 | 73.9 @ 3 mg/kg |
| 257 | 49.7 @ 30 mg/kg |
| 261 | 42.2 @ 30 mg/kg |
| 270 | 68.8 @ 3 mg/kg |
| 271 | 76.9 @ 3 mg/kg |
| 285 | 84.0 @ 3 mg/kg |
| 292 | 58.0 @ 3 mg/kg |
| 293 | 71.0 @ 3 mg/kg |
| 333 | 63.6 @ 3 mg/kg |
| 335 | 50.9 @ 3 mg/kg |
| 346 | 48.6 @ 3 mg/kg |
| 358 | 60.5 @ 3 mg/kg |
| 363 | 42.7 @ 3 mg/kg |
| 367 | 80.0 @ 3 mg/kg |
| 368 | 72.4 @ 3 mg/kg |
| 369 | 38.0 @ 3 mg/kg |
| 371 | 57.6 @ 3 mg/kg |
| 375 | 84.4 @ 3 mg/kg |
| 387 | 54.3 @ 3 mg/kg |
| 400 | 66.4 @ 3 mg/kg |

Xenograft Tumor Growth Inhibition Assay

The effect of example compounds to inhibit growth of human tumor xenografts implanted in mice was evaluated. Briefly, cells obtained from culture (MV4-11 and OPM-2) or tumor brie (MX-1) were suspended in cell culture medium (MEM, Suspension, no Calcium, no Glutamine, Life Technologies Corporation) containing Matrigel (phenol red free, Becton Dickinson Biosciences Discovery Labware) and inoculated subcutaneously (approximately 5 million per site) into the right hind flank of SCID-beige (MV4-11 and OPM-2) or SCID (MX-1) female mice (Charles Rivers Labs) on study day 0. Administration of compound formulated in 2% EtOH, 5% Tween-80, 20% PEG-400, 73% HPMC (Example 240, OPM-2 and MX-1) or 5% DMSO, 5% ETOH, 30% PEG400, 60% Phosal 53 (Example 240, MV4-11 and Examples 290 and 271, OPM-2) was initiated at the time of size match. Examples 285 and 293 were formulated in 2.5% DMSO, 10% ETOH, 27.5% PEG400, 60% Phosal 53 MCT.

Tumors were measured with a pair of calipers twice a week starting at the time of size match and tumor volumes were calculated according to the formula V=L×W²/2 (V: volume, mm³; L: length, mm. W: width, mm). Tumor volume was measured throughout the treatment period or until the mean tumor volume in each group reached an endpoint of >1000 mm³. Results are shown in Tables 4, 5, and 6.

TABLE 4

MX-1 human breast cancer xenograft model

| Treatment | Dose route, regimen | % TGI[a] | % TGD[b] |
|---|---|---|---|
| Compound of Example 240 | 30 mg/kg/day PO, QDx14 | 61*** | 51*** |
| Compound of Example 240 | 10 mg/kg/day PO, QDx14 | 55*** | 35** |
| Compound of Example 240 | 3 mg/kg/day PO, QDx14 | 40* | 20 |
| Compound of Example 285 | 6 mg/kg/day PO, QDx21 | nd[c] | nd[c] |

TABLE 4-continued

MX-1 human breast cancer xenograft model

| Treatment | Dose route, regimen | % TGI[a] | % TGD[b] |
|---|---|---|---|
| Compound of Example 285 | 3 mg/kg/day PO, QDx21 | 84[d]*** | 140[d]** |
| Compound of Example 293 | 3 mg/kg/day PO, QDx21 | 56* | 42 |
| Compound of Example 293 | 1 mg/kg/day PO, QDx21 | 6 | 11 |

[a]Tumor growth inhibition, % TGI = 100 - mean tumor volume of treatment group/mean tumor volume of control group ×100. Dosing began on study day 12. The p values (as indicated by asterisks) are derived from Student's T test comparison of treatment group vs. control group based on tumor volumes on study day 27. *p < 0.05, p < 0.01, *p < 0.001.
[b]Tumor growth delay, % TGD = (T − C)/C × 100, where T = median time to endpoint of treatment group and C = median time to endpoint of control group. The p values (as indicated by asterisks) derived from Kaplan Meier log-rank comparison of treatment group vs. treatment control group based on an endpoint of 1000 mm³. *p < 0.05, p < 0.01, *p < 0.001.
[c]Not determined Group terminated due to 50% morbidity.
[d]40% morbidity.

TABLE 5

MV4-11 human AML xenograft model

| Treatment | Dose route, regimen | % TGI[a] |
|---|---|---|
| Compound of Example 240 | 3 mg/kg/day PO, QDx14 | 0 |
| Compound of Example 240 | 10 mg/kg/day PO, QDx14 | 23 |
| Compound of Example 240 | 30 mg/kg/day PO, QDx14 | 65[b]** |

[a]Tumor growth inhibition, % TGI = 100 - mean tumor volume of treatment group/mean tumor volume of control group ×100. Dosing began on study day 18. The p values (as indicated by asterisks) are derived from Student's T test comparison of treatment group vs. control group based on tumor volumes on study day 31. **p < 0.01.
[b]23% loss inbody weight.

TABLE 6

OPM-2 human multiple myeloma cancer xenograft model

| Treatment | Dose route, regimen | % TGI[a] | % TGD[b] |
|---|---|---|---|
| Compound of Example 240 | 30 mg/kg/day PO, QDx14 | 36** | 113** |
| Compound of Example 270 | 10 mg/kg/day PO, QDx21 | 60 | 59** |
| Compound of Example 270 | 3 mg/kg/day PO, QDx21 | 42* | 17 |
| Compound of Example 271 | 3 mg/kg/day PO, QDx21 | 73* | 93*** |
| Compound of Example 271 | 1 mg/kg/day PO, QDx21 | 66* | 51*** |

[a]Tumor growth inhibition, % TGI = 100 - mean tumor volume of treatment group/mean tumor volume of control group ×100. Dosing began on study day 17 (Example 240) or 18 (Example 270 and 271). The p values (as indicated by asterisks) are derived from Student's T test comparison of treatment group vs. control group based on tumor volumes on study day 38 (Example 270) or 35 (Examples 270 and 271). *p < 0.05,  p < 0.01, *<0.001.
[b]Tumor growth delay, % TGD = (T − C)/C × 100, where T = median time to endpoint of treatment group and C = median time to endpoint of control group. The p values (as indicated by asterisks) derived from Kaplan Meier log-rank comparison of treatment group vs. treatment control group based on an endpoint of 1000 mm³. *p < 0.05, p < 0.01, *p < 0.001.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. All publications, patents, and patent applications cited herein are hereby incorporated by reference in their entirety for all purposes.

The invention claimed is:
1. A compound of formula (I), or a pharmaceutically acceptable salt thereof:

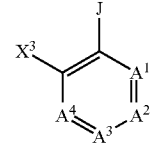

(I)

Wherein J is a group of formula IIa or IIb:

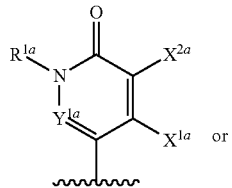

(IIa)

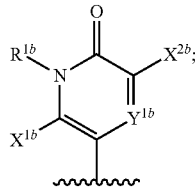

(IIb)

wherein
$R^{1a}$ is $C_1$-$C_3$ alkyl, $C_2$-$C_3$ alkylene-OH, or $C_1$-$C_3$ haloalkyl;
$Y^{1a}$ is N or $CR^{xa}$, wherein $R^{xa}$ is H, halo, $C_1$-$C_3$ alkyl, —O—$C_1$-$C_3$ alkyl, $C_1$-$C_3$ haloalkyl, —O—$C_1$-$C_3$ haloalkyl, aryl, aryl-$C_1$-$C_3$alkylene-OH, aryl-$C_1$-$C_3$alkylene-heterocycloalkyl, $C(O)NR^{10}R^{12}$, wherein heterocycloalkyl of aryl-$C_1$-$C_3$alkylene-heterocycloalkyl may be substituted with one to three $C_1$-$C_3$alkyl,
$R^{1b}$ is H, $C_1$-$C_3$ alkyl, $C_2$-$C_3$ alkylene-OH, or $C_1$-$C_3$ haloalkyl;
$Y^{1b}$ is N or $CR^{xb}$, wherein $R^{xb}$ is heteroaryl, H, halo, $C_1$-$C_3$ alkyl, —O—$C_1$-$C_3$ alkyl, $C_1$-$C_3$ haloalkyl, —O—$C_1$-$C_3$ haloalkyl, aryl, aryl-$C_1$-$C_3$alkylene-OH, aryl-$C_1$-$C_3$alkylene-heterocycloalkyl, $C(O)NR^{10}R^{12}$, wherein heterocycloalkyl of aryl-$C_1$-$C_3$alkylene-heterocycloalkyl may be substituted with one to three $C_1$-$C_3$alkyl; wherein said heteroaryl may be substituted with one to three groups selected from the group consisting of: $C_1$-$C_6$ alkyl, $C_1$-$C_3$alkylene-aryl, $C_1$-$C_3$alkylene-heteroaryl, $C_1$-$C_3$alkylene-heterocycloalkyl, COOH, and COO—$C_1$-$C_4$alkyl,
$X^{2a}$ is selected from the group consisting of: H, —$NR^{10}R^{12}$, halo, OH, —O—$C_1$-$C_4$ alkyl, aryl, heteroaryl, —$NR^{10}C(O)$—$C_1$-$C_4$ alkyl, $NR^{10}C(O)O$—$C_1$-$C_6$ alkyl, and $NR^{10}S(O)_2$—$C_1$-$C_6$ alkyl;
$X^{2b}$ is $C_1$-$C_3$ alkyl, $C_2$-$C_3$ alkylene-OH, or $C_1$-$C_3$ haloalkyl;
$X^{1a}$ and $X^{1b}$ are each selected from the group consisting of: hydrogen, halo, $C_1$-$C_6$ alkyl, $C_1$-$C_4$ haloalkyl, $C_2$-$C_4$ alkenyl, —$C_2$-$C_4$ alkenylene-O—$C_1$-$C_6$ alkyl, $C_2$-$C_4$ alkynyl, —$C_2$-$C_4$ alkynylene-N($C_1$-$C_6$ alkyl)$_2$, —O—$C_1$-$C_6$ alkyl, —O—$CD_2CH_3$, —O—CD$_2$CD$_3$, —O—C$_3$-C$_7$ cycloalkyl, —O-heterocycloalkyl, —O-aryl, —O—C$_1$-C$_3$ alkylene-C$_3$-C$_7$ cycloalkyl, —O—C$_1$-C$_3$ alkylene-heterocycloalkyl, —O—C$_1$-C$_3$ alkylene-aryl, wherein the aryl groups of the —O-aryl and —O—C$_1$-C$_3$ alkylene-aryl, the C$_3$-C$_7$ cycloalkyl groups of the —O—C$_3$-C$_7$ cycloalkyl and —O—C$_1$-C$_3$ alkylene-C$_3$-C$_7$ cycloalkyl, and the heterocycloalkyl groups of the —O-heterocycloalkyl and —O—C$_1$-C$_3$ alkylene-heterocycloalkyl is optionally substituted with 1, 2, or 3 substituents independently selected from the group consisting of oxo, halo, —CN, C$_1$-C$_6$ alkyl, C$_1$-C$_6$ haloalkyl, NH$_2$, N(H)(alkyl), N(alkyl)$_2$, —C(O)OC$_1$-C$_6$ alkyl, and —C$_1$-C$_3$ alkylene-heterocycloalkyl, —O—C$_1$-C$_4$ haloalkyl, OH, —O—C$_1$-C$_6$ alkylene-OH, —O—C$_1$-C$_6$ alkylene-N(R$^{10}$)$_2$, —O—C$_1$-C$_3$ alkylene-C(O)O—C$_1$-C$_4$ alkyl, —NR$^{10}$—C$_1$-C$_6$ alkyl, —NR$^{10}$—C$_1$-C$_6$ haloalkyl, —NR$^{10}$—C(O)OC$_1$-C$_6$ alkyl, —NR$^{10}$—C(O)OC$_1$-C$_6$haloalkyl, —NR$^{10}$—C(O)NR$^{10}$R$^{12}$, —NR$^{10}$—SO$_2$R$^{12}$, —NR$^{10}$—C$_3$-C$_7$ cycloalkyl, —NR$^{10}$—C$_1$-C$_3$ alkylene-C$_3$-C$_7$ cycloalkyl, C$_1$-C$_4$ alkylene-OH, —C$_1$-C$_3$ alkylene-C(O)OC$_1$-C$_4$ alkyl, C$_1$-C$_3$ alkylene-NR$^{10}$C(O)—C$_1$-C$_4$ alkyl, —C$_1$-C$_3$ alkylene-C(O)NR$^{10}$R$^{12}$, —C$_2$-C$_4$ alkenylene-C(O)—O—C$_1$-C$_4$ alkyl, —C(O)—C$_1$-C$_4$ alkyl, C(O)O—C$_1$-C$_4$ alkyl, C(O)NR$^{10}$R$^{12}$, —NR$^{10}$C(O)—C$_1$-C$_4$ alkyl, —NR$^{10}$—C$_1$-C$_3$ alkylene-C(O)—C$_1$-C$_4$ alkyl, —NR$^{10}$—C$_1$-C$_3$ alkylene-C(O)O—C$_1$-C$_4$ alkyl, —SO$_2$NR$^{10}$R$^{12}$, and any of groups i-v:
i) C$_3$-C$_{14}$ cycloalkyl, which is optionally substituted with 1 to 3 of R$^2$, where R$^2$ is selected from the group consisting of: halo, oxo, CN, —O—C$_1$-C$_4$ alkyl, —O—C$_1$-C$_4$ haloalkyl, —NR$^{10}$R$^{12}$, C(O)NR$^{10}$R$^{12}$, C$_1$-C$_4$ alkyl, C$_1$-C$_4$ haloalkyl, C(O)—C$_1$-C$_4$ alkyl, —C(O)O—C$_1$-C$_4$ alkyl, SO$_2$NR$^{10}$R$^{12}$, SO$_2$—C$_1$-C$_4$ alkyl, and aryl, wherein said aryl is optionally substituted with 1 to 3 substituents independently selected from group consisting of: halo, C$_1$-C$_3$ alkyl, C(O)—C$_1$-C$_3$alkyl, C(O)OH, C(O)NR$^{10}$R$^{12}$, and heteroaryl;
ii) heterocycloalkenyl, which is optionally substituted with 1 to 3 of R$^2$, where R$^2$ is selected from the group consisting of: halo, oxo, CN, —O—C$_1$-C$_4$ alkyl, —O—C$_1$-C$_4$ haloalkyl, —NR$^{10}$R$^{12}$, C(O)NR$^{10}$R$^{12}$, C$_1$-C$_4$ alkyl, C$_1$-C$_4$ haloalkyl, C(O)—C$_1$-C$_4$ alkyl, —C(O)O—C$_1$-C$_4$ alkyl, SO$_2$NR$^{10}$R$^{12}$, SO$_2$—C$_1$-C$_4$ alkyl, and aryl, wherein said aryl is optionally substituted with 1 to 3 substituents independently selected from group consisting of: halo, C$_1$-C$_3$ alkyl, C(O)—C$_1$-C$_3$alkyl, C(O)OH, C(O)NR$^{10}$R$^{12}$, and heteroaryl;
iii) heterocycloalkyl, which is optionally substituted with 1 to 3 of R$^3$, where R$^3$ is selected from the group consisting of: halo, oxo, CN, —O—C$_1$-C$_4$ alkyl, —O—C$_1$-C$_4$ haloalkyl, —NR$^{10}$R$^{12}$, C(O)NR$^{10}$R$^{12}$, C$_1$-C$_4$ alkyl, C$_1$-C$_4$ haloalkyl, C(O)—C$_1$-C$_4$ alkyl, —C(O)O—C$_1$-C$_4$ alkyl, SO$_2$NR$^{10}$R$^{12}$, SO$_2$—C$_1$-C$_4$ alkyl, and aryl, wherein said aryl is optionally substituted with 1 to 3 substituents independently selected from group consisting of: halo, C$_1$-C$_3$ alkyl, C(O)—C$_1$-C$_3$alkyl, C(O)OH, C(O)NR$^{10}$R$^{12}$, and heteroaryl;
iv) heteroaryl, which is optionally substituted with 1 to 3 of R$^4$, where R$^4$ is selected from the group consisting of: halo, oxo, CN, —O—C$_1$-C$_4$ alkyl, —O—C$_1$-C$_4$ haloalkyl, —NR$^{10}$R$^{12}$, —C(O)H, C(O)NR$^{10}$R$^{12}$, C$_1$-C$_6$ alkyl, C$_1$-C$_4$ haloalkyl, C$_1$-C$_6$ alkylene-heterocycloalkyl, C$_1$-C$_6$alkylene-aryl, C$_1$-C$_6$ alkylene-heteroaryl, C(O)—C$_1$-C$_4$ alkyl, —C(O)O—C$_1$-C$_4$ alkyl, SO$_2$NR$^{10}$R$^{12}$, SO$_2$—C$_1$-C$_4$ alkyl, —NR$^{14}$C(O)C$_1$-C$_4$-alkyl, heterocycloalkyl, and aryl, wherein said aryl is optionally substituted with 1 to 3 substituents independently selected from group consisting of: halo, C$_1$-C$_3$ alkyl, C(O)—C$_1$-C$_3$alkyl, C(O)OH, C(O)NR$^{10}$R$^{12}$, and heteroaryl,
wherein said heterocycloalkyl or heterocycloalkyl group of C$_1$-C$_6$ alkylene-heterocycloalkyl is optionally substituted with 1 to 3 independently selected C$_1$-C$_3$ alkyl groups, and wherein said heteroaryl group of C$_1$-C$_6$ alkylene-heteroaryl and said aryl groups of C$_1$-C$_6$ alkylene-aryl is optionally substituted with substituents 1 to 3 groups independently selected from C$_1$-C$_3$ alkyl and NR$^{14}$R$^{16}$;
v) aryl, which is optionally substituted with 1 to 3 of R$^6$, where R$^6$ is selected from the group consisting of: halo, CN, —NR$^{14}$R$^{16}$, —N(R$^{14}$)C(O)—C$_1$-C$_4$ alkyl, —NR$^{14}$SO$_2$—C$_1$-C$_4$ alkyl, C(O)H, C(O)C$_1$-C$_6$ alkyl, C(O)heterocycloalkyl, C(O)NR$^{14}$R$^{16}$, —C$_1$-C$_4$ alkylene-NR$^{14}$R$^{16}$, SO$_2$NR$^{14}$R$^{16}$, C(O)OC$_1$-C$_4$ alkyl, —SO$_2$— heterocycloalkyl, —SO$_2$—C$_1$-C$_6$ alkyl, —C$_1$-C$_6$ alkyl, —OH, —O—C$_1$-C$_6$ alkyl, —C$_1$-C$_6$ haloalkyl, —O—C$_1$-C$_6$ haloalkyl, —C$_1$-C$_6$ alkylene-OH, —C(H)(OH)(C$_3$-C$_7$ cycloalkyl), —C(H)(OH)(phenyl), C$_2$-C$_4$ alkenylene-OH, —C$_1$-C$_6$ alkylene-O—C$_1$-C$_6$ alkyl, —C$_1$-C$_6$ alkylene-OC(O)—C$_1$-C$_6$ alkyl, —C$_1$-C$_6$ alkylene-C(O)O—C$_1$-C$_6$ alkyl, —C$_1$-C$_6$ alkylene-N(H)SO$_2$—C$_1$-C$_6$ alkyl, —C$_1$-C$_6$ alkylene-N(H)C(O)—C$_1$-C$_6$ alkyl, —C$_1$-C$_6$ alkylene-CN, —C$_1$-C$_6$ alkylene-heterocycloalkyl, C$_1$-C$_6$ alkylene-aryl, C$_1$-C$_6$ alkylene-heteroaryl, heteroaryl, and heterocycloalkyl,
wherein said heterocycloalkyl and said heterocycloalkyl of said C(O)heterocycloalkyl and said C$_1$-C$_6$ alkylene-heterocycloalkyl is optionally substituted with 1 to 3 groups independently selected from the group consisting of C$_1$-C$_6$ alkyl, and C$_1$-C$_4$ alkylene-aryl,
wherein said heteroaryl and the heteroaryl of said C$_1$-C$_6$ alkylene-heteroaryl, and the aryl of said C$_1$-C$_6$ alkylene-aryl is optionally substituted with 1 to 3 groups independently selected from the group consisting of C$_1$-C$_4$ alkyl, C$_1$-C$_4$ haloalkyl, halo, —C$_1$-C$_3$ alkylene-CN, —C$_1$-C$_3$ alkylene-OH, —C$_1$-C$_3$ alkylene-C(O)O—C$_1$-C$_3$ alkyl, —C$_1$-C$_3$ alkylene-O—C$_1$-C$_3$ alkyl, —C$_1$-C$_3$ alkylene-OC(O)—C$_1$-C$_3$ alkyl, —C$_1$-C$_3$ alkylene-NR$^{14}$-aryl, C$_1$-C$_3$ alkylene-NR$^{14}$—C(O)—C$_1$-C$_4$alkyl, —C$_1$-C$_3$ alkylene-NR$^{14}$SO$_2$—C$_1$-C$_4$ alkyl, —C(O)—C$_1$-C$_3$ alkyl, and —C(O)-heterocycloalkyl, wherein said heterocycloalkyl of C(O)-heterocycloalkyl is optionally substituted with 1 to 3 groups independently selected from the group consisting of: C$_1$-C$_6$ alkyl, —C(O)—NHCH$_2$-aryl, —CH—(OH)—C$_1$-C$_6$ alkyl, —CH(OH)—C$_2$-C$_6$ alkenyl, —CH(OH)—C$_3$-C$_7$ cycloalkyl, —CH(OH)-phenyl, —C(O)NR$^{14}$R$^{16}$—C$_3$-C$_{14}$cycloalkyl, —C(O)NR$^{14}$—C$_1$-C$_3$ alkylene-NR$^{14}$R$^{16}$, —C(O)NR$^{14}$—C$_1$-C$_3$ alkylene-CN, —C(O)NR$^{14}$—C$_1$-C$_3$ alkylene-NR$^{14}$R$^{16}$, —C(O)NR$^{14}$R$^{16}$, —C(O)NH—C$_3$-C$_{14}$ cycloalkyl, —C(O)NH—$C_1$-$C_3$ alkylene-O—$C_1$-$C_3$ alkyl, C(O)NH—$C_1$-$C_3$ alkylene-OH, —$NR^{14}$—$C_3$-$C_{14}$ cycloalkyl, —$NR^{14}$—$C_1$-$C_3$ alkylene-heterocycloalkyl, —$NR^{14}$C(O)—$C_1$-$C_4$ alkyl, heterocycloalkyl, and heteroaryl, wherein said heterocycloalkyl or heteroaryl is optionally substituted with 1-3 substituents independently selected from the group consisting of: halo, $C_1$-$C_4$ alkyl, $C_1$-$C_4$ haloalkyl, and aryl;

where $R^{14}$ and $R^{16}$ are independently selected from the group consisting of: $C_1$-$C_4$ alkyl, $C_3$-$C_7$-cycloalkyl, —$C_1$-$C_3$-alkylene-$NR^{10}R^{12}$, —$C_1$-$C_3$-alkylene-$OR^{12}$, —$C_1$-$C_3$-alkylene-CN, aryl, $C_3$-$C_7$ cycloalkyl, $C_1$-$C_3$-alkylene-aryl, and H, where $R^{10}$ and $R^{12}$ are at each occurrence independently selected from the group consisting of H, $C_1$-$C_6$ alkyl, $C_1$-$C_3$-alkylene-aryl, $C_1$-$C_3$-alkylene-heteroaryl, $C_1$-$C_3$-alkylene-$C_3$-$C_7$-cycloalkyl, —$C_1$-$C_3$-alkylene-heterocycloalkyl, and $C_3$-$C_7$ cycloalkyl;

where $X^3$ is L-G, where L is absent or is selected from the group consisting of:
—O—, —O—$C_1$-$C_3$ alkylene-, —$NR^{30}$—, —$NR^{30}$—$C_1$-$C_3$ alkylene-, —C(O)—, —$C_1$-$C_3$ alkylene- wherein said $C_1$-$C_3$ alkylene is optionally substituted with one to two substituents independently selected from the group consisting of: OH, —$NR^{20}R^{22}$, —NH-heterocycloalkyl, and —O—$C_1$-$C_3$ alkyl, and wherein $R^{30}$ is H, $C_1$-$C_4$ alkyl, or $C_1$-$C_4$ haloalkyl; and G is selected from the group consisting of:

aryl, heteroaryl, $C_2$-$C_6$ alkyl, $C_3$-$C_7$ cycloalkyl, and heterocycloalkyl, wherein G is optionally substituted with 1 to 3 groups independently selected from the group consisting of halo, CN, OH, —$C_1$-$C_4$ alkyl, —$C_2$-$C_4$ alkynyl substituted with a $C_2$-$C_4$ alkenyl or OH, —$C_1$-$C_4$ haloalkyl, —$SO_2$—$R^{32}$, —O—$R^{32}$, —C(O)—$R^{32}$, —C(O)O—$R^{32}$, —C(O)$NR^{20}R^{22}$, —$NR^{20}R^{22}$, —$NR^{20}$C(O)$OR^{32}$, —$NR^{20}$C(O)$R^{32}$, —$NR^{20}SO_2R^{34}$, —$NR^{20}$C(O)$NR^{36}R^{38}$, —O-heterocycloalkyl, aryl, and heterocycloalkyl, and the aryl and the heterocycloalkyl is optionally substituted with one to three groups independently selected from the group consisting of halo, CN, OH, —$C_1$-$C_4$ alkyl, C(O)O$C_1$-$C_6$ alkyl, O—$C_1$-$C_4$ haloalkyl, and —$C_1$-$C_4$ haloalkyl, wherein $R^{32}$ is selected from —$C_1$-$C_4$ alkyl and —$C_1$-$C_4$ haloalkyl, wherein $R^{34}$ is selected from —$C_1$-$C_4$ alkyl and —$C_1$-$C_4$ haloalkyl, wherein $R^{36}$ and $R^{38}$ are independently selected from the group consisting of hydrogen, —$C_1$-$C_4$ alkyl, and —$C_1$-$C_3$ haloalkyl;

where $A^2$ is $CR^{18}$, and $A^1$, $A^3$, and $A^4$ are $CR^{19}$, where $R^{19}$ is H;

wherein $R^{18}$ is selected from the group consisting of:
H, $NO_2$, CN, $C_1$-$C_3$ alkyene-$SO_2$—$C_1$-$C_6$ alkyl, $C_1$-$C_3$ alkyene-$SO_2$—$C_1$-$C_6$ haloalkyl, $C_1$-$C_3$ alkyene-$SO_2$—$NR^{20}R^{22}$, —$NR^{20}R^{22}$, —$NHSO_2$—$NR^{20}R^{22}$, —$NR^{40}SO_2$—$C_1$-$C_4$ alkyl, —$NR^{40}SO_2$—$C_1$-$C_4$ haloalkyl, —$NR^{40}SO_2$—$CH_2$—C(O)OH, —$NR^{40}SO_2$—$CH_2$—C(O)O$C_1$-$C_4$ alkyl, —$NR^{40}SO_2$—$C_3$-$C_7$ cycloalkyl, —$NR^{40}SO_2$-aryl, —$NR^{40}SO_2$-heteroaryl, —$NR^{40}SO_2$—$C_1$-$C_3$ alkylene-$C_3$-$C_{14}$ cycloalkyl, —$NR^{40}SO_2$—$C_1$-$C_3$ alkylene-heterocycloalkyl, —$NR^{40}SO_2$—$C_1$-$C_3$ alkylene-heteroaryl, —$NR^{40}SO_2$—$C_1$-$C_3$ alkylene-aryl, —$SO_2$—$NR^{40}R^{42}$, —$SO_2$—$NR^{40}$—$C_1$-$C_4$ haloalkyl, —$SO_2$—$NR^{40}$—$C_3$-$C_{14}$ cycloalkyl, —$SO_2$—$NR^{40}$—C(O)$NR^{20}R^{22}$, —$SO_2$—$NR^{40}$-heterocycloalkyl, —$SO_2$—$NR^{40}$-heteroaryl, —$SO_2$—$NR^{40}$-aryl, —$SO_2$—$C_1$-$C_6$ alkyl, —$SO_2$—$C_1$-$C_6$ haloalkyl, —$SO_2$—$C_3$-$C_{14}$ cycloalkyl, —$SO_2$-heterocycloalkyl, —$SO_2$-heteroaryl, —$SO_2$-aryl, —$NR^{40}SO_2$—$NR^{20}R^{22}$, —$NR^{40}$C(O)—$C_1$-$C_6$ alkyl, —$NR^{40}$C(O)NH—$C_1$-$C_4$ alkyl, —$NR^{40}$C(O)-heteroaryl, —$NR^{40}$C(O)-heterocycloalkyl, —$NR^{40}$C(O)-aryl, —$NR^{40}$C(O)—$C_3$-$C_{14}$ cycloalkyl, —$NR^{40}$C(O)O—$C_1$-$C_4$ alkyl, —$NR^{40}$C(O)O-heteroaryl, —$NR^{40}$C(O)—$CH_2NH$—C(O)O—$C_1$-$C_4$ alkyl, —$NR^{40}$C(O)—$CH_2NR^{20}R^{22}$, —C(O)$CH_2$—$NR^{20}R^{22}$, —C(O)$NR^{20}R^{22}$, C(O)OH, —$C_1$-$C_3$ alkylene-$NR^{40}$—C(O)—$C_1$-$C_4$ alkyl, —$C_1$-$C_3$ alkylene-$NR^{40}$—C(O)—$C_1$-$C_3$ haloalkyl, —$NR^{40}$-heteroaryl, $C_3$-$C_{14}$ cycloalkyl, heterocycloalkyl, heterocycloalkylaryl, heteroaryl, aryl, —$C_1$-$C_3$ alkylene-cycloalkyl, —$C_1$-$C_3$ alkylene-heterocycloalkyl, —$C_1$-$C_3$ alkylene-heteroaryl, and —$C_1$-$C_3$ alkylene-aryl, wherein any of the cycloalkyl, $C_3$-$C_7$ cycloalkyl, $C_3$-$C_{14}$ cycloalkyl, heterocycloalkyl, heteroaryl, or aryl groups of $R^{18}$ is optionally substituted with 1 to 3 of $C_1$-$C_4$ alkyl, $C_1$-$C_4$ haloalkyl, halo, oxo, —OH, —O—$C_1$-$C_6$ alkyl, —O—$C_1$-$C_6$ haloalkyl, —$OG^1$, —$S(O)_2$—$C_1$-$C_6$ alkyl, —$N(R^{40})_2$, —$N(R^{40})$C(O)$C_1$-$C_6$ alkyl, $G^1$, —$C_1$-$C_6$ alkylene-$G^1$, or —$C_1$-$C_6$ alkylene-$OG^1$, wherein $G^1$ is cycloalkyl, heterocycloalkyl, heteroaryl, or aryl, and each $G^1$ is optionally substituted with 1 to 3 of oxo, $C_1$-$C_4$ alkyl, $C_1$-$C_4$ haloalkyl, or halo, wherein $R^{40}$ and $R^{42}$ are independently selected from the group consisting of: H and $C_1$-$C_4$ alkyl, and wherein $R^{20}$ and $R^{22}$ are at each occurrence independently selected from the group consisting of: H and $C_1$-$C_6$ alkyl.

2. The compound of claim 1, or a pharmaceutically acceptable salt thereof, wherein $R^{18}$ is selected from the group consisting of:

$NO_2$, $C_1$-$C_3$ alkyene-$SO_2$—$C_1$-$C_6$ alkyl, $C_1$-$C_3$ alkyene-$SO_2$—$C_1$-$C_6$ haloalkyl, $C_1$-$C_3$ alkyene-$SO_2$—$NR^{20}R^{22}$, —$NR^{20}R^{22}$, —$NHSO_2$—$NH_2$, —$NR^{40}SO_2$—$C_1$-$C_4$ alkyl, —$NR^{40}SO_2$—$C_1$-$C_4$ haloalkyl, —$NR^{40}SO_2$—$CH_2$—C(O)OH, —$NR^{40}SO_2$—$CH_2$—C(O)O$C_1$-$C_4$, —$NR^{40}SO_2$—$C_1$-$C_4$ alkyl, —$NR^{40}SO_2$—$C_1$-$C_4$ haloalkyl, —$NR^{40}SO_2$—$C_3$-$C_7$ cycloalkyl, —$NR^{40}SO_2$-aryl, —$NR^{40}SO_2$-heteroaryl, —$NR^{40}SO_2$—$C_1$-$C_4$ alkyl, —$NR^{40}SO_2$—$C_1$-$C_4$ haloalkyl, —$NR^{40}SO_2$—$C_1$-$C_3$ alkylene-$C_3$-$C_{14}$ cycloalkyl, —$NR^{40}SO_2$—$C_1$-$C_3$ alkylene-heterocycloalkyl, —$NR^{40}SO_2$—$C_1$-$C_3$ alkylene-heteroaryl, —$NR^{40}SO_2$—$C_1$-$C_3$ alkylene-aryl, —$SO_2$—$NR^{40}R^{42}$, —$SO_2$—$NR^{40}$—$C_1$-$C_4$ alkyl, —$SO_2$—$NR^{40}$—$C_1$-$C_4$ haloalkyl, —$SO_2$—$NR^{40}$—$C_3$-$C_{14}$ cycloalkyl, —$SO_2$—$NR^{40}$—C(O)$NR^{20}R^{22}$, —$SO_2$—$NR^{40}$-heterocycloalkyl, —$SO_2$—$NR^{40}$-heteroaryl, —$SO_2$—$NR^{40}$-aryl, —$SO_2$—$C_1$-$C_6$ alkyl, —$SO_2$—$C_1$-$C_6$ haloalkyl, —$SO_2$—$C_3$-$C_{14}$ cycloalkyl, —$SO_2$-heterocycloalkyl, —$SO_2$-heteroaryl, —$SO_2$-aryl, —$NR^{40}SO_2$—$NR^{20}R^{22}$, —$NR^{40}$C(O)—$C_1$-$C_4$ alkyl, —$NR^{40}$C(O)NH—$C_1$-$C_4$ alkyl, —$NR^{40}$C(O)-heteroaryl, —$NR^{40}$C(O)-aryl, —$NR^{40}$C(O)O—$C_1$-$C_4$ alkyl, —NR⁴⁰C(O)O-heteroaryl, —NR⁴⁰C(O)-aryl, —NR⁴⁰C(O)—CH₂NH—C(O)O—C₁-C₄ alkyl, —C(O)CH₂—NR²⁰R²², —C(O)NR²⁰R²², C(O)OH, C₁-C₃ alkylene-NR⁴⁰—C(O)—C₁-C₄ alkyl, C₁-C₃ alkylene-NR⁴⁰—C(O)—C₁-C₃ haloalkyl, —NR⁴⁰-heteroaryl, C₃-C₁₄ cycloalkyl, heterocycloalkyl, heterocycloalkyl-aryl, heteroaryl, aryl, C₁-C₃ alkylene-cycloalkyl, C₁-C₃ alkylene-heterocycloalkyl, C₁-C₃ alkylene-heteroaryl, and C₁-C₃ alkylene-aryl.

3. The compound of claim 2, or a pharmaceutically acceptable salt thereof, wherein R¹⁸ is selected from the group consisting of:
NR⁴⁰SO₂—C₁-C₄ alkyl, —NR⁴⁰SO₂—C₁-C₄ haloalkyl, —SO₂—NR⁴⁰—C₁-C₄ alkyl, —SO₂—NR⁴⁰—C₁-C₄ haloalkyl, —SO₂—C₁-C₆ alkyl, and —SO₂—C₁-C₆ haloalkyl.

4. The compound of claim 3, or a pharmaceutically acceptable salt thereof, wherein R⁴⁰ is H.

5. The compound of claim 4, or a pharmaceutically acceptable salt thereof, wherein X³ is L-G and L is —O—, or —O—C₁-C₃ alkylene-.

6. The compound of claim 5, or a pharmaceutically acceptable salt thereof, wherein G is aryl or C₃-C₇ cycloalkyl, wherein G is optionally substituted with 1 to 3 groups independently selected from the group consisting of CN, OH, —NR²⁰R²², —C₁-C₄ haloalkyl, —SO₂—C₁-C₄ alkyl, halo, —C(O)—C₁-C₄-alkyl, —O—C₁-C₄ alkyl, —O—C₁-C₄ haloalkyl, —C₁-C₄ alkyl, —NR²⁰C(O)R³², —NR²⁰SO₂OR³⁴, —NR²⁰C(O)NR³⁶R³⁸,
wherein R³² is selected from —C₁-C₄ alkyl and —C₁-C₄ haloalkyl,
wherein R³⁴ is selected from —C₁-C₄ alkyl and —C₁-C₄ haloalkyl,
wherein R³⁶ and R³⁸ are independently selected from the group consisting of hydrogen, —C₁-C₄ alkyl, and —C₁-C₃ haloalkyl.

7. The compound of claim 6, or a pharmaceutically acceptable salt thereof, wherein is L is —O—, and -G is phenyl substituted with 1 to 3 halo.

8. The compound of claim 7, or a pharmaceutically acceptable salt thereof, wherein L is —O—, and -G is phenyl substituted with 1 to 3 fluoro.

9. The compound of claim 8, or a pharmaceutically acceptable salt thereof, wherein said phenyl is 2,4-difluorophenyl.

10. The compound of claim 6, or a pharmaceutically acceptable salt thereof, wherein is L is —O—C₁-C₃ alkyene, and -G is C₃-C₇ cycloalkyl.

11. The compound of claim 1, or a pharmaceutically acceptable salt thereof, wherein J is IIa, Y¹ᵃ is N, R¹ᵃ is methyl, and X²ᵃ is hydrogen.

12. The compound of claim 1, or a pharmaceutically acceptable salt thereof, wherein J is IIa, Y¹ᵃ is CRˣᵃ, wherein Rˣᵃ is H, R¹ᵃ is methyl, and X²ᵃ is hydrogen.

13. The compound of claim 11 or 12, or a pharmaceutically acceptable salt thereof, wherein X¹ᵃ is hydrogen.

14. The compound of claim 11 or 12, a pharmaceutically acceptable salt thereof, wherein X¹ᵃ is selected from the group consisting of:
halo, —O—C₁-C₄ alkyl, and aryl, wherein said aryl is optionally substituted with 1 to 3 of R⁶, where R⁶ is selected from the group consisting of: NR¹⁴SO₂—C₁-C₄ alkyl, —C₁-C₃ alkylene-NR¹⁴R¹⁶, —C₁-C₆ alkylene-heterocycloalkyl, wherein said heterocycloalkyl of said C₁-C₆ alkylene-heterocycloalkyl is optionally substituted with 1 to 3 groups independently selected from the group consisting of C₁-C₆ alkyl and —CH₂- phenyl, wherein said aryl of said C₁-C₆ alkylene-aryl is optionally substituted with 1 to 3 groups independently selected from the group consisting of: —C₁-C₃ alkylene-OH, and heterocycloalkyl, wherein said heterocycloalkyl is optionally substituted with 1-3 substituents independently selected from the group consisting of: C₁-C₄ alkyl, C₁-C₄ haloalkyl and aryl.

15. The compound of claim 6, or a pharmaceutically acceptable salt thereof, wherein J is IIb, R¹ᵇ is hydrogen, X²ᵇ is methyl, Y¹ᵇ is CRˣᵇ, and Rˣᵇ is H.

16. The compound of claim 15, or a pharmaceutically acceptable salt thereof, wherein X¹ᵇ is hydrogen.

17. The compound of claim 16, or a pharmaceutically acceptable salt thereof, wherein is L is —O—, and -G is phenyl substituted with 1 to 3 halo.

18. The compound of claim 17, or a pharmaceutically acceptable salt thereof, wherein G is phenyl substituted with 1 to 3 fluoro.

19. The compound of claim 18, or a pharmaceutically acceptable salt thereof, wherein said phenyl is 2,4-difluorophenyl.

20. The compound of claim 1, or a pharmaceutically acceptable salt thereof, wherein X³ is L-G, L is —NR³⁰— or —NR³⁰—C₁-C₃ alkylene-, and R³⁰ is H.

21. The compound of claim 17, or a pharmaceutically acceptable salt thereof, wherein X¹ᵇ is H, and R¹⁸ is NR⁴⁰SO₂C₁-C₄ alkyl.

22. The compound of claim 1, or a pharmaceutically acceptable salt thereof, wherein J is IIa, R¹ᵃ is methyl, Y¹ᵃ is N or CH, X²ᵃ is H or halo, X³ is L-G, L is —O— or —O—C₁-C₃ alkylene-, G is phenyl or C₃-C₇ cycloalkyl, wherein G is optionally substituted with 1 to 3 halo, and R¹⁸ is selected from the group consisting of H, NR⁴⁰SO₂—C₁-C₄ alkyl, —NR⁴⁰SO₂—C₁-C₄ haloalkyl, —SO₂—NR⁴⁰R⁴², —SO₂—NR⁴⁰—C₁-C₄ haloalkyl, —SO₂—C₁-C₆ alkyl, and —SO₂—C₁-C₆ haloalkyl.

23. The compound of claim 22, or a pharmaceutically acceptable salt thereof, wherein R¹⁸ is selected from the group consisting of H, NR⁴⁰SO₂—C₁-C₄ alkyl, and —SO₂—C₁-C₆ alkyl, and X¹ᵃ is selected from the group consisting of H, —O—C₁-C₆ alkyl, —O—C₁-C₄ haloalkyl, optionally substituted phenyl, optionally substituted heteroaryl, and —O—C₁-C₃ alkylene-C₃-C₇ cycloalkyl wherein said C₃-C₇ cycloalkyl of —O—C₁-C₃ alkylene-C₃-C₇ cycloalkyl is optionally substituted.

24. The compound of claim 1, or a pharmaceutically acceptable salt thereof,

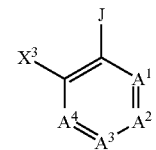

wherein J is a group of formula IIa or IIb:

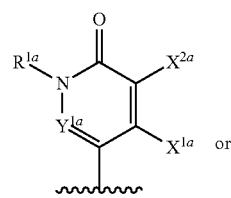

-continued

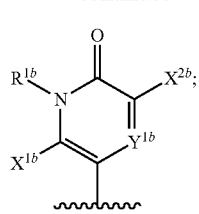
(IIb)

wherein
R$^{1a}$ is C$_1$-C$_3$ alkyl, C$_2$-C$_3$ alkylene-OH, or C$_1$-C$_3$ haloalkyl;
Y$^{1a}$ is N or CR$^{xa}$, wherein R$^{xa}$ is H, halo, C$_1$-C$_3$ alkyl, —O—C$_1$-C$_3$ alkyl, C$_1$-C$_3$ haloalkyl, —O—C$_1$-C$_3$ haloalkyl, aryl, aryl-C$_1$-C$_3$alkylene-OH, aryl-C$_1$-C$_3$alkylene-heterocycloalkyl, C(O)NR$^{10}$R$^{12}$, wherein heterocycloalkyl of aryl-C$_1$-C$_3$alkylene-heterocycloalkyl is optionally substituted with one to three C$_1$-C$_3$alkyl,
R$^{1b}$ is H, C$_1$-C$_3$ alkyl, C$_2$-C$_3$ alkylene-OH, or C$_1$-C$_3$ haloalkyl;
Y$^{1b}$ is N or CR$^{xb}$, wherein R$^{xb}$ is heteroaryl, H, halo, C$_1$-C$_3$ alkyl, —O—C$_1$-C$_3$ alkyl, C$_1$-C$_3$ haloalkyl, —O—C$_1$-C$_3$ haloalkyl, aryl, aryl-C$_1$-C$_3$alkylene-OH, aryl-C$_1$-C$_3$alkylene-heterocycloalkyl, C(O)NR$^{10}$R$^{12}$, wherein heterocycloalkyl of aryl-C$_1$-C$_3$alkylene-heterocycloalkyl is optionally substituted with one to three C$_1$-C$_3$alkyl; wherein said heteroaryl is optionally substituted with one to three groups selected from the group consisting of: C$_1$-C$_6$ alkyl, C$_1$-C$_3$alkylene-aryl, C$_1$-C$_3$alkylene-heteroaryl, C$_1$-C$_3$alkylene-heterocycloalkyl, COOH, and COO—C$_1$-C$_4$alkyl,
X$^{2a}$ is selected from the group consisting of: H, —NR$^{10}$R$^{12}$, halo, OH, —O—C$_1$-C$_4$ alkyl, aryl, heteroaryl, and —NR$^{10}$C(O)—C$_1$-C$_4$ alkyl;
X$^{2b}$ is C$_1$-C$_3$ alkyl, C$_2$-C$_3$ alkylene-OH, or C$_1$-C$_3$ haloalkyl;
X$^{1a}$ and X$^{1b}$ are each selected from the group consisting of: hydrogen, halo, C$_1$-C$_6$ alkyl, C$_1$-C$_4$ haloalkyl, —O—C$_1$-C$_4$ alkyl, —O—C$_1$-C$_6$ cycloalkyl, —O—C$_1$-C$_3$ alkylene-C$_3$-C$_7$ cycloalkyl, —O—C$_1$-C$_4$ haloalkyl, —O—C$_1$-C$_3$ alkylene-heterocycloalkyl, —O—C$_1$-C$_6$ alkylene-OH, —O—C$_1$-C$_3$ alkylene-N(R$^{10}$)$_2$—O—C$_1$-C$_3$ alkylene-C(O)O—C$_1$-C$_4$ alkyl, —NR$^{10}$—C$_1$-C$_6$ alkyl, —NR$^{10}$—C$_1$-C$_6$ haloalkyl, —NR$^{10}$—C(O)OC$_1$-C$_6$ alkyl, —NR$^{10}$—C(O)OC$_1$-C$_6$ haloalkyl, —NR$^{10}$—C(O)NR$^{10}$R$^{12}$, —NR$^{10}$—SO$_2$R$^{12}$, —NR$^{10}$—C$_3$-C$_7$ cycloalkyl, —O—C$_1$-C$_3$ alkylene-C(O)O—C$_1$-C$_4$ alkyl, —NR$^{10}$—C$_1$-C$_6$ alkyl, —NR$^{10}$—C$_1$-C$_6$ haloalkyl, —NR$^{10}$—C$_1$-C$_3$ alkylene-C$_3$-C$_7$ cycloalkyl, C$_1$-C$_4$ alkylene-OH, —C$_1$-C$_3$ alkylene-C(O)O C$_1$-C$_4$ alkyl, C$_1$-C$_3$ alkylene-NR$^{10}$C(O)—C$_1$-C$_4$ alkyl, —C$_1$-C$_3$ alkylene-C(O)NR$^{10}$R$^{12}$, —C$_2$-C$_4$ alkenylene-C(O)—O—C$_1$-C$_4$ alkyl, —C(O)—C$_1$-C$_4$ alkyl, C(O)O—C$_1$-C$_4$ alkyl, C(O)NR$^{10}$R$^{12}$, —NR$^{10}$C(O)—C$_1$-C$_4$ alkyl, —NR$^{10}$SO$_2$—C$_1$-C$_4$ alkyl, —NR$^{10}$—C$_1$-C$_3$ alkylene-C(O)—C$_1$-C$_4$ alkyl, —NR$^{10}$—C$_1$-C$_3$ alkylene-C(O)O—C$_1$-C$_4$ alkyl, —SO$_2$NR$^{10}$R$^{12}$, and any of groups i-v:
i) C$_3$-C$_{14}$ cycloalkyl, which is optionally substituted with 1 to 3 of R$^2$, where R$^2$ is selected from the group consisting of: halo, oxo, CN, —O—C$_1$-C$_4$ alkyl, —O—C$_1$-C$_4$ haloalkyl, —NR$^{10}$R$^{12}$, C(O)NR$^{10}$R$^{12}$, C$_1$-C$_4$ alkyl, C$_1$-C$_4$ haloalkyl, C(O)—C$_1$-C$_4$ alkyl, —C(O)O—C$_1$-C$_4$ alkyl, SO$_2$NR$^{10}$R$^{12}$, SO$_2$—C$_1$-C$_4$ alkyl, and aryl, wherein said aryl is optionally substituted with 1 to 3 substituents independently selected from group consisting of: halo, C$_1$-C$_3$ alkyl, C(O)—C$_1$-C$_3$alkyl, C(O)OH, C(O)NR$^{10}$R$^{12}$, and heteroaryl;
ii) heterocycloalkenyl, which is optionally substituted with 1 to 3 of R$^2$, where R$^2$ is selected from the group consisting of: halo, oxo, CN, —O—C$_1$-C$_4$ alkyl, —O—C$_1$-C$_4$ haloalkyl, —NR$^{10}$R$^{12}$, C(O)NR$^{10}$R$^{12}$, C$_1$-C$_4$ alkyl, C$_1$-C$_4$ haloalkyl, C(O)—C$_1$-C$_4$ alkyl, —C(O)O—C$_1$-C$_4$ alkyl, SO$_2$NR$^{10}$R$^{12}$, SO$_2$—C$_1$-C$_4$ alkyl, and aryl, wherein said aryl is optionally substituted with 1 to 3 substituents independently selected from group consisting of: halo, C$_1$-C$_3$ alkyl, C(O)—C$_1$-C$_3$alkyl, C(O)OH, C(O)NR$^{10}$R$^{12}$, and heteroaryl;
iii) heterocycloalkyl, which is optionally substituted with 1 to 3 of R$^3$, where R$^3$ is selected from the group consisting of: halo, oxo, CN, —O—C$_1$-C$_4$ alkyl, —O—C$_1$-C$_4$ haloalkyl, —NR$^{10}$R$^{12}$, C(O)NR$^{10}$R$^{12}$, C$_1$-C$_4$ alkyl, C$_1$-C$_4$ haloalkyl, C(O)—C$_1$-C$_4$ alkyl, —C(O)O—C$_1$-C$_4$ alkyl, SO$_2$NR$^{10}$R$^{12}$, SO$_2$—C$_1$-C$_4$ alkyl, and aryl, wherein said aryl is optionally substituted with 1 to 3 substituents independently selected from group consisting of: halo, C$_1$-C$_3$ alkyl, C(O)—C$_1$-C$_3$alkyl, C(O)OH, C(O)NR$^{10}$R$^{12}$, and heteroaryl;
iv) heteroaryl, which is optionally substituted with 1 to 3 of R$^4$, where R$^4$ is selected from the group consisting of: halo, oxo, CN, —O—C$_1$-C$_4$ alkyl, —O—C$_1$-C$_4$ haloalkyl, —NR$^{10}$R$^{12}$, C(O)NR$^{10}$R$^{12}$, C$_1$-C$_6$ alkyl, C$_1$-C$_4$ haloalkyl, C$_1$-C$_6$ alkylene-heterocycloalkyl, C$_1$-C$_6$alkylene-aryl, C$_1$-C$_6$alkylene-heteroaryl, C(O)—C$_1$-C$_4$ alkyl, —C(O)O—C$_1$-C$_4$ alkyl, SO$_2$NR$^{10}$R$^{12}$, SO$_2$—C$_1$-C$_4$ alkyl, —NR$^{14}$C(O)C$_1$-C$_4$-alkyl, NH—C$_1$-C$_4$ alkylene-aryl, heterocycloalkyl, and aryl, wherein said aryl is optionally substituted with 1 to 3 substituents independently selected from group consisting of: halo, C$_1$-C$_3$ alkyl, C(O)—C$_1$-C$_3$alkyl, C(O)OH, C(O)NR$^{10}$R$^{12}$, and heteroaryl, wherein said heterocycloalkyl or heterocycloalkyl group of C$_1$-C$_6$ alkylene-heterocycloalkyl is optionally substituted with 1 to 3 independently selected C$_1$-C$_3$ alkyl groups, and wherein said heteroaryl group of C$_1$-C$_6$ alkylene-heteroaryl and said aryl groups of C$_1$-C$_6$ alkylene-aryl and NH—C$_1$-C$_4$ alkylene-aryl is optionally substituted with substituents 1 to 3 groups independently selected from C$_1$-C$_3$ alkyl and NR$^{14}$R$^{16}$;
v) aryl, which is optionally substituted with 1 to 3 of R$^6$, where R$^6$ is selected from the group consisting of: halo, CN, —NR$^{14}$R$^{16}$, —NR$^{14}$SO$_2$—C$_1$-C$_4$ alkyl, C(O)H, —C$_1$-C$_4$ alkylene-NR$^{14}$R$^{16}$, SO$_2$NR$^{14}$R$^{16}$, C(O)OC$_1$-C$_4$ alkyl, —SO$_2$-heterocycloalkyl, —SO$_2$—C$_1$-C$_6$ alkyl, —C$_1$-C$_6$ alkyl, —O—C$_1$-C$_6$ alkyl, —C$_1$-C$_6$ haloalkyl, —O—C$_1$-C$_6$ haloalkyl, —C$_1$-C$_6$ alkylene-heterocycloalkyl, C$_1$-C$_6$alkylene-aryl, and C$_1$-C$_6$alkylene-heteroaryl,
wherein said heterocycloalkyl of said C$_1$-C$_6$ alkylene-heterocycloalkyl is optionally substituted with 1 to 3 groups independently selected from the group consisting of C$_1$-C$_6$ alkyl and —CH$_2$-phenyl, and C$_1$-C$_4$ alkylene-aryl, wherein the heteroaryl of said $C_1$-$C_6$ alkylene-heteroaryl and the aryl of said $C_1$-$C_6$ alkylene-aryl is optionally substituted with 1 to 3 groups independently selected from the group consisting of $C_1$-$C_4$ alkyl, $C_1$-$C_4$ haloalkyl, and halo-$C_1$-$C_3$ alkylene-CN, —$C_1$-$C_3$ alkylene-OH, —$C_1$-$C_3$ alkylene-C(O)O—$C_1$-$C_3$ alkyl, —$C_1$-$C_3$ alkylene-O—$C_1$-$C_3$ alkyl, —$C_1$-$C_3$ alkylene-OC(O)—$C_1$-$C_3$ alkyl, —$C_1$-$C_3$ alkylene-N$R^{14}$-aryl, $C_1$-$C_3$ alkylene-N$R^{14}$—C(O)—$C_1$-$C_4$alkyl, —$C_1$-$C_3$ alkylene-N$R^{14}$S$O_2$—$C_1$-$C_4$ alkyl, —C(O)—$C_1$-$C_3$ alkylene, and —C(O)-heterocycloalkyl, wherein said heterocycloalkyl of C(O)-heterocycloalkyl is optionally substituted with 1 to 3 groups independently selected from the group consisting of: $C_1$-$C_6$ alkyl, —C(O)—NHC$H_2$-aryl, —CH—(OH)—$C_1$-$C_6$ alkyl, —CH(OH)—$C_2$-$C_6$ alkenyl, —CH(OH)—$C_3$-$C_7$ cycloalkyl, —CH(OH)-phenyl, —C(O)N$R^{14}R^{16}$—$C_3$-$C_{14}$cycloalkyl, —C(O)N$R^{14}$$C_1$-$C_3$ alkylene-N$R^{14}R^{16}$, —C(O)N$R^{14}$—$C_1$-$C_3$ alkylene-CN, —C(O)N$R^{14}$—$C_1$-$C_3$ alkylene-N$R^{14}R^{16}$, —C(O)N$R^{14}R^{16}$, —C(O)NH—$C_3$-$C_{14}$ cycloalkyl, —C(O)NH—$C_1$-$C_3$ alkylene-O—$C_1$-$C_3$ alkyl, C(O)NH—$C_1$-$C_3$ alkylene-OH, —N$R^{14}$—$C_3$-$C_{14}$ cycloalkyl, —N$R^{14}$—$C_1$-$C_3$ alkylene-heterocycloalkyl, —$NR^{14}$C(O)—$C_1$-$C_4$ alkyl, heterocycloalkyl, and heteroaryl, wherein said heterocycloalkyl or heteroaryl is optionally substituted with 1-3 substituents independently selected from the group consisting of: halo, $C_1$-$C_4$ alkyl, $C_1$-$C_4$ haloalkyl and aryl;

where $R^{14}$ and $R^{16}$ are independently selected from the group consisting of: $C_1$-$C_4$ alkyl, $C_3$-$C_7$-cycloalkyl, —$C_1$-$C_3$-alkylene-N$R^{10}R^{12}$, aryl, and H, where $R^{10}$ and $R^{12}$ are at each occurrence independently selected from the group consisting of H, $C_1$-$C_4$ alkyl, $C_1$-$C_3$-alkylene-aryl, $C_1$-$C_3$-alkylene-heteroarylaryl, $C_1$-$C_3$-alkylene-$C_3$-$C_7$-cycloalkyl, and cyclopropyl;

where $X^3$ is L-G, where L is absent or is selected from the group consisting of:
—O—, —O—$C_1$-$C_3$ alkylene-, —N$R^{30}$—, —C(O)—, —$C_1$-$C_3$ alkylene-, wherein said $C_1$-$C_3$ alkylene is optionally substituted with one to two substituents independently selected from the group consisting of: OH, —N$R^{20}R^{22}$, —NH-heterocycloalkyl, and —O—$C_1$-$C_3$ alkyl, and wherein $R^{30}$ is H or $C_1$-$C_4$ alkyl, or $C_1$-$C_4$ haloalkyl; and G is selected from the group consisting of:
aryl, heteroaryl, $C_2$-$C_6$ alkyl, $C_3$-$C_7$ cycloalkyl, heterocycloalkyl, wherein G is optionally substituted with 1 to 3 groups independently selected from the group consisting of halo, CN, OH, —$C_1$-$C_4$ alkyl, —$C_1$-$C_4$ haloalkyl, —S$O_2$—$R^{32}$, —O—$R^{32}$, —C(O)—$R^{32}$, —C(O)O—$R^{32}$, —N$R^{20}R^{22}$, —N$R^{20}$C(O)O$R^{32}$, —N$R^{20}$C(O)$R^{32}$, —N$R^{20}$S$O_2$O$R^{34}$, —N$R^{20}$C(O)N$R^{36}R^{38}$, aryl, and aryl substituted with one to three groups independently selected from the group consisting of halo, CN, OH, —$C_1$-$C_4$ alkyl, and —$C_1$-$C_4$ haloalkyl,
wherein $R^{32}$ is selected from —$C_1$-$C_4$ alkyl and —$C_1$-$C_4$ haloalkyl,
wherein $R^{34}$ is selected from —$C_1$-$C_4$ alkyl and —$C_1$-$C_4$ haloalkyl, wherein $R^{36}$ and $R^{38}$ are independently selected from the group consisting of hydrogen, —$C_1$-$C_4$ alkyl, and —$C_1$-$C_3$ haloalkyl;
where $A^2$ is C$R^{18}$, and $A^1$, $A^3$, and $A^4$ are C$R^{19}$, where $R^{19}$ is H;
wherein $R^{18}$ is selected from the group consisting of: H, N$O_2$, $C_1$-$C_3$ alkyene-S$O_2$—$C_1$-$C_6$ alkyl, $C_1$-$C_3$ alkyene-S$O_2$—$C_1$-$C_6$ haloalkyl, $C_1$-$C_3$ alkyene-S$O_2$—N$R^{20}R^{22}$, —N$R^{20}R^{22}$, —NHS$O_2$—N$H_2$, —N$R^{40}$S$O_2$—$C_1$-$C_4$ alkyl, —N$R^{40}$S$O_2$—$C_1$-$C_4$ haloalkyl, —N$R^{40}$S$O_2$—C$H_2$—C(O)OH, —N$R^{40}$S$O_2$—C$H_2$—C(O)O$C_1$-$C_4$, —N$R^{40}$S$O_2$—$C_1$-$C_4$ alkyl, —N$R^{40}$S$O_2$—$C_1$-$C_4$ haloalkyl, —N$R^{40}$S$O_2$—$C_3$-$C_7$ cycloalkyl, —N$R^{40}$S$O_2$-aryl, —N$R^{40}$S$O_2$-heteroaryl, —N$R^{40}$S$O_2$—$C_1$-$C_4$ alkyl, —N$R^{40}$S$O_2$—$C_1$-$C_4$ haloalkyl, —N$R^{40}$S$O_2$—$C_1$-$C_3$ alkylene-$C_3$-$C_{14}$ cycloalkyl, —N$R^{40}$S$O_2$—$C_1$-$C_3$ alkylene-heterocycloalkyl, —N$R^{40}$S$O_2$—$C_1$-$C_3$ alkylene-heteroaryl, —N$R^{40}$S$O_2$—$C_1$-$C_3$ alkylene-aryl, —S$O_2$—N$R^{40}R^{42}$, —S$O_2$—N$R^{40}$—$C_1$-$C_4$ alkyl, —S$O_2$—N$R^{40}$—$C_1$-$C_4$ haloalkyl, —S$O_2$—N$R^{40}$—$C_3$-$C_{14}$ cycloalkyl, —S$O_2$—N$R^{40}$—C(O)N$R^{20}R^{22}$, —S$O_2$—N$R^{40}$-heterocycloalkyl, —S$O_2$—N$R^{40}$-heteroaryl, —S$O_2$—N$R^{40}$-aryl, —S$O_2$—$C_1$-$C_6$ alkyl, —S$O_2$—$C_1$-$C_6$ haloalkyl, —S$O_2$—$C_3$-$C_{14}$ cycloalkyl, —S$O_2$-heterocycloalkyl, —S$O_2$-heteroaryl, —S$O_2$-aryl, —N$R^{40}$S$O_2$—N$R^{20}R^{22}$, —N$R^{40}$C(O)—$C_1$-$C_4$ alkyl, —N$R^{40}$C(O)NH—$C_1$-$C_4$ alkyl, —N$R^{40}$C(O)-heteroaryl, —N$R^{40}$C(O)-aryl, —N$R^{40}$C(O)O—$C_1$-$C_4$ alkyl, —N$R^{40}$C(O)O-heteroaryl, —N$R^{40}$C(O)-aryl, —N$R^{40}$C(O)—C$H_2$NH—C(O)O—$C_1$-$C_4$ alkyl, —C(O)C$H_2$—N$R^{20}R^{22}$, —C(O)N$R^{20}R^{22}$, C(O)OH, $C_1$-$C_3$ alkylene-N$R^{40}$—C(O)—$C_1$-$C_4$ alkyl, $C_1$-$C_3$ alkylene-N$R^{40}$—C(O)—$C_1$-$C_3$ haloalkyl, —N$R^{40}$-heteroaryl, $C_3$-$C_{14}$ cycloalkyl, heterocycloalkyl, heterocycloalkyl-aryl, heteroaryl, aryl, $C_1$-$C_3$ alkylene-cycloalkyl, $C_1$-$C_3$ alkylene-heterocycloalkyl, $C_1$-$C_3$ alkylene-heteroaryl, and $C_1$-$C_3$ alkylene-aryl,
wherein any of the cycloalkyl, heterocycloalkyl, heteroaryl, or aryl groups of $R^{18}$ is optionally substituted with 1 to 3 of $C_1$-$C_4$ alkyl, $C_1$-$C_4$ haloalkyl or halo,
wherein $R^{40}$ and $R^{42}$ are independently selected from the group consisting of: H and $C_1$-$C_4$ alkyl, and
wherein $R^{20}$ and $R^{22}$ are at each occurrence independently selected from the group consisting of: H and $C_1$-$C_4$ alkyl.

25. The compound of claim 1, or a pharmaceutically acceptable salt thereof, wherein said compound is selected from the group consisting of:
1-methyl-5-(2-phenoxyphenyl)pyridin-2(1H)-one;
N-[3-(1-methyl-6-oxo-1,6-dihydropyridin-3-yl)-4-phenoxyphenyl]methanesulfonamide;
methyl {[3-(1-methyl-6-oxo-1,6-dihydropyridin-3-yl)-4-phenoxyphenyl]sulfamoyl}acetate;
{[3-(1-methyl-6-oxo-1,6-dihydropyridin-3-yl)-4-phenoxyphenyl]sulfamoyl}acetic acid;
1-methyl-N-[3-(1-methyl-6-oxo-1,6-dihydropyridin-3-yl)-4-phenoxyphenyl]-1H-imidazole-4-sulfonamide;
N-[3-(1-methyl-6-oxo-1,6-dihydropyridin-3-yl)-4-phenoxyphenyl]-1H-imidazole-4-sulfonamide;
2,2,2-trifluoro-N-[3-(1-methyl-6-oxo-1,6-dihydropyridin-3-yl)-4-phenoxyphenyl]ethanesulfonamide;

N-methyl-N'-[3-(1-methyl-6-oxo-1,6-dihydropyridin-3-yl)-4-phenoxyphenyl]sulfuric diamide;
N-{3-(1-methyl-6-oxo-1,6-dihydropyridin-3-yl)-4-[4-(trifluoromethyl)phenoxy]phenyl}methanesulfonamide;
N-[4-(4-fluorophenoxy)-3-(1-methyl-6-oxo-1,6-dihydropyridin-3-yl)phenyl]methanesulfonamide;
N-[4-(4-chlorophenoxy)-3-(1-methyl-6-oxo-1,6-dihydropyridin-3-yl)phenyl]methanesulfonamide;
N-[3-(1-methyl-6-oxo-1,6-dihydropyridin-3-yl)-4-(pyridin-3-yloxy)phenyl]methanesulfonamide;
N-[4-(2-chlorophenoxy)-3-(1-methyl-6-oxo-1,6-dihydropyridin-3-yl)phenyl]methanesulfonamide;
N-{3-(1-methyl-6-oxo-1,6-dihydropyridin-3-yl)-4-[2-(trifluoromethyl)phenoxy]phenyl}methanesulfonamide;
N-[4-(2-cyanophenoxy)-3-(1-methyl-6-oxo-1,6-dihydropyridin-3-yl)phenyl]methanesulfonamide;
N-[4-(2-methoxyphenoxy)-3-(1-methyl-6-oxo-1,6-dihydropyridin-3-yl)phenyl]methanesulfonamide;
N-[4-(2-fluorophenoxy)-3-(1-methyl-6-oxo-1,6-dihydropyridin-3-yl)phenyl]methanesulfonamide;
N-[4-(2,4-difluorophenoxy)-3-(1-methyl-6-oxo-1,6-dihydropyridin-3-yl)phenyl]methanesulfonamide;
N-[4-(2,4-difluorophenoxy)-3-(1-methyl-6-oxo-1,6-dihydropyridin-3-yl)phenyl]ethanesulfonamide;
N-[4-(3,5-difluorophenoxy)-3-(1-methyl-6-oxo-1,6-dihydropyridin-3-yl)phenyl]methanesulfonamide;
N-[4-(3-chlorophenoxy)-3-(1-methyl-6-oxo-1,6-dihydropyridin-3-yl)phenyl]methanesulfonamide;
N-{3-(1-methyl-6-oxo-1,6-dihydropyridin-3-yl)-4-[3-(trifluoromethyl)phenoxy]phenyl}methanesulfonamide;
N-[4-(3-cyanophenoxy)-3-(1-methyl-6-oxo-1,6-dihydropyridin-3-yl)phenyl]methanesulfonamide;
N-[4-(3-fluorophenoxy)-3-(1-methyl-6-oxo-1,6-dihydropyridin-3-yl)phenyl]methanesulfonamide;
N-[4-(cyclohexyloxy)-3-(1-methyl-6-oxo-1,6-dihydropyridin-3-yl)phenyl]methanesulfonamide;
N-[4-(cyclopentyloxy)-3-(1-methyl-6-oxo-1,6-dihydropyridin-3-yl)phenyl]methanesulfonamide;
N-[3-(1-methyl-6-oxo-1,6-dihydropyridin-3-yl)-4-(tetrahydrofuran-3-yloxy)phenyl]methanesulfonamide;
N-[3-(1-methyl-6-oxo-1,6-dihydropyridin-3-yl)-4-(tetrahydro-2H-pyran-4-ylmethoxy)phenyl]methanesulfonamide;
N-[3-(1-methyl-6-oxo-1,6-dihydropyridin-3-yl)-4-phenoxyphenyl]-1H-pyrrole-2-carboxamide;
tert-butyl (2-{[3-(1-methyl-6-oxo-1,6-dihydropyridin-3-yl)-4-phenoxyphenyl]amino}-2-oxoethyl)carbamate;
N-[3-(1-methyl-6-oxo-1,6-dihydropyridin-3-yl)-4-phenoxyphenyl]glycinamide;
1-methyl-5-[2-phenoxy-5-(pyridin-2-ylamino)phenyl]pyridin-2(1H)-one;
N-ethyl-3-(1-methyl-6-oxo-1,6-dihydropyridin-3-yl)-4-phenoxybenzenesulfonamide;
3-(1-methyl-6-oxo-1,6-dihydropyridin-3-yl)-4-phenoxybenzenesulfonamide;
4-methoxy-1-methyl-5-(2-phenoxyphenyl)pyridin-2(1H)-one;
N-[3-(4-methoxy-1-methyl-6-oxo-1,6-dihydropyridin-3-yl)-4-phenoxyphenyl]methanesulfonamide;
N-{4-(2,4-difluorophenoxy)-3-[1-methyl-6-oxo-4-(trifluoromethyl)-1,6-dihydropyridin-3-yl]phenyl}ethanesulfonamide;
N-[3-(4-chloro-1-methyl-6-oxo-1,6-dihydropyridin-3-yl)-4-(2,4-difluorophenoxy)phenyl]methanesulfonamide;
N-[4-(2,4-difluorophenoxy)-3-(4-methoxy-1-methyl-6-oxo-1,6-dihydropyridin-3-yl)phenyl]methanesulfonamide;
N-[4-(2,4-difluorophenoxy)-3-(4-methoxy-1-methyl-6-oxo-1,6-dihydropyridin-3-yl)phenyl]ethanesulfonamide;
N-[4-(2,4-difluorophenoxy)-3-{4-[4-(hydroxymethyl)phenyl]-1-methyl-6-oxo-1,6-dihydropyridin-3-yl}phenyl]methanesulfonamide;
N-[4-(2,4-difluorophenoxy)-3-(1-methyl-4-{4-[(4-methylpiperazin-1-yl)methyl]phenyl}-6-oxo-1,6-dihydropyridin-3-yl)phenyl]methanesulfonamide;
N-[4-(2,4-difluorophenoxy)-3-{1-methyl-4-[4-(morpholin-4-yl)phenyl]-6-oxo-1,6-dihydropyridin-3-yl}phenyl]methanesulfonamide;
5-[2-(cyclopropylmethoxy)-5-(ethylsulfonyl)phenyl]-4-methoxy-1-methylpyridin-2(1H)-one;
5-{2-(2,4-difluorophenoxy)-5-[(methylsulfonyl)amino]phenyl}-N,1-dimethyl-2-oxo-1,2-dihydropyridine-4-carboxamide;
N-[4-(2,4-difluorophenoxy)-3-(4-ethoxy-1-methyl-6-oxo-1,6-dihydropyridin-3-yl)phenyl]methanesulfonamide;
N-[4-(2,4-difluorophenoxy)-3-{4-[4-(hydroxymethyl)phenyl]-1-methyl-6-oxo-1,6-dihydropyridin-3-yl}phenyl]ethanesulfonamide;
N-[4-(2,4-difluorophenoxy)-3-(1-methyl-4-{4-[(4-methylpiperazin-1-yl)methyl]phenyl}-6-oxo-1,6-dihydropyridin-3-yl)phenyl]ethanesulfonamide;
N-[4-(2,4-difluorophenoxy)-3-(4-{4-[(dimethylamino)methyl]phenyl}-1-methyl-6-oxo-1,6-dihydropyridin-3-yl)phenyl]ethanesulfonamide;
3-chloro-1-methyl-5-(2-phenoxyphenyl)pyridin-2(1H)-one;
N-[3-(5-chloro-1-methyl-6-oxo-1,6-dihydropyridin-3-yl)-4-(2,4-difluorophenoxy)phenyl]methanesulfonamide;
N-[3-(5-chloro-1-methyl-6-oxo-1,6-dihydropyridin-3-yl)-4-(2,4-difluorophenoxy)phenyl]ethanesulfonamide;
N-[4-(2,4-difluorophenoxy)-3-{1-methyl-4-[4-(morpholin-4-yl)phenyl]-6-oxo-1,6-dihydropyridin-3-yl}phenyl]ethanesulfonamide; sss
4-{4-[(ethylsulfonyl)amino]-2-[1-methyl-6-oxo-4-(2,2,2-trifluoroethoxy)-1,6-dihydropyridin-3-yl]phenoxy}benzamide;
N-[4-(2,4-difluorophenoxy)-3-(4-ethoxy-1-methyl-6-oxo-1,6-dihydropyridin-3-yl)phenyl]-2-oxo-1-phenylpyrrolidine-3-carboxamide;
N-[4-(2,4-difluorophenoxy)-3-(4-ethoxy-1-methyl-6-oxo-1,6-dihydropyridin-3-yl)phenyl]-3,3-dimethylbutanamide;
N-[4-(2,4-difluorophenoxy)-3-(4-ethoxy-1-methyl-6-oxo-1,6-dihydropyridin-3-yl)phenyl]-4-(phenoxymethyl)benzamide;
N-[4-(2,4-difluorophenoxy)-3-(4-ethoxy-1-methyl-6-oxo-1,6-dihydropyridin-3-yl)phenyl]-4-methylpentanamide;
N-[4-(2,4-difluorophenoxy)-3-(4-ethoxy-1-methyl-6-oxo-1,6-dihydropyridin-3-yl)phenyl]-1-phenylcyclopropanecarboxamide;
4-(acetylamino)-N-[4-(2,4-difluorophenoxy)-3-(4-ethoxy-1-methyl-6-oxo-1,6-dihydropyridin-3-yl)phenyl]benzamide;

N-[4-(2,4-difluorophenoxy)-3-(4-ethoxy-1-methyl-6-oxo-1,6-dihydropyridin-3-yl)phenyl]-4-(propan-2-yloxy)benzamide;

N-[4-(2,4-difluorophenoxy)-3-(4-ethoxy-1-methyl-6-oxo-1,6-dihydropyridin-3-yl)phenyl]-2-(2-phenylethyl)benzamide;

4-(diethylamino)-N-[4-(2,4-difluorophenoxy)-3-(4-ethoxy-1-methyl-6-oxo-1,6-dihydropyridin-3-yl)phenyl]benzamide;

N-[4-(2,4-difluorophenoxy)-3-(4-ethoxy-1-methyl-6-oxo-1,6-dihydropyridin-3-yl)phenyl]biphenyl-4-carboxamide;

5-{2-(2,4-difluorophenoxy)-5-[(2,2-dimethylpropyl)amino]phenyl}-4-ethoxy-1-methylpyridin-2(1H)-one;

5-{2-(2,4-difluorophenoxy)-5-[(3,3-dimethylbutyl)amino]phenyl}-4-ethoxy-1-methylpyridin-2(1H)-one;

N-[4-(2,4-difluorophenoxy)-3-(4-ethoxy-1-methyl-6-oxo-1,6-dihydropyridin-3-yl)phenyl]-4-(methylsulfonyl)benzenesulfonamide;

N-[4-(2,4-difluorophenoxy)-3-(4-ethoxy-1-methyl-6-oxo-1,6-dihydropyridin-3-yl)phenyl]-4-(trifluoromethoxy)benzenesulfonamide;

N-[4-(2,4-difluorophenoxy)-3-(4-ethoxy-1-methyl-6-oxo-1,6-dihydropyridin-3-yl)phenyl]biphenyl-4-sulfonamide;

N-[4-(2,4-difluorophenoxy)-3-(4-ethoxy-1-methyl-6-oxo-1,6-dihydropyridin-3-yl)phenyl]-1-[(1 S,4R)-7,7-dimethyl-2-oxobicyclo[2.2.1]hept-1-yl]methanesulfonamide;

N-[4-(2,4-difluorophenoxy)-3-(4-ethoxy-1-methyl-6-oxo-1,6-dihydropyridin-3-yl)phenyl]-1-phenylmethanesulfonamide;

5-{2-[2-(but-3-en-1-yn-1-yl)phenoxy]-5-(ethylsulfonyl)phenyl}-4-hydroxy-1-methylpyridin-2(1H)-one;

4-chloro-5-{5-(ethylsulfonyl)-2-[2-(3-hydroxyprop-1-yn-1-yl)phenoxy]phenyl}-1-methylpyridin-2(1H)-one;

N-[4-(2,4-difluorophenoxy)-3-(1-methyl-4-{[4-(morpholin-4-ylmethyl)benzyl]oxy}-6-oxo-1,6-dihydropyridin-3-yl)phenyl]ethanesulfonamide;

N-{4-(2,4-difluorophenoxy)-3-[1-methyl-4-(oxetan-3-yloxy)-6-oxo-1,6-dihydropyridin-3-yl]phenyl}ethanesulfonamide;

4-(2,4-difluorophenoxy)-5-[2-(2,4-difluorophenoxy)-5-(ethylsulfonyl)phenyl]-1-methylpyridin-2(1H)-one;

5-[2-(2,4-difluorophenoxy)-5-(ethylsulfonyl)phenyl]-1-methyl-4-(oxetan-3-yloxy)pyridin-2(1H)-one;

tert-butyl 4-[(5-{2-(2,4-difluorophenoxy)-5-[(ethylsulfonyl)amino]phenyl}-1-methyl-2-oxo-1,2-dihydropyridin-4-yl)oxy]piperidine-1-carboxylate;

tert-butyl 4-{[5-(2-{4-[1-(tert-butoxycarbonyl)piperidin-4-yl]-2-fluorophenoxy}-5-[(ethylsulfonyl)amino]phenyl)-1-methyl-2-oxo-1,2-dihydropyridin-4-yl]oxy}piperidine-1-carboxylate;

N-[4-(2,4-difluorophenoxy)-3-(4-{[trans-4-(dimethylamino)cyclohexyl]oxy}-1-methyl-6-oxo-1,6-dihydropyridin-3-yl)phenyl]ethanesulfonamide;

N-{4-(2,4-difluorophenoxy)-3-[1-methyl-6-oxo-4-(piperidin-4-yloxy)-1,6-dihydropyridin-3-yl]phenyl}ethanesulfonamide;

N-{4-(2,4-difluorophenoxy)-3-{1-methyl-4-[(1-methylpyrrolidin-3-yl)methoxy]-6-oxo-1,6-dihydropyridin-3-yl}phenyl}ethanesulfonamide;

tert-butyl 4-{[(5-{2-(2,4-difluorophenoxy)-5-[(ethylsulfonyl)amino]phenyl}-1-methyl-2-oxo-1,2-dihydropyridin-4-yl)oxy]methyl}piperidine-1-carboxylate;

tert-butyl 6-[(5-{2-(2,4-difluorophenoxy)-5-[(ethylsulfonyl)amino]phenyl}-1-methyl-2-oxo-1,2-dihydropyridin-4-yl)oxy]-2-azaspiro[3.3]heptane-2-carboxylate;

N-{3-[4-(2-azaspiro[3.3]hept-6-yloxy)-1-methyl-6-oxo-1,6-dihydropyridin-3-yl]-4-(2,4-difluorophenoxy)phenyl}ethanesulfonamide;

5-{2-[(cyclopropylmethyl)amino]-5-(methylsulfonyl)phenyl}-4-[(E)-2-ethoxyethenyl]-1-methylpyridin-2(1H)-one;

N-[3-(4-{[4-(diethylamino)but-2-yn-1-yl]oxy}-1-methyl-6-oxo-1,6-dihydropyridin-3-yl)-4-(2,4-difluorophenoxy)phenyl]ethanesulfonamide;

N-[4-(2,4-difluorophenoxy)-3-{1-methyl-6-oxo-4-[(1E)-prop-1-en-1-yl]-1,6-dihydropyridin-3-yl}phenyl]ethanesulfonamide;

N-[4-(2,4-difluorophenoxy)-3-{1-methyl-4-[4-(4-methylpiperazin-1-yl)phenyl]-6-oxo-1,6-dihydropyridin-3-yl}phenyl]ethanesulfonamide;

N-{4-(2,4-difluorophenoxy)-3-[4-(2-hydroxyphenyl)-1-methyl-6-oxo-1,6-dihydropyridin-3-yl]phenyl}ethanesulfonamide;

N-{4-(2,4-difluorophenoxy)-3-[4-(4-formylthiophen-3-yl)-1-methyl-6-oxo-1,6-dihydropyridin-3-yl]phenyl}ethanesulfonamide;

N-[4-(2,4-difluorophenoxy)-3-{4-[(1,1-$^2$H$_2$)ethyloxy]-1-methyl-6-oxo-1,6-dihydropyridin-3-yl}phenyl]ethanesulfonamide;

N-[4-(2,4-difluorophenoxy)-3-{4-[($^2$H$_5$)ethyloxy]-1-methyl-6-oxo-1,6-dihydropyridin-3-yl}phenyl]ethanesulfonamide;

N-[3-{4-[(2,2-difluoro-1-methylcyclopropyl)methoxy]-1-methyl-6-oxo-1,6-dihydropyridin-3-yl}-4-(2,4-difluorophenoxy)phenyl]ethanesulfonamide;

N-{4-[2-fluoro-4-(oxetan-3-yloxy)phenoxy]-3-[1-methyl-4-(oxetan-3-yloxy)-6-oxo-1,6-dihydropyridin-3-yl]phenyl}ethanesulfonamide;

5-{2-[(cyclopropylmethyl)amino]-5-(methylsulfonyl)phenyl}-4-[(Z)-2-ethoxyethenyl]-1-methylpyridin-2(1H)-one;

ethyl {5-[2-(cyclopropylmethoxy)-5-(ethylsulfonyl)phenyl]-1-methyl-2-oxo-1,2-dihydropyridin-3-yl}carbamate;

N-{5-[2-(cyclopropylmethoxy)-5-(ethylsulfonyl)phenyl]-1-methyl-2-oxo-1,2-dihydropyridin-3-yl}methanesulfonamide;

5-{2-[(cyclopropylmethyl)amino]-5-(methylsulfonyl)phenyl}-4-ethoxy-1-methylpyridin-2(1H)-one;

5-{2-[(cyclopropylmethyl)amino]-5-(methylsulfonyl)phenyl}-4-[(3-hydroxy-2,3-dimethylbutan-2-yl)oxy]-1-methylpyridin-2(1H)-one;

N-{4-(2,4-difluorophenoxy)-3-[1-methyl-4-(1-methyl-1H-pyrazol-4-yl)-6-oxo-1,6-dihydropyridin-3-yl]phenyl}ethanesulfonamide;

N-[4-(2,4-difluorophenoxy)-3-(4-ethoxy-1-methyl-6-oxo-1,6-dihydropyridin-3-yl)phenyl]naphthalene-1-sulfonamide;

N-[4-(2,4-difluorophenoxy)-3-(4-ethoxy-1-methyl-6-oxo-1,6-dihydropyridin-3-yl)phenyl]benzenesulfonamide;

N-[4-(2,4-difluorophenoxy)-3-(1-methyl-4-{1-[2-(morpholin-4-yl)ethyl]-1H-pyrazol-4-yl}-6-oxo-1,6-dihydropyridin-3-yl)phenyl]ethanesulfonamide;

N-{4-(2,4-difluorophenoxy)-3-[1-methyl-6-oxo-4-(1H-pyrazol-1-yl)-1,6-dihydropyridin-3-yl]phenyl}ethanesulfonamide;

N-[4-(2,4-difluorophenoxy)-3-(4-ethoxy-1-methyl-6-oxo-1,6-dihydropyridin-3-yl)phenyl]-4-(propan-2-yl)benzenesulfonamide;

4-chloro-N-[4-(2,4-difluorophenoxy)-3-(4-ethoxy-1-methyl-6-oxo-1,6-dihydropyridin-3-yl)phenyl]-2-fluorobenzenesulfonamide;

N-[4-(2,4-difluorophenoxy)-3-(4-ethoxy-1-methyl-6-oxo-1,6-dihydropyridin-3-yl)phenyl]propane-1-sulfonamide;

1-(2-chloro-5-fluorophenyl)-N-[4-(2,4-difluorophenoxy)-3-(4-ethoxy-1-methyl-6-oxo-1,6-dihydropyridin-3-yl)phenyl]methanesulfonamide;

N-[4-(2,4-difluorophenoxy)-3-(4-ethoxy-1-methyl-6-oxo-1,6-dihydropyridin-3-yl)phenyl]-1-(2-fluorophenyl)methanesulfonamide;

N-[4-(2,4-difluorophenoxy)-3-(5-fluoro-1-methyl-6-oxo-1,6-dihydropyridin-3-yl)phenyl]ethanesulfonamide;

N-[3-{4-[(cyclopropylmethyl)amino]-1-methyl-6-oxo-1,6-dihydropyridin-3-yl}-4-(2,4-difluorophenoxy)phenyl]ethanesulfonamide;

3-amino-5-[2-(cyclopropylmethoxy)-5-(ethylsulfonyl)phenyl]-1-methylpyridin-2(1H)-one;

N-[4-(4-cyanophenoxy)-3-(4-ethoxy-1-methyl-6-oxo-1,6-dihydropyridin-3-yl)phenyl]ethanesulfonamide;

N-[4-(2,4-difluorophenoxy)-3-(1-methyl-6-oxo-4-propyl-1,6-dihydropyridin-3-yl)phenyl]ethanesulfonamide;

5-{5-(ethylsulfonyl)-2-[(cis-4-methoxy-4-methylcyclohexyl)oxy]phenyl}-1-methylpyridin-2(1H)-one;

N-{5-[2-(cyclopropylmethoxy)-5-(ethylsulfonyl)phenyl]-1-methyl-2-oxo-1,2-dihydropyridin-3-yl}acetamide;

N-{3-[4-(cyclopropylamino)-1-methyl-6-oxo-1,6-dihydropyridin-3-yl]-4-(2,4-difluorophenoxy)phenyl}ethanesulfonamide;

N-{4-(2,4-difluorophenoxy)-3-[4-(ethylamino)-1-methyl-6-oxo-1,6-dihydropyridin-3-yl]phenyl}ethanesulfonamide;

5-[2-(2,4-difluorophenoxy)-5-(propan-2-ylsulfonyl)phenyl]-1-methylpyridin-2(1H)-one;

N-{3-[4-(cyclobutyloxy)-1-methyl-6-oxo-1,6-dihydropyridin-3-yl]-4-(2,4-difluorophenoxy)phenyl}ethanesulfonamide;

5-{2-[(2,2-difluorocyclopropyl)methoxy]-5-(ethylsulfonyl)phenyl}-4-ethoxy-1-methylpyridin-2(1H)-one;

5-[2-(2,4-difluorophenoxy)-5-(propan-2-ylsulfonyl)phenyl]-4-ethoxy-1-methylpyridin-2(1H)-one;

5-{2-(2,4-difluorophenoxy)-5-[(methylsulfonyl)methyl]phenyl}-4-ethoxy-1-methylpyridin-2(1H)-one;

5-[5-(cyclopropylsulfonyl)-2-(2,4-difluorophenoxy)phenyl]-4-ethoxy-1-methylpyridin-2(1H)-one;

N-{4-(2,4-difluorophenoxy)-3-[4-(3-hydroxy-3-methylbutoxy)-1-methyl-6-oxo-1,6-dihydropyridin-3-yl]phenyl}ethanesulfonamide;

5-[2-(cyclopropylamino)-5-(ethylsulfonyl)phenyl]-4-ethoxy-1-methylpyridin-2(1H)-one;

N-{4-(4-cyanophenoxy)-3-[1-methyl-6-oxo-4-(2,2,2-trifluoroethoxy)-1,6-dihydropyridin-3-yl]phenyl}ethanesulfonamide;

5-[2-(2,4-difluorophenoxy)-5-(ethylsulfonyl)phenyl]-4-ethoxy-1-methylpyridin-2(1H)-one;

N-{4-(2,4-difluorophenoxy)-3-[4-(2-hydroxy-2-methylpropoxy)-1-methyl-6-oxo-1,6-dihydropyridin-3-yl]phenyl}ethanesulfonamide;

4-ethoxy-5-{5-(ethylsulfonyl)-2-[4-(trifluoromethoxy)phenoxy]phenyl}-1-methylpyridin-2(1H)-one;

4-[2-(4-ethoxy-1-methyl-6-oxo-1,6-dihydropyridin-3-yl)-4-(ethylsulfonyl)phenoxy]benzonitrile;

5-{2-(2,4-difluorophenoxy)-5-[(ethylsulfonyl)methyl]phenyl}-4-ethoxy-1-methylpyridin-2(1H)-one;

5-{2-(2,4-difluorophenoxy)-5-[2-(ethylsulfonyl)propan-2-yl]phenyl}-4-ethoxy-1-methylpyridin-2(1H)-one;

N-[4-(cyclopropylmethoxy)-3-(4-ethoxy-1-methyl-6-oxo-1,6-dihydropyridin-3-yl)phenyl]ethanesulfonamide;

4-chloro-5-[2-(2,4-difluorophenoxy)-5-(ethylsulfonyl)phenyl]-1-methylpyridin-2(1H)-one;

N-[4-(2-cyclopropylethoxy)-3-(4-ethoxy-1-methyl-6-oxo-1,6-dihydropyridin-3-yl)phenyl]ethanesulfonamide;

N-[4-(cyclobutyloxy)-3-(4-ethoxy-1-methyl-6-oxo-1,6-dihydropyridin-3-yl)phenyl]ethanesulfonamide;

N-{4-[(4,4-difluorocyclohexyl)oxy]-3-(4-ethoxy-1-methyl-6-oxo-1,6-dihydropyridin-3-yl)phenyl}ethanesulfonamide;

N-{3-(4-ethoxy-1-methyl-6-oxo-1,6-dihydropyridin-3-yl)-4-[4-(trifluoromethyl)phenoxy]phenyl}ethanesulfonamide;

N-{3-(4-ethoxy-1-methyl-6-oxo-1,6-dihydropyridin-3-yl)-4-[4-(trifluoromethoxy)phenoxy]phenyl}ethanesulfonamide;

ethyl 4-{2-(4-ethoxy-1-methyl-6-oxo-1,6-dihydropyridin-3-yl)-4-[(ethylsulfonyl)amino]phenoxy}piperidine-1-carboxylate;

N-{4-[(1-acetylpiperidin-4-yl)oxy]-3-(4-ethoxy-1-methyl-6-oxo-1,6-dihydropyridin-3-yl)phenyl}ethanesulfonamide;

N-{3-[4-(1-benzyl-1H-pyrazol-4-yl)-1-methyl-6-oxo-1,6-dihydropyridin-3-yl]-4-(2,4-difluorophenoxy)phenyl}ethanesulfonamide;

N-{4-(2,4-difluorophenoxy)-3-{1-methyl-4-[1-(2-methylpropyl)-1H-pyrazol-4-yl]-6-oxo-1,6-dihydropyridin-3-yl}phenyl}ethanesulfonamide;

N-{4-(2,4-difluorophenoxy)-3-[4-(furan-2-yl)-1-methyl-6-oxo-1,6-dihydropyridin-3-yl]phenyl}ethanesulfonamide;

N-{4-(2,4-difluorophenoxy)-3-[4-(furan-3-yl)-1-methyl-6-oxo-1,6-dihydropyridin-3-yl]phenyl}ethanesulfonamide;

N-[4-(2,3-dihydro-1H-inden-2-yloxy)-3-(4-ethoxy-1-methyl-6-oxo-1,6-dihydropyridin-3-yl)phenyl]ethanesulfonamide;

tert-butyl (trans-4-{2-(4-ethoxy-1-methyl-6-oxo-1,6-dihydropyridin-3-yl)-4-[(ethylsulfonyl)amino]phenoxy}cyclohexyl)carbamate;

N-[3-(4-ethoxy-1-methyl-6-oxo-1,6-dihydropyridin-3-yl)-4-(4-fluorophenoxy)phenyl]ethanesulfonamide;

5-[2-(cyclopropylmethoxy)-5-(2,3-dihydro-1H-indol-1-ylsulfonyl)phenyl]-4-ethoxy-1-methylpyridin-2(1H)-one;

N-{4-(2,4-difluorophenoxy)-3-[1-methyl-6-oxo-4-(piperidin-4-ylmethoxy)-1,6-dihydropyridin-3-yl]phenyl}ethanesulfonamide;

N-[4-(4-chlorophenoxy)-3-(4-ethoxy-1-methyl-6-oxo-1,6-dihydropyridin-3-yl)phenyl]ethanesulfonamide;

N-[4-(3,4-difluorophenoxy)-3-(4-ethoxy-1-methyl-6-oxo-1,6-dihydropyridin-3-yl)phenyl]ethanesulfonamide;

N-[3-(4-ethoxy-1-methyl-6-oxo-1,6-dihydropyridin-3-yl)-4-(3,4,5-trifluorophenoxy)phenyl]ethanesulfonamide;

N-[4-(4-chloro-2-fluorophenoxy)-3-(4-ethoxy-1-methyl-6-oxo-1,6-dihydropyridin-3-yl)phenyl]ethanesulfonamide;

N-[4-(4-chloro-2,6-difluorophenoxy)-3-(4-ethoxy-1-methyl-6-oxo-1,6-dihydropyridin-3-yl)phenyl]ethanesulfonamide;
N-[3-(4-ethoxy-1-methyl-6-oxo-1,6-dihydropyridin-3-yl)-4-(pyridin-3-yloxy)phenyl]ethanesulfonamide;
5-[5-amino-2-(2,4-difluorophenoxy)phenyl]-4-ethoxy-1-methylpyridin-2(1H)-one;
N-{4-(2,4-difluorophenoxy)-3-[1-methyl-4-(5-methylthiophen-2-yl)-6-oxo-1,6-dihydropyridin-3-yl]phenyl}ethanesulfonamide;
N-[4-(4-cyano-2-fluorophenoxy)-3-(4-ethoxy-1-methyl-6-oxo-1,6-dihydropyridin-3-yl)phenyl]ethanesulfonamide;
5-{2-[(2,4-difluorobenzyl)amino]-5-(methylsulfonyl)phenyl}-4-ethoxy-1-methylpyridin-2(1H)-one;
N-[3-(4-ethoxy-1-methyl-6-oxo-1,6-dihydropyridin-3-yl)-4-({1-[4-(trifluoromethyl)phenyl]piperidin-4-yl}oxy)phenyl]ethanesulfonamide;
N-[4-(2,4-difluorophenoxy)-3-(4-ethoxy-1-methyl-6-oxo-1,6-dihydropyridin-3-yl)phenyl]-1,3-thiazole-5-carboxamide;
2,5-dichloro-N-[4-(2,4-difluorophenoxy)-3-(4-ethoxy-1-methyl-6-oxo-1,6-dihydropyridin-3-yl)phenyl]benzamide;
N-[4-(2,4-difluorophenoxy)-3-(4-ethoxy-1-methyl-6-oxo-1,6-dihydropyridin-3-yl)phenyl]-4-(propan-2-yl)benzamide;
N-[4-(2,4-difluorophenoxy)-3-(4-ethoxy-1-methyl-6-oxo-1,6-dihydropyridin-3-yl)phenyl]-5-methylpyrazine-2-carboxamide;
N-[4-(2,4-difluorophenoxy)-3-(4-ethoxy-1-methyl-6-oxo-1,6-dihydropyridin-3-yl)phenyl]pyridine-2-carboxamide;
4-tert-butyl-N-[4-(2,4-difluorophenoxy)-3-(4-ethoxy-1-methyl-6-oxo-1,6-dihydropyridin-3-yl)phenyl]benzenesulfonamide;
2,4-dichloro-N-[4-(2,4-difluorophenoxy)-3-(4-ethoxy-1-methyl-6-oxo-1,6-dihydropyridin-3-yl)phenyl]benzenesulfonamide;
N-[4-(2,4-difluorophenoxy)-3-(4-ethoxy-1-methyl-6-oxo-1,6-dihydropyridin-3-yl)phenyl]naphthalene-2-sulfonamide;
5-[2-(2,4-difluorophenoxy)-5-(2,3-dihydro-1H-indol-1-ylsulfonyl)phenyl]-4-ethoxy-1-methylpyridin-2(1H)-one; and
N-[4-(2,4-difluorophenoxy)-3-(4-ethoxy-1-methyl-6-oxo-1,6-dihydropyridin-3-yl)phenyl]-N-methyl-1-phenylmethanesulfonamide.

26. The compound of claim 1, or a pharmaceutically acceptable salt thereof, wherein said compound is selected from the group consisting of:
2-methyl-6-(2-phenoxyphenyl)pyridazin-3(2H)-one;
6-[2-(benzyloxy)phenyl]-2-methylpyridazin-3(2H)-one;
-[2-(1-methyl-6-oxo-1,6-dihydropyridazin-3-yl)phenoxy]benzonitrile;
6-[2-(cyclopentyloxy)phenyl]-2-methylpyridazin-3(2H)-one;
6-[2-(4-hydroxybutoxy)phenyl]-2-methylpyridazin-3(2H)-one;
2-methyl-6-[2-(pyridin-2-yloxy)phenyl]pyridazin-3(2H)-one;
2-methyl-6-{2-[4-(trifluoromethyl)phenoxy]phenyl}pyridazin-3(2H)-one;
2-methyl-6-{2-[4-(methylsulfonyl)phenoxy]phenyl}pyridazin-3(2H)-one;
2-methyl-6-(5-nitro-2-phenoxyphenyl)pyridazin-3(2H)-one;
6-(5-amino-2-phenoxyphenyl)-2-methylpyridazin-3(2H)-one;
4-methyl-N-[3-(1-methyl-6-oxo-1,6-dihydropyridazin-3-yl)-4-phenoxyphenyl]benzenesulfonamide;
N-[3-(1-methyl-6-oxo-1,6-dihydropyridazin-3-yl)-4-phenoxyphenyl]acetamide;
3-(1-methyl-6-oxo-1,6-dihydropyridazin-3-yl)-4-phenoxybenzonitrile;
3-(1-methyl-6-oxo-1,6-dihydropyridazin-3-yl)-4-phenoxybenzamide;
3-(1-methyl-6-oxo-1,6-dihydropyridazin-3-yl)-4-phenoxybenzoic acid;
N-[3-(1-methyl-6-oxo-1,6-dihydropyridazin-3-yl)-4-phenoxybenzyl]acetamide;
2,2,2-trifluoro-N-[3-(1-methyl-6-oxo-1,6-dihydropyridazin-3-yl)-4-phenoxybenzyl]acetamide;
5-methoxy-2-methyl-6-(2-phenoxyphenyl)pyridazin-3(2H)-one;
6-(5-amino-2-phenoxyphenyl)-5-methoxy-2-methylpyridazin-3(2H)-one;
N-[3-(4-methoxy-1-methyl-6-oxo-1,6-dihydropyridazin-3-yl)-4-phenoxyphenyl]acetamide;
N-[3-(4-methoxy-1-methyl-6-oxo-1,6-dihydropyridazin-3-yl)-4-phenoxyphenyl]methanesulfonamide;
N-[3-(4-methoxy-1-methyl-6-oxo-1,6-dihydropyridazin-3-yl)-4-phenoxyphenyl]-N-methylmethanesulfonamide;
N-[3-(4-methoxy-1-methyl-6-oxo-1,6-dihydropyridazin-3-yl)-4-phenoxyphenyl]propane-1-sulfonamide;
2,2,2-trifluoro-N-[3-(4-methoxy-1-methyl-6-oxo-1,6-dihydropyridazin-3-yl)-4-phenoxyphenyl]ethanesulfonamide;
N-[3-(4-methoxy-1-methyl-6-oxo-1,6-dihydropyridazin-3-yl)-4-phenoxyphenyl]cyclopentanesulfonamide;
N-[3-(4-methoxy-1-methyl-6-oxo-1,6-dihydropyridazin-3-yl)-4-phenoxyphenyl]-1-phenylmethanesulfonamide;
3,3,3-trifluoro-N-[3-(4-methoxy-1-methyl-6-oxo-1,6-dihydropyridazin-3-yl)-4-phenoxyphenyl]propane-1-sulfonamide;
Ethyl [3-(4-methoxy-1-methyl-6-oxo-1,6-dihydropyridazin-3-yl)-4-phenoxyphenyl]carbamate;
1-ethyl-3-[3-(4-methoxy-1-methyl-6-oxo-1,6-dihydropyridazin-3-yl)-4-phenoxyphenyl]urea;
N'-[3-(4-methoxy-1-methyl-6-oxo-1,6-dihydropyridazin-3-yl)-4-phenoxyphenyl]-N,N-dimethylsulfuric diamide;
4-[2-(4-methoxy-1-methyl-6-oxo-1,6-dihydropyridazin-3-yl)phenoxy]benzonitrile;
6-[2-(4-fluorophenoxy)phenyl]-5-methoxy-2-methylpyridazin-3(2H)-one;
6-[2-(3-chloro-4-fluorophenoxy)phenyl]-5-methoxy-2-methylpyridazin-3(2H)-one;
5-methoxy-6-[2-(4-methoxyphenoxy)phenyl]-2-methylpyridazin-3(2H)-one;
6-[2-(3-fluorophenoxy)phenyl]-5-methoxy-2-methylpyridazin-3(2H)-one;
6-[2-(4-chlorophenoxy)phenyl]-5-methoxy-2-methylpyridazin-3(2H)-one;
methyl {[1-methyl-6-oxo-3-(2-phenoxyphenyl)-1,6-dihydropyridazin-4-yl]oxy}acetate;
6-[2-(cyclohexyloxy)phenyl]-5-methoxy-2-methylpyridazin-3(2H)-one;
5-methoxy-2-methyl-6-[2-(pyridin-2-ylmethoxy)phenyl]pyridazin-3(2H)-one;
6-[2-(1H-indazol-5-ylmethoxy)phenyl]-5-methoxy-2-methylpyridazin-3(2H)-one;

6-[2-(2-cyclohexylethoxy)phenyl]-5-methoxy-2-methyl-pyridazin-3(2H)-one;
tert-butyl 4-{[2-(4-methoxy-1-methyl-6-oxo-1,6-dihydropyridazin-3-yl)phenoxy]methyl}piperidine-1-carboxylate;
5-methoxy-2-methyl-6-[2-(piperidin-4-ylmethoxy)phenyl]pyridazin-3(2H)-one;
5-methoxy-2-methyl-6-[2-(pyridin-4-ylmethoxy)phenyl]pyridazin-3(2H)-one;
6-[2-(cyclopentylmethoxy)phenyl]-5-methoxy-2-methyl-pyridazin-3(2H)-one;
5-methoxy-2-methyl-6-[2-(tetrahydro-2H-pyran-4-ylmethoxy)phenyl]pyridazin-3(2H)-one;
methyl 1-[1-methyl-6-oxo-3-(2-phenoxyphenyl)-1,6-dihydropyridazin-4-yl]pyrrolidine-3-carboxylate;
Ethyl 1-[1-methyl-6-oxo-3-(2-phenoxyphenyl)-1,6-dihydropyridazin-4-yl]pyrrolidine-3-carboxylate;
methyl N-[1-methyl-6-oxo-3-(2-phenoxyphenyl)-1,6-dihydropyridazin-4-yl]glycinate;
2-methyl-5-(4-methyl-3-oxopiperazin-1-yl)-6-(2-phenoxyphenyl)pyridazin-3(2H)-one;
6-(biphenyl-2-yl)-2-methylpyridazin-3(2H)-one;
2'-(1-methyl-6-oxo-1,6-dihydropyridazin-3-yl)biphenyl-3-carbonitrile;
5-(2-fluoropyridin-4-yl)-2-methyl-6-(2-phenoxyphenyl)pyridazin-3(2H)-one;
2-methyl-5-(2-oxo-1,2-dihydropyridin-4-yl)-6-(2-phenoxyphenyl)pyridazin-3(2H)-one;
2-methyl-5-(1-methyl-2-oxo-1,2-dihydropyridin-4-yl)-6-(2-phenoxyphenyl)pyridazin-3(2H)-one;
5-(2-methoxypyridin-4-yl)-2-methyl-6-(2-phenoxyphenyl)pyridazin-3(2H)-one;
N-{3-[4-(2-methoxypyridin-4-yl)-1-methyl-6-oxo-1,6-dihydropyridazin-3-yl]-4-phenoxyphenyl}methanesulfonamide;
Ethyl 3-[1-methyl-6-oxo-3-(2-phenoxyphenyl)-1,6-dihydropyridazin-4-yl]benzoate;
2-methyl-5-{3-[(4-methylpiperazin-1-yl)methyl]phenyl}-6-(2-phenoxyphenyl)pyridazin-3(2H)-one;
2-methyl-5-{4-[(4-methylpiperazin-1-yl)methyl]phenyl}-6-(2-phenoxyphenyl)pyridazin-3(2H)-one;
N-[3-(1-methyl-4-{4-[(4-methylpiperazin-1-yl)methyl]phenyl}-6-oxo-1,6-dihydropyridazin-3-yl)-4-phenoxyphenyl]methanesulfonamide;
N-{3-[1-methyl-4-(4-methylphenyl)-6-oxo-1,6-dihydropyridazin-3-yl]-4-phenoxyphenyl}methanesulfonamide;
5-(3-amino-4-methylphenyl)-2-methyl-6-(2-phenoxyphenyl)pyridazin-3(2H)-one;
4-[1-methyl-6-oxo-3-(2-phenoxyphenyl)-1,6-dihydropyridazin-4-yl]benzaldehyde;
2-methyl-5-[4-(morpholin-4-ylmethyl)phenyl]-6-(2-phenoxyphenyl)pyridazin-3(2H)-one;
2-methyl-6-(2-phenoxyphenyl)-5-[4-(piperidin-1-ylmethyl)phenyl]pyridazin-3(2H)-one;
2-methyl-5-{4-[(4-methylpiperidin-1-yl)methyl]phenyl}-6-(2-phenoxyphenyl)pyridazin-3(2H)-one;
5-{4-[(diethylamino)methyl]phenyl}-2-methyl-6-(2-phenoxyphenyl)pyridazin-3(2H)-one;
2-methyl-6-(2-phenoxyphenyl)-5-[4-(piperazin-1-ylmethyl)phenyl]pyridazin-3(2H)-one;
2-methyl-6-(2-phenoxyphenyl)-5-[4-(pyrrolidin-1-ylmethyl)phenyl]pyridazin-3(2H)-one;
5-[4-(1-hydroxypropyl)phenyl]-2-methyl-6-(2-phenoxyphenyl)pyridazin-3(2H)-one;
5-[4-(1-hydroxy-2-methylpropyl)phenyl]-2-methyl-6-(2-phenoxyphenyl)pyridazin-3(2H)-one;
5-{4-[cyclopentyl(hydroxy)methyl]phenyl}-2-methyl-6-(2-phenoxyphenyl)pyridazin-3(2H)-one;
5-[4-(1-hydroxyethyl)phenyl]-2-methyl-6-(2-phenoxyphenyl)pyridazin-3(2H)-one;
5-{4-[hydroxy(phenyl)methyl]phenyl}-2-methyl-6-(2-phenoxyphenyl)pyridazin-3(2H)-one;
5-[4-(1-hydroxybut-3-en-1-yl)phenyl]-2-methyl-6-(2-phenoxyphenyl)pyridazin-3(2H)-one;
5-[4-(hydroxymethyl)phenyl]-2-methyl-6-(2-phenoxyphenyl)pyridazin-3(2H)-one;
5-[4-(methoxymethyl)phenyl]-2-methyl-6-(2-phenoxyphenyl)pyridazin-3(2H)-one;
4-[1-methyl-6-oxo-3-(2-phenoxyphenyl)-1,6-dihydropyridazin-4-yl]benzyl acetate;
tert-butyl 4-[1-methyl-6-oxo-3-(2-phenoxyphenyl)-1,6-dihydropyridazin-4-yl]-3,6-dihydropyridine-1(2H)-carboxylate;
2-methyl-6-(2-phenoxyphenyl)-5-(1,2,3,6-tetrahydropyridin-4-yl)pyridazin-3(2H)-one;
2-methyl-5-(1-methyl-1,2,3,6-tetrahydropyridin-4-yl)-6-(2-phenoxyphenyl)pyridazin-3(2H)-one;
5-(1-acetyl-1,2,3,6-tetrahydropyridin-4-yl)-2-methyl-6-(2-phenoxyphenyl)pyridazin-3(2H)-one;
2-methyl-5-[1-(methylsulfonyl)-1,2,3,6-tetrahydropyridin-4-yl]-6-(2-phenoxyphenyl)pyridazin-3(2H)-one;
tert-butyl 4-[1-methyl-6-oxo-3-(2-phenoxyphenyl)-1,6-dihydropyridazin-4-yl]piperidine-1-carboxylate;
2-methyl-6-(2-phenoxyphenyl)-5-(piperidin-4-yl)pyridazin-3(2H)-one;
2-methyl-5-(1-methylpiperidin-4-yl)-6-(2-phenoxyphenyl)pyridazin-3(2H)-one;
5-(1-acetylpiperidin-4-yl)-2-methyl-6-(2-phenoxyphenyl)pyridazin-3(2H)-one;
2-methyl-5-[1-(methylsulfonyl)piperidin-4-yl]-6-(2-phenoxyphenyl)pyridazin-3(2H)-one;
2-methyl-5-[4-(5-methyl-1,3,4-oxadiazol-2-yl)phenyl]-6-(2-phenoxyphenyl)pyridazin-3(2H)-one;
methyl 3-{4-[1-methyl-6-oxo-3-(2-phenoxyphenyl)-1,6-dihydropyridazin-4-yl]phenyl}propanoate;
5-(4-benzylphenyl)-2-methyl-6-(2-phenoxyphenyl)pyridazin-3(2H)-one;
{4-[1-methyl-6-oxo-3-(2-phenoxyphenyl)-1,6-dihydropyridazin-4-yl]phenyl}acetonitrile;
5-[4-(5,6-dihydro-4H-1,3-oxazin-2-yl)phenyl]-2-methyl-6-(2-phenoxyphenyl)pyridazin-3(2H)-one;
2-methyl-5-[4-(2-methylpropyl)phenyl]-6-(2-phenoxyphenyl)pyridazin-3(2H)-one;
Ethyl {4-[1-methyl-6-oxo-3-(2-phenoxyphenyl)-1,6-dihydropyridazin-4-yl]phenyl}acetate;
N-{4-[1-methyl-6-oxo-3-(2-phenoxyphenyl)-1,6-dihydropyridazin-4-yl]benzyl}methanesulfonamide;
N-{4-[1-methyl-6-oxo-3-(2-phenoxyphenyl)-1,6-dihydropyridazin-4-yl]benzyl}acetamide;
N-(2-{4-[1-methyl-6-oxo-3-(2-phenoxyphenyl)-1,6-dihydropyridazin-4-yl]phenyl}ethyl)acetamide;
5-[4-(3-hydroxypropyl)phenyl]-2-methyl-6-(2-phenoxyphenyl)pyridazin-3(2H)-one;
methyl 4-[1-methyl-6-oxo-3-(2-phenoxyphenyl)-1,6-dihydropyridazin-4-yl]benzoate;
2-methyl-5-(1-methyl-1H-pyrazol-4-yl)-6-(2-phenoxyphenyl)pyridazin-3(2H)-one;
2-methyl-6-(2-phenoxyphenyl)-5-(pyridin-4-yl)pyridazin-3(2H)-one;
N-{4-[1-methyl-6-oxo-3-(2-phenoxyphenyl)-1,6-dihydropyridazin-4-yl]phenyl}acetamide;
N-{3-[1-methyl-6-oxo-3-(2-phenoxyphenyl)-1,6-dihydropyridazin-4-yl]phenyl}acetamide;

5-(4-ethoxy-3-fluorophenyl)-2-methyl-6-(2-phenoxyphenyl)pyridazin-3(2H)-one;
N,N-dimethyl-4-[1-methyl-6-oxo-3-(2-phenoxyphenyl)-1,6-dihydropyridazin-4-yl]benzamide;
N,N-dimethyl-3-[1-methyl-6-oxo-3-(2-phenoxyphenyl)-1,6-dihydropyridazin-4-yl]benzamide;
2-methyl-5-[3-(2-methylpropoxy)phenyl]-6-(2-phenoxyphenyl)pyridazin-3(2H)-one;
5-[3-fluoro-4-(propan-2-yloxy)phenyl]-2-methyl-6-(2-phenoxyphenyl)pyridazin-3(2H)-one;
4-[1-methyl-6-oxo-3-(2-phenoxyphenyl)-1,6-dihydropyridazin-4-yl]benzenesulfonamide;
5-(1-benzyl-1H-pyrazol-4-yl)-2-methyl-6-(2-phenoxyphenyl)pyridazin-3(2H)-one;
N-cyclopropyl-4-[1-methyl-6-oxo-3-(2-phenoxyphenyl)-1,6-dihydropyridazin-4-yl]benzamide;
5-(3,5-dimethyl-1H-pyrazol-4-yl)-2-methyl-6-(2-phenoxyphenyl)pyridazin-3(2H)-one;
5-(6-methoxypyridin-3-yl)-2-methyl-6-(2-phenoxyphenyl)pyridazin-3(2H)-one;
5-(4-ethoxyphenyl)-2-methyl-6-(2-phenoxyphenyl)pyridazin-3(2H)-one;
5-(isoquinolin-4-yl)-2-methyl-6-(2-phenoxyphenyl)pyridazin-3(2H)-one;
N-{4-[1-methyl-6-oxo-3-(2-phenoxyphenyl)-1,6-dihydropyridazin-4-yl]phenyl}methanesulfonamide;
N-{3-[1-methyl-6-oxo-3-(2-phenoxyphenyl)-1,6-dihydropyridazin-4-yl]phenyl}methanesulfonamide;
N-{5-[1-methyl-6-oxo-3-(2-phenoxyphenyl)-1,6-dihydropyridazin-4-yl]pyridin-3-yl}acetamide;
N-methyl-5-[1-methyl-6-oxo-3-(2-phenoxyphenyl)-1,6-dihydropyridazin-4-yl]pyridine-3-carboxamide;
2-methyl-6-(2-phenoxyphenyl)-5-[6-(propan-2-yloxy)pyridin-3-yl]pyridazin-3(2H)-one;
5-(3-acetyl-2-fluorophenyl)-2-methyl-6-(2-phenoxyphenyl)pyridazin-3(2H)-one;
5-(2,6-dimethoxypyridin-3-yl)-2-methyl-6-(2-phenoxyphenyl)pyridazin-3(2H)-one;
methyl 2-[1-methyl-6-oxo-3-(2-phenoxyphenyl)-1,6-dihydropyridazin-4-yl]benzoate;
N-methyl-4-[1-methyl-6-oxo-3-(2-phenoxyphenyl)-1,6-dihydropyridazin-4-yl]benzamide;
N-methyl-3-[1-methyl-6-oxo-3-(2-phenoxyphenyl)-1,6-dihydropyridazin-4-yl]benzamide;
2-methyl-5-[1-(3-methylbutyl)-1H-pyrazol-4-yl]-6-(2-phenoxyphenyl)pyridazin-3(2H)-one;
2-methyl-6-(2-phenoxyphenyl)-5-[2-(propan-2-yloxy)pyridin-3-yl]pyridazin-3(2H)-one;
5-(1,3-benzothiazol-5-yl)-2-methyl-6-(2-phenoxyphenyl)pyridazin-3(2H)-one;
5-(5-acetyl-2-fluorophenyl)-2-methyl-6-(2-phenoxyphenyl)pyridazin-3(2H)-one;
5-(2,3-dihydro-1,4-benzodioxin-6-yl)-2-methyl-6-(2-phenoxyphenyl)pyridazin-3(2H)-one;
5-[3-(1-methoxyethyl)phenyl]-2-methyl-6-(2-phenoxyphenyl)pyridazin-3(2H)-one;
5-[4-(1-methoxyethyl)phenyl]-2-methyl-6-(2-phenoxyphenyl)pyridazin-3(2H)-one;
5-(3-ethoxy-2-fluorophenyl)-2-methyl-6-(2-phenoxyphenyl)pyridazin-3(2H)-one;
5-(2,1,3-benzothiadiazol-5-yl)-2-methyl-6-(2-phenoxyphenyl)pyridazin-3(2H)-one;
5-[5-(benzylamino)pyridin-3-yl]-2-methyl-6-(2-phenoxyphenyl)pyridazin-3(2H)-one;
2-methyl-5-[3-(morpholin-4-yl)phenyl]-6-(2-phenoxyphenyl)pyridazin-3(2H)-one;
2-methyl-6-(2-phenoxyphenyl)-5-[6-(2,2,2-trifluoroethoxy)pyridin-3-yl]pyridazin-3(2H)-one;
2-methyl-5-[3-(morpholin-4-ylmethyl)phenyl]-6-(2-phenoxyphenyl)pyridazin-3(2H)-one;
2-methyl-6-(2-phenoxyphenyl)-5-[3-(thiomorpholin-4-ylcarbonyl)phenyl]pyridazin-3(2H)-one;
5-[5-(cyclopentylamino)pyridin-3-yl]-2-methyl-6-(2-phenoxyphenyl)pyridazin-3(2H)-one;
N-cyclopropyl-5-[1-methyl-6-oxo-3-(2-phenoxyphenyl)-1,6-dihydropyridazin-4-yl]pyridine-3-carboxamide;
N-cyclopentyl-5-[1-methyl-6-oxo-3-(2-phenoxyphenyl)-1,6-dihydropyridazin-4-yl]pyridine-3-carboxamide;
N,N-diethyl-3-[1-methyl-6-oxo-3-(2-phenoxyphenyl)-1,6-dihydropyridazin-4-yl]benzenesulfonamide;
2-methyl-5-[4-(morpholin-4-ylcarbonyl)phenyl]-6-(2-phenoxyphenyl)pyridazin-3(2H)-one;
N-cyclohexyl-N-methyl-3-[1-methyl-6-oxo-3-(2-phenoxyphenyl)-1,6-dihydropyridazin-4-yl]benzamide;
2-methyl-5-[4-(morpholin-4-yl)phenyl]-6-(2-phenoxyphenyl)pyridazin-3(2H)-one;
N-[3-(dimethylamino)propyl]-4-[1-methyl-6-oxo-3-(2-phenoxyphenyl)-1,6-dihydropyridazin-4-yl]benzamide;
2-methyl-6-(2-phenoxyphenyl)-5-[6-(piperazin-1-yl)pyridin-3-yl]pyridazin-3(2H)-one;
3-fluoro-N,N-dimethyl-5-[1-methyl-6-oxo-3-(2-phenoxyphenyl)-1,6-dihydropyridazin-4-yl]benzamide;
2-methyl-5-[2-(morpholin-4-yl)pyridin-4-yl]-6-(2-phenoxyphenyl)pyridazin-3(2H)-one;
2-methyl-5-{3-[(4-methylpiperidin-1-yl)carbonyl]phenyl}-6-(2-phenoxyphenyl)pyridazin-3(2H)-one;
2-fluoro-N,N-dimethyl-5-[1-methyl-6-oxo-3-(2-phenoxyphenyl)-1,6-dihydropyridazin-4-yl]benzamide;
2-methyl-6-(2-phenoxyphenyl)-5-[3-(pyrrolidin-1-ylsulfonyl)phenyl]pyridazin-3(2H)-one;
2-methyl-6-(2-phenoxyphenyl)-5-[3-(piperidin-1-ylcarbonyl)phenyl]pyridazin-3(2H)-one;
N,N-diethyl-4-[1-methyl-6-oxo-3-(2-phenoxyphenyl)-1,6-dihydropyridazin-4-yl]benzamide;
N-methyl-4-[1-methyl-6-oxo-3-(2-phenoxyphenyl)-1,6-dihydropyridazin-4-yl]benzenesulfonamide;
N,N-diethyl-3-[1-methyl-6-oxo-3-(2-phenoxyphenyl)-1,6-dihydropyridazin-4-yl]benzamide;
2-methyl-5-[4-(4-methylpiperazin-1-yl)phenyl]-6-(2-phenoxyphenyl)pyridazin-3(2H)-one;
2-methyl-5-(6-{[2-(morpholin-4-yl)ethyl]amino}pyridin-3-yl)-6-(2-phenoxyphenyl)pyridazin-3(2H)-one;
N-[3-(dimethylamino)propyl]-3-[1-methyl-6-oxo-3-(2-phenoxyphenyl)-1,6-dihydropyridazin-4-yl]benzamide;
5-[6-(benzylamino)pyridin-3-yl]-2-methyl-6-(2-phenoxyphenyl)pyridazin-3(2H)-one;
N-(2-cyanoethyl)-4-[1-methyl-6-oxo-3-(2-phenoxyphenyl)-1,6-dihydropyridazin-4-yl]benzamide;
2-methyl-5-[5-methyl-6-(morpholin-4-yl)pyridin-3-yl]-6-(2-phenoxyphenyl)pyridazin-3(2H)-one;
N,N-diethyl-3-fluoro-5-[1-methyl-6-oxo-3-(2-phenoxyphenyl)-1,6-dihydropyridazin-4-yl]benzamide;
N-tert-butyl-4-[1-methyl-6-oxo-3-(2-phenoxyphenyl)-1,6-dihydropyridazin-4-yl]benzamide;
N-cyclopentyl-4-[1-methyl-6-oxo-3-(2-phenoxyphenyl)-1,6-dihydropyridazin-4-yl]benzamide;
4-[1-methyl-6-oxo-3-(2-phenoxyphenyl)-1,6-dihydropyridazin-4-yl]-N-(2-methylpropyl)benzamide;
N-(3-methoxypropyl)-4-[1-methyl-6-oxo-3-(2-phenoxyphenyl)-1,6-dihydropyridazin-4-yl]benzamide;

2-methyl-5-{1-[2-(morpholin-4-yl)ethyl]-1H-pyrazol-4-yl}-6-(2-phenoxyphenyl)pyridazin-3(2H)-one;
N-(2-methoxyethyl)-4-[1-methyl-6-oxo-3-(2-phenoxyphenyl)-1,6-dihydropyridazin-4-yl]benzamide;
2-methyl-5-[2-(4-methylpiperazin-1-yl)pyridin-4-yl]-6-(2-phenoxyphenyl)pyridazin-3(2H)-one;
2-methyl-5-[3-(morpholin-4-ylcarbonyl)phenyl]-6-(2-phenoxyphenyl)pyridazin-3(2H)-one;
2-methyl-5-[3-(5-methyl-1,3,4-oxadiazol-2-yl)phenyl]-6-(2-phenoxyphenyl)pyridazin-3(2H)-one;
N-cyclopropyl-3-[1-methyl-6-oxo-3-(2-phenoxyphenyl)-1,6-dihydropyridazin-4-yl]benzamide;
2-methyl-6-(2-phenoxyphenyl)-5-[4-(pyrrolidin-1-ylsulfonyl)phenyl]pyridazin-3(2H)-one;
2-methyl-5-[6-(morpholin-4-yl)pyridin-3-yl]-6-(2-phenoxyphenyl)pyridazin-3(2H)-one;
2-methyl-6-(2-phenoxyphenyl)-5-{4-[4-(propan-2-yl)piperazin-1-yl]phenyl}pyridazin-3(2H)-one;
N,N-diethyl-2-fluoro-5-[1-methyl-6-oxo-3-(2-phenoxyphenyl)-1,6-dihydropyridazin-4-yl]benzamide;
N-benzyl-4-[1-methyl-6-oxo-3-(2-phenoxyphenyl)-1,6-dihydropyridazin-4-yl]benzamide;
2-methyl-6-(2-phenoxyphenyl)-5-[4-(pyrrolidin-1-ylcarbonyl)phenyl]pyridazin-3(2H)-one;
2-methyl-6-(2-phenoxyphenyl)-5-[6-(piperidin-1-yl)pyridin-3-yl]pyridazin-3(2H)-one;
N-cyclohexyl-4-[1-methyl-6-oxo-3-(2-phenoxyphenyl)-1,6-dihydropyridazin-4-yl]benzamide;
N-[2-(dimethylamino)ethyl]-3-[1-methyl-6-oxo-3-(2-phenoxyphenyl)-1,6-dihydropyridazin-4-yl]benzamide;
2-methyl-6-(2-phenoxyphenyl)-5-{4-[(phenylamino)methyl]phenyl}pyridazin-3(2H)-one;
2-methyl-5-[2-(4-methylpiperazin-1-yl)pyrimidin-5-yl]-6-(2-phenoxyphenyl)pyridazin-3(2H)-one;
methyl {4-[1-methyl-6-oxo-3-(2-phenoxyphenyl)-1,6-dihydropyridazin-4-yl]phenyl}acetate;
5-(5-ethoxypyridin-3-yl)-2-methyl-6-(2-phenoxyphenyl)pyridazin-3(2H)-one;
2-methyl-5-[4-(methylamino)phenyl]-6-(2-phenoxyphenyl)pyridazin-3(2H)-one;
5-[2-(dimethylamino)pyrimidin-5-yl]-2-methyl-6-(2-phenoxyphenyl)pyridazin-3(2H)-one;
{3-[1-methyl-6-oxo-3-(2-phenoxyphenyl)-1,6-dihydropyridazin-4-yl]phenyl}acetonitrile;
2-methyl-5-(1-methyl-1H-pyrrol-2-yl)-6-(2-phenoxyphenyl)pyridazin-3(2H)-one;
2-methyl-6-(2-phenoxyphenyl)-5-(pyridin-3-yl)pyridazin-3(2H)-one;
2-methyl-5-(6-methylpyridin-3-yl)-6-(2-phenoxyphenyl)pyridazin-3(2H)-one;
5-(3-methoxyphenyl)-2-methyl-6-(2-phenoxyphenyl)pyridazin-3(2H)-one;
2-methyl-5-(4-methyl-3,4-dihydro-2H-pyrido[3,2-b][1,4]oxazin-7-yl)-6-(2-phenoxyphenyl)pyridazin-3(2H)-one;
5-(4-fluoro-3-methoxyphenyl)-2-methyl-6-(2-phenoxyphenyl)pyridazin-3(2H)-one;
5-(2-aminopyridin-4-yl)-2-methyl-6-(2-phenoxyphenyl)pyridazin-3(2H)-one;
5-(3-acetylphenyl)-2-methyl-6-(2-phenoxyphenyl)pyridazin-3(2H)-one;
N-ethyl-4-[1-methyl-6-oxo-3-(2-phenoxyphenyl)-1,6-dihydropyridazin-4-yl]benzamide;
5-(3-fluoro-4-methoxyphenyl)-2-methyl-6-(2-phenoxyphenyl)pyridazin-3(2H)-one;
5-(1,5-dimethyl-1H-pyrazol-4-yl)-2-methyl-6-(2-phenoxyphenyl)pyridazin-3(2H)-one;
2-methyl-5-(2-methylpyridin-4-yl)-6-(2-phenoxyphenyl)pyridazin-3(2H)-one;
2-methyl-5-[1-(2-methylpropyl)-1H-pyrazol-4-yl]-6-(2-phenoxyphenyl)pyridazin-3(2H)-one;
2-methyl-5-(4-methylpyridin-3-yl)-6-(2-phenoxyphenyl)pyridazin-3(2H)-one;
2-methyl-5-(1-methyl-1H-indol-5-yl)-6-(2-phenoxyphenyl)pyridazin-3(2H)-one;
5-[3-(dimethylamino)phenyl]-2-methyl-6-(2-phenoxyphenyl)pyridazin-3(2H)-one;
5-(2-fluoro-5-methoxyphenyl)-2-methyl-6-(2-phenoxyphenyl)pyridazin-3(2H)-one;
2-methyl-5-(5-methylfuran-2-yl)-6-(2-phenoxyphenyl)pyridazin-3(2H)-one;
5-(1-ethyl-1H-pyrazol-4-yl)-2-methyl-6-(2-phenoxyphenyl)pyridazin-3(2H)-one;
5-(3-methoxypyridin-4-yl)-2-methyl-6-(2-phenoxyphenyl)pyridazin-3(2H)-one;
2-methyl-5-(1-methyl-1H-indol-2-yl)-6-(2-phenoxyphenyl)pyridazin-3(2H)-one;
N,N-dimethyl-5-[1-methyl-6-oxo-3-(2-phenoxyphenyl)-1,6-dihydropyridazin-4-yl]pyridine-3-carboxamide;
5-[5-(dimethylamino)pyridin-3-yl]-2-methyl-6-(2-phenoxyphenyl)pyridazin-3(2H)-one;
5-butyl-2-methyl-6-(2-phenoxyphenyl)pyridazin-3(2H)-one;
methyl 1-methyl-6-oxo-3-(2-phenoxyphenyl)-1,6-dihydropyridazine-4-carboxylate;
methyl (2E)-3-[1-methyl-6-oxo-3-(2-phenoxyphenyl)-1,6-dihydropyridazin-4-yl]prop-2-enoate;
methyl 3-[1-methyl-6-oxo-3-(2-phenoxyphenyl)-1,6-dihydropyridazin-4-yl]propanoate;
5-acetyl-2-methyl-6-(2-phenoxyphenyl)pyridazin-3(2H)-one;
6-(2-benzylphenyl)-2-methylpyridazin-3(2H)-one;
N-[4-(2,4-difluorophenoxy)-3-(4-ethoxy-1-methyl-6-oxo-1,6-dihydropyridin-3-yl)phenyl]ethanesulfonamide;
N-[4-(2,4-difluorophenoxy)-3-{1-methyl-4-[2-(morpholin-4-yl)ethoxy]-6-oxo-1,6-dihydropyridin-3-yl}phenyl]ethanesulfonamide;
N-(3-(4-(cyclopropylmethoxy)-1-methyl-6-oxo-1,6-dihydropyridin-3-yl)-4-(2,4-difluorophenoxy)phenyl)ethanesulfonamide;
N-(4-(2,4-difluorophenoxy)-3-(4-(2-(dimethylamino)ethoxy)-1-methyl-6-oxo-1,6-dihydropyridin-3-yl)phenyl)ethanesulfonamide;
N-{4-(2,4-difluorophenoxy)-3-[1-methyl-6-oxo-4-(propan-2-yloxy)-1,6-dihydropyridin-3-yl]phenyl}ethanesulfonamide;
N-{4-(2,4-difluorophenoxy)-3-[1-methyl-4-(2-methylpropoxy)-6-oxo-1,6-dihydropyridin-3-yl]phenyl}ethanesulfonamide;
N-{4-(2,4-difluorophenoxy)-3-[1-methyl-6-oxo-4-(tetrahydrofuran-3-ylmethoxy)-1,6-dihydropyridin-3-yl]phenyl}ethanesulfonamide;
N-[4-(2,4-difluorophenoxy)-3-(1-methyl-6-oxo-4-propoxy-1,6-dihydropyridin-3-yl)phenyl]ethanesulfonamide; and
N-{4-(2,4-difluorophenoxy)-3-[1-methyl-6-oxo-4-(2,2,2-trifluoroethoxy)-1,6-dihydropyridin-3-yl]phenyl}ethanesulfonamide.

27. The compound of claim 1, or a pharmaceutically acceptable salt thereof, wherein said compound is selected from the group consisting of:

3-methyl-5-(2-phenoxyphenyl)pyridin-2(1H)-one;
N-[3-(5-methyl-6-oxo-1,6-dihydropyridin-3-yl)-4-phenoxyphenyl]methanesulfonamide;
N-[3-(5-methyl-6-oxo-1,6-dihydropyridin-3-yl)-4-phenoxyphenyl]acetamide;
N-[4-(2,4-difluorophenoxy)-3-(5-methyl-6-oxo-1,6-dihydropyridin-3-yl)phenyl]methanesulfonamide;
N-[4-(2,4-difluorophenoxy)-3-(5-methyl-6-oxo-1,6-dihydropyridin-3-yl)phenyl]ethanesulfonamide;
N-[4-(2,4-difluorophenoxy)-3-(5-methyl-6-oxo-1,6-dihydropyridin-3-yl)phenyl]acetamide;
N-{4-[(4,4-difluorocyclohexyl)oxy]-3-(5-methyl-6-oxo-1,6-dihydropyridin-3-yl)phenyl}methanesulfonamide; and
N-{4-[(4,4-difluorocyclohexyl)oxy]-3-(5-methyl-6-oxo-1,6-dihydropyridin-3-yl)phenyl}ethanesulfonamide.

28. A pharmaceutical composition comprising a therapeutically effective amount of a compound of formula (I) according to claim 1, or a pharmaceutically acceptable salt thereof, in combination with a pharmaceutically acceptable carrier.

29. A method for treating cancer in a subject comprising administering a therapeutically effective amount of a compound of formula (I) according to claim 1, or a pharmaceutically acceptable salt thereof, to a subject in need thereof.

30. The method of claim 29, wherein the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

31. The method of claim 30, further comprising administering a therapeutically effective amount of at least one additional therapeutic agent.

32. A method for treating a disease or condition in a subject comprising administering a therapeutically effective amount of a compound of formula (I) according to claim 1, or a pharmaceutically acceptable salt thereof, to a subject in need thereof, wherein said disease or condition is selected from the group consisting of: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis systemic lupus erythematosus, Takayasu's Arteritis, toxic shock, thyroiditis, type I diabetes, ulcerative colitis, uveitis, vitiligo, vasculitis, and Wegener's granulomatosis.

33. The method of claim 32, further comprising administering a therapeutically effective amount of at least one additional therapeutic agent.

34. A method for treating AIDS in a subject comprising administering a therapeutically effective amount of a compound of formula (I) according to claim 1, or a pharmaceutically acceptable salt thereof, to a subject in need thereof.

35. The method of claim 34, further comprising administering a therapeutically effective amount of at least one additional therapeutic agent.

36. A method for treating obesity in a subject comprising administering a therapeutically effective amount of a compound of formula (I) according to claim 1, or a pharmaceutically acceptable salt thereof, to a subject in need thereof.

37. The method of claim 36, further comprising administering a therapeutically effective amount of at least one additional therapeutic agent.

38. A method for treating type II diabetes in a subject comprising administering a therapeutically effective amount of a compound of formula (I) according to claim 1, or a pharmaceutically acceptable salt thereof, to a subject in need thereof.

39. The method of claim 38, further comprising administering a therapeutically effective amount of at least one additional therapeutic agent.

40. A method for treating an acute kidney disease or condition in a subject comprising administering a therapeutically effective amount of a compound of claim 1 or a pharmaceutically acceptable salt thereof, to a subject in need thereof, wherein said acute kidney disease or condition is selected from the group consisting of: ischemia-reperfusion induced kidney disease, cardiac and major surgery induced kidney disease, percutaneous coronary intervention induced kidney disease, radio-contrast agent induced kidney disease, sepsis induced kidney disease, pneumonia induced kidney disease, and drug toxicity induced kidney disease.

41. The method of claim 40, further comprising administering a therapeutically effective amount of at least one additional therapeutic agent.

42. A method of treating a chronic kidney disease or condition in a subject comprising administering a therapeutically effective amount of a compound of claim 1 or a pharmaceutically acceptable salt thereof, to a subject in need thereof, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis.

43. The method of claim 42, further comprising administering a therapeutically effective amount of at least one additional therapeutic agent.

* * * * *

UNITED STATES PATENT AND TRADEMARK OFFICE
CERTIFICATE OF CORRECTION

PATENT NO. : 9,561,231 B2  
APPLICATION NO. : 13/796437  
DATED : February 7, 2017  
INVENTOR(S) : Hubbard et al.

Page 1 of 2

It is certified that error appears in the above-identified patent and that said Letters Patent is hereby corrected as shown below:

In the Claims

Column No: 238, Line(s): 41, Claim: 1, "maybe substituted" to read as --is optionally substituted--

Column No: 238, Line(s): 50, Claim: 1, "maybe substituted" to read as --is optionally substituted--

Column No: 238, Line(s): 52, Claim: 1, "maybe substituted" to read as --is optionally substituted--

Column No: 240, Line(s): 17, Claim: 1, "substituted with substituents 1 to 3 groups" to read as --substituted with 1 to 3 groups--

Column No: 241, Line(s): 58, Claim: 1, "$C_1$-$C_3$ alkyene-$SO_2$-$C_1$-$C_6$ alkyl," to read as --$C_1$-$C_3$ alkylene-$SO_2$-$C_1$-$C_6$ alkyl,--

Column No: 241, Line(s): 59, Claim: 1, "$C_1$-$C_3$ alkyene-$SO_2$-$C_1$-$C_6$ haloalkyl," to read as --$C_1$-$C_3$ alkylene-$SO_2$-$C_1$-$C_6$ haloalkyl,--

Column No: 241, Line(s): 59-60, Claim: 1, "$C_1$-$C_3$ alkyene-$SO_2$-$N^{20}N^{22}$," to read as --$C_1$-$C_3$ alkylene-$SO_2$-$N^{20}N^{22}$,--

Column No: 242, Line(s): 45, Claim: 2, "$C_1$-$C_3$ alkyene-$SO_2$-$C_1$-$C_6$ alkyl," to read as --$C_1$-$C_3$ alkylene-$SO_2$-$C_1$-$C_6$ alkyl,--

Column No: 242, Line(s): 45-46, Claim: 2, "$C_1$-$C_3$ alkyene-$SO_2$-$C_1$-$C_6$ haloalkyl," to read as --$C_1$-$C_3$ alkylene-$SO_2$-$C_1$-$C_6$ haloalkyl,--

Column No: 242, Line(s): 46-47, Claim: 2, "$C_1$-$C_3$ alkyene-$SO_2$-$N^{20}N^{22}$," to read as --$C_1$-$C_3$ alkylene-$SO_2$-$N^{20}N^{22}$,--

Column No: 243, Line(s): 47, Claim: 10, "alkyene" to read as --alkylene--

Signed and Sealed this  
Twenty-second Day of October, 2019

Andrei Iancu  
*Director of the United States Patent and Trademark Office*

CERTIFICATE OF CORRECTION (continued)
U.S. Pat. No. 9,561,231 B2

Column No: 246, Line(s): 50-51, Claim: 24, "substituted with substituents 1 to 3 groups" to read as --substituted with 1 to 3 groups--

Column No: 247, Line(s): 39, Claim: 24, "-heteroarylaryl," to read as -- -heteroaryl,--

Column No: 248, Line(s): 07, Claim: 24, "$C_1$-$C_3$ alkyene-$SO_2$-$C_1$-$C_6$ alkyl," to read as --$C_1$-$C_3$ alkylene-$SO_2$-$C_1$-$C_6$ alkyl,--

Column No: 248, Line(s): 07-08, Claim: 24, "$C_1$-$C_3$ alkyene-$SO_2$-$C_1$-$C_6$ haloalkyl," to read as --$C_1$-$C_3$ alkylene-$SO_2$-$C_1$-$C_6$ haloalkyl,--

Column No: 248, Line(s): 08-09, Claim: 24, "$C_1$-$C_3$ alkyene-$SO_2$-$N^{20}N^{22}$," to read as --$C_1$-$C_3$ alkylene-$SO_2$-$N^{20}N^{22}$,--

Column No: 250, Line(s): 46, Claim: 25, "ethanesulfonamide; sss" to read as --ethanesulfonamide;--

Column No: 255, Line(s): 54-55, Claim: 26, "-[2-(1-methyl-6-oxo-1,6-dihydropyridazin-3-yl)phenoxy]benzonitrile;" to read as --4-[2-(1-methyl-6-oxo-1,6-dihydropyridazin-3-yl)phenoxy]benzonitrile;--